(12) United States Patent
Hadd et al.

(10) Patent No.: US 9,452,167 B2
(45) Date of Patent: *Sep. 27, 2016

(54) HETEROCYCLIC COMPOUNDS AND METHODS OF USE THEREOF

(71) Applicant: AMBIT BIOSCIENCES CORPORATION, San Diego, CA (US)

(72) Inventors: Michael J. Hadd, San Diego, CA (US); Michael D. Hocker, San Diego, CA (US); Mark W. Holladay, San Diego, CA (US); Gang Liu, San Diego, CA (US); Martin W. Rowbottom, San Diego, CA (US); Shimin Xu, San Diego, CA (US)

(73) Assignee: AMBIT BIOSCIENCES CORPORATION, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/580,045

(22) Filed: Dec. 22, 2014

(65) Prior Publication Data

US 2015/0196566 A1 Jul. 16, 2015

Related U.S. Application Data

(63) Continuation of application No. 13/651,312, filed on Oct. 12, 2012, now Pat. No. 8,952,058.

(60) Provisional application No. 61/638,990, filed on Apr. 26, 2012, provisional application No. 61/547,637, filed on Oct. 14, 2011.

(51) Int. Cl.
| | |
|---|---|
| A01N 37/12 | (2006.01) |
| A01N 37/44 | (2006.01) |
| A61K 31/5377 | (2006.01) |
| C07D 413/14 | (2006.01) |
| C07D 413/06 | (2006.01) |
| C07D 417/06 | (2006.01) |
| C07D 417/14 | (2006.01) |
| C07D 471/04 | (2006.01) |
| C07D 487/04 | (2006.01) |
| A61K 31/422 | (2006.01) |
| A61K 31/427 | (2006.01) |
| A61K 31/437 | (2006.01) |
| A61K 31/4439 | (2006.01) |
| A61K 31/454 | (2006.01) |
| A61K 31/52 | (2006.01) |
| A61K 45/06 | (2006.01) |

(52) U.S. Cl.
CPC ......... *A61K 31/5377* (2013.01); *A61K 31/422* (2013.01); *A61K 31/427* (2013.01); *A61K 31/437* (2013.01); *A61K 31/4439* (2013.01); *A61K 31/454* (2013.01); *A61K 31/52* (2013.01); *A61K 45/06* (2013.01); *C07D 413/06* (2013.01); *C07D 413/14* (2013.01); *C07D 417/06* (2013.01); *C07D 417/14* (2013.01); *C07D 471/04* (2013.01); *C07D 487/04* (2013.01)

(58) Field of Classification Search
CPC ............ A61K 31/422; A61K 31/427; A61K 31/437; A61K 31/4439; A61K 31/454; A61K 31/52; A61K 31/5377; A61K 45/06; C07D 413/06; C07D 413/14; C07D 417/06; C07D 417/14; C07D 471/04; C07D 487/04
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,104,385 | A | 8/1978 | Lesher et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,639,480 | A | 6/1997 | Bodmer et al. |
| 5,674,533 | A | 10/1997 | Santus et al. |
| 5,709,874 | A | 1/1998 | Hanson et al. |
| 5,733,566 | A | 3/1998 | Lewis |
| 5,739,108 | A | 4/1998 | Mitchell |
| 5,759,542 | A | 6/1998 | Gurewich |
| 5,840,674 | A | 11/1998 | Yatvin et al. |
| 5,891,474 | A | 4/1999 | Busetti et al. |
| 5,900,252 | A | 5/1999 | Calanchi et al. |
| 5,922,356 | A | 7/1999 | Koseki et al. |
| 5,972,366 | A | 10/1999 | Haynes et al. |

(Continued)

FOREIGN PATENT DOCUMENTS

| | | |
|---|---|---|
| JP | 2006070014 | 3/2006 |
| WO | WO 93/16684 | 9/1993 |

(Continued)

OTHER PUBLICATIONS

Judson, Semin Respir Crit Care Med 2007;28:83-101.*

(Continued)

*Primary Examiner* — Jean Cornet
(74) *Attorney, Agent, or Firm* — Jones Day

(57) ABSTRACT

Provided herein are heterocyclic compounds for treatment of CSF1R, FLT3, KIT, and/or PDGFRβ kinase mediated diseases. Also provided are pharmaceutical compositions comprising the compounds and methods of using the compounds and compositions.

20 Claims, 6 Drawing Sheets

(56) References Cited

U.S. PATENT DOCUMENTS

| | | | |
|---|---|---|---|
| 5,972,891 A | 10/1999 | Kamei et al. | |
| 5,980,945 A | 11/1999 | Ruiz | |
| 5,985,307 A | 11/1999 | Hanson et al. | |
| 5,993,855 A | 11/1999 | Yoshimoto et al. | |
| 6,004,534 A | 12/1999 | Langer et al. | |
| 6,039,975 A | 3/2000 | Shah et al. | |
| 6,045,830 A | 4/2000 | Igari et al. | |
| 6,048,736 A | 4/2000 | Kosak | |
| 6,060,082 A | 5/2000 | Chen et al. | |
| 6,071,495 A | 6/2000 | Unger et al. | |
| 6,087,324 A | 7/2000 | Igari et al. | |
| 6,113,943 A | 9/2000 | Okada et al. | |
| 6,120,751 A | 9/2000 | Unger | |
| 6,131,570 A | 10/2000 | Schuster et al. | |
| 6,139,865 A | 10/2000 | Friend et al. | |
| 6,197,350 B1 | 3/2001 | Yamagata et al. | |
| 6,248,363 B1 | 6/2001 | Patel et al. | |
| 6,253,872 B1 | 7/2001 | Neumann | |
| 6,264,970 B1 | 7/2001 | Hata et al. | |
| 6,267,981 B1 | 7/2001 | Okamoto et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |
| 6,376,461 B1 | 4/2002 | Igari et al. | |
| 6,419,961 B1 | 7/2002 | Igari et al. | |
| 6,589,548 B1 | 7/2003 | Oh et al. | |
| 6,613,358 B2 | 9/2003 | Randolph et al. | |
| 6,699,500 B2 | 3/2004 | Okada et al. | |
| 6,740,634 B1 | 5/2004 | Saikawa et al. | |
| 7,355,052 B2 | 4/2008 | Poitout et al. | |
| 7,449,463 B2 | 11/2008 | Bonfanti et al. | |
| 7,470,712 B2 | 12/2008 | Herpin et al. | |
| 7,863,291 B2 | 1/2011 | Cook, II et al. | |
| 7,910,741 B2 | 3/2011 | Nishizawa et al. | |
| 8,034,835 B2 | 10/2011 | Bonfanti et al. | |
| 8,053,450 B2 | 11/2011 | Herpin et al. | |
| 2007/0066660 A1 | 3/2007 | Stahle et al. | |
| 2007/0099938 A1 | 5/2007 | Ohmoto et al. | |
| 2009/0163464 A1 | 6/2009 | Black et al. | |
| 2010/0099684 A1 | 4/2010 | Cook, II et al. | |
| 2011/0207767 A1 | 8/2011 | Beusker et al. | |

FOREIGN PATENT DOCUMENTS

| | | | | |
|---|---|---|---|---|
| WO | WO 2004/015142 | | 2/2004 | |
| WO | WO 2004/085425 | | 10/2004 | |
| WO | WO 2005/058874 | | 6/2005 | |
| WO | WO 2007/022305 | | 2/2007 | |
| WO | WO 2008/005310 | | 1/2008 | |
| WO | WO 2008/121687 | | 10/2008 | |
| WO | WO 2009/050228 | | 4/2009 | |
| WO | WO 2009050228 A2 * | 4/2009 | ......... A61K 31/4184 |
| WO | WO 2010/100249 | | 9/2010 | |
| WO | WO 2011/153192 | | 12/2011 | |
| WO | WO 2012/018668 | | 2/2012 | |
| WO | WO 2012/088438 | | 6/2012 | |

OTHER PUBLICATIONS

Angelo et al., "$N^2$-1H-Benzimidazol-2-yl-$N^4$-phenyl-2,4-pyrimidinediamines and $N^2$-1H-Benzimidazol-2-yl-5,6,7,8-tetrahydro-$N^4$-phenyl-2,4-quinazolinediamines as Potential Antifilarial Agents[1,2]," J. Med. Chem. 26(9):1311-1316 (1983).

Baiocchi et al., "Expression of the macrophage colony-stimulating factor and its receptor in gynecologic malignancies," Cancer 67(4):990-996 (1991).

Bauknecht et al., "Expression of transcripts for CSF-1 and for the "macrophage" and "epithelial" isoforms of the CSF-1R transcripts in human ovarian carcinomas," Cancer Detect. Prev. 18(3): 231-239 (1994).

Blume-Jensen and Hunter, "Oncogenic kinase signaling," Nature 411(6835):355-365 (2001).

Conway et al., "Effects of the cFMS Kinase Inhibitor 5-(3-Methoxy-4-((4-methoxybenzyl)oxy)benzyl)pyrimidine-2,4-diamine (GW2580) in Normal and Arthritic Rats," J. Pharmacol. Exp. Ther. 326(1):41-50 (2008).(Epub Apr. 23, 2008).

Curtin et al., "Somatic activation of KIT in distinct subtypes of melanoma," J. Clin. Oncol. 24(26):4340-4346 (2006).

De Giorgi and Verweij, "Imatinib and gastrointestinal stromal tumors: Where do we go from here?" Mol. Cancer Ther. (3):495-501 (2005).

Duensing et al., "Biology of gastrointestinal stromal tumors: KIT mutations and beyond," Cancer Invest. 22(1):106-116 (2004).

Errasti et al., "Desymmetrization of hydrazinocyclohexadienes: a new approach for the synthesis of polyhydroxylated aminocyclohexanes," Org. Lett. 11(13):2912-2915 (2009).

Fabian et al., "A small molecule-kinase interaction map for clinical kinase inhibitors," Nat. Biotechnol. 23(3):329-336 (2005).

Heinrich, "Targeting FLT3 kinase in acute myelogenous leukemia: progress, perils, and prospec," Mini. Rev. Med. Chem. 4(3):255-271 (2004).

Kirma et al., "Elevated expression of the oncogene c-fms and its ligand, the macrophage colony-stimulating factor-1, in cervical cancer and the role of transforming growth factor-beta1 in inducing c-fms expression," Cancer Res. 67(5):1918-1926 (2007).

Kiyoi et al., "Clinical significance of FLT3 in leukemia," Int. J. Hematol. 82(2):85-92 (2005).

Kluger et al., "Macrophage colony-stimulating factor-1 receptor expression is associated with poor outcome in breast cancer by large cohort tissue microarray analysis," Clin. Canc. Res. 10(1 Pt 1):173-177 (2004).

Krause and Van Etten, "Tyrosine kinases as targets for cancer therapy," N. Engl. J. Med. 353(2):172-187 (2005).

Levis and Small, "FLT3 tyrosine kinase inhibitors," Int. J. Hematol. 82(2):100-107 (2005).

Lipton, "Pathophysiology of bone metastases: how this knowledge may lead to therapeutic intervention," J. Support Oncol. 2(3):205-220 (2004).

Molinos-Gomez et al., "Tautomeric enhancement of the hyperpolarizability in new acridine-benzothiazolylamine based NLO chromophores," Tetrahedron 61:9075-9081 (2005).

Mroczko et al., "Hematopoietic cytokines in the sera of patients with pancreatic cancer," Clin. Chem. Lab. Med. 43(2):146-150 (2005).

Mroczko et al., "Serum macrophage-colony stimulating factor levels in colorectal cancer patients correlate with lymph node metastasis and poor prognosis," Clin. Chim. Acta 380(1-2):208-212 (2007). (Epub Feb. 27, 2007).

Müller-Tidow et al., "High-throughput analysis of genome-wide receptor tyrosine kinase expression in human cancers identifies potential novel drug targets," Clin. Cancer Res. 10(4):1241-1249 (2004).

Ohno et al., "The orally-active and selective c-Fms tyrosine kinase inhibitor Ki20227 inhibits disease progression in a collagen-induced arthritis mouse model," Eur. J. Immunol. 38(1):283-291 (2008).

Plowman et al., "Receptor Tyosine Kinases as Targets for Drug Intervention," DN&P 7(6):334-339 (1994).

Priceman et al., "Targeting distinct tumor-infiltrating myeloid cells by inhibiting CSF-1 receptor: combating tumor evasion of antiangiogenic therapy," Blood 115(7):1461-1471(2010). (Epub Dec. 11, 2009).

Ritchlin et al., "Mechanisms of TNF-α- and RANKL-mediated osteoclastogenesis and bone resorption in psoriatic arthritis," J. Clin. Invest. 111(6):821-831 (2003).

Rolland et al., "Increased blood myeloid dendritic cells and dendritic cell-poietins in Langerhans cell histiocytosis," J. Immunol. 174(5):3067-3071 (2005).

Sapi, "The Role of CSF-1 in Normal Physiology of Mammary Gland and Breast Cancer: An Update," Exp. Biol. Med. (Maywood) 229(1):1-11 (2004).

Scholl et al., "Anti-colony-stimulating factor-1 antibody staining in primary breast adenocarcinomas correlates with marked inflammatory cell infiltrates and prognosis," J. Natl. Cancer Inst. 86(2):120-126 (1994).

(56) References Cited

OTHER PUBLICATIONS

Scott et al., "The links between joint damage and disability in rheumatoid arthritis," *Rheumatology (Oxford)* 39(2):122-132 (2000).
Shakya et al., "Synthesis and Antibacterial Activity of 2-[5'-Alkyl-1',3',4'-thiadiazol-2'-yl]amino-benzothiazole,-benzoxazole,-benzimidazole and -imidazolidines," *J. Indian Chem. Soc.* 68(3):147-148 (1991).
Sheng et al., "3D-QSAR and molecular docking studies on benzothiazole derivatives as Candida albicans N-myristoyltransferase inhibitors," *Eur. J. Med. Chem.* 42(4):477-486 (2007). (Epub Nov. 18, 2006).
Singh et al., "Studies in antiparasitic agents: Part 13—Synthesis of 4-aryl-2-substitutedamino-thiazoles as potential anthelmintics," *Indian J. Chem., Sec. B* 28B:786-789 (1989).
Sridevi et al., "Synthesis of Some Phenylpyrazolo Benzothiazolo Quinoxaline Derivatives," *Int.J. PharmTech Res.* 1(3):816-821 (2009).
Srivastava and Sharma, "Sutdies in antiparasitic agents: Part 14—Synthesis of 5-aryl-2-(diazacycloalken-2-ylamino)-1,3,4-thiadiazoles and 4-benzylidene-2-(substituted amino)imidazol-5-ones as potential anthelmintics," *Indian J. Chem., Sec. B* 29B:142-147(1990).
Tang et al., "Oncogene amplification correlates with dense lymphocyte infiltration in human breast cancers: a role for hematopoietic growth factor release by tumor cells?" *J. Cell. Biochem.* 44(3):189-198 (1990).
Wan et al., "Phosphonium-mediated cyclization of N-(2-aminophenyl)thioureas:efficient synthesis of 2-aminobenzimidazoles," *Tetrahedron Lett.* 52(32):4149-4152 (2011).
Whartenby et al., "Inhibition of FLT3 signaling targets DCs to ameliorate autoimmune disease," *Proc. Natl. Acad. Sci. U. S. A.* 102(46):16741-16746 (2005). (Epub Nov. 4, 2005).
Office Action mailed Jul. 18, 2013, U.S. Appl. No. 13/651,312.
Office Action mailed Jan. 16, 2014, U.S. Appl. No. 13/651,312.
Notice of Allowance mailed Sep. 22, 2014, U.S. Appl. No. 13/651,312.
Elmore et al., "Colony-Stimulating Factor 1 Receptor Signaling is Necessary for Microglia Viability, Unmasking a Microglia Progenitor Cell in the Adult Brain," *Neuron* 82:3080-397 (2014).
Escamilla et al., "CSF1 receptor targeting in prostate cancer reverses macrophage-mediated resistance to androgen blockade therapy," *Cancer Res.* 75(6):950-962 (2015) (Epub Mar. 3, 2015).
Green, Kim, "Microglial function in the Healthy Brain," The Green Lab, Accessed on Feb. 1, 2016 from URL: http://faculty.sites.uci.edu/kimgreen/bio/microglia-in-the-healthy-brain/.
Habets, Gaston, Zhang, Jiazhong, Burton, Betsy, Zhang, Chao, Ibrahim, Prabha, Wong, Bernice, et al; Efficacy of the Selective CSF1R (Fms) Inhibitor PLX5622 in Mouse Models of Rheumatoid Arthritis. [abstract]. *Arthritis Rheum* 2010;62 Suppl 10 :273.
Mok et al., "Inhibition of CSF-1 Receptor Improves the Antitumor Efficacy of Adoptive Cell Transfer Immunotherapy," *Cancer Res.* 74:153-161 (2014) (Epub Nov. 18, 2013).
Olmos-Alonso et al., "Pharmacological targeting of CSF1R inhibits microglial proliferation and prevents the progression of Alzheimer's-like pathology," *Brain* 1-17 (2016).
Plexxikon, "Plexxikon's PLX3397 Preclinical Data Demonstrate Potential of Novel, "First-in-Class" Cancer Drug; Phase 1 Clinical Trial Under Way in Patients with Metastatic Cancers," Press Release, Apr. 20, 2010.
Pyonteck et al., "CSF-1R inhibition alters macrophage polarization and blocks glioma progression," *Nat. Med.* 19:1264-1272 (2013).
Robert C. Armstrong, Barbara Belli, Martin W. Rowbottom, Ron R. Nepomuceno, Alan Q. Dao, Allison M. Rooks, Dan Brigham, Craig W. McMannus, Michael D. Hocker, Mark W. Holladay, Gang Liu. AC708 is a potent and selective Inhibitor of CSF1R and reduces tumor associated macrophage infiltration in a breast tumor model. [abstract]. In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr 903.

\* cited by examiner

HETEROCYCLIC COMPOUNDS AND METHODS OF USE THEREOF

RELATED APPLICATIONS

This application claims priority under 35 U.S.C. §120 to, and is a continuation of U.S. patent application Ser. No. 13/651,312, filed Oct. 12, 2012, now allowed, which claims priority to U.S. provisional application No. 61/547,637, filed in Oct. 14, 2011 and U.S. provisional application No. 61/638,990, filed in Apr. 26, 2012. The disclosures of each the above referenced applications are incorporated by reference herein in their entireties.

FIELD

Provided herein are heterocyclic compounds, including benzothiazolyl, benzoxazolyl, and quinazolyl compounds. In certain embodiments, the compounds are modulators of type III receptor tyrosine kinase family. In other embodiments, the compounds are modulators of CSF1R, FLT3, KIT, and/or PDGFRβ kinases. Also provided are compositions comprising the compounds and methods of use thereof. The compounds provided are useful in the treatment, prevention, or amelioration of a disease or disorder related to CSF1R, FLT3, KIT, and/or PDGFRβ kinase activity or one or more symptoms associated with such diseases or disorders.

BACKGROUND

Protein kinases (PKs) are enzymes that catalyze the phosphorylation of hydroxy groups on tyrosine, serine and threonine residues of proteins. Receptor tyrosine kinases (RTKs) are a sub-family of protein kinases that play a critical role in cell signaling and are involved in the process of tumorigenesis including cell proliferation, survival, angiogenesis, invasion and metastasis. A class of RTK known as the type III receptor tyrosine kinase family, which includes the receptors PDGFR α, PDGFR β, FLT3, KIT, VEGFR and CSF1R, has been implicated in various proliferative and inflammatory diseases.

CSF1R (also known as macrophage colony stimulating factor receptor (M-CSFR) or fms) is a receptor for the macrophage colony stimulating factor (M-CSF or CSF-1). Binding of the CSF-1 ligand to its receptor results in dimerization and auto-phosphorylation of the receptor and leads to activation of downstream signal transduction pathways including the PI3K/Akt and the mitogen activating protein kinase MAPK pathways. Activation of CSF1R leads to the proliferation, survival, motility and differentiation of cells of the monocyte/macrophage lineage and hence plays a role in normal tissue development and immune defense. Activation of CSF1R also leads to the proliferation and differentiation of osteoclast precursors and therefore mediates the process of bone resorption.

Because of its role in osteoclast biology, CSF1R is believed to be an important therapeutic target for osteoporosis and inflammatory arthritis. For example, elevated M-CFS signaling leads to elevated osteoclast activity, which leads to bone loss attending arthritis and other inflammatory bone erosion. (See Scott et al. *Rheumatology* 2000, 39: 122-132, Ritchlin et al. *J. Clin. Invest.* 2003, 111:821-831). Inhibition of CSF1R therefore represents a promising therapeutic approach for arthritis and other inflammatory bone erosion which is further supported by the efficacy data of known CSF1R inhibitors such as Ki-20227 and GW2580 in arthritic animal models (See Conwat et al. *JPET* 2008, 326:41-50 and Ohno et al. *Eur. J. Immunol.* 2008, 38:283-291). Dysregulation of osteoclast development and disruption in the balance of bone resorption and bone formation that underlie osteoporosis might also be treated with a modulator of CSF1R.

Elevated expression or activation of CSF1R and/or its ligand have been found in patients with acute myeloid leukemia, prostate, breast, ovarian, endometrial, colorectal, pancreatic and a variety of other cancers, and elevated levels of M-CSF is associated with poor prognosis in certain cancers (See, Muller-Tidow et al. *Clin Cancer Res,* 2004, 10:1241-1249, Bauknecht et al. *Cancer Detect. Prev.,* 1994, 18: 231-239; Baiocchi G et al. *Cancer* 1991, 67:990-996; Kirma et al *Cancer Res.* 2007; Sapi et al. *Exp. Biol. Med.,* 2004, 229:1-11; Kluger et al. *Clin. Canc. Res.* 2004 10:173-177; Mroczko et al., *Clin. Chem. Lab. Med.* 2005 43:146-50 and Mroczko et al., *Clin. Chim. Acta* 2007, 380:208-212). The data suggests that CSF1R may be a valuable therapeutic target for these solid tumors.

Early studies have associated elevated expression of M-CSF with increased leukocyte infiltration of solid tumors in human breast and ovarian cancers (Scholl et al. *J. Natl. Cancer Inst.* 1994, 86:120-126, Tang et al. *J. Cell. Biochem.* 1990, 44:189-198). Further studies have shown that M-CSF is one of several cytokines implicated in the recruitment of tumor-associated macrophages (TAMs) that contribute to tumor angiogenesis and tumor progression to metastasis, and more recently, that the preclinical inhibitor GW2580 inhibits tumor metastasis and angiogenesis in mice tumor xenograft experiments (Priceman et al. *Blood* 2010 115(7): 1461-1471). Stimulated osteoclast activity is also believed to underlie the pathophysiology of bone metastases. (Lipton, *J. Support. Oncol.* 2004 2:205-220). Metastatic bone lesions results in significant localized bone loss and lead to skeletal morbidity, symptoms which include bone pain, bone fractures and hypercalcemia. Inhibition of CSF1R therefore may therefore provide therapy for solid tumors and metastatic cancer including metastases to the bone.

Another member of the PDGFR family, FLT3 (also called Flk2), plays an important role in the proliferation and differentiation of hematopoietic stem cells and activating mutation or overexpression of this receptor is found in AML (See, Heinrich Mini-*Reviews in Medicinal Chemistry* 2004, 4(3):255-271, Kiyoi et al. *Int J Hematol,* 2005 82:85-92). More than a dozen known FLT3 inhibitors are being developed and some have shown promising clinical effects against AML (See Levis et al. *Int J Hematol.* 2005 82:100-107). The FLT3 receptor is also expressed in a large portion of dendritic cell progenitors and stimulation of the receptor causes the proliferation and differentiation of these progenitors into dendritic cells (DC). Since dendritic cells are the main initiators of the T-cell mediated immune response, including the autoreactive immune response, FLT3 inhibition is a mechanism for downregulating DC-mediated inflammatory and autoimmune responses. One study shows the FLT3 inhibitor CEP-701 to be effective in reducing myelin loss in experimental autoimmune encephalomyelitis (EAE), a mouse model for multiple sclerosis (See Whartenby et al. *PNAS* 2005 102: 16741-16746). A high level of the FLT3 ligand is found in the serum of patients with Langerhans cell histiocytosis and systemic lupus erythematosus, which further implicates FLT3 signaling in the dysregulation of dendritic cell progenitors in those autoimmune diseases (See Rolland et al. *J. Immunol.* 2005 174: 3067-3071).

KIT (or stem cell factor receptor, or SCFR) is another member of the RTK family, and the presence of kit mutations is a key diagnostic marker for gastrointestinal stromal tumors (GIST) (Duensing et al. *Cancer Investigation* 2004, 22(1):106-116). Gleevec® (imatinib mesylate or STI571), the first FDA-approved RTK inhibitor originally approved for c-Abl-mediated chronic myeloid leukemia, gained FDA-approval for KIT-mediated GIST in 2002 and has validated the molecular-based approach of Kit inhibition for the treatment of GIST. (Giorgi and Verweij, *Mol. Cancer Ther.* 2005 4(3):495-501). Gain of function mutations of the Kit receptor are also associated with mast cell/myeloid leukemia and seminomas/dysgerminomas (Blume-Jensen *Nature* 2001 411(17): 355-365. KIT mutations have been also identified in certain melanomas and is recognized as a potential therapeutic target for melanoma (Curtain et al. *J Clin. Oncol.* 2006 24(26):4340-4346).

There continues to be a need for the identification of small molecules that inhibit RTKs, particularly compounds useful for the treatment of CSF1R-, FLT3, PDGFRβ- and/or KIT-mediated diseases.

SUMMARY

Provided herein are compounds of formula (I) or pharmaceutically acceptable salts, solvates, hydrates, clathrates, single stereoisomers, mixture of stereoisomers or racemic mixture of stereoisomers thereof. In certain embodiment, the compounds have activity as CSF1R, FLT3, KIT, and/or PDGFRβ kinase modulators. The compounds are useful in medical treatments, pharmaceutical compositions and methods for modulating the activity of CSF1R, FLT3, KIT, and/or PDGFRβ kinases, including wildtype and/or mutated forms of CSF1R, FLT3, KIT, and/or PDGFRβ kinases. In certain embodiments, the compounds provided herein have activity as CSF1R, FLT3, KIT, and/or PDGFRβ kinase modulators. In one embodiment, the compounds for use in the compositions and methods provided herein have formula (I).

In certain embodiments, provided herein are compounds of Formula I:

I or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, deuterium, halogen, hydroxyl and alkoxy, or $R^1$ and $R^2$ together form =O;

$R^3$ is hydrogen or alkyl;

$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''S(O)$_t$R$^w$, —R''N(R$^x$)C(J)R$^x$, —R''N(R$^x$)C(J)OR$^x$, —R''N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is —(CR$^5$R$^6$)$_q$—;

$R^5$ and $R^6$ are each independently hydrogen, deuterium, halo, alkyl, haloalkyl or hydroxyalkyl;

Z is O, S or NR$^7$;

$R^7$ is hydrogen, deuterium or alkyl;

each W is independently CR$^8$ or N;

$R^8$ is hydrogen, deuterium, halo, haloalkyl or alkyl;

ring A is a bicyclic or tricyclic aryl, heteroaryl or heterocyclyl optionally substituted with one to four substituents selected from $Q^2$;

$W^1$ is N or C;

$W^2$ is N, NR$^{9a}$ or CR$^{9b}$;

$W^3$ is N, NR$^{10a}$ or CR$^{10b}$;

$W^4$ is N, NR$^{11a}$ or CR$^{11b}$;

$R^{9a}$, $R^{9b}$, $R^{10a}$, $R^{10b}$, $R^{11a}$ and $R^{11b}$ are selected as follows:

i) $R^{9a}$, $R^{10a}$ and $R^{11a}$ are each independently hydrogen, deuterium or alkyl and $R^{9b}$, $R^{10b}$ and $R^{11b}$ are each independently hydrogen or $Q^2$; or ii) $R^{9a}$ and $R^{10b}$, $R^{9a}$ and $R^{10a}$, $R^{9b}$ and $R^{10b}$, $R^{9b}$ and $R^{10a}$, $R^{10b}$ and $R^{11a}$, $R^{10a}$ and $R^{11b}$, $R^{10a}$ and $R^{11b}$ or $R^{10b}$ and $R^{11b}$ together with the atoms to which they are attached form an aryl, heteroaryl or heterocyclyl ring, optionally substituted with one or more, in one embodiment, one to three, in another embodiment, one, two or three groups selected from $Q^2$; and the remainder of $R^{9a}$ or $R^{11a}$ is hydrogen, deuterium or alkyl; and the remainder of $R^{9b}$ or $R^{11b}$ is hydrogen or $Q^2$; or iii) $R^{9a}$ and $R^{10b}$, $R^{9a}$ and $R^{10a}$, $R^{9b}$ and $R^{10b}$, $R^{9b}$ and $R^{10a}$, $R^{10b}$ and $R^{11a}$, $R^{10a}$ and $R^{11b}$, $R^{10a}$ and $R^{11b}$ or $R^{10b}$ and $R^{11b}$ together with the atoms to which they are attached form an aryl, heteroaryl or heterocyclyl ring optionally fused to a phenyl ring optionally substituted with one or more, in one embodiment, one to three, in another embodiment, one, two or three groups selected from $Q^2$; and the remainder of $R^{9a}$ or $R^{11a}$ is hydrogen, deuterium or alkyl and the remainder of $R^{9b}$ or $R^{11b}$ is hydrogen or $Q^2$;

each $Q^2$ is independently halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''OR$^x$, —R''O-R''N(R$^y$)(R$^z$), R''N(R$^y$)(R$^z$), —R''SR$^x$, —R''C(J)R$^x$, —R''C(J)OR$^x$, —R''C(J)N(R$^y$)(R$^z$), —R''C(J)R''N(R$^y$)(R$^z$), —R''C(J)N(R$^y$)OR$^x$, —C(=NOR$^y$)R$^x$, —R''S(O)$_t$R$^w$, —R''N(R$^x$)C(J)R$^x$, —R''N(R$^x$)C(J)OR$^x$, —R''N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more groups $Q^4$; in one embodiment, one to three $Q^4$ groups, each $Q^4$ is independently selected from halo, deuterium, hydroxyl, alkyl, haloalkyl and hydroxyalkyl;

each $R^d$ is independently hydrogen or alkyl;

each R'' is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^x$ or S;

each t is independently an integer from 0-2;

n is 1 or 2; and q is an integer from 0-4, wherein the compounds are selected such that: i) when W is CH; $W^1$ is C; Z is S; $R^1$ is hydrogen, or hydroxyl and $R^2$ is hydrogen, or $R^1$ and $R^2$ together form =O; then ring A is not pyridine; ii) when W is CH; $W^1$ is N; Z is S; $R^1$ and $R^2$ are hydrogen, then ring A is not pyrrolidine; iii) when W is CH, Z is NH, $R^1$ and $R^2$ together form =O, q is 0, and $R^4$ is pyridinyl, then ring A is not phenyl, iv) when W is CH, Z is NH, $R^1$ and $R^2$ together form =O, q is 0, and $R^4$ is phenyl, then ring A is not pyrrolidine, and v) when Z is N, one of $R^1$ and $R^2$ is methyl and the other of $R^1$ and $R^2$ is H, q is 0, and $R^3$ is pyridine, and $W^1$ is N, ring A cannot be piperidine, 1,2,3,4-tetrahydroisoquinoline, or isoindoline.

In one embodiment, the compound provided herein is a compound of formula (I). In one embodiment, the compound provided herein is a pharmaceutically acceptable salt of the compound of formula (I). In one embodiment, the compound provided herein is a solvate of the compound of formula (I). In one embodiment, the compound provided herein is a hydrate of compound of formula (I). In one embodiment, the compound provided herein is a prodrug of the compound of formula (I). In one embodiment, the compound provided herein is a clathrate of the compound of formula (I).

Also provided are pharmaceutical compositions formulated for administration by an appropriate route and means containing effective concentrations of one or more of the compounds provided herein, or pharmaceutically acceptable salts, solvates, hydrates and prodrugs thereof, and optionally comprising at least one pharmaceutical carrier.

In one embodiment, the pharmaceutical compositions deliver amounts effective for the treatment, prevention, or amelioration of diseases or disorders that are modulated or otherwise affected by CSF1R, FLT3, KIT, and/or PDGFRβ kinases, or one or more symptoms or causes thereof. Such diseases or disorders include without limitation, cancers, nonmalignant proliferation diseases, atherosclerosis, restenosis following vascular angioplasty, fibroproliferative disorders, inflammatory diseases or disorders related to immune dysfunction, infectious diseases, and/or diseases or disorders that can be treated, prevented or managed by modulating the activity, binding or sub-cellular distribution of kinases, wherein such methods comprise administering to a subject, e.g., a human, in need of such treatment, prevention or management a therapeutically and prophylactically effective amount of a compound provided herein. Such diseases or disorders are further described herein.

Also provided herein are combination therapies using one or more compounds or compositions provided herein, or pharmaceutically acceptable derivatives thereof, in combination with other pharmaceutically active agents for the treatment of the diseases and disorders described herein.

In one embodiment, such additional pharmaceutical agents include one or more chemotherapeutic agents, antiproliferative agents, anti-inflammatory agents, immunomodulatory agents or immunosuppressive agents.

The compounds or compositions provided herein, or pharmaceutically acceptable derivatives thereof, may be administered simultaneously with, prior to, or after administration of one or more of the above agents. Pharmaceutical compositions containing a compound provided herein and one or more of the above agents are also provided.

In certain embodiments, provided herein are methods of treating, preventing or ameliorating a disease or disorder that is modulated or otherwise affected by CSF1R, FLT3, KIT, and/or PDGFRβ kinases such as wild type and/or mutant CSF1R, FLT3, KIT, and/or PDGFRβ kinases, or one or more symptoms or causes thereof.

In practicing the methods, effective amounts of the compounds or compositions containing therapeutically effective concentrations of the compounds, which are formulated for systemic delivery, including parenteral, oral, or intravenous delivery, or for local or topical application are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

DETAILED DESCRIPTION

Figure 1:
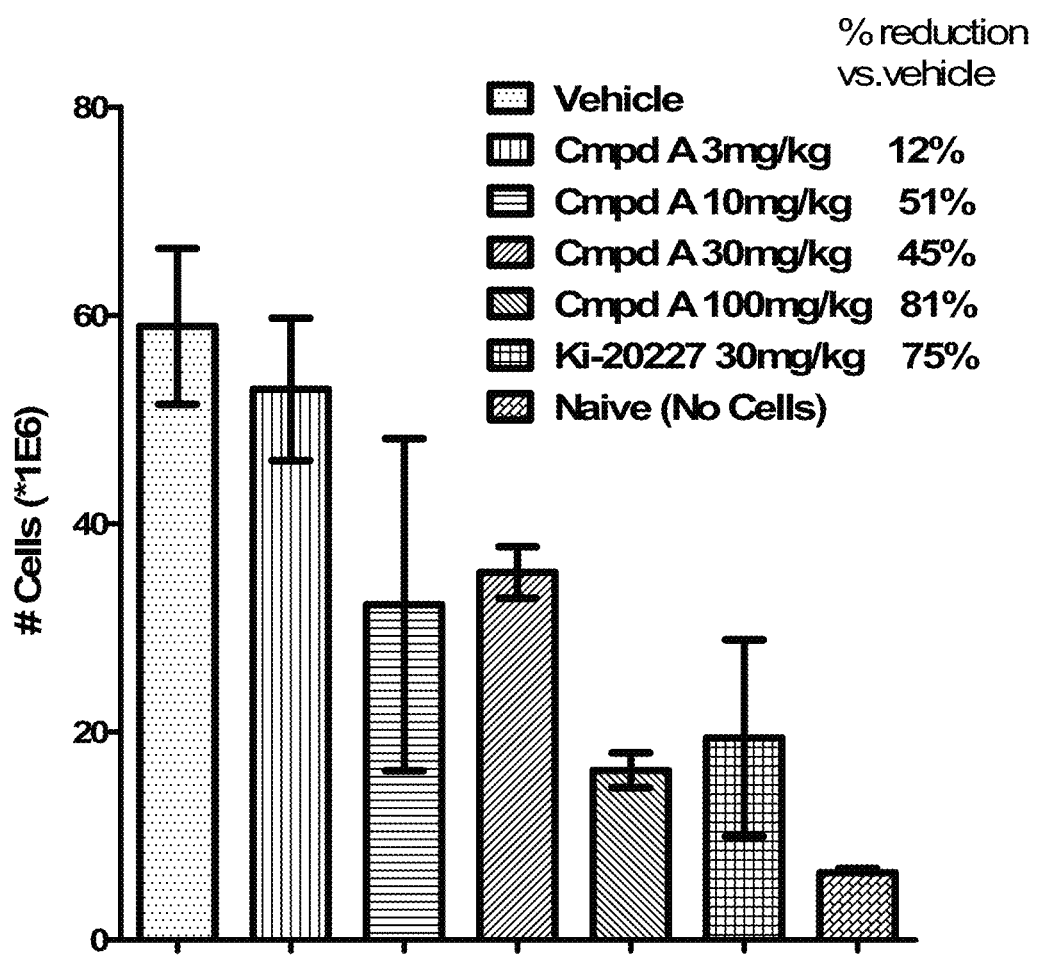
FIG. 1 depicts the in vivo inhibition of CSF-1 dependent M-NFS-60 tumor cell proliferation in the peritoneal cavity of athymic nu/nu mice from the administration of one of the compounds provided herein having the Formula I (Compound A).

Provided herein are compounds of formula I that have activity as CSF1R, FLT3, KIT, and/or PDGFRβ kinase modulators. Further provided are methods of treating, preventing or ameliorating diseases that are modulated by CSF1R, FLT3, KIT, and/or PDGFRβ kinases, and pharmaceutical compositions and dosage forms useful for such methods. The methods and compositions are described in detail in the sections below.

A. DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain group consisting solely of carbon and hydrogen atoms, containing no unsaturation, having from one to ten, one to eight, one to six or one to four carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkenyl" refers to a straight or branched hydrocarbon chain group consisting solely of carbon and hydrogen atoms, containing at least one double bond, having from two to ten carbon atoms, and which is attached to the rest of the molecule by a single bond or a double bond, e.g., ethenyl, prop-1-enyl, but-1-enyl, pent-1-enyl, penta-1,4-dienyl, and the like.

"Alkynyl" refers to a straight or branched hydrocarbon chain group consisting solely of carbon and hydrogen atoms, containing at least one triple bond, having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkenylene" or "alkenylene chain" refers to a straight or branched chain unsaturated divalent radical consisting solely of carbon and hydrogen atoms, having from two to eight carbon atoms, wherein the unsaturation is present only as double bonds and wherein the double bond can exist between any two carbon atoms in the chain, e.g., ethenylene, prop-1-enylene, but-2-enylene and the like. The alkenylene chain may be attached to the rest of the molecule through any two carbons within the chain.

"Alkynylene" or "alkynylene chain" refers to a straight or branched chain unsaturated divalent radical consisting solely of carbon and hydrogen atoms, having from two to eight carbon atoms, wherein the unsaturation is present only as triple bonds and wherein the triple bond can exist between any two carbon atoms in the chain, e.g., ethynylene, prop-1-ynylene, but-2-ynylene, pent-1-ynylene, pent-3-ynylene and the like. The alkynylene chain may be attached to the rest of the molecule through any two carbons within the chain.

"Alkoxy" refers to the group having the formula —OR wherein R is alkyl or haloalkyl. An "optionally substituted alkoxy" refers to the group having the formula —OR wherein R is an optionally substituted alkyl as defined herein.

"Amino" refers to a radical having the formula —NR'R" wherein R' and R" are each independently hydrogen, alkyl or haloalkyl. An "optionally substituted amino" refers to a radical having the formula NR'R" wherein one or both of R' and R" are optionally substituted alkyl as defined herein.

"Aryl" refers to a group of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Cycloalkyl" refers to a stable monovalent monocyclic or bicyclic hydrocarbon group consisting solely of carbon and hydrogen atoms, having from three to ten carbon atoms which is saturated, e.g., cyclopropyl, cyclobutyl, cyclopentyl, cyclohexyl, decalinyl, norbornane, norbornene, adamantyl, bicyclo[2.2.2]octane and the like.

"Cycloalkenyl" refers to a stable monovalent monocyclic or bicyclic hydrocarbon group consisting solely of carbon and hydrogen atoms, having from three to ten carbon atoms, which is partially unsaturated. Examples of cycloalkenyl include cyclopropene, cyclobutylene, cyclopentene and cyclohexene.

"Halo, "halogen" or "halide" refers to F, Cl, Br or I.

"Haloalkyl" refers to an alkyl group, in certain embodiments, $C_{1-6}$alkyl group in which one or more of the hydrogen atoms are replaced by halogen. Such groups include, but are not limited to, chloromethyl, trifluoromethyl 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, 2,2-difluorocyclopropyl, (trifluoromethyl)cyclopropyl, 4,4-difluorocyclohexyl and 2,2,2-trifluoro-1,1-dimethyl-ethyl.

"Heterocycle" or "Heterocyclyl" refers to a stable 3- to 15-membered non-aromatic ring radical which consists of carbon atoms and from one to five heteroatoms selected from a group consisting of nitrogen, oxygen and sulfur. In one embodiment, the heterocyclic ring system radical may be a monocyclic, bicyclic or tricyclic ring or tetracyclic ring system, which may include fused or bridged ring systems; and the nitrogen or sulfur atoms in the heterocyclic ring system radical may be optionally oxidized; the nitrogen atom may be optionally quaternized; and the heterocyclyl radical may be partially or fully saturated. The heterocyclic ring system may be attached to the main structure at any heteroatom or carbon atom which results in the creation of a stable compound. Exemplary heterocylic radicals include, morpholinyl, piperidinyl, piperazinyl, pyranyl, pyrrolidinyl, oxetanyl, azetidinyl, quinuclidinyl, octahydroquinolizinyl, decahydroquinolizinyl, azabicyclo[3.2.1]octanyl, azabicyclo[2.2.2]octanyl, isoindolinyl, indolinyl and others.

"Heteroaryl" refers to a heterocyclyl group as defined above which is aromatic. The heteroaryl groups include, but are not limited to monocyclyl, bicyclyl and tricyclyl groups, and may be attached to the main structure at any heteroatom or carbon atom which results in the creation of a stable compound. Examples of such heteroaryl groups include, but are not limited to: furanyl, imidazolyl, oxazolyl, isoxazolyl, pyrimidinyl, pyridinyl, pyridazinyl, thiazolyl, thienyl, benzimidazolyl, imidazo[4,5-b]pyridinyl, imidazo[1,2-a]pyridinyl, imidazo[1,2-b]pyridazinyl, imidazo[1,2-a]pyrazinyl and others.

"Heterocyclylalkyl" refers to a group of the formula —$R_aR_e$ wherein $R_a$ is an alkyl group as defined above and $R_e$ is a heterocyclyl group as defined herein, where the alkyl group $R_a$ may attach at either the carbon atom or the heteroatom of the heterocyclyl group $R_e$. The alkyl group and the heterocyclyl group may be optionally substituted as defined herein.

"$IC_{50}$" refers to an amount, concentration or dosage of a particular test compound that achieves a 50% inhibition of a maximal response, such as cell growth or proliferation measured via any the in vitro or cell based assay described herein.

"Oxo" refers to the group =O attached to a carbon atom.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

As used herein and unless otherwise indicated, the term "hydrate" means a compound provided herein or a salt thereof, that further includes a stoichiometric or non-stoichiometeric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Unless stated otherwise specifically described in the specification, it is understood that the substitution can occur on any atom of the alkyl, alkenyl, alkynyl, cycloalkyl, heterocyclyl, aryl or heteroaryl group.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein.

Thus, the compounds provided herein may be enantiomerically pure, or be stereoisomeric or diastereomeric mixtures.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

As used herein, "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

Where the number of any given substituent is not specified (e.g., haloalkyl), there may be one or more substituents present. For example, "haloalkyl" may include one or more of the same or different halogens.

In the description herein, if there is any discrepancy between a chemical name and chemical structure, the structure controls.

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxorubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, and radiation treatment.

"Anti-inflammatory agents" refers to matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate, salicylsalicylic acid), COX-1 or COX-2 inhibitors), or glucocorticoid receptor agonists such as corticosteroids, methylprednisone, prednisone, or cortisone.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

B. COMPOUNDS

In certain embodiments, provided herein are compounds of Formula I:

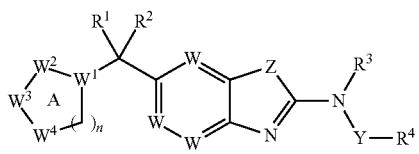

I or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, deuterium, halogen, hydroxyl and alkoxy, or $R^1$ and $R^2$ together form =O;

$R^3$ is hydrogen or alkyl;

$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"S(O)$_t$R$^w$, —R"N(R$^x$)C(J)R$^x$, —R"N(R$^x$)C(J)OR$^x$, —R"N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is —(CR$^5$R$^6$)$_q$—;

$R^5$ and $R^6$ are each independently hydrogen, deuterium, halo, alkyl, haloalkyl or hydroxyalkyl;

Z is O, S or NR$^7$;

$R^7$ is hydrogen, deuterium or alkyl;

each W is independently CR$^8$ or N;

$R^8$ is hydrogen, deuterium, halo or alkyl;

ring A is a monocyclic, bicyclic or tricyclic aryl, heteroaryl or heterocyclyl optionally substituted with one to four substituents selected from $Q^2$;

$W^1$ is N or C;

$W^2$ is N, NR$^{9a}$ or CR$^{9b}$;

$W^3$ is N, NR$^{10a}$ or CR$^{10b}$;

$W^4$ is N, NR$^{11a}$ or CR$^{11b}$;

$R^{9a}$, $R^{9b}$, $R^{10a}$, $R^{10b}$, $R^{11a}$ and $R^{11b}$ are selected as follows:

i) $R^{9a}$, $R^{10a}$ and $R^{11a}$ are each independently hydrogen or alkyl and $R^{9b}$, $R^{10b}$ and $R^{11b}$ are each independently hydrogen, deuterium, oxo, hydroxyl, halo or alkyl; or ii) $R^{9a}$ and $R^{10b}$, $R^{9b}$ and $R^{10b}$, $R^{9b}$ and $R^{10a}$, $R^{10b}$ and $R^{11a}$, $R^{10a}$ and $R^{11b}$ or $R^{10b}$ and $R^{11b}$ together with the atoms to which they are attached form an aryl, heteroaryl or heterocyclyl ring, optionally substituted with one or more, in one embodiment, one to three, in another embodiment, one, two or three groups selected from $Q^2$; and the remainder of $R^{9a}$, $R^{10a}$ and $R^{11a}$ are each independently hydrogen, deuterium or alkyl; and the remainder of $R^{9b}$, $R^{10b}$ and $R^{11b}$ are each independently hydrogen, deuterium, halo or alkyl; or iii) $R^{9a}$ and $R^{10b}$, $R^{9b}$ and $R^{10b}$, $R^{9b}$ and $R^{10a}$, $R^{10b}$ and $R^{11a}$, $R^{10a}$ and $R^{11b}$ or $R^{10b}$ and $R^{11b}$ together with the atoms to which they are attached form an aryl, heteroaryl or heterocyclyl ring optionally fused to a phenyl ring optionally substituted with one or more, in one embodiment, one to three, in another embodiment, one, two or three groups selected from $Q^2$; and the remainder of $R^{9a}$ and $R^{9b}$ or the remainder of $R^{11a}$ and $R^{11b}$ are each independently hydrogen, deuterium or alkyl;

each $Q^2$ is independently halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more groups $Q^4$; in one embodiment, one to three Q⁴ groups, each Q⁴ is independently selected from halo, deuterium, hydroxyl, alkyl, haloalkyl and hydroxyalkyl;

$R^d$ is hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three Q⁷ groups; each Q⁷ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, NR$^x$ or S;

each t is independently an integer from 0-2;

n is 1 or 2; and q is an integer from 0-4, wherein the compounds are selected such that: i) when W is CH; W¹ is C; Z is S; R¹ is hydrogen, or hydroxyl and R² is hydrogen, or R¹ and R² together form =O; then ring A is not pyridine; ii) when W is CH; W¹ is N; Z is S; R¹ and R² are hydrogen, then ring A is not pyrrolidine; iii) when W is CH, Z is NH, R¹ and R² together form =O, q is 0, and R⁴ is pyridinyl, then ring A is not phenyl, iv) when W is CH, Z is NH, R¹ and R² together form =O, q is 0, and R⁴ is phenyl, then ring A is not pyrrolidine, and v) when Z is N, one of R¹ and R² is methyl and the other of R¹ and R² is H, q is 0, and R³ is pyridine, and W¹ is N, ring A cannot be piperidine, 1,2,3,4-tetrahydroisoquinoline, or isoindoline.

In certain embodiments, provided herein are compounds of Formula I or pharmaceutically acceptable salts, solvates, hydrates, clathrates, single stereoisomers, mixture of stereoisomers or racemic mixture of stereoisomers thereof, wherein:

R¹ and R² are each independently selected from hydrogen, halogen, hydroxyl and alkoxy, or R¹ and R² together form =O;

R³ is hydrogen or alkyl;

R⁴ is cycloalkyl, cycloalkenyl, aryl, heterocyclyl or heteroaryl, where R⁴ is optionally substituted with one or more, in one embodiment, one to three, in another embodiment, one, two or three groups selected from Q¹;

each Q¹ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$^u$OR$^x$, —R$^u$OR$^u$N(R$^y$)(R$^z$), —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q³ groups, in one embodiment, one to three Q³ groups; each Q³ is independently selected from halo, hydroxyl, alkyl, haloalkyl and hydroxyalkyl;

Y is —(CR⁵R⁶)$_q$—;

R⁵ and R⁶ are each independently hydrogen, halo, alkyl, haloalkyl or hydroxyalkyl;

Z is O, S or NR⁷;

R⁷ is hydrogen or alkyl;

each W is independently CR⁸ or N;

R⁸ is hydrogen or alkyl;

ring A is aryl or heteroaryl, optionally substituted with one to four substituents selected from Q²;

W¹ is N or C;

W² is N, NR$^{9a}$ or CR$^{9b}$;

W³ is N, NR$^{10a}$ or CR$^{10b}$;

W⁴ is N, NR$^{11a}$ or CR$^{11b}$;

R$^{9a}$, R$^{9b}$, R$^{10a}$, R$^{10b}$, R$^{11a}$ and R$^{11b}$ are selected as follows:

i) R$^{9a}$, R$^{10a}$ and R$^{11a}$ are each independently hydrogen or alkyl and R$^{9b}$, R$^{10b}$ and R$^{11b}$ are each independently hydrogen, oxo, hydroxyl, halo or alkyl; or ii) R$^{9a}$ and R$^{10b}$, R$^{9b}$ and R$^{10b}$, R$^{9b}$ and R$^{10a}$, or R$^{10b}$ and R$^{11b}$ together with the atoms to which they are attached form an aryl or heteroaryl ring, optionally substituted with one or more, in one embodiment, one to three, in another embodiment, one, two or three groups selected from Q²; and the remainder of R$^{9a}$, R$^{10a}$ and R$^{11a}$ are each independently hydrogen or alkyl; and the remainder of R$^{9b}$, R$^{10b}$ and R$^{11b}$ are each independently hydrogen, halo or alkyl;

each Q² is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$^u$OR$^x$, —R$^u$OR$^u$N(R$^y$)(R$^z$), —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$C(J)N(R$^y$)OR$^x$, —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more groups Q⁴; in one embodiment, one to three Q⁴ groups, each Q⁴ is independently selected from halo, hydroxyl, alkyl, haloalkyl and hydroxyalkyl;

$R^d$ is hydrogen or alkyl;

each $R^u$ is independently alkylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^x$ or S;

each t is independently an integer from 0-2;

n is 1 or 2; and q is an integer from 0-4, wherein the compounds are selected such that when W is CH; $W^1$ is C; Z is S; $R^1$ is hydrogen, or hydroxyl and $R^2$ is hydrogen, or $R^1$ and $R^2$ together form =O; then ring A is not pyridine.

In certain embodiments, provided herein are compounds of Formula I wherein ring A is heteroaryl, n is 1 and the other variables are as described elsewhere herein. In certain embodiments, provided herein are compounds of Formula I wherein ring A is heteroaryl, $W^1$ is N, n is 1 or 2 and the other variables are as described elsewhere herein. In certain embodiments, provided herein are compounds of Formula I wherein ring A is heteroaryl, $W^1$ is C or N, n is 1 or 2, provided that when $W^1$ is C, n is 1 and the other variables are as described elsewhere herein.

In certain embodiments, provided herein are compounds of Formula I, wherein ring A is bicyclic or tricyclic heteroaryl, and the other variables are as described elsewhere herein.

In certain embodiments, provided herein are compounds of Formula I or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, halogen, hydroxyl and alkoxy;

$R^3$ is hydrogen or alkyl;

$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —$R''OR^x$ or —$R''C(O)R^x$;

Y is —$(CR^5R^6)_q$—;

$R^5$ and $R^6$ are each independently hydrogen, halo, alkyl, haloalkyl or hydroxyalkyl;

Z is O, S or $NR^7$;

$R^7$ is hydrogen or alkyl;

each W is independently $CR^8$ or N;

$R^8$ is hydrogen, haloalkyl or alkyl;

ring A is aryl or heteroaryl, optionally substituted with one to four substituents selected from $Q^2$;

$W^1$ is N or C;

$W^2$ is N, $NR^{9a}$ or $CR^{9b}$;

$W^3$ is N, $NR^{10a}$ or $CR^{10b}$;

$W^4$ is N, $NR^{11a}$ or $CR^{11b}$;

$R^{9a}$, $R^{9b}$, $R^{10a}$, $R^{10b}$, $R^{11a}$ and $R^{11b}$ are selected as follows:

i) $R^{9a}$, $R^{10a}$ and $R^{11a}$ are each independently hydrogen or alkyl and $R^{9b}$, $R^{10b}$ and $R^{11b}$ are each independently hydrogen, oxo, hydroxyl, halo or alkyl; or ii) $R^{9a}$ and $R^{10b}$, $R^{9a}$ and $R^{10a}$, $R^{9b}$ and $R^{10b}$, $R^{9b}$ and $R^{10a}$, $R^{10a}$ and $R^{11a}$, $R^{10b}$ and $R^{11a}$, $R^{10a}$ and $R^{11b}$ or $R^{10b}$ and $R^{11b}$ together with the atoms to which they are attached form an aryl, heteroaryl or heterocyclyl ring, optionally substituted with one or more, in one embodiment, one to three, in another embodiment, one, two or three groups selected from $Q^2$; and the remainder of $R^{9a}$, $R^{10a}$ and $R^{11a}$ are each independently hydrogen or alkyl; and the remainder of $R^{9b}$ $R^{10b}$ and $R^{11b}$ are each independently hydrogen, halo or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R''OR^x$, —$R''OR''N(R^y)(R^z)$, —$R''N(R^y)(R^z)$, —$R''SR^x$, —$R''C(J)R^x$, —$R''C(J)OR^x$, —$R''C(J)N(R^y)(R^z)$, —$R''C(J)N(R^y)OR^x$, —$R''S(O)_tR^w$, —$R''N(R^x)C(J)R^x$, —$R''N(R^x)C(J)OR^x$, —$R''N(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; in one embodiment, one to three $Q^4$ groups, each $Q^4$ is independently selected from halo, hydroxyl, alkyl, haloalkyl and hydroxyalkyl;

each $R''$ is independently alkylene or a direct bond;

$R^w$ is alkyl;

each $R^x$ is independently hydrogen or alkyl;

$R^y$ and $R^z$ are each independently hydrogen or alkyl;

J is O, $NR^x$ or S;

each t is independently an integer from 0-2;

n is 1 or 2; and q is an integer from 0-4, wherein the compounds are selected such that when W is CH; $W^1$ is C; Z is S; $R^1$ is hydrogen, or hydroxyl and $R^2$ is hydrogen, or $R^1$ and $R^2$ together form =O; then ring A is not pyridine.

In certain embodiments, the compounds of Formula I is selected such that when W is CH; $W^1$ is C; Z is NH; $R^1$ and $R^2$ together form =O; and q is 0, then ring A is not phenyl. In certain embodiments, the compounds of Formula I is selected such that when i) W is CH; $W^1$ is C; Z is S; $R^1$ is hydrogen or hydroxyl and $R^2$ is hydrogen, or $R^1$ and $R^2$ together form =O; then ring A is not pyridine and ii) when W is CH; $W^1$ is C; Z is NH; $R^1$ and $R^2$ together form =O; and q is 0, then ring A is not phenyl.

In certain embodiments, the compounds provided herein are selected such that when W is CH; $W^1$ is C; Z is S; $R^1$ is hydrogen, or hydroxyl and $R^2$ is hydrogen, or $R^1$ and $R^2$ together form =O; then ring A is not a 6 membered heteroaryl ring.

In certain embodiments, the compounds provided herein are selected such that when W is CH; $W^1$ is C; Z is S; $R^1$ is hydrogen, or hydroxyl and $R^2$ is hydrogen, or $R^1$ and $R^2$ together form =O; then ring A is a fused bicyclic ring.

In certain embodiments, the compounds provided herein are selected such that when W is CH; $W^1$ is N; Z is S; $R^1$ and $R^2$ are hydrogen, then ring A is not pyrrolidine.

In certain embodiments, the compounds provided herein are selected such that when W is CH; $W^1$ is N; Z is S; $R^1$ and $R^2$ are hydrogen, then ring A is not 5-membered heterocyclyl.

In certain embodiments, the compounds provided herein are selected such that when W is CH, Z is NH, $R^1$ and $R^2$ together form =O, q is 0, and $R^4$ is pyridinyl, then ring A is not phenyl.

In certain embodiments, the compounds provided herein are selected such that when W is CH, Z is NH, $R^1$ and $R^2$ together form =O, q is 0, and $R^4$ is nitrogen containing heteroaryl, then ring A is not phenyl.

In certain embodiments, the compounds provided herein are selected such that when W is CH, Z is NH, $R^1$ and $R^2$ together form =O, q is 0, and $R^4$ is monocyclic heteroaryl, then ring A is not phenyl.

In certain embodiments, the compounds provided herein are selected such that when W is CH, Z is NH, $R^1$ and $R^2$ together form =O, q is 0, and $R^4$ is phenyl, then ring A is not pyrrolidine.

In certain embodiments, the compounds provided herein are selected such that when W is CH, Z is NH, $R^1$ and $R^2$ together form =O, q is 0, and $R^4$ is phenyl, then ring A is not nitrogen containing heterocyclyl.

In certain embodiments, the compounds provided herein are selected such that when Z is N, one of $R^1$ and $R^2$ is methyl and the other of $R^1$ and $R^2$ is H, q is 0, and $R^3$ is pyridine, and $W^1$ is N, ring A cannot be piperidine, 1,2,3, 4-tetrahydroisoquinoline, or isoindoline.

In certain embodiments, the compounds provided herein are selected such that when Z is N, one of $R^1$ and $R^2$ is methyl and the other of $R^1$ and $R^2$ is H, q is 0, and $R^3$ is pyridine, and $W^1$ is N, ring A cannot be nitrogen containing heterocyclyl. In certain embodiments, the compounds provided herein are selected such that when Z is N, one of $R^1$ and $R^2$ is methyl and the other of $R^1$ and $R^2$ is H, q is 0, and $R^3$ is pyridine, and $W^1$ is N, ring A cannot be heterocyclyl.

In certain embodiments, provided herein are compounds of Formula I, wherein $R^1$ and $R^2$ are each independently selected from hydrogen and halogen. In certain embodiments, $R^1$ and $R^2$ are each hydrogen. In certain embodiments, $R^1$ is hydrogen and $R^2$ is halogen. In certain embodiments, $R^1$ and $R^2$ are each halogen. In certain embodiments, $R^1$ and $R^2$ are each independently selected from hydrogen and fluorine. In certain embodiments, $R^1$ is alkoxy and $R^2$ is hydrogen. In certain embodiments, $R^1$ is hydroxy and $R^2$ is hydrogen.

In certain embodiments, $R^3$ is hydrogen or alkyl. In certain embodiments, $R^3$ is hydrogen or methyl. In certain embodiments, $R^3$ is hydrogen.

In certain embodiments, $R^4$ is cycloalkyl, aryl, heterocyclyl or heteroaryl, where $R^4$ is optionally substituted with one or more, in one embodiment, one to three, in another embodiment, one, two or three groups selected from $Q^1$; each $Q^1$ is independently halo, oxo, alkyl, haloalkyl, hydroxyalkyl, cycloalkyl, =NOH, —$R^uOR^x$ or —$R^uC(O)R^x$, each $R^u$ is independently alkylene or a direct bond; and each $R^x$ is independently hydrogen or alkyl. In certain embodiments, $R^4$ is cycloalkyl or heterocyclyl, where $R^4$ is optionally substituted with one or more $Q^1$.

In certain embodiments, $R^4$ is cyclohexyl, tetrahydrofuryl, pyridinyl, phenyl, morpholinyl, cyclopentyl, piperidinyl, tetrahydro-2H-pyranyl or 2,3-dihydro-1H-indenyl, where $R^4$ is optionally substituted with one or more, in one embodiment, one to three, in another embodiment, one, two or three groups selected from $Q^1$; each $Q^1$ is independently halo, oxo, alkyl, haloalkyl, hydroxyalkyl, cycloalkyl, =NOH, —$R^uOR^x$ or —$R^uC(O)R^x$, each $R^u$ is independently alkylene or a direct bond; and each $R^x$ is independently hydrogen or alkyl.

In certain embodiments, $R^4$ is cycloalkyl, optionally substituted with one, two or three groups selected from $Q^1$; each $Q^1$ is independently halo, oxo, alkyl, haloalkyl, hydroxyalkyl, cycloalkyl, =NOH, —$R^uOR^x$ or —$R^uC(O)R^x$, each $R^u$ is independently alkylene or a direct bond; and each $R^x$ is independently hydrogen or alkyl.

In certain embodiments, $R^4$ is cyclohexyl, optionally substituted with hydroxyl.

In certain embodiments, Y is direct bond or $(CR^5R^6)_q$—; $R^5$ and $R^6$ are each independently hydrogen, halo, alkyl, haloalkyl or hydroxyalkyl. In certain embodiments, Y is direct bond or $(CR^5R^6)_q$—; $R^5$ and $R^6$ are each independently hydrogen, alkyl or hydroxyalkyl. In certain embodiments, Y is direct bond, —$CH_2$—, —$CH(CH_3)$— or —CH($CH_2OH$)—.

In certain embodiments, Z is O, S or NH. In certain embodiments, Z is O or S.

In certain embodiments, each W is independently $CR^8$ or N; and $R^8$ is hydrogen, halo or alkyl. In certain embodiments, each W is $CR^x$; and $R^8$ is hydrogen or alkyl. In certain embodiments, each W is CH.

In certain embodiments, ring A is aryl or heteroaryl, optionally substituted with one or two substituents selected from $Q^2$; where $Q^2$ is heteroaryl, —$R^uC(J)N(R^y)(R^z)$, or —$R^uN(R^x)C(J)R^x$, where when $Q^2$ is the heteroaryl, it is optionally substituted with one or more alkyl;

each $R^u$ is independently alkylene or a direct bond;
each $R^x$ is independently hydrogen or alkyl;
$R^y$ and $R^z$ are each independently hydrogen or alkyl; and
J is O, $NR^x$ or S.

In certain embodiments, ring A is heteroaryl, optionally substituted with one or two substituents selected from $Q^2$; where $Q^2$ is heteroaryl, —$R^uC(J)N(R^y)(R^z)$, or —$R^uN(R^x)C(J)R^x$, where when $Q^2$ heteroaryl, it is optionally substituted with one or more alkyl;

each $R^u$ is independently alkylene or a direct bond;
each $R^x$ is independently hydrogen or alkyl;
$R^y$ and $R^z$ are each independently hydrogen or alkyl; and
J is O, $NR^x$ or S.

In certain embodiments, provided herein are compounds of Formula I:

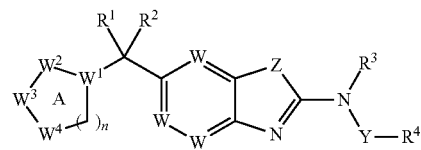

or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, halogen, hydroxyl and alkoxy, or $R^1$ and $R^2$ together form =O;

$R^3$ is hydrogen or alkyl;

$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uS(O)_tR^w$, —$R^uN(R^x)C(J)R^x$, —$R^uN(R^x)C(J)OR^x$, —$R^uN(R^x)S(O)_tR^w$, =$NOR^d$, or —C(=$NR^y$)N($R^y$)$OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from halo, hydroxyl, alkyl, haloalkyl and hydroxyalkyl;

Y is —$(CR^5R^6)_q$—;

$R^5$ and $R^6$ are each independently hydrogen, halo, alkyl, haloalkyl or hydroxyalkyl;

Z is O, S or $NR^7$;

$R^7$ is hydrogen or alkyl;

each W is independently $CR^8$ or N;

$R^8$ is hydrogen, halo, haloalkyl or alkyl;

ring A is a bicyclic or tricyclic heteroaryl or heterocyclyl optionally substituted with one to four substituents selected from $Q^2$;

$W^1$ is N or C;

$W^2$ is N, $NR^{9a}$ or $CR^{9b}$;

$W^3$ is N, $NR^{10a}$ or $CR^{10b}$;

$W^4$ is N, $NR^{11a}$ or $CR^{11b}$;

$R^{9a}$, $R^{9b}$, $R^{10a}$, $R^{10b}$, $R^{11a}$ and $R^{11b}$ are selected as follows:

i) $R^{9a}$ and $R^{10b}$, $R^{9a}$ and $R^{10a}$, $R^{9b}$ and $R^{10b}$, $R^{9b}$ and $R^{10a}$, $R^{10a}$ and $R^{11a}$, $R^{10b}$ and $R^{11a}$, $R^{10a}$ and $R^{11b}$ or $R^{10b}$ and $R^{11b}$ together with the atoms to which they are attached form an aryl, heteroaryl or heterocyclyl ring, optionally substituted with one or more, in one embodiment, one to three, in another embodiment, one, two or three groups selected from $Q^2$; and the remainder of $R^{9a}$, $R^{10a}$ and $R^{11a}$ are each independently hydrogen or alkyl; and the remainder of $R^{9b}$, $R^{10b}$ and $R^{11b}$ are each independently hydrogen, halo or alkyl; or ii) $R^{9a}$ and $R^{10b}$, $R^{9a}$ and $R^{10a}$, $R^{9b}$ and $R^{10b}$, $R^{10a}$ and $R^{11a}$, $R^{10b}$ and $R^{11a}$, $R^{10a}$ and $R^{11b}$ or $R^{10b}$ and $R^{11b}$ together with the atoms to which they are attached form an aryl, heteroaryl or heterocyclyl ring optionally fused to a phenyl ring optionally substituted with one or more, in one embodiment, one to three, in another embodiment, one, two or three groups selected from $Q^2$; and the remainder of $R^{9a}$ and $R^{9b}$ or the remainder of $R^{11a}$ and $R^{11b}$ are each independently hydrogen or alkyl;

each $Q^2$ is independently halo, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)R^uN(R^y)(R^z)$, —$R^uC(J)N(R^y)OR^x$, —C(=$NOR^x$)$R^x$, —$R^uS(O)_tR^w$, —$R^uN(R^x)C(J)R^x$, —$R^uN(R^x)C(J)OR^x$, —$R^uN(R^x)S(O)_tR^w$ or —C(=$NR^y$)N($R^y$)$OR^x$, where the alkyl, haloalkyl, aminoalkyl, alkenyl, alkynyl, cycloalkyl, cycloalkenyl, aryl, heteroaryl, and heterocyclyl groups are optionally substituted with one or more groups $Q^4$; in one embodiment, one to three $Q^4$ groups, each $Q^4$ is independently selected from halo, hydroxyl, alkyl, haloalkyl and hydroxyalkyl;

$R^d$ is hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^x$ or S;

each t is independently an integer from 0-2;

n is 1 or 2; and q is an integer from 0-4, wherein the compound is selected such that when Z is N, one of $R^1$ and $R^2$ is methyl and the other of $R^1$ and $R^2$ is H, q is 0, and $R^3$ is pyridine, and $W^1$ is N, ring A cannot be 1,2,3,4-tetrahydroisoquinoline, or isoindoline In certain embodiments, $W^1$ is N. In certain embodiments, $W^1$ is C.

In certain embodiments, $W^2$ is N or $CR^{9b}$, where $R^{9b}$ is hydrogen oxo, hydroxyl or alkyl. In certain embodiments, $W^3$ is N or $CR^{19b}$, where $R^{10b}$ is hydrogen or alkyl. In certain embodiments, $W^4$ is N or $CR^{11b}$, where $R^{11b}$ is hydrogen or alkyl. In certain embodiments, $W^2$ is $CR^{9b}$; $W^3$ is $CR^{10b}$; $W^4$ is N or $CR^{11b}$; where $R^{9b}$ and $R^{10b}$ together with the carbon atoms on which they are substituted form an aryl or heteroaryl ring, optionally substituted with one or more, in one embodiment, one to three, in another embodiment, one, two or three groups selected from $Q^2$; $R^{11b}$ is hydrogen or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)N(R^y)OR^x$, —$R^uS(O)_tR^w$, —$R^uN(R^x)C(J)R^x$, —$R^uN(R^x)C(J)OR^x$, —$R^uN(R^x)S(O)_tR^w$ or —C(=$NR^y$)N($R^y$)$OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^u$ is independently alkylene or a direct bond;

$R^w$ is alkyl;

each $R^x$ is independently hydrogen or alkyl;

$R^y$ and $R^z$ are each independently hydrogen or alkyl;

J is O, $NR^x$ or S; and each t is independently an integer from 0-2.

In certain embodiments, $W^2$ is $CR^{9b}$; $W^3$ is $CR^{19b}$; $W^4$ is N; where $R^{9b}$ and $R^{10b}$ together with the carbon atoms on which they are substituted form an aryl or heteroaryl ring, optionally substituted with one or two groups selected from $Q^2$, where $Q^2$ is as defined elsewhere herein. In certain embodiments, each $Q^2$ is independently halo, cyano, alkyl, haloalkyl, aminoalkyl, alkenyl, alkynyl, cycloalkyl, heteroaryl, heterocyclyl, —$R^uOR^x$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)N(R^y)OR^x$, —$R^uS(O)_tR^w$, —$R^uN(R^x)C(J)R^x$, —$R^uN(R^x)C(J)OR^x$, —$R^uN(R^x)S(O)_tR^w$ or —C(=$NR^y$)N($R^y$)$OR^x$, where the alkyl, haloalkyl, aminoalkyl, alkenyl, alkynyl, cycloalkyl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^u$ is independently alkylene or a direct bond;
$R^w$ is alkyl;
each $R^x$ is independently hydrogen or alkyl;
$R^y$ and $R^z$ are each independently hydrogen or alkyl;
J is O, $NR^x$ or S; and
each t is independently an integer from 0-2.

In certain embodiments, n is 1 or 2. In certain embodiments, n is 1. In certain embodiments, n is 2.

In certain embodiments, q is an integer from 0-4. In certain embodiments, q is 0-3. In certain embodiments, q is 0-2. In certain embodiments, q is 0, 1 or 2. In certain embodiments, q is 0. In certain embodiments, q is 1. In certain embodiments, q is 2.

In certain embodiments, provided herein are compounds of Formula I or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, alkoxy and halogen;
$R^3$ is hydrogen or alkyl;
$R^4$ is cycloalkyl, aryl, heterocyclyl or heteroaryl, where $R^4$ is optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, $-R^uOR^x$ or $-R^uC(O)R^x$;
Y is direct bond or $-(CR^5R^6)_q-$;
$R^5$ and $R^6$ are each independently hydrogen, halo, alkyl, haloalkyl or hydroxyalkyl;
Z is O, S, or $NR^7$;
$R^7$ is hydrogen or alkyl;
each W is independently $CR^8$ or N;
$R^8$ is hydrogen, haloalkyl or alkyl;
ring A is aryl or heteroaryl;
$W^1$ is N or C;
$W^2$ is N, $NR^{9a}$ or $CR^{9b}$;
$W^3$ is N, $NR^{10a}$ or $CR^{10b}$;
$W^4$ is N, $NR^{11a}$ or $CR^{11b}$;
$R^{9a}$, $R^{9b}$, $R^{10a}$, $R^{10b}$, $R^{11a}$ and $R^{11b}$ are selected as follows:
i) $R^{9a}$, $R^{10a}$ and $R^{11a}$ are each independently hydrogen or alkyl; and $R^{9b}$, $R^{10b}$ and $R^{11b}$ are each independently hydrogen, oxo, hydroxyl, halo or alkyl; or
ii) $R^{9a}$ and $R^{10b}$, $R^{9a}$ and $R^{10a}$, $R^{9b}$ and $R^{10b}$, $R^{9b}$ and $R^{10a}$, $R^{10a}$ and $R^{11a}$, $R^{10b}$ and $R^{11a}$, $R^{10a}$ and $R^{11b}$ or $R^{10b}$ and $R^{11b}$ together with the atoms to which they are attached form an aryl or heteroaryl ring, optionally substituted with one or more, in one embodiment, one to three, in another embodiment, one, two or three groups selected from $Q^2$; the remainder of $R^{9a}$, $R^{10a}$ and $R^{11a}$ are each independently hydrogen or alkyl; the remainder of $R^{9b}$ $R^{10b}$ and $R^{11b}$ are each independently hydrogen, halo or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $-R^uOR^x$, $-R^uOR^uN(R^y)(R^z)$, $-R^uN(R^y)(R^z)$, $-R^uSR^x$, $-R^uC(J)R^x$, $-R^uC(J)OR^x$, $-R^uC(J)N(R^y)(R^z)$, $-R^uC(J)N(R^y)OR^x$, $-R^uS(O)_tR^w$, $-R^uN(R^x)C(J)R^x$, $-R^uN(R^x)C(J)OR^x$, $-R^uN(R^x)S(O)_tR^w$ or $-C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^u$ is independently alkylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2;
n is 1; and
q is an integer from 0-2.

In certain embodiments, provided herein are compounds of Formula II

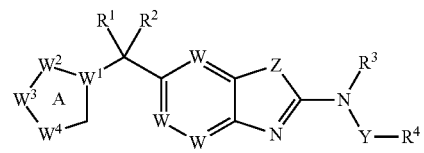

or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, alkoxy and halogen;
$R^3$ is hydrogen or alkyl;
$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;
each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $-R^uOR^x$, $-R^uOR^uN(R^y)(R^z)$, $-R^uN(R^y)(R^z)$, $-R^uSR^x$, $-R^uC(J)R^x$, $-R^uC(J)OR^x$, $-R^uC(J)N(R^y)(R^z)$, $-R^uS(O)_tR^w$, $-R^uN(R^x)C(J)R^x$, $-R^uN(R^x)C(J)OR^x$, $-R^uN(R^x)S(O)_tR^w$, $=NOR^d$, or $-C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is $-(CR^5R^6)_q-$;
$R^5$ and $R^6$ are each independently hydrogen, halo, alkyl, haloalkyl or hydroxyalkyl;
Z is O, S, or $NR^7$;
$R^7$ is hydrogen or alkyl;
each W is independently $CR^8$ or N;
$R^8$ is hydrogen, haloalkyl or alkyl;
ring A is aryl or heteroaryl, optionally substituted with one to four substituents selected from $Q^2$;
$W^1$ is N or C;
$W^2$ is N, $NR^{9a}$ or $CR^{9b}$;
$W^3$ is N, $NR^{10a}$ or $CR^{10b}$;
$W^4$ is N, $NR^{11a}$ or $CR^{11b}$;

$R^{9a}$, $R^{9b}$, $R^{10a}$, $R^{10b}$, $R^{11a}$ and $R^{11b}$ are selected as follows:
  i) $R^{9a}$, $R^{10a}$ and $R^{11a}$ are each independently hydrogen or alkyl and $R^{9b}$, $R^{10b}$ and $R^{11b}$ are each independently hydrogen or $Q^2$; or
  ii) $R^{9a}$ and $R^{10b}$, $R^{9a}$ and $R^{10a}$, $R^{9b}$ and $R^{10b}$, $R^{9b}$ and $R^{10a}$, $R^{10a}$ and $R^{11a}$, $R^{10b}$ and $R^{11a}$, $R^{10a}$ and $R^{11b}$ or $R^{10b}$ and $R^{11b}$ together with the atoms to which they are attached form an aryl or heteroaryl ring, optionally substituted with one or more, in one embodiment, one to three, in another embodiment, one, two or three groups selected from $Q^2$; the remainder of $R^{9a}$ or $R^{11a}$ is hydrogen or alkyl; and the remainder of $R^{9b}$ or $R^{11b}$ is independently hydrogen or $Q^2$;

each $Q^2$ is independently halo, deuterium, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $-R^uOR^x$, $-R^uOR^uOR^x$, $-R^uO-R^uN(R^y)(R^z)$, $-R^uN(R^y)(R^z)$, $-R^uSR^x$, $-R^uC(J)R^x$, $-R^uC(J)OR^x$, $-R^uC(J)N(R^y)(R^z)$, $-R^uC(J)R^uN(R^y)(R^z)$, $-R^uC(J)N(R^y)OR^x$, $-C(=NOR^x)R^x$, $-R^uS(O)_tR^w$, $-R^uN(R^x)C(J)R^x$, $-R^uN(R^x)C(J)OR^x$, $-R^uN(R^x)S(O)_tR^w$ or $-C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^d$ is independently hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:
  (i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or
  (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^x$ or S;

each t is independently an integer from 0-2; and q is an integer from 0-2;

wherein the compounds are selected such that when i) W is CH; $W^1$ is C; Z is S; $R^1$ is hydrogen, or hydroxyl and $R^2$ is hydrogen, or $R^1$ and $R^2$ together form =O; then ring A is not pyridine and ii) when W is CH; $W^1$ is C; Z is NH; $R^1$ and $R^2$ together form =O; and q is 0, then ring A is not phenyl.

In certain embodiments, provided herein are compounds of Formula II wherein each $Q^1$ is independently halo, oxo, alkyl, haloalkyl, hydroxyalkyl, cycloalkyl, =NOH, $-R^uOR^x$ or $-R^uC(O)R^x$; each $R^u$ is independently alkylene or a direct bond; each $R^x$ is independently hydrogen or alkyl; and the other variables are as described elsewhere herein. In certain embodiments, provided herein are compounds of Formula II wherein ring A is heteroaryl optionally substituted with one to four substituents selected from $Q^2$; n is 1 and the other variables are as described elsewhere herein.

In certain embodiments, provided herein are compounds of Formula II

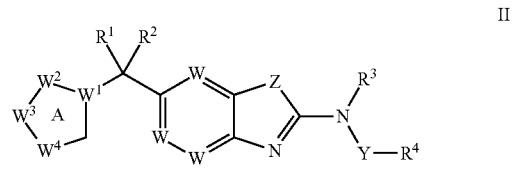

or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, alkoxy and halogen;

$R^3$ is hydrogen or alkyl;

$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, $-R^uOR^x$ or $-R^uC(O)R^x$;

Y is $-(CR^5R^6)_q-$;

$R^5$ and $R^6$ are each independently hydrogen, halo, alkyl, haloalkyl or hydroxyalkyl;

Z is O, S, or $NR^7$;

$R^7$ is hydrogen or alkyl;

each W is independently $CR^8$ or N;

$R^8$ is hydrogen, halo, haloalkyl or alkyl;

ring A is aryl or heteroaryl, optionally substituted with one to four substituents selected from $Q^2$;

$W^1$ is N or C;

$W^2$ is N, $NR^{9a}$ or $CR^{9b}$;

$W^3$ is N, $NR^{10a}$ or $CR^{10b}$;

$W^4$ is N, $NR^{11a}$ or $CR^{11b}$;

$R^{9a}$, $R^{9b}$, $R^{10a}$, $R^{10b}$, $R^{11a}$ and $R^{11b}$ are selected as follows:
  i) $R^{9a}$, $R^{10a}$ and $R^{11a}$ are each independently hydrogen or alkyl and $R^{9b}$, $R^{10b}$ and $R^{11b}$ are each independently hydrogen, oxo, hydroxyl, halo or alkyl; or
  ii) $R^{9a}$ and $R^{10b}$, $R^{9a}$ and $R^{10a}$, $R^{9b}$ and $R^{10b}$, $R^{9b}$ and $R^{10a}$, $R^{10a}$ and $R^{11a}$, $R^{10b}$ and $R^{11a}$, $R^{10a}$ and $R^{11b}$ or $R^{10b}$ and $R^{11b}$ together with the atoms to which they are attached form an aryl or heteroaryl ring, optionally substituted with one or more, in one embodiment, one to three, in another embodiment, one, two or three groups selected from $Q^2$; the remainder of $R^{9a}$, $R^{10a}$ and $R^{11a}$ are each independently hydrogen or alkyl; the remainder of $R^{9b}$, $R^{10b}$ and $R^{11b}$ are each independently hydrogen, halo or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $-R^uOR^x$, $-R^uOR^uN(R^y)(R^z)$, $-R^uN(R^y)(R^z)$, $-R^uSR^x$, $-R^uC(J)R^x$, $-R^uC(J)OR^x$, $-R^uC(J)N(R^y)(R^z)$, —R"C(J)N(R$^y$)OR$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^4$ groups; each Q$^4$ is independently selected from halo, hydroxyl, alkyl, haloalkyl and hydroxyalkyl;

each R$^u$ is independently alkylene or a direct bond;

R$^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2; and q is an integer from 0-2.

In certain embodiments, provided herein are compounds of Formula II wherein ring A is heteroaryl optionally substituted with one to four substituents selected from Q$^2$ and the other variables are as described elsewhere herein.

In certain embodiments, compound of formula II us selected such that: i) when W is CH; W$^1$ is N; Z is S; R$^1$ and R$^2$ are hydrogen, then ring A is not pyrrolidine; ii) when W is CH, Z is NH, R$^1$ and R$^2$ together form =O, q is 0, and R$^4$ is phenyl, then ring A is not pyrrolidine, and iii) when Z is N, one of R$^1$ and R$^2$ is methyl and the other of R$^1$ and R$^2$ is H, q is 0, and R$^3$ is pyridine, and W$^1$ is N, ring A cannot be isoindoline.

In certain embodiments, provided herein are compounds of Formula II, wherein ring A is bicyclic or tricyclic heteroaryl, and the other variables are as described elsewhere herein.

In certain embodiments, provided herein are compounds of Formula II or pharmaceutically acceptable salts, solvates, hydrates, clathrates, single stereoisomers, mixture of stereoisomers or racemic mixture of stereoisomers thereof, wherein:

R$^1$ and R$^2$ are each independently selected from hydrogen, alkoxy and halogen;

R$^3$ is hydrogen or alkyl;

R$^4$ is cycloalkyl, cycloalkenyl, aryl, heterocyclyl or heteroaryl, where R$^4$ is optionally substituted with one or more, in one embodiment, one to three, in another embodiment, one, two or three groups selected from Q$^1$;

each Q$^1$ is independently halo, oxo, alkyl, haloalkyl, hydroxyalkyl, cycloalkyl, =NOH, —R"OR$^x$ or —R"C(O)R$^x$;

Y is —(CR$^5$R$^6$)$_q$—;

R$^5$ and R$^6$ are each independently hydrogen, halo, alkyl, haloalkyl or hydroxyalkyl;

Z is O, S, or NR$^7$;

R$^7$ is hydrogen or alkyl;

each W is independently CR$^8$ or N;

R$^8$ is hydrogen, halo, haloalkyl or alkyl;

ring A is heteroaryl or heterocyclyl, optionally substituted with one to four substituents selected from Q$^2$;

W$^1$ is N or C;

W$^2$ is N, NR$^{9a}$ or CR$^{9b}$;

W$^3$ is N, NR$^{10a}$ or CR$^{10b}$;

W$^4$ is N, NR$^{11a}$ or CR$^{11b}$;

R$^{9a}$, R$^{9b}$, R$^{10a}$, R$^{10b}$, R$^{11a}$ and R$^{11b}$ are selected as follows:

i) R$^{9a}$, R$^{10a}$ and R$^{11a}$ are each independently hydrogen or alkyl and R$^{9b}$, R$^{10b}$ and R$^{11b}$ are each independently hydrogen, oxo, hydroxyl, halo or alkyl; or ii) R$^{9a}$ and R$^{10b}$, R$^{9a}$ and R$^{10a}$, R$^{9b}$ and R$^{10b}$, R$^{9b}$ and R$^{10a}$, R$^{10a}$ and R$^{11a}$, R$^{10b}$ and R$^{11a}$, R$^{10a}$ and R$^{11b}$ or R$^{10b}$ and R$^{11b}$ together with the atoms to which they are attached form an aryl, heteroaryl or heterocyclyl ring, optionally substituted with one or more, in one embodiment, one to three, in another embodiment, one, two or three groups selected from Q$^2$; the remainder of R$^{9a}$, R$^{10a}$ and R$^{11a}$ are each independently hydrogen or alkyl; the remainder of R$^{9b}$ R$^{10b}$ and R$^{11b}$ are each independently hydrogen, halo or alkyl; or iii) R$^{9a}$ and R$^{10b}$, R$^{9a}$ and R$^{10a}$, R$^{9b}$ and R$^{10b}$, R$^{10a}$ and R$^{11a}$, R$^{10b}$ and R$^{11a}$, R$^{10a}$ and R$^{11b}$ or R$^{10b}$ and R$^{11b}$ together with the atoms to which they are attached form an aryl, heteroaryl or heterocyclyl ring optionally fused to a phenyl ring optionally substituted with one or more, in one embodiment, one to three, in another embodiment, one, two or three groups selected from Q$^2$; and the remainder of R$^{9a}$ and R$^{9b}$ or the remainder of R$^{11a}$ and R$^{11b}$ are each independently hydrogen or alkyl;

each Q$^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^4$ groups; each Q$^4$ is independently selected from halo, hydroxyl, alkyl, haloalkyl and hydroxyalkyl;

each R$^u$ is independently alkylene, alkenylene or a direct bond;

R$^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each R$^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

R$^y$ and R$^z$ are each independently selected from (i) or (ii) below:

(i) R$^y$ and R$^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) R$^y$ and R$^z$, together with the nitrogen atom to which they are attached, form a heterocyclyl or heteroaryl, optionally substituted with one or more, in one embodiment, one, two or three Q$^7$ groups; each Q$^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, NR$^x$ or S;

each t is independently an integer from 0-2; and q is an integer from 0-2;

wherein the compounds are selected such that when W is CH; W$^1$ is N; Z is S; R$^1$ and R$^2$ are hydrogen, then ring A is not pyrrolidine.

In certain embodiments, provided herein are compounds of Formula II or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, alkoxy and halogen;

$R^3$ is hydrogen or alkyl;

$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —$R^uOR^x$ or —$R^uC(O)R^x$;

Y is —$(CR^5R^6)_q$—;

$R^5$ and $R^6$ are each independently hydrogen, halo, alkyl, haloalkyl or hydroxyalkyl;

Z is O, S, or $NR^7$;

$R^7$ is hydrogen or alkyl;

each W is independently $CR^8$ or N;

$R^8$ is hydrogen, halo, haloalkyl or alkyl;

ring A is bicyclic heteroaryl or heterocyclyl, optionally substituted with one to four substituents selected from $Q^2$;

$W^1$ is N or C;

$W^2$ is N, $NR^{9a}$ or $CR^{9b}$;

$W^3$ is $CR^{10b}$;

$W^4$ is N;

$R^{9a}$, $R^{9b}$, and $R^{10b}$ are selected as follows:

$R^{9a}$ and $R^{10b}$ or $R^{9b}$ and $R^{10b}$, together with the atoms to which they are attached, form an aryl, heteroaryl or heterocyclyl ring, optionally substituted with one or more, in one embodiment, one to three, in another embodiment, one, two or three groups selected from $Q^2$; the remainder of $R^{9a}$ and $R^{10b}$ is hydrogen or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)R^uN(R^y)(R^z)$, —$R^uC(J)N(R^y)OR^x$, —$C(=NOR^x)R^x$, —$R^uS(O)_tR^w$, —$R^uN(R^x)C(J)R^x$, —$R^uN(R^x)C(J)OR^x$, —$R^uN(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^x$ or S;

each t is independently an integer from 0-2; and q is an integer from 0-2.

In certain embodiments, provided herein are compounds of Formula II wherein $W^4$ is N; $W^2$ is N, $NR^{9a}$ or $CR^{9b}$; $W^3$ is $CR^{10b}$; and $R^{9a}$ and $R^{10b}$ or $R^{9b}$ and $R^{10b}$, together with the atoms to which they are attached, form an aryl, heteroaryl or heterocyclyl ring, optionally substituted with one or more, in one embodiment, one to three, in another embodiment, one, two or three groups selected from $Q^2$ and the other variables are as described elsewhere herein.

In certain embodiments, provided herein are compounds of Formula II wherein $R^4$ is cycloalkyl, optionally substituted with one or more, in one embodiment, one to three, in another embodiment, one, two or three groups selected from $Q^1$; each $Q^1$ is independently halo, oxo, alkyl, haloalkyl, hydroxyalkyl, cycloalkyl, =NOH, —$R^uOR^x$ or —$R^uC(O)R^x$; Y is —$(CR^5R^6)_q$—;

each $R^u$ is independently alkylene, alkenylene or a direct bond;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; and q is 0; and the other variables are as described elsewhere herein.

In certain embodiments, provided herein are compounds of Formula III

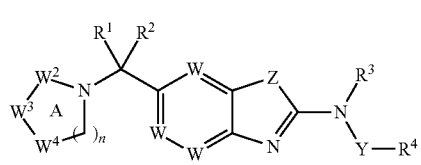

or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, halogen, alkoxy and hydroxyl;

$R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uS(O)_tR^w$, —$R^uN(R^x)C(J)R^x$, —$R^uN(R^x)C(J)OR^x$, —$R^uN(R^x)S(O)_tR^w$, =$NOR^d$, or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is —$(CR^5R^6)_q$—;

$R^5$ and $R^6$ are each independently hydrogen, halo, alkyl, haloalkyl or hydroxyalkyl;

Z is O, S or NH;

each W is independently $CR^8$ or N;

$R^8$ is hydrogen, halo, haloalkyl or alkyl;

ring A is heteroaryl or heterocyclyl, optionally substituted with one to four substituents selected from $Q^2$;

$W^2$ is N or $CR^{9b}$;

$W^3$ is N or $CR^{10b}$;

$W^4$ is N or $CR^{11b}$;

$R^{9b}$, $R^{10b}$ and $R^{11b}$ are selected as follows:

i) $R^{9b}$, $R^{10b}$ and $R^{11b}$ are each independently hydrogen or $Q^2$; or ii) $R^{9b}$ and $R^{10b}$ or $R^{10b}$ and $R^{11b}$ together with the atoms to which they are attached form an aryl or heteroaryl ring, optionally substituted with one or more, in one embodiment, one to three, in another embodiment, one, two or three groups selected from $Q^2$; and the remainder of $R^{9b}$, $R^{10b}$ and $R^{11b}$ is hydrogen or $Q^2$;

each $Q^2$ is independently halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)R^uN(R^y)(R^z)$, —$R^uC(J)N(R^y)OR^x$, —$C(=NOR^x)R^x$, —$R^uS(O)_tR^w$, —$R^uN(R^x)C(J)R^x$, —$R^uN(R^x)C(J)OR^x$, —$R^uN(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

$R^d$ is hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^x$ or S;

each t is independently an integer from 0-2;

n is 1 or 2; and q is an integer from 0-4.

In certain embodiments, provided herein are compounds of Formula III wherein each $Q^1$ is independently halo, oxo, alkyl, haloalkyl, hydroxyalkyl, cycloalkyl, =NOH, —$R^uOR^x$ or —$R^uC(O)R^x$; each $R^u$ is independently alkylene or a direct bond; each $R^x$ is independently hydrogen or alkyl; and the other variables are as described elsewhere herein.

In certain embodiments, provided herein are compounds of Formula III

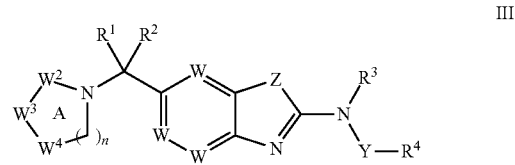

III or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, halogen, alkoxy and hydroxyl;

$R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —$R^uOR^x$ or —$R^uC(O)R^x$;

Y is —$(CR^5R^6)_q$—;

$R^5$ and $R^6$ are each independently hydrogen, halo, alkyl, haloalkyl or hydroxyalkyl;

Z is O, S or NH;

each W is independently $CR^8$ or N;

$R^8$ is hydrogen, halo, haloalkyl or alkyl;

ring A is heteroaryl, optionally substituted with one to four substituents selected from $Q^2$;

$W^2$ is N or $CR^{9b}$;

$W^3$ is N or $CR^{10b}$;

$W^4$ is N or $CR^{11b}$;

$R^{9b}$, $R^{10b}$ and $R^{1b}$ are selected as follows:

i) $R^{9b}$, $R^{10b}$ and $R^{11b}$ are each independently hydrogen, oxo, hydroxyl, halo or alkyl; or ii) $R^{9b}$ and $R^{10b}$ or $R^{10b}$ and $R^{11b}$ together with the atoms to which they are attached form an aryl or heteroaryl ring, optionally substituted with one or more, in one embodiment, one to three, in another embodiment, one, two or three groups selected from $Q^2$; and the remainder of $R^{9b}$, $R^{10b}$ and $R^{11b}$ is hydrogen, halo or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)N(R^y)OR^x$, —$R^uS(O)_tR^w$, —$R^uN(R^x)C(J)R^x$, —$R^uN(R^x)C(J)OR^x$, —$R^uN(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^u$ is independently alkylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2;
n is 1 or 2; and
q is an integer from 0-4.

In certain embodiments, compound of Formula III is selected such that: i) when W is CH; Z is S; $R^1$ and $R^2$ are hydrogen, then ring A is not pyrrolidine; ii) when W is CH, Z is NH, $R^1$ and $R^2$ together form =O, q is 0, and $R^4$ is phenyl, then ring A is not pyrrolidine; and iii) when Z is NH, one of $R^1$ and $R^2$ is methyl and the other of $R^1$ and $R^2$ is H, q is 0, and $R^3$ is pyridine, and $W^1$ is N, ring A cannot be A cannot be piperidine, 1,2,3,4-tetrahydroisoquinoline, or isoindoline.

In certain embodiments, provided herein are compounds of Formula III wherein ring A is heteroaryl and the other variables are as described elsewhere herein. In certain embodiments, provided herein are compounds of Formula III, wherein ring A is bicyclic or tricyclic heteroaryl, and the other variables are as described elsewhere herein.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein $R^1$ and $R^2$ are each independently selected from hydrogen or halogen;
$R^3$ is hydrogen or alkyl;
$R^4$ is cycloalkyl, optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, —$R^u OR^x$ or —$R^u C(O) R^x$;
Y is —$(CR^5 R^6)_q$—;
$R^5$ and $R^6$ are each independently hydrogen, halo, alkyl, haloalkyl or hydroxyalkyl;
Z is O, S, or NH;
each W is independently $CR^8$ or N;
$R^8$ is hydrogen, halo, haloalkyl or alkyl;
ring A is heteroaryl optionally substituted with one to four substituents selected from $Q^2$;
$W^2$ is N or $CR^{9b}$;
$W^3$ is N or $CR^{10b}$;
$W^4$ is N or $CR^{11b}$;
$R^{9b}$, $R^{10b}$ and $R^{1b}$ are selected as follows:
i) $R^{9b}$, $R^{10b}$ and $R^{11b}$ are each independently hydrogen or $Q^2$; or
ii) $R^{9b}$ and $R^{10b}$ or $R^{10b}$ and $R^{11b}$, together with the atoms to which they are attached, form an aryl or heteroaryl ring, optionally substituted with one or more, in one embodiment, one to three, in another embodiment, one, two or three groups selected from $Q^2$; and the remainder of $R^{9b}$, $R^{10b}$ and $R^{11b}$ is hydrogen or $Q^2$;
each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^u OR^x$, —$R^u OR^u N(R^y)(R^z)$, —$R^u N(R^y)(R^z)$, —$R^u SR^x$, —$R^u C(J)R^x$, —$R^u C(J)OR^x$, —$R^u C(J)N(R^y)(R^z)$, —$R^u C(J)N(R^y)OR^x$, —$R^u S(O)_t R^w$, —$R^u N(R^x)C(J)R^x$, —$R^u N(R^x)C(J)OR^x$, —$R^u N(R^x)S(O)_t R^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^u$ is independently alkylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2;
n is 1 or 2; and
q is an integer from 0-2.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein $R^1$ and $R^2$ are each independently selected from hydrogen or halogen;
$R^3$ is hydrogen or alkyl;
$R^4$ is cycloalkyl, optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, —$R^u OR^x$ or —$R^u C(O) R^x$;
Y is —$(CR^5 R^6)_q$—;
$R^5$ and $R^6$ are each independently hydrogen, halo, alkyl, haloalkyl or hydroxyalkyl;
Z is O, S, or NH;
each W is independently $CR^8$ or N;
$R^8$ is hydrogen, halo, haloalkyl or alkyl;
ring A is heteroaryl optionally substituted with one to four substituents selected from $Q^2$;
$W^2$ is N or $CR^{9b}$;
$W^3$ is N or $CR^{10b}$;
$W^4$ is N or $CR^{11b}$;
$R^{9b}$, $R^{10b}$ and $R^{1b}$ are selected as follows:
i) $R^{9b}$, $R^{10b}$ and $R^{11b}$ are each independently hydrogen, oxo, hydroxyl, halo or alkyl; or
ii) $R^{9b}$ and $R^{10b}$ or $R^{10b}$ and $R^{11b}$, together with the atoms to which they are attached, form an aryl or heteroaryl ring, optionally substituted with one or more, in one embodiment, one to three, in another embodiment, one, two or three groups selected from $Q^2$; and the remainder of $R^{9b}$, $R^{10b}$ and $R^{11b}$ is hydrogen, halo or alkyl;
each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^u OR^x$, —$R^u OR^u N(R^y)(R^z)$, —$R^u N(R^y)(R^z)$, —$R^u SR^x$, —$R^u C(J)R^x$, —$R^u C(J)OR^x$, —$R^u C(J)N(R^y)(R^z)$, —$R^u C(J)N(R^y)OR^x$, —$R^u S(O)_t R^w$, —$R^u N(R^x)C(J)R^x$, —$R^u N(R^x)C(J)OR^x$, —$R^u N(R^x)S(O)_t R^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^u$ is independently alkylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2;
n is 1 or 2; and
q is an integer from 0-2.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, halogen, alkoxy and hydroxyl;

$R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''S(O)$_t$R$^w$, —R''N(R$^x$)C(J)R$^x$, —R''N(R$^x$)C(J)OR$^x$, —R''N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is —(CR$^5$R$^6$)$_q$—;

$R^5$ and $R^6$ are each independently hydrogen, halo, alkyl, haloalkyl or hydroxyalkyl;

Z is O, S or NH;

each W is independently CR$^8$ or N;

$R^8$ is hydrogen, halo, haloalkyl or alkyl;

ring A is heteroaryl optionally substituted with one to four substituents selected from $Q^2$;

$W^2$ is N or CR$^{9b}$;

$W^3$ is N or CR$^{10b}$;

$W^4$ is N or CR$^{11b}$;

$R^{9b}$, $R^{10b}$ and $R^{1b}$ are selected as follows:

i) $R^{9b}$, $R^{10b}$ and $R^{11b}$ are each independently hydrogen, or $Q^2$; or ii) $R^{9b}$ and $R^{10b}$ or $R^{10b}$ and $R^{11b}$ together with the atoms to which they are attached form an aryl or heteroaryl ring, optionally substituted with one or more, in one embodiment, one to three, in another embodiment, one, two or three groups selected from $Q^2$; and the remainder of $R^{9b}$, $R^{10b}$ and $R^{11b}$ is hydrogen or $Q^2$;

each $Q^2$ is independently halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''C(J)R''N(R$^y$)(R$^z$), —R''C(J)N(R$^y$)OR$^x$, —C(=NOR$^x$)R$^x$, —R''S(O)$_t$R$^w$, —R''N(R$^x$)C(J)R$^x$, —R''N(R$^x$)C(J)OR$^x$, —R''N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

$R^d$ is hydrogen or alkyl;

each $R''$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, NR$^x$ or S;

each t is independently an integer from 0-2;

n is 1; and q is an integer from 0-4.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen, halogen, alkoxy and hydroxyl;

$R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —R''OR$^x$ or —R''C(O)R$^x$; Y is —(CR$^5$R$^6$)$_q$—;

$R^5$ and $R^6$ are each independently hydrogen, halo, alkyl, haloalkyl or hydroxyalkyl;

Z is O, S or NH;

each W is independently CR$^8$ or N;

$R^8$ is hydrogen, halo, haloalkyl or alkyl;

ring A is heteroaryl or heterocyclyl optionally substituted with one to four substituents selected from $Q^2$;

$W^2$ is N or CR$^{9b}$;

$W^3$ is N or CR$^{10b}$;

$W^4$ is N or CR$^{11b}$;

$R^{9b}$, $R^{10b}$ and $R^{11b}$ are selected as follows:

i) $R^{9b}$, $R^{10b}$ and $R^{11b}$ are each independently hydrogen, oxo, hydroxyl, halo or alkyl; or ii) $R^{9b}$ and $R^{10b}$ or $R^{10b}$ and $R^{11b}$ together with the atoms to which they are attached form an aryl or heteroaryl ring, optionally substituted with one or more, in one embodiment, one to three, in another embodiment, one, two or three groups selected from $Q^2$; and the remainder of $R^{9b}$, $R^{10b}$ and $R^{11b}$ is hydrogen, halo or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''C(J)R''N(R$^y$)(R$^z$), —R''C(J)N(R$^y$)OR$^x$, —C(=NOR$^x$)R$^x$, —R''S(O)$_t$R$^w$, —R''N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^4$ groups; each Q$^4$ is independently selected from halo, hydroxyl, alkyl, haloalkyl and hydroxyalkyl;

each R$^u$ is independently alkylene, alkenylene or a direct bond;

R$^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2;

n is 1 or 2; and q is an integer from 0-4;

wherein the compounds are selected such that when i) when W is CH; W$^1$ is C; Z is S; R$^1$ is hydrogen, or hydroxyl and R$^2$ is hydrogen, or R$^1$ and R$^2$ together form =O; then ring A is not pyridine and ii) W is CH; W$^1$ is N; Z is S; R$^1$ and R$^2$ are hydrogen, then ring A is not pyrrolidine.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein R$^1$ and R$^2$ are each independently selected from hydrogen or halogen;

R$^3$ is hydrogen or alkyl;

R$^4$ is cycloalkyl, optionally substituted with one or more, in one embodiment, one to three, in another embodiment, one, two or three groups selected from Q$^1$;

each Q$^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"S(O)$_t$R$^w$, —R"N(R$^x$)C(J)R$^x$, —R"N(R$^x$)C(J)OR$^x$, —R"N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^3$ groups, in one embodiment, one to three Q$^3$ groups; each Q$^3$ is independently selected from deuterium, halo, hydroxyl, alkyl, haloalkyl and hydroxyalkyl;

Y is —(CR$^5$R$^6$)$_q$—;

R$^5$ and R$^6$ are each independently hydrogen, halo, alkyl, haloalkyl or hydroxyalkyl;

Z is O, S, or NH;

each W is independently CR$^8$ or N;

R$^8$ is hydrogen, halo, haloalkyl or alkyl;

ring A is heteroaryl optionally substituted with one to four substituents selected from Q$^2$;

W$^2$ is N or CR$^{9b}$;

W$^3$ is N or CR$^{10b}$;

W$^4$ is N or CR$^{11b}$;

R$^{9b}$, R$^{10b}$ and R$^{11b}$ are selected as follows:

i) R$^{9b}$, R$^{10b}$ and R$^{11b}$ are each independently hydrogen, oxo, hydroxyl, halo or alkyl; or ii) R$^{9b}$ and R$^{10b}$ or R$^{10b}$ and R$^{11b}$, together with the atoms to which they are attached, form an aryl or heteroaryl ring, optionally substituted with one or more, in one embodiment, one to three, in another embodiment, one, two or three groups selected from Q$^2$; and the remainder of R$^{9b}$, R$^{10b}$ and R$^{11b}$ is hydrogen, halo or alkyl;

each Q$^2$ is independently halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^4$ groups; each Q$^4$ is independently selected from halo, hydroxyl, alkyl, haloalkyl and hydroxyalkyl;

R$^d$ is hydrogen or alkyl;

each R$^u$ is independently alkylene, alkenylene or a direct bond;

R$^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each R$^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

R$^y$ and R$^z$ are each independently selected from (i) or (ii) below:

(i) R$^y$ and R$^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) R$^y$ and R$^z$, together with the nitrogen atom to which they are attached, form a heterocyclyl or heteroaryl, optionally substituted with one or more, in one embodiment, one, two or three Q$^7$ groups; each Q$^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, NR$^x$ or S;

each t is independently an integer from 0-2;

n is 1 or 2; and q is an integer from 0-2.

In certain embodiments, provided herein are compounds of Formula III wherein n is 1 and the other variables are as described elsewhere herein. In certain embodiments, provided herein are compounds of Formula III wherein each Q$^1$ is independently halo, oxo, alkyl, haloalkyl, hydroxyalkyl, cycloalkyl, =NOH, —R"OR$^x$ or —R"C(O)R$^x$; each R$^u$ is independently alkylene or a direct bond; each R$^x$ is independently hydrogen or alkyl; n is 1 and the other variables are as described elsewhere herein.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein R$^1$ and R$^2$ are each independently selected from hydrogen or halogen;

R$^3$ is hydrogen or alkyl;

R$^4$ is cycloalkyl, optionally substituted with one or more, in one embodiment, one to three, in another embodiment, one, two or three groups selected from Q$^1$;

each Q$^1$ is independently halo, oxo, alkyl, haloalkyl, hydroxyalkyl, cycloalkyl, =NOH, —R"OR$^x$ or —R"C(O)R$^x$;

Y is —(CR$^5$R$^6$)$_q$—;

R$^5$ and R$^6$ are each independently hydrogen, halo, alkyl, haloalkyl or hydroxyalkyl;

Z is O, S, or NH;

each W is independently CR$^8$ or N;

R$^8$ is hydrogen, halo, haloalkyl or alkyl;

ring A is heteroaryl optionally substituted with one to four substituents selected from Q$^2$;

W$^2$ is N or CR$^{9b}$;

W$^3$ is N or CR$^{10b}$;

W$^4$ is N or CR$^{11b}$;

R$^{9b}$, R$^{10b}$ and R$^{11b}$ are selected as follows:

i) R$^{9b}$, R$^{10b}$ and R$^{11b}$ are each independently hydrogen, oxo, hydroxyl, halo or alkyl; or ii) R$^{9b}$ and R$^{10b}$ or R$^{10b}$ and R$^{11b}$, together with the atoms to which they are attached, form an aryl or heteroaryl ring, optionally substituted with one or more, in one embodiment, one to three, in another embodiment, one, two or three groups selected from Q$^2$; and the remainder of R$^{9b}$, R$^{10b}$ and R$^{11b}$ is hydrogen, halo or alkyl;

each Q$^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$^u$OR$^x$, —R$^u$OR$^u$N(R$^y$)(R$^z$), —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$C(J)N(R$^y$)OR$^x$, —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^4$ groups; each Q$^4$ is independently selected from halo, hydroxyl, alkyl, haloalkyl and hydroxyalkyl;

each R$^u$ is independently alkylene or a direct bond;

R$^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2;

n is 1 or 2; and q is an integer from 0-2.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein R$^1$ and R$^2$ are each independently selected from hydrogen or halogen;

R$^3$ is hydrogen or alkyl;

R$^4$ is cycloalkyl, optionally substituted with one or more, in one embodiment, one to three, in another embodiment, one, two or three groups selected from Q$^1$;

each Q$^1$ is independently halo, oxo, alkyl, haloalkyl, hydroxyalkyl, cycloalkyl, =NOH, —R$^u$OR$^x$ or —R$^u$C(O)R$^x$;

Y is —(CR$^5$R$^6$)$_q$—;

R$^5$ and R$^6$ are each independently hydrogen, halo, alkyl, haloalkyl or hydroxyalkyl;

Z is O, S, or NH;

each W is independently CR$^8$ or N;

R$^8$ is hydrogen, halo, haloalkyl or alkyl;

ring A is heteroaryl, optionally substituted with one to four substituents selected from Q$^2$;

W$^2$ is N or CR$^{9b}$;

W$^3$ is N or CR$^{10b}$;

W$^4$ is N or CR$^{11b}$;

R$^{9b}$ and R$^{10b}$, together with the atoms to which they are attached, form an aryl or heteroaryl ring, optionally substituted with one or two groups selected from Q$^2$;

each Q$^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$^u$OR$^x$, —R$^u$OR$^u$N(R$^y$)(R$^z$), —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$C(J)N(R$^y$)OR$^x$, —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^4$ groups; each Q$^4$ is independently selected from halo, hydroxyl, alkyl, haloalkyl and hydroxyalkyl;

each R$^u$ is independently alkylene or a direct bond;

R$^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2;

R$^{11b}$ is hydrogen;

n is 1 or 2; and q is an integer from 0-2.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein R$^1$ and R$^2$ are each independently selected from hydrogen or halogen;

R$^3$ is hydrogen or alkyl;

R$^4$ is cycloalkyl, optionally substituted with one or more, in one embodiment, one to three, in another embodiment, one, two or three groups selected from Q$^1$;

each Q$^1$ is independently halo, oxo, alkyl, haloalkyl, hydroxyalkyl, cycloalkyl, =NOH, —R$^u$OR$^x$ or —R$^u$C(O)R$^x$;

Y is —(CR$^5$R$^6$)$_q$—;

R$^5$ and R$^6$ are each independently hydrogen, halo, alkyl, haloalkyl or hydroxyalkyl;

Z is O, S, or NH;

each W is independently CR$^8$ or N;

R$^8$ is hydrogen, halo, haloalkyl or alkyl;

ring A is heteroaryl, optionally substituted with one to four substituents selected from Q$^2$;

W$^2$ is N or CR$^{9b}$;

W$^3$ is N or CR$^{10b}$;

W$^4$ is N or CR$^{11b}$;

R$^{9b}$ and R$^{10b}$, together with the atoms to which they are attached, form an aryl or heteroaryl ring, optionally substituted with one or two groups selected from Q$^2$;

each Q$^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$^u$OR$^x$, —R$^u$OR$^u$N(R$^y$)(R$^z$), —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$C(J)N(R$^y$)OR$^x$, —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^4$ groups; each Q$^4$ is independently selected from halo, hydroxyl, alkyl, haloalkyl and hydroxyalkyl;

each R$^u$ is independently alkylene or a direct bond;

$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2;
$R^{11b}$ is hydrogen;
n is 1 or 2; and
q is an integer from 0-2.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein $R^1$ and $R^2$ are each independently selected from hydrogen or halogen;
$R^3$ is hydrogen or alkyl;
$R^4$ is cycloalkyl, optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, $-R^uOR^x$ or $-R^uC(O)R^x$;
Y is $-(CR^5R^6)_q-$;
$R^5$ and $R^6$ are each independently hydrogen, halo, alkyl, haloalkyl or hydroxyalkyl;
Z is O, S, or NH;
each W is independently $CR^8$ or N;
$R^8$ is hydrogen, halo, haloalkyl or alkyl;
ring A is heteroaryl, optionally substituted with one to four substituents selected from $Q^2$;
$W^2$ is N or $CR^{9b}$;
$W^3$ is N or $CR^{10b}$;
$W^4$ is N or $CR^{11b}$;
$R^{9b}$ and $R^{10b}$, together with the carbon atoms to which they are attached, form an aryl or heteroaryl ring, optionally substituted with one or two groups $Q^2$, each $Q^2$ is independently halo, cyano, alkyl, haloalkyl, aminoalkyl, alkenyl, alkynyl, cycloalkyl, heteroaryl, heterocyclyl, $-R^uOR^x$, $-R^uN(R^y)(R^z)$, $-R^uSR^x$, $-R^uC(J)R^x$, $-R^uC(J)OR^x$, $-R^uC(J)N(R^y)(R^z)$, $-R^uC(J)N(R^y)OR^x$, $-R^uS(O)_tR^w$, $-R^uN(R^x)C(J)R^x$, $-R^uN(R^x)C(J)OR^x$, $-R^uN(R^x)S(O)_tR^w$ or $-C(=NR^y)N(R^y)OR^x$, where the cycloalkyl, heteroaryl, heterocyclyl are optionally substituted with one or more alkyl;
$R^{11b}$ is hydrogen or $Q^2$;
each $R^u$ is independently alkylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2; and
q is an integer from 0-2.

In certain embodiments, provided herein are compounds of Formula III or pharmaceutically acceptable salts, solvates, hydrates, clathrates, single stereoisomers, mixture of stereoisomers or racemic mixture of stereoisomers thereof, wherein $R^1$ and $R^2$ are each independently selected from hydrogen or halogen;
$R^3$ is hydrogen or alkyl;
$R^4$ is cycloalkyl, optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, $-R^uOR^x$ or $-R^uC(O)R^x$;
Y is $-(CR^5R^6)_q-$;
$R^5$ and $R^6$ are each independently hydrogen, halo, alkyl, haloalkyl or hydroxyalkyl;
Z is O, S, or NH;
each W is independently $CR^8$ or N;
$R^8$ is hydrogen, halo, haloalkyl or alkyl;
ring A is heteroaryl, optionally substituted with one to four substituents selected from $Q^2$;
$W^2$ is N or $CR^{9b}$;
$W^3$ is N or $CR^{10b}$;
$W^4$ is N or $CR^{11b}$;
$R^{9b}$ and $R^{10b}$, together with the carbon atoms to which they are attached, form an aryl or heteroaryl ring, optionally substituted with one or two groups $Q^2$, each $Q^2$ is independently halo, cyano, alkyl, haloalkyl, aminoalkyl, alkenyl, alkynyl, cycloalkyl, heteroaryl, heterocyclyl, $-R^uOR^x$, $-R^uN(R^y)(R^z)$, $-R^uSR^x$, $-R^uC(J)R^x$, $-R^uC(J)OR^x$, $-R^uC(J)N(R^y)(R^z)$, $-R^uC(J)N(R^y)OR^x$, $-R^uS(O)_tR^w$, $-R^uN(R^x)C(J)R^x$, $-R^uN(R^x)C(J)OR^x$, $-R^uN(R^x)S(O)_tR^w$ or $-C(=NR^y)N(R^y)OR^x$, where the cycloalkyl, heteroaryl, heterocyclyl are optionally substituted with one or more alkyl;
each $R^u$ is independently alkylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2; and
q is an integer from 0-2.

In certain embodiments, provided herein are compounds of Formula III or pharmaceutically acceptable salts, solvates, hydrates, clathrates, single stereoisomers, mixture of stereoisomers or racemic mixture of stereoisomers thereof wherein:

$R^1$ and $R^2$ are each independently selected from hydrogen, halogen, and hydroxyl;
$R^3$ is hydrogen or alkyl;
$R^4$ is cycloalkyl, where $R^4$ is optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, $-R^uOR^x$ or $-R^uC(O)R^x$;
Y is $-(CR^5R^6)_q-$;
$R^5$ and $R^6$ are each independently hydrogen, halo, alkyl, haloalkyl or hydroxyalkyl;
Z is O, S, or NH;
each W is independently $CR^8$ or N;
$R^8$ is hydrogen, halo, haloalkyl or alkyl;
ring A is heteroaryl, optionally substituted with one to four substituents selected from $Q^2$;
$W^2$ is N or $CR^{9b}$;
$W^3$ is N or $CR^{10b}$;
$W^4$ is N or $CR^{11b}$;
$R^{9b}$, $R^{10b}$ and $R^{1b}$ are selected as follows:
i) $R^{9b}$, $R^{10b}$ and $R^{11b}$ are each independently hydrogen or $Q^2$; or
ii) $R^{9b}$ and $R^{10b}$ or $R^{10b}$ and $R^{11b}$, together with the atoms on which they are substituted form an aryl, heteroaryl ring, optionally substituted with one or two groups selected from $Q^2$; and the remainder of $R^{9b}$ or $R^{11b}$ is hydrogen or $Q^2$;
each $Q^2$ is hydrogen, halo, alkoxy, tetrazole or pyrazole, where the tetrazole and pyrazole rings are optionally substituted with one or more alkyl;
each $R^u$ is independently alkylene or a direct bond;
$R^w$ is alkyl;
each $R^x$ is independently hydrogen or alkyl;

$R^y$ and $R^z$ are each independently hydrogen or alkyl;

J is O, $NR^x$ or S;

each t is independently an integer from 0-2;

n is 1 or 2; and q is an integer from 0-4.

In certain embodiments, provided herein are compounds of Formula III or pharmaceutically acceptable salts, solvates, hydrates, clathrates, single stereoisomers, mixture of stereoisomers or racemic mixture of stereoisomers thereof wherein:

$R^1$ and $R^2$ are each independently selected from hydrogen, halogen, and hydroxyl;

$R^3$ is hydrogen or alkyl;

$R^4$ is cycloalkyl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —$R''OR^x$ or —$R''C(O)R^x$;

Y is —$(CR^5R^6)_q$—;

$R^5$ and $R^6$ are each independently hydrogen, halo, alkyl, haloalkyl or hydroxyalkyl;

Z is O, S, or NH;

each W is independently $CR^8$ or N;

$R^8$ is hydrogen, halo, haloalkyl or alkyl;

ring A is heteroaryl, optionally substituted with one to four substituents selected from $Q^2$;

$W^2$ is N or $CR^{9b}$;

$W^3$ is N or $CR^{10b}$;

$W^4$ is N or $CR^{11b}$;

$R^{9b}$, $R^{10b}$ and $R^{11b}$ are selected as follows:

i) $R^{9b}$, $R^{10b}$ and $R^{11b}$ are each independently hydrogen, oxo, hydroxyl, halo or alkyl; or ii) $R^{9b}$ and $R^{10b}$ or $R^{10b}$ and $R^{11b}$, together with the atoms on which they are substituted form an aryl, heteroaryl ring, optionally substituted with one or two groups selected from $Q^2$; and the remainder of $R^{9b}$, $R^{10b}$ or $R^{11b}$ is hydrogen or alkyl;

each $Q^2$ is hydrogen, halo, alkoxy, tetrazole or pyrazole, where the tetrazole and pyrazole rings are optionally substituted with one or more alkyl;

each $R^u$ is independently alkylene or a direct bond;

$R^w$ is alkyl;

each $R^x$ is independently hydrogen or alkyl;

$R^y$ and $R^z$ are each independently hydrogen or alkyl;

J is O, $NR^x$ or S;

each t is independently an integer from 0-2;

n is 1 or 2; and q is an integer from 0-4.

In certain embodiments, provided herein are compounds of Formula III wherein $W^4$ is N; $W^2$ is $CR^{9b}$; $W^3$ is $CR^{10b}$; $R^{9b}$ and $R^{10b}$, together with the atoms to which they are attached, form an aryl or heteroaryl ring, optionally substituted with one or more, in one embodiment, one to three, in another embodiment, one, two or three groups selected from $Q^2$; and the other variables are as described elsewhere herein.

In certain embodiments, provided herein are compounds of Formula IV

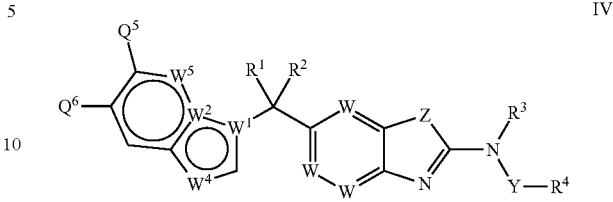

or pharmaceutically acceptable salts, solvates, hydrates, clathrates, single stereoisomers, mixture of stereoisomers or racemic mixture of stereoisomers thereof, wherein the variables are as described elsewhere herein.

In certain embodiments, provided herein are compounds of Formula IV, wherein $R^1$ and $R^2$ are each independently selected from hydrogen or halogen;

$R^3$ is hydrogen or alkyl;

$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R''OR^x$, —$R''OR''N(R^y)(R^z)$, —$R''N(R^y)(R^z)$, —$R''SR^x$, —$R''C(J)R^x$, —$R''C(J)OR^x$, —$R''C(J)N(R^y)(R^z)$, —$R''S(O)_tR^w$, —$R''N(R^x)C(J)R^x$, —$R''N(R^x)C(J)OR^x$, —$R''N(R^x)S(O)_tR^w$, =$NOR^d$, or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is —$(CR^5R^6)_q$—;

$R^5$ and $R^6$ are each independently hydrogen, halo, alkyl, haloalkyl or hydroxyalkyl;

Z is O, S, or NH;

each W is independently $CR^8$ or N;

$R^8$ is hydrogen, halo, haloalkyl or alkyl;

$W^1$ is N or C;

$W^2$ is N or $CR^{9b}$;

$R^{9b}$ is hydrogen or $Q^2$;

$W^4$ is N or $CR^{11b}$;

$W^5$ is N or $CR^{13}$;

$R^{11b}$ and $R^{13}$ are each independently hydrogen or $Q^2$;

$Q^2$ is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R''OR^x$, —$R''OR''OR^x$, —$R''OR''N(R^y)(R^z)$, —$R''N(R^y)(R^z)$, —$R''SR^x$, —$R''C(J)R^x$, —$R''C(J)OR^x$, —$R''C(J)N(R^y)(R^z)$, —$R''C(J)R''N(R^y)(R^z)$, —$R''C(J)N(R^y)OR^x$, —$C(=NOR^x)R^x$, —$R''S(O)_tR^w$, —$R''N(R^x)C(J)R^x$, —$R''N(R^x)C(J)OR^x$, —$R''N(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more groups $Q^4$; in one embodiment, one to three $Q^4$ groups, each $Q^4$ is independently selected from halo, deuterium, hydroxyl, alkyl, haloalkyl and hydroxyalkyl;

$Q^5$ and $Q^6$ are each independently hydrogen, deuterium, halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''C(J)R''N(R$^y$)(R$^z$), —R''C(J)N(R$^y$)OR$^x$, —C(=NOR$^x$)R$^x$, —R''S(O)$_t$R$^w$, —R''N(R$^x$)C(J)R$^x$, —R''N(R$^x$)C(J)OR$^x$, —R''N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^8$ groups; each Q$^8$ is independently selected from halo, deuterium, hydroxyl, alkyl, haloalkyl and hydroxyalkyl;

each R$^d$ is independently hydrogen or alkyl;

R$^d$ is hydrogen or alkyl;

each R$^u$ is independently alkylene, alkenylene or a direct bond;

R$^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each R$^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

R$^y$ and R$^z$ are each independently selected from (i) or (ii) below:

(i) R$^y$ and R$^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) R$^y$ and R$^z$, together with the nitrogen atom to which they are attached, form a heterocyclyl or heteroaryl, optionally substituted with one or more, in one embodiment, one, two or three Q$^7$ groups; each Q$^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, NR$^x$ or S;

each t is independently an integer from 0-2; and q is an integer from 0-4.

In certain embodiments, provided herein are compounds of Formula IV wherein R$^1$ and R$^2$ are both hydrogen. In certain embodiments, provided herein are compounds of Formula IV wherein R$^{9b}$ and R$^{11b}$ are each independently hydrogen, alkyl or haloalkyl and the other variables are as described elsewhere herein. In certain embodiments, provided herein are compounds Formula IV wherein each Q$^1$ is independently halo, oxo, alkyl, haloalkyl, hydroxyalkyl, cycloalkyl, =NOH, —R''OR$^x$ or —R''C(O)R$^x$; each R$^u$ is independently alkylene or a direct bond; each R$^x$ is independently hydrogen or alkyl; and the other variables are as described elsewhere herein. In certain embodiments, provided herein are compounds Formula IV wherein each Q$^1$ is independently halo, oxo, alkyl, haloalkyl, hydroxyalkyl, cycloalkyl, =NOH, —R''OR$^x$ or —R''C(O)R$^x$; each R$^u$ is independently alkylene or a direct bond; each R$^x$ is independently hydrogen or alkyl; R$^{11b}$ and R$^{13}$ are each independently hydrogen, halo or alkyl and the other variables are as described elsewhere herein. In certain embodiments, provided herein are compounds of Formula IV wherein R$^4$ is cycloalkyl.

In certain embodiments, provided herein are compounds of Formula IV wherein R$^{9b}$ and R$^{11b}$ are each independently hydrogen, halo or alkyl and the other variables are as described elsewhere herein. In certain embodiments, provided herein are compounds Formula IV wherein each Q$^1$ is independently halo, oxo, alkyl, haloalkyl, hydroxyalkyl, cycloalkyl, =NOH, —R''OR$^x$ or —R''C(O)R$^x$; each R$^u$ is independently alkylene or a direct bond; each R$^x$ is independently hydrogen or alkyl; and the other variables are as described elsewhere herein. In certain embodiments, provided herein are compounds Formula IV wherein each Q$^1$ is independently halo, oxo, alkyl, haloalkyl, hydroxyalkyl, cycloalkyl, =NOH, —R''OR$^x$ or —R''C(O)R$^x$; each R$^u$ is independently alkylene or a direct bond; each R$^x$ is independently hydrogen or alkyl; R$^{11b}$ and R$^{13}$ are each independently hydrogen, halo or alkyl and the other variables are as described elsewhere herein.

In certain embodiments, provided herein are compounds of Formula IV or pharmaceutically acceptable salts, solvates, hydrates, clathrates, single stereoisomers, mixture of stereoisomers or racemic mixture of stereoisomers thereof, wherein:

R$^1$ and R$^2$ are each independently selected from hydrogen or halogen;

R$^3$ is hydrogen or alkyl;

R$^4$ is cycloalkyl, cycloalkenyl, aryl, heterocyclyl or heteroaryl, where R$^4$ is optionally substituted with one or more, in one embodiment, one to three, in another embodiment, one, two or three groups selected from Q$^1$;

each Q$^1$ is independently halo, oxo, alkyl, haloalkyl, hydroxyalkyl, cycloalkyl, =NOH, —R''OR$^x$ or —R''C(O)R$^x$;

Y is —(CR$^5$R$^6$)$_q$—;

R$^5$ and R$^6$ are each independently hydrogen, halo, alkyl, haloalkyl or hydroxyalkyl;

Z is O, S, or NH;

each W is independently CR$^8$ or N;

R$^8$ is hydrogen, halo, haloalkyl or alkyl;

W$^1$ is N or C;

W$^2$ is N or CR$^{9b}$;

R$^{9b}$ is hydrogen or alkyl;

W$^4$ is N or CR$^{11b}$;

R$^{11b}$ is hydrogen, halo or alkyl;

W$^5$ is N or CR$^{13}$;

R$^{13}$ is hydrogen, halo or alkyl;

Q$^5$ and Q$^6$ are each independently hydrogen, deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''C(J)N(R$^y$)OR$^x$, —R''S(O)$_t$R$^w$, —R''N(R$^x$)C(J)R$^x$, —R''N(R$^x$)C(J)OR$^x$, —R''N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^8$ groups; each Q$^8$ is independently selected from halo, deuterium, hydroxyl, alkyl, haloalkyl and hydroxyalkyl;

each R$^u$ is independently alkylene or a direct bond;

R$^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2; and q is an integer from 0-4.

In certain embodiments, provided herein are compounds of Formula IV or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen or halogen;

$R^3$ is hydrogen or alkyl;

$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —R"OR$^x$ or —R"C(O)R$^x$;

Y is —(CR$^5$R$^6$)$_q$—;

$R^5$ and $R^6$ are each independently hydrogen, halo, alkyl, haloalkyl or hydroxyalkyl;

Z is O, S, or NH;

each W is independently CR$^8$ or N;

$R^8$ is hydrogen, halo, haloalkyl or alkyl;

$W^1$ is N or C;

$W^2$ is N or CR$^{9b}$;

$R^{9b}$ is hydrogen or alkyl;

$W^4$ is N or CR$^{11b}$;

$R^{11b}$ is hydrogen or $Q^2$;

$Q^2$ is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more groups $Q^4$; in one embodiment, one to three $Q^4$ groups, each $Q^4$ is independently selected from halo, deuterium, hydroxyl, alkyl, haloalkyl and hydroxyalkyl;

$W^5$ is N or CR$^{13}$;

$R^{13}$ is hydrogen, halo or alkyl;

$Q^5$ and $Q^6$ are each independently hydrogen, deuterium, halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

each R" is independently alkylene, alkenylene or a direct bond;

$R^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2; and q is an integer from 0-4.

In certain embodiments, provided herein are compounds of Formula IV or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen or halogen;

$R^3$ is hydrogen or alkyl;

$R^4$ is cycloalkyl, cycloalkenyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —R"OR$^x$ or —R"C(O)R$^x$;

Y is —(CR$^5$R$^6$)$_q$—;

$R^5$ and $R^6$ are each independently hydrogen, halo, alkyl, haloalkyl or hydroxyalkyl;

Z is O, S, or NH;

each W is independently CR$^8$ or N;

$R^8$ is hydrogen, halo, haloalkyl or alkyl;

$W^1$ is N or C;

$W^2$ is N or CR$^{9b}$;

$R^{9b}$ is hydrogen or alkyl;

$W^4$ is N or CR$^{11b}$;

$R^{11b}$ is hydrogen, halo or alkyl;

$W^5$ is N or CR$^{13}$;

$R^{13}$ is hydrogen, halo or alkyl;

$Q^5$ and $Q^6$ are each independently hydrogen, deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R" C(J)R$^x$, —R"C(J)OR$^x$, —R"C(J)N(R$^y$)(R$^z$), —R"C(J) R"N(R$^y$)(R$^z$), —R"C(J)N(R$^y$)OR$^x$, —C(=NOR$^x$) R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

each R" is independently alkylene, alkenylene or a direct bond;

$R^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2; and q is an integer from 0-4.

In certain embodiments, provided herein are compounds of Formula IV wherein $R^1$ and $R^2$ are both hydrogen and the other variables are as described elsewhere herein.

In certain embodiments, provided herein are compounds of Formula IV wherein $R^{11b}$ and $R^{13}$ are each independently hydrogen, halo or alkyl and the other variables are as described elsewhere herein.

In certain embodiments, provided herein are compounds of Formula V

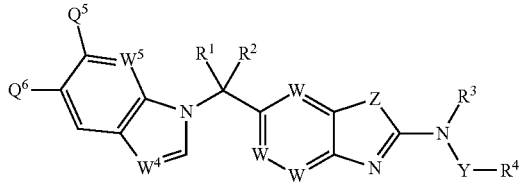

V or pharmaceutically acceptable salts, solvates, hydrates, clathrates, single stereoisomers, mixture of stereoisomers or racemic mixture of stereoisomers thereof, wherein the variables are as described elsewhere herein.

In certain embodiments, provided herein are compounds of Formula V or pharmaceutically acceptable salts, solvates, hydrates, clathrates, single stereoisomers, mixture of stereoisomers or racemic mixture of stereoisomers thereof, wherein $R^1$ and $R^2$ are each independently selected from hydrogen or halogen;

$R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"S(O)$_t$R$^w$, —R"N(R$^x$)C(J)R$^x$, —R"N(R$^x$)C(J)OR$^x$, —R"N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is —(CR$^5$R$^6$)$_q$—;

$R^5$ and $R^6$ are each independently hydrogen, halo, alkyl, haloalkyl or hydroxyalkyl;

Z is O, S, or NH;

each W is independently CR$^8$ or N;

$R^8$ is hydrogen, halo, haloalkyl or alkyl;

$W^4$ is N or CR$^{11b}$;

$W^5$ is N or CR$^{13}$;

$R^{11b}$ and $R^{13}$ are each independently hydrogen or $Q^2$;

$Q^2$ is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more groups $Q^4$; in one embodiment, one to three $Q^4$ groups, each $Q^4$ is independently selected from halo, deuterium, hydroxyl, alkyl, haloalkyl and hydroxyalkyl;

$Q^5$ and $Q^6$ are each independently hydrogen, deuterium, halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

each $R^d$ is independently hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

$R^y$ and $R^z$ are each independently hydrogen or alkyl;

J is O, NR$^x$ or S;

each t is independently an integer from 0-2; and q is an integer from 0-4.

In certain embodiments, provided herein are compounds of Formula V or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen or halogen;

$R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —R"OR$^x$ or —R"C(O)R$^x$;

Y is —(CR$^5$R$^6$)$_q$—;

$R^5$ and $R^6$ are each independently hydrogen, halo, alkyl, haloalkyl or hydroxyalkyl;

Z is O, S, or NH;

each W is independently CR$^8$ or N;

R$^8$ is hydrogen, halo, haloalkyl or alkyl;

W$^4$ is N or CR$^{11b}$;

R$^{11b}$ is hydrogen, halo or alkyl;

W$^5$ is N or CR$^{13}$;

R$^{13}$ is hydrogen, halo or alkyl;

Q$^5$ and Q$^6$ are each independently hydrogen, deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$^u$OR$^x$, —R$^u$OR$^u$N(R$^y$)(R$^z$), —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$C(J)N(R$^y$)OR$^x$, —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^8$ groups; each Q$^8$ is independently selected from halo, deuterium, hydroxyl, alkyl, haloalkyl and hydroxyalkyl;

each R$^u$ is independently alkylene or a direct bond;

R$^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2; and q is an integer from 0-4.

In certain embodiments, provided herein are compounds of Formula V wherein W$^4$ is N and the other variables are as described elsewhere herein.

In certain embodiments, provided herein are compounds of Formula V wherein W$^4$ is N; W$^5$ is N; Q$^5$ and Q$^6$ are each independently hydrogen, halo, or alkoxy; R$^4$ is cycloalkyl, optionally substituted with one or two groups selected from Q$^1$; each Q$^1$ is independently halo, oxo, alkyl, haloalkyl, hydroxyalkyl, cycloalkyl, =NOH, —R$^u$OR$^x$ or —R$^u$C(O)R$^x$; and the other variables are as described elsewhere herein.

In certain embodiments, provided herein are compounds of Formula V wherein W$^4$ is N; W$^5$ is CR$^{11b}$; R$^{11b}$ is hydrogen; Q$^5$ and Q$^6$ are each independently hydrogen, halo, or alkoxy; R$^4$ is cycloalkyl, optionally substituted with one or two groups selected from Q$^1$; each Q$^1$ is independently halo, oxo, alkyl, haloalkyl, hydroxyalkyl, cycloalkyl, =NOH, —R$^u$OR$^x$ or —R$^u$C(O)R$^x$; and the other variables are as described elsewhere herein.

In certain embodiments, provided herein are compound of Formula V wherein Q$^1$ is independently halo, oxo, alkyl, haloalkyl, hydroxyalkyl, cycloalkyl, =NOH, —R$^u$OR$^x$ or —R$^u$C(O)R$^x$; each R$^u$ is independently alkylene or a direct bond; each R$^x$ is independently hydrogen or alkyl; and the other variables are as described elsewhere herein.

In certain embodiments, provided herein are compounds of Formula V wherein W$^4$ is N; W$^5$ is CH or N; Q$^5$ and Q$^6$ are each independently hydrogen, halo, or alkoxy; R$^4$ is cyclohexyl, optionally substituted with one or two hydroxy; and the other variables are as described elsewhere herein.

In certain embodiments, provided herein are compounds of Formula V wherein W is C; Z is S; W$^4$ is N; W$^5$ is CH or N; Q$^5$ and Q$^6$ are each independently hydrogen, halo, alkyl, or alkoxy; R$^3$ is hydrogen or alkyl; Y is —(CR$^5$R$^6$)$_q$—; q is 0; and R$^4$ is cycloalkyl, optionally substituted with one or two hydroxy.

In certain embodiments, provided herein are compounds of Formula V wherein W is C; Z is S; W$^4$ is N; W$^5$ is CH or N; Q$^5$ and Q$^6$ are each independently hydrogen, halo, alkyl, or alkoxy; R$^3$ is hydrogen or alkyl; Y is —(CR$^5$R$^6$)$_q$—; q is 0; and R$^4$ is cyclohexyl, optionally substituted with one or two hydroxy.

In certain embodiments, provided herein are compounds of Formula V or pharmaceutically acceptable salts, solvates, hydrates, clathrates, single stereoisomers, mixture of stereoisomers or racemic mixture of stereoisomers thereof, wherein:

R$^1$ and R$^2$ are each independently selected from hydrogen or halogen;

R$^3$ is hydrogen or alkyl;

R$^4$ is cycloalkyl, aryl, heterocyclyl or heteroaryl, where R$^4$ is optionally substituted with one or more, in one embodiment, one to three, in another embodiment, one, two or three groups selected from Q$^1$;

each Q$^1$ is independently halo, oxo, alkyl, haloalkyl, hydroxyalkyl, cycloalkyl, =NOH, —R$^u$OR$^x$ or —R$^u$C(O)R$^x$;

Y is —(CR$^5$R$^6$)$_q$—;

R$^5$ and R$^6$ are each independently hydrogen, halo, alkyl, haloalkyl or hydroxyalkyl;

Z is O, S, or NH;

each W is independently CR$^8$ or N;

R$^8$ is hydrogen, halo, haloalkyl or alkyl;

W$^4$ is N or CR$^{11b}$;

R$^{11b}$ is hydrogen, halo or alkyl;

W$^5$ is N or CR$^{13}$;

R$^{13}$ is hydrogen, halo or alkyl;

Q$^5$ and Q$^6$ are each independently hydrogen, deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$^u$OR$^x$, —R$^u$OR$^u$N(R$^y$)(R$^z$), —R$^u$OR$^u$OR$^x$, —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$C(J)R$^u$N(R$^y$)(R$^z$), —R$^u$C(J)N(R$^y$)OR$^x$, —C(=NOR$^x$) R$^x$, —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^8$ groups; each Q$^8$ is independently selected from halo, deuterium, hydroxyl, alkyl, haloalkyl and hydroxyalkyl;

each R$^u$ is independently alkylene, alkenylene or a direct bond;

R$^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2; and q is an integer from 0-4.

In certain embodiments, provided herein are compounds of Formula VI

VI or pharmaceutically acceptable salts, solvates, hydrates, clathrates, single stereoisomers, mixture of stereoisomers or racemic mixture of stereoisomers thereof wherein $R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''S(O)$_t$R$^w$, —R''N(R$^x$)C(J)R$^x$, —R''N(R$^x$)C(J)OR$^x$, —R''N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is —(CR$^5$R$^6$)$_q$—;

$R^5$ and $R^6$ are each independently hydrogen, halo, alkyl, haloalkyl or hydroxyalkyl;

Z is O, S, or NH;

$W^5$ is N or CH;

$W^4$ is N or CR$^{11b}$;

$R^{11b}$ is hydrogen or $Q^2$;

$Q^2$ is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''C(J)R''N(R$^y$)(R$^z$), —R''C(J)N(R$^y$)OR$^x$, —C(=NOR$^x$)R$^x$, —R''S(O)$_t$R$^w$, —R''N(R$^x$)C(J)R$^x$, —R''N(R$^x$)C(J)OR$^x$, —R''N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more groups $Q^4$; in one embodiment, one to three $Q^4$ groups, each $Q^4$ is independently selected from halo, deuterium, hydroxyl, alkyl, haloalkyl and hydroxyalkyl;

$Q^5$ and $Q^6$ are each independently hydrogen, deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''C(J)R''N(R$^y$)(R$^z$), —R''C(J)N(R$^y$)OR$^x$, —C(=NOR$^x$)R$^x$, —R''S(O)$_t$R$^w$, —R''N(R$^x$)C(J)R$^x$, —R''N(R$^x$)C(J)OR$^x$, —R''N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

each $R^d$ is independently hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, NR$^x$ or S;

each t is independently an integer from 0-2; and q is an integer from 0-4.

In certain embodiments, provided herein are compounds of Formula VI wherein $W^4$ is N and the other variables are as described elsewhere herein. In certain embodiments, provided herein are compound of Formula VI wherein $Q^1$ is independently halo, oxo, alkyl, haloalkyl, hydroxyalkyl, cycloalkyl, =NOH, —R''OR$^x$ or —R''C(O)R$^x$; each R'' is independently alkylene or a direct bond; each R$^x$ is independently hydrogen or alkyl; and the other variables are as described elsewhere herein.

In certain embodiments, provided herein are compounds of Formula VI or pharmaceutically acceptable salts, solvates, hydrates, clathrates, single stereoisomers, mixture of stereoisomers or racemic mixture of stereoisomers thereof wherein $R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —R''OR$^x$ or —R''C(O)R$^x$;

Y is —(CR$^5$R$^6$)$_q$—;

$R^5$ and $R^6$ are each independently hydrogen, halo, alkyl, haloalkyl or hydroxyalkyl;

Z is O, S, or NH;

$W^5$ is N or CH;

$W^4$ is N or CR$^{11b}$;

$R^{11b}$ is hydrogen, halo or alkyl;

$Q^5$ and $Q^6$ are each independently hydrogen, deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R''OR$^x$, —R''OR''N(R$^y$)(R$^z$), —R''N(R$^y$)(R$^z$), —R''SR$^x$, —R''C(J)R$^x$, —R''C(J)OR$^x$, —R''C(J)N(R$^y$)(R$^z$), —R''C(J)N(R$^y$)OR$^x$, —R''S(O)$_t$R$^w$, —R''N(R$^x$)C(J)R$^x$, —R''N(R$^x$)C(J)OR$^x$, —R''N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

each R'' is independently alkylene or a direct bond;

$R^w$ is alkyl;

each $R^x$ is independently hydrogen or alkyl;
$R^y$ and $R^z$ are each independently hydrogen or alkyl;
J is O, $NR^x$ or S;
each t is independently an integer from 0-2; and
q is an integer from 0-4.

In certain embodiments, provided herein are compounds of Formula VI or pharmaceutically acceptable salts, solvates, hydrates, clathrates, single stereoisomers, mixture of stereoisomers or racemic mixture of stereoisomers thereof wherein
$R^3$ is hydrogen or alkyl;
$R^4$ is cycloalkyl, aryl, heterocyclyl or heteroaryl, where $R^4$ is optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, —$R^uOR^x$ or —$R^uC(O)R^x$;
Y is —$(CR^5R^6)_q$—;
$R^5$ and $R^6$ are each independently hydrogen, halo, alkyl, haloalkyl or hydroxyalkyl;
Z is O, S, or NH;
$W^5$ is N or CH;
$W^4$ is N or $CR^{11b}$;
$R^{11b}$ is hydrogen, halo or alkyl;
$Q^5$ and $Q^6$ are each independently hydrogen, deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uN(R^y)(R^z)$, —$R^uOR^uOR^x$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)R^uN(R^y)(R^z)$, —$R^uC(J)N(R^y)OR^x$, —$R^uS(O)_tR^w$, —$R^uN(R^x)C(J)R^x$, —$R^uN(R^x)C(J)OR^x$, —$C(=NOR^x)R^x$, —$R^uN(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;
each $R^u$ is independently alkylene, alkenylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2;
q is an integer from 0-4.

In certain embodiments, provided herein are compounds of Formula VI or pharmaceutically acceptable salts, solvates, hydrates, clathrates, single stereoisomers, mixture of stereoisomers or racemic mixture of stereoisomers thereof wherein
$R^3$ is hydrogen or alkyl;
$R^4$ is cycloalkyl, aryl, heterocyclyl or heteroaryl, where $R^4$ is optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, —$R^uOR^x$ or —$R^uC(O)R^x$;
Y is —$(CR^5R^6)_q$—;
$R^5$ and $R^6$ are each independently hydrogen, halo, alkyl, haloalkyl or hydroxyalkyl;
Z is O, S, or NH;
$W^5$ is N or CH;
$W^4$ is N or $CR^{11b}$;
$R^{11b}$ is hydrogen, halo or alkyl;
$Q^5$ and $Q^6$ are each independently hydrogen, deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uS(O)_tR^w$, —$R^uN(R^x)C(J)R^x$, —$R^uN(R^x)C(J)OR^x$, —$R^uN(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;
each $R^u$ is independently alkylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2; and
q is an integer from 0-4.

In certain embodiments, provided herein are compounds of Formula VI or pharmaceutically acceptable salts, solvates, hydrates, clathrates, single stereoisomers, mixture of stereoisomers or racemic mixture of stereoisomers thereof wherein
$R^3$ is hydrogen or alkyl;
$R^4$ is cycloalkyl, aryl, heterocyclyl or heteroaryl, where $R^4$ is optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, —$R^uOR^x$ or —$R^uC(O)R^x$;
Y is —$(CR^5R^6)_q$—;
$R^5$ and $R^6$ are each independently hydrogen, halo, alkyl, haloalkyl or hydroxyalkyl;
Z is O, S, or NH;
$W^5$ is N or CH;
$W^4$ is N or $CR^{11b}$;
$R^{11b}$ is hydrogen, halo or alkyl;
$Q^5$ and $Q^6$ are each independently hydrogen, deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uN(R^y)(R^z)$, —$R^uOR^uOR^x$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)R^uN(R^y)(R^z)$, —$R^uC(J)N(R^y)OR^x$, —$R^uS(O)_tR^w$, —$R^uN(R^x)C(J)R^x$, —$R^uN(R^x)C(J)OR^x$, —$C(=NOR^x)R^x$, —$R^uN(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;
each $R^u$ is independently alkylene, alkenylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2;
q is an integer from 0-4.

In certain embodiments, provided herein are compounds of Formulae IV, V or VI wherein $W^4$ is N, $W^5$ is N or $CR^{13}$;

$R^{13}$ is hydrogen, halo or alkyl; and the other variables are as described elsewhere herein. In certain embodiments, provided herein are compounds of Formulae IV, V or VI wherein $W^4$ is N; $W^5$ is N or CH and the other variables are as described elsewhere herein.

In certain embodiments, provided herein are compounds of Formulae IV, V or VI, wherein $Q^5$ and $Q^6$ are each independently hydrogen, deuterium, halo, cyano, alkyl, haloalkyl, aminoalkyl, alkenyl, alkynyl, cycloalkyl, heteroaryl, heteroaralkyl, heterocyclyl, heterocyclylalkyl, —R$''$OR$^x$, —R$''$N(R$^y$)(R$^z$), —R$''$SR$^x$, —R$''$C(J)R$^x$, —R$''$C(J)OR$^x$, —R$''$C(J)N(R$^y$)(R$^z$), —R$''$C(J)N(R$^y$)OR$^x$, —R$''$S(O)$_t$R$^w$, —R$''$N(R$^x$)C(J)R$^x$, —R$''$N(R$^x$)C(J)OR$^x$, —R$''$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^8$ groups; each Q$^8$ is independently selected from halo, deuterium, hydroxyl, alkyl, haloalkyl and hydroxyalkyl;

each R$''$ is independently alkylene or a direct bond;
R$^w$ is alkyl;
each R$^x$ is independently hydrogen or alkyl;
R$^y$ and R$^z$ are each independently hydrogen or alkyl;
J is O, NR$^x$ or S;
each t is independently an integer from 0-2;
n is 1 or 2; and
q is an integer from 0-4, and the other variables are as described elsewhere herein.

In certain embodiments, $Q^5$ and $Q^6$ are each independently hydrogen, deuterium, chloro, fluoro, bromo, cyano, alkyl, alkenyl, alkynyl, cycloalkyl, methoxy or alkylcarbonyl, and the other variables are as described elsewhere herein. In certain embodiments, provided herein are compounds of Formula IV, V or VI, wherein $Q^5$ and $Q^6$ are each independently hydrogen, deuterium, halo, cyano, cycloalkyl, alkoxy, tetrazole or pyrazole, where the tetrazole and pyrazole rings are optionally substituted with one or more alkyl, and the other variables are as described elsewhere herein. In certain embodiments, provided herein are compounds of Formula IV, V or VI, wherein $Q^5$ and $Q^6$ are each independently hydrogen, deuterium, halo, alkoxy, tetrazole or pyrazole, where the tetrazole and pyrazole rings are optionally substituted with one or more alkyl, and the other variables are as described elsewhere herein. In certain embodiments, $Q^5$ and $Q^6$ are each independently hydrogen, deuterium, chloro, fluoro, bromo, cyano, alkyl, alkenyl, alkynyl, cycloalkyl, methoxy or alkylcarbonyl, and the other variables are as described elsewhere herein. In certain embodiments, $Q^5$ and $Q^6$ are each independently hydrogen, deuterium, chloro, fluoro, bromo, cyano, alkyl, alkenyl, alkynyl, cycloalkyl or methoxy, and the other variables are as described elsewhere herein. In certain embodiments, $Q^5$ and $Q^6$ are each independently hydrogen, deuterium, chloro, fluoro, bromo, cyano, cycloalkyl or methoxy, and the other variables are as described elsewhere herein. In certain embodiments, $Q^5$ and $Q^6$ are each independently hydrogen, deuterium, chloro, fluoro, bromo or methoxy, and the other variables are as described elsewhere herein.

In certain embodiments, provided herein are compounds of Formula IV, V or VI, wherein
$R^3$ is hydrogen;
$R^4$ is cyclohexyl, tetrahydrofuryl, pyridinyl, phenyl, morpholinyl, cyclopentyl, piperidinyl, tetrahydro-2H-pyranyl or 2,3-dihydro-1H-indenyl, where $R^4$ is optionally substituted with one or more, in one embodiment, one to three, in another embodiment, one, two or three groups selected from Q$^1$; each Q$^1$ is independently halo, oxo, alkyl, haloalkyl, hydroxyalkyl, cycloalkyl, =NOH, —R$''$OR$^x$ or —R$''$C(O)R$^x$;

each R$''$ is independently alkylene or a direct bond;
each R$^x$ is independently hydrogen or alkyl;
$Q^5$ and $Q^6$ are each independently hydrogen, deuterium, halo, cyano, alkyl, haloalkyl, aminoalkyl, alkenyl, alkynyl, cycloalkyl, heteroaryl, heteroaralkyl, heterocyclyl, heterocyclylalkyl, —R$''$OR$^x$, —R$''$N(R$^y$)(R$^z$), —R$''$SR$^x$, —R$''$C(J)R$^x$, —R$''$C(J)OR$^x$, —R$''$C(J)N(R$^y$)(R$^z$), —R$''$S(O)$_t$R$^w$, —R$''$N(R$^x$)C(J)R$^x$, —R$''$N(R$^x$)C(J)OR$^x$, —R$''$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^8$ groups; each Q$^8$ is independently selected from halo, deuterium, hydroxyl, alkyl, haloalkyl and hydroxyalkyl;

each R$''$ is independently alkylene or a direct bond;
R$^w$ is alkyl;
each R$^x$ is independently hydrogen or alkyl;
R$^y$ and R$^z$ are each independently hydrogen or alkyl;
J is O, NR$^x$ or S;
each t is independently an integer from 0-2;
n is 1 or 2; and
q is an integer from 0-4, and the other variables are as described elsewhere herein.

In certain embodiments, provided herein are compounds of Formula VIIa

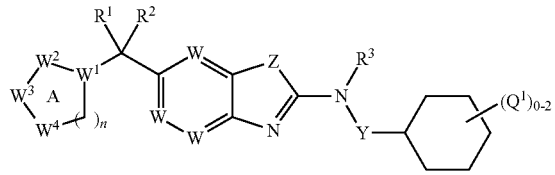

or pharmaceutically acceptable salts, solvates, hydrates, clathrates, single stereoisomers, mixture of stereoisomers or racemic mixture of stereoisomers thereof, wherein:
$R^1$ and $R^2$ are each independently selected from hydrogen or halogen;
$R^3$ is hydrogen or alkyl;
each Q$^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$''$OR$^x$, —R$''$OR$''$N(R$^y$)(R$^z$), —R$''$N(R$^y$)(R$^z$), —R$''$SR$^x$, —R$''$C(J)R$^x$, —R$''$C(J)OR$^x$, —R$''$C(J)N(R$^y$)(R$^z$), —R$''$S(O)$_t$R$^w$, —R$''$N(R$^x$)C(J)R$^x$, —R$''$N(R$^x$)C(J)OR$^x$, —R$''$N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^3$ groups, in one embodiment, one to three Q$^3$ groups; each Q$^3$ is independently selected from deuterium, halo, hydroxyl, alkyl, haloalkyl and hydroxyalkyl;
Y is —(CR$^5$R$^6$)$_q$—;
$R^5$ and $R^6$ are each independently hydrogen, halo, alkyl, haloalkyl or hydroxyalkyl;
Z is O, S, or NH;
each W is independently CR$^8$ or N;
$R^8$ is hydrogen, halo, haloalkyl or alkyl;

ring A is aryl or heteroaryl, optionally substituted with one to four substituents selected from $Q^2$;
$W^1$ is N or C;
$W^2$ is N, $NR^{9a}$ or $CR^{9b}$;
$W^3$ is N, $NR^{10a}$ or $CR^{10b}$;
$W^4$ is N, $NR^{11a}$ or $CR^{11b}$;
$R^{9a}$, $R^{9b}$, $R^{10a}$, $R^{10b}$, $R^{11a}$ and $R^{11b}$ are selected as follows:
  i) $R^{9a}$, $R^{10a}$ and $R^{11a}$ are each independently hydrogen or alkyl and $R^{9b}$, $R^{10b}$ and $R^{11b}$ are each independently hydrogen or $Q^2$; or
  ii) $R^{9a}$ and $R^{10b}$, $R^{9b}$ and $R^{10b}$, $R^{9b}$ and $R^{10a}$, $R^{10b}$ and $R^{11a}$, $R^{10a}$ and $R^{11b}$ or $R^{10b}$ and $R^{11b}$, together with the atoms to which they are attached form an aryl, heteroaryl or heterocyclyl ring, wherein the aryl, heteroaryl or heterocyclyl ring is optionally substituted with one or more, in one embodiment, one to three, in another embodiment, one, two or three groups selected from $Q^2$; and the remainder of $R^{9a}$ or $R^{11a}$ is hydrogen or alkyl and the remainder of $R^{9b}$ or $R^{11b}$ is hydrogen or $Q^2$;
each $Q^2$ is independently halo, deuterium, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $-R^uOR^x$, $-R^uOR^uOR^x$, $-R^uO-R^uN(R^y)(R^z)$, $-R^uN(R^y)(R^z)$, $-R^uSR^x$, $-R^uC(J)R^x$, $-R^uC(J)OR^x$, $-{}^uC(J)N(R^y)(R^z)$, $-R^uC(J)R^uN(R^y)(R^z)$, $-R^uC(J)N(R^y)OR^x$, $-C(=NOR^x)R^x$, $-R^uS(O)_tR^w$, $-R^uN(R^x)C(J)R^x$, $-R^uN(R^x)C(J)OR^x$, $-R^uN(R^x)S(O)_tR^w$ or $-C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;
  each $R^d$ is independently hydrogen or alkyl;
  each $R^u$ is independently alkylene or a direct bond;
  $R^w$ is alkyl;
  each $R^x$ is independently hydrogen or alkyl;
  $R^y$ and $R^z$ are each independently hydrogen or alkyl;
  J is O, $NR^x$ or S;
  each t is independently an integer from 0-2;
  n is 1 or 2; and
  q is an integer from 0-4.

In certain embodiments, provided herein are compounds of Formula VIIa wherein each $Q^1$ is independently halo, oxo, alkyl, haloalkyl, hydroxyalkyl, cycloalkyl, $=$NOH, $-R^uOR^x$ or $-R^uC(O)R^x$; each $R^u$ is independently alkylene or a direct bond; each $R^x$ is independently hydrogen or alkyl; and the other variables are as described elsewhere herein.

In certain embodiments, provided herein are compounds of Formula VIIa or pharmaceutically acceptable salts, solvates, hydrates, clathrates, single stereoisomers, mixture of stereoisomers or racemic mixture of stereoisomers thereof, wherein:
  $R^1$ and $R^2$ are each independently selected from hydrogen or halogen;
  $R^3$ is hydrogen or alkyl;
  each $Q^1$ is independently halo, oxo, alkyl, haloalkyl, hydroxyalkyl, cycloalkyl, $=$NOH, $-R^uOR^x$ or $-R^uC(O)R^x$;
  Y is $-(CR^5R^6)_q-$;
  $R^5$ and $R^6$ are each independently hydrogen, halo, alkyl, haloalkyl or hydroxyalkyl;
  Z is O, S, or NH;
  each W is independently $CR^8$ or N;
  $R^8$ is hydrogen, halo, haloalkyl or alkyl;
  ring A is aryl or heteroaryl, optionally substituted with one to four substituents selected from $Q^2$;
  $W^1$ is N or C;
  $W^2$ is N, $NR^{9a}$ or $CR^{9b}$;
  $W^3$ is N, $NR^{10a}$ or $CR^{10b}$;
  $W^4$ is N, $NR^{11a}$ or $CR^{11b}$;
  $R^{9a}$, $R^{9b}$, $R^{10a}$, $R^{10b}$, $R^{11a}$ and $R^{11b}$ are selected as follows:
    i) $R^{9a}$, $R^{10a}$ and $R^{11a}$ are each independently hydrogen or alkyl and $R^{9b}$, $R^{10b}$ and $R^{11b}$ are each independently hydrogen, oxo, hydroxyl, halo or alkyl; or
    ii) $R^{9a}$ and $R^{10b}$, $R^{9b}$ and $R^{10b}$, $R^{9b}$ and $R^{10a}$, $R^{10b}$ and $R^{11a}$, $R^{10a}$ and $R^{11b}$ or $R^{10b}$ and $R^{11b}$, together with the atoms to which they are attached form an aryl, heteroaryl or heterocyclyl ring, wherein the aryl, heteroaryl or heterocyclyl ring is optionally substituted with one or more, in one embodiment, one to three, in another embodiment, one, two or three groups selected from $Q^2$; and the remainder of $R^{9a}$, $R^{10a}$ or $R^{11a}$ is hydrogen or alkyl and the remainder of $R^{9b}$, $R^{10b}$ or $R^{11b}$ is hydrogen, halo or alkyl;
  each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $-R^uOR^x$, $-R^uOR^uN(R^y)(R^z)$, $-R^uN(R^y)(R^z)$, $-R^uSR^x$, $-R^uC(J)R^x$, $-R^uC(J)OR^x$, $-R^uC(J)N(R^y)(R^z)$, $-R^uC(J)N(R^y)OR^x$, $-R^uS(O)_tR^w$, $-R^uN(R^x)C(J)R^x$, $-R^uN(R^x)C(J)OR^x$, $-R^uN(R^x)S(O)_tR^w$ or $-C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;
    each $R^u$ is independently alkylene or a direct bond;
    $R^w$ is alkyl;
    each $R^x$ is independently hydrogen or alkyl;
    $R^y$ and $R^z$ are each independently hydrogen or alkyl;
    J is O, $NR^x$ or S;
    each t is independently an integer from 0-2;
    n is 1 or 2; and
    q is an integer from 0-4.

In certain embodiments, provided herein are compounds of Formula VIIa or pharmaceutically acceptable salts, solvates, hydrates, clathrates, single stereoisomers, mixture of stereoisomers or racemic mixture of stereoisomers thereof, wherein:
  $R^1$ and $R^2$ are each independently selected from hydrogen or halogen;
  $R^3$ is hydrogen or alkyl;
  each $Q^1$ is independently halo, oxo, alkyl, haloalkyl, hydroxyalkyl, cycloalkyl, $=$NOH, $-R^uOR^x$ or $-R^uC(O)R^x$;
  Y is $-(CR^5R^6)_q-$;
  $R^5$ and $R^6$ are each independently hydrogen, halo, alkyl, haloalkyl or hydroxyalkyl;
  Z is O, S, or NH;
  each W is independently $CR^8$ or N;
  $R^8$ is hydrogen, halo, haloalkyl or alkyl;
  ring A is aryl, heteroaryl or heterocyclyl, optionally substituted with one to four substituents selected from $Q^2$;
  $W^1$ is N or C;
  $W^2$ is N, $NR^{9a}$ or $CR^{9b}$;
  $W^3$ is N, $NR^{10a}$ or $CR^{10b}$;
  $W^4$ is N, $NR^{11a}$ or $CR^{11b}$;

$R^{9a}$, $R^{9b}$, $R^{10a}$, $R^{10b}$, $R^{11a}$ and $R^{11b}$ are selected as follows:
  i) $R^{9a}$, $R^{10a}$ and $R^{11a}$ are each independently hydrogen or alkyl and $R^{9b}$, $R^{10b}$ and $R^{11b}$ are each independently hydrogen, oxo, hydroxyl, halo or alkyl; or
  ii) $R^{9a}$ and $R^{10b}$, $R^{9b}$ and $R^{10b}$, $R^{9b}$ and $R^{10a}$, $R^{10b}$ and $R^{11a}$, $R^{10a}$ and $R^{11b}$ or $R^{10b}$ and $R^{11b}$, together with the atoms to which they are attached form an aryl, heteroaryl or heterocyclyl ring, wherein the aryl, heteroaryl or heterocyclyl ring is optionally substituted with one or more, in one embodiment, one to three, in another embodiment, one, two or three groups selected from $Q^2$; and the remainder of $R^{9a}$, $R^{10a}$ or $R^{11a}$ is hydrogen or alkyl and the remainder of $R^{9b}$, $R^{10b}$ or $R^{11b}$ is hydrogen, halo or alkyl; or
  iii) $R^{9a}$ and $R^{10b}$, $R^{9b}$ and $R^{10b}$, $R^{9b}$ and $R^{10a}$, $R^{10b}$ and $R^{11a}$, $R^{10a}$ and $R^{11b}$, or $R^{10b}$ and $R^{11b}$ together with the atoms to which they are attached form an aryl, heteroaryl or heterocyclyl ring optionally fused to a phenyl ring optionally substituted with one or more, in one embodiment, one to three, in another embodiment, one, two or three groups selected from $Q^2$; and the remainder of $R^{9a}$ and $R^{9b}$ or the remainder of $R^{11a}$ and $R^{11b}$ are each independently hydrogen or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each R" is independently alkylene, alkenylene or a direct bond;

R$^w$ is alkyl;

each R$^x$ is independently hydrogen or alkyl;

R$^y$ and R$^z$ are each independently hydrogen or alkyl;

J is O, NR$^x$ or S;

each t is independently an integer from 0-2;

n is 1 or 2; and q is an integer from 0-4;

wherein the compounds are selected such that: i) when W is CH; W$^1$ is C; Z is S; R$^1$ is hydrogen, or hydroxyl and R$^2$ is hydrogen, or R$^1$ and R$^2$ together form =O; then ring A is not pyridine and ii) when W is CH; W$^1$ is N; Z is S; R$^1$ and R$^2$ are hydrogen, then ring A is not pyrrolidine.

In certain embodiments, provided herein are compounds of Formula VIIb

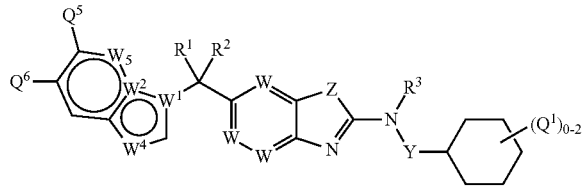

VIIb or pharmaceutically acceptable salts, solvates, hydrates, clathrates, single stereoisomers, mixture of stereoisomers or racemic mixture of stereoisomers thereof, wherein:

$R^1$ and $R^2$ are each independently selected from hydrogen or halogen;

$R^3$ is hydrogen or alkyl;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"S(O)$_t$R$^w$, —R"N(R$^x$)C(J)R$^x$, —R"N(R$^x$)C(J)OR$^x$, —R"N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is —(CR$^5$R$^6$)$_q$—;

$R^5$ and $R^6$ are each independently hydrogen, halo, alkyl, haloalkyl or hydroxyalkyl;

Z is O, S, or NH;

each W is independently CR$^8$ or N;

$R^8$ is hydrogen, halo, haloalkyl or alkyl;

W$^1$ is N or C;

W$^2$ is N or CR$^{9b}$;

$R^{9b}$ is hydrogen or alkyl;

W$^4$ is N or CR$^{11b}$;

W$^5$ is N or CR$^{13}$;

$R^{11b}$ and $R^{13}$ are each independently hydrogen or $Q^2$;

$Q^2$ is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more groups $Q^4$; in one embodiment, one to three $Q^4$ groups, each $Q^4$ is independently selected from halo, deuterium, hydroxyl, alkyl, haloalkyl and hydroxyalkyl;

$Q^5$ and $Q^6$ are each independently hydrogen, deuterium, halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

each R$^d$ is independently hydrogen or alkyl;

each R" is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^x$ or S;

each t is independently an integer from 0-2;

n is 1 or 2; and q is an integer from 0-4.

In certain embodiment, provided herein are compounds of Formula VIIb wherein each $Q^1$ is independently halo, oxo, alkyl, haloalkyl, hydroxyalkyl, cycloalkyl, =NOH, $-R^uOR^x$ or $-R^uC(O)R^x$; each $R^u$ is independently alkylene or a direct bond; each $R^x$ is independently hydrogen or alkyl; and the other variables are as described elsewhere herein.

In certain embodiments, provided herein are compounds of Formula VIIb wherein $R^1$ and $R^2$ are both hydrogen. In certain embodiments, provided herein are compounds of Formula VIIb wherein $Q^5$ and $Q^6$ are each independently hydrogen, deuterium, halo, cyano, alkyl, alkenyl, alkynyl, cycloalkyl, alkoxy or alkylcarbonyl, and the other variables are as described elsewhere herein. In certain embodiments, provided herein are compounds of Formula VIIb, wherein $Q^5$ is hydrogen and $Q^6$ is halo, deuterium, cyano, alkyl, alkenyl, alkynyl, cycloalkyl, alkoxy or alkylcarbonyl. In certain embodiments, provided herein are compounds of Formula VIIb, wherein $Q^5$ is hydrogen and $Q^6$ is halo, alkyl, alkenyl, alkynyl, cycloalkyl, alkoxy or alkylcarbonyl. In certain embodiments, provided herein are compounds of Formula VIIb, wherein $Q^5$ is hydrogen and $Q^6$ is halo, cyano, cycloalkyl, alkoxy or alkylcarbonyl. In certain embodiments, provided herein are compounds of Formula VIIb, wherein $Q^5$ is hydrogen and $Q^6$ is bromo, chloro, fluoro, cyano, cyclopropyl, methoxy or methylcarbonyl.

In certain embodiments, provided herein are compounds of Formula VIII

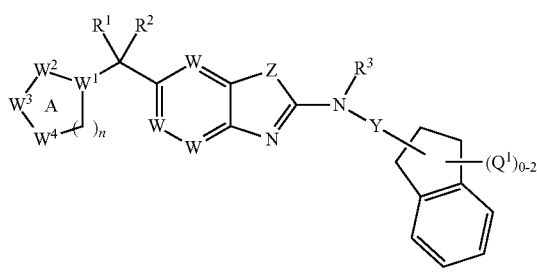

VIII or pharmaceutically acceptable salts, solvates, hydrates, clathrates, single stereoisomers, mixture of stereoisomers or racemic mixture of stereoisomers thereof wherein:

$R^1$ and $R^2$ are each independently selected from hydrogen or halogen;

$R^3$ is hydrogen or alkyl;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $-R^uOR^x$, $-R^uOR^uN(R^y)(R^z)$, $-R^uN(R^y)(R^z)$, $-R^uSR^x$, $-R^uC(J)R^x$, $-R^uC(J)OR^x$, $-R^uC(J)N(R^y)(R^z)$, $-R^uS(O)_tR^w$, $-R^uN(R^x)C(J)R^x$, $-R^uN(R^x)C(J)OR^x$, $-R^uN(R^x)S(O)_tR^w$, =$NOR^d$, or $-C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

Y is $-(CR^5R^6)_q-$;

$R^5$ and $R^6$ are each independently hydrogen, halo, alkyl, haloalkyl or hydroxyalkyl;

Z is O, S, or NH;

each W is independently $CR^8$ or N;

$R^8$ is hydrogen, halo, haloalkyl or alkyl;

ring A is aryl or heteroaryl, optionally substituted with one to four substituents selected from $Q^2$;

$W^1$ is N or C;

$W^2$ is N, $NR^{9a}$ or $CR^{9b}$;

$W^3$ is N, $NR^{10a}$ or $CR^{10b}$;

$W^4$ is N, $NR^{11a}$ or $CR^{11b}$;

$R^{9a}$, $R^{9b}$, $R^{10a}$, $R^{10b}$, $R^{11a}$ and $R^{11b}$ are selected as follows:

i) $R^{9a}$, $R^{10a}$ and $R^{11a}$ are each independently hydrogen or alkyl and $R^{9b}$, $R^{10b}$ and $R^{11b}$ are each independently hydrogen or $Q^2$; or ii) $R^{9a}$ and $R^{10b}$, $R^{9b}$ and $R^{10b}$, $R^{9b}$ and $R^{10a}$, $R^{10b}$ and $R^{11a}$, $R^{10a}$ and $R^{11b}$ or $R^{10b}$ and $R^{11b}$, together with the atoms to which they are attached form an aryl, heteroaryl ring, wherein the aryl, heteroaryl ring is optionally substituted with one or more, in one embodiment, one to three, in another embodiment, one, two or three groups selected from $Q^2$; and the remainder of $R^{9a}$ or $R^{11a}$ is hydrogen or alkyl and the remainder of $R^{9b}$ or $R^{11b}$ is hydrogen or $Q^2$;

each $Q^2$ is independently halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $-R^uOR^x$, $-R^uOR^uOR^x$, $-R^uOR^uN(R^y)(R^z)$, $-R^uN(R^y)(R^z)$, $-R^uSR^x$, $-R^uC(J)R^x$, $-R^uC(J)OR^x$, $-R^uC(J)N(R^y)(R^z)$, $-R^uC(J)R^uN(R^y)(R^z)$, $-R^uC(J)N(R^y)OR^x$, $-C(=NOR^x)R^x$, $-R^uS(O)_tR^w$, $-R^uN(R^x)C(J)R^x$, $-R^uN(R^x)C(J)OR^x$, $-R^uN(R^x)S(O)_tR^w$ or $-C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^d$ is independently hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^x$ or S;
each t is independently an integer from 0-2;
n is 1 or 2; and
q is an integer from 0-4.

In certain embodiments, provided herein are compounds of Formula VIIa, VIIb or VIII, wherein:

$R^1$ and $R^2$ are each hydrogen;
$R^3$ is hydrogen or alkyl;
each $Q^1$ is independently halo, oxo, alkyl, hydroxyl, alkoxy, haloalkyl, hydroxyalkyl, cycloalkyl, =NOH, or $-R^uC(O)R^x$;
Y is $-(CR^5R^6)_q-$;
$R^5$ and $R^6$ are each independently hydrogen, halo, alkyl, haloalkyl or hydroxyalkyl;
Z is O, S, or NH;
each W is CH;
ring A is aryl or heteroaryl, optionally substituted with one to four substituents selected from $Q^2$;
$W^1$ is N or C;
$W^2$ is N, $NR^{9a}$ or $CR^{9b}$;
$W^3$ is N, $NR^{10a}$ or $CR^{10b}$;
$W^4$ is N, $NR^{11a}$ or $CR^{11b}$;
$R^{9a}$, $R^{9b}$, $R^{10a}$, $R^{10b}$, $R^{11a}$ and $R^{11b}$ are selected as follows:

i) $R^{9a}$, $R^{10a}$ and $R^{11a}$ are each independently hydrogen or alkyl and $R^{9b}$, $R^{10b}$ and $R^{11b}$ are each independently hydrogen, oxo, hydroxyl, halo or alkyl; or ii) $R^{9a}$ and $R^{10b}$, $R^{9b}$ and $R^{10b}$, $R^{9b}$ and $R^{10a}$, $R^{10b}$ and $R^{11a}$, $R^{10a}$ and $R^{11b}$ or $R^{10b}$ and $R^{11b}$, together with the atoms to which they are attached form an aryl, heteroaryl or heterocyclyl ring, wherein the aryl, heteroaryl or heterocyclyl ring is optionally substituted with one or more, in one embodiment, one to three, in another embodiment, one, two or three groups selected from $Q^2$; and the remainder of $R^{9a}$, $R^{10a}$ or $R^{11a}$ is hydrogen or alkyl or the remainder of $R^{9b}$, $R^{10b}$ or $R^{11b}$ is hydrogen, halo or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $-R^uOR^x$, $-R^uOR^uN(R^y)(R^z)$, $-R^uN(R^y)(R^z)$, $-R^uSR^x$, $-R^uC(J)R^x$, $-R^uC(J)OR^x$, $-R^uC(J)N(R^y)(R^z)$, $-R^uS(O)_tR^w$, $-R^uN(R^x)C(J)R^x$, $-R^uN(R^x)C(J)OR^x$, $-R^uN(R^x)S(O)_tR^w$ or $-C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; each $Q^4$ is independently selected from halo, hydroxyl, alkyl, haloalkyl and hydroxyalkyl;

each $R^u$ is independently alkylene or a direct bond;
$R^w$ is alkyl;
each $R^x$ is independently hydrogen or alkyl;
$R^y$ and $R^z$ are each independently hydrogen or alkyl;
J is O, $NR^x$ or S;
each t is independently an integer from 0-2;
n is 1 or 2; and
q is an integer from 0-4.

In certain embodiments, provided herein are compounds of Formula VIII

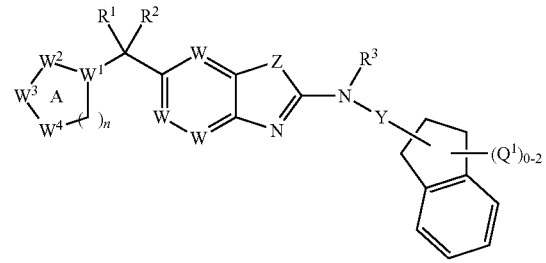

or pharmaceutically acceptable salts, solvates, hydrates, clathrates, single stereoisomers, mixture of stereoisomers or racemic mixture of stereoisomers thereof wherein:

$R^1$ and $R^2$ are each independently selected from hydrogen or halogen;
$R^3$ is hydrogen or alkyl;
each $Q^1$ is independently halo, oxo, alkyl, haloalkyl, hydroxyalkyl, cycloalkyl, =NOH, $-R^uOR^x$ or $-R^uC(O)R^x$;
Y is $-(CR^5R^6)_q-$;
$R^5$ and $R^6$ are each independently hydrogen, halo, alkyl, haloalkyl or hydroxyalkyl;
Z is O, S, or NH;
each W is independently $CR^8$ or N;
$R^8$ is hydrogen, halo, haloalkyl or alkyl;
ring A is aryl or heteroaryl, optionally substituted with one to four substituents selected from $Q^2$;
$W^1$ is N or C;
$W^2$ is N, $NR^{9a}$ or $CR^{9b}$;
$W^3$ is N, $NR^{10a}$ or $CR^{10b}$;
$W^4$ is N, $NR^{11a}$ or $CR^{11b}$;
$R^{9a}$, $R^{9b}$, $R^{10a}$, $R^{10b}$, $R^{11a}$ and $R^{11b}$ are selected as follows:

i) $R^{9a}$, $R^{10a}$ and $R^{11a}$ are each independently hydrogen or alkyl and $R^{9b}$, $R^{10b}$ and $R^{11b}$ are each independently hydrogen, oxo, hydroxyl, halo or alkyl; or ii) $R^{9a}$ and $R^{10b}$, $R^{9b}$ and $R^{10b}$, $R^{9b}$ and $R^{10a}$, $R^{10b}$ and $R^{11a}$, $R^{10a}$ and $R^{11b}$ or $R^{10b}$ and $R^{11b}$, together with the atoms to which they are attached form an aryl, heteroaryl ring, wherein the aryl, heteroaryl ring is optionally substituted with one or more, in one embodiment, one to three, in another embodiment, one, two or three groups selected from $Q^2$; and the remainder of $R^{9a}$, $R^{10a}$ or $R^{11a}$ is hydrogen or alkyl or the remainder of $R^{9b}$, $R^{10b}$ or $R^{11b}$ is hydrogen, halo or alkyl;

each $Q^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^4$ groups; each Q$^4$ is independently selected from halo, hydroxyl, alkyl, haloalkyl and hydroxyalkyl;

each R$^u$ is independently alkylene or a direct bond;
R$^w$ is alkyl;
each R$^x$ is independently hydrogen or alkyl;
R$^y$ and R$^z$ are each independently hydrogen or alkyl;
J is O, NR$^x$ or S;
each t is independently an integer from 0-2;
n is 1 or 2; and
q is an integer from 0-4.

In certain embodiments, provided herein are compounds of Formula VIIa, VIIb or VIII, wherein:
R$^1$ and R$^2$ are each hydrogen;
R$^3$ is hydrogen or alkyl;
each Q$^1$ is independently halo, oxo, alkyl, hydroxyl, alkoxy, haloalkyl, hydroxyalkyl, cycloalkyl, =NOH, or —R"C(O)R$^x$;
Y is —(CR$^5$R$^6$)$_q$—;
R$^5$ and R$^6$ are each independently hydrogen, halo, alkyl, haloalkyl or hydroxyalkyl;
Z is O, S, or NH;
each W is CH;
ring A is aryl or heteroaryl, optionally substituted with one to four substituents selected from Q$^2$;
W$^1$ is N or C;
W$^2$ is N, NR$^{9a}$ or CR$^{9b}$;
W$^3$ is N, NR$^{10a}$ or CR$^{10b}$;
W$^4$ is N, NR$^{11a}$ or CR$^{11b}$;
R$^{9a}$, R$^{9b}$, R$^{10a}$, R$^{10b}$, R$^{11a}$ and R$^{11b}$ are selected as follows:
  i) R$^{9a}$, R$^{10a}$ and R$^{11a}$ are each independently hydrogen or alkyl and R$^{9b}$, R$^{10b}$ and R$^{11b}$ are each independently hydrogen, oxo, hydroxyl, halo or alkyl; or
  ii) R$^{9a}$ and R$^{10b}$, R$^{9b}$ and R$^{10b}$, R$^{9b}$ and R$^{10a}$, R$^{10b}$ and R$^{11a}$, R$^{10a}$ and R$^{11b}$ or R$^{10b}$ and R$^{11b}$, together with the atoms to which they are attached form an aryl, heteroaryl or heterocyclyl ring, wherein the aryl, heteroaryl or heterocyclyl ring is optionally substituted with one or more, in one embodiment, one to three, in another embodiment, one, two or three groups selected from Q$^2$; and the remainder of R$^{9a}$, R$^{10a}$ or R$^{11a}$ is hydrogen or alkyl or the remainder of R$^{9b}$, R$^{10b}$ or R$^{11b}$ is hydrogen, halo or alkyl;

each Q$^2$ is independently halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups optionally substituted with one or more Q$^4$ groups; each Q$^4$ is independently selected from halo, hydroxyl, alkyl, haloalkyl and hydroxyalkyl;
each R$^u$ is independently alkylene or a direct bond;
R$^w$ is alkyl;
each R$^x$ is independently hydrogen or alkyl;

R$^y$ and R$^z$ are each independently hydrogen or alkyl;
J is O, NR$^x$ or S;
each t is independently an integer from 0-2;
n is 1 or 2; and
q is an integer from 0-4.

In certain embodiments, provided herein are compounds of Formula VIII wherein each Q$^1$ is independently halo, oxo, alkyl, haloalkyl, hydroxyalkyl, cycloalkyl, =NOH, —R"OR$^x$ or —R"C(O)R$^x$; each R$^u$ is independently alkylene or a direct bond; each R$^x$ is independently hydrogen or alkyl; and the other variables are as described elsewhere herein.

In certain embodiments, provided herein are compounds of Formula IX

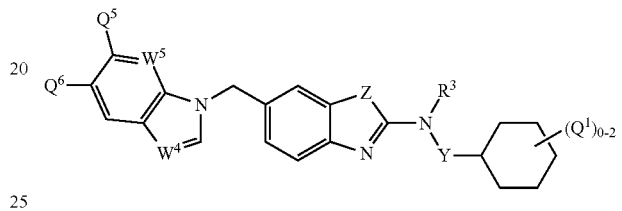

IX or pharmaceutically acceptable salts, solvates, hydrates, clathrates, single stereoisomers, mixture of stereoisomers or racemic mixture of stereoisomers thereof, wherein:
R$^3$ is hydrogen or alkyl;
each Q$^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"S(O)$_t$R$^w$, —R"N(R$^x$)C(J)R$^x$, —R"N(R$^x$)C(J)OR$^x$, —R"N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^3$ groups, in one embodiment, one to three Q$^3$ groups; each Q$^3$ is independently selected from deuterium, halo, hydroxyl, alkyl, haloalkyl and hydroxyalkyl;
Y is —(CR$^5$R$^6$)$_q$—;
R$^5$ and R$^6$ are each independently hydrogen, halo, alkyl, haloalkyl or hydroxyalkyl;
Z is O, S, or NH;
W$^4$ is N or CR$^{11b}$;
W$^5$ is N or CR$^{13}$;
R$^{11b}$ and R$^{13}$ are each independently hydrogen or Q$^2$;
each Q$^2$ is independently halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more groups Q$^4$; in one embodiment, one to three Q$^4$ groups, each Q$^4$ is independently selected from halo, deuterium, hydroxyl, alkyl, haloalkyl and hydroxyalkyl;

$Q^5$ and $Q^6$ are each independently hydrogen, halo, cyano, alkyl, haloalkyl, aminoalkyl, alkenyl, alkynyl, cycloalkyl, heteroaryl, heteroaralkyl, heterocyclyl, heterocyclylalkyl, —R″OR$^x$, —R″N(R$^y$)(R$^z$), —R″SR$^x$, —R″C(J)R$^x$, —R″C(J)OR$^x$, —R″C(J)N(R$^y$)(R$^z$), —R″S(O)$_t$R$^w$, —R″N(R$^x$)C(J)R$^x$, —R″N(R$^x$)C(J)OR$^x$, —R″N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

$R^d$ is hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, NR$^x$ or S;

each t is independently an integer from 0-2;

n is 1 or 2; and q is an integer from 0-4.

In certain embodiments, provided herein are compounds of Formula IX or pharmaceutically acceptable salts, solvates, hydrates, clathrates, single stereoisomers, mixture of stereoisomers or racemic mixture of stereoisomers thereof, wherein:

$R^3$ is hydrogen or alkyl;

each $Q^1$ is independently halo, oxo, alkyl, haloalkyl, hydroxyalkyl, cycloalkyl, =NOH, —R″OR$^x$ or —R″C(O)R$^x$;

Y is —(CR$^5$R$^6$)$_q$—;

$R^5$ and $R^6$ are each independently hydrogen, halo, alkyl, haloalkyl or hydroxyalkyl;

Z is O, S, or NH;

$W^4$ is N or CR$^{11b}$;

$R^{11b}$ is hydrogen, halo or alkyl;

$W^5$ is N or CR$^{13}$;

$R^{13}$ is hydrogen, halo or alkyl;

$Q^5$ and $Q^6$ are each independently hydrogen, halo, cyano, alkyl, haloalkyl, aminoalkyl, alkenyl, alkynyl, cycloalkyl, heteroaryl, heteroaralkyl, heterocyclyl, heterocyclylalkyl, —R″OR$^x$, —R″N(R$^y$)(R$^z$), —R″SR$^x$, —R″C(J)R$^x$, —R″C(J)OR$^x$, —R″C(J)N(R$^y$)(R$^z$), —R″S(O)$_t$R$^w$, —R″N(R$^x$)C(J)R$^x$, —R″N(R$^x$)C(J)OR$^x$, —R″N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

each $R^u$ is independently alkylene or a direct bond;

$R^w$ is alkyl;

each $R^x$ is independently hydrogen or alkyl;

$R^y$ and $R^z$ are each independently hydrogen or alkyl;

J is O, NR$^x$ or S;

each t is independently an integer from 0-2;

n is 1 or 2; and q is an integer from 0-4.

In certain embodiments, provided herein are compounds of Formula IX wherein each $Q^1$ is independently halo, oxo, alkyl, haloalkyl, hydroxyalkyl, cycloalkyl, =NOH, —R″OR$^x$ or —R″C(O)R$^x$; each $R^u$ is independently alkylene or a direct bond; each $R^x$ is independently hydrogen or alkyl; $R^{11b}$ and $R^{13}$ are each independently hydrogen, halo or alkyl; and the other variables are as described elsewhere herein. In certain embodiments, provided herein are compounds of Formula IX, wherein $Q^5$ and $Q^6$ are each independently hydrogen, halo, alkoxy, tetrazole or pyrazole, where the tetrazole and pyrazole rings are optionally substituted with one or more alkyl, and the other variables are as described elsewhere herein. In certain embodiments, $Q^5$ and $Q^6$ are each independently hydrogen, chloro, fluoro, bromo or methoxy, and the other variables are as described elsewhere herein.

In certain embodiments, provided herein are compounds of Formula X

X or pharmaceutically acceptable salts, solvates, hydrates, clathrates, single stereoisomers, mixture of stereoisomers or racemic mixture of stereoisomers thereof, wherein:

$R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R″OR$^x$, —R″OR″N(R$^y$)(R$^z$), —R″N(R$^y$)(R$^z$), —R″SR$^x$, —R″C(J)R$^x$, —R″C(J)OR$^x$, —R″C(J)N(R$^y$)(R$^z$), —R″S(O)$_t$R$^w$, —R″N(R$^x$)C(J)R$^x$, —R″N(R$^x$)C(J)OR$^x$, —R″N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^3$ groups, in one embodiment, one to three $Q^3$ groups; each $Q^3$ is independently selected from deuterium, halo, hydroxyl, alkyl, haloalkyl and hydroxyalkyl;

each $R^d$ is independently hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

Y is —$(CR^5R^6)_q$—;

$R^5$ and $R^6$ are each independently hydrogen, halo, alkyl, haloalkyl or hydroxyalkyl;

Z is O, S, or NH;

$W^4$ is N or $CR^{11b}$;

$R^{11b}$ is hydrogen or $Q^2$;

$Q^2$ is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uOR^x$, —$R^uOR^uN(R^y)$ $(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)R^uN(R^y)(R^z)$, —$R^uC(J)N(R^y)$ $OR^x$, —$C(=NOR^x)R^x$, —$R^uS(O)_tR^w$, —$R^uN(R^x)C(J)R^x$, —$R^uN(R^x)C(J)OR^x$, —$R^uN(R^x)S(O)_tR^w$ or —C=(NR^y)N $(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^4$ groups; in one embodiment, one to three $Q^4$ groups, each $Q^4$ is independently selected from halo, deuterium, hydroxyl, alkyl, haloalkyl and hydroxyalkyl;

$W^5$ is N or $CR^{13}$;

$R^{13}$ is hydrogen, halo or alkyl; and q is an integer from 0-4.

In certain embodiments, provided herein are compounds of Formula X wherein each $Q^1$ is independently halo, oxo, alkyl, haloalkyl, hydroxyalkyl, cycloalkyl, =NOH, —$R^uOR^x$ or —$R^uC(O)R^x$; each $R^u$ is independently alkylene or a direct bond; each $R^x$ is independently hydrogen or alkyl; and the other variables are as described elsewhere herein.

In certain embodiments, provided herein are compounds of Formula X or pharmaceutically acceptable salts, solvates, hydrates, clathrates, single stereoisomers, mixture of stereoisomers or racemic mixture of stereoisomers thereof, wherein:

$R^3$ is hydrogen or alkyl;

$R^4$ is cycloalkyl, aryl, heterocyclyl or heteroaryl, where $R^4$ is optionally substituted with one or more, in one embodiment, one to three, in another embodiment, one, two or three groups selected from $Q^1$;

each $Q^1$ is independently halo, oxo, alkyl, haloalkyl, hydroxyalkyl, cycloalkyl, =NOH, —$R^uOR^x$ or —$R^uC(O)R^x$;

each $R^u$ is independently alkylene or a direct bond;

each $R^x$ is independently hydrogen or alkyl;

Y is —$(CR^5R^6)_q$—;

$R^5$ and $R^6$ are each independently hydrogen, halo, alkyl, haloalkyl or hydroxyalkyl;

Z is O, S, or NH;

$W^4$ is N or $CR^{11b}$;

$R^{11b}$ is hydrogen, halo or alkyl;

$W^5$ is N or $CR^{13}$;

$R^{13}$ is hydrogen, halo or alkyl; and q is an integer from 0-4.

In certain embodiments, provided herein are compounds of Formula XI

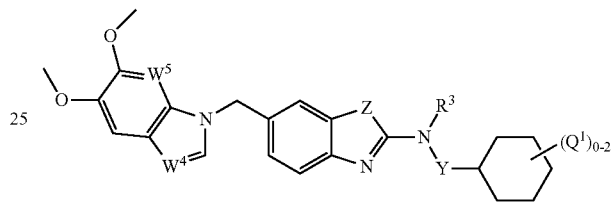

or pharmaceutically acceptable salts, solvates, hydrates, clathrates, single stereoisomers, mixture of stereoisomers or racemic mixture of stereoisomers thereof, wherein:

$R^3$ is hydrogen or alkyl;

each $Q^1$ is independently halo, oxo, alkyl, haloalkyl, hydroxyalkyl, cycloalkyl, =NOH, —$R^uOR^x$ or —$R^uC(O)R^x$;

each $R^u$ is independently alkylene or a direct bond;

each $R^x$ is independently hydrogen or alkyl; Y is —$(CR^5R^6)_q$—;

$R^5$ and $R^6$ are each independently hydrogen, halo, alkyl, haloalkyl or hydroxyalkyl;

Z is O, S, or NH;

$W^4$ is N or $CR^{11b}$;

$R^{11b}$ is hydrogen, halo or alkyl;

$W^5$ is N or $CR^{13}$;

$R^{13}$ is hydrogen, halo or alkyl; and q is an integer from 0-4.

In certain embodiments, provided herein are compounds of Formula XI or pharmaceutically acceptable salts, solvates, hydrates, clathrates, single stereoisomers, mixture of stereoisomers or racemic mixture of stereoisomers thereof, wherein:

$R^3$ is hydrogen or alkyl;

each $Q^1$ is independently halo, oxo, alkyl, haloalkyl, hydroxyalkyl, cycloalkyl, =NOH, —$R^uOR^x$ or —$R^uC(O)R^x$;

Y is —$(CR^5R^6)_q$—;

$R^5$ and $R^6$ are each independently hydrogen, halo, alkyl, haloalkyl or hydroxyalkyl;

Z is O, S, or NH;

$W^4$ is N or $CR^{11b}$;

$R^{11b}$ is hydrogen, halo or alkyl;

$W^5$ is N or $CR^{13}$;

$R^{13}$ is hydrogen, halo or alkyl; and q is an integer from 0-4.

In certain embodiments, provided herein are compounds of Formula XII

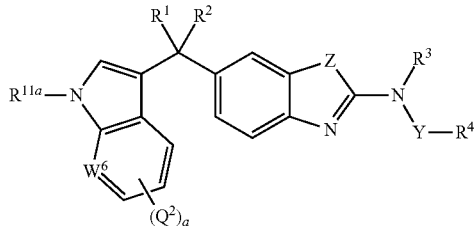

XII or pharmaceutically acceptable salts, solvates, hydrates, clathrates, single stereoisomers, mixture of stereoisomers or racemic mixture of stereoisomers thereof, wherein:
$R^3$ is hydrogen or alkyl;
$R^4$ is cycloalkyl, aryl, heterocyclyl or heteroaryl, where $R^4$ is optionally substituted with one or more, in one embodiment, one to three, in another embodiment, one, two or three groups selected from $Q^1$;
each $Q^1$ is independently halo, oxo, alkyl, haloalkyl, hydroxyalkyl, cycloalkyl, =NOH, $-R^u OR^x$ or $-R^u C(O)R^x$;
each $R^u$ is independently alkylene or a direct bond;
each $R^x$ is independently hydrogen or alkyl;
Y is $-(CR^5R^6)_q-$;
$R^5$ and $R^6$ are each independently hydrogen, halo, alkyl, haloalkyl or hydroxyalkyl;
Z is O, S, or NH;
$R^{11a}$ is hydrogen or alkyl;
$W^6$ is N or $CR^{14}$;
$R^{14}$ is hydrogen or alkyl;
a is 0-4; and
q is an integer from 0-4.

In certain embodiments, provided herein are compounds of Formula XII or pharmaceutically acceptable salts, solvates, hydrates, clathrates, single stereoisomers, mixture of stereoisomers or racemic mixture of stereoisomers thereof, wherein:
$R^3$ is hydrogen or alkyl;
$R^4$ is cycloalkyl, where $R^4$ is optionally substituted with hydroxy;
Y is $-(CR^5R^6)_q-$;
$R^5$ and $R^6$ are each independently hydrogen, halo, alkyl, haloalkyl or hydroxyalkyl;
Z is O, S, or NH;
$R^{11a}$ is hydrogen or alkyl;
$W^6$ is N or $CR^{14}$;
$R^{14}$ is hydrogen or alkyl;
a is 0-2; and
q is an integer from 0-2.

In one embodiment, the compound provided herein is selected from:
2-((6-((1H-benzo[d]imidazol-1-yl)methyl)benzo[d]thiazol-2-yl)amino)cyclohexanol,
(1R,2R)-2-((6-((5,6-dimethoxy-1H-benzo[d]imidazol-1-yl)methyl)benzo[d]thiazol-2-yl)amino)cyclohexanol,
2-((6-((5,6-dimethoxy-1H-benzo[d]imidazol-1-yl)methyl)benzo[d]thiazol-2-yl)amino)cyclohexanol,
(1R,2R)-2-((6-((3H-imidazo[4,5-b]pyridin-3-yl)methyl)benzo[d]thiazol-2-yl)amino)cyclohexanol methanesulfonic acid,
(1R,2R)-2-((6-((3H-imidazo[4,5-b]pyridin-3-yl)methyl)benzo[d]thiazol-2-yl)amino)cyclohexanol
2-((6-((3H-imidazo[4,5-b]pyridin-3-yl)methyl)benzo[d]thiazol-2-yl)amino)cyclohexanol
(1R,2R)-2-((6-((6-methoxy-1H-benzo[d]imidazol-1-yl)methyl)benzo[d]thiazol-2-yl)amino)cyclohexanol,
2-((6-((6-methoxy-1H-benzo[d]imidazol-1-yl)methyl)benzo[d]thiazol-2-yl)amino)cyclohexanol,
(1R,2R)-2-((6-((5-methoxy-1H-benzo[d]imidazol-1-yl)methyl)benzo[d]thiazol-2-yl)amino)cyclohexanol,
2-((6-((5-methoxy-1H-benzo[d]imidazol-1-yl)methyl)benzo[d]thiazol-2-yl)amino)cyclohexanol,
(1R,2R)-2-((6-((1H-imidazo[4,5-b]pyridin-1-yl)methyl)benzo[d]thiazol-2-yl)amino)cyclohexanol,
2-((6-((1H-imidazo[4,5-b]pyridin-1-yl)methyl)benzo[d]thiazol-2-yl)amino)cyclohexanol,
(1R,2R)-2-((6-((1H-benzo[d]imidazol-1-yl)methyl)benzo[d]thiazol-2-yl)amino)cyclohexanol,
2-((6-((1H-imidazo[4,5-b]pyridin-1-yl)methyl)benzo[d]thiazol-2-yl)amino)cyclohexanol,
(1S,2S)-2-((6-((1H-benzo[d]imidazol-1-yl)methyl)benzo[d]thiazol-2-yl)amino)cyclohexanol,
2-((6-((1H-benzo[d]imidazol-1-yl)methyl)benzo[d]thiazol-2-yl)amino)cyclohexanol,
(R)-6-((5,6-dimethoxy-1H-benzo[d]imidazol-1-yl)methyl)-N-((tetrahydrofuran-2-yl)methyl)benzo[d]thiazol-2-amine,
6-((5,6-dimethoxy-1H-benzo[d]imidazol-1-yl)methyl)-N-((tetrahydrofuran-2-yl)methyl)benzo[d]thiazol-2-amine,
6-((5,6-dimethoxy-1H-benzo[d]imidazol-1-yl)methyl)-N-(pyridin-2-ylmethyl)benzo[d]thiazol-2-amine,
(1R,2S)-1-((6-((5,6-dimethoxy-1H-benzo[d]imidazol-1-yl)methyl)benzo[d]thiazol-2-yl)amino)-2,3-dihydro-1H-inden-2-ol,
1-((6-((5,6-dimethoxy-1H-benzo[d]imidazol-1-yl)methyl)benzo[d]thiazol-2-yl)amino)-2,3-dihydro-1H-inden-2-ol,
(S)—N-(2,3-dihydro-1H-inden-1-yl)-6-((5,6-dimethoxy-1H-benzo[d]imidazol-1-yl)methyl)benzo[d]thiazol-2-amine,
N-(2,3-dihydro-1H-inden-1-yl)-6-((5,6-dimethoxy-1H-benzo[d]imidazol-1-yl)methyl)benzo[d]thiazol-2-amine,
(1R,2R)-2-((6-(methoxy(1H-pyrrolo[2,3-b]pyridin-3-yl)methyl)benzo[d]thiazol-2-yl)amino)cyclohexanol,
2-((6-(methoxy(1H-pyrrolo[2,3-b]pyridin-3-yl)methyl)benzo[d]thiazol-2-yl)amino)cyclohexanol,
N-benzyl-6-((5,6-dimethoxy-1H-benzo[d]imidazol-1-yl)methyl)benzo[d]thiazol-2-amine,
6-((5,6-dimethoxy-1H-benzo[d]imidazol-1-yl)methyl)-N-(2-morpholinoethyl)benzo[d]thiazol-2-amine,
6-((5,6-dimethoxy-1H-benzo[d]imidazol-1-yl)methyl)-N-(tetrahydro-2H-pyran-4-yl)benzo[d]thiazol-2-amine,
N-cyclohexyl-6-((5,6-dimethoxy-1H-benzo[d]imidazol-1-yl)methyl)-N-methylbenzo[d]thiazol-2-amine,
(1R,2R)-2-((6-((1H-pyrrolo[2,3-b]pyridin-3-yl)methyl)benzo[d]thiazol-2-yl)amino)cyclohexanol,
2-((6-((1H-pyrrolo[2,3-b]pyridin-3-yl)methyl)benzo[d]thiazol-2-yl)amino)cyclohexanol,
N-cyclohexyl-6-((5,6-dimethoxy-1H-benzo[d]imidazol-1-yl)methyl)benzo[d]thiazol-2-amine,
(1R,2R)-1-((6-((5,6-dimethoxy-1H-benzo[d]imidazol-1-yl)methyl)benzo[d]thiazol-2-yl)amino)-2,3-dihydro-1H-inden-2-ol,
1-((6-((5,6-dimethoxy-1H-benzo[d]imidazol-1-yl)methyl)benzo[d]thiazol-2-yl)amino)-2,3-dihydro-1H-inden-2-ol,
(1R,2R)-2-((6-((5,6-dimethoxy-1H-benzo[d]imidazol-1-yl)methyl)benzo[d]thiazol-2-yl)amino)cyclopentanol,
2-((6-((5,6-dimethoxy-1H-benzo[d]imidazol-1-yl)methyl)benzo[d]thiazol-2-yl)amino)cyclopentanol, 6-((5,6-dimethoxy-1H-benzo[d]imidazol-1-yl)methyl)-N-(pyridin-4-ylmethyl)benzo[d]thiazol-2-amine,
6-((5,6-dimethoxy-1H-benzo[d]imidazol-1-yl)methyl)-N-phenylbenzo[d]thiazol-2-amine,
(1R,2R)-2-((6-((5-methoxy-3H-imidazo[4,5-b]pyridin-3-yl)methyl)benzo[d]thiazol-2-yl)amino)cyclohexanol,
2-((6-((5-methoxy-3H-imidazo[4,5-b]pyridin-3-yl)methyl)benzo[d]thiazol-2-yl)amino)cyclohexanol,
1-(4-((6-((5,6-dimethoxy-1H-benzo[d]imidazol-1-yl)methyl)benzo[d]thiazol-2-yl)amino)piperidin-1-yl)ethanone acetic acid,
1-(4-((6-((5,6-dimethoxy-1H-benzo[d]imidazol-1-yl)methyl)benzo[d]thiazol-2-yl)amino)piperidin-1-yl)ethanone,
(R,S)-6-((5,6-dimethoxy-1H-benzo[d]imidazol-1-yl)methyl)-N-(tetrahydrofuran-3-yl)benzo[d]thiazol-2-amine acetic acid,
(R,S)-6-((5,6-dimethoxy-1H-benzo[d]imidazol-1-yl)methyl)-N-(tetrahydrofuran-3-yl)benzo[d]thiazol-2-amine,
6-((5,6-dimethoxy-1H-benzo[d]imidazol-1-yl)methyl)-N-(tetrahydrofuran-3-yl)benzo[d]thiazol-2-amine,
3-((2-(((1R,2R)-2-hydroxycyclohexyl)amino)benzo[d]thiazol-6-yl)methyl)-3H-imidazo[4,5-b]pyridin-2-aminium acetate,
(1R,2R)-2-((6-((2-amino-3H-imidazo[4,5-b]pyridin-3-yl)methyl)benzo[d]thiazol-2-yl)amino)cyclohexanol,
2-((6-((2-amino-3H-imidazo[4,5-b]pyridin-3-yl)methyl)benzo[d]thiazol-2-yl)amino)cyclohexanol,
6-((5,6-dimethoxy-1H-benzo[d]imidazol-1-yl)methyl)-N-(2-ethoxyphenyl)benzo[d]thiazol-2-amine,
N-(cyclohexylmethyl)-6-((5,6-dimethoxy-1H-benzo[d]imidazol-1-yl)methyl)benzo[d]thiazol-2-amine,
(1R,2R)-2-((6-((6-bromo-3H-imidazo[4,5-b]pyridin-3-yl)methyl)benzo[d]thiazol-2-yl)amino)cyclohexanol,
2-((6-((6-bromo-3H-imidazo[4,5-b]pyridin-3-yl)methyl)benzo[d]thiazol-2-yl)amino)cyclohexanol,
6-((5,6-dimethoxy-1H-benzo[d]imidazol-1-yl)methyl)-N-(2-methoxyphenyl)benzo[d]thiazol-2-amine,
2-((6-((5,6-dimethoxy-1H-benzo[d]imidazol-1-yl)methyl)benzo[d]thiazol-2-yl)amino)phenol,
(1R,2R)-1-((6-((4-(1-methyl-1H-pyrazol-4-yl)-1H-imidazol-1-yl)methyl)benzo[d]thiazol-2-yl)amino)-2,3-dihydro-1H-inden-2-ol,
1-((6-((4-(1-methyl-1H-pyrazol-4-yl)-1H-imidazol-1-yl)methyl)benzo[d]thiazol-2-yl)amino)-2,3-dihydro-1H-inden-2-ol,
(1R,2R)-1-((6-((5-(1-methyl-1H-pyrazol-4-yl)-1H-imidazol-1-yl)methyl)benzo[d]thiazol-2-yl)amino)-2,3-dihydro-1H-inden-2-ol,
1-((6-((5-(1-methyl-1H-pyrazol-4-yl)-1H-imidazol-1-yl)methyl)benzo[d]thiazol-2-yl)amino)-2,3-dihydro-1H-inden-2-ol,
(S)—N-(1-cyclohexylethyl)-6-((5,6-dimethoxy-1H-benzo[d]imidazol-1-yl)methyl)benzo[d]thiazol-2-amine,
N-(1-cyclohexylethyl)-6-((5,6-dimethoxy-1H-benzo[d]imidazol-1-yl)methyl)benzo[d]thiazol-2-amine,
(1R,2R)-2-((6-((5,6-dimethoxy-1H-benzo[d]imidazol-1-yl)methyl)benzo[d]oxazol-2-yl)amino)cyclohexanol,
2-((6-((5,6-dimethoxy-1H-benzo[d]imidazol-1-yl)methyl)benzo[d]oxazol-2-yl)amino)cyclohexanol,
N-(cyclohexylmethyl)-6-((5,6-dimethoxy-1H-benzo[d]imidazol-1-yl)methyl)benzo[d]oxazol-2-amine,
(1R,2R)-2-((6-((4-(1-methyl-1H-pyrazol-4-yl)-1H-imidazol-1-yl)methyl)benzo[d]thiazol-2-yl)amino)cyclohexanol,
2-((6-((4-(1-methyl-1H-pyrazol-4-yl)-1H-imidazol-1-yl)methyl)benzo[d]thiazol-2-yl)amino)cyclohexanol,
1-((2-(((1R,2R)-2-hydroxycyclohexyl)amino)benzo[d]thiazol-6-yl)methyl)-N-methyl-1H-imidazole-4-carboxamide,
1-((2-((2-hydroxycyclohexyl)amino)benzo[d]thiazol-6-yl)methyl)-N-methyl-1H-imidazole-4-carboxamide
(1R,2R)-2-((6-(imidazo[1,2-a]pyridin-3-ylmethyl)benzo[d]thiazol-2-yl)amino)cyclohexanol,
2-((6-(imidazo[1,2-a]pyridin-3-ylmethyl)benzo[d]thiazol-2-yl)amino)cyclohexanol,
(1R,2R)-2-((6-((6-(1-methyl-1H-pyrazol-4-yl)-3H-imidazo[4,5-b]pyridin-3-yl)methyl)benzo[d]thiazol-2-yl)amino)cyclohexanol,
2-((6-((6-(1-methyl-1H-pyrazol-4-yl)-3H-imidazo[4,5-b]pyridin-3-yl)methyl)benzo[d]thiazol-2-yl)amino)cyclohexanol,
(1R,2R)-2-((6-((6-(pyridin-3-yl)-3H-imidazo[4,5-b]pyridin-3-yl)methyl)benzo[d]thiazol-2-yl)amino)cyclohexanol,
2-((6-((6-(pyridin-3-yl)-3H-imidazo[4,5-b]pyridin-3-yl)methyl)benzo[d]thiazol-2-yl)amino)cyclohexanol,
(1R,2R)-2-((6-((5-bromo-6-methoxy-1H-benzo[d]imidazol-1-yl)methyl)benzo[d]thiazol-2-yl)amino)cyclohexanol,
2-((6-((5-bromo-6-methoxy-1H-benzo[d]imidazol-1-yl)methyl)benzo[d]thiazol-2-yl)amino)cyclohexanol,
(1R,2R)-1-((6-((6-bromo-3H-imidazo[4,5-b]pyridin-3-yl)methyl)benzo[d]thiazol-2-yl)amino)-2,3-dihydro-1H-inden-2-ol,
1-((6-((6-bromo-3H-imidazo[4,5-b]pyridin-3-yl)methyl)benzo[d]thiazol-2-yl)amino)-2,3-dihydro-1H-inden-2-ol,
3-((2-(((1R,2R)-2-hydroxycyclohexyl)amino)benzo[d]thiazol-6-yl)methyl)-3H-imidazo[4,5-b]pyridine-6-carbonitrile,
3-((2-((2-hydroxycyclohexyl)amino)benzo[d]thiazol-6-yl)methyl)-3H-imidazo[4,5-b]pyridine-6-carbonitrile,
(1R,2R)-2-((6-((7-methoxyimidazo[1,2-a]pyridin-3-yl)methyl)benzo[d]thiazol-2-yl)amino)cyclohexanol,
2-((6-((7-methoxyimidazo[1,2-a]pyridin-3-yl)methyl)benzo[d]thiazol-2-yl)amino)cyclohexanol,
(1R,2R)-2-((6-((6-cyclopropyl-3H-imidazo[4,5-b]pyridin-3-yl)methyl)benzo[d]thiazol-2-yl)amino)cyclohexanol,
2-((6-((6-cyclopropyl-3H-imidazo[4,5-b]pyridin-3-yl)methyl)benzo[d]thiazol-2-yl)amino)cyclohexanol,
(1R,2R)-1-((6-((3H-imidazo[4,5-b]pyridin-3-yl)methyl)benzo[d]thiazol-2-yl)amino)-2,3-dihydro-1H-inden-2-ol,
1-((6-((3H-imidazo[4,5-b]pyridin-3-yl)methyl)benzo[d]thiazol-2-yl)amino)-2,3-dihydro-1H-inden-2-ol,
(1R,2R)-2-((6-((6-bromo-5-methoxy-1H-benzo[d]imidazol-1-yl)methyl)benzo[d]thiazol-2-yl)amino)cyclohexanol,
2-((6-((6-bromo-5-methoxy-1H-benzo[d]imidazol-1-yl)methyl)benzo[d]thiazol-2-yl)amino)cyclohexanol,
(1R,2R)-2-((6-((9H-purin-9-yl)methyl)benzo[d]thiazol-2-yl)amino)cyclohexanol,
2-((6-((9H-purin-9-yl)methyl)benzo[d]thiazol-2-yl)amino)cyclohexanol,
(1R,2R)-1-((6-((5-bromo-6-methoxy-1H-benzo[d]imidazol-1-yl)methyl)benzo[d]thiazol-2-yl)amino)-2,3-dihydro-1H-inden-2-ol,
1-((6-((5-bromo-6-methoxy-1H-benzo[d]imidazol-1-yl)methyl)benzo[d]thiazol-2-yl)amino)-2,3-dihydro-1H-inden-2-ol,
(±)-(1R,2R)(1S,2S)-2-((6-((5,6-dimethoxy-1H-benzo[d]imidazol-1-yl)methyl)benzo[d]thiazol-2-yl)amino)cycloheptanol,
2-((6-((5,6-dimethoxy-1H-benzo[d]imidazol-1-yl)methyl)benzo[d]thiazol-2-yl)amino)cycloheptanol, (1R,2R)-2-((6-((6-methoxy-5-(1-methyl-1H-pyrazol-4-yl)-1H-benzo[d]imidazol-1-yl)methyl)benzo[d]thiazol-2-yl)amino)cyclohexanol,
2-((6-((6-methoxy-5-(1-methyl-1H-pyrazol-4-yl)-1H-benzo[d]imidazol-1-yl)methyl)benzo[d]thiazol-2-yl)amino)cyclohexanol,
(1R,2R)-2-((6-((5-methoxy-6-(1-methyl-1H-pyrazol-4-yl)-1H-benzo[d]imidazol-1-yl)methyl)benzo[d]thiazol-2-yl)amino)cyclohexanol,
2-((6-((5-methoxy-6-(1-methyl-1H-pyrazol-4-yl)-1H-benzo[d]imidazol-1-yl)methyl)benzo[d]thiazol-2-yl)amino)cyclohexanol,
1-((2-(((1R,2R)-2-hydroxycyclohexyl)amino)benzo[d]thiazol-6-yl)methyl)-5-methoxy-1H-benzo[d]imidazole-6-carbonitrile,
1-((2-((2-hydroxycyclohexyl)amino)benzo[d]thiazol-6-yl)methyl)-5-methoxy-1H-benzo[d]imidazole-6-carbonitrile,
(R)-2-((6-((3H-imidazo[4,5-b]pyridin-3-yl)methyl)benzo[d]thiazol-2-yl)amino)cyclohexanone,
2-((6-((3H-imidazo[4,5-b]pyridin-3-yl)methyl)benzo[d]thiazol-2-yl)amino)cyclohexanone,
(1R,2R)-2-((6-((6-chloro-3H-imidazo[4,5-b]pyridin-3-yl)methyl)benzo[d]thiazol-2-yl)amino)cyclohexanol,
2-((6-((6-chloro-3H-imidazo[4,5-b]pyridin-3-yl)methyl)benzo[d]thiazol-2-yl)amino)cyclohexanol,
(1R,2R)-2-((6-((3H-imidazo[4,5-b]pyridin-3-yl)methyl)benzo[d]oxazol-2-yl)amino)cyclohexanol,
2-((6-((3H-imidazo[4,5-b]pyridin-3-yl)methyl)benzo[d]oxazol-2-yl)amino)cyclohexanol,
(1R,2R)-1-((6-((3H-imidazo[4,5-b]pyridin-3-yl)methyl)benzo[d]oxazol-2-yl)amino)-2,3-dihydro-1H-inden-2-ol,
1-((6-((3H-imidazo[4,5-b]pyridin-3-yl)methyl)benzo[d]oxazol-2-yl)amino)-2,3-dihydro-1H-inden-2-ol,
(R)-2-((6-((3H-imidazo[4,5-b]pyridin-3-yl)methyl)benzo[d]thiazol-2-yl)amino)cyclohexanone oxime,
2-((6-((3H-imidazo[4,5-b]pyridin-3-yl)methyl)benzo[d]thiazol-2-yl)amino)cyclohexanone oxime,
(1S,2R)-2-((6-((3H-imidazo[4,5-b]pyridin-3-yl)methyl)benzo[d]thiazol-2-yl)amino)-1-methylcyclohexanol,
(1R,2R)-2-((6-((3H-imidazo[4,5-b]pyridin-3-yl)methyl)benzo[d]thiazol-2-yl)amino)-1-methylcyclohexanol,
2-((6-((3H-imidazo[4,5-b]pyridin-3-yl)methyl)benzo[d]thiazol-2-yl)amino)-1-methylcyclohexanol,
(1R,2R)-2-((6-((6-bromo-3H-imidazo[4,5-b]pyridin-3-yl)methyl)benzo[d]oxazol-2-yl)amino)cyclohexanol,
2-((6-((6-bromo-3H-imidazo[4,5-b]pyridin-3-yl)methyl)benzo[d]oxazol-2-yl)amino)cyclohexanol,
(1R,2R)-1-((6-((6-bromo-3H-imidazo[4,5-b]pyridin-3-yl)methyl)benzo[d]oxazol-2-yl)amino)-2,3-dihydro-1H-inden-2-ol,
1-((6-((6-bromo-3H-imidazo[4,5-b]pyridin-3-yl)methyl)benzo[d]oxazol-2-yl)amino)-2,3-dihydro-1H-inden-2-ol,
(S)-2-((6-((3H-imidazo[4,5-b]pyridin-3-yl)methyl)benzo[d]thiazol-2-yl)amino)-2-cyclohexylethanol,
2-((6-((3H-imidazo[4,5-b]pyridin-3-yl)methyl)benzo[d]thiazol-2-yl)amino)-2-cyclohexylethanol,
(R)-2-((6-((3H-imidazo[4,5-b]pyridin-3-yl)methyl)benzo[d]thiazol-2-yl)amino)-2-cyclohexylethanol,
1-((2-(((1R,2R)-2-hydroxycyclohexyl)amino)benzo[d]thiazol-6-yl)methyl)-6-methoxy-1H-benzo[d]imidazole-5-carbonitrile,
1-((2-((2-hydroxycyclohexyl)amino)benzo[d]thiazol-6-yl)methyl)-6-methoxy-1H-benzo[d]imidazole-5-carbonitrile,
((1R,2R)-2-((6-((3H-imidazo[4,5-b]pyridin-3-yl)methyl)benzo[d]thiazol-2-yl)amino)cyclohexyl)methanol,
2-((6-((3H-imidazo[4,5-b]pyridin-3-yl)methyl)benzo[d]thiazol-2-yl)amino)cyclohexyl)methanol,
(1R,2R)-2-((6-((6-methoxy-1H-benzo[d]imidazol-1-yl)methyl)benzo[d]thiazol-2-yl)amino)cyclohexanol,
2-((6-((6-methoxy-1H-benzo[d]imidazol-1-yl)methyl)benzo[d]thiazol-2-yl)amino)cyclohexanol,
(1R,2R)-2-((6-((5-methoxy-1H-benzo[d]imidazol-1-yl)methyl)benzo[d]thiazol-2-yl)amino)cyclohexanol,
2-((6-((5-methoxy-1H-benzo[d]imidazol-1-yl)methyl)benzo[d]thiazol-2-yl)amino)cyclohexanol,
(1R,2R)-1-((6-((6-fluoro-3H-imidazo[4,5-b]pyridin-3-yl)methyl)benzo[d]thiazol-2-yl)amino)-2,3-dihydro-1H-inden-2-ol,
1-((6-((6-fluoro-3H-imidazo[4,5-b]pyridin-3-yl)methyl)benzo[d]thiazol-2-yl)amino)-2,3-dihydro-1H-inden-2-ol,
(1R,2R)-2-((6-((6-fluoro-3H-imidazo[4,5-b]pyridin-3-yl)methyl)benzo[d]thiazol-2-yl)amino)cyclohexanol,
2-((6-((6-fluoro-3H-imidazo[4,5-b]pyridin-3-yl)methyl)benzo[d]thiazol-2-yl)amino)cyclohexanol,
(1R,2R)-2-((6-((3H-imidazo[4,5-c]pyridin-3-yl)methyl)benzo[d]thiazol-2-yl)amino)cyclohexanol,
2-((6-((3H-imidazo[4,5-c]pyridin-3-yl)methyl)benzo[d]thiazol-2-yl)amino)cyclohexanol,
(1R,2R)-2-((6-((1H-imidazo[4,5-c]pyridin-1-yl)methyl)benzo[d]thiazol-2-yl)amino)cyclohexanol,
2-((6-((1H-imidazo[4,5-c]pyridin-1-yl)methyl)benzo[d]thiazol-2-yl)amino)cyclohexanol,
1-(3-((2-(((1R,2R)-2-hydroxycyclohexyl)amino)benzo[d]thiazol-6-yl)methyl)-3H-imidazo[4,5-b]pyridin-6-yl)ethanone,
1-(3-((2-((2-hydroxycyclohexyl)amino)benzo[d]thiazol-6-yl)methyl)-3H-imidazo[4,5-b]pyridin-6-yl)ethanone,
(1R,2R)-2-((6-((6-(methylsulfonyl)-3H-imidazo[4,5-b]pyridin-3-yl)methyl)benzo[d]thiazol-2-yl)amino)cyclohexanol,
2-((6-((6-(methylsulfonyl)-3H-imidazo[4,5-b]pyridin-3-yl)methyl)benzo[d]thiazol-2-yl)amino)cyclohexanol,
1-(((6-((3H-imidazo[4,5-b]pyridin-3-yl)methyl)benzo[d]thiazol-2-yl)amino)methyl)cyclohexanol,
(1-(((6-((3H-imidazo[4,5-b]pyridin-3-yl)methyl)benzo[d]thiazol-2-yl)amino)methyl)cyclohexyl)methanol,
(1R,2R)-2-((6-((4-(1-methyl-1H-pyrazol-4-yl)-1H-imidazol-1-yl)methyl)benzo[d]oxazol-2-yl)amino)cyclohexanol,
2-((6-((4-(1-methyl-1H-pyrazol-4-yl)-1H-imidazol-1-yl)methyl)benzo[d]oxazol-2-yl)amino)cyclohexanol,
(1R,2R)-2-((6-((5-bromo-3H-imidazo[4,5-b]pyridin-3-yl)methyl)benzo[d]thiazol-2-yl)amino)cyclohexanol,
2-((6-((5-bromo-3H-imidazo[4,5-b]pyridin-3-yl)methyl)benzo[d]thiazol-2-yl)amino)cyclohexanol,
methyl 3-((2-(((1R,2R)-2-hydroxycyclohexyl)amino)benzo[d]thiazol-6-yl)methyl)-3H-imidazo[4,5-b]pyridine-6-carboxylate,
methyl 3-((2-((2-hydroxycyclohexyl)amino)benzo[d]thiazol-6-yl)methyl)-3H-imidazo[4,5-b]pyridine-6-carboxylate,
(1R,2R)-1-((6-((5-bromo-3H-imidazo[4,5-b]pyridin-3-yl)methyl)benzo[d]thiazol-2-yl)amino)-2,3-dihydro-1H-inden-2-ol,
1-((6-((5-bromo-3H-imidazo[4,5-b]pyridin-3-yl)methyl)benzo[d]thiazol-2-yl)amino)-2,3-dihydro-1H-inden-2-ol,
3-((2-(((1R,2R)-2-hydroxycyclohexyl)amino)benzo[d]thiazol-6-yl)methyl)-3H-imidazo[4,5-b]pyridine-6-carboxylic acid,
3-((2-((2-hydroxycyclohexyl)amino)benzo[d]thiazol-6-yl)methyl)-3H-imidazo[4,5-b]pyridine-6-carboxylic acid, (1R,2R)-2-((6-((6-(morpholinomethyl)-3H-imidazo[4,5-b]pyridin-3-yl)methyl)benzo[d]thiazol-2-yl)amino)cyclohexanol,
2-((6-((6-(morpholinomethyl)-3H-imidazo[4,5-b]pyridin-3-yl)methyl)benzo[d]thiazol-2-yl)amino)cyclohexanol,
(1R,2R)-2-((6-((6-(hydroxymethyl)-3H-imidazo[4,5-b]pyridin-3-yl)methyl)benzo[d]thiazol-2-yl)amino)cyclohexanol,
2-((6-((6-(hydroxymethyl)-3H-imidazo[4,5-b]pyridin-3-yl)methyl)benzo[d]thiazol-2-yl)amino)cyclohexanol,
(1R,2R)-2-((6-((6-(methylthio)-3H-imidazo[4,5-b]pyridin-3-yl)methyl)benzo[d]thiazol-2-yl)amino)cyclohexanol,
2-((6-((6-(methylthio)-3H-imidazo[4,5-b]pyridin-3-yl)methyl)benzo[d]thiazol-2-yl)amino)cyclohexanol,
(1R,2R)-2-((6-((6-((methylthio)methyl)-3H-imidazo[4,5-b]pyridin-3-yl)methyl)benzo[d]thiazol-2-yl)amino)cyclohexanol,
2-((6-((6-((methylthio)methyl)-3H-imidazo[4,5-b]pyridin-3-yl)methyl)benzo[d]thiazol-2-yl)amino)cyclohexanol,
3-((2-(((1R,2R)-2-hydroxycyclohexyl)amino)benzo[d]thiazol-6-yl)methyl)-3H-imidazo[4,5-b]pyridine-5-carbonitrile,
3-((2-((2-hydroxycyclohexyl)amino)benzo[d]thiazol-6-yl)methyl)-3H-imidazo[4,5-b]pyridine-5-carbonitrile,
1-(3-((2-(((1R,2R)-2-hydroxycyclohexyl)amino)benzo[d]thiazol-6-yl)methyl)-3H-imidazo[4,5-b]pyridin-5-yl)ethanone,
1-(3-((2-((2-hydroxycyclohexyl)amino)benzo[d]thiazol-6-yl)methyl)-3H-imidazo[4,5-b]pyridin-5-yl)ethanone,
3-((2-(((1R,2R)-2-hydroxycyclohexyl)amino)benzo[d]thiazol-6-yl)methyl)-N-methyl-3H-imidazo[4,5-b]pyridine-6-carboxamide,
3-((2-((2-hydroxycyclohexyl)amino)benzo[d]thiazol-6-yl)methyl)-N-methyl-3H-imidazo[4,5-b]pyridine-6-carboxamide,
N-hydroxy-3-((2-(((1R,2R)-2-hydroxycyclohexyl)amino)benzo[d]thiazol-6-yl)methyl)-3H-imidazo[4,5-b]pyridine-6-carboximidamide,
(1R,2R)-2-((6-((6-(aminomethyl)-3H-imidazo[4,5-b]pyridin-3-yl)methyl)benzo[d]thiazol-2-yl)amino)cyclohexanol acetic acid,
(1R,2R)-2-((6-((6-(aminomethyl)-3H-imidazo[4,5-b]pyridin-3-yl)methyl)benzo[d]thiazol-2-yl)amino)cyclohexanol,
2-((6-((6-(aminomethyl)-3H-imidazo[4,5-b]pyridin-3-yl)methyl)benzo[d]thiazol-2-yl)amino)cyclohexanol,
3-((2-(((1R,2R)-2-hydroxycyclohexyl)amino)benzo[d]thiazol-6-yl)methyl)-N,N-dimethyl-3H-imidazo[4,5-b]pyridine-6-carboxamide,
3-((2-((2-hydroxycyclohexyl)amino)benzo[d]thiazol-6-yl)methyl)-N,N-dimethyl-3H-imidazo[4,5-b]pyridine-6-carboxamide,
(1R,2R)-2-((6-((6-(2H-tetrazol-5-yl)-3H-imidazo[4,5-b]pyridin-3-yl)methyl)benzo[d]thiazol-2-yl)amino)cyclohexanol,
2-((6-((6-(2H-tetrazol-5-yl)-3H-imidazo[4,5-b]pyridin-3-yl)methyl)benzo[d]thiazol-2-yl)amino)cyclohexanol,
(1R,2R)-2-((6-((6-(2-methyl-2H-tetrazol-5-yl)-3H-imidazo[4,5-b]pyridin-3-yl)methyl)benzo[d]thiazol-2-yl)amino)cyclohexanol,
2-((6-((6-(2-methyl-2H-tetrazol-5-yl)-3H-imidazo[4,5-b]pyridin-3-yl)methyl)benzo[d]thiazol-2-yl)amino)cyclohexanol,
(1R,2R)-2-((6-((6-(1-methyl-1H-tetrazol-5-yl)-3H-imidazo[4,5-b]pyridin-3-yl)methyl)benzo[d]thiazol-2-yl)amino)cyclohexanol,
2-((6-((6-(1-methyl-1H-tetrazol-5-yl)-3H-imidazo[4,5-b]pyridin-3-yl)methyl)benzo[d]thiazol-2-yl)amino)cyclohexanol,
(1R,2R)-1-((6-((9H-purin-9-yl)methyl)benzo[d]thiazol-2-yl)amino)-2,3-dihydro-1H-inden-2-ol,
1-((6-((9H-purin-9-yl)methyl)benzo[d]thiazol-2-yl)amino)-2,3-dihydro-1H-inden-2-ol,
(1R,2R)-2-((6-((6-ethynyl-3H-imidazo[4,5-b]pyridin-3-yl)methyl)benzo[d]thiazol-2-yl)amino)cyclohexanol,
2-((6-((6-ethynyl-3H-imidazo[4,5-b]pyridin-3-yl)methyl)benzo[d]thiazol-2-yl)amino)cyclohexanol,
(1R,2R)-2-((6-((6-morpholino-3H-imidazo[4,5-b]pyridin-3-yl)methyl)benzo[d]thiazol-2-yl)amino)cyclohexanol,
2-((6-((6-morpholino-3H-imidazo[4,5-b]pyridin-3-yl)methyl)benzo[d]thiazol-2-yl)amino)cyclohexanol,
(1R,2R)-2-((6-((6-vinyl-3H-imidazo[4,5-b]pyridin-3-yl)methyl)benzo[d]thiazol-2-yl)amino)cyclohexanol,
2-((6-((6-vinyl-3H-imidazo[4,5-b]pyridin-3-yl)methyl)benzo[d]thiazol-2-yl)amino)cyclohexanol,
N-((3-((2-(((1R,2R)-2-hydroxycyclohexyl)amino)benzo[d]thiazol-6-yl)methyl)-3H-imidazo[4,5-b]pyridin-6-yl)methyl)acetamide,
N-((3-((2-((2-hydroxycyclohexyl)amino)benzo[d]thiazol-6-yl)methyl)-3H-imidazo[4,5-b]pyridin-6-yl)methyl)acetamide,
(1R,2R)-2-((6-((5-bromo-1H-benzo[d]imidazol-1-yl)methyl)benzo[d]thiazol-2-yl)amino)cyclohexanol,
2-((6-((5-bromo-1H-benzo[d]imidazol-1-yl)methyl)benzo[d]thiazol-2-yl)amino)cyclohexanol,
N-(1-((2-(((1R,2R)-2-hydroxycyclohexyl)amino)benzo[d]thiazol-6-yl)methyl)-1H-imidazol-4-yl)acetamide,
N-(1-((2-((2-hydroxycyclohexyl)amino)benzo[d]thiazol-6-yl)methyl)-1H-imidazol-4-yl)acetamide,
(1R,2R)-2-((6-((6-ethyl-3H-imidazo[4,5-b]pyridin-3-yl)methyl)benzo[d]thiazol-2-yl)amino)cyclohexanol,
2-((6-((6-ethyl-3H-imidazo[4,5-b]pyridin-3-yl)methyl)benzo[d]thiazol-2-yl)amino)cyclohexanol,
1-((2-(((1R,2R)-2-hydroxycyclohexyl)amino)benzo[d]thiazol-6-yl)methyl)-3-(1-methyl-1H-pyrazol-4-yl)pyrazin-2(1H)-one, and
1-((2-((2-hydroxycyclohexyl)amino)benzo[d]thiazol-6-yl)methyl)-3-(1-methyl-1H-pyrazol-4-yl)pyrazin-2(1H)-one.

In one embodiment, the compound provided herein is selected from:
(1R,2R)-2-((6-((6-(3-hydroxy-3-methylbut-1-yn-1-yl)-3H-imidazo[4,5-b]pyridin-3-yl)methyl)benzo[d]thiazol-2-yl)amino)cyclohexanol;
2-((6-((6-(3-hydroxy-3-methylbut-1-yn-1-yl)-3H-imidazo[4,5-b]pyridin-3-yl)methyl)benzo[d]thiazol-2-yl)amino)cyclohexanol;
(1R,2R)-2-((6-((2-(trifluoromethyl)-9H-purin-9-yl)methyl)benzo[d]thiazol-2-yl)amino)cyclohexanol;
2-((6-((2-(trifluoromethyl)-9H-purin-9-yl)methyl)benzo[d]thiazol-2-yl)amino)cyclohexanol;
(1R,2R)-2-((6-((5-(methylsulfonyl)-3H-imidazo[4,5-b]pyridin-3-yl)methyl)benzo[d]thiazol-2-yl)amino)cyclohexanol;
2-((6-((5-(methylsulfonyl)-3H-imidazo[4,5-b]pyridin-3-yl)methyl)benzo[d]thiazol-2-yl)amino)cyclohexanol;
(1R,2R)-2-((6-((6-bromo-1H-benzo[d]imidazol-1-yl)methyl)benzo[d]thiazol-2-yl)amino)cyclohexanol;
2-((6-((6-bromo-1H-benzo[d]imidazol-1-yl)methyl)benzo[d]thiazol-2-yl)amino)cyclohexanol;
1-((2-(((1R,2R)-2-hydroxycyclohexyl)amino)benzo[d]thiazol-6-yl)methyl)-1H-benzo[d]imidazole-5-carbonitrile;

1-((2-((2-hydroxycyclohexyl)amino)benzo[d]thiazol-6-yl)
methyl)-1H-benzo[d]imidazole-5-carbonitrile;
(1R,2R)-2-((6-((6-(2-hydroxypropan-2-yl)-3H-imidazo[4,5-
b]pyridin-3-yl)methyl)benzo[d]thiazol-2-yl)amino)cyclo-
hexanol;
2-((6-((6-(2-hydroxypropan-2-yl)-3H-imidazo[4,5-b]pyri-
din-3-yl)methyl)benzo[d]thiazol-2-yl)amino)cyclohexa-
nol;
1-(1-((2-(((1R,2R)-2-hydroxycyclohexyl)amino)benzo[d]
thiazol-6-yl)methyl)-1H-benzo[d]imidazol-5-yl)etha-
none;
1-(1-((2-((2-hydroxycyclohexyl)amino)benzo[d]thiazol-6-
yl)methyl)-1H-benzo[d]imidazol-5-yl)ethanone;
1-(2-(((1R,2R)-2-hydroxycyclohexyl)amino)benzo[d]thi-
azol-6-yl)methyl)-1H-benzo[d]imidazole-6-carbonitrile;
1-(2-((2-hydroxycyclohexyl)amino)benzo[d]thiazol-6-yl)
methyl)-1H-benzo[d]imidazole-6-carbonitrile;
(1R,2R)-2-((6-((5-(methylsulfonyl)-1H-benzo[d]imidazol-
1-yl)methyl)benzo[d]thiazol-2-yl)amino)cyclohexanol;
2-((6-((5-(methylsulfonyl)-1H-benzo[d]imidazol-1-yl)
methyl)benzo[d]thiazol-2-yl)amino)cyclohexanol;
(1R,2R)-2-((6-((6-(methylsulfonyl)-1H-benzo[d]imidazol-
1-yl)methyl)benzo[d]thiazol-2-yl)amino)cyclohexanol;
2-((6-((6-(methylsulfonyl)-1H-benzo[d]imidazol-1-yl)
methyl)benzo[d]thiazol-2-yl)amino)cyclohexanol;
(1R,2R)-2-((6-((3H-imidazo[4,5-b]pyridin-3-yl)methyl)thi-
azolo[4,5-b]pyridin-2-yl)amino)cyclohexanol;
2-((6-((3H-imidazo[4,5-b]pyridin-3-yl)methyl)thiazolo[4,5-
b]pyridin-2-yl)amino)cyclohexanol;
(1R,2R)-2-((6-((6-((R,S)-1-hydroxyethyl)-3H-imidazo[4,5-
b]pyridin-3-yl)methyl)benzo[d]thiazol-2-yl)amino)cyclo-
hexanol;
2-((6-((6-(1-hydroxyethyl)-3H-imidazo[4,5-b]pyridin-3-yl)
methyl)benzo[d]thiazol-2-yl)amino)cyclohexanol;
2-(dimethylamino)-1-(3-((2-(((1R,2R)-2-hydroxycyclo-
hexyl)amino)benzo[d]thiazol-6-yl)methyl)-3H-imidazo
[4,5-b]pyridin-6-yl)ethanone acetate salt;
2-(dimethylamino)-1-(3-((2-((2-hydroxycyclohexyl)amino)
benzo[d]thiazol-6-yl)methyl)-3H-imidazo[4,5-b]pyridin-
6-yl)ethanone;
2-(dimethylamino)-1-(3-((2-(((1R,2R)-2-hydroxycyclo-
hexyl)amino)benzo[d]thiazol-6-yl)methyl)-3H-imidazo
[4,5-b]pyridin-6-yl)ethanone;
3-((2-(((1R,2R)-2-hydroxycyclohexyl)amino)benzo[d]thi-
azol-6-yl)methyl)imidazo[1,2-a]pyridine-7-carbonitrile;
3-((2-((2-hydroxycyclohexyl)amino)benzo[d]thiazol-6-yl)
methyl)imidazo[1,2-a]pyridine-7-carbonitrile;
(1R,2R)-2-((6-((9H-purin-9-yl)methyl)benzo[d]oxazol-2-
yl)amino)cyclohexanol;
2-((6-((9H-purin-9-yl)methyl)benzo[d]oxazol-2-yl)amino)
cyclohexanol;
(1R,2R)-2-((6-((5,6-dimethyl-1H-benzo[d]imidazol-1-yl)
methyl)benzo[d]thiazol-2-yl)amino)cyclohexanol;
2-((6-((5,6-dimethyl-1H-benzo[d]imidazol-1-yl)methyl)
benzo[d]thiazol-2-yl)amino)cyclohexanol;
1-(1-((2-(((1R,2R)-2-hydroxycyclohexyl)amino)benzo[d]
thiazol-6-yl)methyl)-1H-benzo[d]imidazol-6-yl)etha-
none;
1-(1-((2-((2-hydroxycyclohexyl)amino)benzo[d]thiazol-6-
yl)methyl)-1H-benzo[d]imidazol-6-yl)ethanone;
(1R,2R)-2-((6-((5-ethynyl-1H-benzo[d]imidazol-1-yl)
methyl)benzo[d]thiazol-2-yl)amino)cyclohexanol;
2-((6-((5-ethynyl-1H-benzo[d]imidazol-1-yl)methyl)benzo
[d]thiazol-2-yl)amino)cyclohexanol;
(1R,2R)-2-((6-((6-ethynyl-1H-benzo[d]imidazol-1-yl)
methyl)benzo[d]thiazol-2-yl)amino)cyclohexanol;
2-((6-((6-ethynyl-1H-benzo[d]imidazol-1-yl)methyl)benzo
[d]thiazol-2-yl)amino)cyclohexanol;
(1R,2R)-2-((6-((6-bromo-5-methoxy-3H-imidazo[4,5-b]
pyridin-3-yl)methyl)benzo[d]thiazol-2-yl)amino)cyclo-
hexanol;
2-((6-((6-bromo-5-methoxy-3H-imidazo[4,5-b]pyridin-3-
yl)methyl)benzo[d]thiazol-2-yl)amino)cyclohexanol;
3-((2-(((1R,2R)-2-hydroxycyclohexyl)amino)benzo[d]ox-
azol-6-yl)methyl)-3H-imidazo[4,5-b]pyridine-6-carboni-
trile;
3-((2-((2-hydroxycyclohexyl)amino)benzo[d]oxazol-6-yl)
methyl)-3H-imidazo[4,5-b]pyridine-6-carbonitrile;
(1R,2R)-2-((6-(imidazo[1,2-c]pyrazin-3-ylmethyl)benzo[d]
thiazol-2-yl)amino)cyclohexanol;
2-((6-(imidazo[1,2-c]pyrazin-3-ylmethyl)benzo[d]thiazol-
2-yl)amino)cyclohexanol;
3-((2-(((1R,2R)-2-hydroxycyclohexyl)amino)benzo[d]thi-
azol-6-yl)methyl)-5-methoxy-3H-imidazo[4,5-b]pyri-
dine-6-carbonitrile;
3-((2-((2-hydroxycyclohexyl)amino)benzo[d]thiazol-6-yl)
methyl)-5-methoxy-3H-imidazo[4,5-b]pyridine-6-carbo-
nitrile;
(1R,2R)-2-((6-((5-methyl-1H-benzo[d]imidazol-1-yl)
methyl)benzo[d]thiazol-2-yl)amino)cyclohexanol;
2-((6-((5-methyl-1H-benzo[d]imidazol-1-yl)methyl)benzo
[d]thiazol-2-yl)amino)cyclohexanol;
(1R,2R)-2-((6-((5,6-difluoro-1H-benzo[d]imidazol-1-yl)
methyl)benzo[d]thiazol-2-yl)amino)cyclohexanol;
2-((6-((5,6-difluoro-1H-benzo[d]imidazol-1-yl)methyl)
benzo[d]thiazol-2-yl)amino)cyclohexanol;
(1R,2R)-2-((6-((5-fluoro-1H-benzo[d]imidazol-1-yl)
methyl)benzo[d]thiazol-2-yl)amino)cyclohexanol;
2-((6-((5-fluoro-1H-benzo[d]imidazol-1-yl)methyl)benzo
[d]thiazol-2-yl)amino)cyclohexanol;
(1R,2R)-2-((6-((5-(trifluoromethyl)-1H-benzo[d]imidazol-
1-yl)methyl)benzo[d]thiazol-2-yl)amino)cyclohexanol;
2-((6-((5-(trifluoromethyl)-1H-benzo[d]imidazol-1-yl)
methyl)benzo[d]thiazol-2-yl)amino)cyclohexanol;
(1R,2R)-2-((6-(imidazo[1,2-b]pyridazin-3-ylmethyl)benzo
[d]thiazol-2-yl)amino)cyclohexanol;
2-((6-(imidazo[1,2-b]pyridazin-3-ylmethyl)benzo[d]thi-
azol-2-yl)amino)cyclohexanol;
(1R,2R)-2-((6-((6-fluoro-3H-imidazo[4,5-b]pyridin-3-yl)
methyl)benzo[d]oxazol-2-yl)amino)cyclohexanol;
2-((6-((6-fluoro-3H-imidazo[4,5-b]pyridin-3-yl)methyl)
benzo[d]oxazol-2-yl)amino)cyclohexanol;
((1R,2R)-2-((6-((6-bromo-3H-imidazo[4,5-b]pyridin-3-yl)
methyl)benzo[d]thiazol-2-yl)amino)cyclohexyl)metha-
nol;
2-((6-((6-bromo-3H-imidazo[4,5-b]pyridin-3-yl)methyl)
benzo[d]thiazol-2-yl)amino)cyclohexyl)methanol;
(1R,2R)-2-((6-((6-(1-methyl-1H-tetrazol-5-yl)-3H-imidazo
[4,5-b]pyridin-3-yl)methyl)benzo[d]thiazol-2-yl)amino)
cyclohexanol;
2-((6-((6-(1-methyl-1H-tetrazol-5-yl)-3H-imidazo[4,5-b]
pyridin-3-yl)methyl)benzo[d]thiazol-2-yl)amino)cyclo-
hexanol;
(1R,2R)-2-((6-((7-(2-hydroxyethoxy)imidazo[1,2-a]pyri-
din-3-yl)methyl)benzo[d]thiazol-2-yl)amino)cyclohexa-
nol;
2-((6-((7-(2-hydroxyethoxy)imidazo[1,2-a]pyridin-3-yl)
methyl)benzo[d]thiazol-2-yl)amino)cyclohexanol;
((1S,2R)-2-((6-((6-bromo-3H-imidazo[4,5-b]pyridin-3-yl)
methyl)benzo[d]thiazol-2-yl)amino)cyclohexyl)metha-
nol;
2-((6-((6-bromo-3H-imidazo[4,5-b]pyridin-3-yl)methyl)
benzo[d]thiazol-2-yl)amino)cyclohexyl)methanol;

(1R,2R)-2-((6-((5,6-dichloro-3H-imidazo[4,5-b]pyridin-3-yl)methyl)benzo[d]thiazol-2-yl)amino)cyclohexanol;
2-((6-((5,6-dichloro-3H-imidazo[4,5-b]pyridin-3-yl)methyl)benzo[d]thiazol-2-yl)amino)cyclohexanol;
(1R,2R)-2-((6-((5-ethoxy-1H-benzo[d]imidazol-1-yl)methyl)benzo[d]thiazol-2-yl)amino)cyclohexanol;
2-((6-((5-ethoxy-1H-benzo[d]imidazol-1-yl)methyl)benzo[d]thiazol-2-yl)amino)cyclohexanol;
3-((2-(((1R,2R)-2-hydroxycyclohexyl)amino)benzo[d]thiazol-6-yl)methyl)-3H-imidazo[4,5-b]pyridine-5,6-dicarbonitrile;
3-((2-((2-hydroxycyclohexyl)amino)benzo[d]thiazol-6-yl)methyl)-3H-imidazo[4,5-b]pyridine-5,6-dicarbonitrile;
3-((2-(((1R,2R)-2-(hydroxymethyl)cyclohexyl)amino)benzo[d]thiazol-6-yl)methyl)-3H-imidazo[4,5-b]pyridine-6-carbonitrile;
3-((2-((2-(hydroxymethyl)cyclohexyl)amino)benzo[d]thiazol-6-yl)methyl)-3H-imidazo[4,5-b]pyridine-6-carbonitrile;
(1R,2R)-2-((6-((6-(1H-pyrazol-1-yl)-3H-imidazo[4,5-b]pyridin-3-yl)methyl)benzo[d]thiazol-2-yl)amino)cyclohexanol;
2-((6-((6-(1H-pyrazol-1-yl)-3H-imidazo[4,5-b]pyridin-3-yl)methyl)benzo[d]thiazol-2-yl)amino)cyclohexanol;
(1R,2R)-2-((6-(imidazo[1,2-b]pyridazin-3-ylmethyl)benzo[d]oxazol-2-yl)amino)cyclohexanol;
2-((6-(imidazo[1,2-b]pyridazin-3-ylmethyl)benzo[d]oxazol-2-yl)amino)cyclohexanol;
3-((2-(((1R,2R)-2-hydroxycyclohexyl)amino)benzo[d]thiazol-6-yl)methyl)-N-methylimidazo[1,2-b]pyridazine-6-carboxamide;
3-((2-((2-hydroxycyclohexyl)amino)benzo[d]thiazol-6-yl)methyl)-N-methylimidazo[1,2-b]pyridazine-6-carboxamide;
(1R,2R)-2-((6-((6-(hydroxymethyl)imidazo[1,2-b]pyridazin-3-yl)methyl)benzo[d]thiazol-2-yl)amino)cyclohexanol;
2-((6-((6-(hydroxymethyl)imidazo[1,2-b]pyridazin-3-yl)methyl)benzo[d]thiazol-2-yl)amino)cyclohexanol;
(1R,2R)-2-((6-((6-(1H-1,2,4-triazol-1-yl)-3H-imidazo[4,5-b]pyridin-3-yl)methyl)benzo[d]thiazol-2-yl)amino)cyclohexanol;
2-((6-((6-(1H-1,2,4-triazol-1-yl)-3H-imidazo[4,5-b]pyridin-3-yl)methyl)benzo[d]thiazol-2-yl)amino)cyclohexanol;
(1R,2R)-2-((6-((6-iodo-3H-imidazo[4,5-b]pyridin-3-yl)methyl)benzo[d]thiazol-2-yl)amino)cyclohexanol;
2-((6-((6-iodo-3H-imidazo[4,5-b]pyridin-3-yl)methyl)benzo[d]thiazol-2-yl)amino)cyclohexanol;
1-((2-(((1R,2R)-2-hydroxycyclohexyl)amino)benzo[d]thiazol-6-yl)methyl)-1H-benzo[d]imidazol-5-ol;
1-((2-((2-hydroxycyclohexyl)amino)benzo[d]thiazol-6-yl)methyl)-1H-benzo[d]imidazol-5-ol;
(1R,2R)-2-((6-((5,7-difluoro-1H-benzo[d]imidazol-1-yl)methyl)benzo[d]thiazol-2-yl)amino)cyclohexanol;
2-((6-((5,7-difluoro-1H-benzo[d]imidazol-1-yl)methyl)benzo[d]thiazol-2-yl)amino)cyclohexanol;
(1R,2R)-2-((6-((5-(trifluoromethoxy)-1H-benzo[d]imidazol-1-yl)methyl)benzo[d]thiazol-2-yl)amino)cyclohexanol;
2-((6-((5-(trifluoromethoxy)-1H-benzo[d]imidazol-1-yl)methyl)benzo[d]thiazol-2-yl)amino)cyclohexanol;
(1R,2R)-2-((6-((6-methoxyimidazo[1,2-b]pyridazin-3-yl)methyl)benzo[d]thiazol-2-yl)amino)cyclohexanol;
2-((6-((6-methoxyimidazo[1,2-b]pyridazin-3-yl)methyl)benzo[d]thiazol-2-yl)amino)cyclohexanol;
(1R,2R)-2-((6-((5-methoxy-1H-benzo[d]imidazol-1-yl)methyl)benzo[d]oxazol-2-yl)amino)cyclohexanol;
2-((6-((5-methoxy-1H-benzo[d]imidazol-1-yl)methyl)benzo[d]oxazol-2-yl)amino)cyclohexanol;
(1R,2R)-2-((6-((6-methoxy-1H-benzo[d]imidazol-1-yl)methyl)benzo[d]oxazol-2-yl)amino)cyclohexanol;
2-((6-((6-methoxy-1H-benzo[d]imidazol-1-yl)methyl)benzo[d]oxazol-2-yl)amino)cyclohexanol;
(1R,2R)-2-((6-((7-(2-methoxyethoxyl)imidazo[1,2-a]pyridin-3-yl)methyl)benzo[d]thiazol-2-yl)amino)cyclohexanol;
2-((6-((7-(2-methoxyethoxy)imidazo[1,2-a]pyridin-3-yl)methyl)benzo[d]thiazol-2-yl)amino)cyclohexanol;
(1R,2R)-2-((6-((3H-imidazo[4,5-b]pyridin-3-yl)methyl)-5-fluorobenzo[d]thiazol-2-yl)amino)cyclohexanol;
2-((6-((3H-imidazo[4,5-b]pyridin-3-yl)methyl)-5-fluorobenzo[d]thiazol-2-yl)amino)cyclohexanol;
(1R,2R)-2-((6-((6-morpholinoimidazo[1,2-b]pyridazin-3-yl)methyl)benzo[d]thiazol-2-yl)amino)cyclohexanol;
2-((6-((6-morpholinoimidazo[1,2-b]pyridazin-3-yl)methyl)benzo[d]thiazol-2-yl)amino)cyclohexanol;
(1R,2R)-2-((4-chloro-6-((6-morpholinoimidazo[1,2-b]pyridazin-3-yl)methyl)benzo[d]thiazol-2-yl)amino)cyclohexanol;
2-((4-chloro-6-((6-morpholinoimidazo[1,2-b]pyridazin-3-yl)methyl)benzo[d]thiazol-2-yl)amino)cyclohexanol;
(1R,2R)-2-((6-(imidazo[2,1-b]thiazol-5-ylmethyl)benzo[d]thiazol-2-yl)amino)cyclohexanol;
2-((6-(imidazo[2,1-b]thiazol-5-ylmethyl)benzo[d]thiazol-2-yl)amino)cyclohexanol;
(1R,2R)-2-((6-((6-chloroimidazo[1,2-b]pyridazin-3-yl)methyl)benzo[d]thiazol-2-yl)amino)cyclohexanol;
2-((6-((6-chloroimidazo[1,2-b]pyridazin-3-yl)methyl)benzo[d]thiazol-2-yl)amino)cyclohexanol;
(1R,2R)-2-((6-((6-(1H-pyrazol-1-yl)imidazo[1,2-a]pyridin-3-yl)methyl)benzo[d]thiazol-2-yl)amino)cyclohexanol;
2-((6-((6-(1H-pyrazol-1-yl)imidazo[1,2-a]pyridin-3-yl)methyl)benzo[d]thiazol-2-yl)amino)cyclohexanol;
(1R,2R)-2-((6-((5-(1H-pyrazol-1-yl)-1H-benzo[d]imidazol-1-yl)methyl)benzo[d]thiazol-2-yl)amino)cyclohexanol;
2-((6-((5-(1H-pyrazol-1-yl)-1H-benzo[d]imidazol-1-yl)methyl)benzo[d]thiazol-2-yl)amino)cyclohexanol;
(1R,2R)-2-((6-((5-(1H-1,2,4-triazol-1-yl)-1H-benzo[d]imidazol-1-yl)methyl)benzo[d]thiazol-2-yl)amino)cyclohexanol;
2-((6-((5-(1H-1,2,4-triazol-1-yl)-1H-benzo[d]imidazol-1-yl)methyl)benzo[d]thiazol-2-yl)amino)cyclohexanol;
(1S,2R)-2-((6-((6-fluoro-3H-imidazo[4,5-b]pyridin-3-yl)methyl)benzo[d]thiazol-2-yl)amino)cyclohexanol;
2-((6-((6-fluoro-3H-imidazo[4,5-b]pyridin-3-yl)methyl)benzo[d]thiazol-2-yl)amino)cyclohexanol;
trans-4-((6-((6-fluoro-3H-imidazo[4,5-b]pyridin-3-yl)methyl)benzo[d]thiazol-2-yl)amino)cyclohexanol;
4-((6-((6-fluoro-3H-imidazo[4,5-b]pyridin-3-yl)methyl)benzo[d]thiazol-2-yl)amino)cyclohexanol;
(1R,2R)-2-((6-((3H-imidazo[4,5-b]pyridin-3-yl)methyl)-7-fluorobenzo[d]thiazol-2-yl)amino)cyclohexanol;
2-((6-((3H-imidazo[4,5-b]pyridin-3-yl)methyl)-7-fluorobenzo[d]thiazol-2-yl)amino)cyclohexanol;
(1R,2R)-2-((6-((6-methoxyimidazo[1,2-a]pyridin-3-yl)methyl)benzo[d]thiazol-2-yl)amino)cyclohexanol;
2-((6-((6-methoxyimidazo[1,2-a]pyridin-3-yl)methyl)benzo[d]thiazol-2-yl)amino)cyclohexanol;
(1R,2R)-2-((6-((3H-imidazo[4,5-b]pyridin-3-yl)methyl)-4-bromobenzo[d]thiazol-2-yl)amino)cyclohexanol;
2-((6-((3H-imidazo[4,5-b]pyridin-3-yl)methyl)-4-bromobenzo[d]thiazol-2-yl)amino)cyclohexanol;
(1R,2R)-2-((6-((7-(1H-pyrazol-1-yl)imidazo[1,2-a]pyridin-3-yl)methyl)benzo[d]thiazol-2-yl)amino)cyclohexanol;

2-((6-((7-(1H-pyrazol-1-yl)imidazo[1,2-a]pyridin-3-yl)methyl)benzo[d]thiazol-2-yl)amino)cyclohexanol;

(1R,2R)-2-((6-((3H-imidazo[4,5-b]pyridin-3-yl)methyl)-4,7-difluorobenzo[d]thiazol-2-yl)amino)cyclohexanol;

2-((6-((3H-imidazo[4,5-b]pyridin-3-yl)methyl)-4,7-difluorobenzo[d]thiazol-2-yl)amino)cyclohexanol;

(1R,2R)-2-((6-((7-(1H-1,2,4-triazol-1-yl)imidazo[1,2-a]pyridin-3-yl)methyl)benzo[d]thiazol-2-yl)amino)cyclohexanol;

2-((6-((7-(1H-1,2,4-triazol-1-yl)imidazo[1,2-a]pyridin-3-yl)methyl)benzo[d]thiazol-2-yl)amino)cyclohexanol;

1-((2-(((1R,2R)-2-hydroxycyclohexyl)amino)benzo[d]oxazol-6-yl)methyl)-1H-benzo[d]imidazole-5-carbonitrile;

1-((2-((2-hydroxycyclohexyl)amino)benzo[d]oxazol-6-yl)methyl)-1H-benzo[d]imidazole-5-carbonitrile;

(1R,2R)-2-((6-((5-(2-morpholinoethoxy)-1H-benzo[d]imidazol-1-yl)methyl)benzo[d]thiazol-2-yl)amino)cyclohexanol;

2-((6-((5-(2-morpholinoethoxy)-1H-benzo[d]imidazol-1-yl)methyl)benzo[d]thiazol-2-yl)amino)cyclohexanol;

(1R,2R)-2-((6-((5-(2-hydroxyethoxy)-1H-benzo[d]imidazol-1-yl)methyl)benzo[d]thiazol-2-yl)amino)cyclohexanol;

2-((6-((5-(2-hydroxyethoxy)-1H-benzo[d]imidazol-1-yl)methyl)benzo[d]thiazol-2-yl)amino)cyclohexanol;

1-((2-(((1R,2R)-2-hydroxycyclohexyl)amino)benzo[d]thiazol-6-yl)methyl)-N-methyl-1H-benzo[d]imidazole-5-carboxamide;

1-((2-((2-hydroxycyclohexyl)amino)benzo[d]thiazol-6-yl)methyl)-N-methyl-1H-benzo[d]imidazole-5-carboxamide;

(1R,2R)-2-((6-((5-(3,6-dihydro-2H-pyran-4-yl)-1H-benzo[d]imidazol-1-yl)methyl)benzo[d]thiazol-2-yl)amino)cyclohexanol;

2-((6-((5-(3,6-dihydro-2H-pyran-4-yl)-1H-benzo[d]imidazol-1-yl)methyl)benzo[d]thiazol-2-yl)amino)cyclohexanol;

(1R,2R)-2-((6-((5-(3,3,3-trifluoroprop-1-en-2-yl)-1H-benzo[d]imidazol-1-yl)methyl)benzo[d]thiazol-2-yl)amino)cyclohexanol;

2-((6-((5-(3,3,3-trifluoroprop-1-en-2-yl)-1H-benzo[d]imidazol-1-yl)methyl)benzo[d]thiazol-2-yl)amino)cyclohexanol;

(R)—N-(cyclohex-2-en-1-yl)-6-((6-fluoro-3H-imidazo[4,5-b]pyridin-3-yl)methyl)benzo[d]thiazol-2-amine;

N-(cyclohex-2-en-1-yl)-6-((6-fluoro-3H-imidazo[4,5-b]pyridin-3-yl)methyl)benzo[d]thiazol-2-amine;

(1R,2R)-2-((6-((6-bromoimidazo[1,2-b]pyridazin-3-yl)methyl)benzo[d]thiazol-2-yl)amino)cyclohexanol;

2-((6-((6-bromoimidazo[1,2-b]pyridazin-3-yl)methyl)benzo[d]thiazol-2-yl)amino)cyclohexanol;

(1R,2R)-2-((6-((6-(4-methylpiperazin-1-yl)imidazo[1,2-b]pyridazin-3-yl)methyl)benzo[d]thiazol-2-yl)amino)cyclohexanol;

2-((6-((6-(4-methylpiperazin-1-yl)imidazo[1,2-b]pyridazin-3-yl)methyl)benzo[d]thiazol-2-yl)amino)cyclohexanol;

(trans-4-((6-((6-fluoro-3H-imidazo[4,5-b]pyridin-3-yl)methyl)benzo[d]thiazol-2-yl)amino)cyclohexyl)methanol;

(cis-4-((6-((6-fluoro-3H-imidazo[4,5-b]pyridin-3-yl)methyl)benzo[d]thiazol-2-yl)amino)cyclohexyl)methanol;

4-((6-((6-fluoro-3H-imidazo[4,5-b]pyridin-3-yl)methyl)benzo[d]thiazol-2-yl)amino)cyclohexyl)methanol;

6-((6-fluoro-3H-imidazo[4,5-b]pyridin-3-yl)methyl)-N-((1R,2R)-2-(methylthio)cyclohexyl)benzo[d]thiazol-2-amine;

6-((6-fluoro-3H-imidazo[4,5-b]pyridin-3-yl)methyl)-N-(2-(methylthio)cyclohexyl)benzo[d]thiazol-2-amine;

(1R,2R)-2-((6-((5-(oxetan-3-yloxy)-1H-benzo[d]imidazol-1-yl)methyl)benzo[d]thiazol-2-yl)amino)cyclohexanol;

2-((6-((5-(oxetan-3-yloxy)-1H-benzo[d]imidazol-1-yl)methyl)benzo[d]thiazol-2-yl)amino)cyclohexanol;

(1R,2R)-2-((6-((5-vinyl-1H-benzo[d]imidazol-1-yl)methyl)benzo[d]thiazol-2-yl)amino)cyclohexanol;

2-((6-((5-vinyl-1H-benzo[d]imidazol-1-yl)methyl)benzo[d]thiazol-2-yl)amino)cyclohexanol;

(1R,2R)-2-((6-((5-(cyclohex-1-en-1-yl)-1H-benzo[d]imidazol-1-yl)methyl)benzo[d]thiazol-2-yl)amino)cyclohexanol;

2-((6-((5-(cyclohex-1-en-1-yl)-1H-benzo[d]imidazol-1-yl)methyl)benzo[d]thiazol-2-yl)amino)cyclohexanol;

(1R,2R)-2-((6-((5-(1-methyl-3-(trifluoromethyl)-1H-pyrazol-4-yl)-1H-benzo[d]imidazol-1-yl)methyl)benzo[d]thiazol-2-yl)amino)cyclohexanol;

2-((6-((5-(1-methyl-3-(trifluoromethyl)-1H-pyrazol-4-yl)-1H-benzo[d]imidazol-1-yl)methyl)benzo[d]thiazol-2-yl)amino)cyclohexanol;

(1R,2R)-2-((6-((5-fluoroimidazo[1,2-a]pyridin-3-yl)methyl)benzo[d]thiazol-2-yl)amino)cyclohexanol;

2-((6-((5-fluoroimidazo[1,2-a]pyridin-3-yl)methyl)benzo[d]thiazol-2-yl)amino)cyclohexanol;

(1R,2R)-2-((6-((7-morpholinoimidazo[1,2-a]pyridin-3-yl)methyl)benzo[d]thiazol-2-yl)amino)cyclohexanol;

2-((6-((7-morpholinoimidazo[1,2-a]pyridin-3-yl)methyl)benzo[d]thiazol-2-yl)amino)cyclohexanol;

(1R,2R)-2-((6-((7-(4-methylpiperazin-1-yl)imidazo[1,2-a]pyridin-3-yl)methyl)benzo[d]thiazol-2-yl)amino)cyclohexanol;

2-((6-((7-(4-methylpiperazin-1-yl)imidazo[1,2-a]pyridin-3-yl)methyl)benzo[d]thiazol-2-yl)amino)cyclohexanol;

((1R,2R)-2-((6-((5,7-dimethyl-1H-benzo[d]imidazol-1-yl)methyl)benzo[d]thiazol-2-yl)amino)cyclohexanol;

2-((6-((5,7-dimethyl-1H-benzo[d]imidazol-1-yl)methyl)benzo[d]thiazol-2-yl)amino)cyclohexanol;

(1R,2R)-2-((6-((5-bromo-7-methyl-1H-benzo[d]imidazol-1-yl)methyl)benzo[d]thiazol-2-yl)amino)cyclohexanol;

2-((6-((5-bromo-7-methyl-1H-benzo[d]imidazol-1-yl)methyl)benzo[d]thiazol-2-yl)amino)cyclohexanol;

6-((6-fluoro-3H-imidazo[4,5-b]pyridin-3-yl)methyl)-N-phenylbenzo[d]thiazol-2-amine;

((1R,3R)-3-((6-((6-fluoro-3H-imidazo[4,5-b]pyridin-3-yl)methyl)benzo[d]thiazol-2-yl)amino)cyclohexyl)methanol;

3-((6-((6-fluoro-3H-imidazo[4,5-b]pyridin-3-yl)methyl)benzo[d]thiazol-2-yl)amino)cyclohexyl)methanol;

(1R,2S,3R)-3-((6-((6-fluoro-3H-imidazo[4,5-b]pyridin-3-yl)methyl)benzo[d]thiazol-2-yl)amino)cyclohexane-1,2-diol;

3-((6-((6-fluoro-3H-imidazo[4,5-b]pyridin-3-yl)methyl)benzo[d]thiazol-2-yl)amino)cyclohexane-1,2-diol;

((1S,3R)-3-((6-((6-fluoro-3H-imidazo[4,5-b]pyridin-3-yl)methyl)benzo[d]thiazol-2-yl)amino)cyclohexyl)methanol;

3-((6-((6-fluoro-3H-imidazo[4,5-b]pyridin-3-yl)methyl)benzo[d]thiazol-2-yl)amino)cyclohexyl)methanol;

6-chloro-1-((2-(((1R,2R)-2-hydroxycyclohexyl)amino)benzo[d]oxazol-6-yl)methyl)-1H-benzo[d]imidazole-5-carbonitrile;

6-chloro-1-((2-((2-hydroxycyclohexyl)amino)benzo[d]oxazol-6-yl)methyl)-1H-benzo[d]imidazole-5-carbonitrile;

2-((1-((2-(((1R,2R)-2-hydroxycyclohexyl)amino)benzo[d]thiazol-6-yl)methyl)-1H-benzo[d]imidazol-5-yl)oxy)acetonitrile;

2-((1-((2-((2-hydroxycyclohexyl)amino)benzo[d]thiazol-6-yl)methyl)-1H-benzo[d]imidazol-5-yl)oxy)acetonitrile;
6-((6-fluoro-3H-imidazo[4,5-b]pyridin-3-yl)methyl)-N-(2-methoxyphenyl)benzo[d]thiazol-2-amine;
N-((1R,2R)-2-chlorocyclohexyl)-6-((6-fluoro-3H-imidazo[4,5-b]pyridin-3-yl)methyl)benzo[d]thiazol-2-amine;
N-(2-chlorocyclohexyl)-6-((6-fluoro-3H-imidazo[4,5-b]pyridin-3-yl)methyl)benzo[d]thiazol-2-amine;
1-(3-((2-(((1R,2R)-2-hydroxycyclohexyl)amino)benzo[d]thiazol-6-yl)methyl)imidazo[1,2-a]pyridin-7-yl)piperidin-4-ol;
1-(3-((2-((2-hydroxycyclohexyl)amino)benzo[d]thiazol-6-yl)methyl)imidazo[1,2-a]pyridin-7-yl)piperidin-4-ol;
1-(3-((2-(((1R,2R)-2-hydroxycyclohexyl)amino)benzo[d]thiazol-6-yl)methyl)imidazo[1,2-a]pyridin-7-yl)ethanone;
1-(3-((2-((2-hydroxycyclohexyl)amino)benzo[d]thiazol-6-yl)methyl)imidazo[1,2-a]pyridin-7-yl)ethanone;
(1R,2R)-2-((6-((7-(1-hydroxyethyl)imidazo[1,2-a]pyridin-3-yl)methyl)benzo[d]thiazol-2-yl)amino)cyclohexanol;
2-((6-((7-(1-hydroxyethyl)imidazo[1,2-a]pyridin-3-yl)methyl)benzo[d]thiazol-2-yl)amino)cyclohexanol;
1-(3-((2-(((1R,2R)-2-hydroxycyclohexyl)amino)benzo[d]thiazol-6-yl)methyl)imidazo[1,2-a]pyridin-7-yl)ethanone oxime;
1-(3-((2-((2-hydroxycyclohexyl)amino)benzo[d]thiazol-6-yl)methyl)imidazo[1,2-a]pyridin-7-yl)ethanone oxime;
(1R,2R)-2-((6-((5-bromo-7-fluoro-1H-benzo[d]imidazol-1-yl)methyl)benzo[d]thiazol-2-yl)amino)cyclohexanol;
2-((6-((5-bromo-7-fluoro-1H-benzo[d]imidazol-1-yl)methyl)benzo[d]thiazol-2-yl)amino)cyclohexanol;
1-(3-((2-(((1R,2R)-2-hydroxycyclohexyl)amino)benzo[d]thiazol-6-yl)methyl)imidazo[1,2-a]pyridin-7-yl)ethanone O-methyl oxime;
1-(3-((2-((2-hydroxycyclohexyl)amino)benzo[d]thiazol-6-yl)methyl)imidazo[1,2-a]pyridin-7-yl)ethanone O-methyl oxime;
(1R,2R)-2-((6-((9H-benzo[d]imidazo[1,2-c]imidazol-3-yl)methyl)benzo[d]thiazol-2-yl)amino)cyclohexanol;
2-((6-((9H-benzo[d]imidazo[1,2-c]imidazol-3-yl)methyl)benzo[d]thiazol-2-yl)amino)cyclohexanol;
7-fluoro-1-((2-(((1R,2R)-2-hydroxycyclohexyl)amino)benzo[d]thiazol-6-yl)methyl)-1H-benzo[d]imidazole-5-carbonitrile;
7-fluoro-1-((2-((2-hydroxycyclohexyl)amino)benzo[d]thiazol-6-yl)methyl)-1H-benzo[d]imidazole-5-carbonitrile;
(1R,2R)-2-((6-((7-fluoro-5-vinyl-1H-benzo[d]imidazol-1-yl)methyl)benzo[d]thiazol-2-yl)amino)cyclohexanol;
2-((6-((7-fluoro-5-vinyl-1H-benzo[d]imidazol-1-yl)methyl)benzo[d]thiazol-2-yl)amino)cyclohexanol;
(1R,2R)-2-((6-((5-(3,6-dihydro-2H-pyran-4-yl)-7-fluoro-1H-benzo[d]imidazol-1-yl)methyl)benzo[d]thiazol-2-yl)amino)cyclohexanol;
2-((6-((5-(3,6-dihydro-2H-pyran-4-yl)-7-fluoro-1H-benzo[d]imidazol-1-yl)methyl)benzo[d]thiazol-2-yl)amino)cyclohexanol;
(1R,2R)-2-((6-((5-morpholino-1H-benzo[d]imidazol-1-yl)methyl)benzo[d]thiazol-2-yl)amino)cyclohexanol;
2-((6-((5-morpholino-1H-benzo[d]imidazol-1-yl)methyl)benzo[d]thiazol-2-yl)amino)cyclohexanol;
1-(1-((2-(((1R,2R)-2-hydroxycyclohexyl)amino)benzo[d]thiazol-6-yl)methyl)-1H-benzo[d]imidazol-5-yl)piperidin-2-one;
1-(1-((2-((2-hydroxycyclohexyl)amino)benzo[d]thiazol-6-yl)methyl)-1H-benzo[d]imidazol-5-yl)piperidin-2-one;
(1R,2R)-2-((6-((5-(1H-pyrazol-3-yl)-1H-benzo[d]imidazol-1-yl)methyl)benzo[d]thiazol-2-yl)amino)cyclohexanol;
2-((6-((5-(1H-pyrazol-3-yl)-1H-benzo[d]imidazol-1-yl)methyl)benzo[d]thiazol-2-yl)amino)cyclohexanol;
(1R,2R)-2-((6-((6-(trifluoromethyl)-3H-imidazo[4,5-b]pyridin-3-yl)methyl)benzo[d]thiazol-2-yl)amino)cyclohexanol;
2-((6-((6-(trifluoromethyl)-3H-imidazo[4,5-b]pyridin-3-yl)methyl)benzo[d]thiazol-2-yl)amino)cyclohexanol;
(1S,2S)-2-((6-((6-fluoro-3H-imidazo[4,5-b]pyridin-3-yl)methyl)benzo[d]thiazol-2-yl)amino)cyclohexanol;
2-((6-((6-fluoro-3H-imidazo[4,5-b]pyridin-3-yl)methyl)benzo[d]thiazol-2-yl)amino)cyclohexanol;
(1R,2R)-2-((6-((7-(1H-imidazol-1-yl)imidazo[1,2-a]pyridin-3-yl)methyl)benzo[d]thiazol-2-yl)amino)cyclohexanol;
2-((6-((7-(1H-imidazol-1-yl)imidazo[1,2-a]pyridin-3-yl)methyl)benzo[d]thiazol-2-yl)amino)cyclohexanol;
(1R,2R)-2-((6-((7-(2H-1,2,3-triazol-2-yl)imidazo[1,2-a]pyridin-3-yl)methyl)benzo[d]thiazol-2-yl)amino)cyclohexanol;
2-((6-((7-(2H-1,2,3-triazol-2-yl)imidazo[1,2-a]pyridin-3-yl)methyl)benzo[d]thiazol-2-yl)amino)cyclohexanol;
(1R,2R)-2-((6-((7-vinylimidazo[1,2-a]pyridin-3-yl)methyl)benzo[d]thiazol-2-yl)amino)cyclohexanol;
2-((6-((7-vinylimidazo[1,2-a]pyridin-3-yl)methyl)benzo[d]thiazol-2-yl)amino)cyclohexanol;
(1R,2R)-2-((6-((7-(allyloxy)imidazo[1,2-a]pyridin-3-yl)methyl)benzo[d]thiazol-2-yl)amino)cyclohexanol;
2-((6-((7-(allyloxy)imidazo[1,2-a]pyridin-3-yl)methyl)benzo[d]thiazol-2-yl)amino)cyclohexanol;
(1R,2R)-2-((6-((7-(1H-1,2,3-triazol-1-yl)imidazo[1,2-a]pyridin-3-yl)methyl)benzo[d]thiazol-2-yl)amino)cyclohexanol;
2-((6-((7-(1H-1,2,3-triazol-1-yl)imidazo[1,2-a]pyridin-3-yl)methyl)benzo[d]thiazol-2-yl)amino)cyclohexanol;
N-((1R,2S)-2-chlorocyclohexyl)-6-((6-fluoro-3H-imidazo[4,5-b]pyridin-3-yl)methyl)benzo[d]thiazol-2-amine;
N-(2-chlorocyclohexyl)-6-((6-fluoro-3H-imidazo[4,5-b]pyridin-3-yl)methyl)benzo[d]thiazol-2-amine;
3-amino-1-((2-(((1R,2R)-2-hydroxycyclohexyl)amino)benzo[d]thiazol-6-yl)methyl)pyrazin-2(1H)-one acetate salt;
3-amino-1-((2-(((1R,2R)-2-hydroxycyclohexyl)amino)benzo[d]thiazol-6-yl)methyl)pyrazin-2(1H)-one;
3-amino-1-((2-((2-hydroxycyclohexyl)amino)benzo[d]thiazol-6-yl)methyl)pyrazin-2(1H)-one;
3-((2-(((1R,2R)-2-hydroxycyclohexyl)amino)benzo[d]thiazol-6-yl)methyl)imidazo[1,2-b]pyridazine-6-carbonitrile;
3-((2-((2-hydroxycyclohexyl)amino)benzo[d]thiazol-6-yl)methyl)imidazo[1,2-b]pyridazine-6-carbonitrile;
1-((2-(((1R,2R)-2-hydroxycyclohexyl)amino)benzo[d]thiazol-6-yl)methyl)-3-morpholinopyrazin-2(1H)-one;
1-((2-((2-hydroxycyclohexyl)amino)benzo[d]thiazol-6-yl)methyl)-3-morpholinopyrazin-2(1H)-one;
(3-((2-(((1R,2R)-2-hydroxycyclohexyl)amino)benzo[d]thiazol-6-yl)methyl)imidazo[1,2-a]pyridin-7-yl)(pyrrolidin-1-yl)methanone;
(3-((2-((2-hydroxycyclohexyl)amino)benzo[d]thiazol-6-yl)methyl)imidazo[1,2-a]pyridin-7-yl)(pyrrolidin-1-yl)methanone;
(E)-3-(1-((2-(((1R,2R)-2-hydroxycyclohexyl)amino)benzo[d]thiazol-6-yl)methyl)-1H-benzo[d]imidazol-5-yl)acrylic acid;
(E)-3-(1-((2-((2-hydroxycyclohexyl)amino)benzo[d]thiazol-6-yl)methyl)-1H-benzo[d]imidazol-5-yl)acrylic acid;

3-(1-((2-((2-hydroxycyclohexyl)amino)benzo[d]thiazol-6-yl)methyl)-1H-benzo[d]imidazol-5-yl)acrylic acid;

(1R,2R)-2-((6-((5-(1,2,3,6-tetrahydropyridin-4-yl)-1H-benzo[d]imidazol-1-yl)methyl)benzo[d]thiazol-2-yl)amino)cyclohexanol;

2-((6-((5-(1,2,3,6-tetrahydropyridin-4-yl)-1H-benzo[d]imidazol-1-yl)methyl)benzo[d]thiazol-2-yl)amino)cyclohexanol;

(1R,2R)-2-((6-((5-(1H-imidazol-1-yl)-1H-benzo[d]imidazol-1-yl)methyl)benzo[d]thiazol-2-yl)amino)cyclohexanol;

2-((6-((5-(1H-imidazol-1-yl)-1H-benzo[d]imidazol-1-yl)methyl)benzo[d]thiazol-2-yl)amino)cyclohexanol;

(1R,2R)-2-((6-((5-(2-methyl-2H-tetrazol-5-yl)-1H-benzo[d]imidazol-1-yl)methyl)benzo[d]thiazol-2-yl)amino)cyclohexanol;

2-((6-((5-(2-methyl-2H-tetrazol-5-yl)-1H-benzo[d]imidazol-1-yl)methyl)benzo[d]thiazol-2-yl)amino)cyclohexanol;

(1S,2R,3R)-3-((6-((6-fluoro-3H-imidazo[4,5-b]pyridin-3-yl)methyl)benzo[d]thiazol-2-yl)amino)cyclohexane-1,2-diol;

3-((6-((6-fluoro-3H-imidazo[4,5-b]pyridin-3-yl)methyl)benzo[d]thiazol-2-yl)amino)cyclohexane-1,2-diol;

(1R,2S,3R)-3-((6-((7-(1H-pyrazol-1-yl)imidazo[1,2-a]pyridin-3-yl)methyl)benzo[d]thiazol-2-yl)amino)cyclohexane-1,2-diol;

3-((6-((7-(1H-pyrazol-1-yl)imidazo[1,2-a]pyridin-3-yl)methyl)benzo[d]thiazol-2-yl)amino)cyclohexane-1,2-diol;

(1R,2S,3R)-3-((6-((5-methoxy-1H-benzo[d]imidazol-1-yl)methyl)benzo[d]thiazol-2-yl)amino)cyclohexane-1,2-diol;

3-((6-((5-methoxy-1H-benzo[d]imidazol-1-yl)methyl)benzo[d]thiazol-2-yl)amino)cyclohexane-1,2-diol;

(1R,2S,3R)-3-((6-((7-(2H-1,2,3-triazol-2-yl)imidazo[1,2-a]pyridin-3-yl)methyl)benzo[d]thiazol-2-yl)amino)cyclohexane-1,2-diol;

3-((6-((7-(2H-1,2,3-triazol-2-yl)imidazo[1,2-a]pyridin-3-yl)methyl)benzo[d]thiazol-2-yl)amino)cyclohexane-1,2-diol;

(1R,2S,3R)-3-((6-((5-vinyl-1H-benzo[d]imidazol-1-yl)methyl)benzo[d]thiazol-2-yl)amino)cyclohexane-1,2-diol;

3-((6-((5-vinyl-1H-benzo[d]imidazol-1-yl)methyl)benzo[d]thiazol-2-yl)amino)cyclohexane-1,2-diol;

(1R,2S,3R)-3-((6-((5-(oxetan-3-yloxy)-1H-benzo[d]imidazol-1-yl)methyl)benzo[d]thiazol-2-yl)amino)cyclohexane-1,2-diol;

3-((6-((5-(oxetan-3-yloxy)-1H-benzo[d]imidazol-1-yl)methyl)benzo[d]thiazol-2-yl)amino)cyclohexane-1,2-diol;

(1R,2S,3R)-3-((6-((6-(1H-1,2,4-triazol-1-yl)-3H-imidazo[4,5-b]pyridin-3-yl)methyl)benzo[d]thiazol-2-yl)amino)cyclohexane-1,2-diol;

3-((6-((6-(1H-1,2,4-triazol-1-yl)-3H-imidazo[4,5-b]pyridin-3-yl)methyl)benzo[d]thiazol-2-yl)amino)cyclohexane-1,2-diol;

(1R,2S,3R)-3-((6-((5-morpholino-1H-benzo[d]imidazol-1-yl)methyl)benzo[d]thiazol-2-yl)amino)cyclohexane-1,2-diol;

3-((6-((5-morpholino-1H-benzo[d]imidazol-1-yl)methyl)benzo[d]thiazol-2-yl)amino)cyclohexane-1,2-diol;

(1R,2S,3R)-3-((6-((5-(2-methyl-2H-tetrazol-5-yl)-1H-benzo[d]imidazol-1-yl)methyl)benzo[d]thiazol-2-yl)amino)cyclohexane-1,2-diol; and 3-((6-((5-(2-methyl-2H-tetrazol-5-yl)-1H-benzo[d]imidazol-1-yl)methyl)benzo[d]thiazol-2-yl)amino)cyclohexane-1,2-diol.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a CH bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

In another embodiment, provided herein are methods of using the disclosed compounds and compositions, or pharmaceutically acceptable salts, solvates, hydrates, clathrates, single stereoisomers, mixture of stereoisomers or racemic mixture of stereoisomers thereof, for the local or systemic treatment or prophylaxis of human and veterinary diseases, disorders and conditions modulated or otherwise affected mediated via CSF1R, FLT3, KIT, and/or PDGFRβ kinase activity.

C. FORMULATION OF PHARMACEUTICAL COMPOSITIONS

The pharmaceutical compositions provided herein contain therapeutically effective amounts of one or more of compounds provided herein that are useful in the prevention, treatment, or amelioration of CSF1R, FLT3, KIT, and/or PDGFRβ kinase mediated diseases or one or more of the symptoms thereof.

The compositions contain one or more compounds provided herein. The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art.

In the compositions, effective concentrations of one or more compounds or pharmaceutically acceptable salts, solvates, hydrates, clathrates, single stereoisomers, mixture of stereoisomers or racemic mixture of stereoisomers or prodrug is (are) mixed with a suitable pharmaceutical carrier or vehicle. The concentrations of the compounds in the compositions are effective for delivery of an amount, upon administration, that treats, prevents, or ameliorates one or more of the symptoms of CSF1R, FLT3, KIT, and/or PDGFRβ kinase mediated diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of CSF1R, FLT3, KIT, and/or PDGFRβ kinase mediated diseases.

Typically a therapeutically effective dosage should produce a serum concentration of active ingredient of from about 1 ng/ml to about 5-100 μg/ml. The pharmaceutical compositions typically should provide a dosage of from about 10 mg to about 4000 mg of compound per kilogram of body weight per day. Pharmaceutical dosage unit forms are prepared to provide from about 10 mg to about 1000 mg and in certain embodiments, from about 10 mg to about 500 mg, from about 20 mg to about 250 mg or from about 25 mg to about 100 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing CSF1R, FLT3, KIT, and/or PDGFRβ kinase mediated diseases. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including, but not limited to, orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. In one embodiment, the effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001%-100% active ingredient, in certain embodiments, about 0.1-85%, typically about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as CSF1R, FLT3, KIT, and/or PDGFRβ kinase mediated diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. In one embodiment, the composition is administered as an aqueous solution with hydroxypropyl-beta-cyclodextrin (HPBCD) as an excipient. In one embodiment, the aqueous solution contains about 1% to about 50% HPBCD. In one embodiment, the aqueous solution contains about 1%, 3%, 5%, 10% or about 20% HPBCD.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose, hydroxypropyl-beta-cyclodextrin (HPBCD) or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, 100-500 mg, 10-500 mg, 5-250 mg or 25-100 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used. In another embodiment, polymeric materials can be used. In yet another embodiment, a controlled release system can be placed in proximity of the therapeutic target, i.e., thus requiring only a fraction of the systemic dose. In some embodiments, a controlled release device is introduced into a subject in proximity of the site of inappropriate immune activation or a tumor. The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

D. EVALUATION OF THE ACTIVITY OF THE COMPOUNDS

Standard physiological, pharmacological and biochemical procedures are available for testing the compounds to identify those that possess biological activities that modulate the activity of CSF1R, FLT3, KIT, and/or PDGFRβ kinase.

Such assays include, for example, biochemical assays such as binding assays, radioactivity incorporation assays, as well as a variety of cell based assays.

In certain embodiments, the compounds disclosed herein are tested in an M-NFS-60 cell proliferation assay to determine their cellular potency against CSF1R. M-NFS-60s are mouse monocytic cells that depend on the binding of the ligand M-CSF to its receptor, CSF1R, to proliferate. Inhibition of CSF1R kinase activity will cause reduced growth and/or cell death. This assay assesses the potency of compounds as CSF1R inhibitors by measuring the reduction of Alamar Blue reagent by viable cells. An exemplary assay is described in the Examples section.

In certain embodiments, competition binding assays were performed as described in Fabian et al., *Nature Biotechnology* 2005, 23, 329-336.

In one embodiment, the compounds provided herein were found to have Kds of about or less than about 150 nM against FLT3 kinase. In one embodiment, the compounds provided herein have Kds of about 1 nM or less, 3 nM or less, 5 nM or less, 0.1-2 nM, 2-5 nM, 5-10 nM, 10-25 nM, 25-50 nM, or 5-150 nM, against FLT3 kinase. In one embodiment, the compounds provided herein have Kds of less than about 50, 25, 10, 5, 4, 3, 2, or 1 nM against FLT3 kinase. In another embodiment, the compounds provided herein have Kds of about or less than about 5 nM, 3 nM or 1 nM against FLT3 kinase.

In one embodiment, the compounds provided herein were found to have Kds of about or less than about 50 nM against KIT kinase. In one embodiment, the compounds provided herein have Kds of about 1 nM or less, 3 nM or less, 0.1-2 nM, 2-5 nM, 5-10 nM, or 10-25 M, against KIT kinase. In one embodiment, the compounds provided herein have Kds of less than about 10, 5, 4, 3, 2 or 1 nM against KIT kinase. In another embodiment, the compounds provided herein have Kds of about or less than about 5 nM, 3 nM or 1 nM against KIT kinase.

In one embodiment, the compounds provided herein were found to have Kds of about or less than about 100 nM or 50 nM against PDGFRβ kinase. In one embodiment, the compounds provided herein have Kds of about 1 nM or less, 3 nM or less, 0.1-2 nM, 2-5 nM, 5-10 nM, or 10-25 M, against PDGFRβ kinase. In one embodiment, the compounds provided herein have Kds of less than about 10, 5, 4, 3, 2 or 1 nM against PDGFRβ kinase. In another embodiment, the compounds provided herein have Kds of about or less than about 5 nM, 3 nM or 1 nM against PDGFRβ kinase.

In one embodiment, the compounds provided herein were found to have Kds of about or less than about 1 µM against CSF1R kinase. In one embodiment, the compounds provided herein were found to have Kds of less than about 1, 0.5, 0.1 or 0.01 µM against CSF1R kinase. In one embodiment, the compounds provided herein were found to have Kds of less than about 300, 200, 100, 50, 10, 5, 4, 3, 2, or 1 nM against CSF1R kinase. In another embodiment, the compounds provided herein were found to have Kds of about or less than about 5 nM, 3 nM or 1 nM against CSF1R kinase.

E. METHODS OF USE OF THE COMPOUNDS AND COMPOSITIONS

Also provided herein are methods of using the disclosed compounds and compositions, or pharmaceutically acceptable salts, solvates, hydrates, clathrates, single stereoisomers, mixture of stereoisomers, racemic mixture of stereoisomers or prodrugs thereof, for the treatment, prevention, or amelioration of a disease or disorder that is mediated or otherwise affected via protein kinase activity or one or more symptoms of diseases or disorders that are mediated or otherwise affected via protein kinase activity (see, Krause and Van Etten, *N Engl J Med* (2005) 353(2):172-187, Blume-Jensen and Hunter, *Nature* (2001) 411(17): 355-365 and Plowman et al., DN&P, 7:334-339 (1994)).

In certain embodiments, provided herein are methods of treating the following diseases or disorders:

1) carcinomas include Kit-mediated and/or CSF1R-mediated carcinomas, adenocarcinoma, squamous cell carcinoma, adenosquamous carcinoma, teratocarcinoma, head and neck cancer, brain cancer, intracranial carcinoma, glioblastoma including PDGFR-mediated glioblastoma, glioblastoma multiforme including PDGFR-mediated glioblastoma multiforme, neuroblastoma, cancer of the larynx, multiple endocrine neoplasias 2A and 2B (MENS 2A and MENS 2B) including RET-mediated MENS, thyroid cancer, including sporadic and familial medullary thyroid carcinoma, papillary thyroid carcinoma, parathyroid carcinoma including any RET-mediated thyroid carcinoma, follicular thyroid cancer, anaplastic thyroid cancer, bronchial carcinoid, oat cell carcinoma, lung cancer, small-cell lung cancer including flt-3 and/or Kit-mediated small cell lung cancer, stomach/gastric cancer, gastrointestinal cancer, gastrointestinal stromal tumors (GIST) including Kit-mediated GIST and PDGFRα-mediated GIST, colon cancer, colorectal cancer, pancreatic cancer, islet cell carcinoma, hepatic/liver cancer, metastases to the liver, bladder cancer, renal cell cancer including PDGFR-mediated renal cell cancer, cancers of the genitourinary tract, ovarian cancer including Kit-mediated and/or PDGFR-mediated and/or CSF1R-mediated ovarian cancer, endometrial cancer including CSF1R-mediated endometrial cancer, cervical cancer, breast cancer including Flt-3-mediated and/or PDGFR-mediated and/or CSF1R-mediated breast cancer, prostate cancer including Kit-mediated prostate cancer, germ cell tumors including Kit-mediated germ cell tumors, seminomas including Kit-mediated seminomas, dysgerminomas, including Kit-mediated dysgerminomas, melanoma including PDGFR-mediated melanoma, metastases to the bone including CSF1R-mediated bone metastases, metastatic tumors including VEGFR-mediated and/or CSF1R metastatic tumors, stromal tumors, neuroendocrine tumors, tumor angiogenesis including VEGFR-mediated and/or CSF1R-mediated tumor angiogenesis, mixed mesodermal tumors;

2) sarcomas including PDGFR-mediated sarcomas, osteosarcoma, osteogenic sarcoma, bone cancer, glioma including PDGFR-mediated and/or CSF1R-mediated glioma, astrocytoma, vascular tumors including VEGFR-mediated vascular tumors, Kaposi's sarcoma, carcinosarcoma, hemangiosarcomas including VEGFR3-mediated hemangiosarcomas, lymphangiosarcoma including VEGFR3-mediated lymphangiosarcoma;

3) liquid tumors, myeloma, multiple myeloma, leukemia, myeloproliferative diseases (MPD), acute myeloid leukemia (AML) including flt-3 mediated and/or KIT-mediated and/or CSF1R-mediated acute myeloid leukemia, chronic myeloid leukemias (CML) including Flt-3-mediated and/or PDGFR-mediated chronic myeloid leukemia, myelodysplastic leukemias including Flt-3-mediated myelodysplastic leukemia, acute megakaryoblastic leukemia CSF1R-mediated acute megakaryoblastic leukemia, myelodysplastic syndrome, including Flt-3 mediated and/or Kit-mediated myelodysplastic syndrome (MDS), idiopathic hypereosinophilic syndrome (HES) including PDGFR-mediated HES, chronic eosinophilic leukemia (CEL) including PDGFR-mediated CEL, chronic myelomonocytic leukemia (CMML), mast cell leukemia including Kit-mediated mast cell leukemia, or systemic mastocytosis including Kit-mediated systemic mastocytosis; and 4) lymphoma, Hodgkin's lymphoma, lymphoproliferative diseases, acute lymphoblastic leukemia (ALL), B-cell acute lymphoblastic leukemias, T-cell acute lymphoblastic leukemias, natural killer (NK) cell leukemia, B-cell lymphoma, T-cell lymphoma, and natural killer (NK) cell lymphoma, any of which may be Flt-3 mediated and/or PDGFR-mediated, Langerhans cell histiocytosis including CSF1R-mediated and flt-3-mediated Langerhans cell histiocytosis, mast cell tumors and mastocytosis;

2) Nonmalignant proliferation diseases; atherosclerosis including CSF1R-mediated atherosclerosis or PDGFR-mediated atherosclerosis, restenosis following vascular angioplasty including PDGFR-mediated restenosis, and fibroproliferative disorders such as obliterative bronchiolitis and idiopathic myelofibrosis, both of which may be PDGFR-mediated, pulmonary fibrosis and also obesity and obesity-induced insulin resistance, either of which may be CSF1R mediated;

5) Inflammatory diseases or immune disorders including autoimmune diseases, which include, but is not limited to, tissue transplant rejection, graft-versus-host disease, wound healing, kidney disease, multiple sclerosis, thyroiditis, type 1 diabetes, sarcoidosis, allergic rhinitis, nephritis, Alzheimer's disease, inflammatory bowel disease including Crohn's disease and ulcerative colitis (UC), systemic lupus erythematosis (SLE), cutaneous lupus erythematosis (SLE), lupus nephritis, glomerular nephritis, arthritis, osteoarthritis, rheumatoid arthritis, psoriatic arthritis, inflammatory arthritis, osteoporosis, asthma and chronic obstructive pulmonary disease (COPD), allergic asthma, ankylosing spondylitis, including any of the aforementioned diseases which are flt-3-mediated and/or CSF1R-mediated and/or KIT-mediated;

6) Bone diseases including disorders relating to the mineralization, formation and resorption of the bone, including but not limited to osteoporosis, glucocorticoid-induced osteoporosis, periodontitis, bone loss due to cancer therapy, periprosthetic osteolysis, Paget's disease, hypercalcemia, hypercalcemia of malignancy, osteomyelitis, and bone pain; and 7) Infectious diseases mediated either via viral or bacterial pathogens and sepsis, including KIT-mediated and/or CSF1R-mediated sepsis.

Also provided are methods of modulating the activity, or subcellular distribution, of kinases in a cell, tissue or whole organism, using the compounds and compositions provided herein, or pharmaceutically acceptable derivatives thereof. In one embodiment, provided herein are methods of modulating the activity of FLT3 activity in a cell, tissue or whole organism using the compounds and compositions provided herein, or pharmaceutically acceptable derivatives thereof. In one embodiment, provided herein are methods of modulating the activity of CSF1R activity in a cell, tissue or whole organism using the compounds and compositions provided herein, or pharmaceutically acceptable derivatives thereof. In one embodiment, provided herein are methods of modulating the activity of KIT activity in a cell, tissue or whole organism using the compounds and compositions provided herein, or pharmaceutically acceptable derivatives thereof.

In one embodiment, the methods provided herein are for treating tumor-associated osteolysis, osteoporosis including ovariectomy-induced bone loss, orthopedic implant failure, renal inflammation and glomerulonephritis, transplant rejection including renal and bone marrow allografts and skin xenograft, obesity, Alzheimer's Disease and Langerhans cell histiocytosis. In one embodiment, the methods provided herein are for treating chronic skin disorders including psoriasis.

In another embodiment, a method for treating periodontitis, Langerhans cell histiocytosis, osteoporosis, Paget's disease of bone (PDB), bone loss due to cancer therapy, periprosthetic osteolysis, glucocorticoid-induced osteoporosis, rheumatoid arthritis, psoriatic arthritis, osteoarthritis, and/or inflammatory arthritis is provided herein.

In one embodiment, the methods provided herein are for treating bone diseases including disorders relating to the mineralization, formation and resorption of the bone, including but not limited to osteoporosis, Paget's disease, hypercalcemia, hypercalcemia of malignancy, osteolysis, osteomyelitis, and bone pain.

In one embodiment, the methods provided herein are for treating cancers, including, but not limited to liquid tumors, head and neck cancer, (originating in lip, oral cavity, oropharynx, hypopharynx, larynx, nasopharynx, nasal cavity and paranasal sinuses or salivary glands); lung cancer, including small cell lung cancer, non-small cell lung cancer; gastrointestinal tract cancers, including esophageal cancer, gastric cancer, colorectal cancer, anal cancer, pancreatic cancer, liver cancer, gallbladder cancer, extrahepatic bile duct cancer, cancer of the ampulla of water; breast cancer; gynecologic cancers, including, cancer of uterine cervix, cancer of the uterine body, vaginal cancer, vulvar cancer, ovarian cancer, gestational trophoblastic cancer neoplasia; testicular cancer; urinary tract cancers, including, renal cancer, urinary bladder cancer, prostate cancer, penile cancer, urethral cancer; neurologic tumors; tenosynovial giant cell tumors, endocrine neoplasms, including carcinoid and islet cell tumors, pheochromocytoma, adrenal cortical carcinoma, parathyroid carcinoma and metastases to endocrine glands. In another embodiment, the methods provided herein are for treating carcinoma, breast cancer, ovarian cancer, bone metastases, osteoporosis, Paget's disease, hypercalcemia, hypercalcemia of malignancy, osteolysis, osteomyelitis, bone pain, inflammatory bowel disease (IBD), Crohn's disease, ulcerative colitis (UC), systemic lupus erythematosis (SLE), lupus nephritis, glomerular nephritis, arthritis, osteoarthritis, rheumatoid arthritis, osteoporosis, asthma, allergic asthma, chronic obstructive pulmonary disease (COPD), psoriasis, ankylosing spondylitis, and multiple sclerosis. In another embodiment, provided herein are methods for treating inflammatory diseases of the eye including conjunctivitis, uveitis, iritis, scleritis, blepheritis, meibomitis and optical neuritis. In yet another embodiment, provided herein are methods for treating glaucoma, diabetic retinopathy and macular degeneration.

Further examples of cancers are basal cell carcinoma; squamous cell carcinoma; chondrosarcoma (a cancer arising in cartilage cells); mesenchymal-chondrosarcoma; soft tissue sarcomas, including, malignant tumours that may arise in any of the mesodermal tissues (muscles, tendons, vessels that carry blood or lymph, joints and fat); soft tissue sarcomas include; alveolar soft-part sarcoma, angiosarcoma, fibrosarcoma, leiomyosarcoma, liposarcoma, malignant fibrous histiocytoma, hemangiopericytoma, mesenchymoma, schwannoma, peripheral neuroectodermal tumours, rhabdomyosarcoma, synovial sarcoma; gestational trophoblastic tumour (malignancy in which the tissues formed in the uterus following conception become cancerous); Hodgkin's lymphoma and laryngeal cancer.

In one embodiment, the cancer is a leukemia. In one embodiment, the leukemia is chronic lymphocytic leukemia, chronic myelocytic leukemia, acute lymphoblastic leukemia, acute myeloid leukemia, and acute myeloblastic leukemia.

In another embodiment, the leukemia is acute leukemia. In one embodiment, the acute leukemia is acute myeloid leukemia (AML). In one embodiment, acute myeloid leukemia is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the acute myeloid leukemia is undifferentiated AML (M0). In yet another embodiment, the acute myeloid leukemia is myeloblastic leukemia (M1). In yet another embodiment, the acute myeloid leukemia is myeloblastic leukemia (M2). In yet another embodiment, the acute myeloid leukemia is promyelocytic leukemia (M3 or M3 variant [M3V]). In yet another embodiment, the acute myeloid leukemia is myelomonocytic leukemia (M4 or M4 variant with eosinophilia [M4E]). In yet another embodiment, the acute myeloid leukemia is monocytic leukemia (M5). In yet another embodiment, the acute myeloid leukemia is erythroleukemia (M6). In yet another embodiment, the acute myeloid leukemia is megakaryoblastic leukemia (M7). In yet another embodiment, the acute myeloid leukemia is promyelocytic leukemia In another embodiment, the acute leukemia is acute lymphocytic leukemia (ALL). In one embodiment, the acute lymphocytic leukemia is leukemia that originates in the blast cells of the bone marrow (B-cells), thymus (T-cells), or lymph nodes. The acute lymphocytic leukemia is categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In another embodiment, the acute lymphocytic leukemia originates in the blast cells of the bone marrow (B-cells). In yet another embodiment, the acute lymphocytic leukemia originates in the thymus (T-cells). In yet another embodiment, the acute lymphocytic leukemia originates in the lymph nodes. In yet another embodiment, the acute lymphocytic leukemia is L1 type characterized by mature-appearing lymphoblasts (T-cells or pre-B-cells). In yet another embodiment, the acute lymphocytic leukemia is L2 type characterized by immature and pleomorphic (variously shaped) lymphoblasts (T-cells or pre-B-cells). In yet another embodiment, the acute lymphocytic leukemia is L3 type characterized by lymphoblasts (B-cells; Burkitt's cells).

In yet another embodiment, the leukemia is T-cell leukemia. In one embodiment, the T-cell leukemia is peripheral T-cell leukemia, T-cell lymphoblastic leukemia, cutaneous T-cell leukemia, and adult T-cell leukemia. In another embodiment, the T-cell leukemia is peripheral T-cell leukemia. In yet another embodiment, the T-cell leukemia is T-cell lymphoblastic leukemia. In yet another embodiment, the T-cell leukemia is cutaneous T-cell leukemia. In still another embodiment, the T-cell leukemia is adult T-cell leukemia.

In yet another embodiment, the leukemia is Philadelphia positive. In one embodiment, the Philadelphia positive leukemia is Philadelphia positive AML, including, but not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the Philadelphia positive leukemia is Philadelphia positive ALL.

In still another embodiment, the leukemia is drug resistant. In still another embodiment, the gastrointestinal stromal tumor (GIST) is drug resistant. In still another embodiment, the melanoma is drug resistant. In one embodiment, the subject has developed drug resistance to the anticancer therapy.

The cancers to be treated herein may be primary or metastatic. In one embodiment, the cancer is a solid or blood born metastatic tumor. In another embodiment, the cancer is metastatic cancer of bone.

Also provided are methods of modulating the activity, or subcellular distribution, of CSF1R kinase in a cell, tissue or whole organism, using the compounds and compositions provided herein, or pharmaceutically acceptable salts, solvates, hydrates, clathrates, single stereoisomers, mixture of stereoisomers or racemic mixture of stereoisomers thereof.

The active ingredient(s) in one embodiment are administered in an amount sufficient to deliver to a patient a therapeutically effective amount of the active compound in order to e.g., treat the diseases described herein, without causing serious toxic effects in a treated subject.

A typical dose of the compound may be in the range of from about 1 to about 50 mg/kg, from about 1 to about 20 mg/kg, from about 0.1 to about 10 mg/kg, from about 0.5 mg/kg to about 10 mg/kg, of body weight per day, more generally from about 0.1 to about 100 mg/kg body weight of the recipient per day. Alternatively, a typical dose of the compound may be in the range of from about 50 mg to about 500 mg. Lower dosages may be used, for example, doses of about 0.5-100 mg, 0.5-10 mg, or 0.5-5 mg per kilogram body weight per day. Even lower doses may be useful, and thus ranges can include from about 0.1-0.5 mg/kg body weight of the recipient per day. The effective dosage range of the pharmaceutically acceptable derivatives is calculated based on the weight of the parent compound to be delivered. If the derivative compound itself exhibits activity, then the effective dosage can be estimated as above using the weight of the derivative, or by other means known to those of skill in the art.

The compounds are conveniently administered in units of any suitable dosage form, including but not limited to one containing from about 1 to 2000 mg, from about 10 to 1000 mg, or from about 25 to 700 mg of active ingredient per unit dosage form. In one embodiment, the unit dose is selected from 12, 18, 25, 27, 40, 50, 60, 90, 100, 135, 200, 250, 300, 400, 450, 500, 600, 675, 700, 800, 900 and 1000 mgs. For example, an oral dosage of from about 25 to 1000 mg is usually convenient, including in one or multiple dosage forms of 10, 12, 18, 25, 27, 40, 50, 60, 90, 100, 135, 200, 250, 300, 400, 450, 500, 600, 675, 700, 800, 900 or 1000 mgs. In certain embodiments, lower dosages may be used, for example, from about 10-100 or 1-50 mgs. Also contemplated are doses of 0.1-50 mg, 0.1-20 mg, or 0.1-10 mg. Furthermore, lower doses may be utilized in the case of administration by a non-oral route, as for example, by injection or inhalation.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compositions provided herein.

In certain embodiments, the compound or composition provided herein can be administered as a single once-a-day dose (QD) or as divided doses throughout a day. In particular embodiments, the compound or composition is administered four times per day (QID). In particular embodiments, the compound or composition is administered three times per day (TID). In particular embodiments, the compound or composition is administered two times per day (BID). In particular embodiments, the compound or composition is administered once per day (QD).

The administration can also be continuous (i.e., daily for consecutive days or every day) or intermittent. The term "intermittent" or "intermittently" as used herein is intended to mean stopping and starting at either regular or irregular intervals. For example, intermittent administration of the compound of Formula I may be administration for one to six days per week or administration on alternate days.

In one embodiment, the compound or composition provided herein is administered intermittently. In yet another embodiment, the compound or composition provided herein is administered intermittently once weekly, twice weekly or three times weekly. In yet another embodiment, the compound or composition provided herein is administered once weekly. In yet another embodiment, the compound or composition provided herein is administered twice weekly. In yet another embodiment, the compound or composition provided herein is administered three times weekly. In one embodiment, the compound or composition provided herein is administered QD intermittently once weekly, twice weekly or three times weekly. In yet another embodiment, the compound or composition provided herein is administered QD once weekly. In another embodiment, the compound or composition provided herein is administered QD twice weekly. In another embodiment, the compound or composition provided herein is administered QD three times weekly.

In one embodiment, the active ingredient is administered to achieve peak plasma concentrations of the active compound of from about 0.02 to 20 μM, from about 0.2 to about 5 μM or from about 0.5 to 10 μM. For example, this can be achieved by intravenous injection of a 0.1 to 5% solution of active ingredient, optionally in saline, or administered as a bolus of active ingredient. It is to be understood that for any particular subject, specific dosage regimens should be adjusted over time to meet individual needs, and will vary depending upon absorption, inactivation and excretion rates of the drug. The concentrations set forth here are exemplary only and are not intended to limit the scope or practice of the claimed composition. The active ingredient may be administered all at once, or may be divided into a number of smaller doses to be administered at varying intervals of time.

The subject matter has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the examples may be substituted with other suitable reagents. See, e.g., Smith & March, *Advanced Organic Chemistry*, 5$^{th}$ ed. (2001).

F. COMBINATION THERAPY

Furthermore, it will be understood by those skilled in the art that the compounds, isomers, and pharmaceutically acceptable salts, hydrates, solvates provided herein, including pharmaceutical compositions and formulations containing these compounds, can be used in a wide variety of combination therapies to treat the conditions and diseases described above. Thus, also contemplated herein is the use of compounds, and pharmaceutically acceptable salts provided herein in combination with other active pharmaceutical agents for the treatment of the disease/conditions described herein.

In one embodiment, such additional pharmaceutical agents include without limitation anti-cancer agents (including chemotherapeutic agents and anti-proliferative agents), anti-inflammatory agents, immunomodulatory agents or immunosuppressive agents.

In certain embodiments, the anti-cancer agents include anti-metabolites (e.g., 5-fluoro-uracil, cytarabine, clofarabine, methotrexate, fludarabine and others), antimicrotubule agents (e.g., vinca alkaloids such as vincristine, vinblastine; taxanes such as paclitaxel and docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, satraplatin and CI-973), anthracyclines (e.g., doxrubicin and daunorubicin), antitumor antibiotics (e.g., mitomycin, idarubicin, adriamycin and daunomycin), topoisomerase inhibitors (e.g., etoposide and camptothecins), anti-angiogenesis agents (e.g. Sutent®, sorafenib and Bevacizumab) or any other cytotoxic agents, (e.g. estramustine phosphate, prednimustine), hormones or hormone agonists, antagonists, partial agonists or partial antagonists, kinase inhibitors (such as imatinib), and radiation treatment.

In certain embodiments, the anti-inflammatory agents include matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate and salicylsalicyclic acid), COX-1 or COX-2 inhibitors, glucocorticoid receptor agonists (e.g., corticosteroids, methylprednisone, prednisone, and cortisone) or antifolates such as methotrexate.

The compound or composition provided herein, or pharmaceutically acceptable salt of the compound, may be administered simultaneously with, prior to, or after administration of one or more of the above agents.

Pharmaceutical compositions containing a compound provided herein or pharmaceutically acceptable salt thereof, and one or more of the above agents are also provided.

Also provided, in one embodiment, is a combination therapy that treats or prevents the onset of the symptoms, or associated complications of cancer and related diseases and disorders, said therapy comprising the administration to a subject in need thereof, one of the compounds or compositions disclosed herein, or pharmaceutically acceptable salts thereof, with one or more anti-cancer agents. Also provided, in another embodiment, is a combination therapy that treats or prevents the onset of the symptom of osteoporosis and related diseases and disorders, said therapy comprising the administration to a subject in need thereof, one of the compounds or compositions disclosed herein, or pharmaceutically acceptable salts thereof, with one or more anti-inflammatory or immunomodulatory agents. Also provided, in yet another embodiment, is a combination therapy that treats or prevents the onset of the symptom of rheumatoid arthritis and related diseases and disorders, said therapy comprising the administration to a subject in need thereof, one of the compounds or compositions disclosed herein, or pharmaceutically acceptable salts thereof, with one or more anti-inflammatory or immunomodulatory agents.

G. PREPARATION OF COMPOUNDS

Starting materials in the synthesis examples provided herein are either available from commercial sources or via literature procedures (e.g., March *Advanced Organic Chemistry: Reactions, Mechanisms, and Structure*, (1992) 4th Ed.; Wiley Interscience, New York). All commercially available compounds were used without further purification unless otherwise indicated. 300 MHz Proton ($^{1}$H) nuclear magnetic resonance (NMR) spectra were recorded on a Bruker Avance 300 NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low resolution mass spectra (MS) were obtained as electrospray ionization (ESI) mass spectra, which were recorded on a Shimadzu HPLC/MS instrument using reverse-phase conditions (acetonitrile/water, 0.05% acetic acid). Preparative reverse phase HPLC was typically performed using a Varian HPLC system equipped with a Phenomenex phenylhexyl, a Phenomenex Luna C18, or a Varian Pursuit diphenyl reverse phase column; typical elution conditions utilized a gradient containing an increasing composition of organic cosolvent (0.05% HOAc/CH$_3$CN or 0.05% HOAc/MeOH) to aqueous cosolvent (0.05% aq HOAc). Silica gel chromatography was either performed manually, typically following the published procedure for flash chromatography (Still et al. (1978) *J. Org. Chem.* 43:2923), or on an automated system (for example, Biotage SP instrument) using pre-packed silica gel columns.

It is understood that in the following description, combinations of substituents and/or variables of the depicted formulae are permissible only if such contributions result in stable compounds under standard conditions.

It will also be appreciated by those skilled in the art that in the process described below, the functional groups of intermediate compounds may need to be protected by suitable protecting groups. Such functional groups include hydroxy, amino, mercapto and carboxylic acid. Suitable protecting groups for hydroxy include trialkylsilyl or diaryl-alkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T.W. and P.G.M. Wutz, *Protective Groups in Organic Synthesis* (1991), 2nd Ed., Wiley-Interscience.

One of ordinary skill in the art could easily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that the compounds provided herein could exist as one or more isomers, that is, E/Z isomers, enantiomers and/or diastereomers.

Compounds of formula (I) may be generally prepared as depicted in the following schemes, unless otherwise noted, the various substituents are as defined elsewhere herein.

Standard abbreviations and acronyms as defined in *J. Org. Chem.* 2007 72(1): 23A-24A are used herein. Other abbreviations and acronyms used herein are as follows:

| | |
|---|---|
| AcOH | acetic acid |
| DIEA | diisopropylethylamine |
| DCM | dichloromethane |
| DMA | N,N-dimethylacetamide |
| EDCI | N-(3-Dimemylaminopropyl)-N'-ethylcarbodiimide hydrochloride |
| EtOAc | ethyl acetate |
| EtOH | ethanol |
| HATU | O-(7-azabenzotriazol-1yl)-N,N,N',N'-tetramethyluronium hexafluorophosphate |
| HOAc | acetic acid |
| LCMS | liquid chromatography mass spectrometry |
| MeOH | methanol |
| t-BuOK | potassium tert-butoxide |
| TEA | Triethylamine |

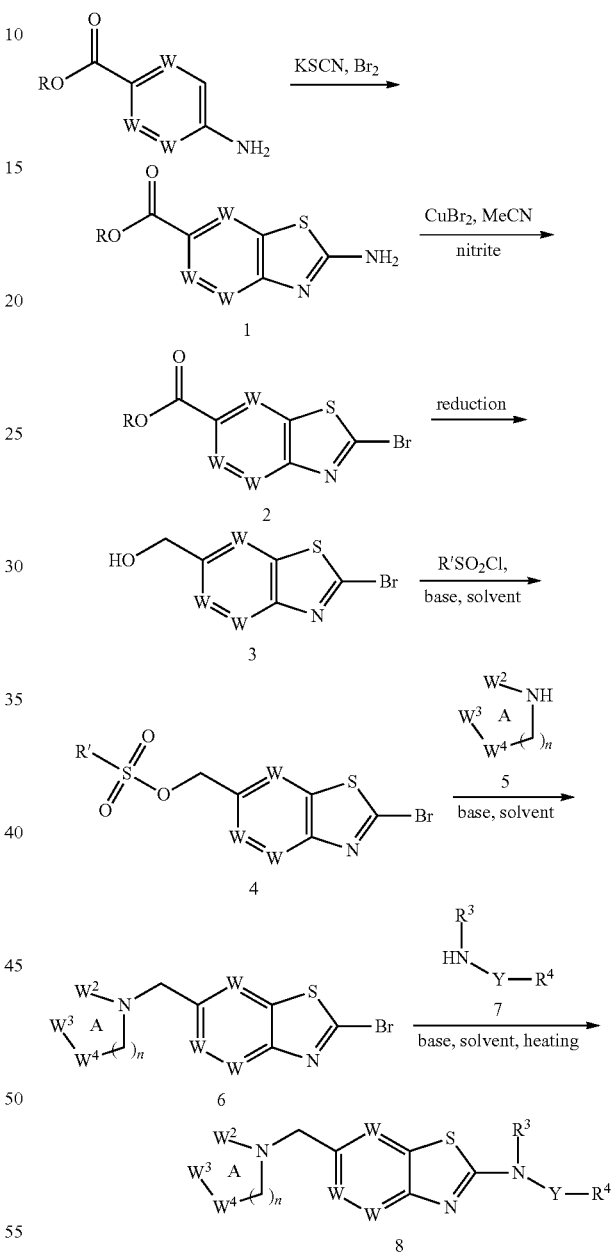

Scheme 1: General synthesis of compounds of formula (I).

R = alkyl
R' = alkyl or aryl, etc.

In an illustrative method, certain compounds of formula (I) may be routinely prepared according to the synthetic route outlined in Scheme 1. The readily available 2-amino-substituted azole compounds 1 are either commercially available or can be prepared from corresponding 4-amino-arylcarboxylates or 4-aminoheteroarylcarboxylates using procedures analogous to those described by Molinos-Gomez, et al. Tetrahedron 61, 9075 (2005). Amines 1 can be converted to bromides 2 under Sandmeyer conditions with a bromine source such as, but not limited to, cupric bromide, using an organic nitrite such as, but not limited to, tert-butyl nitrite or iso-amyl nitrite. The reaction can be conducted in a solvent such as, but not limited to, MeCN. The carboxylates of 2 can be reduced to give alcohols 3 using a reducing nuclear Overhauser effect (NOE) in the NMR of products. The bromides 6 can be treated with amine 7 under nucleophilic substitution conditions at elevated temperature in a solvent such as, but not limited to, DMA or DMF, and promoted with a base such as, but not limited to, DIEA or TEA to afford compounds 8.

Scheme 2: General synthesis of compounds of formula (I).

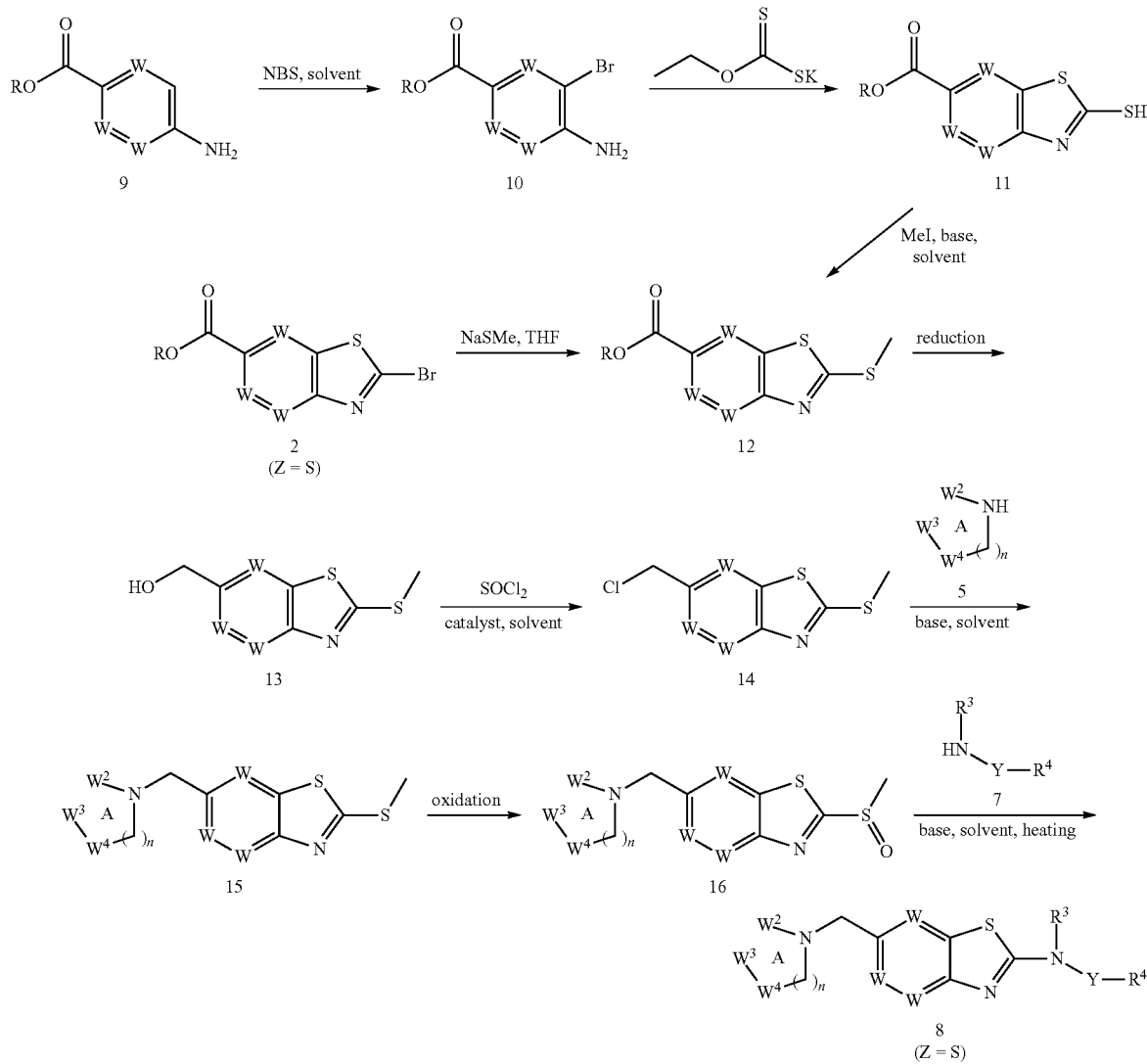

agent such as, but not limited to, DIBAL-H or LiBH$_4$, in a solvent such as, but not limited to, DCM or THF. The alcohols 3 can be converted to sulfonates 4 using a sulfonating agent such as, but not limited to, methanesulfonyl chloride or p-toluenesulfonyl chloride. The reaction can be conducted in a solvent such as, but not limited to, DCM or THF and promoted with a base such as, but not limited to, TEA or pyridine. Alkylation of heteroaryls/heterocyclyls 5 with sulfonate 4 to give compounds 6 can be effected in the presence of a base, such as, but not limited to, NaH or t-BuOK. The alkylation can be conducted in a solvent such as, but not limited to, DMF or THF, at elevated temperature if necessary. The regiochemistry of the alkylation can be discerned by careful examination of the 2-dimensional In an illustrative method, certain compounds of formula (I) may be routinely prepared according to the synthetic route outlined in Scheme 2. The readily available aminoaryl/heteroaryl compounds 9 can be converted to bromides 10 with a bromination agent such as, but not limited to, N-bromosuccimide or bromine. The reaction can be conducted in a solvent such as, but not limited to, MeCN or DCM. Condensation of bromides 10 with potassium O-ethyl carbonodithioate in a solvent such as, but not limited to, DMF under refluxing conditions can afford mercaptan compounds 11, which can be alkylated with iodomethane to give methylsulfides 12. The reaction can be run in a solvent such as, but not limited to, DMF or DMA and promoted with a base such as, but not limited to, K$_2$CO$_3$ or Cs$_2$CO$_3$ at elevated temperature if necessary. Alternatively, methylsulfides 12 can be prepared starting from bromides 2 by treating with sodium thiomethoxide in a solvent, such as, but not limited to, THF or MeCN. The carboxylate group of 12 can be reduced to give alcohols 13 using a reducing agent such as, but not limited to, DIBAL-H or LiBH₄, in a solvent such as, but not limited to, DCM or THF. The alcohols 13 can be converted to chlorides 14 using an agent such as, but not limited to, thionyl chloride or oxalyl chloride, in a solvent such as, but not limited to, DCM. The reaction can be catalyzed by the addition of a small amount of DMF. Alkylation of heteroaryls/heterocyclyls 5 with chlorides 14 to give compounds 15 can be effected using a base such as, but not limited to, NaH or t-BuOK. The alkylation can be conducted in a solvent such as, but not limited to, DMF or THF, at elevated temperature if necessary. The sulfide moiety of 15 can be oxidized to the corresponding sulfoxide using an oxidizing agent such as, but not limited to, m-CPBA or peracetic acid. The oxidation can be conducted in a solvent such as, but not limited to, DCM or AcOH. The sulfinyl group of 16 can be displaced with an amine 7 under nucleophilic substitution conditions at elevated temperature to afford compounds 8. The reaction can be run in a solvent such as, but not limited to, DMA or DMF, and promoted with a base such as, but not limited to, DIEA or TEA.

Scheme 3: General synthesis of compounds of formula (I).

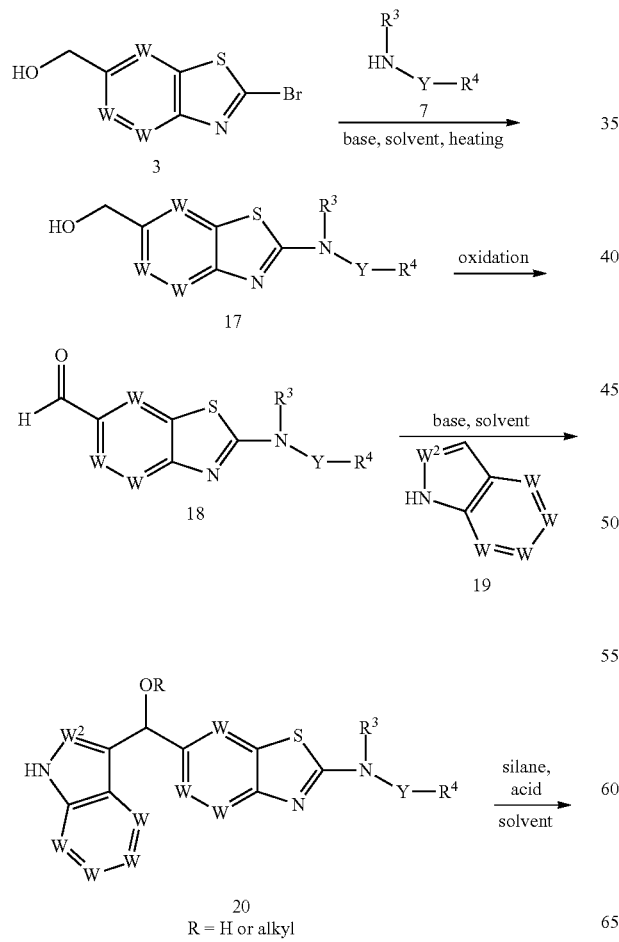

20
R = H or alkyl

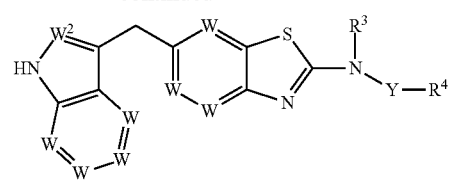

21

In another illustrative method, compounds of formula (I) may also be routinely prepared according to the synthetic route outlined in Scheme 3. Heteroaryl bromides 3 can react with amines 7 as previously described to give products 17, which can be oxidized to the corresponding aldehydes 18 with an oxidizing agent such as, but not limited to, Dess-Martin periodinane or MnO₂, in a solvent such as, but not limited to, DCM or MeCN. Condensation of aldehydes 18 and heteroaryls 19 can provide carbinol compounds 20 (R=H). The condensation can be promoted with a base such as, but not limited to, KOH or NaOH, in a solvent such as, but not limited to, MeOH or EtOH. When the reaction is conducted in an alcohol solvent, products 20 (R=alkyl) can also be isolated. Reduction of compounds 20 with a silane such as, but not limited to, Et₃SiH, promoted with the addition of an acid such as, but not limited to, trifluoroacetic acid or methanesulfonic acid will provide compounds 21. The reduction reaction can be conducted in a solvent such as, but not limited to, DCM or MeCN.

Scheme 4: General synthesis of compounds of formula (I).

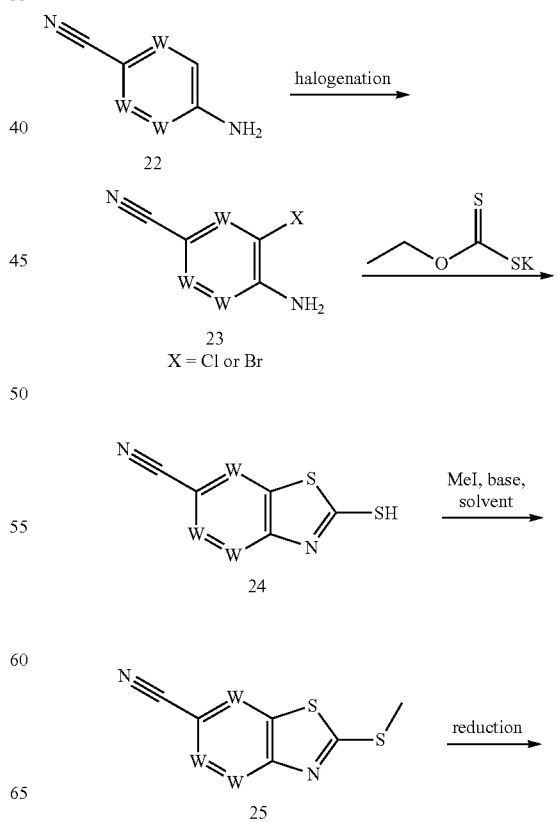

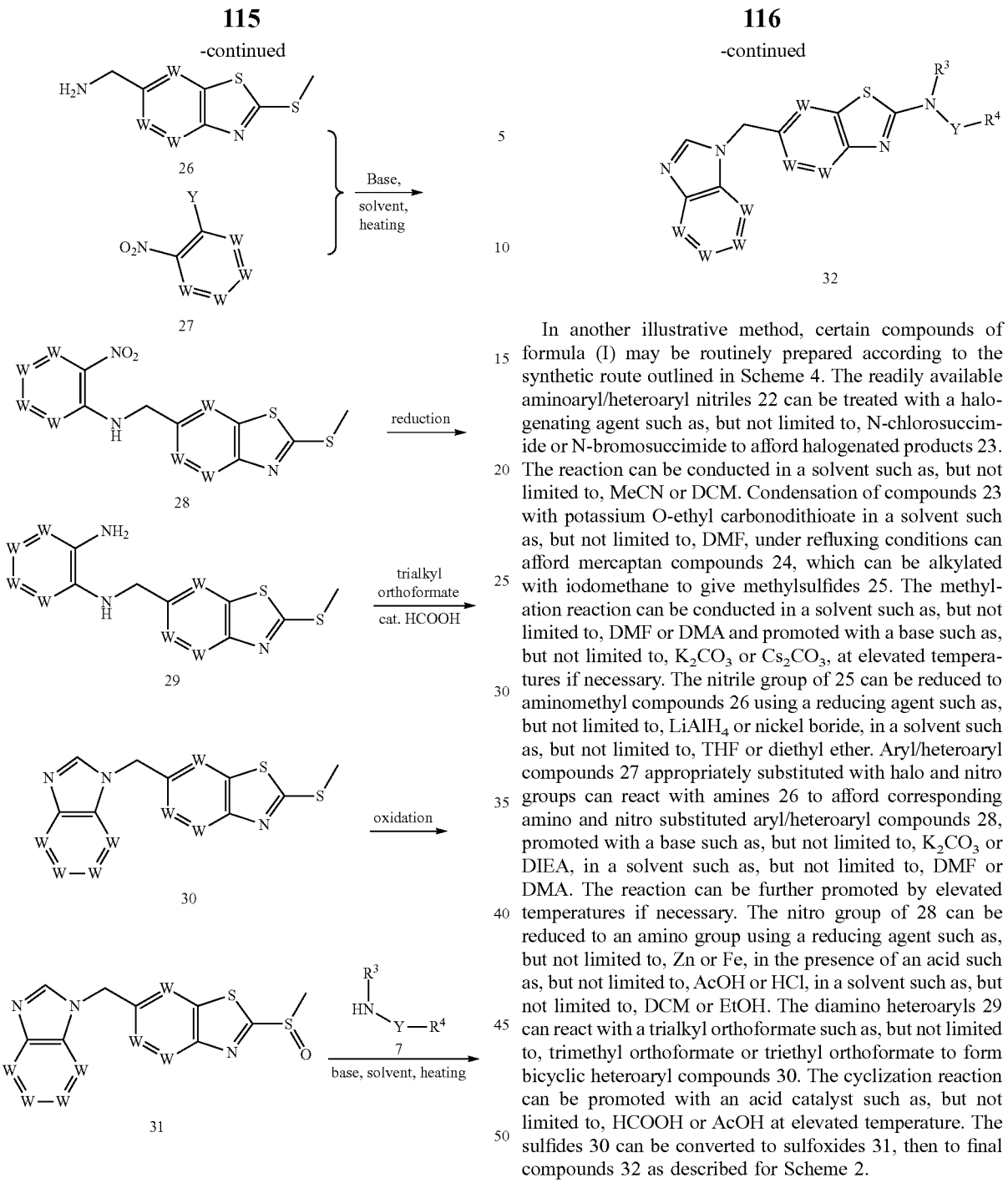

In another illustrative method, certain compounds of formula (I) may be routinely prepared according to the synthetic route outlined in Scheme 4. The readily available aminoaryl/heteroaryl nitriles 22 can be treated with a halogenating agent such as, but not limited to, N-chlorosuccimide or N-bromosuccimide to afford halogenated products 23. The reaction can be conducted in a solvent such as, but not limited to, MeCN or DCM. Condensation of compounds 23 with potassium O-ethyl carbonodithioate in a solvent such as, but not limited to, DMF, under refluxing conditions can afford mercaptan compounds 24, which can be alkylated with iodomethane to give methylsulfides 25. The methylation reaction can be conducted in a solvent such as, but not limited to, DMF or DMA and promoted with a base such as, but not limited to, $K_2CO_3$ or $Cs_2CO_3$, at elevated temperatures if necessary. The nitrile group of 25 can be reduced to aminomethyl compounds 26 using a reducing agent such as, but not limited to, $LiAlH_4$ or nickel boride, in a solvent such as, but not limited to, THF or diethyl ether. Aryl/heteroaryl compounds 27 appropriately substituted with halo and nitro groups can react with amines 26 to afford corresponding amino and nitro substituted aryl/heteroaryl compounds 28, promoted with a base such as, but not limited to, $K_2CO_3$ or DIEA, in a solvent such as, but not limited to, DMF or DMA. The reaction can be further promoted by elevated temperatures if necessary. The nitro group of 28 can be reduced to an amino group using a reducing agent such as, but not limited to, Zn or Fe, in the presence of an acid such as, but not limited to, AcOH or HCl, in a solvent such as, but not limited to, DCM or EtOH. The diamino heteroaryls 29 can react with a trialkyl orthoformate such as, but not limited to, trimethyl orthoformate or triethyl orthoformate to form bicyclic heteroaryl compounds 30. The cyclization reaction can be promoted with an acid catalyst such as, but not limited to, HCOOH or AcOH at elevated temperature. The sulfides 30 can be converted to sulfoxides 31, then to final compounds 32 as described for Scheme 2.

Scheme 5: General synthesis of compounds of formula (I).

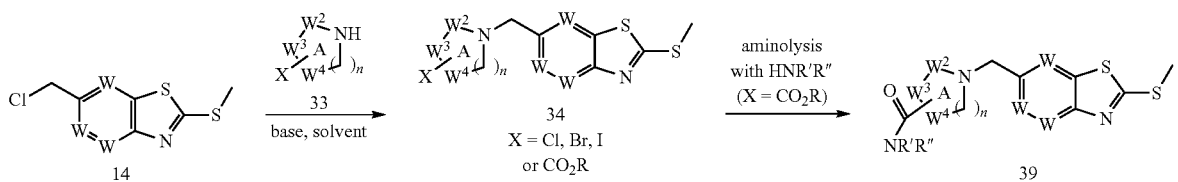

-continued

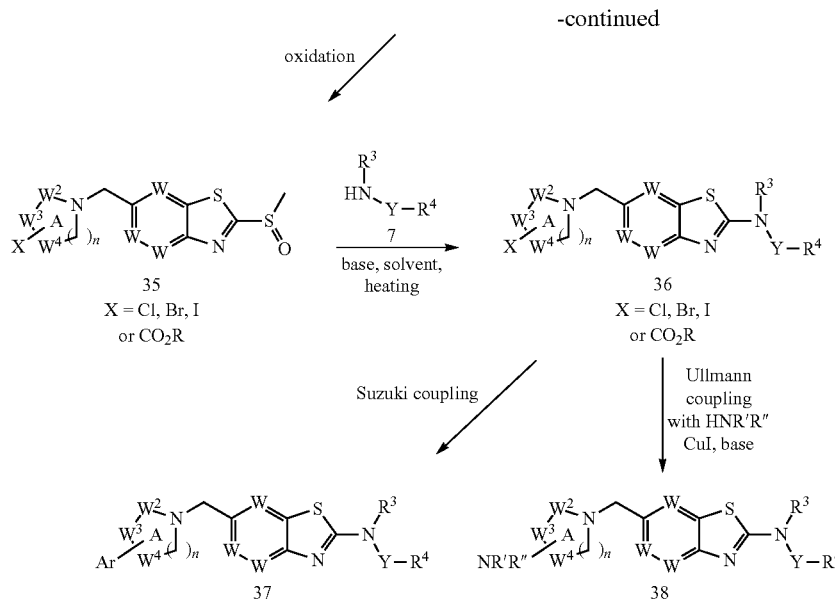

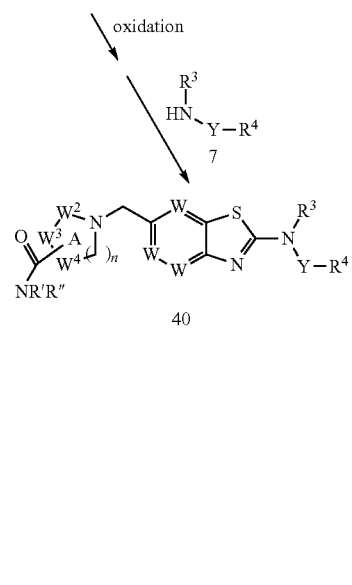

In another illustrative method, compounds of formula (I) may also be routinely prepared according to the synthetic route outlined in Scheme 5. Alkylation of heteroaryls/heterocyclyls 33 with chlorides 14 to give compounds 34 can be effected using a base such as, but not limited to, NaH or t-BuOK. The alkylation can be conducted in a solvent such as, but not limited to, DMF or THF, at elevated temperatures if necessary. Following a two step sequence of oxidation and nucleophilic substitution as described in Scheme 2, the sulfides 34 can be converted first to sulfoxides 35 and then to compounds 36. Suzuki coupling of 36 with aryl or heteroaryl boronic acids or boronate esters catalyzed by a palladium catalyst such as, but not limited to, Pd(dppf)Cl$_2$ or PdCl$_2$(PPh$_3$)$_2$, in a solvent such as, but not limited to, MeCN or 1,4-dioxane, can provide the aryl-heteroaryl/biheteroaryl compounds 37. The Suzuki reaction can be promoted with a base such as, but not limited to, Na$_2$CO$_3$ or KOAc, at elevated temperatures as needed. Compounds 36 can also undergo Ullmann-type coupling with a NH-containing nucleophile such as, but not limited to, an amine or carboxamide, to yield compounds 38. The reaction can be catalyzed with a catalyst such as, but not limited to, copper (I) iodide or copper, promoted with a base such as, but not limited to, K$_2$CO$_3$ or Cs$_2$CO$_3$, and conducted in a solvent such as, but not limited to, DMF or NMP, at elevated temperature. Alternatively, compounds 34 (X=CO$_2$R) can undergo aminolysis with any of various amines to give carboxamides 39. The reaction can be promoted with a reagent such as, but not limited to, trimethylaluminum or triethylaluminum, and conducted in a solvent such as, but not limited to, DCE or DCM. Following a two step sequence of oxidation and nucleophilic substitution as described in Scheme 2, compounds 39 can be converted to final compounds 40.

Scheme 6: General synthesis of compounds of formula (I).

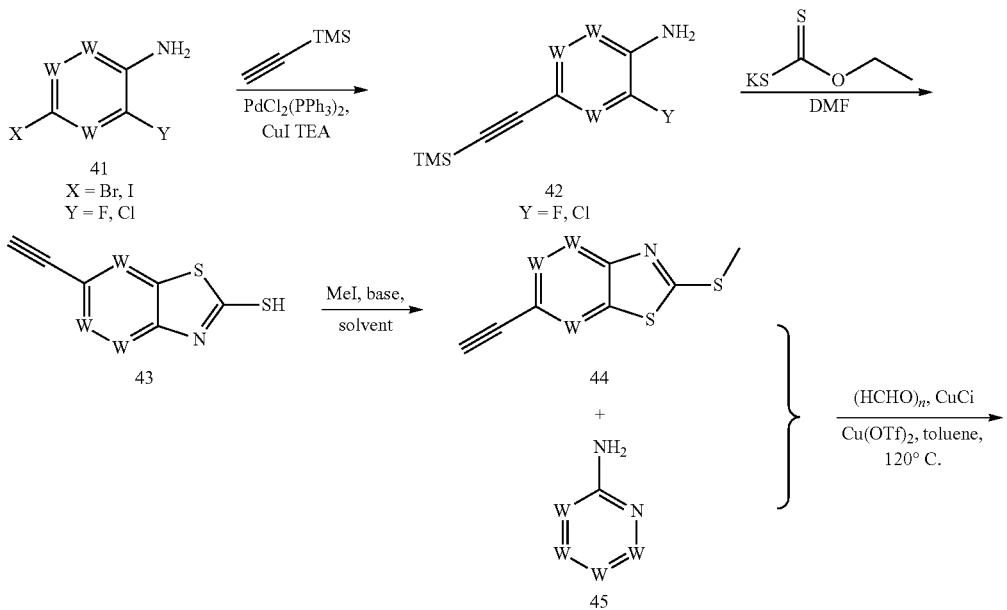

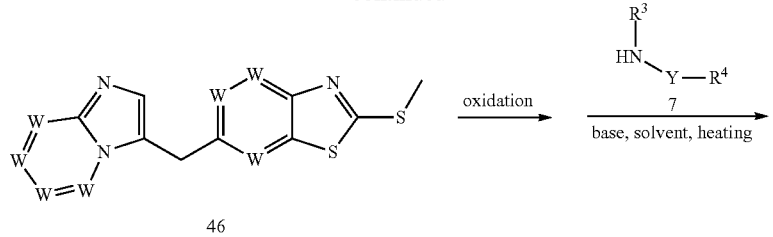

In another illustrative method, compounds of formula (I) may also be routinely prepared according to the synthetic route outlined in Scheme 6. Starting from appropriate aminoaryl/heteroaryl dihalides 41, Sonogashira coupling with ethynyltrimethylsilane catalyzed by a catalyst such as $PdCl_2(PPh_3)_2$ or $PdCl_2(dppf)$ can afford the acetylenes 42. The coupling reaction can be promoted with a base such as, but not limited to, DIEA or TEA, and conducted in a solvent such as, but not limited to, DMF or MeCN, at elevated temperatures if necessary. Condensation of 42 with potassium O-ethyl carbonodithioate in a solvent such as, but not limited to, DMF, with heating can afford mercaptan compounds 43, which can be alkylated with iodomethane to give methylsulfides 44. The reaction can be conducted in a solvent such as, but not limited to, DMF or DMA and promoted with bases such as, but not limited to, $K_2CO_3$ or $Cs_2CO_3$, at elevated temperatures if necessary. Three component cyclization using acetylenes 44, aminoaryl/heteroaryl compounds 45, and paraformaldehyde in a solvent such as, but not limited to, toluene at elevated temperature provides compounds 46. The cyclization can be promoted with a catalyst such as, but not limited to, copper (I) chloride and copper (II) triflate. Following a two step sequence of oxidation and nucleophilic substitution as described in Scheme 2, compounds 46 can be converted to final compounds 47.

Scheme 7: General synthesis of compounds of formula (I).

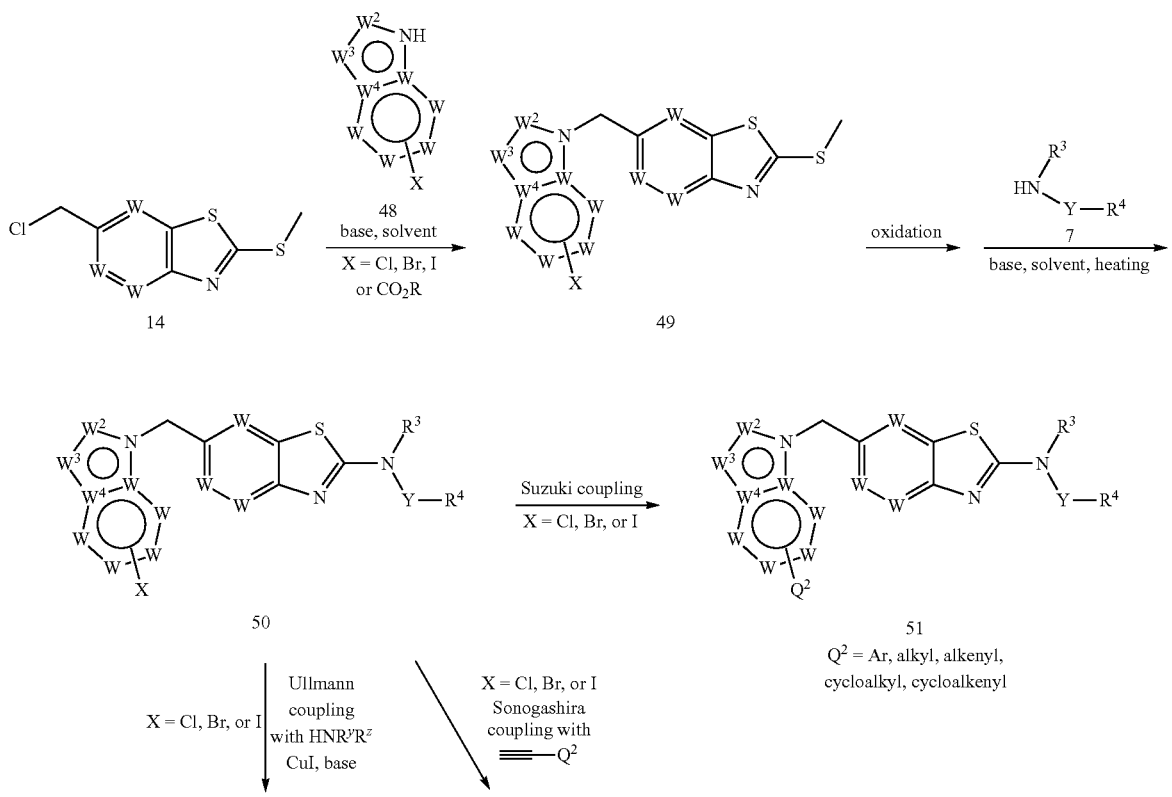

-continued

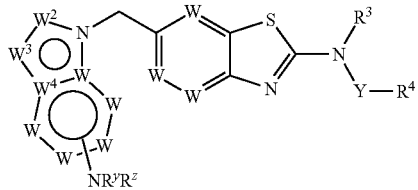

52

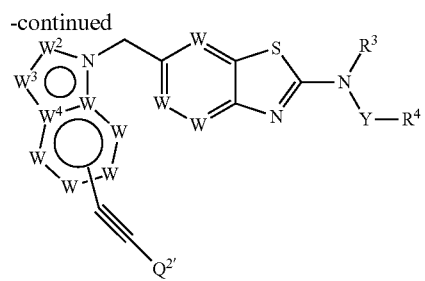

53

In another illustrative method, compounds of formula (I) may also be routinely prepared according to the synthetic route outlined in Scheme 7. Alkylation of heteroaryls 48 (wherein X is connected to W=carbon) with chlorides 14 from Scheme 2 using conditions described in Scheme 2 can provide compounds 49. Following a two step sequence of oxidation and nucleophilic substitution as described in Scheme 2, compounds 49 can be converted to common intermediates 50. As described in Scheme 5, Suzuki coupling of 50 with coupling partners such as, but not limited to, boronic acids, boronate esters, or Molander trifluoroborates can yield compounds 51. Ullmann coupling of 50 with NH-containing nucleophiles such as, but not limited to, amines or carboxamides, under conditions described for Scheme 5 can lead to compounds 52. Sonogashira coupling of 50 with acetylenes under conditions described for Scheme 6 can yield compounds 53.

Scheme 8: General synthesis of compounds of formula (I).

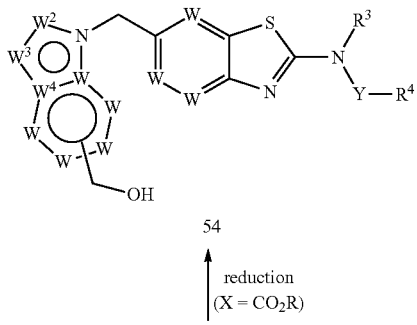

54

↑ reduction
(X = CO$_2$R)

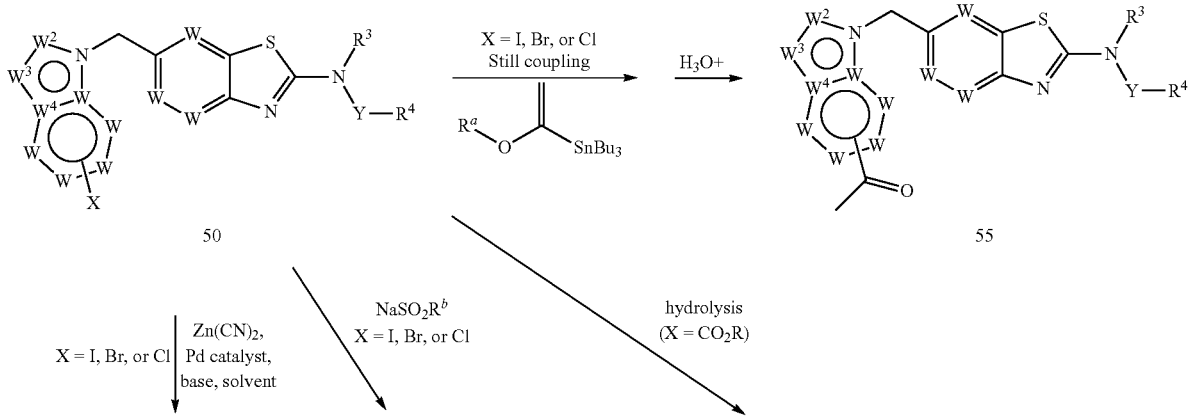

123 124

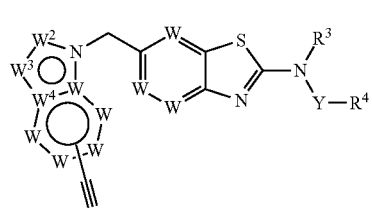

56

-continued

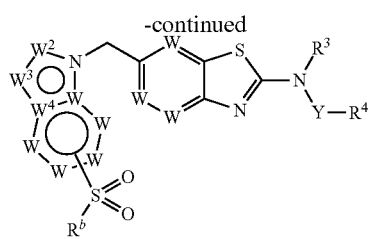

57

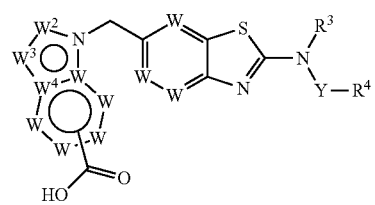

58

HNR^yR^z, amide coupling reagent, base

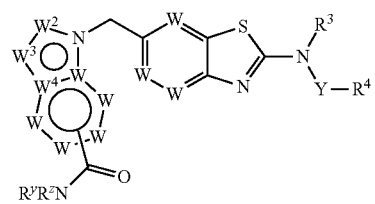

59

$R^a$ and $R^b$ are alkyl, aryl, etc.

In another illustrative method, compounds of formula (I) may also be routinely prepared according to the synthetic route outlined in Scheme 8. Starting from the common intermediates 50 described in Scheme 7, reduction of the carboxylates of 50 (X=CO₂R) using a reducing agent such as, but not limited to, DIBAL-H or LiBH₄, in a solvent such as, but not limited to, DCM or THF, can afford alcohols 54. Stille coupling of 50 (X=I, Br, or Cl) with an appropriate tributyl alkoxyvinyl stannane followed by acidic hydrolysis can yield the acetyl compounds 55. The reaction is typically catalyzed by a catalyst such as Pd(PPh₃)₄ and conducted in a solvent such as, but not limited to, DMF or DMA. Similarly, palladium-mediated cyanation of 50 (X=I, Br, or Cl) with a reagent such as, but not limited to, Zn(CN)₂, can provide the cyano compounds 56. The reaction is catalyzed by catalysts such as PdCl₂(PPh₃)₂ or PdCl₂(dppf), promoted with bases such as, but not limited to, DIEA or TEA, and conducted in solvents such as, but not limited to, DMF or MeCN, at elevated temperature. Analogously, palladium-mediated sulfonylation of 50 (X=I, Br, or Cl) with a reagent such as, but not limited to, sodium methanesulfinate, can generate sulfonyl compounds 57. The reaction is catalyzed by a catalyst such as, but not limited to, copper (I) trifluoromethane-sulfonate benzene complex, promoted with an amine such as, but not limited to, unsymmetrical N,N-dimethylethylene diamine, and conducted in a solvent such as, but not limited to, DMF or DMSO, at elevated temperature. The carboxylate of common intermediates 50 (X=CO₂R) can be hydrolyzed using a base such as, but not limited to, NaOH or KOH, in a solvent such as, but not limited to, MeOH or THF, to give carboxylic acids 58. Coupling of acids 58 with any of various amines using peptide coupling agents such as, but not limited to, EDCI or HATU, can afford the carboxamides 59. The reaction can be promoted with a base such as, but not limited to, DIEA or TEA and conducted in a solvent such as, but not limited to, DMF or THF.

Scheme 9: General synthesis of compounds of formula (I).

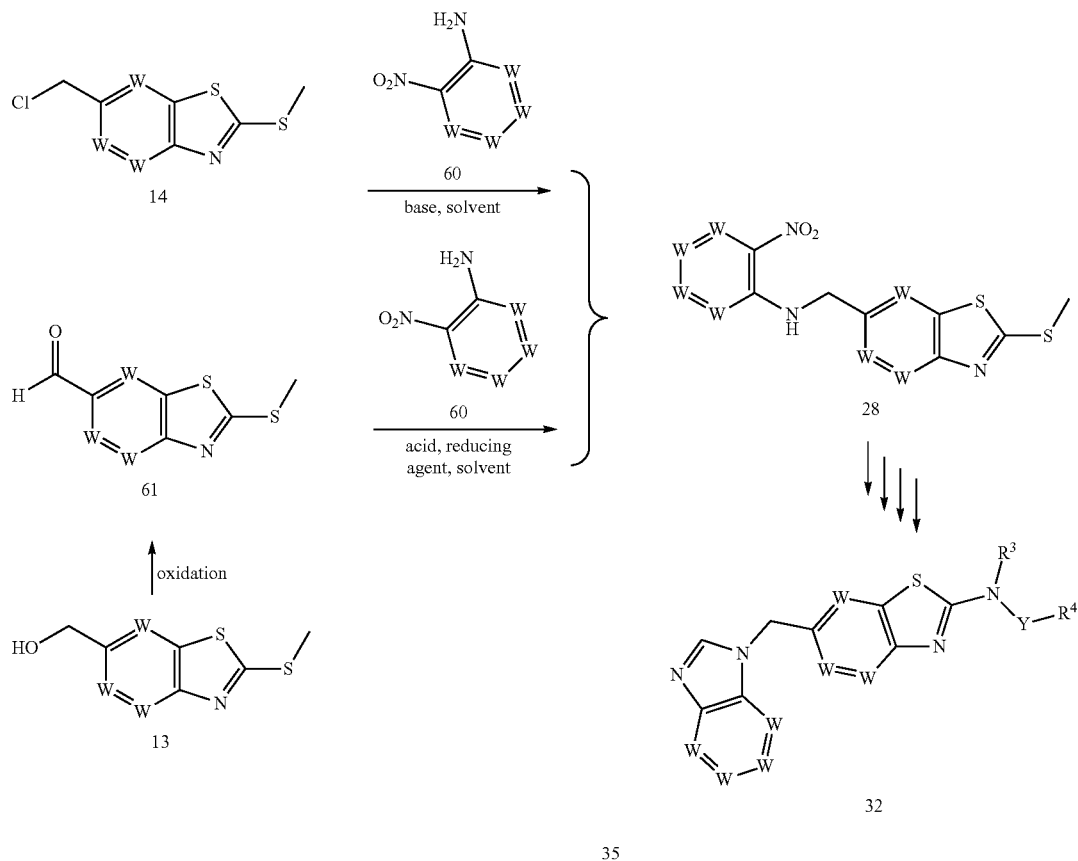

In another illustrative method, compounds of formula (I) may also be routinely prepared according to the synthetic route outlined in Scheme 9. Alkylation of amino nitro aryls/heteroaryls 60 with chlorides 14 can be effected using a base such as, but not limited to, NaH or t-BuOK to give compounds 28. The alkylation can be conducted in a solvent such as, but not limited to, DMF or THF. Alternatively, alcohols 13 can be oxidized to aldehydes 61 using an oxidizing agent such as, but not limited to, Dess-Martin periodinane or $MnO_2$, in a solvent such as, but not limited to, DCM or MeCN. Reductive alkylation of amino nitro aryls/heteroaryls 60 with aldehydes 61 can be effected using a reducing agent such as, but not limited to, $NaCNBH_3$ or $Na(OAc)_3BH$, usually in the presence of an acid such as, but not limited to, TFA or AcOH, to give compounds 28. The reductive alkylation reaction can be conducted in a solvent such as, but not limited to, DCM or DCE. Compounds 28 can be converted to the final compounds 32 as described in Scheme 4.

Scheme 10: General synthesis of compounds of formula (I).

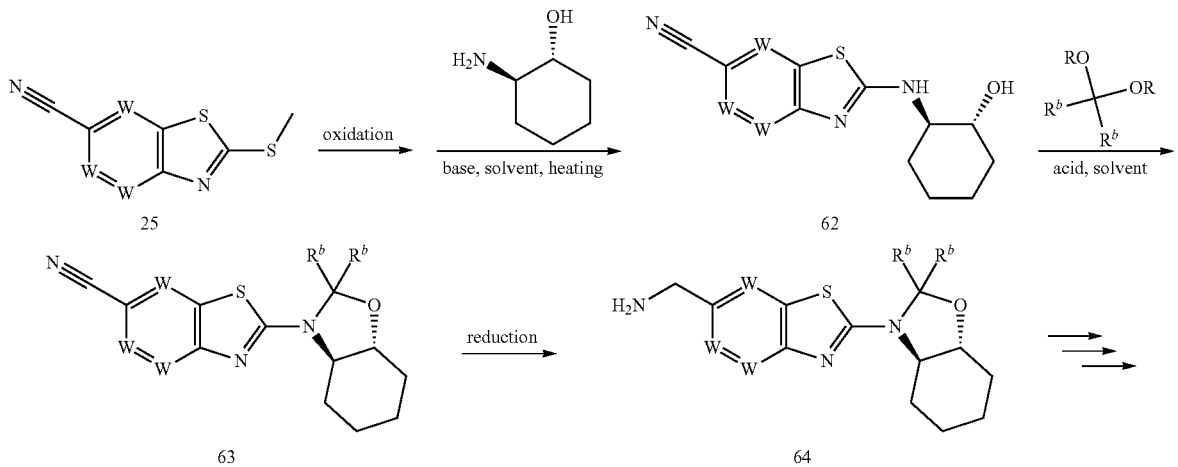

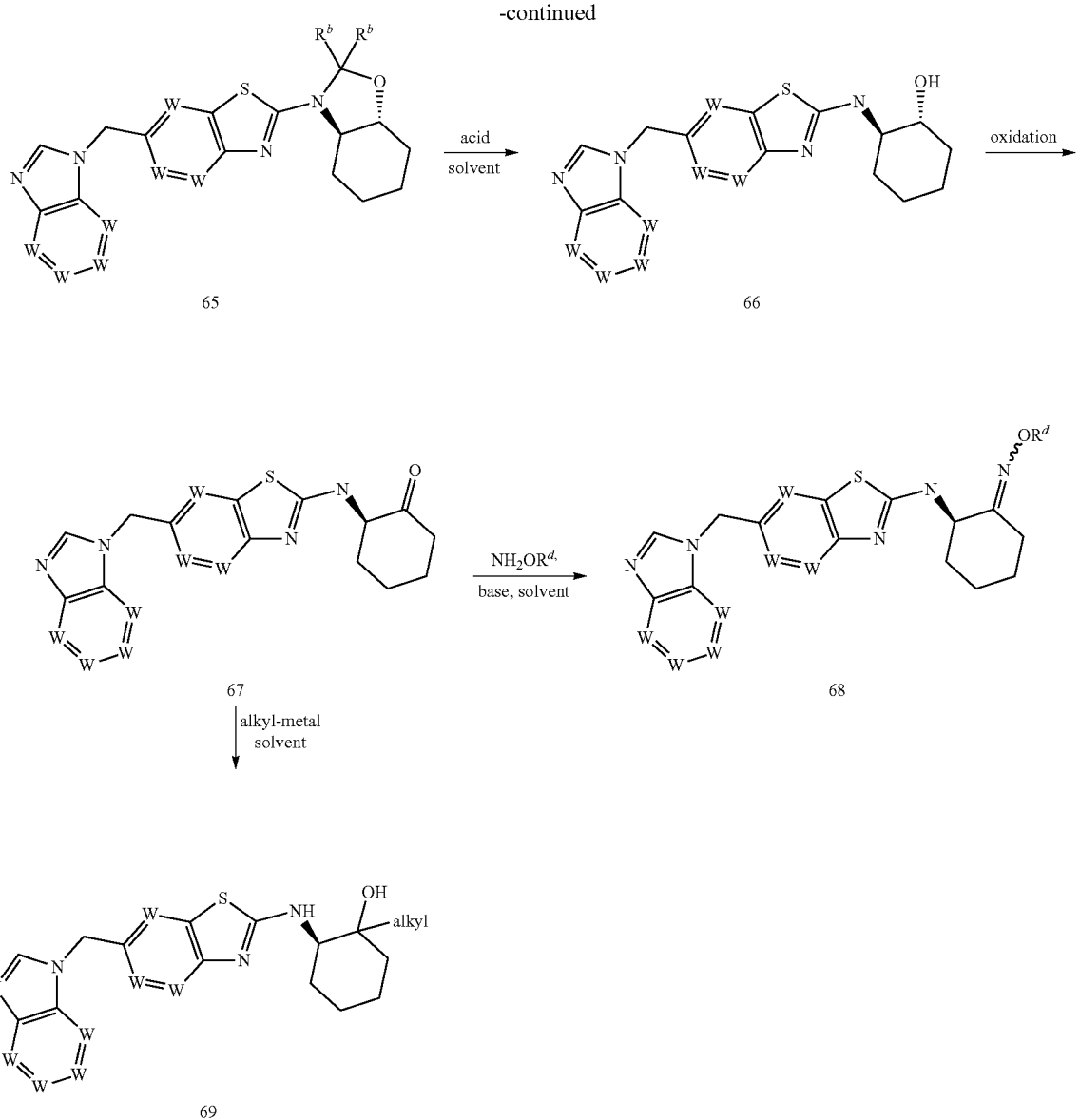

In another illustrative method, compounds of formula (I) may also be routinely prepared according to the synthetic route outlined in Scheme 10. Starting with nitriles 25 from Scheme 4, oxidation of the sulfide moiety and nucleophilic substitution with amino alcohols such as, but not limited to, a single stereoisomer of 2-aminocyclohexanol, can provide the compounds 62. Simultaneous protection of the NH and OH groups of 62 by treatment with a ketal such as, but not limited to, 2,2-dimethoxypropane in the presence of an acid catalyst such as, but not limited to, p-toluenesulfonic acid or camphorsulfonic acid, in a solvent such as, but not limited to, toluene or 1,4-dioxane, with heating as required can afford compounds 63. Reduction of the nitrile group of 63 can be realized using a metal hydride such as, but not limited to, LiAlH$_4$ or nickel boride, in a solvent such as THF or diethyl ether to give amines 64. Using procedures analogous to those described in Scheme 4 for conversion of compounds 26 to compounds 30, a three step sequence can convert compounds 64 to compounds 65, after which the protecting group can be removed using an acid such as, but not limited to, TFA in DCM or HCl in 1,4-dioxane, to give compounds of the invention 66. Compounds 66 can furthermore be oxidized to ketones 67 using an oxidizing agent such as, but not limited to, Dess-Martin periodinane or 2-iodoxybenzoic acid, in a solvent such as, but not limited to, DCM or MeCN. Treatment of ketones 67 with hydroxylamine or an alkoxylamine at elevated temperature in a solvent such as, but not limited to, EtOH or MeOH can generate oximes 68. The reaction can be promoted with a base such as, but not limited to, pyridine. On the other hand, ketones 67 can react with organometallic agents such as, but not limited to, Grignard reagents or organolithium agents, in a solvent such as, but not limited to, THF or diethyl ether, to give compounds 69, which may be formed as a mixture of diastereoisomers.

Scheme 11: General synthesis of compounds of formula (I).

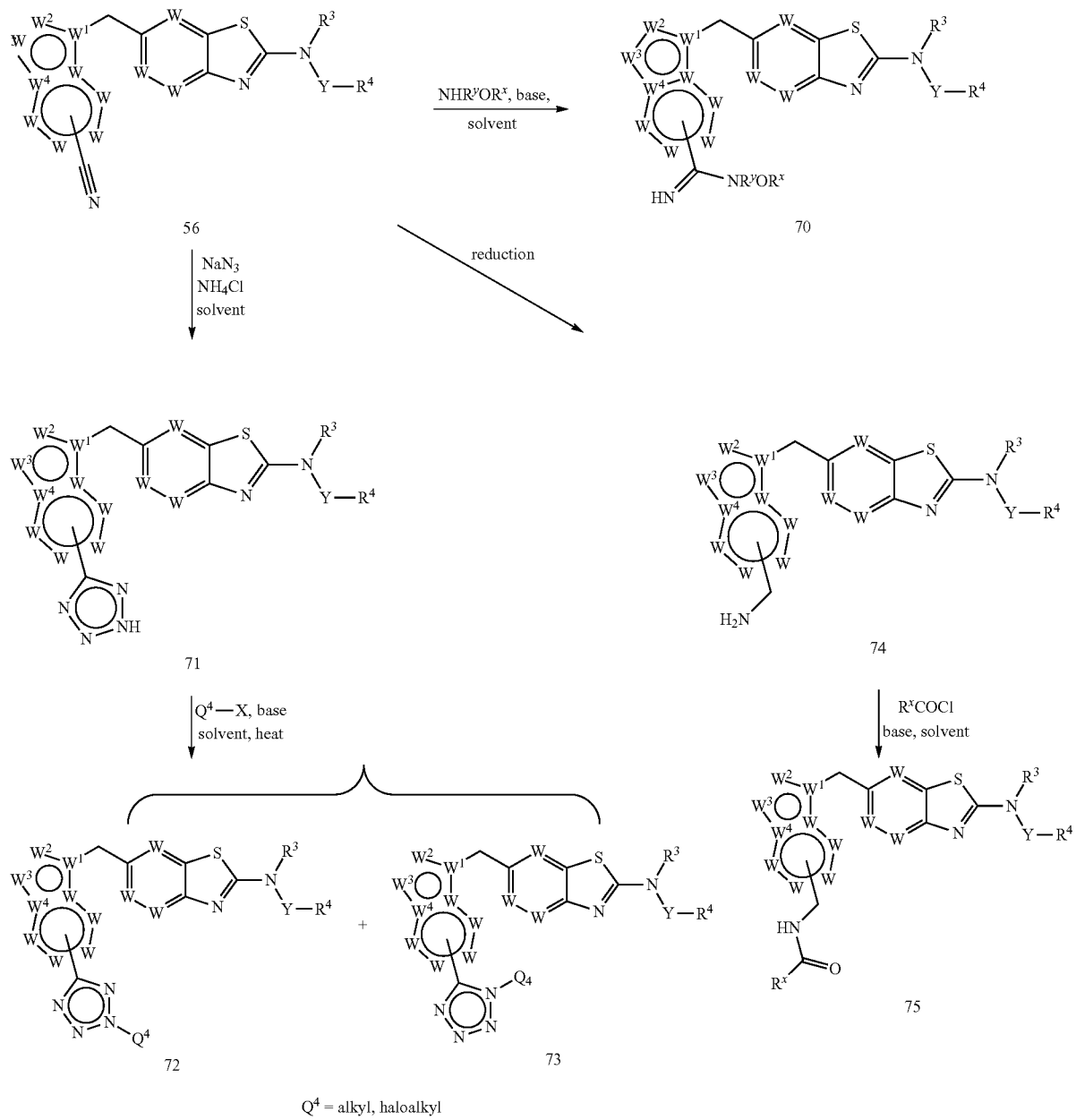

$Q^4$ = alkyl, haloalkyl

In another illustrative method, compounds of formula (I) may also be routinely prepared according to the synthetic route outlined in Scheme 11. Reaction of nitriles 56 from Scheme 8 with hydroxylamine derivatives at elevated temperature in a solvent such as, but not limited to, EtOH or MeOH can generate hydroxyl or alkoxyl amidines 70. The reaction can be promoted with a base such as, but not limited to, pyridine. Reaction of nitriles 56 with azide, for example with NaN$_3$ and NH$_4$Cl, in a solvent such as, but not limited to, DMF or DMA, can provide tetrazole compounds 71. Alkylation of the tetrazoles with alkyl or haloalkyl halides using bases such as, but not limited to, K$_2$CO$_3$ or Cs$_2$CO$_3$, in solvents such as, but not limited to, DMF or DMA, at elevated temperature can yield tetrazole derivatives 72 and 73. Reduction of the nitrile group of 56 can be realized using metal hydrides such as, but not limited to, LiAlH$_4$ or nickel boride, in a solvent such as THF or diethyl ether to give amino compounds 74. Acylation of the amino group of 74 with an acylating group in the presence of a base such as, but not limited to, pyridine or DIEA, in a solvent such as DCM or DCE, can afford amides 75; corresponding carbamates or ureas can be prepared similarly, by using a chloroformate or an isocyanate, respectively, as the acylating agent.

Scheme 12: General synthesis of oxazole compounds

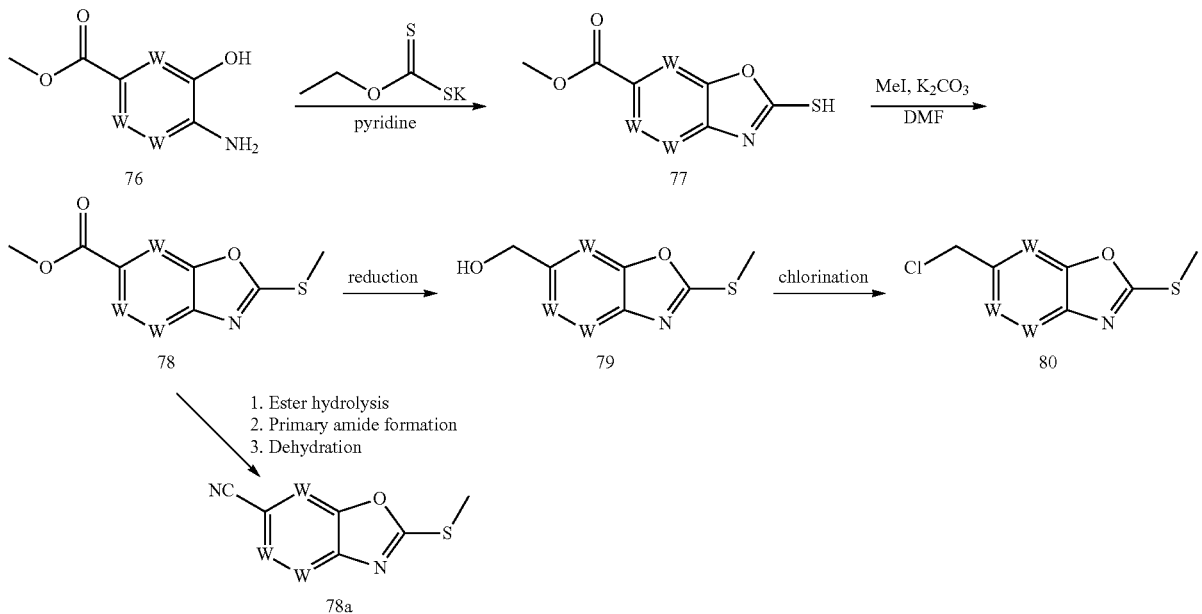

In an illustrative method, the oxazole derivatives used herein may be routinely prepared according to the synthetic route outlined in Scheme 12. Heating of aminophenols 76 with potassium O-ethyl carbonodithioate in solvent such as, but not limited to, pyridine can yield compounds 77. As described in Scheme 2, a three step sequence of alkylation, reduction, and chlorination can generate chloride derivatives 80. Intermediate 78 from the above sequence can alternatively be converted to nitrile 78a by a standard three-step sequence consisting of ester hydrolysis, primary amide formation, and dehydration. Final oxazole compounds of the invention can be prepared by substituting oxazoles 79 in place of thiazoles 13 in Scheme 9 and conducting the remainder of the synthetic sequence using procedures analogous to those in Scheme 9; additional final oxazole compounds of the invention can be prepared by substituting oxazoles 80 in place of thiazoles 14 in Schemes 2, 5, 7, and 9 and conducting the remainder of the respective synthetic sequences using procedures analogous to those in Scheme 2, 5, 7, or 9; and additional final oxazole compounds of the invention can also be prepared by substituting oxazoles 78a in place of thiazoles 25 in Schemes 4 and 10 and conducting the remainder of the respective synthetic sequences using procedures analogous to those in Scheme 4 or 10.

Scheme 13: General synthesis of bicyclic imidazole derivatives (examples of heteroaryls 48)

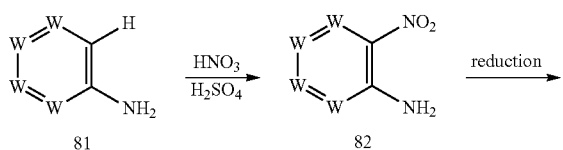

-continued

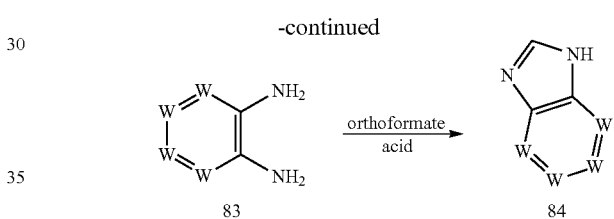

In an illustrative method, bicyclic imidazole derivatives used herein may be routinely prepared according to the synthetic route outlined in Scheme 13. Nitration of amino aryl/heteroaryl compounds 81 can be realized using reagents such as, but not limited to, a mixture of concentrated sulfuric acid and nitric acid, to give amino nitro compounds 82. Reduction of compounds 82 using a reducing agent such as, but not limited to, Zn or Fe in the presence of an acid such as, but not limited to, AcOH or HCl, in a solvent such as, but not limited to, DCM or EtOH can give diamino compounds 83. Compounds 83 can be converted to bicyclic imidazole derivatives 84 by reaction with an orthoformate such as, but not limited to, trimethyl orthoformate or triethyl orthoformate. The reaction can be promoted with an acid catalyst such as, but not limited to, HCOOH or AcOH at elevated temperature.

Scheme 14: General synthesis of amino alcohol derivatives (examples of amines 7)

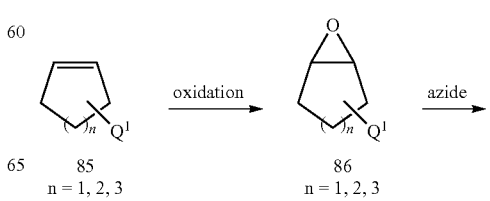

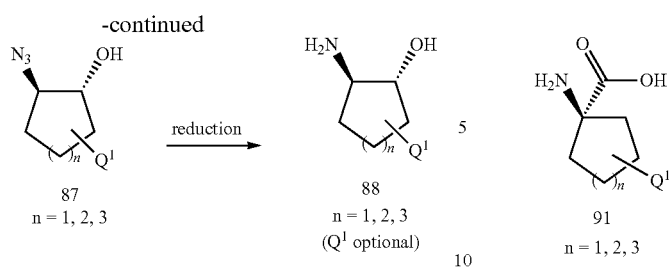
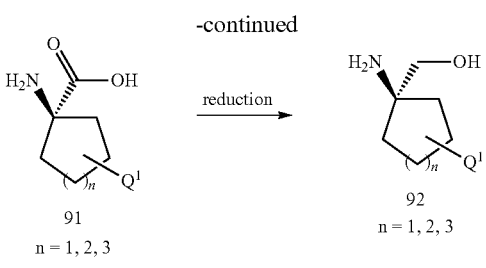

In an illustrative method, amino alcohol derivatives used herein may be routinely prepared according to the synthetic route outlined in Scheme 14. Cycloalkenes 85 can be oxidized using reagents such as, but not limited to, mCPBA or NaOCl to give epoxides 86, which can react with an azide such as, but not limited to, $TMSN_3$ or $n$-$Bu_4NN_3$, in a solvent such as, but not limited to, THF or DCM, to give azido alcohols 87. The azido group of 87 can be reduced to an amino group using hydrogenation or Staudinger reduction conditions to afford amino alcohols 88.

Scheme 15: General synthesis of amino alcohol derivatives (examples of amines 7)

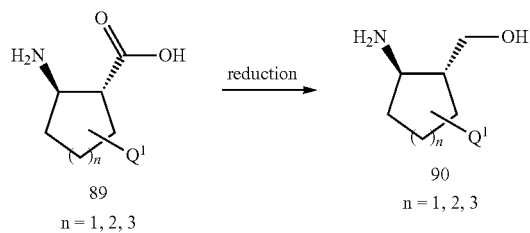

In another illustrative method, amino alcohol derivatives used herein may also be routinely prepared according to the synthetic route outlined in Scheme 15. Amino acids 89 and 91 can be reduced to amino alcohols 90 and 92, respectively, using a reagent such as, but not limited to, $LiAlH_4$ or diborane, in a solvent such as THF or diethyl ether. Similarly, cyanohydrins 93 can be reduced to amino alcohols 94 using a metal hydride such as, but not limited to, $LiAlH_4$ or nickel boride, in a solvent such as THF or diethyl ether.

Scheme 16: General synthesis of 5-membered heteroaryl derivatives (examples of heterocyclyl compounds 5)

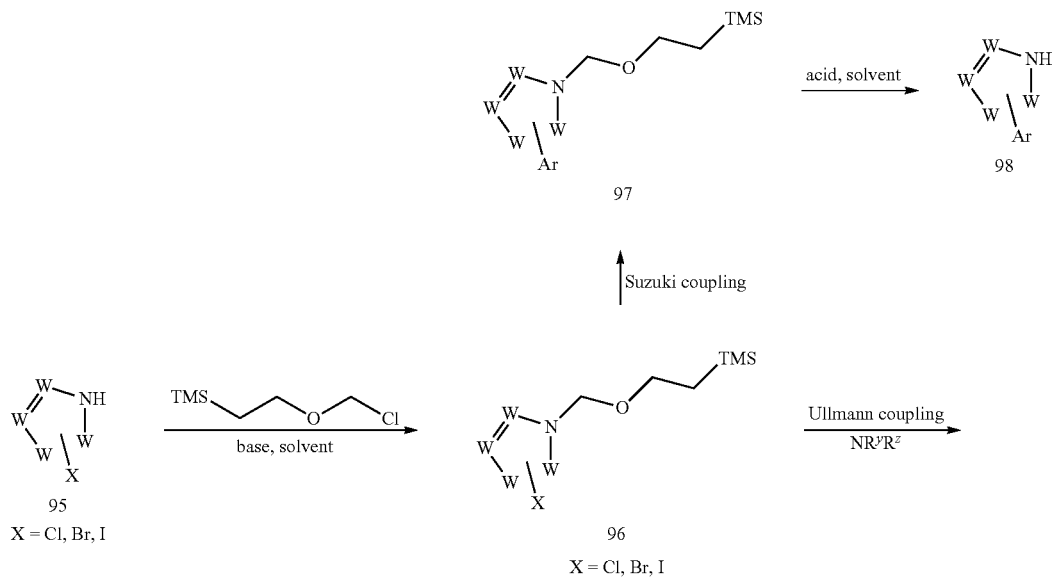

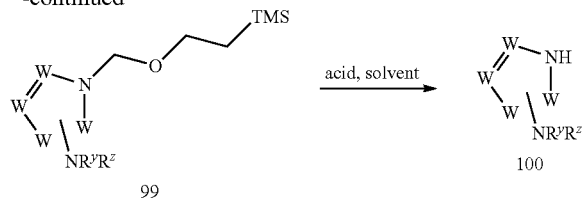

In an illustrative method, certain 5-membered heteroaryl derivatives used herein may be routinely prepared according to the synthetic route outlined in Scheme 16. Heteroaryls 95 containing an appropriate halo substituent can be protected with a protecting group such as, but not limited to, trimethylsilylethoxymethylene group, to give compounds 96. The protection can be effected using a base such as, but not limited to, NaH or t-BuOK, and conducted in a solvent such as, but not limited to, DMF or THF, at elevated temperature if necessary. Haloheteroaryl compounds 96 can undergo Suzuki coupling as described in Scheme 5 with coupling partners such as, but not limited to, boronic acids, boronate esters, or Molander trifluoroborates to yield compounds 97. Subsequent removal of the protecting group using a reagent such as, but not limited to, TFA in DCM or HCl in 1,4-dioxane can provide heteroaryl derivatives 98. Similarly, Ullmann-type coupling of 96 with NH-containing nucleophiles such as, but not limited to, amine or carboxamides, can lead to compounds 99, from which the protecting group can be removed as above to afford heteroaryl derivatives 100.

Scheme17: General synthesis of 6-membered heteroaryl/heterocyclyl derivatives (examples of heteroaryl/heterocyclyl compounds 5)

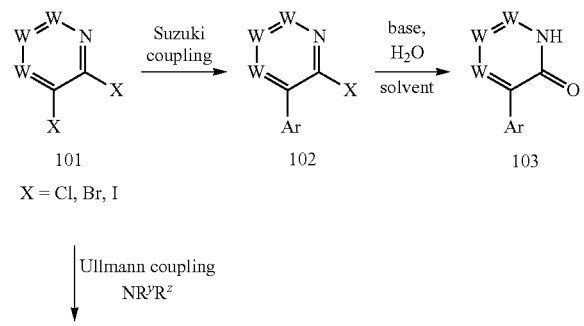

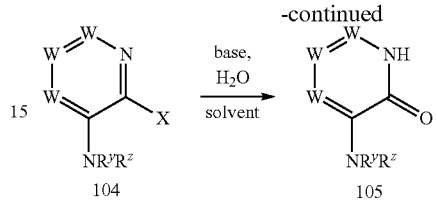

In an illustrative method, certain 6-membered heteroaryl/heterocyclyl derivatives used herein may be routinely prepared according to the synthetic route outlined in Scheme 17. Halogenated heteroaryl/heterocyclyl compounds 101 can undergo Suzuki coupling as described in Scheme 5 with coupling partners such as, but not limited to, boronic acids, boronate esters, or Molander trifluoroborates to yield compounds 102. Subsequent alkaline hydrolysis with, for example, KOH or NaOH, in a solvent such as, but not limited to, DMSO or THF can provide heterocyclyl derivatives 103. Similarly, Ullmann-type coupling of halides 101 with a NH-containing nucleophile such as, but not limited to, an amine or carboxamide, can lead to compounds 104, from which subsequent hydrolysis can lead to heteroaryl/heterocyclyl derivatives 105.

Scheme 18: General synthesis of compounds of formula (I).

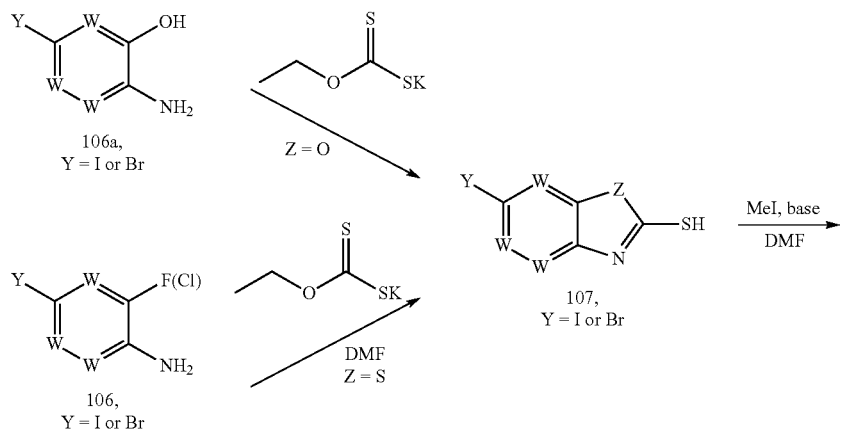

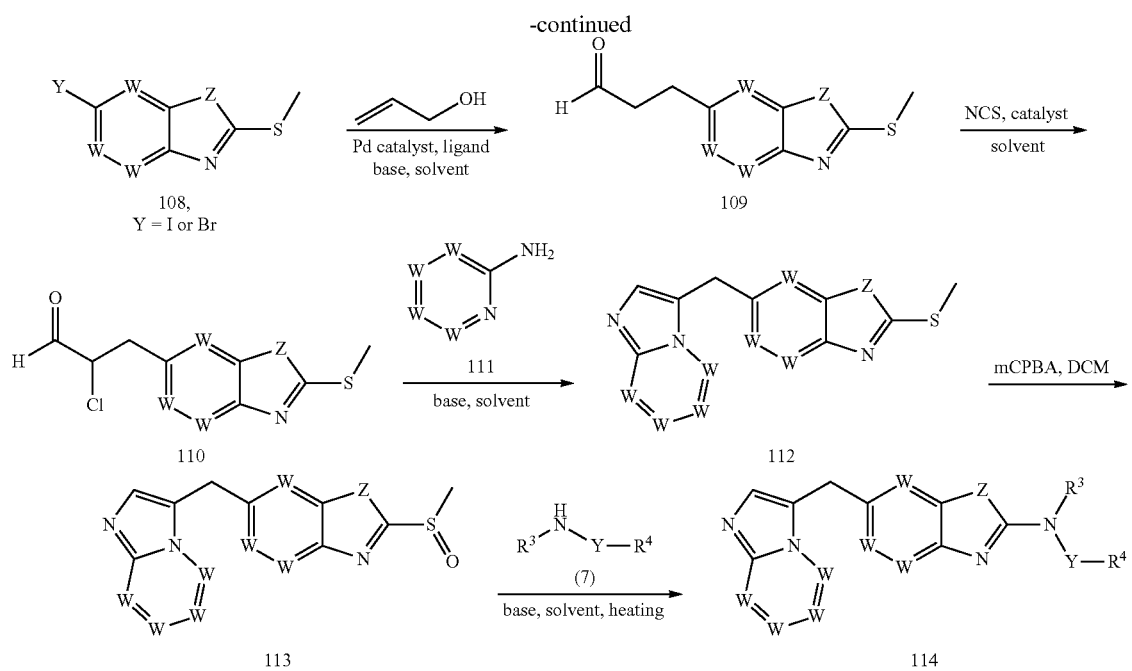

In an illustrative method, compounds of formula (I) may also be routinely prepared according to the synthetic route outlined in Scheme 18. The readily available aminoaryl/heteroaryl derivatives 106 and 106a can react with potassium O-ethyl carbonodithioate in solvent such as, but not limited to, DMF or pyridine with heating to give fused mercaptan derivatives 107. Methylation of compounds 107 can be realized using MeI promoted with a base such as, but not limited to, $K_2CO_3$ or $Cs_2CO_3$ in a solvent such as, but not limited to, DMF or DMA, to give compounds 108. Heck coupling of halides 108 with allyl alcohol catalyzed with a palladium-based catalyst such as, but not limited to, $Pd(OAc)_2$ or $Pd(dba)_2$ provides the propanals 109. The reaction can be promoted with a palladium ligand such as, but not limited to, $P(o\text{-tolyl})_3$ or $As(PPh_3)_3$ and accelerated with a base such as, but not limited to, $NaHCO_3$ or $KHCO_3$. The reaction can be conducted in a solvent such as, but not limited to, MeCN or DMF. Chlorination of propanals 109 can be effected using a chlorinating agent such as, but not limited to, N-chlorosuccinimide and catalyzed with an amine such as, but not limited to, L-proline or piperidine to give chlorides 110. Condensation of compounds 110 with six-membered 2-amino heteroaryl derivatives 111 at elevated temperature promoted with a base such as, but not limited to, $NaHCO_3$ or triethylamine in a solvent such as, but not limited to, n-BuOH or DMF yields bicyclic heteroaryls 112. The sulfides of 112 can be oxidized to sulfoxides using an oxidizing agent such as, but not limited to, m-CPBA or peracetic acid. The oxidation can be conducted in solvent such as, but not limited to, DCM or AcOH. Sulfoxides 113 may react with amines 7 under nucleophilic substitution conditions at elevated temperature to afford compounds 114. The reaction can be conducted in a solvent such as, but not limited to, DMA or NMP and promoted with a base such as, but not limited to, DIEA or TEA.

Scheme 19: General synthesis of compounds of formula (I).

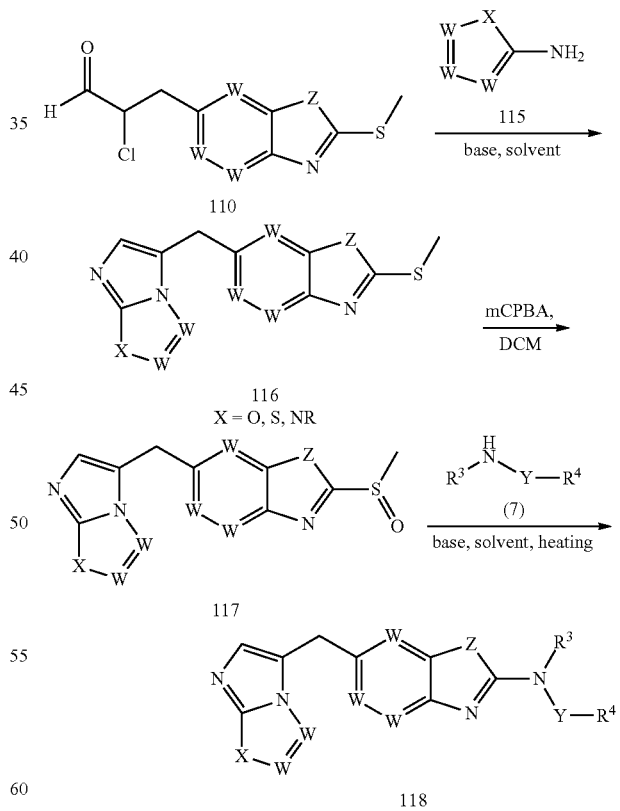

In an illustrative method, compounds of formula (I) may also be routinely prepared according to the synthetic route outlined in Scheme 19. Condensation of compounds 110 from Scheme 18 with five-membered aminoheteroaryl derivatives 115 at elevated temperature promoted with a base such as, but not limited to, NaHCO₃ or triethylamine in a solvent such as, but not limited to, n-BuOH or DMF yields bicyclic heteroaryls 116. Using procedures analogous to those described in Scheme 18, oxidation of compounds 116 to give sulfoxides 117, followed by reaction with amines 7 provides compounds 118.

121 using NCS affords compounds 122. Condensation of compounds 122 with six-membered aminoheteroaryl derivatives 111 gives compounds 114, using procedures analogous to those described in Scheme 18. Alternatively, condensation of chloroaldehydes 122 with bicyclic amino heteroaryls 123 provides tricyclic compounds 124.

Scheme 20: General synthesis of compounds of formula (I).

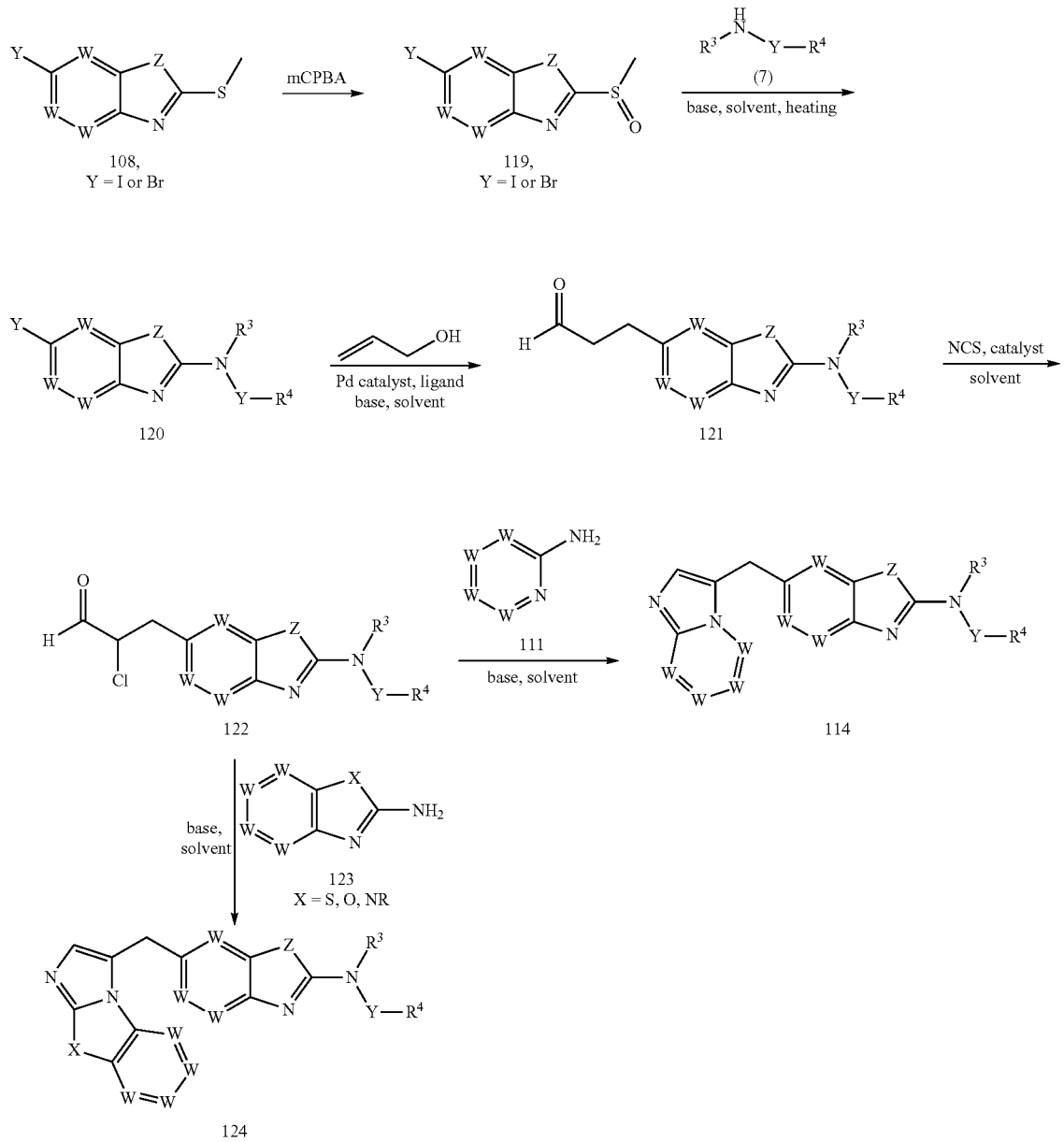

In an illustrative method, compounds of formula (I) may also be routinely prepared according to the synthetic route outlined in Scheme 20. Sulfides 108 from Scheme 18 can be oxidized to sulfoxides 119 using an oxidizing agent such as, but not limited to, m-CPBA or peracetic acid, as described in Scheme 18. Reaction of sulfoxides 119 with amines 7 provides compounds 120, using a procedure analogous to that described in Scheme 18. Heck coupling of halides 120 with allyl alcohol yields propanals 121, using a procedure analogous to that described in Scheme 18. Chlorination of Scheme 21: General synthesis of compounds of formula (I).

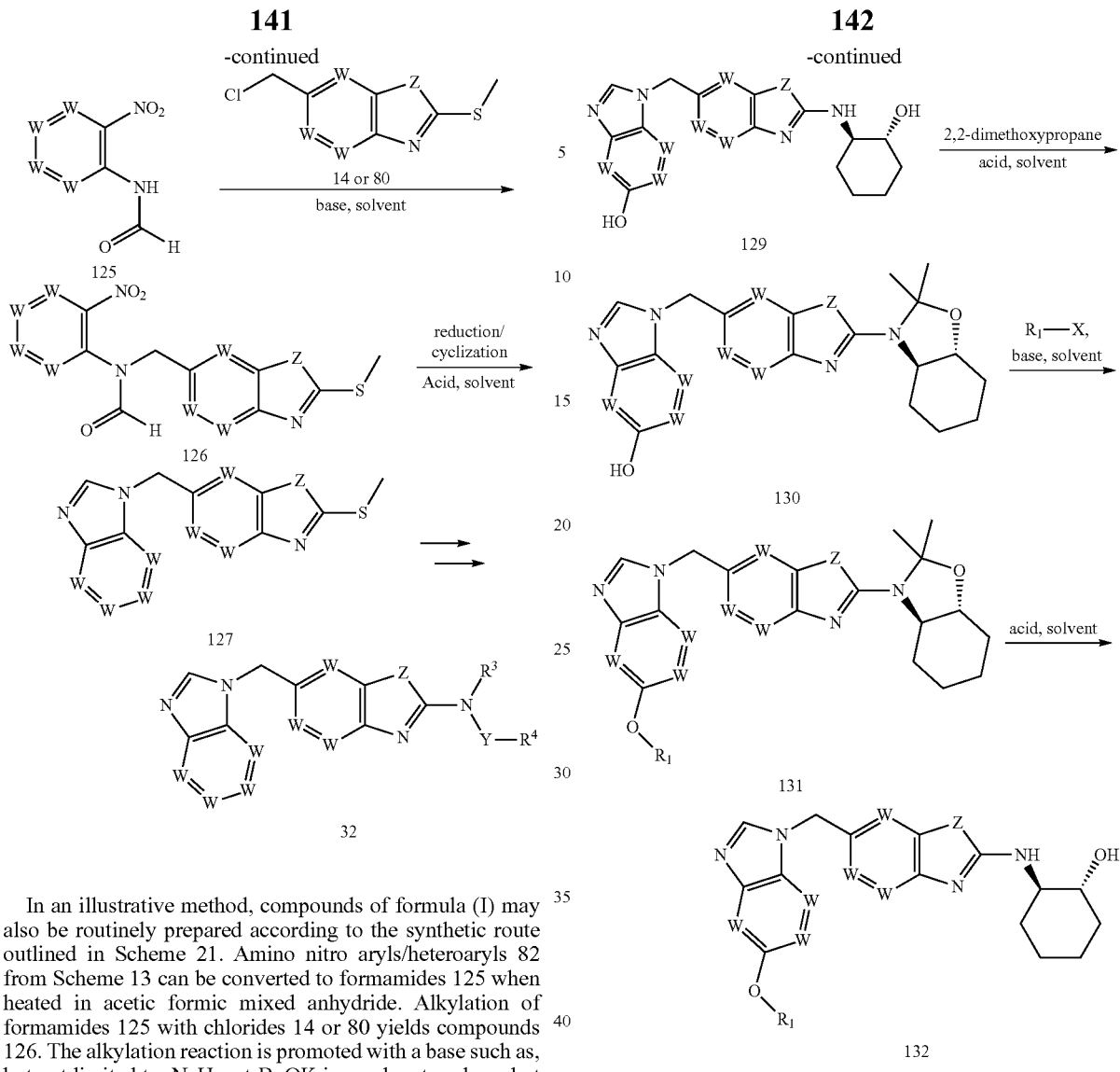

In an illustrative method, compounds of formula (I) may also be routinely prepared according to the synthetic route outlined in Scheme 21. Amino nitro aryls/heteroaryls 82 from Scheme 13 can be converted to formamides 125 when heated in acetic formic mixed anhydride. Alkylation of formamides 125 with chlorides 14 or 80 yields compounds 126. The alkylation reaction is promoted with a base such as, but not limited to, NaH or t-BuOK in a solvent such as, but not limited to, DMF or THF. Reduction of the nitro group to an amino group, accompanied by cyclization to compounds 127 may be effected utilizing a reducing agent such as, but not limited to, iron or zinc, in the presence of an acid such as, but not limited to, AcOH or trifluoroacetic acid. The reaction is conducted in a solvent such as, but not limited to, EtOH or MeOH and may be promoted by heating at elevated temperature. Compound 127 can be converted to the requisite compounds 32 using procedures analogous to those described in Scheme 18 for conversion of 112 to 114.

Scheme 22: General synthesis of compounds of formula (I).

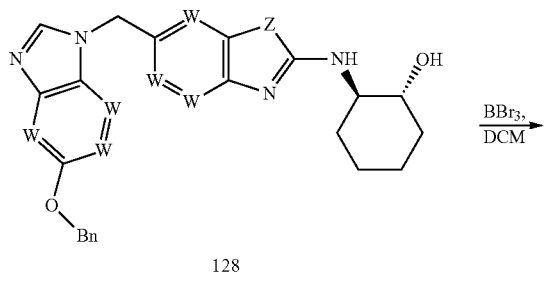

In an illustrative method, compounds of formula (I) may also be routinely prepared according to the synthetic route outlined in Scheme 22. The benzyl groups of compounds 128, which are prepared by methods described above, are removed using a reagent such as, but not limited to, BBr$_3$ or TMSI in a solvent such as, but not limited to, DCM or CH$_3$CN, to give hydroxyl compounds 129. The vicinal amino alcohol functionality of 129 is protected, for example as an acetonide, by reacting with a reagent such as, but not limited to, 2,2-dimethoxypropane to give compounds 130. The reaction is catalyzed by acid such as, but not limited to, p-toluenesulfonic acid or camphor sulfonic acid in a solvent such as, but not limited to, 1,4-dioxane or toluene. Alkylation of the hydroxyl group of 130 with alkyl halides is promoted with a base such as, but not limited to, Cs$_2$CO$_3$ or NaH in a solvent such as, but not limited to, NMP or THF to afford ethers 131. Deprotection of 131 with acid such as, but not limited to, HCl or trifluoroacetic acid in a solvent such as, but not limited to, DCM or CH$_3$CN provides compounds 132.

Scheme 23: General synthesis of compounds of formula (I).

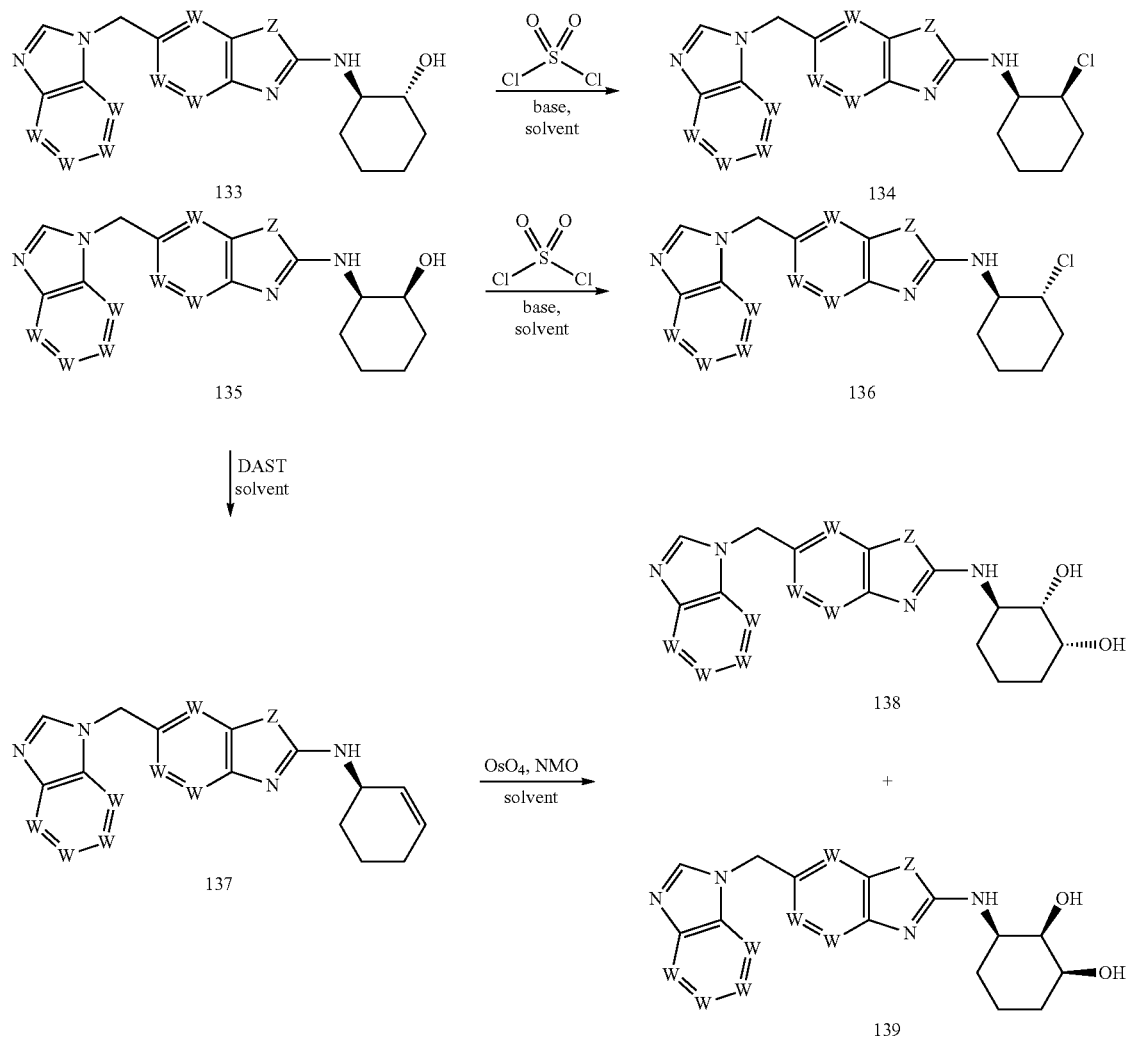

In an illustrative method, compounds of formula (I) may also be routinely prepared according to the synthetic route outlined in Scheme 23. Compounds 133, prepared as described above, can be converted to chlorides 134 by the treatment with sulfuryl chloride in a solvent such as, but not limited to, DCM or CH₃CN. Analogously, compounds 135 can be converted to chlorides 136 under the similar conditions. Furthermore, treatment of compounds 135 with an agent such as, but not limited to, diethylaminosulfur trifluoride (DAST) or Deoxo-fluor in a solvent such as, but not limited to, DCM, can afford cyclohexenes 137. Dihydroxylation at the isolated double bond of 137 with OsO₄ and N-methylmorpholine oxide (NMO) in a solvent such as, but not limited to, H₂O/acetone/t-BuOH provides diol compounds 138 and 139.

Scheme 24: General synthesis of compounds of formula (I).

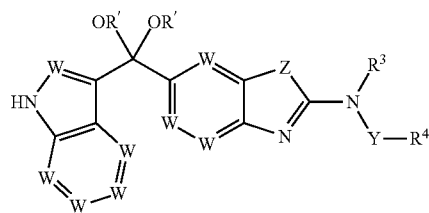

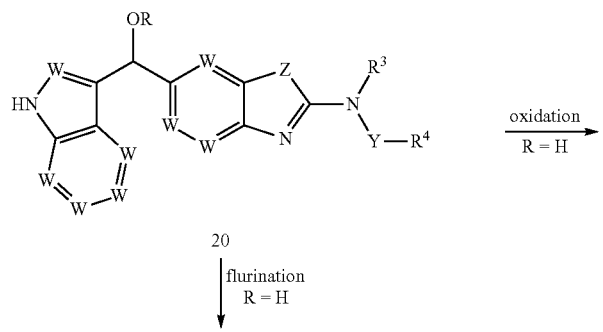

20

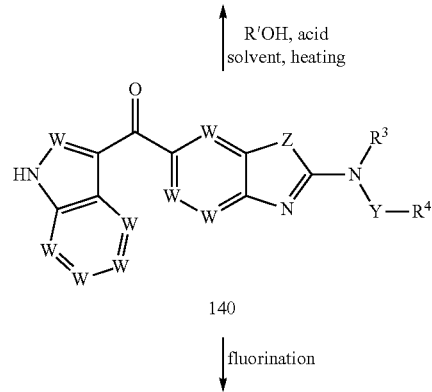

140

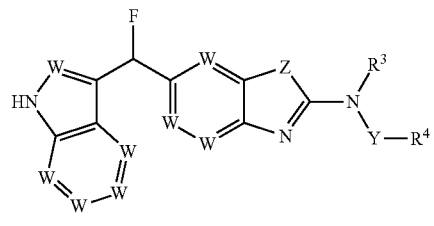

142a

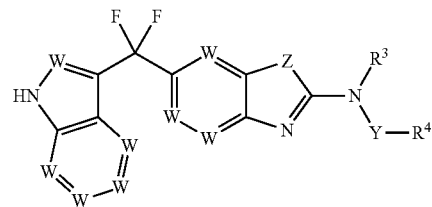

142

In an illustrative method, compounds of formula (I) may also be routinely prepared according to the synthetic route outlined in Scheme 24. Compounds 20 (R=H) from Scheme 3 can be oxidized to ketones 140 with a reagent, such as, but not limited to, Dess-Martin periodinane or Jones reagent in a solvent such as, but not limited to, $CH_3CN$ or acetone. Ketals 141 can be prepared by heating ketones 140 with an alcohol or diol in a solvent such as, but not limited to, toluene or benzene. The reaction can be catalyzed with an acid such as, but not limited to, p-toluene sulfonic acid or camphorsulfonic acid. Ketones 140 can also be bis-fluorinated to give compounds 142 using a fluorinating reagent such as, but not limited to, diethylaminosulfur trifluoride (DAST) or Deoxo-Fluor. Alcohols 20 can also be converted to fluorides 142a using a fluorinating reagent, such as, but not limited to, diethylaminosulfur trifluoride (DAST) or Deoxo-Fluor.

Scheme 25: General synthesis of compounds of formula (I).

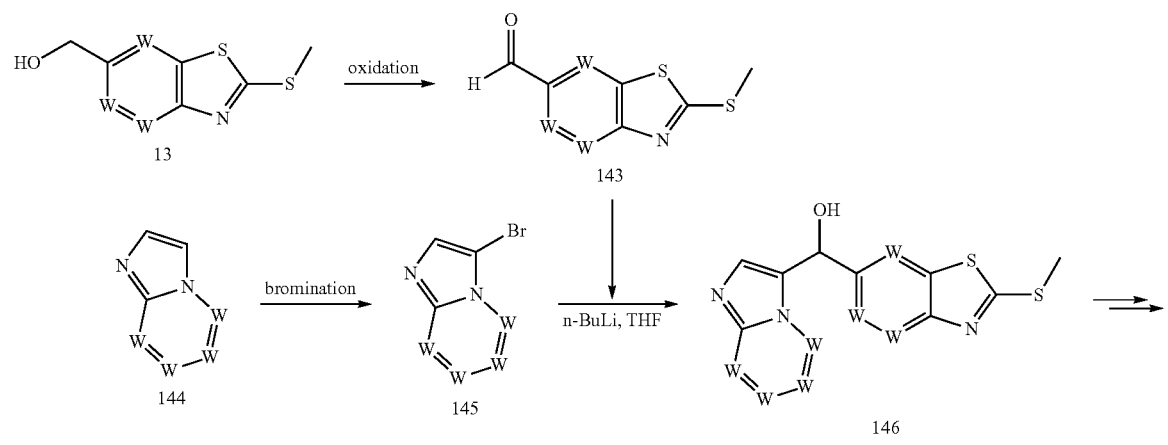

W = CH or N

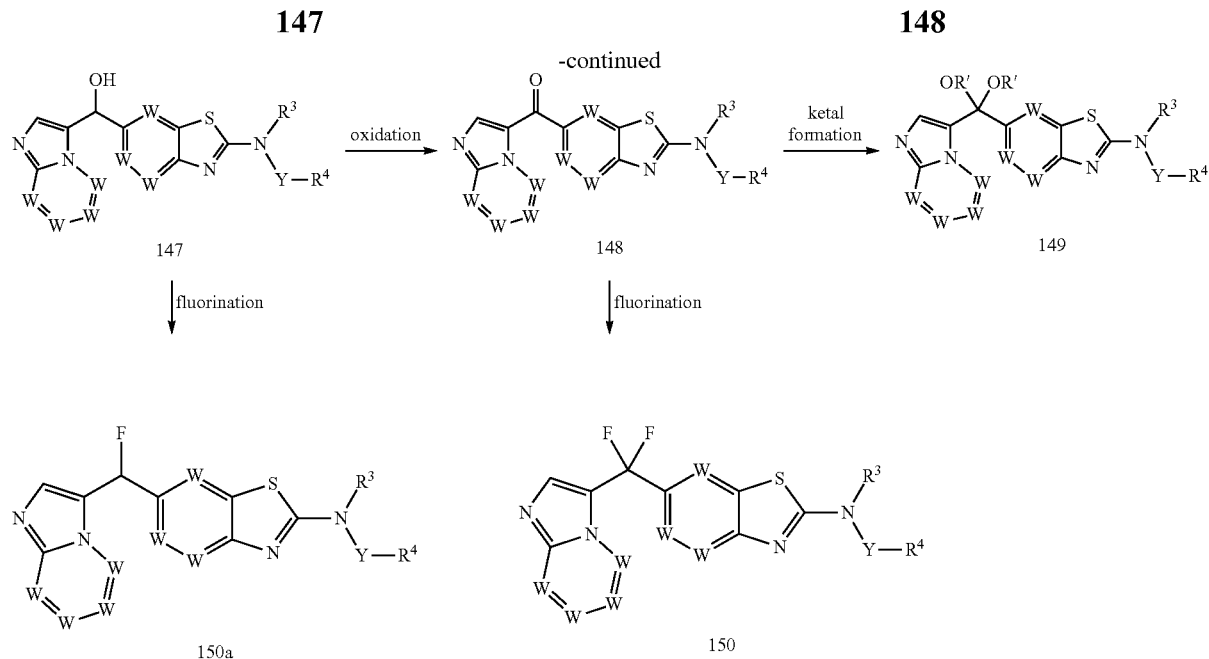

In an illustrative method, the compounds of formula (I) may also be routinely prepared according to the synthetic route outlined in Scheme 25. Compounds 13 from Scheme 2 can be oxidized to aldehydes 143 with a reagent such as, but not limited to, Dess-Martin periodinane, in a solvent such as, but not limited to, $CH_3CN$ or DCM. Meanwhile, readily available compounds 144 can be brominated with a reagent such as, but not limited to, bromine or N-bromosuccimide to give compounds 145. Trans-metallation of 145 with a reagent such as, but not limited to, n-butyl lithium followed by treatment with aldehydes 143 can yield alcohols 146, which can be converted to compounds 147 using procedures analogous to those described in Scheme 4 for conversion of 30 to 32. The alcohols 147 can further be converted to ketones 148, fluorides 150a, ketals 149, and difluoro compounds 150 using procedures analogous to those described in Scheme 24.

The subject matter has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the following examples may be substituted with other suitable reagents. See, e.g., Smith & March, *Advanced Organic Chemistry*, 5$^{th}$ ed. (2001). Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

EXAMPLES

Example 1

Preparation of 2-((6-((1H-benzo[d]imidazol-1-yl) methyl)benzo[d]thiazol-2-yl)amino)cyclohexanol

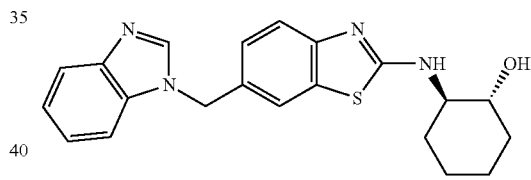

Step 1:
6-((1H-Benzo[d]imidazol-1-yl)methyl)-2-bromobenzo[d] thiazole (150 mg, 44%) was obtained as a white solid using a procedure analogous to that described in Step 5 of Example 2, substituting 1H-benzo[d]imidazole for 5,6-dimethoxy-1H-benzo[d]imidazole used in Example 2. $^1$H NMR (300 MHz, DMSO-$d_6$) δ 8.45 (s, 1H), 8.06 (s, 1H), 7.97 (d, J=8.5 Hz, 1H), 7.62-7.72 (m, 1H), 7.45-7.58 (m, 2H), 7.13-7.28 (m, 2H), 5.65 (s, 2H). LCMS (ESI) m/z 344, 346 (M+H)$^+$.

Step 2:
2-((6-((1H-Benzo[d]imidazol-1-yl)methyl)benzo[d]thiazol-2-yl)amino)cyclohexanol was obtained as a white solid (12 mg, 22%) using a procedure analogous to that described in Step 4 of Example 2, substituting 6-((1H-benzo[d]imidazol-1-yl)methyl)-2-bromobenzo[d]thiazole from Step 1 of this Example for 2-bromo-6-((5,6-dimethoxy-1H-benzo[d] imidazol-1-yl)methyl)benzo[d]thiazole, and racemic trans-2-aminocyclohexanol for (1R,2R)-2-aminocyclohexanol used in Example 2. $^1$H NMR (300 MHz, DMSO-$d_6$) δ 8.40 (s, 1H), 7.98 (d, J=7.5 Hz, 1H), 7.61-7.69 (m, 2H), 7.49-7.59 (m, 1H), 7.25-7.34 (m, 1H), 7.13-7.24 (m, 3H), 5.46 (s, 2H), 4.75 (br s, 1H), 3.47-3.59 (m, 2H), 2.02 (d, J=10.9 Hz, 1H), 1.87 (d, J=9.2 Hz, 1H), 1.61 (br s, 2H), 1.04-1.36 (m, 4H). LCMS (ESI) m/z 379 (M+H)$^+$.

Example 2

Preparation of (1R,2R)-2-((6-((5,6-dimethoxy-1H-benzo[d]imidazol-1-yl)methyl)benzo[d]thiazol-2-yl)amino)cyclohexanol

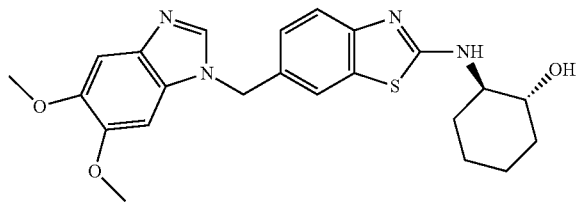 [SMILES: COc1cc2ncn(Cc3ccc4nc(N[C@@H]5CCCC[C@H]5O)sc4c3)c2cc1OC]

Step 1:

To a solution of tert-butyl nitrite (4.5 mL, 37.5 mmol) and copper(II) bromide (6.0 g, 27 mmol) in CH₃CN (100 mL) at rt was added a mixture of ethyl 2-aminobenzo[d]thiazole-6-carboxylate (5.0 g, 22.5 mmol) in CH₃CN (50 mL). The reaction suspension was stirred at rt for 1 h. The resulting reaction mixture was quenched with 300 mL of 1 N HCl aqueous solution and extracted with CH₂Cl₂ (3×200 mL). The combined organic layers were dried over MgSO₄, and concentrated under reduced pressure. The crude product was purified on a silica gel column using a mixture of CH₂Cl₂-hexanes (4:1, v/v) as eluent to give ethyl 2-bromobenzo[d]thiazole-6-carboxylate as a white solid (6.2 g, 96%). $^1$H NMR (300 MHz, CDCl₃) δ 8.54 (d, J=1.1 Hz, 1H), 8.16 (dd, J=1.5, 8.7 Hz, 1H), 8.02 (d, J=8.7 Hz, 1H), 4.43 (q, J=7.2 Hz, 2H), 1.43 (t, J=7.2 Hz, 3H). LCMS (ESI) m/z 288, 286 (M+H)⁺.

Step 2:

To a solution of ethyl 2-bromobenzo[d]thiazole-6-carboxylate (5.0 g, 17.5 mmol) from Step 1 of this Example in anhydrous CH₂Cl₂ was added DIBAL-H (1.0 M in CH₂Cl₂, 36.7 mL, 36.7 mmol) slowly at −78° C. The solution was stirred at −78° C. for 2 h. The resulting mixture was quenched with 10 mL of saturated aq sodium potassium tartrate at −78° C. After slowly warming to 0° C., the mixture was further treated with 50 mL of saturated aq sodium potassium tartrate and stirred at rt for 2 h. The aqueous layer was separated and extracted with CH₂Cl₂ (3×100 mL). The combined organic layers were washed with brine, dried over MgSO₄, and concentrated under reduced pressure. The crude product was purified on a silica gel column using a mixture of EtOAc-hexanes (2:3, v/v) as eluent to give (2-bromobenzo[d]thiazol-6-yl)methanol as a white solid (3.4 g, 80%). $^1$H NMR (300 MHz, CDCl₃) δ 7.96 (d, J=8.3 Hz, 1H), 7.85 (s, 1H), 7.45 (dd, J=1.4, 8.4 Hz, 1H), 4.83 (s, 2H), 1.86 (br s, 1H). LCMS (ESI) m/z 244, 246 (M+H)⁺.

Step 3:

To a solution of (2-bromobenzo[d]thiazol-6-yl)methanol (205 mg, 0.83 mmol) from Step 2 of this Example and DIEA (118 mg, 0.92 mmol) in CH₂Cl₂ (20 mL) cooled in an ethylene glycol-water (4:1, v/v) dry ice bath was added methanesulfonyl chloride (105 mg, 0.92 mmol) slowly. The reaction solution was warmed to rt and stirred at rt for 1 h. The resulting mixture was quenched with 20 mL of water. The separated aqueous layer was extracted with CH₂Cl₂ (3×20 mL). The combined organic layers were washed with brine, dried over MgSO₄, and concentrated under reduced pressure to give (2-bromobenzo[d]thiazol-6-yl)methyl methanesulfonate as a light yellow solid (267 mg, 100%). LCMS (ESI) m/z 322, 324 (M+H)⁺.

Step 4:

To a solution of (2-bromobenzo[d]thiazol-6-yl)methyl methanesulfonate (460 mg, 1.4 mmol) from Step 3 of this Example in DMF (5 mL) was added 5,6-dimethoxy-1H-benzo[d]imidazole (560 mg, 3.14 mmol) portion wise at rt. The mixture was stirred at rt overnight. The resulting solution was diluted with 40 mL of EtOAc and washed with water, brine. The separated organic layer was dried over MgSO₄, and concentrated under reduced pressure The crude product was purified on a silica gel column using a mixture of MeOH—CH₂Cl₂ (1:20, v/v) as eluent to give 2-bromo-6-((5,6-dimethoxy-1H-benzo[d]imidazol-1-yl)methyl)benzo[d]thiazole as a light yellow solid (427 mg, 75%). LCMS (ESI) m/z 404, 406 (M+H)⁺.

Step 5:

To a suspension of 2-bromo-6-((5,6-dimethoxy-1H-benzo[d]imidazol-1-yl)methyl)benzo[d]thiazole (202 mg, 0.5 mmol) from Step 4 of this Example in DMA (4 mL) were added DIEA (129 mg, 1.0 mmol) and (1R,2R)-2-aminocyclohexanol (69 mg, 0.6 mmol) at rt. The mixture was stirred in a sealed tube at 120° C. overnight. After cooling to rt, the mixture was concentrated under reduced pressure. The crude product was purified by HPLC using a mixture of water (5% CH₃CN, 0.05% AcOH) and CH₃CN (0.05% AcOH) as the mobile phase and Varian Pursuit XRs Diphenyl column as the stationary phase to afford (1R,2R)-2-((6-((5,6-dimethoxy-1H-benzo[d]imidazol-1-yl)methyl)benzo[d]thiazol-2-yl)amino)cyclohexanol as a white solid (127 mg, 58%). $^1$H NMR (300 MHz, DMSO-d₆) δ 8.14 (s, 1H), 7.99 (d, J=7.5 Hz, 1H), 7.62 (s, 1H), 7.04-7.34 (m, 4H), 5.40 (s, 2H), 4.77 (br s, 1H), 3.76 (s, 6H), 3.51 (br s, 1H), 1.77-2.14 (m, 3H), 1.61 (br, 2H), 1.04-1.38 (m, 4H). LCMS (ESI) m/z 439 (M+H)⁺.

Example 3

Preparation of (1R,2R)-2-((6-((3H-imidazo[4,5-b]pyridin-3-yl)methyl)benzo[d]thiazol-2-yl)amino)cyclohexanol methanesulfonic acid

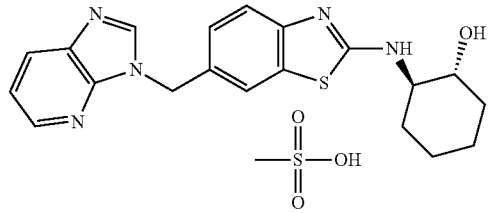

Step 1:

To a solution of ethyl 2-bromobenzo[d]thiazole-6-carboxylate (4.8 g, 16.8 mmol) from Step 1 of Example 2 in THF (100 mL) was added sodium thiomethoxide (1.74 g, 25.2 mmol) slowly at 0° C. The reaction mixture was stirred at rt overnight. The mixture was diluted with Et₂O (200 mL) and washed with saturated aq NaHCO₃ and brine. The organic layer was dried over MgSO₄ and concentrated under reduced pressure to give ethyl 2-(methylthio)benzo[d]thiazole-6-carboxylate as a white solid (4.18 g, 98%). $^1$H NMR (300 MHz, CDCl₃) δ 8.48 (d, J=1.5 Hz, 1H), 8.11 (dd, J=1.6, 8.6 Hz, 1H), 7.87 (d, J=8.5 Hz, 1H), 4.41 (q, J=7.1 Hz, 2H), 2.82 (s, 3H), 1.42 (t, J=7.1 Hz, 3H) LCMS (ESI) m/z 254 (M+H)⁺.

Step 2:

(2-(Methylthio)benzo[d]thiazol-6-yl)methanol (4.1 g, 88%) was obtained as a white solid using a procedure analogous to that described in Step 2 of Example 2, substituting ethyl 2-(methylthio)benzo[d]thiazole-6-carboxylate from Step 1 of this Example for ethyl 2-bromobenzo[d]thiazole-6-carboxylate used in Example 2. LCMS (ESI) m/z 212 (M+H)$^+$.

Step 3:

To a solution of (2-(methylthio)benzo[d]thiazol-6-yl) methanol (4.1 g, 19.4 mmol) from Step 2 of this Example and DIEA (3.26 g, 25.3 mmol) in $CH_2Cl_2$ (200 mL) was added methanesulfonyl chloride (2.88 g, 25.3 mmol) slowly at 0° C. The mixture was then treated with 2 drops of DMF and stirred at rt overnight. The mixture was quenched with 300 mL of saturated aq $NaHCO_3$. The separated aqueous layer was extracted with $CH_2Cl_2$ (2×250 mL). The combined organic layers were washed with brine, dried over $MgSO_4$, and concentrated under reduced pressure to give 6-(chloromethyl)-2-(methylthio)benzo[d]thiazole as a light brown solid (4.4 g, 99%). $^1$H NMR (300 MHz, DMSO-$d_6$) δ 8.10 (d, J=1.5 Hz, 1H), 7.84 (d, J=8.5 Hz, 1H), 7.53 (dd, J=1.6, 8.4 Hz, 1H), 4.89 (s, 2H), 2.80 (s, 3H). LCMS (ESI) m/z 231 (M+H)$^+$.

Step 4:

To a solution of 3H-imidazo[4,5-b]pyridine (2.99 g, 25 mmol) in DMF (100 mL) was added sodium hydride (60% in mineral oil, 1.0 g, 25 mmol) slowly at 0° C. After the reaction mixture was stirred at rt for 20 min, it was treated with a solution of 6-(chloromethyl)-2-(methylthio)benzo[d]thiazole from Step 3 of this Example (4.8 g, 21 mmol) in DMF (20 mL) at 0° C. The reaction mixture was then stirred at rt overnight. The mixture was quenched with 3 mL of saturated aq $NH_4Cl$ and concentrated under reduced pressure. The residue was diluted with 600 mL of EtOAc and washed with water and brine. The organic layer was dried over $MgSO_4$ and concentrated under reduced pressure The crude product was purified on a silica gel column using a mixture of MeOH—$CH_2Cl_2$ (1:30, v/v) as eluent to give 6-((3H-imidazo[4,5-b]pyridin-3-yl)methyl)-2-(methylthio) benzo[d]thiazole as a tan solid (2.5 g, 38%). The regiochemistry of the alkylation was determined by a 2-dimensional nuclear Overhauser effect (NOE) experiment. $^1$H NMR (300 MHz, DMSO-$d_6$) δ 8.65 (s, 1H), 8.38 (dd, J=1.2, 4.8 Hz, 1H), 8.11 (dd, J=1.3, 8.1 Hz, 1H), 8.00 (d, J=1.1 Hz, 1H), 7.81 (d, J=8.3 Hz, 1H), 7.46 (dd, J=1.6, 8.4 Hz, 1H), 7.30 (dd, J=4.8, 8.0 Hz, 1H), 5.62 (s, 2H), 2.77 (s, 3H). LCMS (ESI) m/z 313 (M+H)$^+$.

Step 5:

To a solution of 6-((3H-imidazo[4,5-b]pyridin-3-yl) methyl)-2-(methylthio)benzo[d]thiazole (2.5 g, 8 mmol) in $CH_2Cl_2$ (150 mL) was added mCPBA (70%, 2.36 g, 9.6 mmol) slowly at 0° C. The mixture was stirred at rt overnight. The resulting solution was diluted with 150 mL $CH_2Cl_2$ and washed sequentially with saturated aq $Na_2S_2O_3$, saturated aq $NaHCO_3$ and brine. The organic layer was dried over $MgSO_4$, and concentrated under reduced pressure to give 6-((3H-imidazo[4,5-b]pyridin-3-yl)methyl)-2-(methylsulfinyl)benzo[d]thiazole as a white solid (2.6 g, 99%). $^1$H NMR (300 MHz, DMSO-$d_6$) δ 8.68 (s, 1H), 8.37 (dd, J=1.3, 4.7 Hz, 1H), 8.23 (d, J=0.9 Hz, 1H), 7.99-8.18 (m, 2H), 7.63 (dd, J=1.7, 8.5 Hz, 1H), 7.30 (dd, J=4.7, 8.1 Hz, 1H), 5.70 (s, 2H), 3.06 (s, 3H). LCMS (ESI) m/z 339 (M+H)$^+$.

Step 6:

To a suspension of 6-((3H-imidazo[4,5-b]pyridin-3-yl) methyl)-2-(methylsulfinyl)benzo[d]thiazole (1.3 g, 3.96 mmol) from Step 5 of this Example in DMA (6 mL) were added DIEA (511 mg, 3.96 mmol) and (1R,2R)-2-aminocyclohexanol (1.36 g, 11.9 mmol) at rt. The reaction mixture was stirred in a sealed tube at 120° C. for 6 h. After cooling to rt, the mixture was diluted with 120 mL of EtOAc and washed with 120 mL of water. The organic layer was dried over $MgSO_4$ and concentrated under reduced pressure. The crude product was purified on a silica gel column using a mixture of acetone-EtOAc (1:12, v/v) as eluent to give (1R,2R)-2-((6-((3H-imidazo[4,5-b]pyridin-3-yl)methyl) benzo[d]thiazol-2-yl)amino)cyclohexanol as an off white solid (864 mg, 58%). $^1$H NMR (300 MHz, DMSO-$d_6$) δ 8.60 (s, 1H), 8.38 (dd, J=1.3, 4.7 Hz, 1H), 8.09 (dd, J=1.2, 8.0 Hz, 1H), 7.95 (d, J=7.5 Hz, 1H), 7.67 (s, 1H), 7.17-7.35 (m, 3H), 5.49 (s, 2H), 4.73 (d, J=5.3 Hz, 1H), 3.52 (d, J=8.5 Hz, 1H), 3.32 (br s, 1H), 1.76-2.12 (m, 2H), 1.61 (br s, 2H), 1.07-1.38 (m, 4H). LCMS (ESI) m/z 380 (M+H)$^+$.

Step 7:

To a suspension of (1R,2R)-2-4643H-imidazo[4,5-b]pyridin-3-yl)methyl)benzo[d]thiazol-2-yl)amino)cyclohexanol (1.84 g, 4.88 mmol) in EtOH (100 mL) was added methanesulfonic acid (478 mg, 4.98 mmol) at rt. The reaction mixture was stirred at 55° C. for 2 h. After cooling to rt, the mixture was concentrated under reduced pressure. The residue was diluted with 15 mL of water and freeze dried overnight to give (1R,2R)-2-((6-((3H-imidazo[4,5-b]pyridin-3-yl)methyl)benzo[d]thiazol-2-yl)amino)cyclohexanol methanesulfonate as a tan solid (2.32 g, 100%). $^1$H NMR (300 MHz, MeOH-$d_4$) δ 8.80 (s, 1H), 8.50 (dd, J=1.1, 4.7 Hz, 1H), 8.15 (dd, J=1.1, 8.1 Hz, 1H), 7.82 (s, 1H), 7.36-7.59 (m, 3H), 5.68 (s, 2H), 3.40-3.65 (m, 2H), 2.71 (s, 3H), 2.06 (d, J=12.2 Hz, 2H), 1.79 (d, J=6.6 Hz, 2H), 1.24-1.55 (m, 4H). LCMS (ESI) m/z 380 (M+H)$^+$.

Example 4

Preparation of a Mixture of (1R,2R)-2-((6-((6-methoxy-1H-benzo[d]imidazol-1-yl)methyl)benzo[d]thiazol-2-yl)amino)cyclohexanol and (1R,2R)-2-((6-((5-methoxy-1H-benzo[d]imidazol-1-yl)methyl) benzo[d]thiazol-2-yl)amino)cyclohexanol

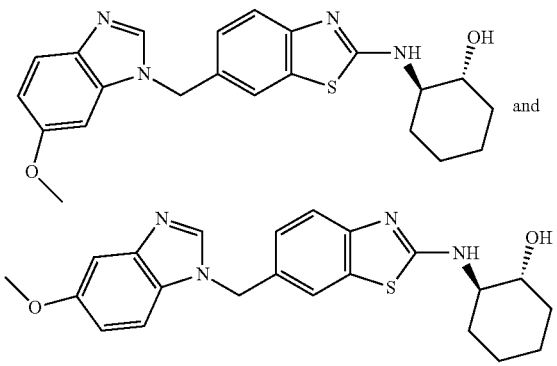

Step 1:

A mixture of 2-bromo-6-((6-methoxy-1H-benzo[d]imidazol-1-yl)methyl)benzo[d]thiazole and 2-bromo-6-((5-methoxy-1H-benzo[d]imidazol-1-yl)methyl)benzo[d]thiazole (846 mg, 81%) was obtained as white solid using a procedure analogous to that described in Step 4 of Example 2, substituting 6-methoxy-1H-benzo[d]imidazole for 5,6-dimethoxy-1H-benzo[d]imidazole used in Example 2. LCMS (ESI) m/z 374, 376 (M+H)$^+$.

Step 2:

A mixture of (1R,2R)-2-((6-(((6-methoxy-1H-benzo[d]imidazol-1-yl)methyl)benzo[d]thiazol-2-yl)amino)cyclohexanol and (1R,2R)-2-((6-((5-methoxy-1H-benzo[d]imidazol-1-yl)methyl)benzo[d]thiazol-2-yl)amino)cyclohexanol (119 mg, 51%) was obtained as a white solid using a procedure analogous to that described in Step 5 of Example 2, substituting the mixture of 2-bromo-6-((6-methoxy-1H-benzo[d]imidazol-1-yl)methyl)benzo[d]thiazole and 2-bromo-6-((5-methoxy-1H-benzo[d]imidazol-1-yl)methyl)benzo[d]thiazole from Step 1 of this Example for 2-bromo-6-((5,6-dimethoxy-1H-benzo[d]imidazol-1-yl)methyl)benzo[d]thiazole used in Example 2. $^1$H NMR (300 MHz, DMSO-$d_6$) δ 8.31 (s, 1H), 8.24 (s, 1H), 7.98 (d, J=7.3 Hz, 2H), 7.5-7.69 (m, 2H), 7.52 (d, J=8.7 Hz, 1H), 7.35-7.46 (m, 1H), 7.25-7.34 (m, 2H), 7.06-7.24 (m, 4H), 6.82 (ddd, J=2.3, 6.8, 8.8 Hz, 2H), 5.42 (s, 4H), 4.78 (br s, 2H), 3.76 (d, J=2.3 Hz, 6H), 3.51 (br s, 3H), 3.27-3.40 (m, 2H), 1.77-2.18 (m, 4H), 1.62 (d, J=5.1 Hz, 4H), 1.04-1.42 (m, 7H). LCMS (ESI) m/z 409 (M+H)$^+$.

Example 5

Preparation of (1R,2R)-2-((6-((1H-imidazo[4,5-b]pyridin-1-yl)methyl)benzo[d]thiazol-2-yl)amino)cyclohexanol

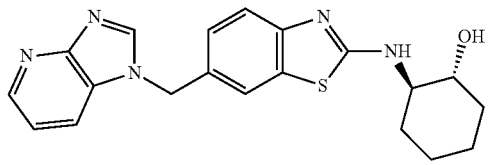 [SMILES: O[C@@H]1CCCC[C@H]1Nc1nc2ccc(Cn3cnc4ncccc43)cc2s1]

Step 1:

To a solution of (2-bromobenzo[d]thiazol-6-yl)methyl methanesulfonate (900 mg, 2.79 mmol) from Step 3 of Example 2 and 1H-imidazo[4,5-b]pyridine (365 mg, 3.07 mmol) in DMF (8 mL) was added potassium carbonate (560 mg, 3.14 mmol) at rt. The reaction mixture was stirred at rt overnight. It was then diluted with 80 mL of EtOAc and the resulting mixture was washed with water and brine. The organic layer was separated and dried over MgSO$_4$, and concentrated under reduced pressure. The crude product was purified on a silica gel column using a mixture of MeOH—CH$_2$Cl$_2$ (1:20, v/v) as eluent to give three isomers:

Isomer 1: 6-((3H-Imidazo[4,5-b]pyridin-3-yl)methyl)-2-bromobenzo[d]thiazole

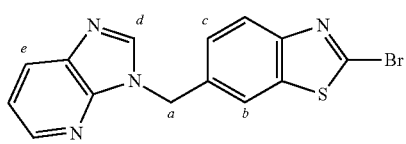 [SMILES: Brc1nc2ccc(Cn3cnc4cccnc43)cc2s1]

$^1$H NMR (300 MHz, DMSO-$d_6$) δ 8.67 (s, 1H), 8.37 (dd, J=1.3, 4.7 Hz, 1H), 8.12 (dd, J=1.2, 8.0 Hz, 1H), 8.06 (d, J=0.9 Hz, 1H), 7.93-8.00 (m, 1H), 7.55 (dd, J=1.5, 8.5 Hz, 1H), 7.31 (dd, J=4.8, 8.0 Hz, 1H), 5.67 (s, 2H). NOESY: a-b, a-c, a-d. LCMS (ESI) m/z 345, 347 (M+H)$^+$.

Isomer 2: 6-((1H-Imidazo[4,5-b]pyridin-1-yl)methyl)-2-bromobenzo[d]thiazole

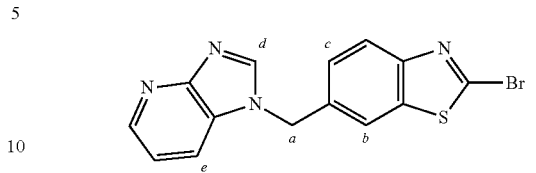

$^1$H NMR (300 MHz, DMSO-$d_6$) δ 8.72 (s, 1H), 8.42 (dd, J=1.5, 4.7 Hz, 1H), 8.08 (d, J=0.9 Hz, 1H), 7.99 (td, J=1.7, 8.1 Hz, 2H), 7.5-7.60 (m, 1H), 7.25 (dd, J=4.7, 8.1 Hz, 1H), 5.70 (s, 2H). NOESY: a-b, a-c, a-d, a-e. LCMS (ESI) m/z 345, 347 (M+H)$^+$.

Isomer 3: 6-((4H-Imidazo[4,5-b]pyridin-4-yl)methyl)-2-bromobenzo[d]thiazole

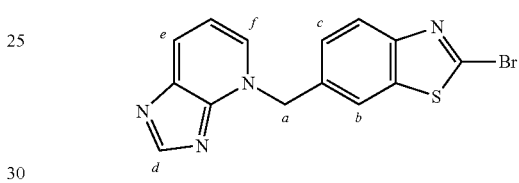

$^1$H NMR (300 MHz, DMSO-$d_6$) δ 8.42-8.51 (m, 1H), 8.28-8.40 (m, 2H), 8.20 (d, J=0.9 Hz, 1H), 7.99 (d, J=8.5 Hz, 1H), 7.68 (dd, J=1.6, 8.4 Hz, 1H), 7.21-7.35 (m, 1H), 6.04 (s, 2H). NOESY: a-b, a-c, a-f. LCMS (ESI) m/z 345, 347 (M+H)$^+$.

Step 2:

(1R,2R)-2-((6-((1H-Imidazo[4,5-b]pyridin-1-yl)methyl)benzo[d]thiazol-2-yl)amino)cyclohexanol (41 mg, 42%) was obtained as a white solid using a procedure analogous to that described in Step 5 of Example 2, substituting the 6-((1H-Imidazo[4,5-b]pyridin-1-yl)methyl)-2-bromobenzo[d]thiazole (Isomer 2) from Step 1 of this Example for 2-bromo-6-((5,6-dimethoxy-1H-benzo[d]imidazol-1-yl)methyl)benzo[d]thiazole used in Example 2. $^1$H NMR (300 MHz, DMSO-$d_6$) δ 8.66 (s, 1H), 8.35-8.44 (m, 1H), 8.00 (d, J=7.0 Hz, 2H), 7.69 (s, 1H), 7.12-7.36 (m, 3H), 5.50 (s, 2H), 4.77 (br s, 1H), 3.24-3.40 (m, 2H), 2.02 (d, J=10.2 Hz, 1H), 1.87 (d, J=9.4 Hz, 1H), 1.62 (d, J=4.9 Hz, 2H), 1.22 (d, J=6.0 Hz, 4H). LCMS (ESI) m/z 380 (M+H)$^+$.

Example 6

Preparation of (1R,2R)-2-((6-((1H-benzo[d]imidazol-1-yl)methyl)benzo[d]thiazol-2-yl)amino)cyclohexanol

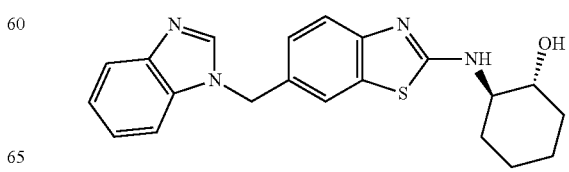

To a suspension of 6-((1H-benzo[d]imidazol-1-yl)methyl)-2-bromobenzo[d]thiazole from Step 1 of Example 1 (34.4 mg, 0.1 mmol) in DMA (3 mL) were added DIEA (15 mg, 0.12 mmol) and (1R,2R)-2-aminocyclohexanol (13.8 mg, 0.12 mmol) at rt. The reaction mixture was stirred in a sealed tube at 120° C. overnight. After cooling to rt, the mixture was concentrated under reduced pressure. The crude product was purified by preparative HPLC using a mixture of water (containing 5% $CH_3CN$, 0.05% HCOOH) and $CH_3CN$ (containing 0.05% HCOOH) as the mobile phase and Varian Pursuit XRs C-18 column as the stationary phase to afford (1R,2R)-2-((6-((1H-benzo[d]imidazol-1-yl)methyl)benzo[d]thiazol-2-yl)amino)cyclohexanol (22 mg, 58%) as a white solid. $^1$H NMR (300 MHz, DMSO-$d_6$) δ 8.40 (s, 1H), 7.99 (d, J=7.3 Hz, 1H), 7.60-7.72 (m, 2H), 7.55 (dd, J=2.6, 6.0 Hz, 1H), 7.26-7.34 (m, 1H), 7.12-7.25 (m, 3H), 5.47 (s, 2H), 4.76 (br s, 1H), 3.26-3.39 (m, 2H), 2.03 (d, J=10.0 Hz, 1H), 1.87 (d, J=9.4 Hz, 1H), 1.62 (d, J=4.7 Hz, 2H), 1.03-1.39 (m, 4H). LCMS (ESI) m/z 379 (M+H)$^+$.

Example 7

Preparation of (1S,2S)-2-((6-((1H-benzo[d]imidazol-1-yl)methyl)benzo[d]thiazol-2-yl)amino)cyclohexanol

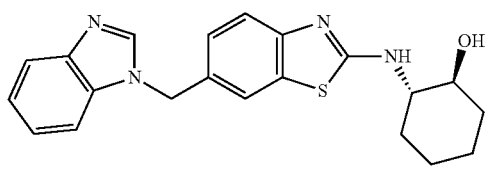 [SMILES: O[C@H]1CCCC[C@@H]1Nc1nc2ccc(Cn3cnc4ccccc43)cc2s1]

(1S,2S)-2-((6-((1H-Benzo[d]imidazol-1-yl)methyl)benzo[d]thiazol-2-yl)amino)cyclohexanol (27 mg, 71%) was obtained as a white solid using a procedure analogous to that described in Example 6, substituting (1S,2S)-2-aminocyclohexanol for (1R,2R)-2-aminocyclohexanol used in Example 6. $^1$H NMR (300 MHz, DMSO-$d_6$) δ 8.40 (s, 1H), 8.03 (d, J=7.3 Hz, 1H), 7.60-7.72 (m, 2H), 7.55 (dd, J=2.6, 6.0 Hz, 1H), 7.25-7.34 (m, 1H), 7.11-7.24 (m, 3H), 5.46 (s, 2H), 4.82 (br s, 1H), 3.50 (br s, 2H), 1.82-2.15 (m, 2H), 1.61 (br s, 2H), 1.02-1.41 (m, 4H). LCMS (ESI) m/z 379 (M+H)$^+$.

Example 8

Preparation of (R)-6-((5,6-dimethoxy-1H-benzo[d]imidazol-1-yl)methyl)-N-((tetrahydrofuran-2-yl)methyl)benzo[d]thiazol-2-amine

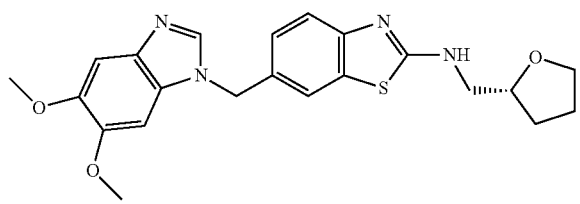 [SMILES: COc1cc2ncn(Cc3ccc4nc(NC[C@H]5CCCO5)sc4c3)c2cc1OC]

(R)-6-((5,6-Dimethoxy-1H-benzo[d]imidazol-1-yl)methyl)-N-((tetrahydrofuran-2-yl)methyl)benzo[d]thiazol-2-amine (33 mg, 65%) was obtained as a white solid using a procedure analogous to that described in Step 5 of Example 2, substituting (R)-(tetrahydrofuran-2-yl)methanamine for (1R,2R)-2-aminocyclohexanol used in Example 2. $^1$H NMR (300 MHz, DMSO-$d_6$) δ 8.05-8.22 (m, 2H), 7.64 (d, J=1.1 Hz, 1H), 7.27-7.37 (m, 1H), 7.11-7.25 (m, 3H), 5.41 (s, 2H), 3.95-4.07 (m, 1H), 3.70-3.83 (m, 7H), 3.5-3.68 (m, 2H), 3.43-3.52 (m, 1H), 1.72-2.00 (m, 3H), 1.48-1.64 (m, 1H). LCMS (ESI) m/z 425 (M+H)$^+$.

Example 9

Preparation of 6-((5,6-dimethoxy-1H-benzo[d]imidazol-1-yl)methyl)-N-(pyridin-2-ylmethyl)benzo[d]thiazol-2-amine

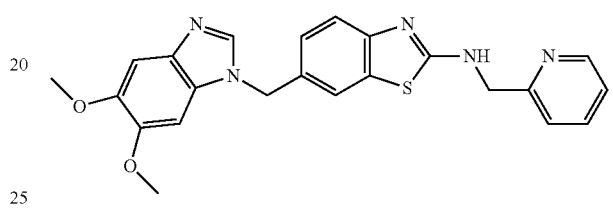

6-((5,6-Dimethoxy-1H-benzo[d]imidazol-1-yl)methyl)-N-(pyridin-2-ylmethyl)benzo[d]thiazol-2-amine (31 mg, 60%) was obtained as a white solid using a procedure analogous to that described in Step 5 of Example 2, substituting pyridin-2-ylmethanamine for (1R,2R)-2-aminocyclohexanol used in Example 2. $^1$H NMR (300 MHz, DMSO-$d_6$) δ 8.67 (t, J=5.5 Hz, 1H), 8.52 (d, J=4.3 Hz, 1H), 8.15 (s, 1H), 7.5-7.85 (m, 2H), 7.05-7.46 (m, 6H), 5.42 (s, 2H), 4.67 (d, J=5.3 Hz, 2H), 3.76 (s, 6H). LCMS (ESI) m/z 432 (M+H)$^+$.

Example 10

Preparation of (1R,2S)-1-((6-((5,6-dimethoxy-1H-benzo[d]imidazol-1-yl)methyl)benzo[d]thiazol-2-yl)amino)-2,3-dihydro-1H-inden-2-ol

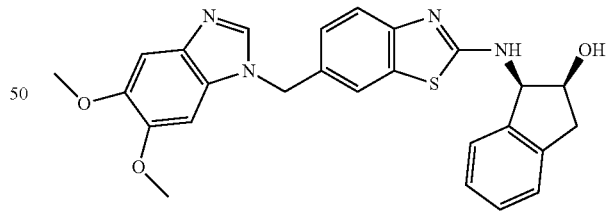

(1R,2S)-1-((6-((5,6-Dimethoxy-1H-benzo[d]imidazol-1-yl)methyl)benzo[d]thiazol-2-yl)amino)-2,3-dihydro-1H-inden-2-ol (27 mg, 39%) was obtained as a white solid using a procedure analogous to that described in Step 5 of Example 2, substituting (1R,2S)-1-amino-2,3-dihydro-1H-inden-2-ol for (1R,2R)-2-aminocyclohexanol used in Example 2. $^1$H NMR (300 MHz, DMSO-$d_6$) δ 8.33 (d, J=8.5 Hz, 1H), 8.16 (s, 1H), 7.69 (s, 1H), 7.31-7.39 (m, 1H), 7.10-7.29 (m, 7H), 5.35-5.50 (m, 3H), 4.5-4.63 (m, 1H), 3.77 (d, J=3.2 Hz, 6H), 3.08 (dd, J=4.8, 16.1 Hz, 2H), 2.83 (d, J=16.0 Hz, 1H). LCMS (ESI) m/z 473 (M+H)$^+$.

Example 11

Preparation of (S)—N-(2,3-dihydro-1H-inden-1-yl)-6-((5,6-dimethoxy-1H-benzo[d]imidazol-1-yl)methyl)benzo[d]thiazol-2-amine

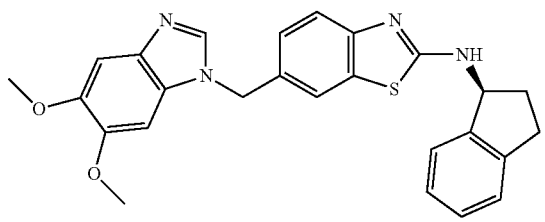 [SMILES: COc1cc2ncn(Cc3ccc4nc(N[C@H]5CCc6ccccc65)sc4c3)c2cc1OC]

(S)—N-(2,3-dihydro-1H-inden-1-yl)-6-((5,6-dimethoxy-1H-benzo[d]imidazol-1-yl)methyl)benzo[d]thiazol-2-amine (22 mg, 33%) was obtained as a white solid using a procedure analogous to that described in Step 5 of Example 2, substituting (S)-2,3-dihydro-1H-inden-1-amine for (1R,2R)-2-aminocyclohexanol used in Example 2. $^1$H NMR (300 MHz, DMSO-$d_6$) δ 8.43 (d, J=7.9 Hz, 1H), 8.17 (s, 1H), 7.68 (d, J=0.9 Hz, 1H), 7.05-7.46 (m, 7H), 5.35-5.53 (m, 3H), 3.77 (d, J=2.6 Hz, 2H), 3.36 (s, 6H), 2.74-3.08 (m, 2H), 1.79-2.02 (m, 1H). LCMS (ESI) m/z 457 (M+H)$^+$.

Example 12

Preparation of (1R,2R)-2-((6-(methoxy(1H-pyrrolo[2,3-b]pyridin-3-yl)methyl)benzo[d]thiazol-2-yl)amino)cyclohexanol

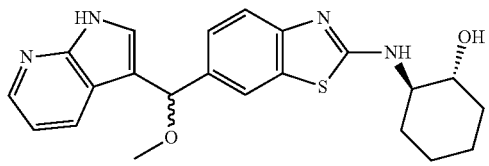 [SMILES: COC(c1ccc2nc(N[C@@H]3CCCC[C@H]3O)sc2c1)c1c[nH]c2ncccc12]

Step 1:

To a suspension of (2-bromobenzo[d]thiazol-6-yl)methanol (400 mg, 1.6 mmol) from Step 2 of Example 2 in DMA (6 mL) were added DIEA (258 mg, 2.0 mmol) and (1R,2R)-2-aminocyclohexanol (226 mg, 2.0 mmol) at rt. The reaction mixture was stirred in a sealed tube at 120° C. overnight. After cooling to rt, the mixture was concentrated under reduced pressure to give crude (1R,2R)-2-((6-(hydroxymethyl)benzo[d]thiazol-2-yl)amino)cyclohexanol as a brown oil (445 mg, 100%), which was used for the next step without any further purification. LCMS (ESI) m/z 279 (M+H)$^+$.

Step 2:

To a solution of (1R,2R)-2-((6-(hydroxymethyl)benzo[d]thiazol-2-yl)amino)cyclohexanol from Step 1 of this Example (445 mg, 1.6 mmol) in $CH_2Cl_2$ (40 mL) was added manganese(IV) oxide (696 mg, 8.0 mmol) at rt. The reaction suspension was heated under reflux overnight. After cooling to rt, the reaction mixture was filtered through a Celite pad. The filtrate was concentrated under reduced pressure to give crude 2-(((1R,2R)-2-hydroxycyclohexyl)amino)benzo[d]thiazole-6-carbaldehyde as a brown oil (440 mg, 99%), which was used to next step without further purification. LCMS (ESI) m/z 277 (M+H)$^+$.

Step 3:

To a solution of 1H-pyrrolo[2,3-b]pyridine (205 mg, 1.74 mmol) in MeOH (20 mL) were added potassium hydroxide (162 mg, 2.9 mmol) and 2-(((1R,2R)-2-hydroxycyclohexyl)amino)benzo[d]thiazole-6-carbaldehyde from Step 2 of this Example (400 mg, 1.45 mmol) sequentially at rt. The reaction mixture was stirred at rt for 14 d. The resulting mixture was diluted with EtOAc (80 mL) and washed with water, brine. The organic layer was dried over $MgSO_4$, and concentrated under reduced pressure. The crude product was purified by HPLC using a mixture of water (5% $CH_3CN$, 0.05% HCOOH) and $CH_3CN$ (0.05% HCOOH) as the mobile phase and Varian Pursuit XRs C-18 column as the stationary phase to afford (1R,2R)-2-((6-(methoxy(1H-pyrrolo[2,3-b]pyridin-3-yl)methyl)benzo[d]thiazol-2-yl)amino)cyclohexanol as a white solid (32 mg, 5.4%). $^1$H NMR (300 MHz, CDCl$_3$) δ 9.70 (br s, 1H), 8.26 (dd, J=1.4, 4.8 Hz, 1H), 7.85 (dd, J=1.3, 7.7 Hz, 1H), 7.64 (d, J=1.3 Hz, 1H), 7.44-7.54 (m, 1H), 7.34 (d, J=8.3 Hz, 1H), 6.97-7.11 (m, 2H), 5.64 (br s, 1H), 5.56 (s, 1H), 3.44-3.67 (m, 3H), 3.42 (s, 3H), 2.06-2.27 (m, 2H), 1.65-1.87 (m, 2H), 1.14-1.53 (m, 4H). LCMS (ESI) m/z 409 (M+H)$^+$.

Example 13

Preparation of N-benzyl-6-((5,6-dimethoxy-1H-benzo[d]imidazol-1-yl)methyl)benzo[d]thiazol-2-amine

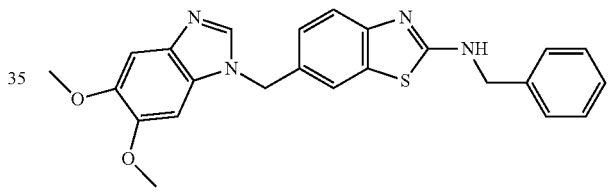

N-Benzyl-6-((5,6-dimethoxy-1H-benzo[d]imidazol-1-yl)methyl)benzo[d]thiazol-2-amine (21 mg, 33%) was obtained as a white solid using a procedure analogous to that described in Step 5 of Example 2, substituting phenylmethanamine for (1R,2R)-2-aminocyclohexanol used in Example 2. $^1$H NMR (300 MHz, DMSO-$d_6$) δ 8.54 (t, J=5.7 Hz, 1H), 8.15 (s, 1H), 7.66 (d, J=1.3 Hz, 1H), 7.07-7.47 (m, 9H), 5.41 (s, 2H), 4.57 (d, J=5.7 Hz, 2H), 3.76 (s, 6H). LCMS (ESI) m/z 431 (M+H)$^+$.

Example 14

Preparation of 6-((5,6-dimethoxy-1H-benzo[d]imidazol-1-yl)methyl)-N-(2-morpholinoethyl)benzo[d]thiazol-2-amine

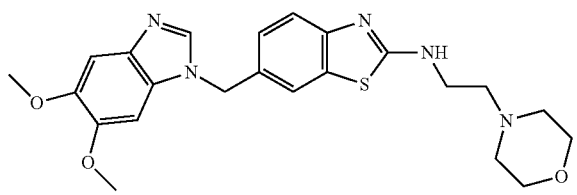 [SMILES: COc1cc2ncn(Cc3ccc4nc(NCCN5CCOCC5)sc4c3)c2cc1OC]

6-((5,6-Dimethoxy-1H-benzo[d]imidazol-1-yl)methyl)-N-(2-morpholinoethyl)benzo[d]thiazol-2-amine (14 mg, 21%) was obtained as a white solid using a procedure analogous to that described in Step 5 of Example 2, substituting 2-morpholinoethanamine for (1R,2R)-2-aminocyclohexanol used in Example 2. $^1$H NMR (300 MHz, DMSO-$d_6$) δ 8.15 (s, 1H), 7.99 (t, J=5.0 Hz, 1H), 7.64 (s, 1H), 7.27-7.36 (m, 1H), 7.11-7.26 (m, 3H), 5.41 (s, 2H), 3.76 (s, 6H), 3.52-3.66 (m, 4H), 3.38-3.51 (m, 4H), 2.33-2.45 (m, 4H). LCMS (ESI) m/z 454 (M+H)$^+$.

Example 15

Preparation of 6-((5,6-dimethoxy-1H-benzo[d]imidazol-1-yl)methyl)-N-(tetrahydro-2H-pyran-4-yl)benzo[d]thiazol-2-amine

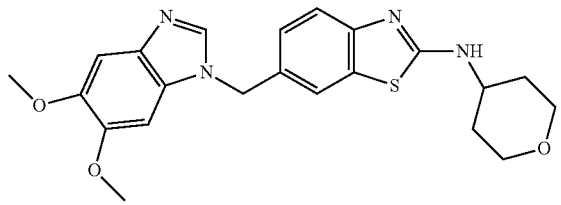 [SMILES: COc1cc2ncn(Cc3ccc4nc(NC5CCOCC5)sc4c3)c2cc1OC]

6-((5,6-Dimethoxy-1H-benzo[d]imidazol-1-yl)methyl)-N-(tetrahydro-2H-pyran-4-yl)benzo[d]thiazol-2-amine (34 mg, 54%) was obtained as a white solid using a procedure analogous to that described in Step 5 of Example 2, substituting tetrahydro-2H-pyran-4-amine for (1R,2R)-2-aminocyclohexanol used in Example 2. $^1$H NMR (300 MHz, DMSO-$d_6$) δ 8.15 (s, 1H), 8.09 (d, J=7.2 Hz, 1H), 7.65 (d, J=1.1 Hz, 1H), 7.30-7.37 (m, 1H), 7.13-7.25 (m, 3H), 5.41 (s, 2H), 3.81-4.00 (m, 2H), 3.76 (s, 6H), 3.37-3.51 (m, 3H), 1.93 (d, J=10.5 Hz, 2H), 1.37-1.56 (m, 2H). LCMS (ESI) m/z 425 (M+H)$^+$.

Example 16

Preparation of N-cyclohexyl-6-((5,6-dimethoxy-1H-benzo[d]imidazol-1-yl)methyl)-N-methylbenzo[d]thiazol-2-amine

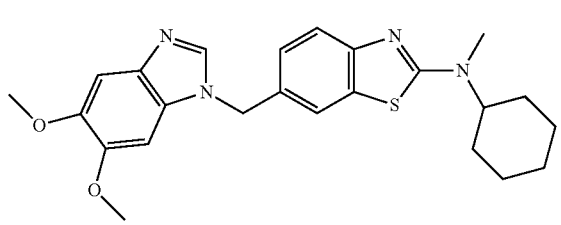 [SMILES: COc1cc2ncn(Cc3ccc4nc(N(C)C5CCCCC5)sc4c3)c2cc1OC]

N-Cyclohexyl-6-((5,6-dimethoxy-1H-benzo[d]imidazol-1-yl)methyl)-N-methylbenzo[d]thiazol-2-amine (47 mg, 73%) was obtained as a white solid using a procedure analogous to that described in Step 5 of Example 2, substituting N-methylcyclohexanamine for (1R,2R)-2-aminocyclohexanol used in Example 2. $^1$H NMR (300 MHz, DMSO-$d_6$) δ 8.16 (s, 1H), 7.75 (d, J=1.1 Hz, 1H), 7.37 (d, J=8.3 Hz, 1H), 7.24 (dd, J=1.5, 8.3 Hz, 1H), 7.18 (d, J=3.0 Hz, 2H), 5.43 (s, 2H), 3.88 (br s, 1H), 3.76 (s, 6H), 2.98 (s, 3H), 1.47-1.90 (m, 7H), 1.35 (q, J=12.5 Hz, 2H), 1.03-1.22 (m, 1H). LCMS (ESI) m/z 437 (M+H)$^+$.

Example 17

Preparation of (1R,2R)-2-((6-((1H-pyrrolo[2,3-b]pyridin-3-yl)methyl)benzo[d]thiazol-2-yl)amino)cyclohexanol

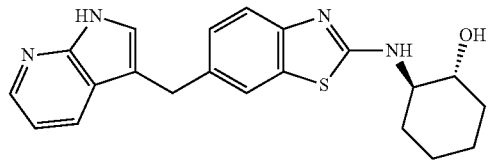 [SMILES: O[C@@H]1CCCC[C@H]1Nc1nc2ccc(Cc3c[nH]c4ncccc34)cc2s1]

To a solution of (1R,2R)-2-((6-(methoxy(1H-pyrrolo[2,3-b]pyridin-3-yl)methyl)benzo[d]thiazol-2-yl)amino)cyclohexanol (20 mg, 0.049 mmol) from Step 3 of Example 12 in CH$_3$CN (10 mL) were added triethylsilane (11.4 mg, 0.092 mmol) and TFA (10.4 mg, 0.092 mmol) at rt. The mixture was stirred at 60° C. overnight. After cooling to rt, the reaction mixture was concentrated under reduced pressure. The crude product was purified by HPLC using a mixture of water (5% CH$_3$CN, 0.05% AcOH) and CH$_3$CN (0.05% AcOH) as the mobile phase and Varian Pursuit XRs Diphenyl column as the stationary phase to afford (1R,2R)-2-((6-((1H-pyrrolo[2,3-b]pyridin-3-yl)methyl)benzo[d]thiazol-2-yl)amino)cyclohexanol (5.7 mg, 31%) as a brown solid. $^1$H NMR (300 MHz, DMSO-$d_6$) δ 11.71 (br s, 1H), 9.56 (br s, 1H), 8.23 (d, J=4.1 Hz, 1H), 7.93 (d, J=7.0 Hz, 1H), 7.70 (s, 1H), 7.26-7.42 (m, 3H), 7.07 (dd, J=4.9, 7.9 Hz, 1H), 4.11 (s, 2H), 3.53 (br s, 1H), 3.27-3.43 (m, 2H), 1.83-2.12 (m, 2H), 1.66 (br s, 2H), 1.27 (br s, 4H). LCMS (ESI) m/z 379 (M+H)$^+$.

Example 18

Preparation of N-cyclohexyl-6-((5,6-dimethoxy-1H-benzo[d]imidazol-1-yl)methyl)benzo[d]thiazol-2-amine

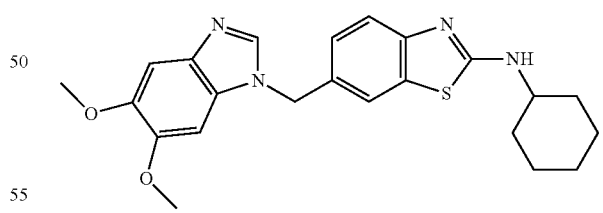

N-Cyclohexyl-6-((5,6-dimethoxy-1H-benzo[d]imidazol-1-yl)methyl)benzo[d]thiazol-2-amine (41 mg, 66%) was obtained as a white solid using a procedure analogous to that described in Step 5 of Example 2, substituting cyclohexanamine for (1R,2R)-2-aminocyclohexanol used in Example 2. $^1$H NMR (300 MHz, DMSO-$d_6$) δ 8.15 (s, 1H), 7.97 (d, J=7.5 Hz, 1H), 7.63 (s, 1H), 7.27-7.36 (m, 1H), 7.08-7.25 (m, 3H), 5.40 (s, 2H), 3.76 (s, 6H), 3.60-3.71 (m, 1H), 1.95 (d, J=10.4 Hz, 2H), 1.49-1.80 (m, 3H), 1.06-1.46 (m, 5H). LCMS (ESI) m/z 423 (M+H)$^+$.

Example 19

Preparation of (1R,2R)-1-((6-((5,6-dimethoxy-1H-benzo[d]imidazol-1-yl)methyl)benzo[d]thiazol-2-yl)amino)-2,3-dihydro-1H-inden-2-ol

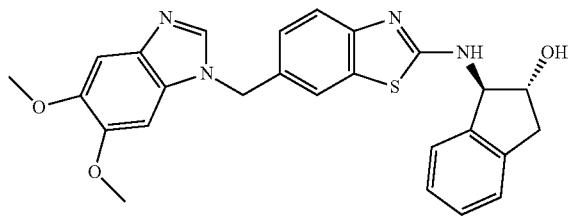 [SMILES: COc1cc2ncn(Cc3ccc4nc(N[C@@H]5c6ccccc6C[C@H]5O)sc4c3)c2cc1OC]

(1R,2R)-1-((6-((5,6-Dimethoxy-1H-benzo[d]imidazol-1-yl)methyl)benzo[d]thiazol-2-yl)amino)-2,3-dihydro-1H-inden-2-ol (41 mg, 66%) was obtained as a white solid using a procedure analogous to that described in Step 5 of Example 2, substituting (1R,2R)-1-amino-2,3-dihydro-1H-inden-2-ol for (1R,2R)-2-aminocyclohexanol used in Example 2. $^1$H NMR (300 MHz, DMSO-$d_6$) δ 8.49 (d, J=7.9 Hz, 1H), 8.17 (s, 1H), 7.69 (s, 1H), 7.32-7.43 (m, 1H), 7.05-7.31 (m, 7H), 5.44 (s, 2H), 5.18 (t, J=6.9 Hz, 1H), 4.30 (q, J=6.9 Hz, 1H), 3.77 (d, J=3.0 Hz, 6H), 3.38 (br s, 1H), 3.16 (dd, J=7.0, 15.4 Hz, 1H), 2.75 (dd, J=7.2, 15.4 Hz, 1H). LCMS (ESI) m/z 473 (M+H)$^+$.

Example 20

Preparation of (1R,2R)-2-((6-((5,6-dimethoxy-1H-benzo[d]imidazol-1-yl)methyl)benzo[d]thiazol-2-yl)amino)cyclopentanol

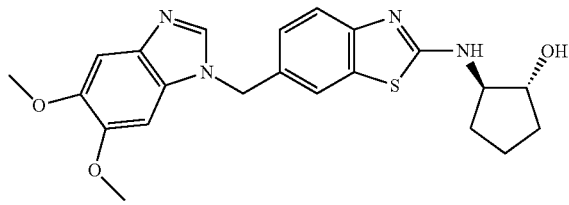 [SMILES: COc1cc2ncn(Cc3ccc4nc(N[C@@H]5CCC[C@H]5O)sc4c3)c2cc1OC]

(1R,2R)-2-((6-((5,6-Dimethoxy-1H-benzo[d]imidazol-1-yl)methyl)benzo[d]thiazol-2-yl)amino)cyclopentanol (31 mg, 49%) was obtained as a white solid using a procedure analogous to that described in Step 5 of Example 2, substituting (1R,2R)-2-aminocyclopentanol for (1R,2R)-2-aminocyclohexanol used in Example 2. $^1$H NMR (300 MHz, DMSO-$d_6$) δ 8.15 (s, 1H), 8.05 (d, J=6.6 Hz, 1H), 7.64 (d, J=1.1 Hz, 1H), 7.28-7.37 (m, 1H), 7.11-7.26 (m, 3H), 5.41 (s, 2H), 4.95 (br. s., 1H), 3.91-4.03 (m, 1H), 3.81-3.91 (m, 1H), 3.76 (s, 6H), 1.75-1.94 (m, 2H), 1.5-1.74 (m, 2H), 1.39-1.55 (m, 2H). LCMS (ESI) m/z 425 (M+H)$^+$.

Example 21

Preparation of 6-((5,6-dimethoxy-1H-benzo[d]imidazol-1-yl)methyl)-N-(pyridin-4-ylmethyl)benzo[d]thiazol-2-amine

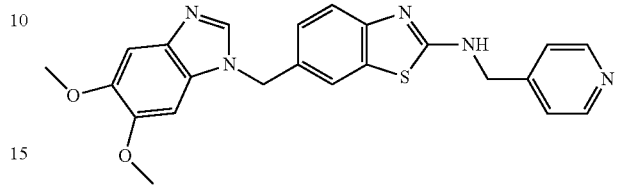

6-((5,6-Dimethoxy-1H-benzo[d]imidazol-1-yl)methyl)-N-(pyridin-4-ylmethyl)benzo[d]thiazol-2-amine (29 mg, 45%) was obtained as a white solid using a procedure analogous to that described in Step 5 of Example 2, substituting pyridin-4-ylmethanamine for (1R,2R)-2-aminocyclohexanol used in Example 2. $^1$H NMR (300 MHz, DMSO-$d_6$) δ 8.67 (t, J=5.8 Hz, 1H), 8.50 (d, J=5.7 Hz, 2H), 8.15 (s, 1H), 7.68 (d, J=0.9 Hz, 1H), 7.06-7.42 (m, 6H), 5.42 (s, 2H), 4.62 (d, J=5.5 Hz, 2H), 3.76 (s, 6H). LCMS (ESI) m/z 432 (M+H)$^+$.

Example 22

Preparation of 6-((5,6-dimethoxy-1H-benzo[d]imidazol-1-yl)methyl)-N-phenylbenzo[d]thiazol-2-amine

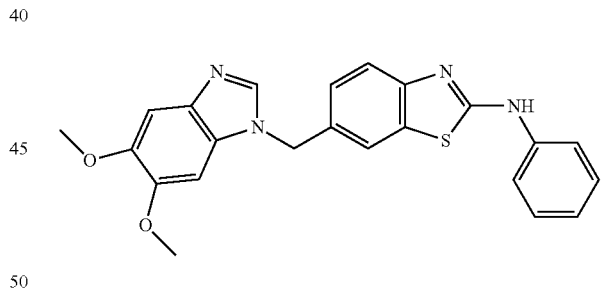

To a suspension of 2-bromo-6-((5,6-dimethoxy-1H-benzo[d]imidazol-1-yl)methyl)benzo[d]thiazole (60 mg, 0.148 mmol) from Step 4 of Example 2 in aniline (0.6 mL) was added DIEA (23 mg, 0.178 mmol) at rt. The reaction mixture was stirred in a sealed tube at 120° C. for 48 h. After cooling to rt, the reaction mixture was concentrated under reduced pressure. The crude product was purified by HPLC using a mixture of water (5% CH$_3$CN, 0.05% HCOOH) and CH$_3$CN (0.05% HCOOH) as the mobile phase and Varian Pursuit XRs C18 column as the stationary phase to afford 6-((5,6-dimethoxy-1H-benzo[d]imidazol-1-yl)methyl)-N-phenylbenzo[d]thiazol-2-amine (31 mg, 50%) as a white solid. $^1$H NMR (300 MHz, DMSO-$d_6$) δ 10.53 (br s, 1H), 8.18 (s, 1H), 7.71-7.82 (m, 3H), 7.56 (d, J=8.3 Hz, 1H), 7.26-7.42 (m, 3H), 7.19 (d, J=3.2 Hz, 2H), 7.01 (t, J=7.3 Hz, 1H), 5.48 (s, 2H), 3.77 (s, 6H). LCMS (ESI) m/z 417 (M+H)$^+$.

Example 23

Preparation of (1R,2R)-2-((6-((5-methoxy-3H-imidazo[4,5-b]pyridin-3-yl)methyl)benzo[d]thiazol-2-yl)amino)cyclohexanol

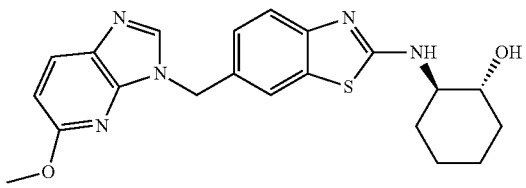 [SMILES: COc1ccc2ncn(Cc3ccc4nc(N[C@@H]5CCCC[C@H]5O)sc4c3)c2n1]

Step 1:

To a stirred solution of 4-aminobenzonitrile (10.0 g, 84.7 mmol) in MeCN (100 mL) at 90° C. was slowly added N-chlorosuccinimide (12.4 g, 93 mmol). After the addition of N-chlorosuccinimide, the reaction mixture was stirred at 90° C. for 2 h. The reaction mixture was then cooled to rt and concentrated under reduced pressure. The residue was dissolved in 500 mL of $CH_2Cl_2$ and washed with 5% aq NaOH. The organic layer was dried over $MgSO_4$ and concentrated under reduced pressure to give 4-amino-3-chlorobenzonitrile as a tan solid (12.2 g, 95%). $^1H$ NMR (300 MHz, $CDCl_3$) δ 7.54 (d, J=1.7 Hz, 1H), 7.35 (dd, J=1.8, 8.4 Hz, 1H), 6.77 (d, J=8.5 Hz, 1H), 4.63 (br s, 2H).

Step 2:

To a solution of 4-amino-3-chlorobenzonitrile (12.2 g, 80.2 mmol) from Step 1 of this Example in DMF (60 mL) was added potassium O-ethyl carbonodithioate (28.9 g, 180.7 mmol) at rt. The mixture was refluxed for 4 h. After cooling to rt, the reaction mixture was poured into ice water and acidified with 2N aq HCl. The tan solids were collected and dried in vacuum oven overnight. Then the solids were refluxed with 500 mL of $CHCl_3$ for 10 min. After cooling to rt, the mixture was treated with 200 mL of hexanes and sonicated for 20 min. The pale brown solid was collected by filtration to give 2-mercaptobenzo[d]thiazole-6-carbonitrile (12.9 g, 84%). $^1H$ NMR (300 MHz, DMSO-$d_6$) δ 14.16 (br s, 1H), 8.23 (d, J=0.9 Hz, 1H), 7.83 (dd, J=1.3, 8.5 Hz, 1H), 7.31-7.51 (m, 1H).

Step 3:

Sodium hydride (60% in mineral oil, 1.92 g, 48 mmol) was suspended in DMF (60 mL) at 0° C. and 2-mercaptobenzo[d]thiazole-6-carbonitrile (5.76 g, 30 mmol) from Step 2 of this Example was added slowly. After gas evolution ceased, iodomethane (8.4 mL, 135 mmol) was added and the reaction mixture was stirred at rt overnight. To the reaction mixture was added 300 mL of water and the precipitate was collected by filtration to give 2-(methylthio)benzo[d]thiazole-6-carbonitrile as a light yellow solid (5.47 g, 89%). $^1H$ NMR (300 MHz, $CDCl_3$) δ 8.08 (d, J=1.1 Hz, 1H), 7.91 (d, J=8.3 Hz, 1H), 7.67 (dd, J=1.5, 8.5 Hz, 1H), 2.83 (s, 3H).

Step 4:

To a solution of 2-(methylthio)benzo[d]thiazole-6-carbonitrile (10.0 g, 48.5 mmol) from Step 3 of this Example in THF (150 mL) was added lithium aluminum hydride solution (2.0 M in THF, 50.9 mL, 101.9 mmol) slowly at −78° C. The reaction mixture was slowly warmed to 0° C. and stirred at 0° C. for 3 h treated with 4 mL of water, 4 mL of 10% aq NaOH and 12 mL of water. The resulting reaction mixture was stirred at rt for 1 h before it was filtered through a Celite pad and the precipitates were washed with 100 of mL EtOAc. The combined filtrates were concentrated under reduced pressure. The crude product was purified on a silica gel column using a mixture of MeOH—$CH_2Cl_2$ (1:2, v/v) as eluent to give (2-(methylthio)benzo[d]thiazol-6-yl)methanamine as an yellow oil (3.5 g, 34%). $^1H$ NMR (300 MHz, $CDCl_3$) δ 7.82 (d, J=8.3 Hz, 1H), 7.73 (s, 1H), 7.35 (dd, J=1.4, 8.4 Hz, 1H), 3.97 (s, 2H), 2.79 (s, 3H), 1.55 (s, 2H). LCMS (ESI) m/z 211 (M+H)$^+$.

Step 5:

To a solution of 2-chloro-6-methoxy-3-nitropyridine (430 mg, 2.3 mmol) in DMF (6 mL) was added (2-(methylthio)benzo[d]thiazol-6-yl)methanamine (437 mg, 2.1 mmol) from Step 4 of this Example slowly at 0° C. The reaction mixture was stirred at rt overnight. The resulting reaction mixture was diluted with 60 mL of EtOAc and washed with saturated aq $NaHCO_3$ and brine. The organic layer was dried over $MgSO_4$, and concentrated under reduced pressure. The crude product was purified on a silica gel column using $CH_2Cl_2$ as eluent to give 6-methoxy-N-((2-(methylthio)benzo[d]thiazol-6-yl)methyl)-3-nitropyridin-2-amine as a yellow solid (431 mg, 57%). LCMS (ESI) m/z 363 (M+H)$^+$.

Step 6:

To a mixture of 6-methoxy-N-((2-(methylthio)benzo[d]thiazol-6-yl)methyl)-3-nitropyridin-2-amine (431 mg, 1.19 mmol) from Step 5 of this Example in acetic acid (6 mL) was added zinc powder (235 mg, 3.57 mmol) slowly at 0° C. The reaction mixture was stirred at 0° C. for 20 min and then stirred at rt for 4 h. The resulting reaction mixture was diluted with 30 mL of EtOAc and filtered through a Celite pad. The filtrate was neutralized with saturated aq $NaHCO_3$. The organic layer was separated, dried over $MgSO_4$, and concentrated under reduced pressure. The crude product was purified on a silica gel column using a mixture of EtOAc-$CH_2Cl_2$ (1:3, v/v) as eluent to give 6-methoxy-$N^2$-((2-(methylthio)benzo[d]thiazol-6-yl)methyl)pyridine-2,3-diamine as a brown oil (389 mg, 98%). LCMS (ESI) m/z 333 (M+H)$^+$.

Step 7:

To a solution of triethoxymethane (5 mL) was added 6-methoxy-$N^2$-((2-(methylthio)benzo[d]thiazol-6-yl)methyl)pyridine-2,3-diamine (332 mg, 1.0 mmol) from Step 6 of this Example at rt. The reaction mixture was heated under reflux overnight. After cooling to rt, the mixture was concentrated under reduced pressure. The crude product was purified on a silica gel column using a mixture of EtOAc-$CH_2Cl_2$ (0 to 100%, v/v) as eluent to give 6-((5-methoxy-3H-imidazo[4,5-b]pyridin-3-yl)methyl)-2-(methylthio)benzo[d]thiazole as a brown solid (180 mg, 53%). $^1H$ NMR (300 MHz, $CDCl_3$) δ 7.95 (d, J=8.7 Hz, 1H), 7.87 (s, 1H), 7.82 (d, J=8.5 Hz, 1H), 7.70 (d, J=1.1 Hz, 1H), 7.41 (dd, J=1.7, 8.3 Hz, 1H), 6.71 (d, J=8.7 Hz, 1H), 5.47 (s, 2H), 3.99 (s, 3H), 2.78 (s, 3H). LCMS (ESI) m/z 343 (M+H)$^+$.

Step 8:

(6-((5-Methoxy-3H-imidazo[4,5-b]pyridin-3-yl)methyl)-2-(methylsulfinyl)benzo[d]thiazole (180 mg, 100%) was obtained as an off white solid using a procedure analogous to that described in Step 5 of Example 3, substituting 6-((5-methoxy-3H-imidazo[4,5-b]pyridin-3-yl)methyl)-2-(methylthio)benzo[d]thiazole from Step 7 of this Example for 6-((3H-imidazo[4,5-b]pyridin-3-yl)methyl)-2-(methylthio)benzo[d]thiazole used in Example 3. LCMS (ESI) m/z 359 (M+H)$^+$.

Step 9:

(1R,2R)-2-((6-((5-Methoxy-3H-imidazo[4,5-b]pyridin-3-yl)methyl)benzo[d]thiazol-2-yl)amino)cyclohexanol (36 mg, 35%) was obtained as a white solid using a procedure analogous to that described in Step 5 of Example 2, substituting 6-((5-methoxy-3H-imidazo[4,5-b]pyridin-3-yl)methyl)-2-(methylsulfinyl)benzo[d]thiazole from Step 8 of this Example for 2-bromo-6-((5,6-dimethoxy-1H-benzo[d]imidazol-1-yl)methyl)benzo[d]thiazole used in Example 2. ¹H NMR (300 MHz, DMSO-d₆) δ 8.34 (s, 1H), 7.90-8.08 (m, 2H), 7.73 (s, 1H), 7.29 (s, 2H), 6.69 (d, J=8.5 Hz, 1H), 5.39 (s, 2H), 4.76 (br s, 1H), 3.94 (s, 3H), 3.51 (br s, 2H), 1.76-2.17 (m, 2H), 1.61 (br s, 2H), 1.04-1.42 (m, 4H). LCMS (ESI) m/z 410 (M+H)⁺.

Example 24

Preparation of 1-(4-((6-((5,6-dimethoxy-1H-benzo[d]imidazol-1-yl)methyl)benzo[d]thiazol-2-yl)amino)piperidin-1-yl)ethanone acetic acid

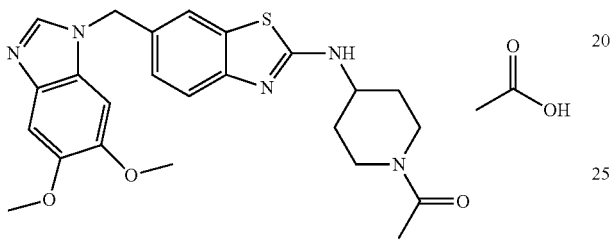

A stirred mixture of 2-bromo-6-((5,6-dimethoxy-1H-benzo[d]imidazol-1-yl)methyl)benzo[d]thiazole (80 mg, 0.198 mmol) from Example 2, 1-(4-aminopiperidin-1-yl)ethanone (56 mg, 0.396 mmol) and DIEA (77 mg, 0.594 mmol) in anhydrous DMA (1 mL) was heated at 120° C. for 15 h. After cooling to rt, the mixture was purified directly by reverse-phase HPLC using a mixture of water (5% CH₃CN, 0.05% HCOOH) and CH₃CN (0.05% HCOOH) as the mobile phase and Varian Pursuit XRs C-18 column as the stationary phase to afford 1-(4-((6-((5,6-dimethoxy-1H-benzo[d]imidazol-1-yl)methyl)benzo[d]thiazol-2-yl)amino)piperidin-1-yl)ethanone acetate (7 mg, 7%) as a white solid. ¹H NMR (300 MHz, DMSO-d₆) δ 8.15 (s, 1H), 8.08 (d, J=7.2 Hz, 1H), 7.65 (s, 1H), 7.30-7.37 (m, 1H), 7.14-7.25 (m, 3H), 5.41 (s, 2H), 4.18 (m, 1H), 3.94 (m, 1H), 3.75-3.77 (m, 7H), 3.11-3.24 (m, 2H), 2.78-2.85 (m, 1H), 1.95-2.05 (m, 4H), 1.89 (s, 3H), 1.19-1.48 (m, 2H). LCMS (ESI) m/z 466 (M+H)⁺.

Example 25

Preparation of (R,S)-6-((5,6-dimethoxy-1H-benzo[d]imidazol-1-yl)methyl)-N-(tetrahydrofuran-3-yl)benzo[d]thiazol-2-amine acetic acid

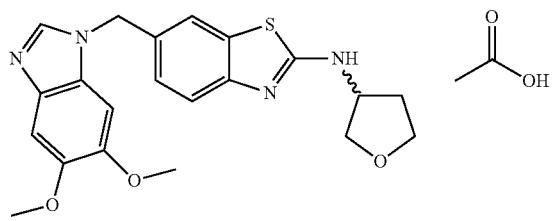

A stirred mixture of 2-bromo-6-((5,6-dimethoxy-1H-benzo[d]imidazol-1-yl)methyl)benzo[d]thiazole (80 mg, 0.198 mmol) from Example 2, (R,S)-tetrahydrofuran-3-amine (34 mg, 0.396 mmol) and DIEA (77 mg, 0.594 mmol) in anhydrous DMA (1 mL) was heated at 120° C. for 3 h. After cooling to rt, the mixture was purified directly by reverse-phase HPLC using a mixture of water (5% CH₃CN, 0.05% HCOOH) and CH₃CN (0.05% HCOOH) as the mobile phase and Varian Pursuit XRs C-18 column as the stationary phase to afford (R,S)-6-((5,6-dimethoxy-1H-benzo[d]imidazol-1-yl)methyl)-N-(tetrahydrofuran-3-yl)benzo[d]thiazol-2-amine acetate (15 mg, 16%) as a white solid. ¹H NMR (300 MHz, DMSO-d₆) δ 8.28 (d, J=6.0 Hz, 1H), 8.15 (s, 1H), 7.66 (d, J=1.1 Hz, 1H), 7.36 (d, J=8.1 Hz, 1H), 7.14-7.26 (m, 3H), 5.42 (s, 2H), 4.39 (br s, 1H), 3.5-3.88 (m, 11H), 2.12-2.26 (m, 1H), 1.88 (s, 3H). LCMS (ESI) m/z 411 (M+H)⁺.

Example 26

Preparation of 3-((2-(((1R,2R)-2-hydroxycyclohexyl)amino)benzo[d]thiazol-6-yl)methyl)-3H-imidazo[4,5-b]pyridin-2-aminium acetic acid

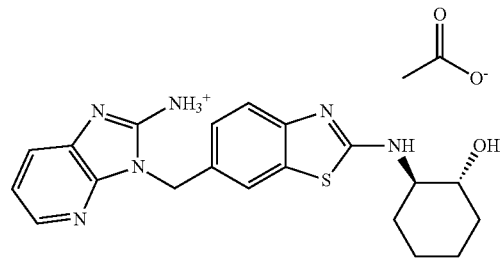

Step 1:

3-((2-Bromobenzo[d]thiazol-6-yl)methyl)-3H-imidazo[4,5-b]pyridin-2-amine (34 mg, 20%) was obtained as a white solid using a procedure analogous to that described in Step 4 of Example 2, substituting 3H-imidazo[4,5-b]pyridin-2-amine for 5,6-dimethoxy-1H-benzo[d]imidazole used in Example 2. ¹H NMR (300 MHz, CDCl₃): δ 7.97 (d, J=8.5 Hz, 1H), 7.51 (d, J=5.5 Hz, 2H), 7.35 (dd, J=8.3, 1.5 Hz, 1H), 7.14-7.23 (m, 1H), 7.05-7.14 (m, 3H), 5.28 (s, 2H).

Step 2:

(1R,2R)-2-((6-((2-Amino-3H-imidazo[4,5-b]pyridin-3-yl)methyl)benzo[d]thiazol-2-yl)amino)cyclohexanol (14 mg, 36%) was obtained as a white solid using a procedure analogous to that described in Step 5 of Example 2, substituting 3-((2-bromobenzo[d]thiazol-6-yl)methyl)-3H-imidazo[4,5-b]pyridin-2-amine from Step 1 of this Example for 2-bromo-6-((5,6-dimethoxy-1H-benzo[d]imidazol-1-yl)methyl)benzo[d]thiazole used in Example 2. ¹H NMR (300 MHz, DMSO-d₆) δ 7.95 (d, J=7.5 Hz, 1H), 7.48 (d, J=1.1 Hz, 1H), 7.27 (d, J=8.3 Hz, 1H), 7.02-7.19 (m, 3H), 6.91 (t, J=7.1 Hz, 1H), 6.76-6.85 (m, 1H), 6.54 (s, 2H), 5.22 (s, 2H), 4.77 (br. s., 1H), 3.11 (br. s., 2H), 1.95-2.16 (m, 2H), 1.87 (s, 3H), 1.62 (d, J=4.5 Hz, 2H), 1.01-1.41 (m, 4H). LCMS (ESI) m/z 395 (M+H)⁺.

Example 27

Preparation of 6-((5,6-dimethoxy-1H-benzo[d]imidazol-1-yl)methyl)-N-(2-ethoxyphenyl)benzo[d]thiazol-2-amine

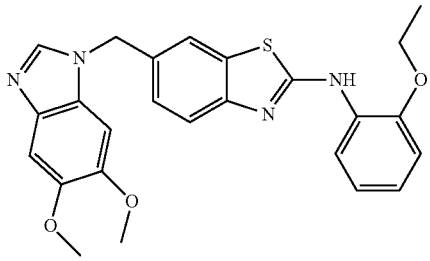 [SMILES: CCOc1ccccc1Nc1nc2ccc(Cn3cnc4cc(OC)c(OC)cc43)cc2s1]

To a suspension of 2-bromo-6-((5,6-dimethoxy-1H-benzo[d]imidazol-1-yl)methyl)benzo[d]thiazole (60 mg, 0.15 mmol) from Example 2 and 2-ethoxyaniline (61 mg, 0.46 mmol) in anhydrous DMA (600 μL) at rt was added DIEA (155 μL, 0.90 mmol). The mixture was heated in a sealed tube at 110° C. for 72 h. After cooling to rt, the resulting reaction solution was purified by reverse-phase preparative HPLC using a mixture of water (5% $CH_3CN$, 0.05% HCOOH) and $CH_3CN$ (0.05% HCOOH) as the mobile phase and Varian Pursuit XRs C18 column as the stationary phase to afford 6-((5,6-dimethoxy-1H-benzo[d]imidazol-1-yl)methyl)-N-(2-ethoxyphenyl)benzo[d]thiazol-2-amine (15.2 mg, 22%) as a white solid. $^1$H NMR (300 MHz, DMSO-$d_6$) δ 9.69 (s, 1H), 8.31-8.44 (m, 1H), 8.18 (s, 1H), 7.76 (d, J=1.1 Hz, 1H), 7.51 (d, J=8.1 Hz, 1H), 7.29 (dd, J=1.5, 8.3 Hz, 1H), 7.19 (d, J=2.4 Hz, 2H), 6.91-7.07 (m, 3H), 5.47 (s, 2H), 4.12 (q, J=6.8 Hz, 2H), 3.76 (s, 6H), 1.37 (t, J=7.0 Hz, 3H). LCMS (ESI) m/z 461 (M+H)$^+$.

Example 28

Preparation of N-(cyclohexylmethyl)-6-((5,6-dimethoxy-1H-benzo[d]imidazol-1-yl)methyl)benzo[d]thiazol-2-amine

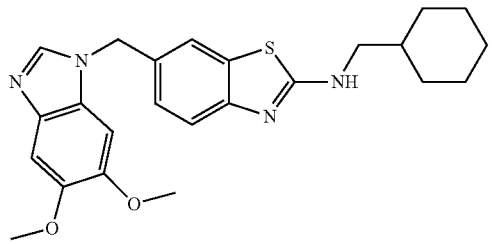 [SMILES: COc1cc2ncn(Cc3ccc4nc(NCC5CCCCC5)sc4c3)c2cc1OC]

A stirred mixture of 2-bromo-6-((5,6-dimethoxy-1H-benzo[d]imidazol-1-yl)methyl)benzo[d]thiazole (70 mg, 0.173 mmol) from Example 2, cyclohexanemethylamine (39 mg, 0.346 mmol) and DIEA (67 mg, 0.519 mmol) in anhydrous DMA (1.5 mL) was heated at 100° C. for 2.5 h. After cooling to rt, the mixture was purified directly by reverse-phase HPLC using a mixture of water (5% $CH_3CN$, 0.05% HCOOH) and $CH_3CN$ (0.05% HCOOH) as the mobile phase and Varian Pursuit XRs C-18 column as the stationary phase to afford N-(cyclohexylmethyl)-6-((5,6-dimethoxy-1H-benzo[d]imidazol-1-yl)methyl)benzo[d]thiazol-2-amine (25 mg, 33%) as a white solid. $^1$H NMR (300 MHz, DMSO-$d_6$) δ 8.15 (br s, 1H), 8.04 (t, J=5.4 Hz, 1H), 7.63 (s, 1H), 7.31 (m, 1H), 7.12-7.24 (m, 3H), 5.40 (s, 2H), 3.76 (s, 6H), 3.17 (t, J=6.1 Hz, 2H), 1.49-1.78 (m, 6H), 1.07-1.27 (m, 3H), 0.84-1.02 (m, 2H). LCMS (ESI) m/z 437 (M+H)$^+$.

Example 29

Preparation of (1R,2R)-2-((6-((6-bromo-3H-imidazo[4,5-b]pyridin-3-yl)methyl)benzo[d]thiazol-2-yl)amino)cyclohexanol

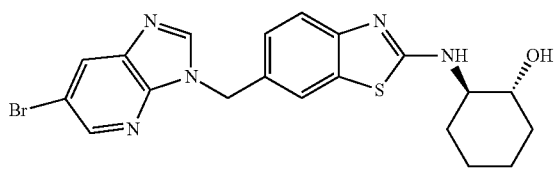 [SMILES: O[C@@H]1CCCC[C@H]1Nc1nc2ccc(Cn3cnc4cc(Br)cnc43)cc2s1]

Step 1:
5-Bromo-N-((2-(methylthio)benzo[d]thiazol-6-yl)methyl)-3-nitropyridin-2-amine (605 mg, 44%) was obtained as a yellow solid using a procedure analogous to that described in Step 5 of Example 23, substituting 5-bromo-2-chloro-3-nitropyridine for 2-chloro-6-methoxy-3-nitropyridine used in Example 23. LCMS (ESI) m/z 409, 411 (M+H)$^+$.

Step 2:
5-Bromo-N$^2$-((2-(methylthio)benzo[d]thiazol-6-yl)methyl)pyridine-2,3-diamine (170 mg, 30%) was obtained as an yellow oil using a procedure analogous to that described in Step 6 of Example 23, substituting 5-bromo-N-((2-(methylthio)benzo[d]thiazol-6-yl)methyl)-3-nitropyridin-2-amine from Step 1 of this Example for 6-methoxy-N-((2-(methylthio)benzo[d]thiazol-6-yl)methyl)-3-nitropyridin-2-amine used in Example 23. LCMS (ESI) m/z 381, 383 (M+H)$^+$.

Step 3:
6-((6-Bromo-3H-imidazo[4,5-b]pyridin-3-yl)methyl)-2-(methylthio)benzo[d]thiazole (71 mg, 40%) was obtained as an off white solid using a procedure analogous to that described in Step 7 of Example 23, substituting 5-bromo-N$^2$-((2-(methylthio)benzo[d]thiazol-6-yl)methyl)pyridine-2,3-diamine from Step 2 of this Example for 6-methoxy-N$^2$-((2-(methylthio)benzo[d]thiazol-6-yl)methyl)pyridine-2,3-diamine used in Example 23. LCMS (ESI) m/z 391, 393 (M+H)$^+$.

Step 4:
6-((6-Bromo-3H-imidazo[4,5-b]pyridin-3-yl)methyl)-2-(methylsulfinyl)benzo[d]thiazole (73 mg, 100%) was obtained as an off white solid using a procedure analogous to that described in Step 8 of Example 23, substituting 6-((6-bromo-3H-imidazo[4,5-b]pyridin-3-yl)methyl)-2-(methylthio)benzo[d]thiazole from Step 3 of this Example for 6-((5-methoxy-3H-imidazo[4,5-b]pyridin-3-yl)methyl)-2-(methylthio)benzo[d]thiazole used in Example 23. LCMS (ESI) m/z 407, 409 (M+H)$^+$.

Step 5:
(1R,2R)-2-((6-((6-Bromo-3H-imidazo[4,5-b]pyridin-3-yl)methyl)benzo[d]thiazol-2-yl)amino)cyclohexanol (22 mg, 27%) was obtained as a white solid using a procedure analogous to that described in Step 5 of Example 2, substituting 6-((6-bromo-3H-imidazo[4,5-b]pyridin-3-yl)methyl)-2-(methylsulfinyl)benzo[d]thiazole from Step 4 of this Example for 2-bromo-6-((5,6-dimethoxy-1H-benzo[d]imidazol-1-yl)methyl)benzo[d]thiazole used in Example 2. $^1$H NMR (300 MHz, DMSO-d$_6$) δ 8.66 (s, 1H), 8.48 (d, J=2.1 Hz, 1H), 8.40 (d, J=2.1 Hz, 1H), 8.00 (d, J=7.5 Hz, 1H), 7.65 (s, 1H), 7.15-7.36 (m, 2H), 5.48 (s, 2H), 4.78 (br s, 1H), 3.51 (br s, 1H), 1.96-2.13 (m, 1H), 1.87 (d, J=9.6 Hz, 1H), 1.61 (br s, 2H), 1.01-1.40 (m, 4H). LCMS (ESI) m/z 458, 460 (M+H)$^+$.

Example 30

Preparation of 6-((5,6-dimethoxy-1H-benzo[d]imidazol-1-yl)methyl)-N-(2-methoxyphenyl)benzo[d]thiazol-2-amine

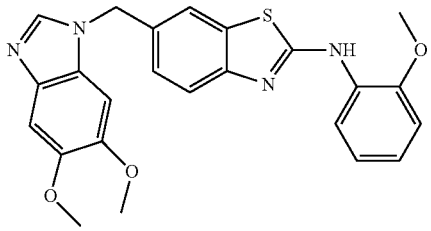 [SMILES: COc1ccccc1Nc1nc2ccc(Cn3cnc4cc(OC)c(OC)cc43)cc2s1]

To a suspension of 2-bromo-6-((5,6-dimethoxy-1H-benzo[d]imidazol-1-yl)methyl)benzo[d]thiazole (26 mg, 0.063 mmol) from Example 2 and 2-methoxyaniline (15.5 mg, 0.13 mmol) in anhydrous 1,4-dioxane (0.30 mL) at rt was added Cs$_2$CO$_3$ (41 mg, 0.13 mmol). Argon was bubbled into the mixture for 5 min followed by the addition of 4,5-bis(diphenylphosphino)-9,9-dimethylxanthene (3.0 mg, 0.005 mmol) and tris(dibenzylideneacetone)dipalladium (0) (2.3 mg, 0.003 mmol). Argon was bubbled into the mixture for an additional 5 min and then the mixture was heated in a sealed tube at 100° C. for 4 h. After cooling to rt, the reaction mixture was filtered through a Celite plug and the filtrate was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford 6-((5,6-dimethoxy-1H-benzo[d]imidazol-1-yl)methyl)-N-(2-methoxyphenyl)benzo[d]thiazol-2-amine (9.4 mg, 33%) as a white solid. $^1$H NMR (300 MHz, DMSO-d$_6$) δ 9.85 (s, 1H), 8.42 (d, J=7.3 Hz, 1H), 8.18 (s, 1H), 7.76 (d, J=1.1 Hz, 1H), 7.51 (d, J=8.1 Hz, 1H), 7.28 (dd, J=1.5, 8.3 Hz, 1H), 7.19 (d, J=2.1 Hz, 2H), 6.92-7.09 (m, 3H), 5.46 (s, 2H), 3.86 (s, 3H), 3.76 (d, J=0.8 Hz, 6H). LCMS (ESI) m/z 447 (M+H)$^+$.

Example 31

Preparation of 2-((6-((5,6-dimethoxy-1H-benzo[d]imidazol-1-yl)methyl)benzo[d]thiazol-2-yl)amino)phenol

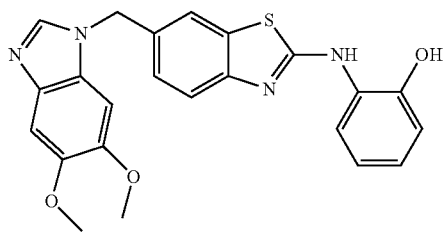 [SMILES: COc1cc2ncn(Cc3ccc4nc(Nc5ccccc5O)sc4c3)c2cc1OC]

To a suspension of 2-bromo-6-((5,6-dimethoxy-1H-benzo[d]imidazol-1-yl)methyl)benzo[d]thiazole (70 mg, 0.17 mmol) from Example 2 and 2-aminophenol (95 mg, 0.87 mmol) in anhydrous DMA (300 μL) at rt was added DIEA (90 μL, 0.52 mmol). The mixture was stirred and heated in a sealed tube at 110° C. for 96 h. After cooling to rt, the mixture was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford 2-((6-((5,6-dimethoxy-1H-benzo[d]imidazol-1-yl)methyl)benzo[d]thiazol-2-yl)amino)phenol (12 mg, 16%) as a white solid. $^1$H NMR (300 MHz, DMSO-d$_6$) δ 9.77 (br s, 1H), 8.14-8.26 (m, 2H), 7.75 (s, 1H), 7.49 (d, J=8.3 Hz, 1H), 7.24-7.29 (m, 1H), 7.16-7.22 (m, 2H), 6.79-6.92 (m, 3H), 5.46 (s, 2H), 3.76 (s, 6H). LCMS (ESI) m/z 461 (M+H)$^+$.

Example 32

Preparation of (1R,2R)-1-((6-((4-(1-methyl-1H-pyrazol-4-yl)-1H-imidazol-1-yl)methyl)benzo[d]thiazol-2-yl)amino)-2,3-dihydro-1H-inden-2-ol or (1R,2R)-1-((6-((5-(1-methyl-1H-pyrazol-4-yl)-1H-imidazol-1-yl)methyl)benzo[d]thiazol-2-yl)amino)-2,3-dihydro-1H-inden-2-ol (Alternative of Example 83)

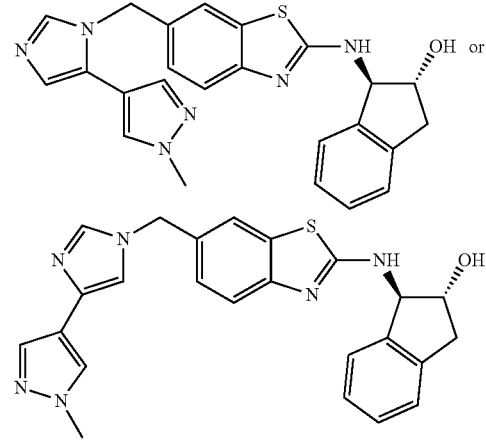

Step 1:

To a stirred mixture of DMF (15 mL) and NaH (60% dispersion in mineral oil, 539 mg, 21 mmol) at 0° C. under argon was added 4-bromo-1H-imidazole (3 g, 20 mmol) in one portion. The mixture was stirred for 5 min at 0° C. A solution of 2-(trimethylsilyl)ethoxymethyl chloride (4.3 mL, 24 mmol) in DMF (3 mL) was added dropwise. After stirring at 0° C. for 1 h, the mixture was warmed slowly to rt and stirred for 6 h. The mixture was then partitioned between EtOAc (100 mL) and water (50 mL). The EtOAc layer was separated and washed with brine, dried over Na$_2$SO$_4$, filtered, and the filtrate was concentrated under reduced pressure. The residue was purified via silica gel flash chromatography (eluting with a gradient of 100% hexanes to 100% EtOAc) to afford a regioisomeric mixture of 4-bromo-1-((2-(trimethylsilyl)ethoxy)methyl)-1H-imidazole and 5-bromo-1-((2-(trimethylsilyl)ethoxy)methyl)-1H-imidazole as an oil (2.9 g, 53%). LCMS (ESI) m/z 277 and 279 (M+H)$^+$.

Step 2:

To a mixture of 4-bromo-1-((2-(trimethylsilyl)ethoxy)methyl)-1H-imidazole and 5-bromo-1-((2-(trimethylsilyl)ethoxy)methyl)-1H-imidazole (345 mg, 1.3 mmol) from Step 1 of this Example, and 1-methylpyrazole-4-boronic acid pinacol ester (390 mg, 1.9 mmol) in DME (3 mL) was added $K_2CO_3$ (691, 5 mmol). Argon was bubbled into the mixture for 5 min followed by the addition of $Pd(PPh_3)_2Cl_2$ (44 mg, 0.06 mmol). Argon was bubbled into the mixture for an additional 5 min. Then the reaction vessel was sealed and the mixture was heated at 100° C. for 15 h. The mixture was cooled to rt, then partitioned between EtOAc (100 mL) and water (50 mL). The EtOAc layer was separated and washed with brine, dried over $Na_2SO_4$, filtered, and concentrated under reduced pressure. The residue was purified via silica gel flash chromatography eluting with a gradient of 100% $CH_2Cl_2$ to 10% MeOH in $CH_2Cl_2$ to afford a regioisomeric mixture of 1-methyl-4-(1-((2-(trimethylsilyl)ethoxy)methyl)-1H-imidazol-4-yl)-1H-pyrazole and 1-methyl-4-(1-((2-(trimethylsilyl)ethoxy)methyl)-1H-imidazol-5-yl)-1H-pyrazole as an oil (280 mg, 82%). LCMS (ESI) m/z 280 $(M+H)^+$.

Step 3:

A mixture of 1-methyl-4-(1-((2-(trimethylsilyl)ethoxy)methyl)-1H-imidazol-4-yl)-1H-pyrazole and 1-methyl-4-(1-((2-(trimethylsilyl)ethoxy)methyl)-1H-imidazol-5-yl)-1H-pyrazole (170 mg, 0.7 mmol) from Step 2 of this Example were stirred in a 1:1 mixture of TFA and $CH_2Cl_2$ (5 mL) for 15 h. The mixture was then concentrated under reduced pressure to afford 4-(1H-imidazol-4-yl)-1-methyl-1H-pyrazole (248 mg) as an oil and was used in the next step without further purification. LCMS (ESI) m/z 149 $(M+H)^+$.

Step 4:

To a stirred mixture of 6-(chloromethyl)-2-(methylthio)benzo[d]thiazole (209 mg, 0.9 mmol) from Step 4 of Example 36 and 4-(1H-imidazol-4-yl)-1-methyl-1H-pyrazole (248 mg, 1.0 mmol) from Step 3 of this Example, in anhydrous DMF (3.0 mL) was added $K_2CO_3$ (700 mg, 5 mmol). After stirring for 3 h at 80° C., the reaction mixture was cooled to rt and partitioned between EtOAc (150 mL) and water (50 mL). The EtOAc layer was separated, washed with brine (50 ml), dried over $Na_2SO_4$, filtered, and concentrated under reduced pressure. The residue was purified via silica gel flash chromatography (eluting isocratically with 1% MeOH in $CH_2Cl_2$) to afford separately 6-((5-(1-methyl-1H-pyrazol-4-yl)-1H-imidazol-1-yl)methyl)-2-(methylthio)benzo[d]thiazole and 6-((4-(1-methyl-1H-pyrazol-4-yl)-1H-imidazol-1-yl)methyl)-2-(methylthio)benzo[d]thiazole as white solids. The first eluting regioisomer is referred to as regioisomer 1 (55 mg, 16%) and the second eluting regioisomer is referred to as regioisomer 2 (142 mg, 42%). The regiochemistry of the alkylation was examined by 2-dimensional nuclear Overhauser effect (NOE) experiment but was inconclusive. Regioisomer 1: $^1$H NMR (300 MHz, $CDCl_3$) δ 7.81 (d, J=8.3 Hz, 1H), 7.60 (s, 1H), 7.37 (s, 1H), 7.31 (s, 1H), 7.19 (s, 1H), 7.08-7.14 (m, 2H), 5.23 (s, 2H), 3.85 (s, 3H), 2.78 (s, 3H). LCMS (ESI) m/z 342 $(M+H)^+$. Regioisomer 2: $^1$H NMR (300 MHz, $CDCl_3$) δ 7.81 (d, J=8.3 Hz, 1H), 7.60-7.71 (m, 2H), 7.47-7.56 (m, 2H), 7.22 (dd, J=1.6, 8.4 Hz, 1H), 6.94 (s, 1H), 5.15 (s, 2H), 3.87 (s, 3H), 2.76 (s, 3H). LCMS (ESI) m/z 342 $(M+H)^+$.

Step 5:

To a stirred mixture of regioisomer 1 from Step 4 of this Example (55 mg, 0.2 mmol) in $CH_2Cl_2$ (15 mL) at 0° C. was added 70-75% 3-chloroperoxybenzoic acid (40 mg, 0.2 mmol). After the mixture was stirred at 0° C. for 2 h, saturated aq $NaHCO_3$ (10 mL) was added. The mixture was stirred for 10 min and the $CH_2Cl_2$ layer was separated, dried over $Na_2SO_4$, filtered, and concentrated under reduced pressure to afford either 6-((5-(1-methyl-1H-pyrazol-4-yl)-1H-imidazol-1-yl)methyl)-2-(methylsulfinyl)benzo[d]thiazole or 6-((4-(1-methyl-1H-pyrazol-4-yl)-1H-imidazol-1-yl)methyl)-2-(methylsulfinyl)benzo[d]thiazole (55 mg) as a white foam. The material was used in the next step without further purification. LCMS (ESI) m/z 356 $(M+H)^+$.

Step 6:

To a mixture of either 6-((5-(1-methyl-1H-pyrazol-4-yl)-1H-imidazol-1-yl)methyl)-2-(methylsulfinyl)benzo[d]thiazole or 6-((4-(1-methyl-1H-pyrazol-4-yl)-1H-imidazol-1-yl)methyl)-2-(methylsulfinyl)benzo[d]thiazole (55 mg, 0.2 mmol) from Step 5 of this Example and (1R,2R)-1-amino-2,3-dihydro-1H-inden-2-ol (48 mg, 0.4 mmol) NMP (1.5 mL) was added DIEA (112 μL, 0.8 mmol). The reaction vessel was sealed and heated at 150° C. in the Biotage microwave reactor for 2 h. The mixture was directly purified by reverse-phase preparative HPLC using a mixture of water (5% $CH_3CN$, 0.05% HCOOH) and $CH_3CN$ (0.05% HCOOH) as the mobile phase and Varian Pursuit XRs C18 column as the stationary phase to afford a single compound identified as either (1R,2R)-1-((6-((4-(1-methyl-1H-pyrazol-4-yl)-1H-imidazol-1-yl)methyl)benzo[d]thiazol-2-yl)amino)-2,3-dihydro-1H-inden-2-ol or (1R,2R)-1-((6-((5-(1-methyl-1H-pyrazol-4-yl)-1H-imidazol-1-yl)methyl)benzo[d]thiazol-2-yl)amino)-2,3-dihydro-1H-inden-2-ol (alternative to Example 83) (6 mg, 7%) as a white powder. $^1$H NMR (300 MHz, DMSO-$d_6$) δ 8.47 (d, J=7.9 Hz, 1H), 7.72-7.86 (m, 2H), 7.49 (s, 1H), 7.28-7.39 (m, 2H), 7.12-7.26 (m, 4H), 7.01 (s, 1H), 6.92 (dd, J=1.7, 8.3 Hz, 1H), 5.52 (m, 1H), 5.28 (s, 2H), 5.17 (t, J=7.1 Hz, 1H), 4.30 (m, 1H), 3.82 (s, 3H), 3.16 (m, 1H), 2.74 (m, 1H). LCMS (ESI) m/z 443 $(M+H)^+$.

Example 33

Preparation of (S)—N-(1-cyclohexylethyl)-6-((5,6-dimethoxy-1H-benzo[d]imidazol-1-yl)methyl)benzo[d]thiazol-2-amine

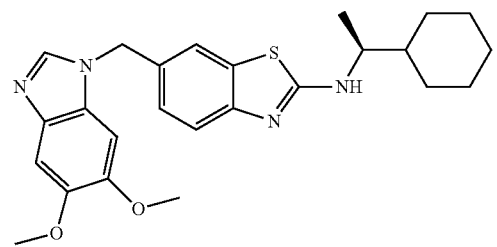 [SMILES: COc1cc2ncn(Cc3ccc4nc(N[C@@H](C)C5CCCCC5)sc4c3)c2cc1OC]

A stirred mixture of 2-bromo-6-((5,6-dimethoxy-1H-benzo[d]imidazol-1-yl)methyl)benzo[d]thiazole from Example 2 (80 mg, 0.198 mmol), (S)-(+)-1-cyclohexylethylamine (50 mg, 0.396 mmol) and DIEA (77 mg, 0.594 mmol) in anhydrous DMA (2 mL) was heated at 100° C. for 72 h. After cooling to rt, the mixture was purified directly by reverse-phase HPLC using a mixture of water (5% $CH_3CN$, 0.05% HOAc) and $CH_3CN$ (0.05% HOAc) as the mobile phase and Varian Pursuit XRs diphenyl column as the stationary phase to afford (S)—N-(1-cyclohexylethyl)-6-((5,6-dimethoxy-1H-benzo[d]imidazol-1-yl)methyl)benzo[d]thiazol-2-amine (48 mg, 54%) as a white solid. $^1$H NMR (300 MHz, DMSO-$d_6$) δ 8.14 (s, 1H), 7.89 (d, J=8.3 Hz, 1H), 7.62 (s, 1H), 7.29 (m, 1H), 7.12-7.23 (m, 3H), 5.40 (s, 2H), 3.76 (2×s, 6H), 1.5-1.79 (m, 6H), 1.32 (m, 1H), 0.93-1.22 (m, 8H). LCMS (ESI) m/z 451 (M+H)+.

Example 34

Preparation of (1R,2R)-2-((6-((5,6-dimethoxy-1H-benzo[d]imidazol-1-yl)methyl)benzo[d]oxazol-2-yl)amino)cyclohexanol

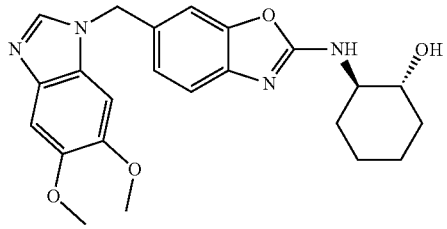 [SMILES: COc1cc2ncn(Cc3ccc4nc(N[C@@H]5CCCC[C@H]5O)oc4c3)c2cc1OC]

Step 1:

To a stirred solution of (2-(methylthio)benzo[d]oxazol-6-yl)methanol (1.2 g, 6.15 mmol) from Example 56 and DIEA (1.19 g, 9.23 mmol) in anhydrous DCM (40 mL) at 0° C. was added dropwise methanesulfonyl chloride (771 mg, 6.77 mmol). The mixture was allowed to warm to rt and was stirred for a further 2 h. The mixture was partitioned between saturated aq NaHCO₃ and DCM. The organic layer was separated and washed with 2 M aq HCl. The organic layer was separated, dried over MgSO₄, filtered, and concentrated under reduced pressure to afford a 9:1 mixture of (2-(methylthio)benzo[d]oxazol-6-yl)methyl methanesulfonate and 6-(chloromethyl)-2-(methylthio)benzo[d]oxazole (1.45 g) as a light pink solid which was not purified further. (2-(Methylthio)benzo[d]oxazol-6-yl)methyl methanesulfonate: ¹H NMR (300 MHz, DMSO-d₆) δ 7.78 (m, 1H), 7.68 (d, J=8.1 Hz, 1H), 7.45 (m, 1H), 5.36 (s, 2H), 3.25 (s, 3H), 2.78 (s, 3H); 6-(chloromethyl)-2-(methylthio)benzo[d]oxazole: ¹H NMR (300 MHz, DMSO-d₆) δ 7.75 (d, J=1.3 Hz, 1H), 7.63 (d, J=8.1 Hz, 1H), 7.43 (dd, J=1.3, 8.1 Hz, 1H), 4.89 (s, 2H), 2.77 (s, 3H).

Step 2:

To a stirred solution of a 9:1 mixture of (2-(methylthio)benzo[d]oxazol-6-yl)methyl methanesulfonate and 6-(chloromethyl)-2-(methylthio)benzo[d]oxazole (1.45 g) from Step 1 of this Example and 5,6-dimethoxybenzimidazole (945 mg, 5.31 mmol) in anhydrous DMF (10 mL) at rt was added solid K₂CO₃ (1.47 g, 10.62 mmol). The mixture was stirred at rt for 3 h. The mixture was partitioned between water and DCM. The organic layer was separated and washed with water. The organic layer was separated, dried over MgSO₄, filtered, and concentrated under reduced pressure. The residue was purified by silica gel flash chromatography eluting with 100% DCM to 10% MeOH in DCM to afford 6-((5,6-dimethoxy-1H-benzo[d]imidazol-1-yl)methyl)-2-(methylthio)benzo[d]oxazole (430 mg) as a solid. ¹H NMR (300 MHz, DMSO-d₆) δ 8.20 (s, 1H), 7.66 (m, 1H), 7.60 (d, J=9.0 Hz, 1H), 7.32 (dd, J=9.0, 3.0 Hz, 1H), 7.19 (s, 2H), 5.53 (s, 2H), 3.76 (s, 6H), 2.73 (s, 3H). LCMS (ESI) m/z 356 (M+H)+.

Step 3:

To a stirred solution of 6-((5,6-dimethoxy-1H-benzo[d]imidazol-1-yl)methyl)-2-(methylthio)benzo[d]oxazole (160 mg, 0.451 mmol) from Step 2 of this Example in DCM (2 mL) at 0° C. was added 70% meta-chloroperbenzoic acid (114 mg, 0.496 mmol) and the mixture was allowed to warm to rt and stirred for a further 2.5 h. To the mixture was added saturated aq NaHCO₃ and the organic layer was separated. The aqueous layer was extracted with DCM and the combined organic layers were washed with saturated aq NaHCO₃. The organic layer was separated, dried over MgSO₄, filtered, and concentrated under reduced pressure to afford a solid (121 mg). The solid was dissolved in anhydrous DMA (2 mL) and then (1R,2R)-(−)-2-aminocyclohexanol (38 mg, 0.324 mmol) and DIEA (63 mg, 0.486 mmol) were added. The reaction vessel was sealed and the mixture was heated at 90° C. for 15 h. After cooling to rt, the reaction mixture was purified directly by reverse-phase HPLC using a mixture of water (5% CH₃CN, 0.05% HCOOH), CH₃CN (0.05% HCOOH) as the mobile phase and Varian Pursuit XRs C-18 column as the stationary phase to afford (1R,2R)-2-((6-((5,6-dimethoxy-1H-benzo[d]imidazol-1-yl)methyl)benzo[d]oxazol-2-yl)amino)cyclohexanol (35 mg) as a white solid. ¹H NMR (300 MHz, DMSO-d₆) δ 8.16 (s, 1H), 7.81 (m, 1H), 7.35 (s, 1H), 7.11-7.21 (m, 4H), 5.41 (s, 2H), 4.70 (br s, 1H), 3.76 (s, 6H), 1.80-2.00 (m, 2H), 1.5-1.67 (m, 2H), 1.15-1.30 (m, 4H). LCMS (ESI) m/z 423 (M+H)+.

Example 35

Preparation of N-(cyclohexylmethyl)-6-((5,6-dimethoxy-1H-benzo[d]imidazol-1-yl)methyl)benzo[d]oxazol-2-amine

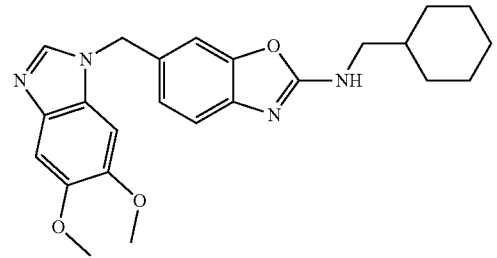 [SMILES: COc1cc2ncn(Cc3ccc4nc(NCC5CCCCC5)oc4c3)c2cc1OC]

Step 1:

To a stirred solution of 6-((5,6-dimethoxy-1H-benzo[c]imidazol-1-yl)methyl)-2-(methylthio)benzo[d]oxazole (270 mg, 0.761 mmol) from Step 2 of Example 34 in DCM (5 mL) at 0° C. was added 70% meta-chloroperbenzoic acid (262 mg, 1.14 mmol), and the mixture was allowed to warm to rt and stirred for a further 4.5 h. To the mixture was added saturated aq NaHCO₃ and the organic layer was separated. The aqueous layer was extracted with DCM and the combined organic layers were washed with saturated aq NaHCO₃. The organic layer was separated, dried over MgSO₄, filtered, and concentrated under reduced pressure. The residue was purified via silica gel flash chromatography eluting with 100% DCM to 10% MeOH in DCM to afford 6-((5,6-dimethoxy-1H-benzo[d]imidazol-1-yl)methyl)-2-(methylsulfinyl)benzo[d]oxazole (127 mg, 45%) as a solid. ¹H NMR (300 MHz, DMSO-d₆) δ 8.24 (s, 1H), 7.85-7.92 (m, 2H), 7.48 (d, J=8.3 Hz, 1H), 7.21 (s, 1H), 7.20 (s, 1H), 5.62 (s, 2H), 3.76 (s, 6H), 3.18 (s, 3H). LCMS (ESI) m/z 372 (M+H)+.

Step 2:

A stirred mixture of 6-((5,6-dimethoxy-1H-benzo[d]imidazol-1-yl)methyl)-2-(methylsulfinyl)benzo[d]oxazole (60 mg, 0.162 mmol), cyclohexylmethylamine (36 mg, 0.323 mmol), and DIEA (63 mg, 0.485 mmol) in anhydrous DMA (2 mL) was heated at 90° C. for 15 h. After cooling to rt, the reaction mixture was purified directly by reverse-phase HPLC using a mixture of water (5% CH$_3$CN, 0.05% HOAc), CH$_3$CN (0.05% HOAc) as the mobile phase and Varian Pursuit XRs diphenyl column as the stationary phase to afford N-(cyclohexylmethyl)-6-((5,6-dimethoxy-1H-benzo [d]imidazol-1-yl)methyl)benzo[d]oxazol-2-amine (20 mg) as a white solid. $^1$H NMR (300 MHz, DMSO-d$_6$) δ 8.17 (s, 1H), 7.99 (t, J=5.7 Hz, 1H), 7.37 (s, 1H), 7.11-7.24 (m, 4H), 5.42 (s, 2H), 3.77 (s, 3H), 3.76 (s, 3H), 3.11 (t, J=6.2 Hz, 2H), 1.5-1.79 (m, 7H), 1.07-1.26 (m, 2H), 0.81-1.00 (m, 2H). LCMS (ESI) m/z 421 (M+H)$^+$.

Example 36

Preparation of (1R,2R)-2-((6-((4-(1-methyl-1H-pyrazol-4-yl)-1H-imidazol-1-yl)methyl)benzo[d]thiazol-2-yl)amino)cyclohexanol

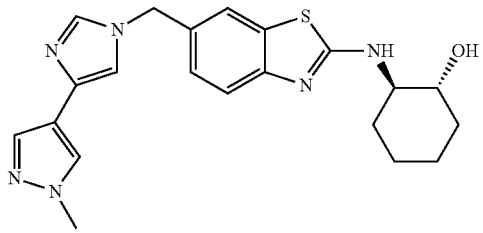 [SMILES: Cn1cc(-c2cn(Cc3ccc4nc(N[C@@H]5CCCC[C@H]5O)sc4c3)cn2)cn1]

Step 1:
To a stirred mixture of CuBr$_2$ (6.5 g, 0.03 mol) and t-butylnitrite (3.9 g, 0.04 mol) in CH$_3$CN (100 mL) at 0° C. under argon was added ethyl 2-aminobenzo[d]thiazole-6-carboxylate (5.0 g, 0.02 mol) portionwise. After stirring at 0° C. for 15 min, the mixture was allowed to warm to rt and stirred under argon for 2 h. 2 N HCl (300 ml) was added and the resulting solution was extracted with EtOAc (2×200 mL). The combined EtOAc layers were washed with brine (100 mL), dried over MgSO$_4$, filtered, and concentrated under reduced pressure. The residue was purified by silica gel flash chromatography eluting with a gradient of 100% hexanes to 50% EtOAc in hexanes to afford ethyl 2-bromobenzo[d]thiazole-6-carboxylate (3.94 g, 61%) as a yellow solid. $^1$H NMR (300 MHz, DMSO-d$_6$) δ 8.81 (s, 1H), 8.05-8.12 (m, 2H), 4.37 (q, J=7.2 Hz, 2H), 1.36 (t, J=7.1 Hz, 3H). LCMS (ESI) m/z 286 and 288 (M+H)$^+$.

Step 2:
To a stirred mixture of 2-bromobenzo[d]thiazole-6-carboxylate (2.3 g, 7.9 mmol) from Step 1 of this Example in THF (15 mL) at 0° C. was added sodium thiomethoxide (607 mg, 8.7 mmol) in one portion. The mixture was allowed to warm to rt and stirred for 20 h. The mixture was partitioned between EtOAc (150 mL) and water (100 mL). The EtOAc layer was separated and washed with water (100 mL) and brine (100 mL), dried over MgSO$_4$, filtered, and concentrated under reduced pressure to afford ethyl 2-(methylthio) benzo[d]thiazole-6-carboxylate (1.7 g, 83%) as a yellow solid which did not require further purification. $^1$H NMR (300 MHz, DMSO-d$_6$) δ 8.69 (d, J=1.3 Hz, 1H), 8.02 (m, 1H), 7.92 (m, 1H), 4.35 (q, J=7.0 Hz, 2H), 2.83 (s, 3H), 1.35 (t, J=7.1 Hz, 3H). LCMS (ESI) m/z 254 (M+H)$^+$.

Step 3:
To a stirred mixture of ethyl 2-(methylthio)benzo[d]thiazole-6-carboxylate (1.7 g, 6.6 mmol) from Step 2 of this Example in CH$_2$Cl$_2$ (50 mL) at −78° C. under argon was added 1 M diisobutyl aluminum hydride in CH$_2$Cl$_2$ (13.8 mL, 13.8 mmol) dropwise. After the mixture was stirred at −78° C. under argon for 3 h, it was allowed to warm slowly to 0° C. To the stirring mixture was added a saturated aq potassium sodium tartrate (50 mL) and the mixture was allowed to slowly warm to rt. After the mixture was stirred for 12 h, the organic layer was separated, dried over Na$_2$SO$_4$, filtered, and concentrated under reduced pressure. The residue was purified by silica gel flash chromatography eluting with a gradient of 100% hexanes to 100% EtOAc to afford (2-(methylthio)benzo[d]thiazol-6-yl)methanol (1.05 g, 76%) as a white solid. $^1$H NMR (300 MHz, DMSO-d$_6$) δ 7.93 (m, 1H), 7.79 (d, J=8.3 Hz, 1H), 7.40 (dd, J=1.3, 8.3 Hz, 1H), 5.32 (t, J=5.7 Hz, 1H), 4.60 (d, J=5.8 Hz, 2H), 2.78 (s, 3H). LCMS (ESI) m/z 212 (M+H)$^+$.

Step 4:
To a stirred mixture of (2-(methylthio)benzo[d]thiazol-6-yl)methanol (1.05 g, 5 mmol) from Step 3 of this Example and DIEA (1.3 mL, 7.5 mmol) in anhydrous CH$_2$Cl$_2$ (20 mL) under argon at −10° C. was added dropwise a solution of methanesulfonyl chloride (0.6 g, 5.5 mmol) in CH$_2$Cl$_2$ (10 mL). The mixture was allowed to warm to rt and stirred for 3 h. Additional methanesulfonyl chloride (190 mg, 1.7 mmol) was added, and the mixture was stirred for a further 2 h. Water (50 mL) was added, and the mixture was stirred for 10 min. The resulting mixture was then extracted with CH$_2$Cl$_2$ (200 mL). The CH$_2$Cl$_2$ layer was separated, dried over Na$_2$SO$_4$, filtered, and concentrated under reduced pressure to afford 6-(chloromethyl)-2-(methylthio)benzo[d]thiazole (1.0 g, 88%) as a light red solid. The material was used in the next step without further purification. LCMS (ESI) m/z 230 (M+H)$^+$.

Step 5:
To a stirred mixture of 6-(chloromethyl)-2-(methylthio) benzo[d]thiazole (0.2 g, 0.9 mmol) from Step 4 of this Example and 4-bromo-1H-imidazole (0.2 g, 1.3 mmol) in anhydrous DMF (3.0 mL) was added K$_2$CO$_3$ (0.37 g, 2.7 mmol). After stirred for 3 h at rt, the reaction mixture was partitioned between EtOAc (100 mL) and water (50 mL). The EtOAc layer was separated, washed with brine (50 ml), dried over Na$_2$SO$_4$, filtered, and concentrated under reduced pressure. The residue was purified by silica gel flash chromatography eluting with a gradient of 30% EtOAc in hexanes to 100% EtOAc to afford 6-((4-bromo-1H-imidazol-1-yl)methyl)-2-(methylthio)benzo[d]thiazole (160 mg, 54%) as a yellow oil. The regiochemistry of the alkylation was determined by 2-dimensional nuclear Overhauser effect (NOE) experiment. $^1$H NMR (300 MHz, CDCl$_3$) δ 7.85 (d, J=8.3 Hz, 1H), 7.54 (d, J=1.1 Hz, 1H), 7.45 (d, J=1.3 Hz, 1H), 7.24 (dd, J=1.7, 8.5 Hz, 1H), 6.88 (d, J=1.5 Hz, 1H), 5.17 (s, 2H), 2.80 (s, 3H). LCMS (ESI) m/z 340 and 342 (M+H)$^+$.

Step 6:
To a stirred mixture of 6-((4-bromo-1H-imidazol-1-yl) methyl)-2-(methylthio)benzo[d]thiazole (105 mg, 0.3 mmol) from Step 5 of this Example in CH$_2$Cl$_2$ (15 mL) at 0° C. was added 70-75% 3-chloroperoxybenzoic acid (91 mg, 0.4 mmol). After the mixture was stirred at 0° C. for 2 h, saturated aq NaHCO$_3$ (10 mL) was added. The mixture was stirred for 10 min and the CH$_2$Cl$_2$ layer was separated, dried over Na$_2$SO$_4$, filtered, and concentrated under reduced pressure to afford 6-((4-bromo-1H-imidazol-1-yl)methyl)-2-(methylsulfinyl)benzo[d]thiazole (130 mg) as a white foam. The material was used in the next step without further purification. LCMS (ESI) m/z 356 and 358 (M+H)$^+$.

Step 7:

To a suspension of 6-(4-bromo-1H-imidazol-1-yl) methyl)-2-(methylsulfinyl)benzo[d]thiazole (130 mg, 0.37 mmol) from Step 6 of this Example and (1R,2R)-2-aminocyclohexanol (126 mg, 1 mmol) in anhydrous DMA (1.0 mL) was added DIEA (320 µL, 1.8 mmol). The mixture was heated in a sealed tube at 110° C. for 7 h. The mixture was cooled to rt and water was slowly added while stirring to give a precipitate. The mixture stirred for 10 min and the solid was collected by filtration to afford (1R,2R)-2-((6-((4-bromo-1H-imidazol-1-yl)methyl)benzo[d]thiazol-2-yl) amino)cyclohexanol (100 mg, 68%) as a tan solid. The material was used in the next step without further purification. LCMS (ESI) m/z 407 and 409 (M+H)$^+$.

Step 8:

To a suspension of (1R,2R)-2-((6-((4-bromo-1H-imidazol-1-yl)methyl)benzo[d]thiazol-2-yl)amino)cyclohexanol (50 mg, 0.12 mmol) from Step 7 of this Example and 1-methylpyrazole-4-boronic acid pinacol ester (51 mg, 0.25 mmol) in a mixture of DME (0.7 mL) and H$_2$O (0.3 mL) was added K$_2$CO$_3$ (68 mg, 0.5 mmol). Argon was bubbled into the mixture for 5 min. To the mixture was added tetrakis (triphenylphosphine)palladium (0) (14 mg, 0.01 mmol). Argon was bubbled into the mixture for 5 min. The reaction vessel was sealed and the mixture was heated at 100° C. for 16 h. Additional portions of 1-methylpyrazole-4-boronic acid pinacol ester (51 mg, 0.25 mmol) and tetrakis(triphenylphosphine)palladium (0) (14 mg, 0.01 mmol) were added to the mixture and argon was bubbled into the mixture for 5 min. The reaction vessel was sealed and the mixture was heated at 110° C. for 4 h. The mixture was cooled to rt and partitioned between EtOAc (100 mL) and aq 1 N K$_2$CO$_3$ (50 mL). The EtOAc layer was separated and washed with water (50 mL) and brine (50 mL), dried over Na$_2$SO$_4$, filtered, and concentrated under reduced pressure. The residue was purified by preparative reverse-phase HPLC using a mixture of water (5% CH$_3$CN, 0.05% HCOOH) and CH$_3$CN (0.05% HCOOH) as the mobile phase and Varian Pursuit XRs C18 column as the stationary phase to afford (1R,2R)-2-((6-((4-(1-methyl-1H-pyrazol-4-yl)-1H-imidazol-1-yl)methyl)benzo[d]thiazol-2-yl)amino)cyclohexanol (10.3 mg, 20%) as a white solid. $^1$H NMR (300 MHz, DMSO-d$_6$) δ 7.97 (d, J=7.5 Hz, 1H), 7.80 (s, 1H), 7.71 (s, 1H), 7.5-7.62 (m, 2H), 7.32 (d, J=8.3 Hz, 1H), 7.24 (s, 1H), 7.16 (dd, J=1.3, 8.3 Hz, 1H), 5.13 (s, 2H), 4.75 (brm, 1H), 3.80 (s, 3H), 3.52 (br s, 1H), 3.34 (br s, 1H), 2.04 (d, J=10.2 Hz, 1H), 1.88 (d, J=9.4 Hz, 1H), 1.5-1.66 (m, 2H), 1.10-1.33 (m, 4H). LCMS (ESI) m/z 409 (M+H)$^+$.

Example 37

Preparation of 1-((2-(((1R,2R)-2-hydroxycyclohexyl)amino)benzo[d]thiazol-6-yl)methyl)-N-methyl-1H-imidazole-4-carboxamide

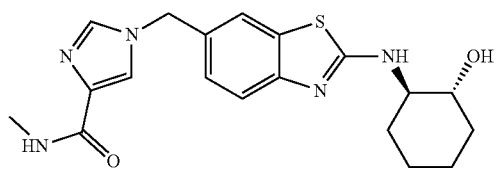 [SMILES: CNC(=O)c1cn(Cc2ccc3nc(N[C@@H]4CCCC[C@H]4O)sc3c2)cn1]

Step 1:

To a stirred mixture of 6-(chloromethyl)-2-(methylthio) benzo[d]thiazole (500 mg, 2.2 mmol) from Example 36 and methyl 4-imidazole carboxylate (400 mg, 3.3 mmol) in DMF (15 mL) was added K$_2$CO$_3$ (0.9 g, 6.5 mmol). After the mixture was stirred for 3 h at rt, it was partitioned between EtOAc (100 mL) and water (50 mL). The EtOAc layer was separated and washed with water (50 mL) and brine (50 mL), then dried over Na$_2$SO$_4$, filtered, and concentrated under reduced pressure. The residue was purified by silica gel flash chromatography eluting with 2% MeOH in CH$_2$Cl$_2$ to afford methyl 1-((2-(methylthio)benzo[d]thiazol-6-yl) methyl)-1H-imidazole-4-carboxylate (130 mg, 19%) as a white solid. The regiochemistry of the alkylation was determined by 2-dimensional nuclear Overhauser effect (NOE) experiment. $^1$H NMR (300 MHz, DMSO-d$_6$) δ 8.01 (d, J=0.9 Hz, 1H), 7.98 (d, J=1.1 Hz, 1H), 7.93 (d, J=0.9 Hz, 1H), 7.84 (d, J=8.3 Hz, 1H), 7.43 (dd, J=1.7, 8.3 Hz, 1H), 5.35 (s, 2H), 3.72 (s, 3H), 2.78 (s, 3H). LCMS (ESI) m/z 322 (M+H)$^+$.

Step 2:

To a stirred solution of methylamine (623 µL of a 2 M solution in THF, 1.3 mmol) at 0° C. was added trimethylaluminum (623 µL of a 2 M solution in toluene, 1.2 mmol). The mixture was stirred for 2 min and then a solution of 1-((2-(methylthio)benzo[d]thiazol-6-yl)methyl)-1H-imidazole-4-carboxylate (80 mg, 0.25 mmol) from Step 1 of this Example in DCE (1 mL) was added dropwise. The reaction vessel was sealed and the mixture was heated at 70° C. for 20 h. The mixture was then concentrated under reduced pressure and the residue was purified by silica gel flash chromatography eluting with 5% MeOH in EtOAc to afford N-methyl-1-((2-(methylthio)benzo[d]thiazol-6-yl)methyl)-1H-imidazole-4-carboxamide (46 mg, 58%) as a white solid. $^1$H NMR (300 MHz, DMSO-d$_6$) δ 7.98 (d, J=1.3 Hz, 1H), 7.81-7.94 (m, 3H), 7.71 (d, J=1.1 Hz, 1H), 7.42 (dd, J=1.6, 8.4 Hz, 1H), 5.33 (s, 2H), 2.78 (s, 3H), 2.70 (d, J=4.9 Hz, 3H). LCMS (ESI) m/z 319 (M+H)$^+$.

Step 3:

N-Methyl-1-((2-(methylsulfinyl)benzo[d]thiazol-6-yl) methyl)-1H-imidazole-4-carboxamide was synthesized as a white foam (76 mg, 100%) using a procedure analogous to that described in Step 6 of Example 36, substituting N-methyl-1-((2-(methylthio)benzo[d]thiazol-6-yl)methyl)-1H-imidazole-4-carboxamide from Step 2 of this Example for 6-((4-bromo-1H-imidazol-1-yl)methyl)-2-(methylthio) benzo[d]thiazole used in Example 36. LCMS (ESI) m/z 335 (M+H)$^+$.

Step 4:

1-((2-(((1R,2R)-2-Hydroxycyclohexyl)amino)benzo[d] thiazol-6-yl)methyl)-N-methyl-1H-imidazole-4-carboxamide was synthesized as a white powder (26 mg, 46%) using a procedure analogous to that described in Step 7 of Example 36, substituting N-methyl-1-((2-(methylsulfinyl) benzo[d]thiazol-6-yl)methyl)-1H-imidazole-4-carboxamide from Step 3 of this Example for 6-((4-bromo-1H-imidazol-1-yl)methyl)-2-(methylsulfinyl)benzo[d]thiazole used in Example 36 and subjecting the crude residue to purification by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase. $^1$H NMR (300 MHz, DMSO-d$_6$) δ 8.01 (d, J=7.5 Hz, 1H), 7.84-7.92 (m, 1H), 7.80 (d, J=1.1 Hz, 1H), 7.62-7.67 (m, 2H), 7.31 (d, 1H), 7.18 (dd, J=1.7, 8.3 Hz, 1H), 5.18 (s, 2H), 4.77 (br m, 1H), 3.55 (br m, 1H), 3.35 (br m, 1H), 2.69 (br m, 3H), 2.04 (br m 1H), 1.86 (br m, 1H), 1.61 (br m, 2H), 1.10-1.35 (br m, 4H). LCMS (ESI) m/z 386 (M+H)$^+$.

Example 38

Preparation of (1R,2R)-2-((6-(imidazo[1,2-a]pyridin-3-ylmethyl)benzo[d]thiazol-2-yl)amino)cyclohexanol

Step 1:

A stirred mixture of 2-fluoro-4-iodoaniline (5.0 g, 21.1 mmol), CuI (90 mg, 0.42 mmol), and PdCl$_2$(PPh$_3$)$_2$ (300 mg, 0.42 mmol) in a pressure tube was flushed with argon. Ethynyltrimethylsilane (2.28 g, 23.2 mmol) in TEA (20 mL) was added and the resulting mixture was stirred at rt overnight. The reaction mixture was then diluted with Et$_2$O and filtered through a Celite pad. The filtrate was concentrated under reduced pressure and the residue was purified by silica gel chromatography eluting with 5% EtOAc in hexanes to afford 2-fluoro-4-((trimethylsilyl)ethynyl)aniline (4.4 g, 100%) as a brown solid. LCMS (ESI) m/z 208 (M+H)$^+$.

Step 2:

To a solution of 2-fluoro-4-((trimethylsilyl)ethynyl)aniline (4.4 g, 21.2 mmol) from Step 1 of this Example in 20 mL of DMF was added potassium O-ethyl carbonodithioate (7.48 g, 46.8 mmol). The resulting mixture was heated under reflux for 4 h. After cooling to rt, the reaction mixture was treated with water (30 mL) and 1N HCl (100 mL). The mixture was stirred at rt for 2 h before the precipitates were collected by filtration and washed with water to give the crude 6-ethynylbenzo[d]thiazole-2-thiol (4.0 g, 99%) as a dark brown solid. LCMS (ESI) m/z 192 (M+H)$^+$.

Step 3:

To a stirred solution of 6-ethynylbenzo[d]thiazole-2-thiol (4.0 g, 21 mmol) from Step 2 of this Example in 20 mL of DMF at 0° C. were added K$_2$CO$_3$ (7.25 g, 5.25 mmol), and MeI (5 mL). The mixture was stirred at rt for 2 h before it was partitioned between EtOAc and water, the organic layer was washed with brine, dried over Na$_2$SO$_4$, and concentrated under reduced pressure. The residue was purified by silica gel chromatography eluting with 3:1 DCM/hexanes to afford 6-ethynyl-2-(methylthio)benzo[d]thiazole (1.5 g, 35%) as an off-white solid. LCMS (ESI) m/z 206 (M+H)$^+$.

Step 4:

A stirred mixture of 2-aminopyridine (100 mg, 1.1 mmol), paraformaldehyde (34 mg, 1.1 mmol), CuCl (5 mg, 0.06 mmol), and Cu(OTf)$_2$ (19 mg, 0.06 mmol) in 3 mL of toluene in a pressure tube was flushed with argon. 6-Ethynyl-2-(methylthio)benzo[d]thiazole (327 mg, 1.6 mmol) from Step 3 of this Example was added. The reaction vessel was sealed and the mixture was heated in an oil bath at 120° C. for 6 h. LCMS analysis showed that the reaction was mostly complete. The reaction mixture was partitioned between EtOAc and saturated aq NaHCO$_3$. The organic layer was washed with brine, dried over Na$_2$SO$_4$, and concentrated under reduced pressure. The residue was purified by silica gel chromatography eluting with 0-100% EtOAc in hexanes to afford 6-(imidazo[1,2-a]pyridin-3-ylmethyl)-2-(methylthio)benzo[d]thiazole (127 mg, 38%) as a brown oil. LCMS (ESI) m/z 312 (M+H)$^+$.

Step 5:

(1R,2R)-2-((6-(Imidazo[1,2-a]pyridin-3-ylmethyl)benzo[d]thiazol-2-yl)amino)cyclohexanol (28 mg, 18%) was obtained as a yellow powder using procedures analogous to those described in Step 5 of Example 3 and Step 5 of Example 2, sequentially, substituting 6-(imidazo[1,2-a]pyridin-3-ylmethyl)-2-(methylthio)benzo[d]thiazole from Step 4 of this Example for 6-((3H-imidazo[4,5-b]pyridin-3-yl)methyl)-2-(methylthio)benzo[d]thiazole used in Example 3. $^1$H NMR (300 MHz, DMSO-d$_6$) δ 8.20 (d, J=6.4 Hz, 1H), 7.89 (d, J=7.5 Hz, 1H), 7.48-7.62 (m, 2H), 7.43 (br s, 1H), 7.27 (d, J=8.1 Hz, 1H), 7.14-7.23 (m, 1H), 7.09 (dd, J=1.2, 8.2 Hz, 1H), 6.86 (t, J=6.7 Hz, 1H), 4.75 (br s, 1H), 4.29 (s, 2H), 3.47-3.59 (m, 1H), 2.03 (d, J=10.4 Hz, 1H), 1.88 (br s, 2H), 1.61 (br s, 2H), 1.23 (d, J=5.5 Hz, 4H). LCMS (ESI) m/z 379 (M+H)$^+$.

Example 39

Preparation of (1R,2R)-2-((6-((6-(1-methyl-1H-pyrazol-4-yl)-3H-imidazo[4,5-b]pyridin-3-yl)methyl)benzo[d]thiazol-2-yl)amino)cyclohexanol

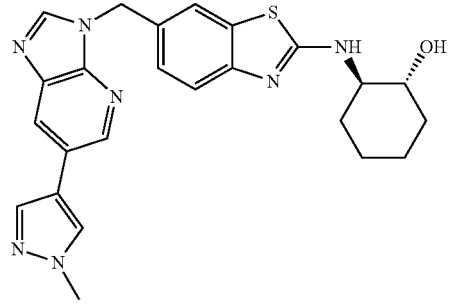 [SMILES: Cn1cc(-c2cnc3c(c2)ncn3Cc2ccc3nc(N[C@@H]4CCCC[C@H]4O)sc3c2)cn1]

A stirred mixture of (1R,2R)-2-((6-((6-bromo-3H-imidazo[4,5-b]pyridin-3-yl)methyl)benzo[d]thiazol-2-yl)amino)cyclohexanol from Example 29 (80 mg, 0.175 mmol), 1-methylpyrazole-4-boronic acid pinacol ester (73 mg, 0.351 mmol), 2M aq Na$_2$CO$_3$ (400 μL, 0.40 mmol), and anhydrous DME (1.5 mL) was degassed under argon for 15 min. Bis(triphenylphosphine)palladium (II) dichloride (12 mg, 0.0171 mmol) was added and the reaction vessel was sealed and the mixture was heated at 100° C. for 15 h. After cooling to rt, the mixture was purified directly by reverse-phase HPLC using a mixture of water (5% CH$_3$CN, 0.05% HOAc) and CH$_3$CN (0.05% HOAc) as the mobile phase and Varian Pursuit XRs diphenyl column as the stationary phase to afford (1R,2R)-2-((6-((6-(1-methyl-1H-pyrazol-4-yl)-3H-imidazo[4,5-b]pyridin-3-yl)methyl)benzo[d]thiazol-2-yl)amino)cyclohexanol (33 mg, 41%) as a white solid. $^1$H NMR (300 MHz, DMSO-d$_6$) δ 8.64 (d, J=1.9 Hz, 1H), 8.56 (s, 1H), 8.26 (d, J=1.9 Hz, 1H), 8.23 (s, 1H), 7.95-8.01 (m, 2H), 7.67 (d, J=1.1 Hz, 1H), 7.20-7.32 (m, 2H), 5.47 (s, 2H), 4.76 (br s, 1H), 3.88 (s, 3H), 3.51 (m, 1H), 3.35 (m, 1H), 2.03 (m, 1H), 1.90 (m, 1H), 1.62 (d, J=4.7 Hz, 2H), 1.10-1.33 (m, 4H). LCMS (ESI) m/z 460 (M+H)$^+$.

Example 40

Preparation of (1R,2R)-2-((6-((6-(pyridin-3-yl)-3H-imidazo[4,5-b]pyridin-3-yl)methyl)benzo[d]thiazol-2-yl)amino)cyclohexanol

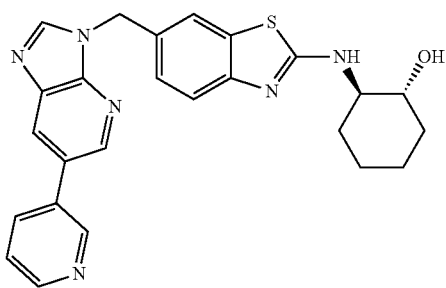 [SMILES: O[C@@H]1CCCC[C@H]1Nc1nc2ccc(Cn3cnc4cc(-c5cccnc5)cnc43)cc2s1]

A stirred mixture of (1R,2R)-2-((6-((6-bromo-3H-imidazo[4,5-b]pyridin-3-yl)methyl)benzo[d]thiazol-2-yl)amino)cyclohexanol (80 mg, 0.175 mmol) from Example 29, pyridine-3-ylboronic acid (43 mg, 0.350 mmol), 2M aq Na$_2$CO$_3$ (400 µt, 0.40 mmol), and anhydrous DME (1.5 mL) was degassed under argon for 15 min. Bis(triphenylphosphine)palladium (II) dichloride (12 mg, 0.0171 mmol) was added and the reaction vessel was sealed and the mixture was heated at 100° C. for 15 h. After cooling to rt, the mixture was purified directly by reverse-phase HPLC using a mixture of water (5% CH$_3$CN, 0.05% HOAc) and CH$_3$CN (0.05% HOAc) as the mobile phase and Varian Pursuit XRs diphenyl column as the stationary phase to afford (1R,2R)-2-((6-((6-(pyridin-3-yl)-3H-imidazo[4,5-b]pyridin-3-yl)methyl)benzo[d]thiazol-2-yl)amino)cyclohexanol (25 mg, 31%) as a white solid. $^1$H NMR (300 MHz, DMSO-d$_6$) δ 8.99 (br s, 1H), 8.66-8.77 (m, 2H), 8.60 (br s, 1H), 8.46 (s, 1H), 8.19 (d, J=7.9 Hz, 1H), 8.00 (d, J=7.3 Hz, 1H), 7.69 (s, 1H), 7.52 (dd, J=4.7, 7.7 Hz, 1H), 7.21-7.34 (m, 2H), 5.53 (s, 2H), 4.77 (br s, 1H), 3.51 (m, 1H), 3.35 (m, 1H), 2.03 (m, 1H), 1.87 (m, 1H), 1.5-1.66 (m, 2H), 1.11-1.34 (m, 4H). LCMS (ESI) m/z 457 (M+H)$^+$.

Example 41

Preparation of (1R,2R)-2-((6-((5-bromo-6-methoxy-1H-benzo[d]imidazol-1-yl)methyl)benzo[d]thiazol-2-yl)amino)cyclohexanol

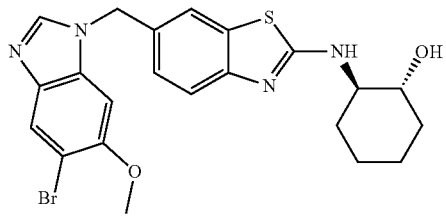

Step 1:

To a stirred mixture of DMF (15 mL) and NaH (60% in mineral oil, 75 mg 1.9 mmol) at −10° C. under argon was added 4-bromo-5-methoxy-2-nitroaniline (490 mg, 2.2 mmol) in one portion. The mixture was stirred for 5 min at −10° C. A solution of 6-(chloromethyl)-2-(methylthio)benzo[d]thiazole from Example 36 (500 mg, 2.2 mmol) in DMF (5 mL) was added dropwise. After stirring at −10° C. for 1 h, the mixture was allowed to warm slowly to rt. The mixture was stirred at rt for 58 h and then partitioned between EtOAc (150 mL) and 1 M aq Na$_2$CO$_3$ (50 mL). The EtOAc layer was separated and washed with water (50 mL) and brine, dried over Na$_2$SO$_4$, filtered, and the filtrate was concentrated under reduced pressure. The residue was purified by silica gel flash chromatography eluting with a gradient of 100% hexanes to 100% EtOAc to afford 4-bromo-5-methoxy-N-((2-(methylthio)benzo[d]thiazol-6-yl)methyl)-2-nitroaniline (239 mg, 25%) as an orange solid. $^1$H NMR (300 MHz, DMSO-d$_6$) δ 9.02 (t, J=5.8 Hz, 1H), 8.23 (s, 1H), 8.06 (s, 1H), 7.83 (d, J=8.5 Hz, 1H), 7.53 (d, J=8.3 Hz, 1H), 6.40 (s, 1H), 4.80 (d, J=5.8 Hz, 2H), 3.77 (s, 3H), 2.78 (s, 3H). LCMS (ESI) m/z 440 and 442 (M+H)$^+$.

Step 2:

To a stirred suspension of 4-bromo-5-methoxy-N-((2-(methylthio)benzo[d]thiazol-6-yl)methyl)-2-nitroaniline (212 mg, 0.5 mmol) from Step 1 of this Example in EtOH (4 mL) and HOAc (2 mL) at 0° C. under argon was added zinc powder (160 mg, 2.4 mmol) in one portion. After 1.5 h at 0° C., MeOH (5 mL), additional HOAc (2 mL), and zinc powder (160 mg, 2.4 mmol) were added. The mixture was allowed to warm to rt and stirred for 18 h. The mixture was filtered and the filtrate was cooled to 0° C. The pH of the filtrate was adjusted to pH~9 by addition of solid Na$_2$CO$_3$. The mixture was then partitioned between EtOAc (150 mL) and water (100 mL). The EtOAc layer was separated, dried over Na$_2$SO$_4$, filtered, and concentrated under reduced pressure. The residue was purified by silica gel flash chromatography eluting with a gradient of 100% hexanes to 100% EtOAc to afford 4-bromo-5-methoxy-N1-((2-(methylthio)benzo[d]thiazol-6-yl)methyl)benzene-1,2-diamine (120 mg, 61%). LCMS (ESI) m/z 410 and 412 (M+H)$^+$.

Step 3:

To a stirred mixture of 4-bromo-5-methoxy-N$^1$-((2-(methylthio)benzo[d]thiazol-6-yl)methyl)benzene-1,2-diamine (120 mg, 0.3 mmol) from Step 2 of this Example and triethylorthoformate (20 mL) was added formic acid (1 mL). The mixture was heated under reflux for 2 h, then concentrated under reduced pressure. The residue was purified by silica gel flash chromatography eluting with 100% EtOAc to afford 6-((5-bromo-6-methoxy-1H-benzo[d]imidazol-1-yl)methyl)-2-(methylthio)benzo[d]thiazole (50 mg, 40%) as an oil. $^1$H NMR (300 MHz, CDCl$_3$) δ 8.01 (s, 1H), 7.78-7.91 (m, 2H), 7.46 (s, 1H), 7.25 (m, 1H), 6.69 (s, 1H), 5.42 (s, 2H), 3.81 (s, 3H), 2.78 (s, 3H). LCMS (ESI) m/z 420 and 422 (M+H)$^+$.

Step 4:

6-((5-Bromo-6-methoxy-1H-benzo[d]imidazol-1-yl)methyl)-2-(methylsulfinyl)benzo[d]thiazole was synthesized as a white foam (75 mg) using a procedure analogous to that described in Step 6 of Example 36, substituting 6-((5-bromo-6-methoxy-1H-benzo[d]imidazol-1-yl)methyl)-2-(methylthio)benzo[d]thiazole from Step 3 of this Example for 6-((4-bromo-1H-imidazol-1-yl)methyl)-2-(methylthio)benzo[d]thiazole used in Example 36. LCMS (ESI) m/z 436 and 438 (M+H)$^+$.

Step 5:

(1R,2R)-2-((6-((5-Bromo-6-methoxy-1H-benzo[d]imidazol-1-yl)methyl)benzo[d]thiazol-2-yl)amino)cyclohexanol was synthesized as a white powder (15 mg, 26%) using a procedure analogous to that described in Step 4 of Example 37, substituting 6-((5-bromo-6-methoxy-1H-benzo[d]imidazol-1-yl)methyl)-2-(methylsulfinyl)benzo[d]thiazole from Step 4 of this Example for N-methyl-1-((2-(methylsulfinyl)

benzo[d]thiazol-6-yl)methyl)-1H-imidazole-4-carboxamide used in Example 37. $^1$H NMR (300 MHz, DMSO-d$_6$) δ 8.29 (s, 1H), 7.98 (d, J=7.5 Hz, 1H), 7.85 (s, 1H), 7.66 (d, J=1.1 Hz, 1H), 7.37 (s, 1H), 7.27-7.33 (m, 1H), 7.22 (dd, J=9, 1.5 Hz, 1H), 5.46 (s, 2H), 4.75 (d, J=4.9 Hz, 1H), 3.85 (s, 3H), 3.52 (br m, 1H), 3.33 (br m, 1H), 2.02 (br m, 1H), 1.85 (br m, 1H), 1.55-1.68 (br m, 2H), 1.10-1.34 (br m, 4H). LCMS (ESI) m/z 487 and 489 (M+H)$^+$.

Example 42

Preparation of (1R,2R)-1-((6-((6-bromo-3H-imidazo[4,5-b]pyridin-3-yl)methyl)benzo[d]thiazol-2-yl)amino)-2,3-dihydro-1H-inden-2-ol

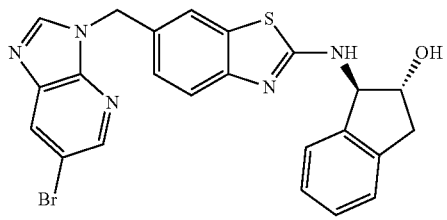 [SMILES: O[C@@H]1Cc2ccccc2[C@H]1Nc1nc2ccc(Cn3cnc4cc(Br)cnc43)cc2s1]

A stirred mixture of 6-((6-bromo-3H-imidazo[4,5-b]pyridin-3-yl)methyl)-2-(methylsulfinyl)benzo[d]thiazole from Example 29 (210 mg, 0.3 mmol), (1R,2R)-1-amino-2,3-dihydro-1H-inden-2-ol (92 mg, 0.6 mmol), and DIEA (267 μL, 1.5 mmol) in DMA (3 mL) was heated at 130° C. for 120 h in a sealed tube. The mixture was cooled to rt and subjected to purification by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford (1R,2R)-1-((6-((6-bromo-3H-imidazo[4,5-b]pyridin-3-yl)methyl)benzo[d]thiazol-2-yl)amino)-2,3-dihydro-1H-inden-2-ol (5.4 mg, 4%) as a white powder. $^1$H NMR (300 MHz, DMSO-d$_6$) δ 8.68 (s, 1H), 8.36-8.54 (m, 3H), 7.71 (s, 1H), 7.35 (m, 1H), 7.11-7.30 (m, 5H), 5.51 (s, 2H), 5.18 (t, J=7.0 Hz, 1H), 4.30 (m, 1H), 3.16 (dd, J=7.2, 15.8 Hz, 1H), 2.74 (dd, J=7.3, 15.4 Hz, 1H). LCMS (ESI) m/z 492 and 494 (M+H)$^+$.

Example 43

Preparation of 3-((2-(((1R,2R)-2-hydroxycyclohexyl)amino)benzo[d]thiazol-6-yl)methyl)-3H-imidazo[4,5-b]pyridine-6-carbonitrile

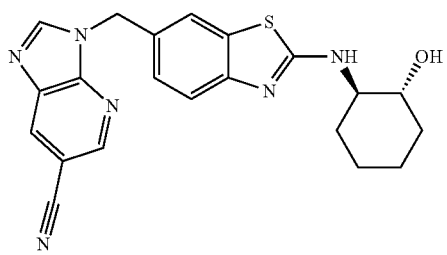 [SMILES: N#Cc1cnc2c(c1)ncn2Cc1ccc2nc(N[C@@H]3CCCC[C@H]3O)sc2c1]

A stirred mixture of (1R,2R)-2-((6-((6-bromo-3H-imidazo[4,5-b]pyridin-3-yl)methyl)benzo[d]thiazol-2-yl)amino)cyclohexanol from Example 29 (170 mg, 0.372 mmol), zinc cyanide (131 mg, 1.12 mmol), 1,1'-bis(diphenylphosphino)ferrocene (31 mg, 0.0558 mmol) and anhydrous DMF (2 mL) was degassed under argon for 15 min. Tris(dibenzylideneacetone)dipalladium (0) (34 mg, 0.0372 mmol) was added. The reaction vessel was sealed and the mixture was heated at 100° C. for 6 h. After cooling to rt, the mixture was purified directly by reverse-phase HPLC using a mixture of water (5% CH$_3$CN, 0.05% HCOOH) and CH$_3$CN (0.05% HCOOH) as the mobile phase and Varian Pursuit XRs C-18 column as the stationary phase to afford ((2-(((1R,2R)-2-hydroxycyclohexyl)amino)benzo[d]thiazol-6-yl)methyl)-3H-imidazo[4,5-b]pyridine-6-carbonitrile (51 mg, 34%) as a white solid. $^1$H NMR (300 MHz, DMSO-d$_6$) δ 8.80-8.91 (m, 2H), 8.72 (d, J=1.5 Hz, 1H), 7.99 (d, J=7.3 Hz, 1H), 7.68 (s, 1H), 7.20-7.34 (m, 2H), 5.53 (s, 2H), 4.74 (br s, 1H), 3.29-3.38 (m, 2H), 2.04 (m, 1H), 1.88 (m, 1H), 1.5-1.70 (m, 2H), 1.10-1.35 (m, 4H). LCMS (ESI) m/z 405 (M+H)$^+$.

Example 44

Preparation of (1R,2R)-2-((6-((7-methoxyimidazo[1,2-a]pyridin-3-yl)methyl)benzo[d]thiazol-2-yl)amino)cyclohexanol

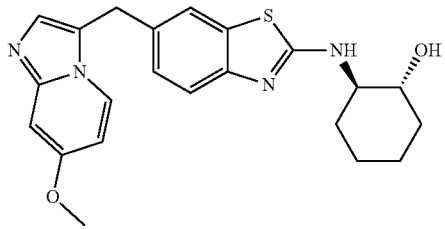 [SMILES: COc1ccn2c(Cc3ccc4nc(N[C@@H]5CCCC[C@H]5O)sc4c3)cnc2c1]

(1R,2R)-2-((6-((7-Methoxyimidazo[1,2-a]pyridin-3-yl)methyl)benzo[d]thiazol-2-yl)amino)cyclohexanol (25 mg) was obtained as a yellow powder using procedures analogous to those described in Steps 4-5 of Example 38, substituting 4-methoxypyridin-2-amine for 2-aminopyridine used in Example 38. $^1$H NMR (300 MHz, DMSO-d$_6$) δ 8.03 (d, J=7.3 Hz, 1H), 7.87 (d, J=7.5 Hz, 1H), 7.49 (s, 1H), 7.17-7.33 (m, 2H), 7.07 (dd, J=1.2, 8.2 Hz, 1H), 6.92 (d, J=2.3 Hz, 1H), 6.59 (dd, J=2.4, 7.4 Hz, 1H), 4.73 (br s, 1H), 4.22 (s, 2H), 3.80 (s, 3H), 3.41-3.63 (m, 2H), 2.03 (d, J=10.2 Hz, 1H), 1.88 (d, J=9.6 Hz, 1H), 1.61 (br s, 2H), 1.23 (d, J=5.3 Hz, 4H). LCMS (ESI) m/z 409 (M+H)$^+$.

Example 45

Preparation of (1R,2R)-2-((6-((6-cyclopropyl-3H-imidazo[4,5-b]pyridin-3-yl)methyl)benzo[d]thiazol-2-yl)amino)cyclohexanol

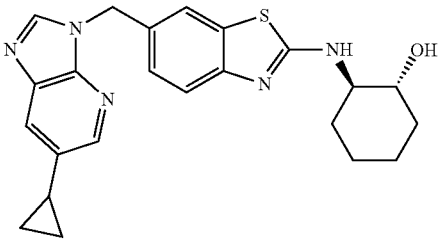 [SMILES: O[C@@H]1CCCC[C@H]1Nc1nc2ccc(Cn3cnc4cc(C5CC5)cnc43)cc2s1]

A stirred mixture of (1R,2R)-2-((6-((6-bromo-3H-imidazo[4,5-b]pyridin-3-yl)methyl)benzo[d]thiazol-2-yl)amino)cyclohexanol from Example 29 (30 mg, 0.0656 mmol), cyclopropylboronic acid (11 mg, 0.131 mmol), $K_2CO_3$ (36 mg, 0.262 mmol), 2-dicyclohexylphosphino-2',4',6'-triisopropylbiphenyl (16 mg, 0.0328 mmol) and anhydrous toluene (1 mL) was degassed under argon for 15 min. Tris(dibenzylideneacetone)dipalladium (0) (6 mg, 0.0066 mmol) was added. The reaction vessel was sealed and the mixture was heated at 100° C. for 15 h. After cooling to rt, the mixture was purified directly by reverse-phase HPLC using a mixture of water (5% $CH_3CN$, 0.05% HOAc) and $CH_3CN$ (0.05% HOAc) as the mobile phase and Phenomenex Luna C-18 column as the stationary phase to afford (1R,2R)-2-((6-((6-cyclopropyl-3H-imidazo[4,5-b]pyridin-3-yl)methyl)benzo[d]thiazol-2-yl)amino)cyclohexanol (1 mg, 4%) as a white solid. $^1$H NMR (300 MHz, DMSO-$d_6$) δ 8.51 (s, 1H), 8.24 (d, J=1.5 Hz, 1H), 8.03 (d, J=7.3 Hz, 1H), 7.70 (d, J=1.5 Hz, 1H), 7.63 (s, 1H), 7.28 (m, 1H), 7.19 (m, 1H), 5.44 (s, 2H), 4.82 (br s, 1H), 1.97-2.13 (m, 2H), 1.85 (m, 1H), 1.5-1.74 (m, 3H), 1.09-1.34 (m, 4H), 0.92-1.02 (m, 2H), 0.70-0.80 (m, 2H). LCMS (ESI) m/z 420 (M+H)$^+$.

Example 46

Preparation of (1R,2R)-1-((6-((3H-imidazo[4,5-b]pyridin-3-yl)methyl)benzo[d]thiazol-2-yl)amino)-2,3-dihydro-1H-inden-2-ol

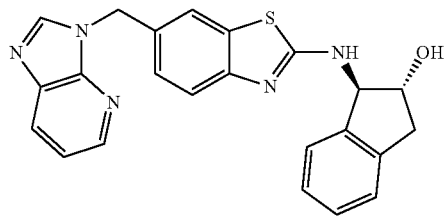 [SMILES: O[C@@H]1Cc2ccccc2[C@H]1Nc1nc2ccc(Cn3cnc4cccnc43)cc2s1]

(1R,2R)-1-((6-((3H-Imidazo[4,5-b]pyridin-3-yl)methyl)benzo[d]thiazol-2-yl)amino)-2,3-dihydro-1H-inden-2-ol was synthesized as a white powder (8 mg, 6%) using a procedure analogous to that described in Example 42, substituting 6-((3H-imidazo[4,5-b]pyridin-3-yl)methyl)-2-(methylsulfinyl)benzo[d]thiazole from Example 3 for 6-((6-bromo-3H-imidazo[4,5-b]pyridin-3-yl)methyl)-2-(methylsulfinyl)benzo[d]thiazole used in Example 42. $^1$H NMR (300 MHz, DMSO-$d_6$) δ 8.62 (s, 1H), 8.46 (d, J=8.1 Hz, 1H), 8.39 (dd, J=1.3, 4.7 Hz, 1H), 8.10 (dd, J=1.3, 8.1 Hz, 1H), 7.73 (d, J=1.1 Hz, 1H), 7.10-7.40 (m, 7H), 5.51 (s, 2H), 5.17 (t, J=7.2 Hz, 1H), 4.29 (m, 1H), 3.16 (dd, J=7.0, 15.6 Hz, 1H), 2.74 (m, 1H). LCMS (ESI) m/z 414 (M+H)$^+$.

Example 47

Preparation of (1R,2R)-2-((6-((6-bromo-5-methoxy-1H-benzo[d]imidazol-1-yl)methyl)benzo[d]thiazol-2-yl)amino)cyclohexanol

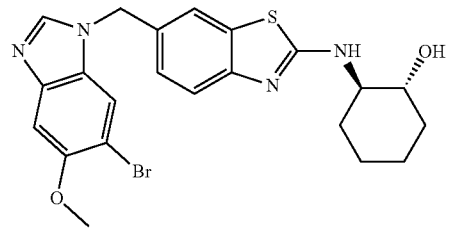 [SMILES: COc1cc2ncn(Cc3ccc4nc(N[C@@H]5CCCC[C@H]5O)sc4c3)c2cc1Br]

Step 1:
To a stirred mixture of 4-bromo-5-methoxy-2-nitroaniline (5 g, 20 mmol) in MeOH (50 mL) and HOAc (20 mL) at 0° C. under argon was added zinc powder (5.3 g, 80 mmol) portionwise. The mixture was stirred for 2 h, then filtered, and the filtrate was cooled to 0° C. The pH of the filtrate was adjusted to pH~9 by addition of solid $Na_2CO_3$. The mixture was then partitioned between EtOAc (250 mL) and water (200 mL). The EtOAc layer was separated, dried over $Na_2SO_4$, filtered, and concentrated under reduced pressure to afford 4-bromo-5-methoxybenzene-1,2-diamine (3.8 g, 88%) as a dark purple solid. The material was used in the next step without further purification. $^1$H NMR (300 MHz, DMSO-$d_6$) δ 6.66 (s, 1H), 6.34 (s, 1H), 4.08-4.83 (m, 4H), 3.63 (s, 3H). LCMS (ESI) m/z 217 and 219 (M+H)$^+$.

Step 2:
To a stirred mixture of 4-bromo-5-methoxybenzene-1,2-diamine (3.8 g, 18 mmol) from Step 1 of this Example and triethyl orthoformate (50 mL) was added formic acid (1 mL). The mixture was heated at reflux for 3 h, then concentrated under reduced pressure. The residue was partitioned between EtOAc (200 mL) and a 1 N aq $Na_2CO_3$ (100 mL). The EtOAc layer was separated, washed with brine (100 mL), dried over $Na_2SO_4$, filtered, and concentrated under reduced pressure to afford 5-bromo-6-methoxy-1H-benzo[d]imidazole (4.0 g) as a brown oil. The material was used in the next step without further purification. LCMS (ESI) m/z 228 and 230 (M+H)$^+$.

Step 3:
To a stirred mixture of DMF (3 mL) and NaH (60% in mineral oil, 67 mg, 1.6 mmol) at 0° C. under argon was added 5-bromo-6-methoxy-1H-benzo[d]imidazole (346 mg, 1.5 mmol) from Step 2 of this Example in one portion. The mixture was stirred for 5 min at 0° C. A solution of 6-(chloromethyl)-2-(methylthio)benzo[d]thiazole (500 mg, 2.2 mmol) from Step 4 of Example 36 in DMF (3 mL) was added dropwise. The mixture was stirred at 0° C. for 1 h, then allowed to warm slowly to rt and stirred for 6 h. The mixture was then partitioned between EtOAc (100 mL) and water (50 mL). The EtOAc layer was separated and washed with brine, dried over $Na_2SO_4$, filtered, and concentrated under reduced pressure. The residue was purified by silica gel flash chromatography eluting with 100% EtOAc to afford the two regioisomers: Regioisomer 1; 6-((5-bromo-6-methoxy-1H-benzo[d]imidazol-1-yl)methyl)-2-(methylthio)benzo[d]thiazole (127 mg, 20%). The structure was confirmed by comparison with NMR from the regiospecific synthesis of the same compound described in Step 3 of Example 41. $^1$H NMR (300 MHz, CDCl$_3$) δ 8.02 (s, 1H), 7.78-7.91 (m, 2H), 7.47 (s, 1H), 7.25 (m, 1H), 6.70 (s, 1H), 5.43 (s, 2H), 3.82 (s, 3H), 2.79 (s, 3H). LCMS (ESI) m/z 420 and 422 (M+H)+. Regioisomer 2; 6-((6-bromo-5-methoxy-1H-benzo[d]imidazol-1-yl)methyl)-2-(methylthio)benzo[d]thiazole (81 mg, 13%). $^1$H NMR (300 MHz, CDCl$_3$) δ 7.92 (s, 1H), 7.84 (d, J=8.5 Hz, 1H), 7.48 (m, 2H), 7.34 (s, 1H), 7.25 (m, 1H), 5.40 (s, 2H), 3.94 (s, 3H), 2.79 (s, 3H). LCMS (ESI) m/z 420 and 422 (M+H)+.

Step 4:

6-((6-Bromo-5-methoxy-1H-benzo[d]imidazol-1-yl)methyl)-2-(methylsulfinyl)benzo[d]thiazole was synthesized as a white foam (115 mg) using a procedure analogous to that described in Step 6 of Example 36, substituting 6-((6-bromo-5-methoxy-1H-benzo[d]imidazol-1-yl)methyl)-2-(methylthio)benzo[d]thiazole (regioisomer 2 from Step 3 of this Example) for 6-((4-bromo-1H-imidazol-1-yl)methyl)-2-(methylthio)benzo[d]thiazole used in Example 36. LCMS (ESI) m/z 436 and 438 (M+H)+.

Step 5:

(1R,2R)-2-((6-((6-Bromo-5-methoxy-1H-benzo[d]imidazol-1-yl)methyl)benzo[d]thiazol-2-yl)amino)cyclohexanol was synthesized as a white powder (15 mg, 19%) using a procedure analogous to that described in Step 4 of Example 37, substituting 6-((5-bromo-5-methoxy-1H-benzo[d]imidazol-1-yl)methyl)-2-(methylsulfinyl)benzo[d]thiazole from Step 4 of this Example for N-methyl-1-((2-(methylsulfinyl)benzo[d]thiazol-6-yl)methyl)-1H-imidazole-4-carboxamide used in Example 37. $^1$H NMR (300 MHz, DMSO-d$_6$) δ 8.37 (s, 1H), 7.98 (d, J=7.5 Hz, 1H), 7.79-7.91 (m, 2H), 7.63 (s, 1H), 7.35 (s, 1H), 7.17 (dd, J=1.6, 8.2 Hz, 1H), 5.43 (s, 2H), 4.75 (br s, 1H), 3.84 (s, 3H), 3.51 (m, 1H), 3.33 (m, 1H), 2.03 (m, 1H), 1.87 (m, 1H), 1.13-1.35 (br m, 2H), 1.09-1.35 (m, 4H). LCMS (ESI) m/z 487 and 489 (M+H)+.

Example 48

Preparation of (1R,2R)-2-((6-((9H-purin-9-yl)methyl)benzo[d]thiazol-2-yl)amino)cyclohexanol

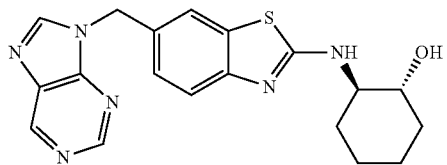

Step 1:

2-(Methylsulfinyl)benzo[d]thiazole-6-carbonitrile was synthesized as a tan solid (6.0 g) using a procedure analogous to that described in Step 5 of Example 3, substituting 2-(methylthio)benzo[d]thiazole-6-carbonitrile from Step 3 of Example 23 for 6-((3H-imidazo[4,5-b]pyridin-3-yl)methyl)-2-(methylthio)benzo[d]thiazole used in Example 3. LCMS (ESI) m/z 223 (M+H)+.

Step 2:

2-(((1R,2R)-2-Hydroxycyclohexyl)amino)benzo[d]thiazole-6-carbonitrile was synthesized as a white solid (1.8 g, 69%) using a procedure analogous to that described in Step 6 of Example 3, substituting 2-(methylsulfinyl)benzo[d]thiazole-6-carbonitrile from Step 1 of this Example for 6-((3H-imidazo[4,5-b]pyridin-3-yl)methyl)-2-(methylsulfinyl)benzo[d]thiazole used in Example 3. LCMS (ESI) m/z 274 (M+H)+.

Step 3:

To a stirred mixture of 2-(((1R,2R)-2-hydroxycyclohexyl)amino)benzo[d]thiazole-6-carbonitrile (1.2 g, 4.5 mmol) from Step 2 of this Example and 2,2-dimethoxypropane (4.7 g, 45 mmol) in 1,4-dioxane (30 mL) were added para-toluenesulfonic acid (89 mg, 0.5 mmol) and molecular sieves (4 Å) and the mixture was heated at reflux for 15 h. The mixture was cooled to rt, filtered, and the filtrate was concentrated under reduced pressure. The residue was purified via silica gel flash chromatography to afford 2-((3aR,7aR)-2,2-dimethylhexahydrobenzo[d]oxazol-3(2H)-yl)benzo[d]thiazole-6-carbonitrile (700 mg, 50%) as a white solid. LCMS (ESI) m/z 314 (M+H)+.

Step 4:

To a stirred mixture of 2-((3aR,7aR)-2,2-dimethylhexahydrobenzo[d]oxazol-3(2H)-yl)benzo[d]thiazole-6-carbonitrile (260 mg, 0.8 mmol) from Step 3 of this Example in THF (10 mL) at 0° C. was added LAH (3.3 mL of a 1M solution in THF, 3.3 mmol). The mixture was allowed to warm slowly to rt and stirred for 15 h. The mixture was again cooled to 0° C. and Na$_2$SO$_4$.10H$_2$O was added slowly. The mixture was stirred for 2 h, filtered, and the filtrate was concentrated under reduced pressure to afford (2-((3aR,7aR)-2,2-dimethylhexahydrobenzo[d]oxazol-3(2H)-yl)benzo[d]thiazol-6-yl)methanamine (237 mg). The material was used in the next step without further purification. LCMS (ESI) m/z 318 (M+H)+.

Step 5:

To a stirred mixture of (2-((3aR,7aR)-2,2-dimethylhexahydrobenzo[d]oxazol-3(2H)-yl)benzo[d]thiazol-6-yl)methanamine (236 mg, 0.7 mmol) from Step 4 of this Example and DIEA (388 μL, 2.2 mmol) at 0° C. under argon was added 4,6-dichloro-5-nitropyrimidine (159 mg, 0.8 mmol) in one portion. The mixture was stirred for 4 h and then concentrated under reduced pressure. The residue was purified by silica gel flash chromatography (eluting with a gradient of 100% hexanes to 50% EtOAc in hexanes) to afford 6-chloro-N-((2-((3aR,7aR)-2,2-dimethylhexahydrobenzo[d]oxazol-3(2H)-yl)benzo[d]thiazol-6-yl)methyl)-5-nitropyrimidin-4-amine (153 mg, 43%) as an oil. $^1$H NMR (300 MHz, CDCl$_3$) δ 8.45 (s, 1H), 7.81 (br s, 1H), 7.5-7.63 (m, 2H), 7.22-7.31 (m, 1H), 4.85 (d, J=5.7 Hz, 2H), 3.11 (m, 1H), 2.82 (m, 1H), 2.11-2.16 (m, 1H), 1.90 (m, 1H), 1.80 (s, 3H), 1.5-1.69 (m, 5H), 1.19-1.49 (m, 4H). LCMS (ESI) m/z 475 (M+H)+.

Step 6:

To a stirred mixture of 6-chloro-N-((2-((3aR,7aR)-2,2-dimethylhexahydrobenzo[d]oxazol-3(2H)-yl)benzo[d]thiazol-6-yl)methyl)-5-nitropyrimidin-4-amine (153 mg, 0.3 mmol) from Step 5 of this Example in MeOH (5 mL) and EtOAc (5 mL) was added Pd 10% wt. on carbon (20 mg, 0.02 mmol). Hydrogen gas was bubbled through the stirred mixture for 2 min, then stirring was continued for 15 h under 1 atm of H$_2$. The mixture was filtered and the filtrate was concentrated under reduced pressure to afford N$^4$-((2-((3aR,7aR)-2,2-dimethylhexahydrobenzo[d]oxazol-3(2H)-yl)benzo[d]thiazol-6-yl)methyl)pyrimidine-4,5-diamine as an oil (155 mg). The material was used in the next step without further purification. LCMS (ESI) m/z 411 (M+H)+.

Step 7:

(3aR,7aR)-3-(6-((9H-Purin-9-yl)methyl)benzo[d]thiazol-2-yl)-2,2-dimethyloctahydrobenzo[d]oxazole was synthesized as an oil (220 mg) using a procedure analogous to that described in Step 3 of Example 41, substituting N$^4$-((2-((3aR,7aR)-2,2-dimethylhexahydrobenzo[d]oxazol-3(2H)-yl)benzo[d]thiazol-6-yl)methyl)pyrimidine-4,5-diamine from Step 6 of this Example for 4-bromo-5-methoxy-N$^1$-

((2-(methylthio)benzo[d]thiazol-6-yl)methyl)benzene-1,2-diamine used in Example 41. LCMS (ESI) m/z 421 (M+H)⁺.

Step 8:
A solution of (3aR,7aR)-3-(6-((9H-purin-9-yl)methyl)benzo[d]thiazol-2-yl)-2,2-dimethyloctahydrobenzo[d]oxazole (220 mg, 0.5 mmol) from Step 7 of this Example in TFA (5 mL) and CH$_2$Cl$_2$ (5 mL) was stirred for 2 h at rt. The mixture was concentrated under reduced pressure and the residue was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford (1R,2R)-2-((6-((9H-purin-9-yl)methyl)benzo[d]thiazol-2-yl)amino)cyclohexanol (7 mg, 4%) as a white powder. $^1$H NMR (300 MHz, DMSO-d$_6$) δ 9.17 (s, 1H), 8.96 (s, 1H), 8.74 (s, 1H), 8.01 (d, J=7.5 Hz, 1H), 7.68 (d, J=1.1 Hz, 1H), 7.17-7.36 (m, 2H), 5.50 (s, 2H), 4.78 (d, J=4.5 Hz, 1H), 3.52 (m, 1H), 3.33 (m, 1H), 2.03 (m, 1H), 1.87 (m, 1H), 1.5-1.67 (m, 2H), 1.11-1.34 (m, 4H). LCMS (ESI) m/z 381 (M+H)⁺.

Example 49

Preparation of (1R,2R)-1-((6-((5-bromo-6-methoxy-1H-benzo[d]imidazol-1-yl)methyl)benzo[d]thiazol-2-yl)amino)-2,3-dihydro-1H-inden-2-ol

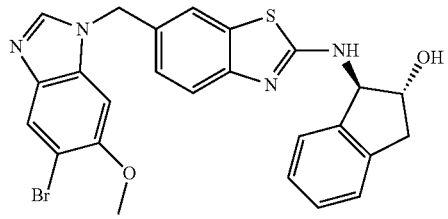 [SMILES: COc1cc2c(cc1Br)ncn2Cc1ccc2nc(N[C@@H]3c4ccccc4C[C@H]3O)sc2c1]

Step 1:
6-((5-Bromo-6-methoxy-1H-benzo[d]imidazol-1-yl)methyl)-2-(methylsulfinyl)benzo[d]thiazole was synthesized as a white foam (200 mg) using a procedure analogous to that described in Step 6 of Example 36, substituting 6-((5-bromo-6-methoxy-1H-benzo[d]imidazol-1-yl)methyl)-2-(methylthio)benzo[d]thiazole regioisomer 1 from Step 3 of Example 47 for 6-((4-bromo-1H-imidazol-1-yl)methyl)-2-(methylthio)benzo[d]thiazole used in Example 36. LCMS (ESI) m/z 436 and 438 (M+H)⁺.

Step 2:
To a suspension of 6-((5-bromo-6-methoxy-1H-benzo[d]imidazol-1-yl)methyl)-2-(methylsulfinyl)benzo[d]thiazole (279 mg, 0.07 mmol) and (1R,2R)-1-amino-2,3-dihydro-1H-inden-2-ol (30 mg, 0.2 mmol) was added DIEA (60 μL, 0.3 mmol). The mixture was heated in a Biotage microwave synthesizer at 160° C. in a sealed tube for 30 min. The mixture was then subjected to purification by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford (1R,2R)-1-((6-((5-bromo-6-methoxy-1H-benzo[d]imidazol-1-yl)methyl)benzo[d]thiazol-2-yl)amino)-2,3-dihydro-1H-inden-2-ol (7 mg, 20%) as a white powder. $^1$H NMR (300 MHz, DMSO-d$_6$) δ 8.48 (d, J=7.9 Hz, 1H), 8.31 (s, 1H), 7.86 (s, 1H), 7.72 (s, 1H), 7.33-7.41 (m, 2H), 7.28 (m, 1H), 7.12-7.24 (m, 4H), 5.49 (s, 2H), 5.17 (t, J=7.1 Hz, 1H), 4.29 (br s, 1H), 3.87 (s, 3H), 3.16 (dd, J=7.0, 15.6 Hz, 1H), 2.74 (dd, J=7.3, 15.5 Hz, 1H). LCMS (ESI) m/z 522 and 524 (M+H)⁺.

Example 50

Preparation of (±)-2-((6-((5,6-dimethoxy-1H-benzo[d]imidazol-1-yl)methyl)benzo[d]thiazol-2-yl)amino)cycloheptanol

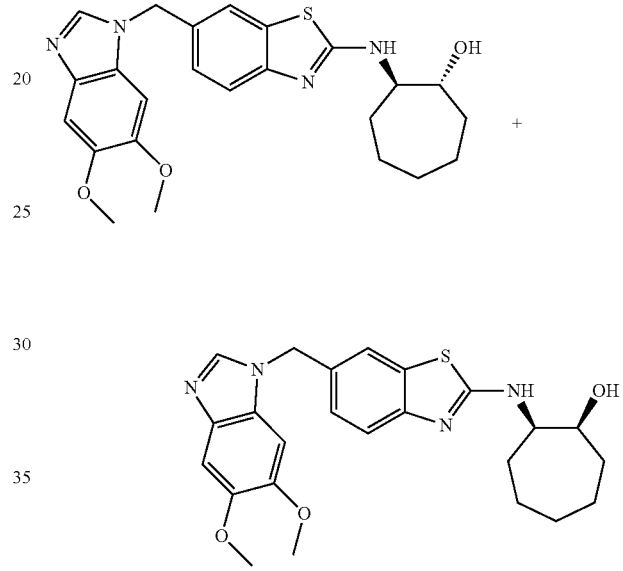

Step 1:
To a stirred mixture of (±)-2-azidocycloheptanol (190 mg, 1.2 mmol) in THF (1 mL) and H$_2$O (100 μL) was added PPh$_3$ (321 mg, 1.2 mmol). The mixture was stirred at rt for 15 h, then concentrated under reduced pressure. The residue was purified via silica gel flash chromatography eluting with 100:15:1, CH$_2$Cl$_2$:MeOH:TEA to afford (±)-2-aminocycloheptanol (103 mg, 50%) as a white solid. LCMS(ELSD) (ESI) m/z 130 (M+H)⁺.

Step 2:
(±)-2-((6-((5,6-Dimethoxy-1H-benzo[d]imidazol-1-yl)methyl)benzo[d]thiazol-2-yl)amino)cycloheptanol was synthesized as a white powder (39 mg, 16%) using a procedure analogous to that described in Example 27, substituting (±)-2-aminocycloheptanol from Step 1 of this Example for 2-ethoxyaniline used in Example 27. $^1$H NMR (300 MHz, DMSO-d$_6$) δ 8.15 (s, 1H), 8.05 (d, J=7.3 Hz, 1H), 7.63 (d, J=1.1 Hz, 1H), 7.30 (m, 1H), 7.13-7.24 (m, 3H), 5.41 (s, 2H), 4.80 (d, J=4.1 Hz, 1H), 3.64-3.81 (m, 8H), 3.58 (br s, 1H), 1.23-1.99 (m, 9H). LCMS (ESI) m/z 453 (M+H)⁺.

Example 51

Preparation of (1R,2R)-2-((6-((6-methoxy-5-(1-methyl-1H-pyrazol-4-yl)-1H-benzo[d]imidazol-1-yl)methyl)benzo[d]thiazol-2-yl)amino)cyclohexanol

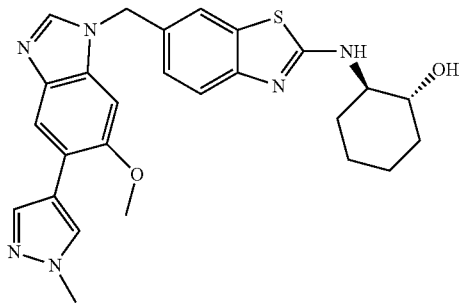 [SMILES: COc1cc2c(cc1-c1cnn(C)c1)ncn2Cc1ccc2nc(N[C@@H]3CCCC[C@H]3O)sc2c1]

Step 1:
To a suspension of 6-((5-bromo-6-methoxy-1H-benzo[d]imidazol-1-yl)methyl)-2-(methylsulfinyl)benzo[d]thiazole (502 mg, 1 mmol) from Step 1 of Example 49 and (1R,2R)-2-aminocyclohexanol in DMA (4 mL) was added DIEA (1 mL, 6 mmol). The mixture was heated in a sealed tube at 110° C. for 16 h. The mixture was cooled to rt and added dropwise with stirring to H$_2$O (200 mL). After the mixture was stirred for 30 min, the solid was collected by filtration to afford (1R,2R)-2-((6-((5-bromo-6-methoxy-1H-benzo[d]imidazol-1-yl)methyl)benzo[d]thiazol-2-yl)amino)cyclohexanol (443 mg, 80%) as a tan solid. $^1$H NMR (300 MHz, DMSO-d$_6$) δ 8.30 (s, 1H), 7.99 (d, J=7.5 Hz, 1H), 7.86 (s, 1H), 7.66 (d, J=1.1 Hz, 1H), 7.37 (s, 1H), 7.30 (m, 1H), 7.22 (m, 1H), 5.46 (s, 2H), 4.76 (d, J=5.1 Hz, 1H), 3.86 (s, 3H), 3.53 (m, 1H), 3.33 (m, 1H), 2.03 (m, 1H), 1.88 (m 1H), 1.5-1.69 (m 2H), 1.11-1.33 (m, 4H). LCMS (ESI) m/z 486 and 488 (M+H)$^+$.

Step 2:
A suspension of (1R,2R)-2-((6-((5-bromo-6-methoxy-1H-benzo[d]imidazol-1-yl)methyl)benzo[d]thiazol-2-yl)amino)cyclohexanol (30 mg, 0.06 mmol) from Step 1 of this Example and 1-methylpyrazole-4-boronic acid pinacol ester (26 mg, 0.1 mmol) in DME (300 μL) was added aq 2M K$_2$CO$_3$ (150 μL, 0.2 mmol). Argon was bubbled into the mixture for 5 min followed by the addition of dichlorobis(triphenylphosphine)palladium II (4 mg, 0.006 mmol). Argon was bubbled into the mixture for an additional 5 min and then the mixture was heated in a sealed tube for 15 h. The mixture was cooled to rt and then partitioned between EtOAc (100 mL) and water (50 mL). The EtOAc layer was separated and concentrated under reduced pressure. The residue was purified by reverse-phase preparative HPLC, using a mixture of water (5% CH$_3$CN, 0.05% HCOOH) and CH$_3$CN (0.05% HCOOH) as the mobile phase and Varian Pursuit XRs C18 column as the stationary phase to afford (1R,2R)-2-((6-((6-methoxy-5-(1-methyl-1H-pyrazol-4-yl)-1H-benzo[d]imidazol-1-yl)methyl)benzo[d]thiazol-2-yl)amino)cyclohexanol (16 mg, 53%) as a white powder. $^1$H NMR (300 MHz, DMSO-d$_6$) δ 8.21 (s, 1H), 7.97-8.06 (m, 2H), 7.87 (s, 1H), 7.80 (s, 1H), 7.66 (d, J=1.1 Hz, 1H), 7.27-7.33 (m, 1H), 7.19-7.25 (m, 2H), 5.44 (s, 2H), 4.78 (d, J=4.3 Hz, 1H), 3.85 (s, 6H), 3.51 (m, 1H), 3.33 (m, 1H), 2.03 (m, 1H), 1.87 (m, 1H), 1.5-1.66 (m, 2H), 1.12-1.32 (m, 4H). LCMS (ESI) m/z 489 (M+H)$^+$.

Example 52

Preparation of (1R,2R)-2-((6-((5-methoxy-6-(1-methyl-1H-pyrazol-4-yl)-1H-benzo[d]imidazol-1-yl)methyl)benzo[d]thiazol-2-yl)amino)cyclohexanol

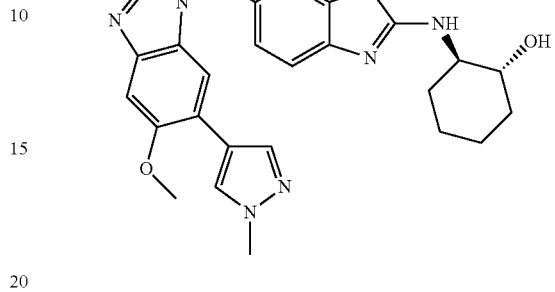

(1R,2R)-2-((6-((5-Methoxy-6-(1-methyl-1H-pyrazol-4-yl)-1H-benzo[d]imidazol-1-yl)methyl)benzo[d]thiazol-2-yl)amino)cyclohexanol (19 mg, 55%) was synthesized as a white powder using a procedure analogous to that described in Step 2 of Example 51, substituting (1R,2R)-2-((6-((6-bromo-5-methoxy-1H-benzo[d]imidazol-1-yl)methyl)benzo[d]thiazol-2-yl)amino)cyclohexanol from Step 5 of Example 47 for (1R,2R)-2-((6-((5-bromo-6-methoxy-1H-benzo[d]imidazol-1-yl)methyl)benzo[d]thiazol-2-yl)amino)cyclohexanol used in Example 51. $^1$H NMR (300 MHz, DMSO-d$_6$) δ 8.27 (s, 1H), 8.06 (s, 1H), 7.99 (d, J=7.3 Hz, 1H), 7.88 (s, 1H), 7.77 (s, 1H), 7.68 (d, J=1.1 Hz, 1H), 7.18-7.33 (m, 3H), 5.44 (s, 2H), 4.77 (d, J=4.5 Hz, 1H), 3.86 (s, 6H), 3.50 (m, 1H), 3.33 (m, 1H), 2.02 (m, 1H), 1.86 (m, 1H), 1.5-1.65 (m, 2H), 1.10-1.31 (m, 4H). LCMS (ESI) m/z 489 (M+H)$^+$.

Example 53

Preparation of 1-((2-(((1R,2R)-2-hydroxycyclohexyl)amino)benzo[d]thiazol-6-yl)methyl)-5-methoxy-1H-benzo[d]imidazole-6-carbonitrile

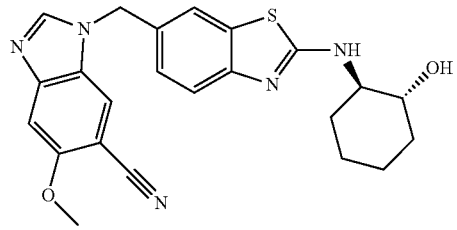 [SMILES: COc1cc2ncn(Cc3ccc4nc(N[C@@H]5CCCC[C@H]5O)sc4c3)c2cc1C#N]

To a suspension of (1R,2R)-2-((6-((6-bromo-5-methoxy-1H-benzo[d]imidazol-1-yl)methyl)benzo[d]thiazol-2-yl)amino)cyclohexanol (50 mg, 0.1 mmol) from Step 5 of Example 47 in DMF (1.5 mL) was added zinc cyanide (24 mg, 0.2 mmol). Argon was bubbled into the mixture for 5 min followed by the addition of 1,1'-bis(diphenylphosphino)ferrocene (9 mg, 0.02 mmol) and tris(dibenzylideneacetone)dipalladium (9 mg, 0.01 mmol). Argon was bubbled into the mixture for an additional 5 min. The reaction vessel was sealed and the mixture was heated at 110° C. for 15 h. The mixture was cooled to rt and argon was again bubbled into the mixture for 5 min. Additional zinc cyanide (24 mg, 0.2 mmol), 1,1'-Bis(diphenylphosphino)ferrocene (9 mg, 0.02 mmol) and tris(dibenzylideneacetone)dipalladium (9 mg, 0.01 mmol) were added to the mixture, and the reaction vessel was resealed and heated for 5 h. The mixture was cooled to rt, filtered, and the filtrate was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford 1-((2-(((1R,2R)-2-hydroxycyclohexyl)amino)benzo[d]thiazol-6-yl)methyl)-5-methoxy-1H-benzo[d]imidazole-6-carbonitrile (18 mg, 41%) as a white powder. $^1$H NMR (300 MHz, DMSO-d$_6$) δ 8.60 (s, 1H), 8.12 (s, 1H), 8.01 (d, J=7.3 Hz, 1H), 7.70 (d, J=0.9 Hz, 1H), 7.43 (s, 1H), 7.20-7.34 (m, 2H), 5.46 (s, 2H), 4.76 (d, J=4.9 Hz, 1H), 3.90 (s, 3H), 3.51 (m, 1H), 3.33 (m, 1H), 2.03 (m, 1H), 1.87 (m, 1H), 1.5-1.67 (m, 2H), 1.15-1.34 (m, 4H). LCMS (ESI) m/z 434 (M+H)$^+$

Example 54

Preparation of (R)-2-((6-((3H-imidazo[4,5-b]pyridin-3-yl)methyl)benzo[d]thiazol-2-yl)amino)cyclohexanone

(1R,2R)-2-((6-((3H-Imidazo[4,5-b]pyridin-3-yl)methyl) benzo[d]thiazol-2-yl)amino)cyclohexanol from Example 3 (188 mg, 0.50 mmol) was stirred in a mixture of DCM/MeCN/DMA (4:4:2, v/v/v) at rt. Dess-Martin periodinane (254 mg, 0.60 mmol) was added and the mixture was stirred at rt for 30 min before another batch of periodinane (254 mg, 0.60 mmol) was added. The resulting mixture was heated at 55° C. for 4 h, then another batch of periodinane (254 mg, 0.60 mmol) was added and the reaction mixture was heated at 60° C. for 6 h. LCMS showed that the reaction was mostly complete. The mixture was then cooled to rt and partitioned between DCM and 3% aq NaOH, and then the organic layer was washed with brine, dried over MgSO$_4$, and concentrated under reduced pressure. The residue was purified by silica gel chromatography eluting with 0-100% EtOAc in hexanes to give (R)-2-((6-((3H-imidazo[4,5-b]pyridin-3-yl)methyl) benzo[d]thiazol-2-yl)amino)cyclohexanone (150 mg, 80%) as a white solid. $^1$H NMR (300 MHz, DMSO-d$_6$) δ 8.60 (s, 1H), 8.38 (dd, J=1.2, 4.8 Hz, 1H), 8.22 (d, J=7.3 Hz, 1H), 8.09 (dd, J=1.3, 8.1 Hz, 1H), 7.70 (d, J=1.1 Hz, 1H), 7.26-7.35 (m, 2H), 7.19-7.26 (m, 1H), 5.49 (s, 2H), 4.68 (td, J=6.5, 12.8 Hz, 1H), 2.5-2.67 (m, 1H), 2.42 (ddd, J=2.7, 5.9, 12.3 Hz, 1H), 2.30 (d, J=13.4 Hz, 1H), 1.94-2.12 (m, 1H), 1.82 (br s, 2H), 1.38-1.66 (m, 2H). LCMS (ESI) m/z 378 (M+H)$^+$.

Example 55

Preparation of (1R,2R)-2-((6-(((6-chloro-3H-imidazo [4,5-b]pyridin-3-yl)methyl)benzo[d]thiazol-2-yl) amino)cyclohexanol

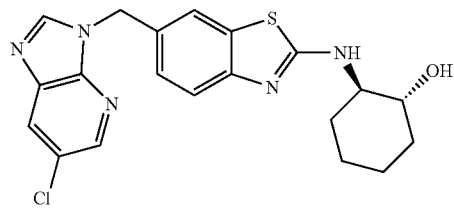 [SMILES: O[C@@H]1CCCC[C@H]1Nc1nc2ccc(Cn3cnc4cc(Cl)cnc43)cc2s1]

Step 1:
5-Chloro-N-((2-(methylthio)benzo[d]thiazol-6-yl) methyl)-3-nitropyridin-2-amine was synthesized as a yellow foam (126 mg, 29%) using a procedure analogous to that described in Step 1 of Example 41, substituting 5-chloro-3-nitropyridin-2-amine for 4-bromo-5-methoxy-2-nitroaniline used in Example 41. LCMS (ESI) m/z 367 (M+H)$^+$.

Step 2:
Crude 5-chloro-N$^2$-((2-(methylthio)benzo[d]thiazol-6-yl) methyl)pyridine-2,3-diamine was synthesized as a yellow solid using a procedure analogous to that describe in Step 2 of Example 41, substituting 5-chloro-N-((2-(methylthio) benzo[d]thiazol-6-yl)methyl)-3-nitropyridin-2-amine from Step 1 of this Example for 4-bromo-5-methoxy-N-((2-(methylthio)benzo[d]thiazol-6-yl)methyl)-2-nitroaniline used in Example 41. The residue was purified by silica gel flash chromatography eluting with a gradient of 100% hexanes to 100% EtOAc to afford 5-chloro-N$^2$-((2-(methylthio)benzo[d]thiazol-6-yl)methyl)pyridine-2,3-diamine (75 mg, 65%). LCMS (ESI) m/z 337 (M+H)$^+$.

Step 3:
6-((6-Chloro-3H-imidazo[4,5-b]pyridin-3-yl)methyl)-2-(methylthio)benzo[d]thiazole was synthesized as a white foam (62 mg, 80%) using a procedure analogous to that described in Step 3 of Example 41, substituting 5-chloro-N$^2$-(2-(methylthio)benzo[d]thiazol-6-yl)methyl)pyridine-2,3-diamine from Step 2 of this Example for 4-bromo-5-methoxy-N$^1$-((2-(methylthio)benzo[d]thiazol-6-yl)methyl) benzene-1,2-diamine used in Example 41. LCMS (ESI) m/z 347 (M+H)$^+$.

Step 4:
6-((6-Chloro-3H-imidazo[4,5-b]pyridin-3-yl)methyl)-2-(methylsulfinyl)benzo[d]thiazole was synthesized as a white foam (111 mg) using a procedure analogous to that described in Step 6 of Example 36, substituting 6-((6-chloro-3H-imidazo[4,5-b]pyridin-3-yl)methyl)-2-(methylthio)benzo[d] thiazole from Step 3 of this Example for 6-((4-bromo-1H-imidazol-1-yl)methyl)-2-(methylthio)benzo[d]thiazole used in Example 36. LCMS (ESI) m/z 363 (M+H)$^+$.

Step 5:
(1R,2R)-2-((6-(((6-Chloro-3H-imidazo[4,5-b]pyridin-3-yl)methyl)benzo[d]thiazol-2-yl)amino)cyclohexanol was synthesized as a white powder (35 mg, 47%) using a procedure analogous to that described in Step 7 of Example 36, substituting 6-((6-chloro-3H-imidazo[4,5-b]pyridin-3-yl)methyl)-2-(methylsulfinyl)benzo[d]thiazole from Sep 4 of this Example for 6-((4-bromo-1H-imidazol-1-yl)methyl)-2-(methylsulfinyl)benzo[d]thiazole used in Example 36. $^1$H NMR (300 MHz, DMSO-d$_6$) δ 8.69 (s, 1H), 8.42 (d, J=2.1 Hz, 1H), 8.28 (d, J=2.3 Hz, 1H), 7.97 (d, J=7.5 Hz, 1H), 7.66

(d, J=1.3 Hz, 1H), 7.29 (m, 1H), 7.21 (m, 1H), 5.48 (s, 2H), 4.74 (d, J=5.1 Hz, 1H), 3.51 (m, 1H), 3.33 (m, 1H), 2.02 (m, 1H), 1.87 (m, 1H), 1.5-1.65 (m, 2H), 1.12-1.31 (m, 4H). LCMS (ESI) m/z 414 (M+H)+.

Example 56

Preparation of (1R,2R)-2-((6-((3H-imidazo[4,5-b]pyridin-3-yl)methyl)benzo[d]oxazol-2-yl)amino)cyclohexanol

Step 1:
To a stirred mixture of methyl 2-mercaptobenzo[d]oxazole-6-carboxylate (5 g, 23.92 mmol) and solid $K_2CO_3$ (9.9 g, 71.76 mmol) in anhydrous DMF (50 mL) at rt was added methyl iodide (10.2 g, 71.76 mmol). The mixture was stirred at rt for 15 h. The reaction mixture was diluted with water then extracted with DCM (×3). The combined organic layers were washed with water and 2 M aq HCl. The organic layer was separated and dried over $MgSO_4$, filtered, and concentrated under reduced pressure to afford methyl 2-(methylthio)benzo[d]oxazole-6-carboxylate (4.24 g, 80%) as a light pink solid that did not require further purification. $^1$H NMR (300 MHz, CDCl$_3$) δ 8.12 (d, J=1.1 Hz, 1H), 8.04 (dd, J=1.1, 8.3 Hz, 1H), 7.61 (d, J=8.3 Hz, 1H), 3.95 (s, 3H), 2.79 (s, 3H). LCMS (ESI) m/z 224 (M+H)+.

Step 2:
To a stirred solution of methyl 2-(methylthio)benzo[d]oxazole-6-carboxylate (4.24 g, 19 mmol) from Step 1 of this Example in anhydrous DCM (100 mL) under an argon atmosphere at −78° C. was added dropwise diisobutylaluminum hydride (1.0 M solution in DCM, 40 mL, 40 mmol). The mixture was allowed to warm to −30° C. over 2 h. The reaction was quenched by addition of saturated aq sodium potassium tartrate and the resulting mixture stirred at rt for an additional 15 h. The organic layer was separated and the aqueous layer extracted with additional DCM (×2). The combined organic layers were washed with water dried over $MgSO_4$, filtered, and concentrated under reduced pressure to afford (2-(methylthio)benzo[d]oxazol-6-yl)methanol (2 g, 54%) as a tan solid that did not require further purification. $^1$H NMR (300 MHz, DMSO-d$_6$) δ 7.5-7.61 (m, 2H), 7.28 (d, J=8.3 Hz, 1H), 5.34 (t, J=5.7 Hz, 1H), 4.59 (d, J=5.7 Hz, 2H), 2.76 (s, 3H). LCMS (ESI) m/z 196 (M+H)+.

Step 3:
To a stirred solution of (2-(methylthio)benzo[d]oxazol-6-yl)methanol (2 g, 10.26 mmol) from Step 2 of this Example in a mixture of anhydrous DMF (0.5 mL) and anhydrous DCM (100 mL) at 0° C. was added dropwise thionyl chloride (4 mL, 55 mmol). The mixture was allowed to warm to rt and stirred for a further 40 min. The mixture was concentrated under reduced pressure and the residue was partitioned between saturated aq NaHCO$_3$ and a 10:1 mixture of DCM:MeOH. The organic layer was separated and dried over MgSO$_4$, filtered, and concentrated under reduced pressure to afford 6-(chloromethyl)-2-(methylthio)benzo[d]oxazole (2 g, 92%) as a light pink solid which did not require further purification. $^1$H NMR (300 MHz, DMSO-d$_6$) δ ppm 7.75 (d, J=1.3 Hz, 1H), 7.63 (d, J=8.1 Hz, 1H), 7.43 (dd, J=1.3, 8.1 Hz, 1H), 4.89 (s, 2H), 2.77 (s, 3H). LCMS (ESI) m/z 214 (M+H)+.

Step 4:
To a stirred solution of 4-azabenzimidazole (304 mg, 2.55 mmol) in anhydrous DMF (10 mL) at 0° C. was added in one portion sodium hydride (60% dispersion in mineral oil, 107 mg, 2.68 mmol) and the mixture was stirred at 0° C. for 20 min. The mixture was allowed to warm to rt and stirred for a further 20 min. To the reaction mixture was added a solution of 6-(chloromethyl)-2-(methylthio)benzo[d]oxazole (600 mg, 2.81 mmol) from Step 3 of this Example in DMF (5 mL). The mixture was stirred at rt for 15 h. To the reaction mixture was added water and the mixture was extracted with DCM. The combined organic layers were washed with brine. The organic layer was separated, dried over MgSO$_4$, filtered, and the filtrate was concentrated under reduced pressure. The crude material was purified by silica gel flash chromatography eluting with 100% DCM followed by 1% MeOH in DCM to afford 6-((3H-imidazo[4,5-b]pyridin-3-yl)methyl)-2-(methylthio)benzo[d]oxazole (290 mg, 38%) as a white solid. The regiochemistry of the alkylation was determined by 2-dimensional nuclear Overhauser effect (NOE) experiment. $^1$H NMR (300 MHz, DMSO-d$_6$) δ 8.64 (s, 1H), 8.38 (dd, J=1.2, 4.6 Hz, 1H), 8.10 (dd, J=1.2, 8.0 Hz, 1H), 7.69 (s, 1H), 7.58 (d, J=8.1 Hz, 1H), 7.25-7.41 (m, 2H), 5.61 (s, 2H), 2.73 (s, 3H). LCMS (ESI) m/z 297 (M+H)+.

Step 5:
To a stirred solution of 6-((3H-imidazo[4,5-b]pyridin-3-yl)methyl)-2-(methylthio)benzo[d]oxazole (290 mg, 0.979 mmol) from Step 4 of this Example in DCM (25 mL) at 0° C. was added 70% meta-chloroperbenzoic acid (582 mg, 2.36 mmol), and the mixture was stirred at 0° C. for 2.5 h. To the mixture was added saturated aq NaHCO$_3$ and the organic layer was separated. The aqueous layer was extracted with DCM and the combined organic layers were washed with saturated aq NaHCO$_3$. The organic layer was separated, dried over MgSO$_4$, filtered, and concentrated under reduced pressure to afford 6-((3H-imidazo[4,5-b]pyridin-3-yl)methyl)-2-(methylsulfinyl)benzo[d]oxazole (305 mg, 100%) as a solid which did not require further purification. $^1$H NMR (300 MHz, DMSO-d$_6$) δ 8.67 (s, 1H), 8.38 (d, J=4.5 Hz, 1H), 8.11 (d, J=7.2 Hz, 1H), 7.84-7.94 (m, 2H), 7.52 (d, J=8.3 Hz, 1H), 7.30 (dd, J=4.8, 8.0 Hz, 1H), 5.69 (s, 2H), 3.18 (s, 3H). LCMS (ESI) m/z 313 (M+H)+.

Step 6:
A stirred mixture of 6-((3H-imidazo[4,5-b]pyridin-3-yl)methyl)-2-(methylthio)benzo[d]oxazole (165 mg, 0.53 mmol) from Step 5 of this Example, (1R,2R)-(−)-2-aminocyclohexanol (122 mg, 1.06 mmol), and DIEA (137 mg, 1.06 mmol) in anhydrous DMA (3 mL) was sealed and heated at 100° C. for 15 h. The reaction mixture was cooled to rt and purified directly by reverse-phase HPLC using a mixture of water (5% CH$_3$CN, 0.05% HOAc), CH$_3$CN (0.05% HOAc) as the mobile phase and Varian Pursuit XRs diphenyl column as the stationary phase to afford (1R,2R)-2-((6-((3H-imidazo[4,5-b]pyridin-3-yl)methyl)benzo[d]oxazol-2-yl)amino)cyclohexanol (44 mg, 23%) as a white solid. $^1$H NMR (300 MHz, DMSO-d$_6$) δ 8.60 (s, 1H), 8.39 (dd, J=1.1, 4.7 Hz, 1H), 8.08 (dd, J=1.2, 8.0 Hz, 1H), 7.81 (d, J=7.5 Hz, 1H), 7.40 (s, 1H), 7.29 (dd, J=4.7, 8.1 Hz, 1H), 7.10-7.19 (m, 2H), 5.50 (s, 2H), 4.70 (br s, 1H), 3.25-3.45

(m, 2H), 1.83-1.97 (m, 2H), 1.5-1.67 (m, 2H), 1.14-1.32 (m, 4H). LCMS (ESI) m/z 364 (M+H)⁺.

Example 57

Preparation of (1R,2R)-1-((6-((3H-imidazo[4,5-b]pyridin-3-yl)methyl)benzo[d]oxazol-2-yl)amino)-2,3-dihydro-1H-inden-2-ol

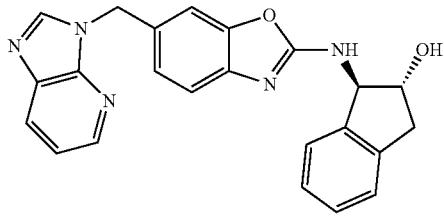 [SMILES: O[C@@H]1Cc2ccccc2[C@H]1Nc1nc2ccc(Cn3cnc4cccnc43)cc2o1]

A stirred mixture of 6-((3H-imidazo[4,5-b]pyridin-3-yl)methyl)-2-(methylthio)benzo[d]oxazole (108 mg, 0.346 mmol) from Step 5 of Example 56, (1R,2R)-(−)-trans-1-amino-2-indanol (104 mg, 0.698 mmol), and DIEA (90 mg, 0.698 mmol) in anhydrous DMA (1.5 mL) was sealed and heated in a Biotage microwave synthesizer at 120° C. for 30 min. The reaction mixture was cooled to rt and purified directly by reverse-phase HPLC using a mixture of water (5% CH₃CN, 0.05% HCOOH) and CH₃CN (0.05% HCOOH) as the mobile phase and Varian Pursuit XRs C-18 column as the stationary phase to afford (1R,2R)-1-((6-((3H-imidazo[4,5-b]pyridin-3-yl)methyl)benzo[d]oxazol-2-yl)amino)-2,3-dihydro-1H-inden-2-ol (35 mg, 26%) as a white solid. ¹H NMR (300 MHz, DMSO-d₆) δ 8.62 (s, 1H), 8.36-8.45 (m, 2H), 8.09 (dd, J=1.3, 8.1 Hz, 1H), 7.47 (s, 1H), 7.29 (dd, J=4.7, 8.1 Hz, 1H), 7.12-7.25 (m, 6H), 5.52 (s, 2H), 5.47 (d, J=5.1 Hz, 1H), 5.02 (m, 1H), 4.34 (m, 1H), 3.15 (dd, J=7.2, 15.6 Hz, 1H), 2.73 (dd, J=7.6, 15.4 Hz, 1H). LCMS (ESI) m/z 398 (M+H)⁺.

Example 58

Preparation of (R)-2-((6-((3H-imidazo[4,5-b]pyridin-3-yl)methyl)benzo[d]thiazol-2-yl)amino)cyclohexanone oxime

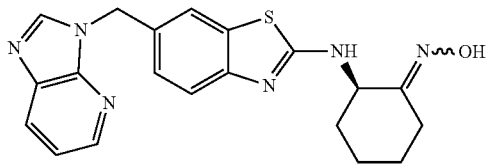 [SMILES: ON=C1CCCC[C@H]1Nc1nc2ccc(Cn3cnc4cccnc43)cc2s1]

(R)-2-((6-((3H-Imidazo[4,5-b]pyridin-3-yl)methyl)benzo[d]thiazol-2-yl)amino)cyclohexanone from Example 54 (70 mg, 0.19 mmol) was stirred in EtOH. Pyridine (100 μL, excess) and NH₂OH.HCl (100 mg, excess) were added and the resulting mixture was heated at 88° C. for 1 h. LCMS showed that the reaction was complete. The mixture was then cooled to rt and purified by HPLC using a mixture of water (5% CH₃CN, 0.05% HCOOH) and CH₃CN (0.05% HCOOH) as the mobile phase and Varian Pursuit XRs C-18 column as the stationary phase to afford (R)-2-((6-((3H-imidazo[4,5-b]pyridin-3-yl)methyl)benzo[d]thiazol-2-yl)amino)cyclohexanone oxime (53 mg, 73%) as a white powder. ¹H NMR (300 MHz, DMSO-d₆) δ 10.57 (s, 1H), 8.60 (s, 1H), 8.38 (d, J=4.0 Hz, 1H), 8.13-8.27 (m, 1H), 8.09 (dd, J=0.8, 7.9 Hz, 1H), 7.5-7.76 (m, 1H), 7.10-7.39 (m, 3H), 5.49 (s, 2H), 4.33-4.77 (m, 1H), 2.69-2.95 (m, 1H), 1.92-2.38 (m, 2H), 1.26-1.86 (m, 5H). LCMS (ESI) m/z 393 (M+H)⁺.

Example 59

Preparation of either (1S,2R)-2-((6-((3H-imidazo[4,5-b]pyridin-3-yl)methyl)benzo[d]thiazol-2-yl)amino)-1-methylcyclohexanol or (1R,2R)-2-((6-((3H-imidazo[4,5-b]pyridin-3-yl)methyl)benzo[d]thiazol-2-yl)amino)-1-methylcyclohexanol Either

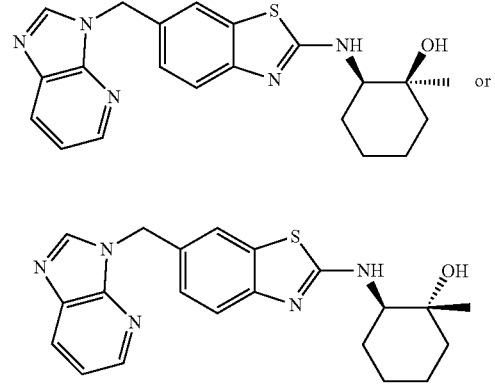

(R)-2-((6-((3H-Imidazo[4,5-b]pyridin-3-yl)methyl)benzo[d]thiazol-2-yl)amino)cyclohexanone from Example 54 (60 mg, 0.16 mmol) was stirred in 5 mL of THF at 0° C. under argon. Methyl lithium in THF (1.6 M, 99 μL, 0.16 mmol) was dropped in slowly. The resulting mixture was stirred at rt for 30 min before more methyl lithium in THF (495 μL, 0.80 mmol) was added. After 90 min, the reaction was quenched with sat. NH₄Cl (20 mL) and the resulting mixture was extracted with DCM (2×50 mL). The combined organic layers were washed with brine, dried over MgSO₄, and concentrated under reduced pressure. The residue was purified by silica gel preparative TLC, eluting with 5:95 2N NH₃/MeOH: EtOAc, followed by HPLC using a mixture of water (5% CH₃CN, 0.05% HCOOH) and CH₃CN (0.05% HCOOH) as the mobile phase and Varian Pursuit XRs C-18 column as the stationary phase to afford two separate diastereoisomers:

The first eluting isomer on reverse-phase HPLC is one of (1S,2R)-2-((6-((3H-imidazo[4,5-b]pyridin-3-yl)methyl)benzo[d]thiazol-2-yl)amino)-1-methylcyclohexanol or (1R,2R)-2-((6-((3H-imidazo[4,5-b]pyridin-3-yl)methyl)benzo[d]thiazol-2-yl)amino)-1-methylcyclohexanol (5 mg, 8%) as a white powder. ¹H NMR (300 MHz, MeOH-d₄) δ 8.40-8.51 (m, 2H), 8.10 (dd, J=0.9, 8.1 Hz, 1H), 7.64 (s, 1H), 7.23-7.43 (m, 3H), 5.57 (s, 2H), 3.78-3.92 (m, 1H), 1.5-1.84 (m, 4H), 1.31-1.55 (m, 4H), 1.22 (s, 3H). LCMS (ESI) m/z 394 (M+H)⁺.

Example 60

Preparation of either (1R,2R)-2-((6-((3H-imidazo[4,5-b]pyridin-3-yl)methyl)benzo[d]thiazol-2-yl)amino)-1-methylcyclohexanol or (1S,2R)-2-((6-((3H-imidazo[4,5-b]pyridin-3-yl)methyl)benzo[d]thiazol-2-yl)amino)-1-methylcyclohexanol Either

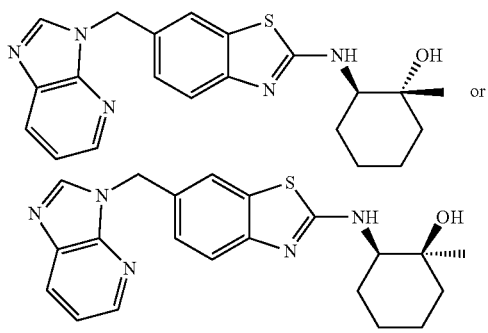

For the two diastereoisomers obtained in Example 59, the second eluting isomer on reverse-phase HPLC is one of (1R,2R)-2-((6-((3H-imidazo[4,5-b]pyridin-3-yl)methyl)benzo[d]thiazol-2-yl)amino)-1-methylcyclohexanol or (1S,2R)-2-((6-((3H-imidazo[4,5-b]pyridin-3-yl)methyl)benzo[d]thiazol-2-yl)amino)-1-methylcyclohexanol and is the alternative to Example 59; obtained as a white powder (4 mg, 6%). $^1$H NMR (300 MHz, MeOH-d$_4$) δ 8.28-8.40 (m, 2H), 7.99 (dd, J=1.1, 8.1 Hz, 1H), 7.52 (d, J=0.9 Hz, 1H), 7.13-7.35 (m, 3H), 5.45 (s, 2H), 3.58 (dd, J=3.9, 11.2 Hz, 1H), 1.17-1.74 (m, 8H), 1.12 (s, 3H). LCMS (ESI) m/z 394 (M+H)$^+$.

Example 61

Preparation of (1R,2R)-2-((6-((6-bromo-3H-imidazo[4,5-b]pyridin-3-yl)methyl)benzo[d]oxazol-2-yl)amino)cyclohexanol

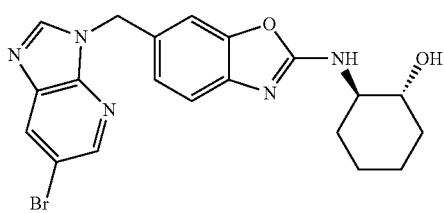 [SMILES: O[C@@H]1CCCC[C@H]1Nc1nc2ccc(Cn3cnc4cc(Br)cnc43)cc2o1]

Step 1:

A stirred mixture of 5-bromopyridine-2,3-diamine (5 g, 26.6 mmol), formic acid (2.5 mL), and triethylorthoformate (70 mL) was heated at 100° C. for 2.5 h. The reaction mixture was cooled to rt and the solid precipitate was collected by filtration, washed with Et$_2$O and dried to afford 6-bromo-3H-imidazo[4,5-b]pyridine as a solid (3.22 g, 61%) which did not require further purification. $^1$H NMR (300 MHz, DMSO-d$_6$) δ 13.14 (br s, 1H), 8.50 (s, 1H), 8.44 (d, J=2.1 Hz, 1H), 8.31 (d, J=1.9 Hz, 1H). LCMS (ESI) m/z 198 and 200 (M+H)$^+$.

Step 2:

To a stirred solution of 6-bromo-3H-imidazo[4,5-b]pyridine (506 mg, 2.55 mmol) from Step 1 of this Example in anhydrous DMF (10 mL) at 0° C. was added in one portion sodium hydride (60% dispersion in mineral oil, 107 mg, 2.68 mmol), and the mixture was stirred at 0° C. for 30 min. To the reaction mixture was added a solution of 6-(chloromethyl)-2-(methylthio)benzo[d]oxazole (600 mg, 2.81 mmol) from Step 3 of Example 56 in DMF (2 mL). The mixture was allowed to warm to rt, then stirred for a further 15 h. To the reaction mixture was added water and the mixture was extracted with EtOAc. The organic layer was separated and the aq layer extracted with additional EtOAc. The combined organic layers were washed with water then brine. The organic layer was separated, dried over MgSO$_4$, filtered, and concentrated under reduced pressure. The residue was purified by silica gel flash chromatography eluting with 100% DCM, followed by 1% MeOH in DCM to afford 6-((6-bromo-3H-imidazo[4,5-b]pyridin-3-yl)methyl)-2-(methylthio)benzo[d]oxazole (460 mg, 48%) as a white solid. The regiochemistry of the alkylation was determined by 2-dimensional nuclear Overhauser effect (NOE) experiment. $^1$H NMR (300 MHz, DMSO-d$_6$) δ 8.70 (s, 1H), 8.48 (d, J=1.9 Hz, 1H), 8.40 (d, J=1.9 Hz, 1H), 7.68 (s, 1H), 7.58 (d, J=8.1 Hz, 1H), 7.34 (d, J=8.1 Hz, 1H), 5.59 (s, 2H), 2.73 (s, 3H). LCMS (ESI) m/z 375 and 377 (M+H)$^+$.

Step 3:

To a stirred solution of 6-((6-bromo-3H-imidazo[4,5-b]pyridin-3-yl)methyl)-2-(methylthio)benzo[d]oxazole (460 mg, 1.23 mmol) from Step 2 of this Example in DCM (25 mL) at 0° C. was added 70% meta-chloroperbenzoic acid (333 mg, 1.35 mmol), and the mixture was allowed to warm to rt and stirred for a further 30 min. To the mixture was added saturated aq NaHCO$_3$ and the organic layer was separated. The aqueous layer was re-extracted with DCM and the combined organic layers were washed with saturated aq NaHCO$_3$. The organic layer was separated, dried over MgSO$_4$, filtered, and concentrated under reduced pressure to afford 6-((6-bromo-3H-imidazo[4,5-b]pyridin-3-yl)methyl)-2-(methylsulfinyl)benzo[d]oxazole (481 mg, 100%) as a cream solid which did not require further purification. $^1$H NMR (300 MHz, DMSO-d$_6$) δ 8.73 (s, 1H), 8.40-8.50 (m, 2H), 7.84-7.95 (m, 2H), 7.50 (d, J=8.3 Hz, 1H), 5.68 (s, 2H), 3.18 (s, 3H). LCMS (ESI) m/z 391 and 393 (M+H)$^+$.

Step 4:

A stirred mixture of 6-((6-bromo-3H-imidazo[4,5-b]pyridin-3-yl)methyl)-2-(methylsulfinyl)benzo[d]oxazole (150 mg, 0.384 mmol) from Step 3 of this Example, (1R,2R)-(−)-2-aminocyclohexanol (88 mg, 0.768 mmol), and DIEA (99 mg, 0.768 mmol) in anhydrous DMA (3 mL) in a sealed vial was heated in a Biotage microwave synthesizer at 120° C. for 30 min. After the reaction mixture was cooled to rt, it was purified directly by reverse-phase HPLC using a mixture of water (5% CH$_3$CN, 0.05% HCOOH) and CH$_3$CN (0.05% HCOOH) as the mobile phase and Varian Pursuit XRs C-18 column as the stationary phase to afford (1R,2R)-2-((6-((6-bromo-3H-imidazo[4,5-b]pyridin-3-yl)methyl)benzo[d]oxazol-2-yl)amino)cyclohexanol (64 mg, 38%) as a white solid. $^1$H NMR (500 MHz, DMSO-d$_6$) δ 8.66 (s, 1H), 8.49 (d, J=2.0 Hz, 1H), 8.38 (d, J=1.7 Hz, 1H), 7.81 (d, J=7.6 Hz, 1H), 7.39 (s, 1H), 7.10-7.16 (m, 2H), 5.48 (s, 2H), 4.69 (d, J=4.2 Hz, 1H), 3.30-3.40 (m, 2H), 1.83-1.97 (m, 2H), 1.5-1.67 (m, 2H), 1.15-1.30 (m, 4H). LCMS (ESI) m/z 442 and 444 (M+H)$^+$.

Example 62

Preparation of (1R,2R)-1-((6-((6-bromo-3H-imidazo[4,5-b]pyridin-3-yl)methyl)benzo[d]oxazol-2-yl)amino)-2,3-dihydro-1H-inden-2-ol

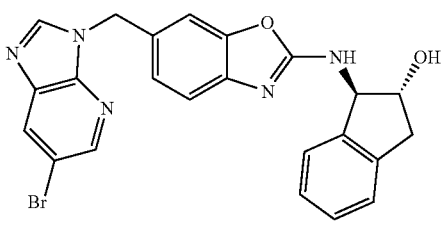 [SMILES: O[C@@H]1Cc2ccccc2[C@H]1Nc1nc2ccc(Cn3cnc4cc(Br)cnc43)cc2o1]

A stirred mixture of 6-((6-bromo-3H-imidazo[4,5-b]pyridin-3-yl)methyl)-2-(methylsulfinyl)benzo[d]oxazole (150 mg, 0.384 mmol) from Step 3 of Example 61, (1R,2R)-(−)-trans-1-amino-2-indanol (114 mg, 0.768 mmol), and DIEA (99 mg, 0.768 mmol) in anhydrous DMA (3 mL) in a sealed vial was heated in a Biotage microwave synthesizer at 120° C. for 30 min. After the reaction mixture was cooled to rt, it was purified directly by reverse-phase HPLC using a mixture of water (5% $CH_3CN$, 0.05% HCOOH) and $CH_3CN$ (0.05% HCOOH) as the mobile phase and Varian Pursuit XRs C-18 column as the stationary phase to afford (1R,2R)-1-((6-((6-bromo-3H-imidazo[4,5-b]pyridin-3-yl)methyl)benzo[d]oxazol-2-yl)amino)-2,3-dihydro-1H-inden-2-ol (40 mg, 22%) as a white solid. $^1$H NMR (499 MHz, DMSO-$d_6$) δ 8.68 (s, 1H), 8.49 (d, J=2.0 Hz, 1H), 8.36-8.44 (m, 2H), 7.45 (s, 1H), 7.12-7.24 (m, 6H), 5.51 (s, 2H), 5.47 (d, J=5.2 Hz, 1H), 5.01 (t, J=7.6 Hz, 1H), 4.34 (m, 1H), 3.15 (dd, J=7.1, 15.5 Hz, 1H), 2.73 (dd, J=7.6, 15.5 Hz, 1H). LCMS (ESI) m/z 476 and 478 (M+H)$^+$.

Example 63

Preparation of (S)-2-((6-((3H-imidazo[4,5-b]pyridin-3-yl)methyl)benzo[d]thiazol-2-yl)amino)-2-cyclohexylethanol

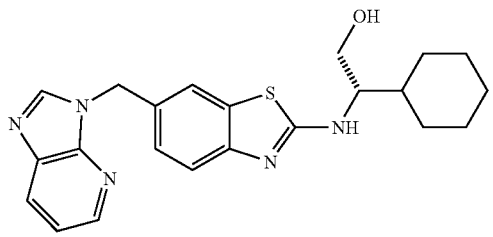 [SMILES: OC[C@@H](Nc1nc2ccc(Cn3cnc4cccnc43)cc2s1)C1CCCCC1]

Step 1:
To a stirred solution of 4-azabenzimidazole (613 mg, 5.15 mmol) in anhydrous DMF (20 mL) at 0° C. was added in one portion sodium hydride (60% dispersion in mineral oil, 216 mg, 5.41 mmol) and the mixture was stirred at 0° C. for 20 min. The mixture was allowed to warm to rt and stirred for a further 20 min. To the reaction mixture was added a solution of 6-(chloromethyl)-2-(methylthio)benzo[d]thiazole (1.3 g, 5.66 mmol) from Step 4 of Example 36 in DMF (5 mL). The mixture was stirred at rt for 15 h. To the reaction mixture was added water (300 mL) and the mixture was extracted with DCM (3×50 mL). The combined organic layers were washed with brine. The organic layer was separated, dried over $MgSO_4$, filtered, and concentrated under reduced pressure. The residue was purified by silica gel flash chromatography (eluting with 100% DCM followed by 1% MeOH in DCM) to afford 6-((3H-imidazo[4,5-b]pyridin-3-yl)methyl)-2-(methylthio)benzo[d]thiazole (670 mg, 41%) as a white solid. The regiochemistry of the alkylation was determined by 2-dimensional nuclear Overhauser effect (NOE) experiment. $^1$H NMR (300 MHz, DMSO-$d_6$) δ 8.65 (s, 1H), 8.38 (dd, J=1.3, 4.7 Hz, 1H), 8.11 (dd, J=1.2, 8.0 Hz, 1H), 8.00 (d, J=1.1 Hz, 1H), 7.81 (d, J=8.5 Hz, 1H), 7.46 (dd, J=1.6, 8.4 Hz, 1H), 7.30 (dd, J=4.7, 8.1 Hz, 1H), 5.62 (s, 2H), 2.77 (s, 3H). LCMS (ESI) m/z 313 (M+H)$^+$.

Step 2:
To a stirred solution of 6-((3H-imidazo[4,5-b]pyridin-3-yl)methyl)-2-(methylthio)benzo[d]thiazole (670 mg, 2.15 mmol) in DCM (25 mL) at 0° C. was added 70% meta-chloroperbenzoic acid (582 mg, 2.36 mmol) and the mixture was stirred at 0° C. for 1 h. To the mixture was added saturated aqueous $NaHCO_3$ and the organic layer was separated. The aqueous layer was extracted with DCM and the combined organic layers were washed with saturated aq $NaHCO_3$. The organic layer was separated, dried over $MgSO_4$, filtered, and under reduced pressure to afford 670 mg of a 4:1 mixture of 6-((3H-imidazo[4,5-b]pyridin-3-yl)methyl)-2-(methylsulfinyl)benzo[d]thiazole and 6-((3H-imidazo[4,5-b]pyridin-3-yl)methyl)-2-(methylsulfonyl)benzo[d]thiazole as a solid that was not purified further. LCMS (ESI) m/z 329 (M+H)$^+$ (consistent with 6-((3H-imidazo[4,5-b]pyridin-3-yl)methyl)-2-(methylsulfinyl)benzo[d]thiazole) and m/z 345 (M+H)$^+$ (consistent with 6-((3H-imidazo[4,5-b]pyridin-3-yl)methyl)-2-(methylsulfonyl)benzo[d]thiazole).

Step 3:
To a stirred mixture of $LiAlH_4$ (724 mg, 19.08 mmol) in anhydrous THF (20 mL) at rt was added portionwise L-(+)-2-cyclohexyglycine (1 g, 6.36 mmol). The mixture was heated at 80° C. for 4 h. The mixture was cooled to 0° C. and then water (1 mL), 1M aq NaOH (1 mL), and water (3 mL) were added sequentially. The mixture was filtered and the filtrate was partitioned between a mixture of DCM, 1M aq NaOH, and saturated aq sodium potassium tartrate. The organic layer was separated and further washed with 1M aq NaOH. The organic layer was separated, dried over $MgSO_4$, filtered, and concentrated under reduced pressure to afford (S)-2-amino-2-cyclohexylethanol (500 mg) which was not purified further. LCMS (ESI) m/z 144 (M+H)$^+$.

Step 4:
A 4:1 mixture of 6-((3H-imidazo[4,5-b]pyridin-3-yl)methyl)-2-(methylsulfinyl)benzo[d]thiazole and 6-((3H-imidazo[4,5-b]pyridin-3-yl)methyl)-2-(methylsulfonyl)benzo[d]thiazole (60 mg) from Step 2 of this Example was dissolved in anhydrous DMA (1.5 mL) and to this solution were added (S)-2-amino-2-cyclohexylethanol (52 mg, 0.366 mmol) from Step 3 of this Example and DIEA (94 mg, 0.732 mmol). The reaction vessel was sealed and the mixture was heated in a Biotage microwave synthesizer at 150° C. for 30 min. LCMS analysis indicated that the reaction was not complete. To the reaction mixture was added additional (S)-2-amino-2-cyclohexylethanol (52 mg, 0.366 mmol). The reaction vessel was sealed and the mixture was heated in a Biotage microwave synthesizer at 150° C. for 40 min. After cooling to rt, the mixture was purified directly by reverse-phase HPLC using a mixture of water (5% $CH_3CN$, 0.05% HCOOH) and $CH_3CN$ (0.05% HCOOH) as the mobile

Example 64

Preparation of (R)-2-((6-((3H-imidazo[4,5-b]pyridin-3-yl)methyl)benzo[d]thiazol-2-yl)amino)-2-cyclohexylethanol

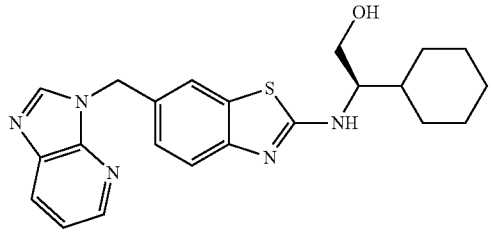 [SMILES: OC[C@H](Nc1nc2ccc(Cn3cnc4cccnc43)cc2s1)C1CCCCC1]

Step 1:

To a stirred mixture of LiAlH$_4$ (724 mg, 19.08 mmol) in anhydrous THF (20 mL) at rt was added portionwise 2-cyclohexyl-D-glycine (1 g, 6.36 mmol). The mixture was heated at 80° C. for 4 h. The mixture was cooled to 0° C. and then water (1 mL), 1M aq NaOH (1 mL), and water (3 mL) were added sequentially. The mixture was filtered and the filtrate was partitioned between a mixture of DCM, 1M aq NaOH, and saturated aq sodium potassium tartrate. The organic layer was separated and further washed with 1M aq NaOH. The organic was separated, dried over MgSO$_4$, filtered, and concentrated under reduced pressure to afford (R)-2-amino-2-cyclohexylethanol (400 mg) which was not purified further. LCMS (ESI) m/z 144 (M+H)$^+$.

Step 2:

A 4:1 mixture of 6-((3H-imidazo[4,5-b]pyridin-3-yl)methyl)-2-(methylsulfinyl)benzo[d]thiazole and 6-((3H-imidazo[4,5-b]pyridin-3-yl)methyl)-2-(methylsulfonyl)benzo[d]thiazole (120 mg) from Step 2 of Example 63 was dissolved in anhydrous DMA (2 mL), and then (R)-2-amino-2-cyclohexylethanol (209 mg, 1.46 mmol) from Step 1 of this Example and DIEA (188 mg, 1.46 mmol) were added. The reaction vessel was sealed and the mixture was heated with stirring at 120° C. for 15 h. After cooling to rt, the mixture was purified directly by reverse-phase HPLC using a mixture of water (5% CH$_3$CN, 0.05% HCOOH) and CH$_3$CN (0.05% HCOOH) as the mobile phase and Varian Pursuit XRs C-18 column as the stationary phase to afford (R)-2-((6-((3H-imidazo[4,5-b]pyridin-3-yl)methyl)benzo[d]thiazol-2-yl)amino)-2-cyclohexylethanol (18 mg) as a white solid. $^1$H NMR (300 MHz, DMSO-d$_6$) δ 8.59 (s, 1H), 8.38 (m, 1H), 8.09 (dd, J=1.0, 8.0 Hz, 1H), 7.85 (d, J=8.9 Hz, 1H), 7.66 (s, 1H), 7.18-7.32 (m, 3H), 5.48 (s, 2H), 4.70 (br s, 1H), 3.72 (m, 1H), 3.50 (m, 2H), 1.5-1.77 (m, 6H), 0.94-1.23 (m, 5H). LCMS (ESI) m/z 408 (M+H)$^+$.

phase and Varian Pursuit XRs C-18 column as the stationary phase to afford (S)-2-((6-((3H-imidazo[4,5-b]pyridin-3-yl)methyl)benzo[d]thiazol-2-yl)amino)-2-cyclohexylethanol (4 mg) as a white solid. $^1$H NMR (500 MHz, DMSO-d$_6$) δ 8.58 (s, 1H), 8.37 (m, 1H), 8.08 (m, 1H), 7.84 (d, J=8.9 Hz, 1H), 7.66 (s, 1H), 7.18-7.31 (m, 3H), 5.48 (s, 2H), 3.71 (m, 1H), 3.50 (m, 1H), 1.5-1.77 (m, 7H), 0.95-1.24 (m, 6H). LCMS (ESI) m/z 408 (M+H)$^+$.

Example 65

Preparation of 1-((2-(((1R,2R)-2-hydroxycyclohexyl)amino)benzo[d]thiazol-6-yl)methyl)-6-methoxy-1H-benzo[d]imidazole-5-carbonitrile

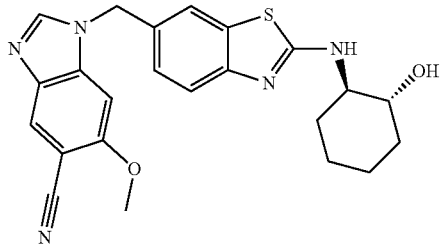 [SMILES: COc1cc2c(cc1C#N)ncn2Cc1ccc2nc(N[C@@H]3CCCC[C@H]3O)sc2c1]

1-((2-(((1R,2R)-2-Hydroxycyclohexyl)amino)benzo[d]thiazol-6-yl)methyl)-6-methoxy-1H-benzo[d]imidazole-5-carbonitrile was synthesized as a white powder (20 mg, 45%) using a procedure analogous to that described in Example 53, substituting (1R,2R)-2-((6-((5-bromo-6-methoxy-1H-benzo[d]imidazol-1-yl)methyl)benzo[d]thiazol-2-yl)amino)cyclohexanol for (1R,2R)-2-((6-((6-bromo-5-methoxy-1H-benzo[d]imidazol-1-yl)methyl)benzo[d]thiazol-2-yl)amino)cyclohexanol used in example 53. $^1$H NMR (300 MHz, DMSO-d$_6$) δ 8.60 (s, 1H), 8.12 (s, 1H), 8.01 (d, J=7.3 Hz, 1H), 7.70 (d, J=0.9 Hz, 1H), 7.43 (s, 1H), 7.20-7.34 (m, 2H), 5.46 (s, 2H), 4.76 (d, J=4.9 Hz, 1H), 3.90 (s, 3H), 3.51 (m, 1H), 3.33 (m, 1H), 2.03 (m, 1H), 1.87 (m, 1H), 1.5-1.67 (m, 2H), 1.15-1.34 (m, 4H). LCMS (ESI) m/z 434 (M+H)$^+$.

Example 66

Preparation of ((1R,2R)-2-((6-((3H-imidazo[4,5-b]pyridin-3-yl)methyl)benzo[d]thiazol-2-yl)amino)cyclohexyl)methanol

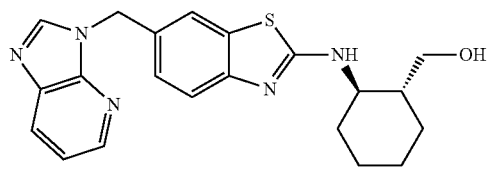 [SMILES: OC[C@@H]1CCCC[C@H]1Nc1nc2ccc(Cn3cnc4cccnc43)cc2s1]

Step 1:

To a stirred mixture of LiAlH$_4$ (796 mg, 20.97 mmol) in anhydrous THF (20 mL) at rt was added portion-wise (1R,2R)-2-aminocyclohexanecarboxylic acid (1 g, 6.99 mmol). The mixture was heated at 80° C. for 4 h before it was cooled to 0° C. Water (1 mL), 1M aq NaOH (1 mL), and water (3 mL) were added sequentially. The mixture was filtered and the filtrate partitioned between a mixture of DCM, 1M aq NaOH, and saturated aq sodium potassium tartrate. The organic layer was separated and washed with 1M aq NaOH. The organic layer was separated, dried over MgSO$_4$, filtered, and under reduced pressure to afford ((1R,2R)-2-aminocyclohexyl)methanol (180 mg) which was not purified further. LCMS (ESI) m/z 130 (M+H)$^+$.

Step 2:

A 4:1 mixture of 6-((3H-imidazo[4,5-b]pyridin-3-yl)methyl)-2-(methylsulfinyl)benzo[d]thiazole and 6-((3H-imidazo[4,5-b]pyridin-3-yl)methyl)-2-(methylsulfonyl)benzo[d]thiazole (120 mg) from Step 2 of Example 63 was dissolved in anhydrous DMA (2 mL), and then ((1R,2R)-2-aminocyclohexyl)methanol (180 mg, 1.40 mmol) from Step 1 of this Example and DIEA (188 mg, 1.46 mmol) were added. The reaction vessel was sealed and the mixture was heated with stirring at 120° C. for 4.5 h. After cooling to rt, the mixture was purified directly by reverse-phase HPLC using a mixture of water (5% $CH_3CN$, 0.05% HCOOH) and $CH_3CN$ (0.05% HCOOH) as the mobile phase and Varian Pursuit XRs C-18 column as the stationary phase to afford ((1R,2R)-2-((6-((3H-imidazo[4,5-b]pyridin-3-yl)methyl)benzo[d]thiazol-2-yl)amino)cyclohexyl)methanol.

(41 mg) as a white solid. $^1$H NMR (300 MHz, DMSO-$d_6$) δ 8.59 (s, 1H), 8.38 (dd, J=1.1, 4.7 Hz, 1H), 8.09 (dd, J=1.2, 8.0 Hz, 1H), 8.00 (d, J=8.3 Hz, 1H), 7.67 (s, 1H), 7.20-7.32 (m, 3H), 5.49 (s, 2H), 4.48 (br s, 1H), 3.55 (m, 2H), 1.99 (m, 1H), 1.82 (m, 1H), 1.60-1.75 (m, 2H), 1.10-1.43 (m, 6H). LCMS (ESI) m/z 394 (M+H)$^+$.

Example 67

Preparation of (1R,2R)-2-((6-((6-methoxy-1H-benzo[d]imidazol-1-yl)methyl)benzo[d]thiazol-2-yl)amino)cyclohexanol

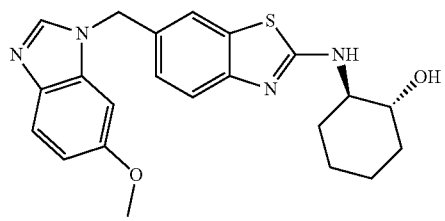 [SMILES: COc1ccc2ncn(Cc3ccc4nc(N[C@@H]5CCCC[C@H]5O)sc4c3)c2c1]

To a mixture of (1R,2R)-2-((6-((5-bromo-6-methoxy-1H-benzo[d]imidazol-1-yl)methyl)benzo[d]thiazol-2-yl)amino)cyclohexanol (100 mg, 0.2 mmol) from Step 1 of Example 51 in 1,4-dioxane (1.4 mL) and aq 1 N NaOH (300 μL) was added zinc powder (134 mg, 2 mmol). The mixture was heated at 80° C. for 55 h. The mixture was cooled to rt, filtered, and the filtrate was purified by reverse-phase preparative HPLC using a mixture of water (5% $CH_3CN$, 0.05% HCOOH) and $CH_3CN$ (0.05% HCOOH) as the mobile phase and Varian Pursuit XRs C18 column as the stationary phase to afford (1R,2R)-2-((6-((6-methoxy-1H-benzo[d]imidazol-1-yl)methyl)benzo[d]thiazol-2-yl)amino)cyclohexanol (45 mg, 56%) as a white powder. $^1$H NMR (500 MHz, DMSO-$d_6$) δ 8.23 (s, 1H), 7.98 (d, J=7.6 Hz, 1H), 7.64 (d, J=1.0 Hz, 1H), 7.51 (d, J=8.6 Hz, 1H), 7.29 (d, J=8.4 Hz, 1H), 7.20 (dd, J=1.4, 8.2 Hz, 1H), 7.12 (d, J=2.2 Hz, 1H), 6.80 (dd, J=2.3, 8.7 Hz, 1H), 5.41 (s, 2H), 4.76 (m, 1H), 3.76 (s, 3H), 3.51 (m, 1H), 3.33 (m, 1H), 2.03 (m, 1H), 1.87 (m, 1H), 1.5-1.66 (m, 2H), 1.14-1.29 (m, 4H). LCMS (ESI) m/z 410 (M+H)$^+$.

Example 68

Preparation of (1R,2R)-2-((6-((5-methoxy-1H-benzo[d]imidazol-1-yl)methyl)benzo[d]thiazol-2-yl)amino)cyclohexanol

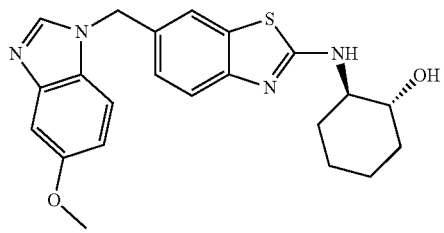 [SMILES: COc1ccc2c(c1)ncn2Cc1ccc2nc(N[C@@H]3CCCC[C@H]3O)sc2c1]

(1R,2R)-2-((6-((5-Methoxy-1H-benzo[d]imidazol-1-yl)methyl)benzo[d]thiazol-2-yl)amino)cyclohexanol was synthesized as a white powder (39 mg, 53%) using a procedure analogous to that described in Example 67, substituting (1R,2R)-2-((6-((6-bromo-5-methoxy-1H-benzo[d]imidazol-1-yl)methyl)benzo[d]thiazol-2-yl)amino)cyclohexanol from Step 5 of Example 47 for (1R,2R)-2-((6-((5-bromo-6-methoxy-1H-benzo[d]imidazol-1-yl)methyl)benzo[d]thiazol-2-yl)amino)cyclohexanol used in Example 67. $^1$H NMR (500 MHz, DMSO-$d_6$) δ 8.31 (s, 1H), 7.99 (d, J=7.6 Hz, 1H), 7.62 (s, 1H), 7.40 (d, J=8.9 Hz, 1H), 7.28 (d, J=8.4 Hz, 1H), 7.13-7.19 (m, 2H), 6.82 (dd, J=2.2, 8.9 Hz, 1H), 5.41 (s, 2H), 4.78 (m, 1H), 3.75 (s, 3H), 3.50 (m, 1H), 3.33 (m, 1H), 2.03 (m, 1H), 1.87 (m, 1H), 1.5-1.66 (m, 2H), 1.13-1.29 (m, 4H). LCMS (ESI) m/z 410 (M+H)$^+$.

Example 69

Preparation of (1R,2R)-1-((6-((6-fluoro-3H-imidazo[4,5-b]pyridin-3-yl)methyl)benzo[d]thiazol-2-yl)amino)-2,3-dihydro-1H-inden-2-ol

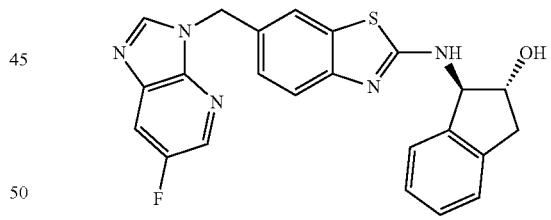

A stirred mixture of 6-((6-fluoro-3H-imidazo[4,5-b]pyridin-3-yl)methyl)-2-(methylsulfinyl)benzo[d]thiazole (120 mg, 0.346 mmol) from Step 4 of Example 70, (1R,2R)-(−)-trans-1-amino-2-indanol (103 mg, 0.692 mmol), and DIEA (89 mg, 0.692 mmol) in anhydrous DMA (2.5 mL) was heated in a Biotage microwave synthesizer at 150° C. for 30 min. LCMS analysis indicated that the reaction was incomplete. Additional (1R,2R)-(−)-trans-1-amino-2-indanol (103 mg, 0.692 mmol) and DIEA (89 mg, 0.692 mmol) were added and the mixture was further heated in a Biotage microwave synthesizer at 150° C. for 2 h. After the reaction mixture was cooled to rt, it was purified directly by reverse-phase HPLC using a mixture of water (5% $CH_3CN$, 0.05% HCOOH) and $CH_3CN$ (0.05% HCOOH) as the mobile phase and Varian Pursuit XRs C-18 column as the stationary phase to afford (1R,2R)-1-((6-((6-fluoro-3H-imidazo[4,5-b]pyridin-3-yl)methyl)benzo[d]thiazol-2-yl)amino)-2,3-dihydro-1H-inden-2-ol (24 mg, 16%) as a white solid. $^1$H NMR (300 MHz, DMSO-d$_6$) δ 8.70 (s, 1H), 8.40-8.50 (m, 2H), 8.09 (dd, J=2.6, 9.4 Hz, 1H), 7.73 (d, J=1.1 Hz, 1H), 7.32-7.39 (m, 1H), 7.10-7.31 (m, 5H), 5.47-6.00 (m, 3H), 5.18 (t, J=7.1 Hz, 1H), 4.30 (d, J=3.6 Hz, 1H), 3.16 (dd, J=7.0, 15.6 Hz, 1H), 2.74 (dd, J=7.1, 15.5 Hz, 1H). LCMS (ESI) m/z 432 (M+H)$^+$.

Example 70

Preparation of (1R,2R)-2-((6-((6-fluoro-3H-imidazo[4,5-b]pyridin-3-yl)methyl)benzo[d]thiazol-2-yl)amino)cyclohexanol

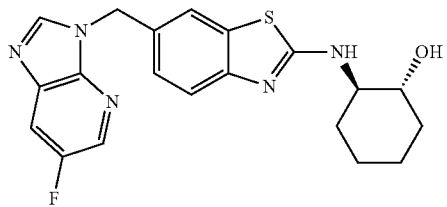 [SMILES: O[C@@H]1CCCC[C@H]1Nc1nc2ccc(Cn3cnc4cc(F)cnc43)cc2s1]

Step 1:
To a stirred mixture of 2-amino-5-fluoro-3-nitropyridine (2.46 g, 15.66 mmol) in a mixture of glacial HOAc (10 mL) and MeOH (20 mL) at 0° C. was added zinc dust (5.09 g, 78.3 mmol) portion-wise, and the mixture was allowed to warm slowly to rt. After stirring at rt for 15 h, the mixture was filtered through Celite and the filtrate was concentrated under reduced pressure. The residue was partitioned between EtOAc and saturated aq NaHCO$_3$. The organic layer was separated and the aqueous layer was extracted with additional EtOAc. The combined organic layers were dried over MgSO$_4$, filtered, and concentrated under reduced pressure to afford 5-fluoropyridine-2,3-diamine (1.13 g) as a solid which was not purified further. LCMS (ESI) m/z 128 (M+H)$^+$.

Step 2:
A stirred mixture of 5-fluoropyridine-2,3-diamine (1.13 g) from Step 1 of this Example, formic acid (0.5 mL), and triethylorthoformate (15 mL) was heated at 100° C. for 1 h. The reaction mixture was cooled to rt, filtered, and the filtrate was concentrated under reduced pressure. The residue was purified via silica gel flash chromatography eluting with 100% DCM to 10% MeOH in DCM to afford 6-fluoro-3H-imidazo[4,5-b]pyridine (760 mg, 36% over two steps) as a yellow solid. $^1$H NMR (500 MHz, DMSO-d$_6$) δ 13.09 (br s, 1H), 8.49 (s, 1H), 8.37 (s, 1H), 7.97 (d, J=7.9 Hz, 1H). LCMS (ESI) m/z 138 (M+H)$^+$.

Step 3:
To a stirred solution of 6-fluoro-3H-imidazo[4,5-b]pyridine (325 mg, 2.37 mmol) from Step 2 of this Example in anhydrous DMF (10 mL) at 0° C. was added in one portion sodium hydride (60% dispersion in mineral oil, 100 mg, 2.49 mmol), and the mixture was stirred at 0° C. for 30 min. To the reaction mixture was added a solution of 6-(chloromethyl)-2-(methylthio)benzo[d]thiazole (600 mg, 2.61 mmol) from Step 4 of Example 36 in DMF (2 mL). The mixture was allowed to warm to rt then stirred for a further 15 h. To the reaction mixture was added water (250 mL) and the mixture was extracted with DCM (3×100 mL). The combined organic layers were washed with water and brine, dried over MgSO$_4$, filtered, and concentrated under reduced pressure. The residue was purified by silica gel flash chromatography eluting with 100% DCM followed by 1% MeOH in DCM to afford 6-((6-fluoro-3H-imidazo[4,5-b]pyridin-3-yl)methyl)-2-(methylthio)benzo[d]thiazole (356 mg, 45%) as a white solid. The regiochemistry of the alkylation was determined by 2-dimensional nuclear Overhauser effect (NOE) experiment. $^1$H NMR (300 MHz, DMSO-d$_6$) δ 8.73 (s, 1H), 8.41 (t, J=2.0 Hz, 1H), 8.10 (dd, J=2.6, 9.4 Hz, 1H), 7.99 (s, 1H), 7.81 (d, J=8.3 Hz, 1H), 7.46 (dd, J=1.3, 8.3 Hz, 1H), 5.62 (s, 2H), 2.77 (s, 3H). LCMS (ESI) m/z 331 (M+H)$^+$.

Step 4:
To a stirred solution of 6-((6-fluoro-3H-imidazo[4,5-b]pyridin-3-yl)methyl)-2-(methylthio)benzo[d]thiazole (350 mg, 1.06 mmol) from Step 3 of this Example in DCM (15 mL) at 0° C. was added 70% meta-chloroperbenzoic acid (287 mg, 1.17 mmol), and the mixture was allowed to warm to rt and stirred for a further 2 h. To the mixture was added saturated aq NaHCO$_3$ and the organic layer was separated. The aqueous layer was extracted with DCM and the combined organic layers were washed with saturated aq NaHCO$_3$. The organic layer was separated, dried over MgSO$_4$, filtered, and concentrated under reduced pressure to afford a solid. The solid was triturated with Et$_2$O, filtered, then dried to afford 6-((6-fluoro-3H-imidazo[4,5-b]pyridin-3-yl)methyl)-2-(methylsulfinyl)benzo[d]thiazole (336 mg, 92%) as a white solid. $^1$H NMR (300 MHz, DMSO-d$_6$) δ 8.76 (s, 1H), 8.41 (br s, 1H), 8.22 (s, 1H), 8.04-8.15 (m, 2H), 7.63 (d, J=8.3 Hz, 1H), 5.70 (s, 2H), 3.06 (s, 3H). LCMS (ESI) m/z 347 (M+H)$^+$.

Step 5:
A stirred mixture of 6-((6-fluoro-3H-imidazo[4,5-b]pyridin-3-yl)methyl)-2-(methylsulfinyl)benzo[d]thiazole (90 mg, 0.260 mmol) from Step 4 of this Example, (1R,2R)-(−)-2-aminocyclohexanol (120 mg, 1.03 mmol), and DIEA (133 mg, 1.03 mmol) in anhydrous DMA (3 mL) was heated at 125° C. for 15 h. After the reaction mixture had cooled to rt, the mixture was purified directly by reverse-phase HPLC using a mixture of water (5% CH$_3$CN, 0.05% HCOOH) and CH$_3$CN (0.05% HCOOH) as the mobile phase and Varian Pursuit XRs C-18 column as the stationary phase to afford (1R,2R)-2-((6-((6-fluoro-3H-imidazo[4,5-b]pyridin-3-yl)methyl)benzo[d]thiazol-2-yl)amino)cyclohexanol (41 mg) as a white solid. $^1$H NMR (300 MHz, DMSO-d$_6$) δ 8.68 (s, 1H), 8.42 (s, 1H), 8.08 (dd, J=2.4, 9.4 Hz, 1H), 7.98 (d, J=7.5 Hz, 1H), 7.66 (s, 1H), 7.17-7.33 (m, 2H), 5.48 (s, 2H), 4.76 (br s, 1H), 3.45-3.55 (m, 2H), 2.03 (m, 1H), 1.87 (m, 1H), 1.5-1.67 (m, 2H), 1.10-1.33 (m, 4H). LCMS (ESI) m/z 398 (M+H)$^+$.

Example 71

Preparation of (1R,2R)-2-((6-((3H-imidazo[4,5-c]pyridin-3-yl)methyl)benzo[d]thiazol-2-yl)amino)cyclohexanol

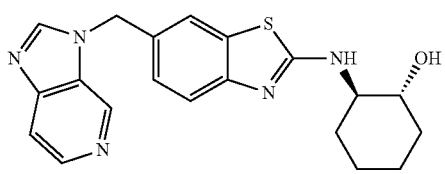 [SMILES: O[C@@H]1CCCC[C@H]1Nc1nc2ccc(Cn3cnc4ccncc43)cc2s1]

Step 1:

6-((3H-Imidazo[4,5-c]pyridin-3-yl)methyl)-2-(methylthio)benzo[d]thiazole (162 mg, 21%) was obtained as a white solid using a procedure analogous to that described in Step 4 of Example 3, substituting 1H-imidazo[4,5-c]pyridine for 3H-imidazo[4,5-b]pyridine used in Example 3. The regiochemistry of the alkylation was determined by 2-dimensional nuclear Overhauser effect (NOE) experiment. $^1$H NMR (300 MHz, MeOH-$d_4$) δ 8.82 (d, J=0.8 Hz, 1H), 8.62 (s, 1H), 8.37 (d, J=5.8 Hz, 1H), 7.92 (d, J=1.1 Hz, 1H), 7.81 (d, J=8.3 Hz, 1H), 7.75 (dd, J=0.8, 5.7 Hz, 1H), 7.46 (dd, J=1.7, 8.3 Hz, 1H), 5.74 (s, 2H), 2.79 (s, 3H). LCMS (ESI) m/z 313 (M+H)$^+$.

Step 2:

(1R,2R)-2-((6-((3H-Imidazo[4,5-c]pyridin-3-yl)methyl)benzo[d]thiazol-2-yl)amino)cyclohexanol (30 mg, 15% over two steps) was obtained as a yellow powder using procedures analogous to those described in Step 5 of Example 3 followed by procedures analogous to those described in Step 5 of Example 2, substituting 6-((3H-imidazo[4,5-c]pyridin-3-yl)methyl)-2-(methylthio)benzo[d]thiazole from Step 1 of this Example for 6-((3H-imidazo[4,5-b]pyridin-3-yl)methyl)-2-(methylthio)benzo[d]thiazole used in Example 3 and substituting the product of that reaction for the 2-bromo-6-((5,6-dimethoxy-1H-benzo[d]imidazol-1-yl)methyl)benzo[d]thiazole used in Example 2. $^1$H NMR (300 MHz, DMSO-$d_6$) δ 8.94 (s, 1H), 8.63 (s, 1H), 8.30 (d, J=5.7 Hz, 1H), 8.01 (d, J=7.3 Hz, 1H), 7.74 (s, 1H), 7.65 (d, J=5.1 Hz, 1H), 7.18-7.36 (m, 2H), 5.56 (s, 2H), 4.76 (br s, 1H), 3.53 (d, J=14.5 Hz, 2H), 2.02 (d, J=10.2 Hz, 1H), 1.86 (s, 1H), 1.61 (br s, 2H), 1.03-1.37 (m, 4H). LCMS (ESI) m/z 380 (M+H)$^+$.

Example 72

Preparation of (1R,2R)-2-((6-((1H-imidazo[4,5-c]pyridin-1-yl)methyl)benzo[d]thiazol-2-yl)amino)cyclohexanol

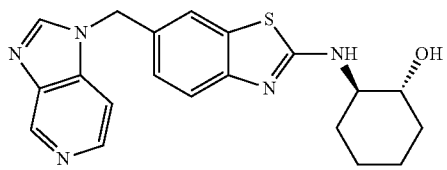 [SMILES: O[C@@H]1CCCC[C@H]1Nc1nc2ccc(Cn3cnc4cnccc43)cc2s1]

Step 1:

6-((1H-Imidazo[4,5-c]pyridin-1-yl)methyl)-2-(methylthio)benzo[d]thiazole (206 mg, 26%) was obtained as a white solid using a procedure analogous to that described in Step 4 of Example 3, substituting 1H-imidazo[4,5-c]pyridine for 3H-imidazo[4,5-b]pyridine used in Example 3. The regiochemistry of the alkylation was determined by 2-dimensional nuclear Overhauser effect (NOE) experiment. $^1$H NMR (300 MHz, MeOH-$d_4$) δ 8.95 (s, 1H), 8.53 (s, 1H), 8.31 (d, J=5.8 Hz, 1H), 7.84 (s, 1H), 7.77 (d, J=8.3 Hz, 1H), 7.59 (d, J=5.3 Hz, 1H), 7.41 (dd, J=1.4, 8.4 Hz, 1H), 5.65 (s, 2H), 2.76 (s, 3H). LCMS (ESI) m/z 313 (M+H)$^+$.

Step 2:

(1R,2R)-2-((6-((1H-Imidazo[4,5-c]pyridin-1-yl)methyl)benzo[d]thiazol-2-yl)amino)cyclohexanol (85 mg, 42% over two steps) was obtained as a yellow powder using procedures analogous to those described in Step 5 of Example 3 followed by procedures analogous to those described in Step 5 of Example 2, substituting 6-((1H-imidazo[4,5-c]pyridin-1-yl)methyl)-2-(methylthio)benzo[d]thiazole from Step 1 of this Example for 6-((3H-imidazo[4,5-b]pyridin-3-yl)methyl)-2-(methylthio)benzo[d]thiazole used in Example 3 and substituting the product of that reaction for the 2-bromo-6-((5,6-dimethoxy-1H-benzo[d]imidazol-1-yl)methyl)benzo[d]thiazole used in Example 2. $^1$H NMR (300 MHz, DMSO-$d_6$) δ 8.95 (br s, 1H), 8.56 (s, 1H), 8.31 (d, J=4.9 Hz, 1H), 8.00 (d, J=7.2 Hz, 1H), 7.69 (d, J=1.1 Hz, 1H), 7.64 (d, J=5.5 Hz, 1H), 7.26-7.37 (m, 1H), 7.11-7.26 (m, 1H), 5.51 (s, 2H), 4.74 (br s, 1H), 3.34 (d, J=4.1 Hz, 2H), 2.02 (d, J=10.2 Hz, 1H), 1.86 (br s, 1H), 1.60 (d, J=4.0 Hz, 2H), 0.90-1.37 (m, 4H). LCMS (ESI) m/z 380 (M+H)$^+$.

Example 73

Preparation of 1-(3-((2-(((1R,2R)-2-hydroxycyclohexyl)amino)benzo[d]thiazol-6-yl)methyl)-3H-imidazo[4,5-b]pyridin-6-yl)ethanone

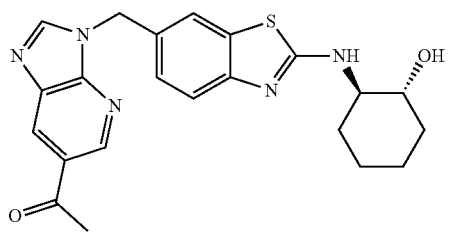 [SMILES: CC(=O)c1cnc2c(c1)ncn2Cc1ccc2nc(N[C@@H]3CCCC[C@H]3O)sc2c1]

A stirred mixture of (1R,2R)-2-((6-((6-bromo-3H-imidazo[4,5-b]pyridin-3-yl)methyl)benzo[d]thiazol-2-yl)amino)cyclohexanol (50 mg, 0.109 mmol) from Example 29, tributyl(1-ethoxyvinyl)tin (79 mg, 0.218 mmol) and TEA (22 mg, 0.218 mmol) in anhydrous DMF (1 mL) at rt was flushed with a stream of argon for 15 min. To the resulting mixture was added tetrakis(triphenylphosphine)palladium (0) (19 mg, 0.0165 mmol). The reaction vessel was sealed and the mixture was heated with stirring at 110° C. for 1.5 h. After cooling to rt, aq 2 M HCl (500 µL) was added and the mixture was stirred for 1 h. The reaction mixture was purified directly by reverse-phase HPLC using a mixture of water (5% CH$_3$CN, 0.05% HCOOH) and CH$_3$CN (0.05% HCOOH) as the mobile phase and Varian Pursuit XRs C18 column as the stationary phase to afford 1-(3-((2-(((1R,2R)-2-hydroxycyclohexyl)amino)benzo[d]thiazol-6-yl)methyl)-3H-imidazo[4,5-b]pyridin-6-yl)ethanone (8 mg, 17%) as a white solid. $^1$H NMR (300 MHz, DMSO-$d_6$) δ 9.00 (d, J=1.5 Hz, 1H), 8.76 (s, 1H), 8.64 (s, 1H), 7.99 (d, J=7.5 Hz, 1H), 7.68 (s, 1H), 7.20-7.32 (m, 2H), 5.53 (s, 2H), 4.76 (br s, 1H), 3.50 (m, 1H), 3.30 (m, 1H), 2.68 (s, 3H), 2.04 (m, 1H), 1.87 (m, 1H), 1.5-1.65 (m, 2H), 1.10-1.30 (m, 4H). LCMS (ESI) m/z 422 (M+H)$^+$.

Example 74

Preparation of (1R,2R)-2-((6-((6-(methylsulfonyl)-3H-imidazo[4,5-b]pyridin-3-yl)methyl)benzo[d]thiazol-2-yl)amino)cyclohexanol

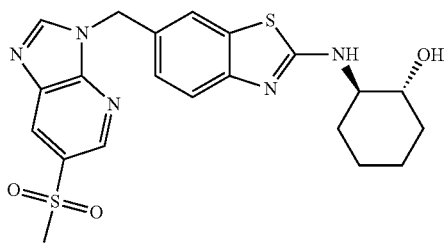 [SMILES: CS(=O)(=O)c1cnc2c(c1)ncn2Cc1ccc2nc(N[C@@H]3CCCC[C@H]3O)sc2c1]

A stirred mixture of (1R,2R)-2-((6-((6-bromo-3H-imidazo[4,5-b]pyridin-3-yl)methyl)benzo[d]thiazol-2-yl)amino)cyclohexanol (100 mg, 0.218 mmol) from Example 29, sodium methanesulfinate (90 mg, 0.436 mmol) and unsymmetrical N,N-dimethylethylene diamine (6 mg, 0.066 mmol) in anhydrous DMSO (1 mL) at rt was flushed with a stream of argon for 15 min. To the resulting mixture was added copper (I) trifluoromethane-sulfonate benzene complex (20 mg, 0.0328 mmol). The reaction vessel was sealed and the mixture was heated with stirring at 125° C. for 5 h. After cooling to rt, the reaction mixture was purified directly by reverse-phase HPLC using a mixture of water (5% $CH_3CN$, 0.05% HOAc) and $CH_3CN$ (0.05% HOAc) as the mobile phase and Varian Pursuit XRs diphenyl column as the stationary phase to afford (1R,2R)-2-((6-((6-(methylsulfonyl)-3H-imidazo[4,5-b]pyridin-3-yl)methyl)benzo[d]thiazol-2-yl)amino)cyclohexanol (12 mg, 12%) as a white solid. $^1$H NMR (300 MHz, DMSO-$d_6$) δ 8.85-8.95 (br m, 2H), 8.61 (s, 1H), 8.02 (d, J=7.3 Hz, 1H), 7.69 (s, 1H), 7.18-7.35 (m, 2H), 5.56 (s, 2H), 4.79 (br s, 1H), 3.25-3.60 (m, 5H), 2.03 (m, 1H), 1.87 (m, 1H), 1.5-1.70 (m, 2H), 1.08-1.36 (m, 4H). LCMS (ESI) m/z 458 (M+H)$^+$.

Example 75

Preparation of 1-(((6-((3H-imidazo[4,5-b]pyridin-3-yl)methyl)benzo[d]thiazol-2-yl)amino)methyl)cyclohexanol

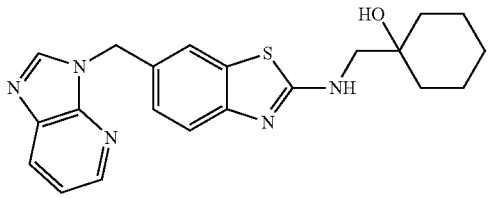 [SMILES: OC1(CNc2nc3ccc(Cn4cnc5cccnc54)cc3s2)CCCCC1]

Step 1:

To a stirred solution of cyclohexanone cyanohydrin (2 g, 15.98 mmol) in anhydrous THF (40 mL) at rt was added portion-wise $LiAlH_4$ (1.82 g, 47.94 mmol). The reaction vessel was sealed and the mixture was heated at 80° C. for 5 h. The mixture was cooled to 0° C. and water (1 mL), 1M aq NaOH (1 mL), and water (3 mL) were added sequentially. To the resulting mixture was added DCM and saturated aq sodium potassium tartrate, and the mixture stirred for 3 h. The organic layer was separated and further washed with brine. The organic layer was separated, dried over $MgSO_4$, filtered, and concentrated under reduced pressure to afford 1-(aminomethyl)cyclohexanol (1.3 g) which was not purified further. LCMS (ESI) m/z 130 (M+H)$^+$.

Step 2:

A 4:1 mixture of 6-((3H-imidazo[4,5-b]pyridin-3-yl)methyl)-2-(methylsulfinyl)benzo[d]thiazole and 6-((3H-imidazo[4,5-b]pyridin-3-yl)methyl)-2-(methylsulfonyl)benzo[d]thiazole (50 mg) from Step 2 of Example 63 was dissolved in anhydrous DMA (1.5 mL), and then 1-(aminomethyl)cyclohexanol (79 mg, 0.608 mmol) from Step 1 of this Example and DIEA (98 mg, 0.760 mmol) were added. The reaction vessel was sealed and the mixture was heated with stirring at 125° C. for 15 h. LCMS analysis indicated that the reaction was not complete. Further amounts of 1-(aminomethyl)cyclohexanol (79 mg, 0.608 mmol) from Step 1 of this Example and DIEA (98 mg, 0.760 mmol) were added and the mixture stirred at 125° C. for further 5 h. After cooling to rt, the mixture was purified directly by reverse-phase HPLC using a mixture of water (5% $CH_3CN$, 0.05% HOAc) and $CH_3CN$ (0.05% HOAc) as the mobile phase and Varian Pursuit XRs Diphenyl column as the stationary phase to afford 1-(((6-((3H-imidazo[4,5-b]pyridin-3-yl)methyl)benzo[d]thiazol-2-yl)amino)methyl)cyclohexanol (10 mg) as a white solid. $^1$H NMR (300 MHz, DMSO-$d_6$) δ 8.60 (s, 1H), 8.38 (dd, J=1.1, 4.7 Hz, 1H), 8.09 (dd, J=1.2, 8.0 Hz, 1H), 7.96 (t, J=5.6 Hz, 1H), 7.67 (s, 1H), 7.19-7.33 (m, 3H), 5.48 (s, 2H), 4.42 (br s, 1H), 1.12-1.62 (m, 12H). LCMS (ESI) m/z 394 (M+H)$^+$.

Example 76

Preparation of (1-(((6-((3H-imidazo[4,5-b]pyridin-3-yl)methyl)benzo[d]thiazol-2-yl)amino)methyl)cyclohexyl)methanol

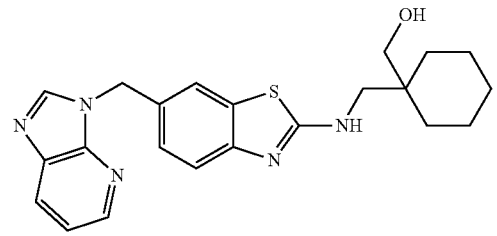 [SMILES: OCC1(CNc2nc3ccc(Cn4cnc5cccnc54)cc3s2)CCCCC1]

Step 1:

To a stirred solution of methyl 1-cyanocyclohexanecarboxylate (2 g, 11.96 mmol) in anhydrous THF (40 mL) at rt was added portionwise $LiAlH_4$ (1.36 g, 35.88 mmol). The reaction vessel was sealed and the mixture was heated at 80° C. for 5 h. The mixture was cooled to 0° C. and water (1 mL), 1M aq NaOH (1 mL), and water (3 mL) were added sequentially. To the resulting mixture were added DCM and saturated aq sodium potassium tartrate, and the mixture was stirred for 3 h. The organic layer was separated and further washed with brine. The organic layer was separated, dried over $MgSO_4$, filtered, and concentrated under reduced pressure to afford (1-(aminomethyl)cyclohexyl)methanol (1 g) which was not purified further. LCMS (ESI) m/z 144 (M+H)$^+$.

Step 2:

A 4:1 mixture of 6-((3H-imidazo[4,5-b]pyridin-3-yl)methyl)-2-(methylsulfinyl)benzo[d]thiazole and 6-((3H-imidazo[4,5-b]pyridin-3-yl)methyl)-2-(methylsulfonyl)benzo[d]thiazole (80 mg) from Step 2 of Example 63 was dissolved in anhydrous DMA (2 mL), and (1-(aminomethyl)cyclohexyl)methanol (175 mg, 1.22 mmol) from Step 1 of this Example and DIEA (157 mg, 1.22 mmol) were added. The reaction vessel was sealed and the mixture was heated with stirring at 125° C. for 15 h. After cooling to rt, the mixture was purified directly by reverse-phase HPLC using a mixture of water (5% CH$_3$CN, 0.05% HOAc) and CH$_3$CN (0.05% HOAc) as the mobile phase and Varian Pursuit XRs Diphenyl column as the stationary phase to afford 1-(((6-((3H-imidazo[4,5-b]pyridin-3-yl)methyl)benzo[d]thiazol-2-yl)amino)methyl)cyclohexanol (22 mg) as a white solid. $^1$H NMR (300 MHz, DMSO-d$_6$) δ 8.60 (s, 1H), 8.38 (dd, J=1.1, 4.7 Hz, 1H), 8.09 (dd, J=1.3, 7.9 Hz, 1H), 7.99 (t, J=5.7 Hz, 1H), 7.68 (s, 1H), 7.20-7.33 (m, 3H), 5.49 (s, 2H), 3.33 (d, J=5.8 Hz, 2H), 3.21 (s, 1H), 1.21-1.49 (m, 12H). LCMS (ESI) m/z 408 (M+H)$^+$.

Example 77

Preparation of (1R,2R)-2-((6-((4-(1-methyl-1H-pyrazol-4-yl)-1H-imidazol-1-yl)methyl)benzo[d]oxazol-2-yl)amino)cyclohexanol

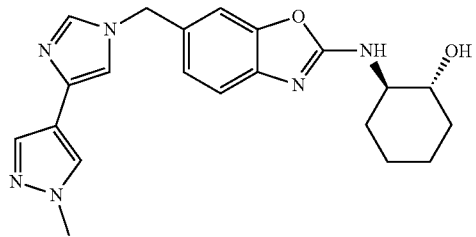 [SMILES: Cn1cc(-c2cn(Cc3ccc4nc(N[C@@H]5CCCC[C@H]5O)oc4c3)cn2)cn1]

Step 1:
6-((4-Bromo-1H-imidazol-1-yl)methyl)-2-(methylthio)benzo[d]oxazole was synthesized as an oil (241 mg, 79%) using a procedure analogous to that described in Step 5 of Example 36, substituting the 9:1 mixture of (2-(methylthio)benzo[d]oxazol-6-yl)methyl methanesulfonate and 6-(chloromethyl)-2-(methylthio)benzo[d]oxazole from Step 1 of Example 34 for 6-(chloromethyl)-2-(methylthio)benzo[d]thiazole used in Example 36. The regiochemistry of the alkylation was determined by 2-dimensional nuclear Overhauser effect (NOE) experiment. $^1$H NMR (300 MHz, DMSO-d$_6$) δ 7.81 (d, J=1.3 Hz, 1H), 7.65 (m, 2H), 7.41 (d, J=1.3 Hz, 1H), 7.32 (dd, J=1.3, 8.1 Hz, 1H), 5.27 (s, 2H), 2.76 (s, 3H). LCMS (ESI) m/z 324 and 326 (M+H)$^+$.

Step 2:
6-((4-Bromo-1H-imidazol-1-yl)methyl)-2-(methylsulfinyl)benzo[d]oxazole was synthesized as a white foam (443 mg) using a procedure analogous to that described in Step 6 of Example 36, substituting 6-((4-bromo-1H-imidazol-1-yl)methyl)-2-(methylthio)benzo[d]oxazole from Step 1 of this Example for 6-((4-bromo-1H-imidazol-1-yl)methyl)-2-(methylthio)benzo[d]thiazole used in Example 36. LCMS (ESI) m/z 340 and 342 (M+H)$^+$.

Step 3:
(1R,2R)-2-((6-((4-Bromo-1H-imidazol-1-yl)methyl)benzo[d]oxazol-2-yl)amino)cyclohexanol was synthesized as an orange solid (280 mg, 96%) using a procedure analogous to that described in Step 7 of Example 36, substituting 6-((4-bromo-1H-imidazol-1-yl)methyl)-2-(methylsulfinyl)benzo[d]oxazole from Step 2 of this Example for 6-((4-bromo-1H-imidazol-1-yl)methyl)-2-(methylsulfinyl)benzo[d]thiazole used in Example 36. LCMS (ESI) m/z 392 and 394 (M+H)$^+$.

Step 4:
(1R,2R)-2-((6-((4-(1-Methyl-1H-pyrazol-4-yl)-1H-imidazol-1-yl)methyl)benzo[d]oxazol-2-yl)amino)cyclohexanol was synthesized as a white powder (27 mg, 10%) using a procedure analogous to that described in Step 8 of Example 36, substituting (1R,2R)-2-((6-((4-bromo-1H-imidazol-1-yl)methyl)benzo[d]oxazol-2-yl)amino)cyclohexanol from Step 3 of this Example for (1R,2R)-2-((6-((4-bromo-1H-imidazol-1-yl)methyl)benzo[d]thiazol-2-yl)amino)cyclohexanol used in Example 36. $^1$H NMR (300 MHz, DMSO-d$_6$) δ 7.78-7.86 (m, 2H), 7.75 (s, 1H), 7.57 (s, 1H), 7.32 (s, 1H), 7.26 (s, 1H), 7.17 (m, 1H), 7.09 (m, 1H), 5.15 (s, 2H), 4.71 (d, J=4.3 Hz, 1H), 3.80 (s, 3H), 3.27-3.42 (m, 2H), 1.81-2.03 (m, 2H), 1.5-1.70 (m, 2H), 1.10-1.34 (m, 4H). LCMS (ESI) m/z 393 (M+H)$^+$.

Example 78

Preparation of (1R,2R)-2-((6-((5-bromo-3H-imidazo[4,5-b]pyridin-3-yl)methyl)benzo[d]thiazol-2-yl)amino)cyclohexanol

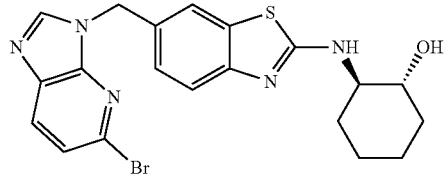 [SMILES: O[C@@H]1CCCC[C@H]1Nc1nc2ccc(Cn3cnc4ccc(Br)nc43)cc2s1]

Step 1:
To a stirred mixture of 6-bromo-3-nitro-2-pyridinamine (2.5 g, 11.47 mmol) in a mixture of glacial HOAc (10 mL), MeOH (10 mL) and EtOH (10 mL) at 0° C. was added portionwise zinc dust (3.73 g, 57.35 mmol). The mixture was stirred at rt for 15 h. The mixture was filtered through Celite, and the filtrate was concentrated under reduced pressure. The residue was partitioned between saturated aq NaHCO$_3$ and EtOAc. The organic layer was separated and the aqueous layer was extracted with additional EtOAc. The combined organic layers were washed with brine, separated and dried over MgSO$_4$, filtered, and concentrated under reduced pressure to afford 6-bromopyridine-2,3-diamine (1.30 g, 60%) as a solid that did not require further purification. $^1$H NMR (300 MHz, DMSO-d$_6$) δ 6.61 (d, J=7.7 Hz, 1H), 6.47 (d, J=7.7 Hz, 1H), 5.82 (s, 2H), 4.79 (s, 2H). LCMS (ESI) m/z 188 and 190 (M+H)$^+$.

Step 2:
A stirred mixture of 6-bromopyridine-2,3-diamine (1.30 g, 6.91 mmol) from Step 1 of this Example, formic acid (0.7 mL), and triethylorthoformate (28 mL) was heated at 100° C. for 1.5 h. After the reaction mixture was cooled to rt, the mixture was concentrated under reduced pressure. The residue was triturated with a mixture of 5% MeOH in DCM. The solid was collected by filtration and dried to afford 5-bromo-3H-imidazo[4,5-b]pyridine (245 mg, 18%) as a tan solid which did not require further purification. The filtrate was concentrated under reduced pressure, and the residue was purified by silica gel flash chromatography (eluting with 100% DCM to 10% MeOH in DCM) to afford additional 5-bromo-3H-imidazo[4,5-b]pyridine (756 mg, 55%) as a tan solid. ¹H NMR (300 MHz, DMSO-d₆) δ 13.08 (br s, 1H), 8.50 (s, 1H), 8.00 (d, J=8.3 Hz, 1H), 7.43 (d, J=8.3 Hz, 1H). LCMS (ESI) m/z 198 and 200 (M+H)⁺.

Step 3:

To a stirred solution of 5-bromo-3H-imidazo[4,5-b]pyridine (1 g, 5.05 mmol) from Step 2 of this Example in anhydrous DMF (25 mL) at 0° C. was added in one portion sodium hydride (60% dispersion in mineral oil, 222 mg 5.56 mmol), and the mixture was stirred at 0° C. for 30 min. To the reaction mixture was added a solution of 6-(chloromethyl)-2-(methylthio)benzo[d]thiazole (1.39 g, 6.06 mmol) from Step 4 of Example 36 in DMF (5 mL). The mixture was allowed to warm to rt and stirred for a further 15 h. To the reaction mixture was added water (300 mL) and the mixture was extracted with EtOAc (3×50 mL). The combined organic layers were washed with water and then brine. The organic layer was separated, dried over MgSO₄, filtered, and concentrated under reduced pressure. The residue was purified by silica gel flash chromatography eluting with 100% DCM, followed by 1% MeOH in DCM to afford 6-((5-bromo-3H-imidazo[4,5-b]pyridin-3-yl)methyl)-2-(methylthio)benzo[d]thiazole (1.02 g, 52%) as a white solid. The regiochemistry of the alkylation was determined by 2-dimensional nuclear Overhauser effect (NOE) experiment. ¹H NMR (300 MHz, DMSO-d₆) δ 8.65 (s, 1H), 8.09 (d, J=8.3 Hz, 1H), 7.96 (d, J=0.9 Hz, 1H), 7.83 (d, J=8.3 Hz, 1H), 7.49 (d, J=8.3 Hz, 1H), 7.43 (dd, J=1.5, 8.3 Hz, 1H), 5.60 (s, 2H), 2.77 (s, 3H). LCMS (ESI) m/z 391 and 393 (M+H)⁺.

Step 4:

To a stirred solution of 6-((5-bromo-3H-imidazo[4,5-b]pyridin-3-yl)methyl)-2-(methylthio)benzo[d]thiazole (1.02 g, 2.61 mmol) from Step 3 of this Example in DCM (50 mL) at 0° C. was added 70% meta-chloroperbenzoic acid (707 mg, 2.87 mmol) and the mixture was allowed to warm to rt and stirred for a further 45 min. To the mixture was added saturated aq NaHCO₃ and the organic layer was separated. The aqueous layer was extracted with DCM and the combined organic layers were washed with saturated aq NaHCO₃. The organic layer was separated, dried over MgSO₄, filtered, and the filtrate was concentrated under reduced pressure to afford 6-((5-bromo-3H-imidazo[4,5-b]pyridin-3-yl)methyl)-2-(methylsulfinyl)benzo[d]thiazole (1.06 g, 100%) as a cream solid which did not require further purification. ¹H NMR (300 MHz, DMSO-d₆) δ 8.68 (s, 1H), 8.18 (s, 1H), 8.08-8.12 (m, 2H), 7.61 (m, 1H), 7.50 (d, J=9 Hz, 1H), 5.68 (s, 2H), 3.07 (s, 3H); LCMS (ESI) m/z 407 and 409 (M+H)⁺.

Step 5:

A stirred mixture of 6-((5-bromo-3H-imidazo[4,5-b]pyridin-3-yl)methyl)-2-(methylsulfinyl)benzo[d]thiazole (50 mg, 0.123 mmol) from Step 4 of this Example, (1R,2R)-(−)-2-aminocyclohexanol (42 mg, 0.369 mmol), and DIEA (46 mg, 0.369 mmol) in anhydrous DMA (1 mL) was heated in a sealed vessel at 100° C. for 15 h. The reaction was allowed to cool to rt and then was purified directly by reverse-phase HPLC using a mixture of water (5% CH₃CN, 0.05% HOAc) and CH₃CN (0.05% HOAc) as the mobile phase and Varian Pursuit XRs diphenyl column as the stationary phase to afford (1R,2R)-2-((6-((5-bromo-3H-imidazo[4,5-b]pyridin-3-yl)methyl)benzo[d]thiazol-2-yl)amino)cyclohexanol (12 mg, 21%) as a white solid. ¹H NMR (300 MHz, DMSO-d₆) δ 8.60 (s, 1H), 7.98-8.10 (m, 2H), 7.64 (d, J=1.1 Hz, 1H), 7.48 (d, J=8.5 Hz, 1H), 7.31 (m, 1H), 7.18 (dd, J=1.6, 8.2 Hz, 1H), 5.46 (s, 2H), 4.79 (br s, 1H), 3.50 (m, 1H), 3.30 (m, 1H), 2.04 (m, 1H), 1.87 (m, 1H), 1.65-1.67 (m, 2H), 1.12-1.34 (m, 4H). LCMS (ESI) m/z 458 and 460 (M+H)⁺.

Example 79

Preparation of methyl 3-((2-(((1R,2R)-2-hydroxycyclohexyl)amino)benzo[d]thiazol-6-yl)methyl)-3H-imidazo[4,5-b]pyridine-6-carboxylate

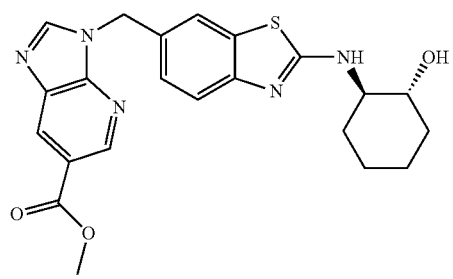 [SMILES: COC(=O)c1cnc2c(c1)ncn2Cc1ccc2nc(N[C@@H]3CCCC[C@H]3O)sc2c1]

Step 1:

To a stirred mixture of methyl 6-amino-5-nitronicotinate (2 g, 10.15 mmol) in a mixture of THF (30 mL) and MeOH (10 mL) at rt was added palladium (10 wt % on activated carbon, 100 mg), and the mixture stirred under hydrogen gas (1 atmosphere) for 15 h. The mixture was filtered through Celite, and the filtrate was concentrated under reduced pressure to afford methyl 5,6-diaminonicotinate (1.69 g, 100%) as a yellow solid which did not require further purification. ¹H NMR (300 MHz, DMSO-d₆) δ 7.94 (d, J=2.1 Hz, 1H), 7.16 (d, J=2.1 Hz, 1H), 6.27 (br s, 2H), 4.92 (br s, 2H), 3.74 (s, 3H). LCMS (ESI) m/z 168 (M+H)⁺.

Step 2:

A stirred mixture of methyl 5,6-diaminonicotinate (1.69 g, 10.12 mmol) from Step 1 of this Example, formic acid (0.5 mL), and triethylorthoformate (25 mL) was heated at 90° C. for 2.5 h. The reaction mixture was cooled to rt and then the precipitated solid was collected by filtration and dried to afford methyl 3H-imidazo[4,5-b]pyridine-6-carboxylate (588 mg, 33%) as a cream solid which did not require further purification. The filtrate was concentrated under reduced pressure, and the residue purified by silica gel flash chromatography eluting with 100% DCM to 10% MeOH in DCM to afford additional methyl 3H-imidazo[4,5-b]pyridine-6-carboxylate (550 mg, 31%) as a cream solid. ¹H NMR (300 MHz, DMSO-d₆) δ 13.33 (br s, 1H), 8.95 (d, J=1.5 Hz, 1H), 8.64 (s, 1H), 8.50 (d, J=1.5 Hz, 1H), 3.91 (s, 3H). LCMS (ESI) m/z 178 (M+H)⁺.

Step 3:

To a stirred solution of methyl 3H-imidazo[4,5-b]pyridine-6-carboxylate (1.34 g, 7.56 mmol) from Step 2 of this Example in anhydrous DMF (25 mL) at 0° C. was added in one portion sodium hydride (60% dispersion in mineral oil, 333 mg, 8.32 mmol) and the mixture was stirred at 0° C. for 30 min. To the reaction mixture was added a solution of 6-(chloromethyl)-2-(methylthio)benzo[d]thiazole (1.3 g, 5.66 mmol) from Step 4 of Example 36 in DMF (5 mL). The mixture was allowed to warm to rt then stirred for a further 15 h. To the reaction mixture was added water (300 mL) and the mixture was extracted with EtOAc (3×50 mL). The combined organic layers were washed with water and then brine, dried over MgSO₄, filtered, and concentrated under reduced pressure. The residue was purified by silica gel flash chromatography eluting with 100% DCM followed by 1% MeOH in DCM to afford methyl 3-((2-(methylthio)benzo[d]thiazol-6-yl)methyl)-3H-imidazo[4,5-b]pyridine-6-carboxylate (1.3 g, 46%) as a white solid. The regiochemistry of the alkylation was determined by 2-dimensional nuclear Overhauser effect (NOE) experiment. ¹H NMR (300 MHz, DMSO-d₆) δ 8.95 (d, J=1.9 Hz, 1H), 8.81 (s, 1H), 8.56 (d, J=1.7 Hz, 1H), 8.00 (d, J=1.1 Hz, 1H), 7.80 (d, J=8.5 Hz, 1H), 7.47 (dd, J=1.6, 8.4 Hz, 1H), 5.66 (s, 2H), 3.90 (s, 3H), 2.76 (s, 3H). LCMS (ESI) m/z 371 (M+H)⁺.

Step 4:

To a stirred solution of methyl 3-((2-(methylthio)benzo[d]thiazol-6-yl)methyl)-3H-imidazo[4,5-b]pyridine-6-carboxylate (300 mg, 0.811 mmol) from Step 3 of this Example in DCM (10 mL) at 0° C. was added 70% meta-chloroperbenzoic acid (154 mg, 0.892 mmol) and the mixture was allowed to warm to rt and stirred for a further 4 h. To the mixture was added saturated aq NaHCO₃ and the organic layer was separated. The aqueous layer was extracted with DCM and the combined organic layers were washed with saturated aq NaHCO₃. The organic layer was separated, dried over MgSO₄, filtered, and concentrated under reduced pressure to afford 370 mg of a 2:1 mixture of methyl 3-((2-(methylsulfinyl)benzo[d]thiazol-6-yl)methyl)-3H-imidazo[4,5-b]pyridine-6-carboxylate and methyl 3-((2-(methylsulfonyl)benzo[d]thiazol-6-yl)methyl)-3H-imidazo[4,5-b]pyridine-6-carboxylate as an oil that was not purified further. LCMS (ESI) m/z 387 (M+H)⁺ (consistent with methyl 3-((2-(methylsulfinyl)benzo[d]thiazol-6-yl)methyl)-3H-imidazo[4,5-b]pyridine-6-carboxylate) and m/z 403 (M+H)⁺ (consistent with methyl 3-((2-(methylsulfonyl)benzo[d]thiazol-6-yl)methyl)-3H-imidazo[4,5-b]pyridine-6-carboxylate).

Step 5:

A 2:1 mixture of methyl 3-((2-(methylsulfinyl)benzo[d]thiazol-6-yl)methyl)-3H-imidazo[4,5-b]pyridine-6-carboxylate and methyl 3-((2-(methylsulfonyl)benzo[d]thiazol-6-yl)methyl)-3H-imidazo[4,5-b]pyridine-6-carboxylate (360 mg) from Step 4 of this Example was dissolved in anhydrous DMA (10 mL), and (1R,2R)-(−)-2-aminocyclohexanol (322 mg, 2.79 mmol) and DIEA (360 mg, 2.79 mmol) were added. The reaction vessel was sealed and the mixture was heated with stirring at 100° C. for 19 h. LCMS indicated the reaction was not complete. To the reaction mixture was added additional (1R,2R)-(−)-2-aminocyclohexanol (100 mg, 0.870 mmol) and the reaction vessel was sealed and the mixture was heated at 100° C. for a further 15 h. After the reaction mixture was cooled to rt, one half of the reaction mixture was purified directly by reverse-phase HPLC using a mixture of water (5% CH₃CN, 0.05% HOAc) and CH₃CN (0.05% HOAc) as the mobile phase and Varian Pursuit XRs diphenyl column as the stationary phase to afford methyl 3-((2-(((1R,2R)-2-hydroxycyclohexyl)amino)benzo[d]thiazol-6-yl)methyl)-3H-imidazo[4,5-b]pyridine-6-carboxylate (19 mg) as a white solid. ¹H NMR (300 MHz, DMSO-d₆) δ 8.96 (d, J=7.3 Hz, 1H), 8.76 (m, 1H), 8.54 (m, 1H), 7.99 (br s, 1H), 7.66 (d, J=7.2 Hz, 1H), 7.16-7.33 (m, 2H), 5.51 (br s, 2H), 4.76 (br s, 1H), 3.89 (s, 3H), 3.30-3.50 (m, 2H), 2.02 (m, 1H), 1.86 (m, 1H), 1.5-1.70 (m, 2H), 1.10-1.30 (m, 4H). LCMS (ESI) m/z 438 (M+H)⁺.

Example 80

Preparation of (1R,2R)-1-((6-((5-bromo-3H-imidazo[4,5-b]pyridin-3-yl)methyl)benzo[d]thiazol-2-yl)amino)-2,3-dihydro-1H-inden-2-ol

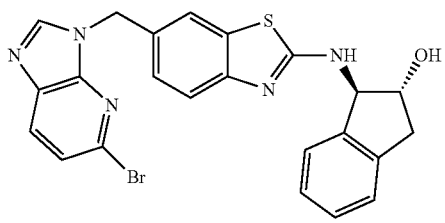 [SMILES: O[C@@H]1Cc2ccccc2[C@H]1Nc1nc2ccc(Cn3cnc4ccc(Br)nc43)cc2s1]

A stirred mixture of 6-((5-bromo-3H-imidazo[4,5-b]pyridin-3-yl)methyl)-2-(methylsulfinyl)benzo[d]thiazole (130 mg, 0.332 mmol) from Step 4 of Example 78, (1R,2R)-(−)-trans-1-amino-2-indanol (198 mg, 1.33 mmol), and DIEA (214 mg, 1.66 mmol) in anhydrous DMA (2 mL) in a sealed reaction vessel was heated in a Biotage microwave synthesizer at 140° C. for 1.5 h. LCMS indicated that the reaction was incomplete. Additional (1R,2R)-(−)-trans-1-amino-2-indanol (50 mg, 0.335 mmol) was added, and the mixture was heated in a Biotage microwave synthesizer at 140° C. for a further 45 min. The reaction mixture was cooled to rt and purified directly by reverse-phase HPLC using a mixture of water (5% CH₃CN, 0.05% HOAc) and CH₃CN (0.05% HOAc) as the mobile phase and Varian Pursuit XRs diphenyl column as the stationary phase to afford (1R,2R)-1-((6-((5-bromo-3H-imidazo[4,5-b]pyridin-3-yl)methyl)benzo[d]thiazol-2-yl)amino)-2,3-dihydro-1H-inden-2-ol (24 mg, 15%) as a white solid. ¹H NMR (300 MHz, DMSO-d₆) δ 8.62 (s, 1H), 8.47 (d, J=7.9 Hz, 1H), 8.08 (d, J=8.3 Hz, 1H), 7.69 (s, 1H), 7.49 (d, J=8.3 Hz, 1H), 7.37 (d, J=8.3 Hz, 1H), 7.11-7.28 (m, 5H), 5.45-5.54 (m, 3H), 5.18 (t, J=7.1 Hz, 1H), 4.24-4.35 (m, 1H), 3.16 (dd, J=6.9, 15.5 Hz, 1H), 2.74 (dd, J=7.1, 15.5 Hz, 1H). LCMS (ESI) m/z 492 and 494 (M+H)⁺.

Example 81

Preparation of 3-((2-(((1R,2R)-2-hydroxycyclohexyl)amino)benzo[d]thiazol-6-yl)methyl)-3H-imidazo[4,5-b]pyridine-6-carboxylic acid

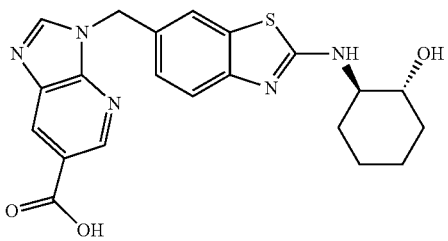 [SMILES: O=C(O)c1cnc2c(c1)ncn2Cc1ccc2nc(N[C@@H]3CCCC[C@H]3O)sc2c1]

A mixture of methyl 3-((2-(((1R,2R)-2-hydroxycyclohexyl)amino)benzo[d]thiazol-6-yl)methyl)-3H-imidazo[4,5-b]pyridine-6-carboxylate (210 mg, 0.48 mmol) from Example 79 in THF (5 mL) and 1 M aq LiOH (5 mL) was stirred at rt for 3 h. The reaction mixture was acidified to pH~1.0 with 2 M aq HCl, and the mixture was purified directly by reverse-phase HPLC using a mixture of water

Example 82

Preparation of (1R,2R)-2-((6-(((6-(morpholinomethyl)-3H-imidazo[4,5-b]pyridin-3-yl)methyl)benzo[d]thiazol-2-yl)amino)cyclohexanol

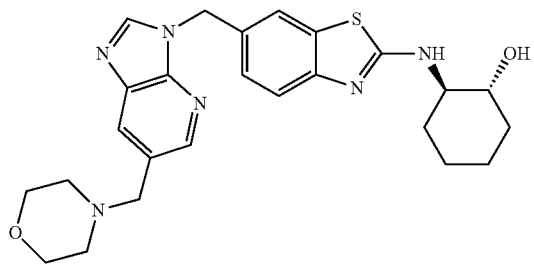 [SMILES: O[C@@H]1CCCC[C@H]1Nc1nc2ccc(Cn3cnc4cc(CN5CCOCC5)cnc43)cc2s1]

A stirred mixture of (1R,2R)-2-((6-((6-bromo-3H-imidazo[4,5-b]pyridin-3-yl)methyl)benzo[d]thiazol-2-yl)amino)cyclohexanol (100 mg, 0.22 mmol) from Example 29, potassium (morpholin-4-yl)methyltrifluoroborate (59 mg, 0.28 mmol), Pd(OAc)$_2$ (1.5 mg, 0.007 mmol), 2-dicyclohexylphosphino-2',4',6'-triisopropylbiphenyl (6.2 mg, 0.013 mmol) and Cs$_2$CO$_3$ (213 mg, 0.66 mmol) in THF/H$_2$O (1.5 mL, 4:1, v/v) was purged with argon for 10 min. The mixture was then heated at 85° C. in a sealed reaction vessel overnight. LCMS showed the reaction complete. After cooling to rt, the reaction mixture was filtered through a Celite plug and the filtrate was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford (1R,2R)-2-((6-((6-(morpholinomethyl)-3H-imidazo[4,5-b]pyridin-3-yl)methyl)benzo[d]thiazol-2-yl)amino)cyclohexanol as a white powder (36 mg, 35%). $^1$H NMR (300 MHz, DMSO-d$_6$) δ 8.57 (s, 1H), 8.31 (d, J=1.5 Hz, 1H), 7.88-8.04 (m, 2H), 7.67 (d, J=0.9 Hz, 1H), 7.26-7.33 (m, 1H), 7.17-7.26 (m, 1H), 5.46 (s, 2H), 4.75 (br s, 1H), 3.60 (s, 2H), 3.45-3.58 (m, 5H), 2.36 (br s, 4H), 2.03 (d, J=10.4 Hz, 1H), 1.79-1.89 (m, 1H), 1.62 (d, J=5.1 Hz, 2H), 1.05-1.37 (m, 4H). LCMS (ESI) m/z 479 (M+H)$^+$.

Example 83

Preparation of either (1R,2R)-1-((6-((4-(1-methyl-1H-pyrazol-4-yl)-1H-imidazol-1-yl)methyl)benzo[d]thiazol-2-yl)amino)-2,3-dihydro-1H-inden-2-ol or (1R,2R)-1-((6-((5-(1-methyl-1H-pyrazol-4-yl)-1H-imidazol-1-yl)methyl)benzo[d]thiazol-2-yl)amino)-2,3-dihydro-1H-inden-2-ol (Alternative to Product of Example 32)

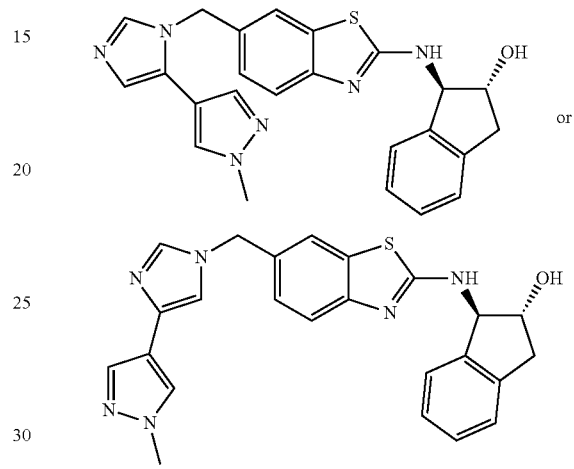

Step 1:

6-((5-(1-Methyl-1H-pyrazol-4-yl)-1H-imidazol-1-yl)methyl)-2-(methylsulfinyl)benzo[d]thiazole or 6-((4-(1-methyl-1H-pyrazol-4-yl)-1H-imidazol-1-yl)methyl)-2-(methylsulfinyl)benzo[d]thiazole was synthesized as a white foam (140 mg) using a procedure analogous to that described in Step 5 of Example 32, substituting regioisomer 2 from Step 4 of Example 32, (either 6-((5-(1-methyl-1H-pyrazol-4-yl)-1H-imidazol-1-yl)methyl)-2-(methylthio)benzo[d]thiazole or 6-((4-(1-methyl-1H-pyrazol-4-yl)-1H-imidazol-1-yl)methyl)-2-(methylthio)benzo[d]thiazole) for regioisomer 1, used in Example 32. LCMS (ESI) m/z 356 (M+H)$^+$.

Step 2:

(1R,2R)-1-((6-((4-(1-Methyl-1H-pyrazol-4-yl)-1H-imidazol-1-yl)methyl)benzo[d]thiazol-2-yl)amino)-2,3-dihydro-1H-inden-2-ol or (1R,2R)-1-((6-((5-(1-methyl-1H-pyrazol-4-yl)-1H-imidazol-1-yl)methyl)benzo[d]thiazol-2-yl)amino)-2,3-dihydro-1H-inden-2-ol (alternative of starting material in Step 6 of Example 32) was synthesized as a white powder (10 mg, 8%) using a procedure analogous to that described in Step 6 of Example 32, substituting the product from Step 1 of this Example for 6-((5-(1-methyl-1H-pyrazol-4-yl)-1H-imidazol-1-yl)methyl)-2-(methylsulfinyl)benzo[d]thiazole or 6-((4-(1-methyl-1H-pyrazol-4-yl)-1H-imidazol-1-yl)methyl)-2-(methylsulfinyl)benzo[d]thiazole used in Example 32. $^1$H NMR (300 MHz, DMSO-d$_6$) δ 8.50 (d, J=7.9 Hz, 1H), 7.81 (s, 1H), 7.73 (d, J=0.9 Hz, 1H), 7.66 (s, 1H), 7.58 (s, 1H), 7.38 (d, J=8.3 Hz, 1H), 7.11-7.30 (m, 6H), 5.54 (m, 1H), 5.11-5.25 (m, 3H), 4.31 (m, 1H), 3.81 (s, 3H), 3.17 (m, 1H), 2.75 (m, 1H). LCMS (ESI) m/z 443 (M+H)$^+$.

---

(from previous column, top)

(5% CH$_3$CN, 0.05% HOAc) and CH$_3$CN (0.05% HOAc) as the mobile phase and Varian Pursuit XRs diphenyl column as the stationary phase to afford 3-((2-(((1R,2R)-2-hydroxycyclohexyl)amino)benzo[d]thiazol-6-yl)methyl)-3H-imidazo[4,5-b]pyridine-6-carboxylic acid (37 mg, 18%) as a white solid. $^1$H NMR (300 MHz, DMSO-d$_6$) δ 13.15 (br s, 1H), 8.96 (d, J=1.7 Hz, 1H), 8.74 (s, 1H), 8.52 (d, J=1.9 Hz, 1H), 7.98 (d, J=7.3 Hz, 1H), 7.67 (d, J=1.1 Hz, 1H), 7.19-7.33 (m, 2H), 5.53 (s, 2H), 4.75 (br s, 1H), 3.51 (m, 1H), 3.33 (m, 1H), 2.03 (m, 1H), 1.87 (m, 1H), 1.5-1.68 (m, 2H), 1.09-1.35 (m, 4H). LCMS (ESI) m/z 424 (M+H)$^+$.

Example 84

Preparation of (1R,2R)-2-((6-((6-(hydroxymethyl)-3H-imidazo[4,5-b]pyridin-3-yl)methyl)benzo[d]thiazol-2-yl)amino)cyclohexanol

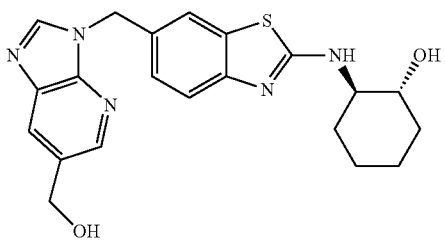 [SMILES: OCc1cnc2c(c1)ncn2Cc1ccc2nc(N[C@@H]3CCCC[C@H]3O)sc2c1]

To a stirred mixture of methyl 3-((2-(((1R,2R)-2-hydroxycyclohexyl)amino)benzo[d]thiazol-6-yl)methyl)-3H-imidazo[4,5-b]pyridine-6-carboxylate (76 mg, 0.174 mmol) from Example 79 in anhydrous DCM (1 mL) at −50° C. under argon was added dropwise diisobutylaluminum hydride (1 M solution in DCM, 0.696 μL, 696 mmol). The mixture was allowed to warm to −20° C. and stirred for 10 min. The reaction mixture was acidified to pH~1.0 with 2 M aq HCl, and the mixture was purified directly by reverse-phase HPLC using a mixture of water (5% CH$_3$CN, 0.05% HOAc) and CH$_3$CN (0.05% HOAc) as the mobile phase and Varian Pursuit XRs diphenyl column as the stationary phase to afford (1R,2R)-2-((6-((6-(hydroxymethyl)-3H-imidazo[4,5-b]pyridin-3-yl)methyl)benzo[d]thiazol-2-yl)amino)cyclohexanol (20 mg, 28%) as a white solid. $^1$H NMR (300 MHz, DMSO-d$_6$) δ 8.56 (s, 1H), 8.35 (d, J=1.3 Hz, 1H), 7.93-8.01 (m, 2H), 7.65 (s, 1H), 7.28 (m, 1H), 7.20 (m, 1H), 5.47 (s, 2H), 5.29 (br s, 1H), 4.75 (d, J=4.0 Hz, 1H), 4.62 (br s, 2H), 3.50 (m, 1H), 3.30 (m, 1H), 2.03 (m, 1H), 1.87 (m, 1H), 1.5-1.65 (m, 2H), 1.10-1.35 (m, 4H). LCMS (ESI) m/z 410 (M+H)$^+$.

Example 85

Preparation of (1R,2R)-2-((6-((6-(methylthio)-3H-imidazo[4,5-b]pyridin-3-yl)methyl)benzo[d]thiazol-2-yl)amino)cyclohexanol

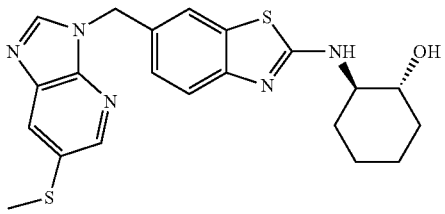 [SMILES: CSc1cnc2c(c1)ncn2Cc1ccc2nc(N[C@@H]3CCCC[C@H]3O)sc2c1]

(1R,2R)-2-((6-((6-(Methylthio)-3H-imidazo[4,5-b]pyridin-3-yl)methyl)benzo[d]thiazol-2-yl)amino)cyclohexanol (25 mg, 18%) was obtained as a tan powder using a procedure analogous to that described in Example 82, substituting potassium (thiomethyl)methyltrifluoroborate for potassium (morpholin-4-yl)methyltrifluoroborate, substituting dioxane/H$_2$O for THF/H$_2$O used in Example 82, and running the reaction at 100° C. instead of 85° C. $^1$H NMR (300 MHz, MeOH-d$_4$) δ 8.37-8.50 (m, 2H), 8.07 (d, J=1.7 Hz, 1H), 7.64 (s, 1H), 7.34-7.40 (m, 1H), 7.25-7.34 (m, 1H), 5.53 (s, 2H), 3.58 (dd, J=3.4, 9.8 Hz, 1H), 3.39-3.51 (m, 1H), 2.56 (s, 3H), 2.10-2.24 (m, 1H), 2.03 (d, J=10.9 Hz, 1H), 1.64-1.85 (m, 2H), 1.13-1.51 (m, 4H). LCMS (ESI) m/z 426 (M+H)$^+$.

Example 86

Preparation of (1R,2R)-2-((6-((6-((methylthio)methyl)-3H-imidazo[4,5-b]pyridin-3-yl)methyl)benzo[d]thiazol-2-yl)amino)cyclohexanol

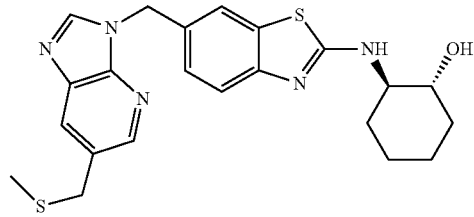 [SMILES: CSCc1cnc2c(c1)ncn2Cc1ccc2nc(N[C@@H]3CCCC[C@H]3O)sc2c1]

(1R,2R)-2-((6-((6-((methylthio)methyl)-3H-imidazo[4,5-b]pyridin-3-yl)methyl)benzo[d]thiazol-2-yl)amino)cyclohexanol (5 mg, 4%) was obtained as a tan powder using a procedure analogous to that described in Example 82, substituting potassium (thiomethyl)methyltrifluoroborate for potassium (morpholin-4-yl)methyltrifluoroborate used in Example 82, substituting dioxane/H$_2$O for THF/H$_2$O used in Example 82, and running the reaction at 100° C. instead of 85° C. $^1$H NMR (300 MHz, MeOH-d$_4$) δ 8.29 (s, 2H), 7.95 (br s, 1H), 7.52 (s, 1H), 7.22-7.30 (m, 1H), 7.13-7.22 (m, 1H), 5.43 (s, 2H), 3.76 (s, 2H), 3.47 (dd, J=3.4, 9.8 Hz, 1H), 3.27-3.40 (m, 1H), 2.04 (d, J=11.7 Hz, 1H), 1.93 (br s, 1H), 1.90 (s, 3H), 1.5-1.74 (m, 2H), 1.01-1.40 (m, 4H). LCMS (ESI) m/z 440 (M+H)$^+$.

Example 87

Preparation of 3-((2-(((1R,2R)-2-hydroxycyclohexyl)amino)benzo[d]thiazol-6-yl)methyl)-3H-imidazo[4,5-b]pyridine-5-carbonitrile

A stirred mixture of (1R,2R)-2-((6-((5-bromo-3H-imidazo[4,5-b]pyridin-3-yl)methyl)benzo[d]thiazol-2-yl)amino)cyclohexanol (100 mg, 0.218 mmol) from Example 78, zinc cyanide (77 mg, 0.654 mmol), and 1,1'-bis(diphenylphosphino)ferrocene (18 mg, 0.0327 mmol) in anhydrous DMF (2 mL) at rt was purged for 15 min with a stream of argon. To the resulting mixture was added tris(dibenzylideneacetone)dipalladium (18 mg, 0.0218 mmol). The reaction vessel was sealed and the mixture was stirred at 100° C. for 2 h. After cooling to rt, the reaction mixture was purified directly by reverse-phase HPLC using a mixture of water (5% CH$_3$CN, 0.05% HOAc) and CH$_3$CN (0.05% HOAc) as the mobile phase and Varian Pursuit XRs diphenyl column as the stationary phase to afford 3-((2-(((1R,2R)-2-hydroxycyclohexyl)amino)benzo[d]thiazol-6-yl)methyl)-3H-imidazo[4,5-b]pyridine-5-carbonitrile (34 mg, 39%) as a white solid. $^1$H NMR (300 MHz, DMSO-d$_6$) δ 8.91 (s, 1H), 8.34 (d, J=8.3 Hz, 1H), 8.01 (d, J=7.3 Hz, 1H), 7.92 (d, J=8.1 Hz, 1H), 7.67 (d, J=1.1 Hz, 1H), 7.32 (m, 1H), 7.22 (m, 1H), 5.53 (s, 2H), 4.77 (br s, 1H), 3.51 (m, 1H), 3.30 (m, 1H), 2.03 (m, 1H), 1.85 (m, 1H), 1.65-1.67 (m, 2H), 1.08-1.37 (m, 4H). LCMS (ESI) m/z 405 (M+H)$^+$.

Example 88

Preparation of 1-(3-((2-(((1R,2R)-2-hydroxycyclohexyl)amino)benzo[d]thiazol-6-yl)methyl)-3H-imidazo[4,5-b]pyridin-5-yl)ethanone

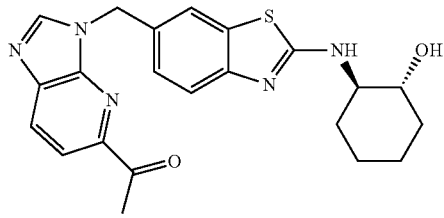 [SMILES: CC(=O)c1ccc2ncn(Cc3ccc4nc(N[C@@H]5CCCC[C@H]5O)sc4c3)c2n1]

A stirred mixture of (1R,2R)-2-((6-((5-bromo-3H-imidazo[4,5-b]pyridin-3-yl)methyl)benzo[d]thiazol-2-yl)amino)cyclohexanol (100 mg, 0.218 mmol) from Example 78, tributyl(1-ethoxyvinyl)tin (157 mg, 0.436 mmol) in anhydrous DMF (2 mL) at rt was purged for 15 min with a stream of argon. To the resulting mixture was added tetrakis(triphenylphosphine)palladium (0) (38 mg, 0.0327 mmol). The reaction vessel was sealed and the mixture was stirred at 110° C. for 2 h. After cooling to rt, 2 M aq HCl (0.5 mL) was added, and the mixture was stirred at rt for 1.5 h. The mixture was purified directly by reverse-phase HPLC using a mixture of water (5% CH$_3$CN, 0.05% HOAc) and CH$_3$CN (0.05% HOAc) as the mobile phase and Varian Pursuit XRs diphenyl column as the stationary phase to afford crude 1-(3-((2-(((1R,2R)-2-hydroxycyclohexyl)amino)benzo[d]thiazol-6-yl)methyl)-3H-imidazo[4,5-b]pyridin-5-yl)ethanone. The crude product was triturated with Et$_2$O and the solid was collected by filtration and dried to afford 1-(3-((2-(((1R,2R)-2-hydroxycyclohexyl)amino)benzo[d]thiazol-6-yl)methyl)-3H-imidazo[4,5-b]pyridin-5-yl)ethanone (19 mg, 21%) as a white solid. $^1$H NMR (300 MHz, DMSO-d$_6$) δ 8.84 (s, 1H), 8.22 (d, J=8.5 Hz, 1H), 8.00 (d, J=7.5 Hz, 1H), 7.92 (d, J=8.3 Hz, 1H), 7.80 (s, 1H), 7.26-7.39 (m, 2H), 5.55 (s, 2H), 4.77 (d, J=4.9 Hz, 1H), 3.50 (m, 1H), 3.30 (m, 1H), 2.74 (s, 3H), 2.02 (m, 1H), 1.87 (m, 1H), 1.5-1.67 (m, 2H), 1.12-1.32 (m, 4H). LCMS (ESI) m/z 422 (M+H)$^+$.

Example 89

Preparation of 3-((2-(((1R,2R)-2-hydroxycyclohexyl)amino)benzo[d]thiazol-6-yl)methyl)-N-methyl-3H-imidazo[4,5-b]pyridine-6-carboxamide

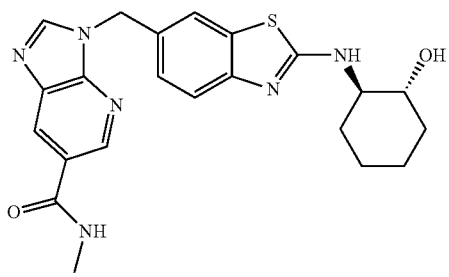 [SMILES: CNC(=O)c1cnc2c(c1)ncn2Cc1ccc2nc(N[C@@H]3CCCC[C@H]3O)sc2c1]

To a stirred mixture of 3-((2-(((1R,2R)-2-hydroxycyclohexyl)amino)benzo[d]thiazol-6-yl)methyl)-3H-imidazo[4,5-b]pyridine-6-carboxylic acid (70 mg, 0.165 mmol) from Example 81 and TEA (67 mg, 0.660 mmol) in anhydrous THF (2.5 mL) at rt was added methylamine (2 M solution in THF, 413 μL, 0.825 mmol) followed by benzotriazol-1-yloxytris(dimethylamino)phosphonium hexafluorophosphate (109 mg, 0.248 mmol). The mixture was stirred at rt for 4.5 h. The mixture was purified by reverse-phase HPLC using a mixture of water (5% CH$_3$CN, 0.05% HOAc) and CH$_3$CN (0.05% HOAc) as the mobile phase and Varian Pursuit XRs diphenyl column as the stationary phase to afford 3-((2-(((1R,2R)-2-hydroxycyclohexyl)amino)benzo[d]thiazol-6-yl)methyl)-N-methyl-3H-imidazo[4,5-b]pyridine-6-carboxamide (26 mg, 36%) as a white solid. $^1$H NMR (300 MHz, DMSO-d$_6$) δ 8.86 (d, J=1.88 Hz, 1H), 8.69 (s, 1H), 8.59 (d, J=4.52 Hz, 1H), 8.49 (d, J=1.88 Hz, 1H), 7.97 (d, J=7.54 Hz, 1H), 7.67 (d, J=1.13 Hz, 1H), 7.19-7.32 (m, 2H), 5.51 (s, 2H), 4.73 (br. s., 1H), 3.51 (m, 1H), 3.30 (m, 1H), 2.82 (d, J=4.33 Hz, 3H), 2.02 (m, 1H), 1.88 (m, 1H), 1.55-1.65 (m 2H), 1.10-1.30 (m, 4H). LCMS (ESI) m/z 437 (M+H)$^+$.

Example 90

Preparation of N-hydroxy-3-((2-(((1R,2R)-2-hydroxycyclohexyl)amino)benzo[d]thiazol-6-yl)methyl)-3H-imidazo[4,5-b]pyridine-6-carboximidamide

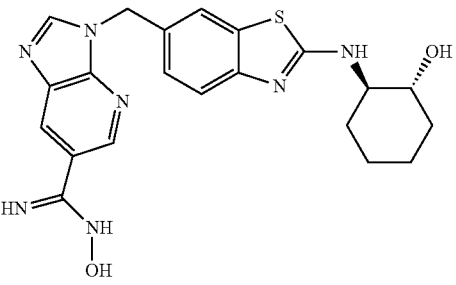 [SMILES: N=C(NO)c1cnc2c(c1)ncn2Cc1ccc2nc(N[C@@H]3CCCC[C@H]3O)sc2c1]

A stirred mixture of 3-((2-(((1R,2R)-2-hydroxycyclohexyl)amino)benzo[d]thiazol-6-yl)methyl)-3H-imidazo[4,5-b]pyridine-6-carbonitrile from Example 43 (55 mg, 0.14 mmol) and excess 50% NH₂OH in H₂O (300 µL) in EtOH (3 mL) was heated at 80° C. for 1 h. LCMS analysis showed that the reaction was complete. The crude product was purified by preparative HPLC using a mixture of water (5% CH₃CN, 0.05% AcOH) and CH₃CN (0.05% AcOH) as the mobile phase and Varian Pursuit XRs Diphenyl column as the stationary phase to afford N-hydroxy-3-((2-(((1R,2R)-2-hydroxycyclohexyl)amino)benzo[d]thiazol-6-yl)methyl)-3H-imidazo[4,5-b]pyridine-6-carboximidamide (8 mg, 13%) as a tan powder. ¹H NMR (300 MHz, MeOH-d₄) δ 8.73 (d, J=1.7 Hz, 1H), 8.50 (s, 1H), 8.29 (d, J=1.7 Hz, 1H), 7.63 (s, 1H), 7.32-7.39 (m, 1H), 7.25-7.32 (m, 1H), 5.55 (s, 2H), 3.5-3.65 (m, 1H), 3.37-3.49 (m, 1H), 2.13 (d, J=12.1 Hz, 1H), 2.02 (d, J=10.4 Hz, 1H), 1.62-1.82 (m, 2H), 1.15-1.49 (m, 4H). LCMS (ESI) m/z 438 (M+H)⁺.

Example 91

Preparation of (1R,2R)-2-((6-((6-(aminomethyl)-3H-imidazo[4,5-b]pyridin-3-yl)methyl)benzo[d]thiazol-2-yl)amino)cyclohexanol acetate

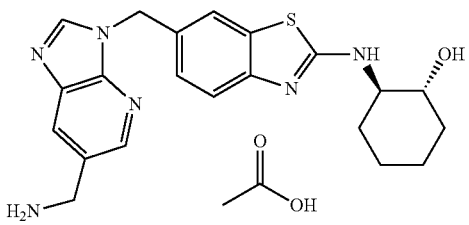

To a stirred mixture of 3-((2-(((1R,2R)-2-hydroxycyclohexyl)amino)benzo[d]thiazol-6-yl)methyl)-3H-imidazo[4,5-b]pyridine-6-carbonitrile from Example 43 (85 mg, 0.21 mmol) in THF (3 mL) at 0° C. was added dropwise LAH in diethyl ether (2.0 M, 0.4 mL, 0.4 mmol). The resulting mixture was stirred at rt for 1 h, before another 0.4 mL of 2.0 M LAH in diethyl ether was added. After stirring at rt overnight, the reaction mixture was treated with sequential addition of 61 µL of H₂O, 61 µL of 10% NaOH, and 183 µL of H₂O. The resulting mixture was filtered through a Celite plug and concentrated under reduced pressure. The residue was purified by preparative HPLC using a mixture of water (5% CH₃CN, 0.05% AcOH) and CH₃CN (0.05% AcOH) as the mobile phase and Varian Pursuit XRs Diphenyl column as the stationary phase to afford (1R,2R)-2-((6-((6-(aminomethyl)-3H-imidazo[4,5-b]pyridin-3-yl)methyl)benzo[d]thiazol-2-yl)amino)cyclohexanol acetate (4 mg, 5%) as a tan powder. ¹H NMR (300 MHz, MeOH-d₄) δ 8.54 (d, J=9.2 Hz, 2H), 8.19 (s, 1H), 7.63 (s, 1H), 7.19-7.42 (m, 2H), 5.56 (s, 2H), 4.27 (s, 2H), 3.57 (d, J=9.6 Hz, 1H), 3.37-3.50 (m, 1H), 2.13 (d, J=11.3 Hz, 1H), 2.01 (br s, 1H), 1.92 (s, 3H), 1.62-1.81 (m, 2H), 1.17-1.49 (m, 4H). LCMS (ESI) m/z 409 (M+H)⁺.

Example 92

Preparation of 3-((2-(((1R,2R)-2-hydroxycyclohexyl)amino)benzo[d]thiazol-6-yl)methyl)-N,N-dimethyl-3H-imidazo[4,5-b]pyridine-6-carboxamide

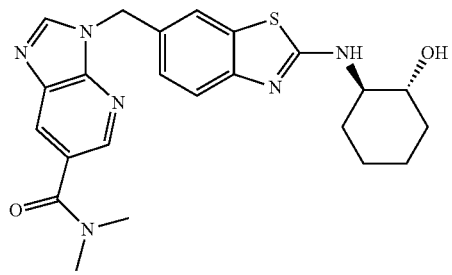 [SMILES: CN(C)C(=O)c1cnc2c(c1)ncn2Cc1ccc2nc(N[C@@H]3CCCC[C@H]3O)sc2c1]

To a stirred mixture of 3-((2-(((1R,2R)-2-hydroxycyclohexyl)amino)benzo[d]thiazol-6-yl)methyl)-3H-imidazo[4,5-b]pyridine-6-carboxylic acid (65 mg, 0.153 mmol) from Example 81 and TEA (77 mg, 0.767 mmol) in a mixture of anhydrous THF (1.5 mL) and anhydrous DMF (0.5 mL) at rt was added dimethylamine (2 M solution in MeOH, 383 µL, 0.767 mmol) followed by benzotriazol-1-yloxytris(dimethylamino)phosphonium hexafluorophosphate (102 mg, 0.230 mmol). The resulting mixture was stirred at rt for 2 h. The mixture was purified directly by reverse-phase HPLC using a mixture of water (5% CH₃CN, 0.05% HOAc) and CH₃CN (0.05% HOAc) as the mobile phase and Varian Pursuit XRs diphenyl column as the stationary phase to afford 3-((2-(((1R,2R)-2-hydroxycyclohexyl)amino)benzo[d]thiazol-6-yl)methyl)-N,N-dimethyl-3H-imidazo[4,5-b]pyridine-6-carboxamide (33 mg, 48%) as a white solid. ¹H NMR (300 MHz, DMSO-d₆) δ 8.70 (s, 1H), 8.45 (s, 1H), 8.16 (s, 1H), 7.96 (d, J=7.54 Hz, 1H), 7.68 (s, 1H), 7.20-7.33 (m, 2H), 5.50 (s, 2H), 4.73 (d, J=4.90 Hz, 1H), 3.51 (m, 1H), 3.30 (m, 1H), 2.99 (br. s., 6H), 2.02 (m, 1H), 1.87 (m, 1H), 1.5-1.65 (m, 2H), 1.10-1.30 (m, 4H). LCMS (ESI) m/z 451 (M+H)⁺.

Example 93

Preparation of (1R,2R)-2-((6-((6-(2H-tetrazol-5-yl)-3H-imidazo[4,5-b]pyridin-3-yl)methyl)benzo[d]thiazol-2-yl)amino)cyclohexanol

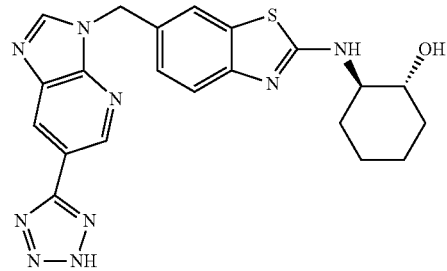 [SMILES: O[C@@H]1CCCC[C@H]1Nc1nc2ccc(Cn3cnc4cc(-c5nn[nH]n5)cnc43)cc2s1]

A stirred mixture of 3-((2-(((1R,2R)-2-hydroxycyclohexyl)amino)benzo[d]thiazol-6-yl)methyl)-3H-imidazo[4,5-b]pyridine-6-carbonitrile from Example 43 (120 mg, 0.30 mmol), NaN₃ (29 mg, 0.45 mmol) and NH₄Cl (24 mg, 0.45 mmol) in DMF (1.5 mL) was heated at 100° C. overnight.

LCMS showed the reaction mostly completed. A portion of the reaction mixture (~⅓) was cooled to rt and purified by preparative HPLC using a mixture of water (5% CH$_3$CN, 0.05% AcOH) and CH$_3$CN (0.05% AcOH) as the mobile phase and Varian Pursuit XRs Diphenyl column as the stationary phase to afford (1R,2R)-2-((6-((6-(2H-tetrazol-5-yl)-3H-imidazo[4,5-b]pyridin-3-yl)methyl)benzo[d]thiazol-2-yl)amino)cyclohexanol (4 mg, 9%) as a white powder. $^1$H NMR (300 MHz, MeOH-d$_4$) δ 9.13 (s, 1H), 8.67 (s, 1H), 8.60 (s, 1H), 7.76 (dd, J=7.5, 10.9 Hz, 2H), 7.69 (s, 1H), 5.60 (s, 2H), 3.56 (d, J=9.6 Hz, 1H), 3.37-3.50 (m, 1H), 1.92-2.21 (m, 2H), 1.72 (d, J=8.9 Hz, 2H), 1.17-1.49 (m, 4H). LCMS (ESI) m/z 448 (M+H)$^+$.

Example 94

Preparation of (1R,2R)-2-((6-((6-(2-methyl-2H-tetrazol-5-yl)-3H-imidazo[4,5-b]pyridin-3-yl)methyl)benzo[d]thiazol-2-yl)amino)cyclohexanol

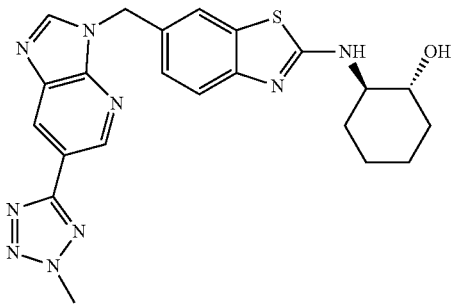 [SMILES: Cn1nnc(-c2cnc3c(c2)ncn3Cc2ccc3nc(N[C@@H]4CCCC[C@H]4O)sc3c2)n1]

To the remaining portion of the reaction mixture from Example 93 were added excess Cs$_2$CO$_3$ (300 mg) and excess MeI (200 μL). The resulting mixture was heated at 90° C. for 4 h. LCMS showed that the reaction was mostly completed. After cooling to rt, the mixture was purified by preparative HPLC using a mixture of water (5% CH$_3$CN, 0.05% AcOH) and CH$_3$CN (0.05% AcOH) as the mobile phase and Varian Pursuit XRs Diphenyl column as the stationary phase to afford (1R,2R)-2-((6-((6-(2-methyl-2H-tetrazol-5-yl)-3H-imidazo[4,5-b]pyridin-3-yl)methyl)benzo[d]thiazol-2-yl)amino)cyclohexanol (8 mg) as a white powder. The regiochemistry assignment of the compound was consistent with the result from a NMR Nuclear Overhauser Effect (NOE) experiment. $^1$H NMR (300 MHz, MeOH-d$_4$) δ 9.17 (s, 1H), 8.69 (s, 1H), 8.55 (s, 1H), 7.67 (s, 1H), 7.25-7.41 (m, 2H), 5.58 (s, 2H), 4.36-4.51 (m, 3H), 3.57 (d, J=9.6 Hz, 1H), 3.36-3.49 (m, 1H), 2.13 (d, J=11.3 Hz, 1H), 2.01 (br s, 1H), 1.71 (d, J=10.0 Hz, 2H), 1.12-1.48 (m, 4H). LCMS (ESI) m/z 462 (M+H)$^+$.

Example 95

Preparation of (1R,2R)-1-((6-((9H-purin-9-yl)methyl)benzo[d]thiazol-2-yl)amino)-2,3-dihydro-1H-inden-2-ol

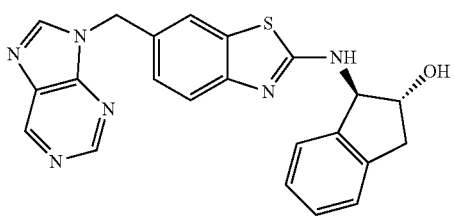 [SMILES: O[C@@H]1Cc2ccccc2[C@H]1Nc1nc2ccc(Cn3cnc4cncnc43)cc2s1]

Step 1:
6-((9H-Purin-9-yl)methyl)-2-(methylthio)benzo[d]thiazole was synthesized as a white solid (690 mg, 30%) using a procedure analogous to that described in Step 3 of Example 47, substituting 9H-purine for 5-bromo-6-methoxy-1H-benzo[d]-imidazole used in Example 47. The regiochemistry of the alkylation was determined by 2-dimensional nuclear Overhauser effect (NOE) experiment. $^1$H NMR (300 MHz, DMSO-d$_6$) δ 9.19 (s, 1H), 8.96 (s, 1H), 8.80 (s, 1H), 8.01 (d, J=0.9 Hz, 1H), 7.82 (d, J=8.3 Hz, 1H), 7.49 (dd, J=1.5, 8.5 Hz, 1H), 5.64 (s, 2H), 2.77 (s, 3H). LCMS (ESI) m/z 314 (M+H)$^+$.

Step 2:
6-((9H-Purin-9-yl)methyl)-2-(methylsulfinyl)benzo[d]thiazole was synthesized as a white foam (473 mg) using a procedure analogous to that described in Step 6 of Example 36, substituting 6-((9H-purin-9-yl)methyl)-2-(methylthio)benzo[d]thiazole from Step 1 of this Example for 6-((4-bromo-1H-imidazol-1-yl)methyl)-2-(methylthio)benzo[d]thiazole used in Example 36. LCMS (ESI) m/z 330 (M+H)$^+$.

Step 3:
To a mixture of 6-((9H-purin-9-yl)methyl)-2-(methylsulfinyl)benzo[d]thiazole (270 mg, 0.8 mmol) from Step 2 of the this Example and (1R,2R)-1-amino-2,3-dihydro-1H-inden-2-ol (246 mg, 1.6 mmol) in NMP (1.5 mL) was added DIEA (570 μL, 3.3 mmol). The reaction vessel was sealed and the mixture was heated at 150° C. in the Biotage microwave reactor for 1.5 h. The mixture was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford (1R,2R)-1-((6-((9H-purin-9-yl)methyl)benzo[d]thiazol-2-yl)amino)-2,3-dihydro-1H-inden-2-ol (71 mg, 21%) as a white powder. $^1$H NMR (300 MHz, DMSO-d$_6$) δ 9.18 (s, 1H), 8.97 (s, 1H), 8.77 (s, 1H), 8.47 (d, J=8.1 Hz, 1H), 7.74 (d, J=1.3 Hz, 1H), 7.37 (m, 1H), 7.30 (m, 1H), 7.11-7.25 (m, 4H), 5.45-5.57 (m, 3H), 5.18 (t, J=7.1 Hz, 1H), 4.28 (m, 1H), 3.16 (dd, J=6.9, 15.5 Hz, 1H), 2.74 (m, 1H). LCMS (ESI) m/z 415 (M+H)$^+$.

Example 96

Preparation of (1R,2R)-2-((6-((6-ethynyl-3H-imidazo[4,5-b]pyridin-3-yl)methyl)benzo[d]thiazol-2-yl)amino)cyclohexanol

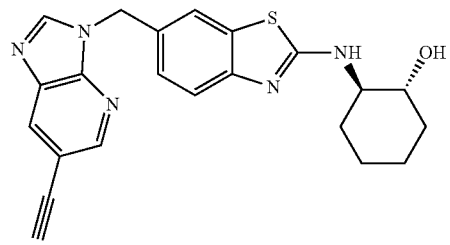 [SMILES: C#Cc1cnc2c(c1)ncn2Cc1ccc2nc(N[C@@H]3CCCC[C@H]3O)sc2c1]

Step 1:
6-Iodo-3H-imidazo[4,5-b]pyridine (3.78 g) was obtained using a procedure analogous to that described in Step 7 of Example 23, substituting 5-iodopyridine-2,3-diamine for 6-methoxy-N$^2$-((2-(methylthio)benzo[d]thiazol-6-yl)methyl)pyridine-2,3-diamine used in Example 23. LCMS (ESI) m/z 246 (M+H)$^+$.

Step 2:

(1R,2R)-2-((6-((6-Iodo-3H-imidazo[4,5-b]pyridin-3-yl)methyl)benzo[d]thiazol-2-yl)amino)cyclohexanol was obtained as an off-white solid using procedures analogous to those described in Steps 4-5 of Example 3 and Step 5 of Example 2, sequentially, substituting 6-iodo-3H-imidazo[4,5-b]pyridine from Step 1 of this Example for 3H-imidazo[4,5-b]pyridine used in Step 4 of Example 3, and then making the analogous substitutions for the starting materials used in Step 5 of Example 3 and Step 5 of Example 2. LCMS (ESI) m/z 506 (M+H)$^+$.

Step 3:

To a stirred suspension of (1R,2R)-2-((6-((6-iodo-3H-imidazo[4,5-b]pyridin-3-yl)methyl)benzo[d]thiazol-2-yl)amino)cyclohexanol (152 mg, 0.30 mmol) from Step 2 of this Example in DMF (3 mL) were added CuI (6 mg, 0.032 mmol) and PdCl$_2$(PPh$_3$)$_2$ (11 mg, 0.015 mmol). The mixture was purged with argon while ethynyltrimethylsilane (85 μL, 0.60 mmol) and TEA (127 μL, 0.90 mmol) were added sequentially. The resulting mixture was stirred at rt for 1 h. LCMS analysis showed that the reaction was complete. Water (30 mL) was added and the resulting dark brown solid was collected by filtration and dried to give crude (1R,2R)-2-((6-((6-((trimethylsilyl)ethynyl)-3H-imidazo[4,5-b]pyridin-3-yl)methyl)benzo[d]thiazol-2-yl)amino)cyclohexanol (100 mg, 70%). LCMS (ESI) m/z 476 (M+H)$^+$.

Step 4:

To a stirred solution of (1R,2R)-2-((6-((6-((trimethylsilyl)ethynyl)-3H-imidazo[4,5-b]pyridin-3-yl)methyl)benzo[d]thiazol-2-yl)amino)cyclohexanol (100 mg, 0.21 mmol) from Step 3 of this Example in MeOH (5 mL) was added excess K$_2$CO$_3$ (150 mg). The resulting mixture was stirred at rt for 30 min. LCMS analysis showed that the reaction was complete. The reaction mixture was filtered through a Celite plug and the filtrate was purified by preparative HPLC using a mixture of water (5% CH$_3$CN, 0.05% AcOH) and CH$_3$CN (0.05% AcOH) as the mobile phase and Varian Pursuit XRs Diphenyl column as the stationary phase to afford (1R,2R)-2-((6-((6-ethynyl-3H-imidazo[4,5-b]pyridin-3-yl)methyl)benzo[d]thiazol-2-yl)amino)cyclohexanol as a tan powder (40 mg, 47%). $^1$H NMR (300 MHz, DMSO-d$_6$) δ 8.69 (s, 1H), 8.50 (d, J=1.5 Hz, 1H), 8.23 (d, J=1.7 Hz, 1H), 8.02 (d, J=6.6 Hz, 1H), 7.66 (s, 1H), 7.26-7.34 (m, 1H), 7.15-7.26 (m, 1H), 5.49 (s, 2H), 4.29 (s, 1H), 3.26-3.38 (m, 2H), 2.03 (d, J=10.4 Hz, 1H), 1.85 (br s, 1H), 1.62 (d, J=4.7 Hz, 2H), 1.00-1.38 (m, 4H). LCMS (ESI) m/z 404 (M+H)$^+$.

Example 97

Preparation of (1R,2R)-2-((6-((6-morpholino-3H-imidazo[4,5-b]pyridin-3-yl)methyl)benzo[d]thiazol-2-yl)amino)cyclohexanol

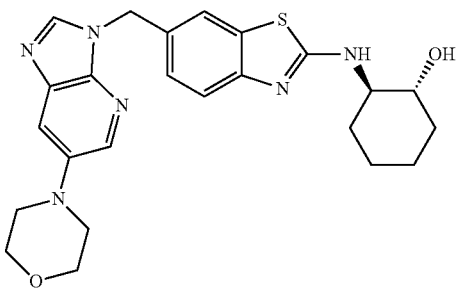 [SMILES: O[C@@H]1CCCC[C@H]1Nc1nc2ccc(Cn3cnc4cc(N5CCOCC5)cnc43)cc2s1]

To a stirred solution of (1R,2R)-2-((6-((6-iodo-3H-imidazo[4,5-b]pyridin-3-yl)methyl)benzo[d]thiazol-2-yl)amino)cyclohexanol from Step 2 of Example 96 (150 mg, 0.30 mmol) in DMSO (3 mL) were added morpholine (156 μL, 1.78 mmol), CuI (23 mg, 0.12 mmol), L-proline (14 mg, 0.12 mmol), and K$_2$CO$_3$ (123 mg, 0.89 mmol). The resulting mixture was flushed with argon, the reaction vessel was sealed and the mixture was heated at 100° C. for 2 h, then at 110° C. for 2 h. LCMS analysis showed that the reaction complete. The reaction mixture was cooled to rt, filtered through a Celite plug, and the filtrate was purified by preparative HPLC using a mixture of water (5% CH$_3$CN, 0.05% AcOH) and CH$_3$CN (0.05% AcOH) as the mobile phase and Varian Pursuit XRs Diphenyl column as the stationary phase to afford (1R,2R)-2-((6-((6-morpholino-3H-imidazo[4,5-b]pyridin-3-yl)methyl)benzo[d]thiazol-2-yl)amino)cyclohexanol (15 mg, 11%) as a tan powder. $^1$H NMR (300 MHz, DMSO-d$_6$) δ 8.46 (s, 1H), 8.22 (d, J=2.3 Hz, 1H), 8.03 (d, J=7.2 Hz, 1H), 7.63 (br s, 2H), 7.24-7.34 (m, 1H), 7.14-7.22 (m, 1H), 5.42 (s, 2H), 3.70-3.83 (m, 4H), 3.48-3.55 (m, 2H), 3.07-3.15 (m, 4H), 2.03 (d, J=10.2 Hz, 1H), 1.87 (d, J=9.6 Hz, 1H), 1.61 (br s, 2H), 1.22 (d, J=7.3 Hz, 4H). LCMS (ESI) m/z 465 (M+H)$^+$.

Example 98

Preparation of (1R,2R)-2-((6-((6-vinyl-3H-imidazo[4,5-b]pyridin-3-yl)methyl)benzo[d]thiazol-2-yl)amino)cyclohexanol

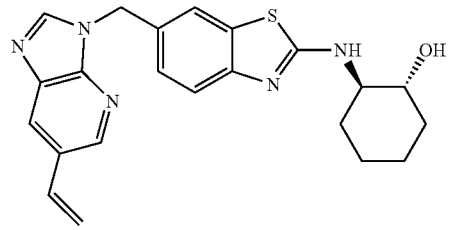 [SMILES: C=Cc1cnc2c(c1)ncn2Cc1ccc2nc(N[C@@H]3CCCC[C@H]3O)sc2c1]

To a stirred mixture of (1R,2R)-2-((6-((6-bromo-3H-imidazo[4,5-b]pyridin-3-yl)methyl)benzo[d]thiazol-2-yl)amino)cyclohexanol (200 mg, 0.44 mmol) from Example 29 in n-PrOH were added potassium vinyltrifluoroborate (117 mg, 0.88 mmol), PdCl$_2$(dppf).DCM (18 mg, 0.022 mmol), and TEA (122 μL, 0.88 mmol). The resulting mixture was purged with argon for 5 min, the reaction vessel was sealed and the mixture was heated at 100° C. overnight. LCMS analysis showed that the reaction was complete. The reaction mixture was cooled to rt and purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford (1R,2R)-2-((6-((6-vinyl-3H-imidazo[4,5-b]pyridin-3-yl)methyl)benzo[d]thiazol-2-yl)amino)cyclohexanol as a tan powder (40 mg, 23%). $^1$H NMR (300 MHz, MeOH-d$_4$) δ 8.50 (d, J=1.7 Hz, 1H), 8.43 (s, 1H), 8.15 (d, J=1.7 Hz, 1H), 7.63 (s, 1H), 7.32-7.41 (m, 1H), 7.25-7.32 (m, 1H), 6.91 (dd, J=10.9, 17.7 Hz, 1H), 5.91 (d, J=17.5 Hz, 1H), 5.53 (s, 2H), 5.35 (d, J=11.1 Hz, 1H), 3.5-3.66 (m, 1H), 3.37-3.49 (m, 1H), 2.14 (d, J=12.1 Hz, 1H), 2.01 (br s, 1H), 1.63-1.82 (m, 2H), 1.13-1.50 (m, 4H). LCMS (ESI) m/z 406 (M+H)$^+$.

Example 99

Preparation of N-((3-((2-(((1R,2R)-2-hydroxycyclohexyl)amino)benzo[d]thiazol-6-yl)methyl)-3H-imidazo[4,5-b]pyridin-6-yl)methyl)acetamide

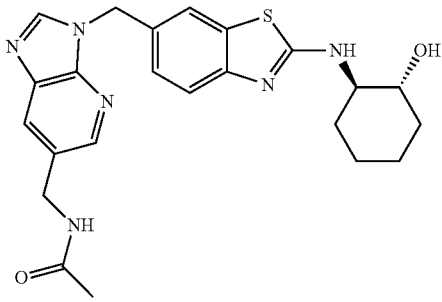 [SMILES: CC(=O)NCc1cnc2c(c1)ncn2Cc1ccc2nc(N[C@@H]3CCCC[C@H]3O)sc2c1]

To a stirred solution of (1R,2R)-2-((6-((6-(aminomethyl)-3H-imidazo[4,5-b]pyridin-3-yl)methyl)benzo[d]thiazol-2-yl)amino)cyclohexanol (50 mg, 0.12 mmol) from Example 91 in DCM (2 mL) were added pyridine (40 µL, 0.48 mmol) and AcCl (27 µL, 0.36 mmol). The resulting mixture was stirred at rt for 3 h before it was concentrated under reduced pressure. The residue was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford N-((3-((2-(((1R,2R)-2-hydroxycyclohexyl)amino)benzo[d]thiazol-6-yl)methyl)-3H-imidazo[4,5-b]pyridin-6-yl)methyl)acetamide (45 mg, 82%) as a white powder. $^1$H NMR (300 MHz, DMSO-d$_6$) δ 8.58 (s, 1H), 8.40 (br s, 1H), 8.31 (s, 1H), 7.84-8.10 (m, 2H), 7.65 (s, 1H), 7.24-7.41 (m, 1H), 7.10-7.24 (m, 1H), 5.47 (s, 2H), 4.37 (d, J=5.5 Hz, 2H), 3.34 (d, J=8.7 Hz, 2H), 1.97-2.16 (m, 1H), 1.89 (br s, 1H), 1.86 (s, 3H), 1.61 (br s, 2H), 0.99-1.39 (m, 4H). LCMS (ESI) m/z 451 (M+H)$^+$.

Example 100

Preparation of (1R,2R)-2-((6-((5-bromo-1H-benzo[d]imidazol-1-yl)methyl)benzo[d]thiazol-2-yl)amino)cyclohexanol

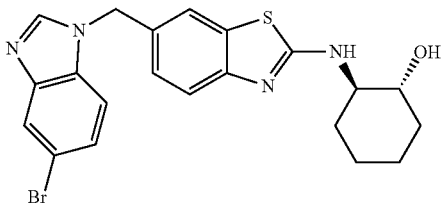

Step 1:

To a stirred mixture of (2-(methylthio)benzo[d]thiazol-6-yl)methanol (958 mg, 4.5 mmol) from Step 3 of Example 36 in CH$_2$Cl$_2$ (20 mL) at 0° C. under argon was added Dess-Martin periodinane (2.0 g, 5.0 mmol) portionwise. The mixture was stirred for 1 h and then diluted with CH$_2$Cl$_2$ (100 mL). To this mixture was added a 50/50 mixture of saturated aq sodium sulfite and saturated aq sodium bicarbonate (40 mL). This mixture was stirred for 10 min and then the CH$_2$Cl$_2$ layer was separated, washed with a saturated aq sodium bicarbonate (50 mL), dried over Na$_2$SO$_4$, filtered, and concentrated under reduced pressure to afford 2-(methylthio)benzo[d]thiazole-6-carbaldehyde (937 mg, 99%) as a white solid. LCMS (ESI) m/z 210 (M+H)$^+$.

Step 2:

To a stirred mixture of 4-bromo-2-nitroaniline (694 mg, 3.2 mmol) in TFA (5 mL) at −15° C. under argon was added NaBH(OAc)$_3$ (1.1 g, 5.3 mmol) portionwise. The mixture was stirred for 10 min. To the stirred mixture was added dropwise 2-(methylthio)benzo[d]thiazole-6-carbaldehyde (735 mg, 3.5 mmol) from Step 1 of this Example in CH$_2$Cl$_2$ (3 mL). The mixture was stirred for 1 h and then concentrated under reduced pressure. The residue was purified by silica gel flash chromatography eluting with a gradient of 100% hexanes to 100% EtOAc to afford 4-bromo-N-((2-(methylthio)benzo[d]thiazol-6-yl)methyl)-2-nitroaniline (1.0 g, 77%) as a yellow solid. $^1$H NMR (300 MHz, DMSO-d$_6$) δ 8.84 (t, J=6.0 Hz, 1H), 8.19 (d, J=2.4 Hz, 1H), 7.98 (s, 1H), 7.81 (d, J=8.3 Hz, 1H), 7.56 (dd, J=2.4, 9.3 Hz, 1H), 7.46 (d, J=8.3 Hz, 1H), 6.88 (d, J=9.2 Hz, 1H), 4.75 (d, J=6.0 Hz, 2H), 2.77 (s, 3H). LCMS (ESI) m/z 410 and 412 (M+H)$^+$.

Step 3:

4-Bromo-N$^1$-((2-(methylthio)benzo[d]thiazol-6-yl)methyl)benzene-1,2-diamine was synthesized as an oil (1 g) using a procedure analogous to that described in Step 2 of Example 41, substituting 4-bromo-N-((2-(methylthio)benzo[d]thiazol-6-yl)methyl)-2-nitroaniline from Step 2 of this Example for 4-bromo-5-methoxy-N-((2-(methylthio)benzo[d]thiazol-6-yl)methyl)-2-nitroaniline used in Example 41. LCMS (ESI) m/z 379 and 381 (M+H)$^+$.

Step 4:

6-((5-Bromo-1H-benzo[d]imidazol-1-yl)methyl)-2-(methylthio)benzo[d]thiazole was synthesized as a white solid (630 mg, 57%) using a procedure analogous to that described in Step 3 of Example 41, substituting 4-bromo-N$^1$-((2-(methylthio)benzo[d]thiazol-6-yl)methyl)benzene-1,2-diamine from Step 3 of this Example for 4-bromo-5-methoxy-N$^2$-((2-(methylthio)benzo[d]thiazol-6-yl)methyl)benzene-1,2-diamine used in Example 41. $^1$H NMR (300 MHz, DMSO-d$_6$) δ 8.51 (s, 1H), 8.00 (s, 1H), 7.75-7.91 (m, 2H), 7.54 (d, J=8.5 Hz, 1H), 7.33-7.45 (m, 2H), 5.62 (s, 2H), 2.77 (s, 3H). LCMS (ESI) m/z 389 and 391 (M+H)$^+$.

Step 5:

6-((5-Bromo-1H-benzo[d]imidazol-1-yl)methyl)-2-(methylsulfinyl)benzo[d]thiazole was synthesized as a white foam (1.0 g) using a procedure analogous to that described in Step 6 of Example 36, substituting 6-((5-bromo-1H-benzo[d]imidazol-1-yl)methyl)-2-(methylthio)benzo[d]thiazole from Step 4 of this Example for the 6-((4-bromo-1H-imidazol-1-yl)methyl)-2-(methylthio)benzo[d]thiazole used in Example 36. LCMS (ESI) m/z 405 and 407 (M+H)$^+$.

Step 6:

(1R,2R)-2-((6-((5-Bromo-1H-benzo[d]imidazol-1-yl)methyl)benzo[d]thiazol-2-yl)amino)cyclohexanol was synthesized as a white powder (36 mg, 36%) using a procedure analogous to that described in Step 7 of Example 36, substituting 6-((5-bromo-1H-benzo[d]imidazol-1-yl)methyl)-2-(methylsulfinyl)benzo[d]thiazole from Step 5 of this Example for 6-((4-bromo-1H-imidazol-1-yl)methyl)-2-(methylsulfinyl)benzo[c]thiazole used in Example 36. $^1$H NMR (300 MHz, DMSO-d$_6$) δ 8.46 (s, 1H), 8.00 (d, J=7.5 Hz, 1H), 7.85 (d, J=1.7 Hz, 1H), 7.64 (d, J=1.3 Hz, 1H), 7.54 (d, J=8.7 Hz, 1H), 7.25-7.39 (m, 2H), 7.18 (dd, J=1.5, 8.3 Hz, 1H), 5.47 (s, 2H), 4.76 (m, 1H), 3.50 (m, 1H), 3.33 (m, 1H), 2.02 (m, 1H), 1.87 (m, 1H), 1.5-1.65 (m, 2H), 1.12-1.32 (m, 4H). LCMS (ESI) m/z 456 and 458 (M+H)⁺.

Example 101

Preparation of N-(1-((2-(((1R,2R)-2-hydroxycyclohexyl)amino)benzo[d]thiazol-6-yl)methyl)-1H-imidazol-4-yl)acetamide

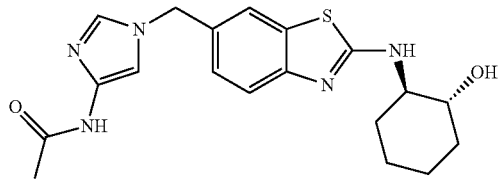 [SMILES: CC(=O)Nc1cn(Cc2ccc3nc(N[C@@H]4CCCC[C@H]4O)sc3c2)cn1]

Step 1:

To a mixture of the regioisomers 4-bromo-1-((2-(trimethylsilyl)ethoxy)methyl)-1H-imidazole and 5-bromo-1-((2-(trimethylsilyl)ethoxy)methyl)-1H-imidazole (643 mg, 2.3 mmol) from Step 1 of Example 32, acetamide (275 mg, 5.0 mmol), and Cs₂CO₃ (1.5 g, 5 mmol) in 1,4-dioxane (7 mL) was added N,N'-dimethylethylenediamine (500 µL, 5 mmol). Argon was bubbled into the mixture for 5 min followed by the addition of CuI (221 mg, 1.1 mmol). Argon was bubbled into the mixture for an additional 5 min. Then the reaction vessel was sealed and the mixture was heated at 100° C. for 15 h. The mixture was cooled to rt, then partitioned between EtOAc (100 mL) and water (50 mL). The EtOAc layer was separated, washed with brine, dried over Na₂SO₄, filtered, and concentrated under reduced pressure. The residue was purified by silica gel flash chromatography eluting with a gradient of 100% hexanes to 100% EtOAc to afford a mixture of regioisomers N-(1-((2-(trimethylsilyl)ethoxy)methyl)-1H-imidazol-4-yl)acetamide and N-(1-((2-(trimethylsilyl)ethoxy)methyl)-1H-imidazol-5-yl)acetamide (170 mg, 29%) as an oil. LCMS (ESI) m/z 256 (M+H)⁺.

Step 2:

The mixture of regioisomers N-(1-((2-(trimethylsilyl)ethoxy)methyl)-1H-imidazol-4-yl)acetamide and N-(1-((2-(trimethylsilyl)ethoxy)methyl)-1H-imidazol-5-yl)acetamide (170 mg, 0.7 mmol) from Step 1 of this Example was stirred in 70% TFA in CH₂Cl₂ (10 mL) at rt for 4 h. The mixture was concentrated under reduced pressure to afford N-(1H-imidazol-4-yl)acetamide (147 mg) as a yellow film which was used in the next step without further purification. LCMS (ESI) m/z 126 (M+H)⁺.

Step 3:

N-(1-((2-(Methylthio)benzo[d]thiazol-6-yl)methyl)-1H-imidazol-4-yl)acetamide was synthesized as a white solid (58 mg, 15%) using a procedure analogous to that described in Step 5 of Example 36, substituting N-(1H-imidazol-4-yl)acetamide from Step 2 of this Example for 4-bromo-1H-imidazole used in Example 36. The regiochemistry of the alkylation was determined by 2-dimensional nuclear Overhauser effect (NOE) experiment. ¹H NMR (300 MHz, DMSO-d₆) δ 10.27 (s, 1H), 7.94 (s, 1H), 7.83 (d, J=8.5 Hz, 1H), 7.60 (s, 1H), 7.38 (d, J=8.5 Hz, 1H), 7.20 (s, 1H), 5.24 (s, 2H), 2.78 (s, 3H), 1.94 (s, 3H). LCMS (ESI) m/z 319 (M+H)⁺.

Step 4:

N-(1-((2-(Methylsulfinyl)benzo[d]thiazol-6-yl)methyl)-1H-imidazol-4-yl)acetamide was synthesized as a white foam (106 mg) using a procedure analogous to that described in Step 6 of Example 36, substituting N-(1-((2-(methylthio)benzo[d]thiazol-6-yl)methyl)-1H-imidazol-4-yl)acetamide from Step 3 of this Example for 6-((4-bromo-1H-imidazol-1-yl)methyl)-2-(methylthio)benzo[d]thiazole used in Example 36. LCMS (ESI) m/z 351 (M+H)⁺

Step 5:

N-(1-((2-(((1R,2R)-2-Hydroxycyclohexyl)amino)benzo[d]thiazol-6-yl)methyl)-1H-imidazol-4-yl)acetamide was synthesized as a white powder (4 mg) using a procedure analogous to that described in Step 7 of Example 36, substituting N-(1-((2-(methylsulfinyl)benzo[d]thiazol-6-yl)methyl)-1H-imidazol-4-yl)acetamide from Step 4 of this Example for 6-((4-bromo-1H-imidazol-1-yl)methyl)-2-(methylsulfinyl)benzo[d]thiazole used in Example 36. The powder was further purified by preparative TLC eluting with 10% MeOH in CH₂Cl₂ to afford N-(1-((2-(((1R,2R)-2-hydroxycyclohexyl)amino)benzo[d]thiazol-6-yl)methyl)-1H-imidazol-4-yl)acetamide (2 mg, 2%) as a white solid. ¹H NMR (300 MHz, MeOH-d₄) δ 7.50 (s, 2H), 7.35 (d, J=8.1 Hz, 1H), 7.12-7.25 (m, 2H), 5.13 (s, 2H), 3.60 (m, 1H), 3.43 (m, 1H), 1.96-2.20 (m, 5H), 1.67-1.80 (m, 2H), 1.20-1.47 (m, 4H). LCMS (ESI) m/z 386 (M+H)⁺.

Example 102

Preparation of (1R,2R)-2-((6-((6-ethyl-3H-imidazo[4,5-b]pyridin-3-yl)methyl)benzo[d]thiazol-2-yl)amino)cyclohexanol

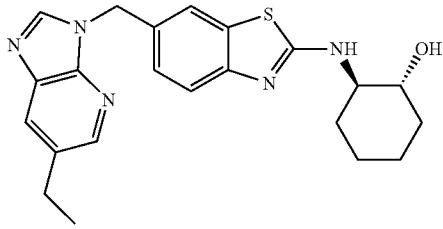 [SMILES: CCc1cnc2c(c1)ncn2Cc1ccc2nc(N[C@@H]3CCCC[C@H]3O)sc2c1]

To a stirred solution of (1R,2R)-2-((6-((6-vinyl-3H-imidazo[4,5-b]pyridin-3-yl)methyl)benzo[d]thiazol-2-yl)amino)cyclohexanol (20 mg, 0.049 mmol) from Example 98 in 1:1 MeOH/THF (2 mL) was added Raney Ni (10 mg). The resulting mixture was stirred under a H₂ balloon at rt for 4 h. LCMS analysis showed that the reaction was complete. The reaction mixture was filtered through a Celite plug and the filtrate was purified with preparative TLC to give (1R,2R)-2-((6-((6-ethyl-3H-imidazo[4,5-b]pyridin-3-yl)methyl)benzo[d]thiazol-2-yl)amino)cyclohexanol (6 mg, 30%). ¹H NMR (300 MHz, DMSO-d₆) δ 8.53 (br s, 1H), 8.26 (br s, 1H), 7.95 (d, J=12.4 Hz, 2H), 7.66 (br s, 1H), 7.25-7.42 (m, 1H), 7.06-7.25 (m, 1H), 5.45 (br s, 2H), 4.74 (d, J=4.5 Hz, 1H), 3.51 (br s, 1H), 2.73 (d, J=7.2 Hz, 2H), 2.04 (br s, 1H), 1.86 (br s, 1H), 1.62 (br s, 2H), 1.23 (t, J=6.8 Hz, 7H). LCMS (ESI) m/z 408 (M+H)⁺.

Example 103

Preparation of 1-((2-(((1R,2R)-2-hydroxycyclohexyl)amino)benzo[d]thiazol-6-yl)methyl)-3-(1-methyl-1H-pyrazol-4-yl)pyrazin-2(1H)-one

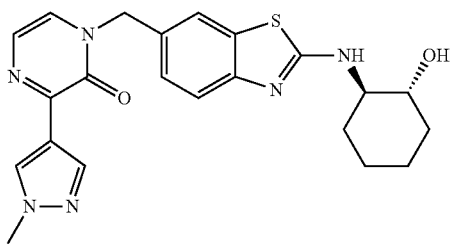 [SMILES: Cn1cc(-c2nccn(Cc3ccc4nc(N[C@@H]5CCCC[C@H]5O)sc4c3)c2=O)cn1]

Step 1:
To 2,3-dichloropyrazine (1.12 g, 7.52 mmol), 1-methyl-4-(4,4,5,5-tetramethyl-1,3,2-dioxaborolan-2-yl)-1H-pyrazole (1.56 g, 7.52 mmol), bis(triphenylphosphine)palladium (II) dichloride (270 mg, 0.38 mmol), and Na$_2$CO$_3$ (2.4 g, 22.56 mmol) in a pressure tube were added 1,2-dimethoxyethane (15 mL) and water (2 mL). The flask was evacuated and flushed with argon (3×) and then sealed and heated at 90° C. overnight. The mixture was concentrated under reduced pressure and purified by silica gel chromatography eluting with 20-100% EtOAc/hexanes to afford 2-chloro-3-(1-methyl-1H-pyrazol-4-yl)pyrazine (780 mg, 53%). LCMS (ESI) m/z 195 (M+H)$^+$.

Step 2:
To 2-chloro-3-(1-methyl-1H-pyrazol-4-yl)pyrazine (200 mg, 1.03 mmol) from Step 1 of this Example in DMSO (1.5 mL) and water (1.5 mL) was added KOH (890 mg, 15.4 mmol) and the mixture was heated at 80° C. for 3 h. The mixture was cooled and partitioned between EtOAc and 4 N HCl. The aqueous layer was concentrated under reduced pressure and then a mixture of MeOH and EtOH was added and the suspension was filtered through Celite. The filtrate was concentrated under reduced pressure and then Et$_2$O was added and the mixture again concentrated under reduced pressure. The residue was triturated with DCM and filtered to afford crude 3-(1-methyl-1H-pyrazol-4-yl)pyrazin-2(1H)-one (300 mg, quantitative) as a yellow solid. $^1$H NMR (300 MHz, DMSO-d$_6$) δ 8.60 (s, 1H), 8.18 (s, 1H), 7.24-7.39 (m, 2H), 3.91 (s, 3H).

Step 3:
To 3-(1-methyl-1H-pyrazol-4-yl)pyrazin-2(1H)-one (139 mg, 0.78 mmol) from Step 2 of this Example in DMF (3 mL) was added NaH (60% in mineral oil, 32 mg, 0.78 mmol) and the mixture was stirred at rt for 10 min. 6-(Chloromethyl)-2-(methylthio)benzo[d]thiazole (180 mg, 0.78 mmol) from Step 4 of Example 36 was then added. The mixture was stirred at rt overnight and then concentrated under reduced pressure. The residue was purified by silica gel chromatography eluting with 0-15% MeOH/DCM to afford impure 3-(1-methyl-1H-pyrazol-4-yl)-1-((2-(methylthio)benzo[d]thiazol-6-yl)methyl)pyrazin-2(1H)-one (80 mg, 27%) which was used without further purification. LCMS (ESI) m/z 370 (M+H)$^1$.

Step 4:
To 3-(1-Methyl-1H-pyrazol-4-yl)-1-((2-(methylthio)benzo[d]thiazol-6-yl)methyl)pyrazin-2(1H)-one (80 mg, 0.21 mmol) from Step 3 of this Example in DCM (5 mL) at 0° C. was added 3-chloroperbenzoic acid (70%, 75 mg, 0.3 mmol) and the mixture was stirred for 20 min. The mixture was diluted with DCM and then washed with aq sodium thiosulfate and saturate aq sodium bicarbonate. The organic layer was dried over sodium sulfate and concentrated under reduced pressure. To the residue was added N,N-dimethylacetamide (4 mL), DIEA (0.075 mL, 0.43 mmol) and (1R,2R)-2-aminocyclohexanol (50 mg, 0.43 mmol). The mixture was heated at 100° C. for 3 d and then purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford 1-((2-(((1R,2R)-2-hydroxycyclohexyl)amino)benzo[d]thiazol-6-yl)methyl)-3-(1-methyl-1H-pyrazol-4-yl)pyrazin-2(1H)-one (7 mg, 8%). $^1$H NMR (300 MHz, DMSO-d$_6$) δ 8.55 (s, 1H), 8.09 (s, 1H), 8.00 (d, J=7.54 Hz, 1H), 7.66-7.71 (m, 2H), 7.35 (d, J=4.33 Hz, 1H), 7.29-7.33 (m, 1H), 7.22-7.27 (m, 1H), 5.14 (s, 2H), 4.77 (br. s., 1H), 3.89 (s, 3H) 3.52 (br. s., 1H), 2.04 (d, J=10.36 Hz, 1H), 1.89 (br. s., 1H), 1.63 (br. s., 2H), 1.23 (d, J=5.84 Hz, 4H). LCMS (ESI) m/z 437 (M+H)$^+$.

Example 104

Preparation of (1R,2R)-2-((6-((6-(3-hydroxy-3-methylbut-1-yn-1-yl)-3H-imidazo[4,5-b]pyridin-3-yl)methyl)benzo[d]thiazol-2-yl)amino)cyclohexanol

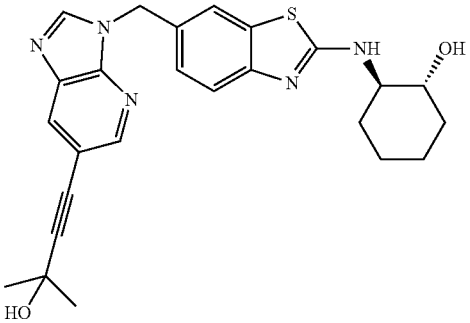 [SMILES: CC(C)(O)C#Cc1cnc2c(c1)ncn2Cc1ccc2nc(N[C@@H]3CCCC[C@H]3O)sc2c1]

(1R,2R)-2-((6-((6-(3-Hydroxy-3-methylbut-1-yn-1-yl)-3H-imidazo[4,5-b]pyridin-3-yl)methyl)benzo[d]thiazol-2-yl)amino)cyclohexanol (125 mg, 91%) was obtained as a white powder using a procedure analogous to that described in Step 3 of Example 96, substituting 2-methylbut-3-yn-2-ol for ethynyltrimethylsilane used in Example 96. $^1$H NMR (300 MHz, DMSO-d$_6$) δ 8.67 (br s, 1H), 8.41 (s, 1H), 8.10 (br s, 1H), 7.99 (d, J=7.3 Hz, 1H), 7.66 (s, 1H), 7.26-7.36 (m, 1H), 7.17-7.26 (m, 1H), 5.48 (s, 2H), 4.77 (br s, 1H), 3.48-3.61 (m, 2H), 2.03 (d, J=10.2 Hz, 1H), 1.88 (d, J=10.0 Hz, 1H), 1.62 (d, J=4.5 Hz, 2H), 1.49 (s, 6H), 1.22 (d, J=5.8 Hz, 4H). LCMS (ESI) m/z 462 (M+H)$^+$.

Example 105

Preparation of (1R,2R)-2-((6-((2-(trifluoromethyl)-9H-purin-9-yl)methyl)benzo[d]thiazol-2-yl)amino)cyclohexanol

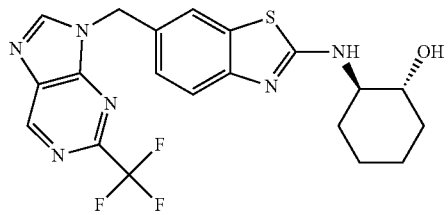 [SMILES: O[C@@H]1CCCC[C@H]1Nc1nc2ccc(Cn3cnc4cnc(C(F)(F)F)nc43)cc2s1]

Step 1:

2-(Trifluoromethyl)-9H-purine (940 mg, 94%) was obtained as a white solid using a procedure analogous to that described in Step 7 of Example 23, substituting 2-(trifluoromethyl)pyrimidine-4,5-diamine for 6-methoxy-$N^2$-((2-(methylthio)benzo[d]thiazol-6-yl)methyl)pyridine-2,3-diamine used in Example 23. LCMS (ESI) m/z 189 (M+H)$^+$.

Step 2:

2-(Methylthio)-6-((2-(trifluoromethyl)-9H-purin-9-yl)methyl)benzo[d]thiazole (480 mg, 47%) was obtained as an oil using a procedure analogous to that described in Step 1 of Example 63, substituting 2-(trifluoromethyl)-9H-purine from Step 1 of this Example for 4-azabenzimidazole used in Example 63. LCMS (ESI) m/z 382 (M+H)$^+$.

Step 3:

(1R,2R)-2-((6-((2-(Trifluoromethyl)-9H-purin-9-yl)methyl)benzo[d]thiazol-2-yl)amino)cyclohexanol was obtained as a light brown solid using procedures analogous to those described in Step 5 of Example 3 followed by procedures analogous to those used in Step 5 of Example 2, substituting 2-(methylthio)-6-((2-(trifluoromethyl)-9H-purin-9-yl)methyl)benzo[d]thiazole from Step 2 of this Example for 6-((3H-imidazo[4,5-b]pyridin-3-yl)methyl)-2-(methylthio)benzo[d]thiazole used in Example 3, and substituting the product of that reaction for the 2-bromo-6-((5,6-dimethoxy-1H-benzo[d]imidazol-1-yl)methyl)benzo[d]thiazole used in Example 2. $^1$H NMR (300 MHz, DMSO-d$_6$) δ 9.39 (s, 1H), 8.97 (s, 1H), 8.05 (d, J=7.5 Hz, 1H), 7.69 (s, 1H), 7.29-7.39 (m, 1H), 7.14-7.28 (m, 1H), 5.56 (s, 2H), 4.81 (br s, 1H), 3.50 (d, J=7.7 Hz, 2H), 1.96-2.17 (m, 1H), 1.88 (d, J=9.6 Hz, 1H), 1.62 (br s, 2H), 0.93-1.41 (m, 4H). LCMS (ESI) m/z 449 (M+H)$^+$.

Example 106

Preparation of (1R,2R)-2-((6-((5-(methylsulfonyl)-3H-imidazo[4,5-b]pyridin-3-yl)methyl)benzo[d]thiazol-2-yl)amino)cyclohexanol

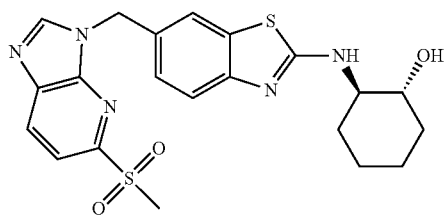 [SMILES: CS(=O)(=O)c1ccc2ncn(Cc3ccc4nc(N[C@@H]5CCCC[C@H]5O)sc4c3)c2n1]

A stirred mixture of (1R,2R)-2-((6-((5-bromo-3H-imidazo[4,5-b]pyridin-3-yl)methyl)benzo[d]thiazol-2-yl)amino)cyclohexanol (89 mg, 0.194 mmol) from Example 78, sodium methane sulfinate (80 mg, 0.777 mmol), and N,N-dimethylethylenediamine (7 mg, 0.078 mmol) in anhydrous DMSO (2 mL) at rt was purged for 15 min with a stream of argon. To the resulting mixture was added copper (I) trifluoromethane-sulfonate benzene complex (20 mg, 0.038 mmol). The reaction vessel was sealed and the mixture was stirred at 125° C. for 5 h. After cooling to rt, the reaction mixture was purified directly by reverse-phase HPLC using a mixture of water (5% CH$_3$CN, 0.05% HOAc) and CH$_3$CN (0.05% HOAc) as the mobile phase and Varian Pursuit XRs diphenyl column as the stationary phase to afford (1R,2R)-2-((6-((5-(methylsulfonyl)-3H-imidazo[4,5-b]pyridin-3-yl)methyl)benzo[d]thiazol-2-yl)amino)cyclohexanol (33 mg, 37%) as a white solid. $^1$H NMR (300 MHz, DMSO-d$_6$) δ 8.91 (s, 1H), 8.39 (d, J=8.3 Hz, 1H), 7.90-8.02 (m, 2H), 7.78 (s, 1H), 7.25-7.36 (m, 2H), 5.54 (s, 2H), 4.74 (br s, 1H), 3.50 (br s, 1H), 3.33-3.34 (m, 4H), 2.02 (m, 1H), 1.87 (m, 1H), 1.5-1.65 (m, 2H), 1.15-1.30 (m, 4H); LCMS (ESI) m/z 458 (M+H)$^+$.

Example 107

Preparation of (1R,2R)-2-((6-((6-bromo-1H-benzo[d]imidazol-1-yl)methyl)benzo[d]thiazol-2-yl)amino)cyclohexanol

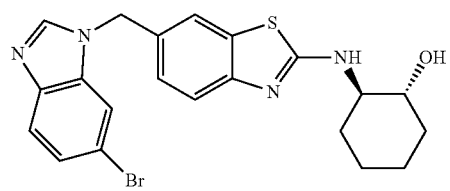 [SMILES: O[C@@H]1CCCC[C@H]1Nc1nc2ccc(Cn3cnc4ccc(Br)cc43)cc2s1]

Step 1:

To a stirred mixture of (2-(methylthio)benzo[d]thiazol-6-yl)methanol (958 mg, 4.5 mmol) from Step 3 of Example 36 in CH$_2$Cl$_2$ (20 mL) at 0° C. under argon was added Dess-Martin periodinane (2.1 g, 5.0 mmol) in small portions. After the mixture was stirred for 1 hr at 0° C., it was diluted with CH$_2$Cl$_2$ (100 mL) followed by the addition of a 1:1 mixture of saturated aq Na$_2$SO$_3$ and saturated aq NaHCO$_3$ (40 mL). The mixture was stirred for 10 min. The layers were separated and the CH$_2$Cl$_2$ layer was sequentially washed with saturated aq NaHCO$_3$ (50 mL) and brine (50 mL). The organic layer was separated and dried over Na$_2$SO$_4$, filtered, and concentrated under reduced pressure to yield 2-(methylthio)benzo[d]thiazole-6-carbaldehyde (937 mg, 99%) as an off white solid which did not require further purification. $^1$H NMR (300 MHz, DMSO-d$_6$) δ 10.06 (s, 1H), 8.62 (s, 1H), 7.99 (s, 2H), 2.84 (s, 3H); LCMS (ESI) m/z 210 (M+H)$^+$.

Step 2:

To a stirred mixture of 5-bromo-2-nitroaniline (714 mg, 4.0 mmol) in TFA (7 mL) at −15° C. under argon, was added NaBH(OAc)$_3$ (1.2 g, 5.4 mmol) in small portions. The mixture was stirred for 15 min, then a solution of 2-(methylthio)benzo[d]thiazole-6-carbaldehyde in CH$_2$Cl$_2$ (2 mL) was added dropwise. The mixture was stirred for 30 min then concentrated under reduced pressure to give a red oil. The oil was partitioned between EtOAc (200 mL) and saturated aq NaHCO$_3$ (100 mL). The organic layer was separated and washed with brine (100 mL). The organic layer was separated, dried over Na$_2$SO$_4$, filtered, and concentrated under reduced pressure. The residue was purified by silica gel flash chromatography eluting with a gradient of 100% hexanes to 50% hexanes in EtOAc to afford 5-bromo-N-((2-(methylthio)benzo[d]thiazol-6-yl)methyl)-2-nitroaniline (1.1 g, 73%) as a yellow solid. LCMS (ESI) m/z 409, 411 (M+H)$^+$.

Step 3:

5-Bromo-$N^1$-((2-(methylthio)benzo[d]thiazol-6-yl)methyl)benzene-1,2-diamine was synthesized as a brown solid (920 mg) using a procedure analogous to that described in Step 2 of Example 41, substituting 5-bromo-N-((2-(methylthio)benzo[d]thiazol-6-yl)methyl)-2-nitroaniline from the previous step for 4-bromo-5-methoxy-N-((2-(methylthio)

benzo[d]thiazol-6-yl)methyl)-2-nitroaniline used in Example 41. LCMS (ESI) m/z 379, 381 (M+H)+.

Step 4:

6-((6-Bromo-1H-benzo[d]imidazol-1-yl)methyl)-2-(methylthio)benzo[d]thiazole was synthesized as a yellow solid (701 mg, 70%) using a procedure analogous to that described in Step 3 of Example 41, substituting 5-bromo-$N^1$-((2-(methylthio)benzo[d]thiazol-6-yl)methyl)benzene-1,2-diamine from the previous step for 4-bromo-5-methoxy-$N^1$-((2-(methylthio)benzo[d]thiazol-6-yl)methyl)benzene-1,2-diamine used in Example 41. LCMS (ESI) m/z 389, 391 (M+H)+.

Step 5:

6-((6-Bromo-1H-benzo[d]imidazol-1-yl)methyl)-2-(methylsulfinyl)benzo[d]thiazole was synthesized as a yellow foam (811 mg) using a procedure analogous to that described in Step 6 of Example 36, substituting 6-((6-bromo-1H-benzo[d]imidazol-1-yl)methyl)-2-(methylthio)benzo[d]thiazole from the previous step for 6-((4-bromo-1H-imidazol-1-yl)methyl)-2-(methylthio)benzo[d]thiazole used in Example 36. LCMS (ESI) m/z 405, 407 (M+H)+.

Step 6:

(1R,2R)-2-((6-((6-Bromo-1H-benzo[d]imidazol-1-yl)methyl)benzo[d]thiazol-2-yl)amino)cyclohexanol was synthesized using a procedure analogous to that described in Step 7 of Example 36, substituting 6-((6-bromo-1H-benzo[d]imidazol-1-yl)methyl)-2-(methylsulfinyl)benzo[d]thiazole from the previous step for 6-((4-bromo-1H-imidazol-1-yl)methyl)-2-(methylsulfinyl)benzo[d]thiazole used in Example 36. A portion of crude product was purified by preparative HPLC using a mixture of water (5% CH$_3$CN, 0.05% HCOOH) and CH$_3$CN (0.05% HCOOH) as the mobile phase and a Varian Diphenyl column as the stationary phase to yield (1R,2R)-2-((6-((6-bromo-1H-benzo[d]imidazol-1-yl)methyl)benzo[d]thiazol-2-yl)amino)cyclohexanol as a white powder (33 mg) $^1$H NMR (300 MHz, DMSO-d$_6$) δ 8.44 (s, 1H), 8.00 (d, J=7.5 Hz, 1H), 7.85 (d, J=1.5 Hz, 1H), 7.5-7.68 (m, 2H), 7.26-7.36 (m, 2H), 7.15-7.24 (m, 1H), 5.47 (s, 2H), 4.76 (d, J=4.5 Hz, 1H), 3.52 (m, 1H), 3.32 (m, 1H), 1.99 (m, 1H), 1.88 (m, 1H), 1.5-1.67 (m, 2H), 1.12-1.30 (m, 4H); LCMS (ESI) m/z 456, 458 (M+H)+.

Example 108

Preparation of 1-((2-(((1R,2R)-2-hydroxycyclohexyl)amino)benzo[d]thiazol-6-yl)methyl)-1H-benzo[d]imidazole-5-carbonitrile

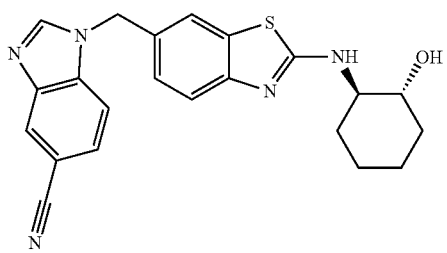 [SMILES: N#Cc1ccc2c(c1)ncn2Cc1ccc2nc(N[C@@H]3CCCC[C@H]3O)sc2c1]

Step 1:

4-Bromo-N-((2-(methylthio)benzo[d]thiazol-6-yl)methyl)-2-nitroaniline was synthesized as a yellow solid (1.08 g, 77%) using a procedure analogous to that described in Step 2 of Example 107, substituting 4-bromo-2-nitroaniline for 5-bromo-2-nitroaniline used in Example 107. $^1$H NMR (300 MHz, DMSO-d$_6$) δ 8.84 (t, J=6.0 Hz, 1H), 8.19 (d, J=2.4 Hz, 1H), 7.98 (s, 1H), 7.81 (d, J=8.3 Hz, 1H), 7.56 (dd, J=2.4, 9.3 Hz, 1H), 7.46 (d, J=8.3 Hz, 1H), 6.88 (d, J=9.2 Hz, 1H), 4.75 (d, J=6.0 Hz, 2H), 2.77 (s, 3H); LCMS (ESI) m/z 410, 412 (M+H)+.

Step 2:

4-Bromo-$N^1$-((2-(methylthio)benzo[d]thiazol-6-yl)methyl)benzene-1,2-diamine was synthesized as a red oil using a procedure analogous to that described in Step 2 of Example 41, substituting 4-bromo-N-((2-(methylthio)benzo[d]thiazol-6-yl)methyl)-2-nitroaniline from the previous step for 4-bromo-5-methoxy-N-((2-(methylthio)benzo[d]thiazol-6-yl)methyl)-2-nitro aniline used in Example 41. LCMS (ESI) m/z 380, 382 (M+H)+.

Step 3:

6-((5-Bromo-1H-benzo[d]imidazol-1-yl)methyl)-2-(methylthio)benzo[d]thiazole was synthesized as a white solid (630 mg, 62% over two steps) using a procedure analogous to that described in Step 3 of Example 41, substituting 4-bromo-$N^1$-((2-(methylthio)benzo[d]thiazol-6-yl)methyl)benzene-1,2-diamine from the previous step for 4-bromo-5-methoxy-$N^1$-((2-(methylthio)benzo[d]thiazol-6-yl)methyl)benzene-1,2-diamine used in Example 41. $^1$H NMR (300 MHz, DMSO-d$_6$) δ 8.51 (s, 1H), 8.00 (s, 1H), 7.87 (d, J=1.7 Hz, 1H), 7.81 (d, J=8.5 Hz, 1H), 7.54 (d, J=8.5 Hz, 1H), 7.33-7.45 (m, 2H), 5.62 (s, 2H), 2.77 (s, 3H); LCMS (ESI) m/z 390, 392 (M+H)+.

Step 4:

6-((5-Bromo-1H-benzo[d]imidazol-1-yl)methyl)-2-(methylsulfinyl)benzo[d]thiazole was synthesized as a white foam (830 mg) using a procedure analogous to that described in Step 6 of Example 36, substituting 6-((5-bromo-1H-benzo[d]imidazol-1-yl)methyl)-2-(methylthio)benzo[d]thiazole from the previous step for 6-((4-bromo-1H-imidazol-1-yl)methyl)-2-(methylthio)benzo[d]thiazole used in Example 36. LCMS (ESI) m/z 405, 407 (M+H)+.

Step 5:

To a suspension of 6-((5-bromo-1H-benzo[d]imidazol-1-yl)methyl)-2-(methylsulfinyl)benzo[d]thiazole (655 mg, 1.6 mmol) and (1R,2R)-2-aminocyclohexanol (558 mg, 4.8 mmol) in anhydrous DMA (3.0 mL) was added DIEA (842 µL, 4.8 mmol). The mixture was heated in a sealed tube at 110° C. for 18 h. The mixture was cooled to rt and added dropwise to a stirred solution of water causing a precipitate to form. After stirring for 10 min, the solid was collected by filtration to afford (1R,2R)-2-((6-((5-bromo-1H-benzo[d]imidazol-1-yl)methyl)benzo[d]thiazol-2-yl)amino)cyclohexanol (837 mg) as a tan solid. The material was used in the next step without further purification. $^1$H NMR (300 MHz, DMSO-d$_6$) δ 8.46 (s, 1H), 7.97 (d, J=7.5 Hz, 1H), 7.85 (d, J=1.7 Hz, 1H), 7.65 (s, 1H), 7.54 (d, J=8.5 Hz, 1H), 7.26-7.39 (m, 2H), 7.19 (m, 1H), 5.47 (s, 2H), 4.74 (d, J=5.1 Hz, 1H), 3.51 (m, 1H), 3.32 (m, 1H), 2.01 (m, 1H), 1.87 (m, 1H), 1.5-1.67 (m, 2H), 1.13-1.32 (m, 4H); LCMS (ESI) m/z 457, 459 (M+H)+.

Step 6:

1-((2-(((1R,2R)-2-Hydroxycyclohexyl)amino)benzo[d]thiazol-6-yl)methyl)-1H-benzo[d]imidazole-5-carbonitrile was synthesized as a white powder (32 mg, 6%) using a procedure analogous to that described in Step 1 of Example 53, substituting (1R,2R)-2-((6-((5-bromo-1H-benzo[d]imidazol-1-yl)methyl)benzo[d]thiazol-2-yl)amino)cyclohexanol from the previous step for (1R,2R)-2-((6-((6-bromo-5-methoxy-1H-benzo[d]imidazol-1-yl)methyl)benzo[d]thiazol-2-yl)amino)cyclohexanol used in Example 53. The product was further purified by silica gel flash chromatography eluting with 5% MeOH in CH$_2$Cl$_2$. $^1$H NMR (300

MHz, DMSO-d$_6$) δ 8.66 (s, 1H), 8.22 (s, 1H), 7.98 (d, J=7.5 Hz, 1H), 7.79 (d, J=8.5 Hz, 1H), 7.68 (s, 1H), 7.62 (m, 1H), 7.29 (m, 1H), 7.21 (m, 1H), 5.54 (s, 2H), 4.73 (d, J=5.3 Hz, 1H), 3.51 (m, 1H), 3.33 (m, 1H), 2.03 (m, 1H), 1.88 (m, 1H), 1.5-1.67 (m, 2H), 1.10-1.35 (m, 4H); LCMS (ESI) m/z 404 (M+H)$^+$.

Example 109

Preparation of (1R,2R)-2-((6-((6-(2-hydroxypropan-2-yl)-3H-imidazo[4,5-b]pyridin-3-yl)methyl)benzo[d]thiazol-2-yl)amino)cyclohexanol

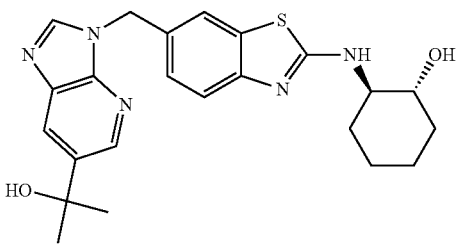 [SMILES: CC(C)(O)c1cnc2c(c1)ncn2Cc1ccc2nc(N[C@@H]3CCCC[C@H]3O)sc2c1]

Step 1:

To a stirred solution of methyl 3-((2-(methylthio)benzo[d]thiazol-6-yl)methyl)-3H-imidazo[4,5-b]pyridine-6-carboxylate (253 mg, 0.684 mmol) from Step 3 of Example 79 in a mixture of anhydrous DCM (2.5 mL) and anhydrous THF (6.4 mL) at 0° C. under an inert atmosphere was added dropwise methyl magnesium bromide (3M solution in diethyl ether, 0.49 mL, 1.47 mmol). The mixture was allowed to slowly warm to rt and stir for 1.5 h. Additional methyl magnesium bromide (3M solution in diethyl ether, 0.49 mL, 1.47 mmol) was added and the mixture was stirred at rt for an additional 48 h. Additional methyl magnesium bromide (3M solution in diethyl ether, 0.25 mL, 0.74 mmol) was added and the mixture was stirred at rt for an additional 4 h. The reaction mixture was partitioned between EtOAc and a 1:1 mixture of saturated aq NH$_4$Cl and saturated aq NaHCO$_3$. The organic layer was separated, dried over MgSO$_4$, filtered, and concentrated under reduced pressure. The residue was purified by silica gel flash chromatography eluting with 100% DCM to 15% MeOH in DCM to afford 2-(3-((2-(methylthio)benzo[d]thiazol-6-yl)methyl)-3H-imidazo[4,5-b]pyridin-6-yl)propan-2-ol (191 mg, 75%) as a solid. $^1$H NMR (300 MHz, DMSO-d$_6$) δ 8.59 (s, 1H), 8.52 (d, J=3.0 Hz, 1H), 8.12 (d, J=3.0 Hz, 1H), 8.00 (m, 1H), 7.81 (d, J=9.0 Hz, 1H), 7.45 (dd, J=9.0, 3.0 Hz, 1H), 5.59 (s, 2H), 5.20 (s, 1H), 2.77 (s, 3H), 1.51 (s, 6H); LCMS (ESI) m/z 371 (M+H)$^+$.

Step 2:

2-(3-((2-(Methylsulfinyl)benzo[d]thiazol-6-yl)methyl)-3H-imidazo[4,5-b]pyridin-6-yl)propan-2-ol (140 mg, 70%) was obtained as a yellow solid using a procedure analogous to that described in Step 5 of Example 3, substituting 2-(3-((2-(methylthio)benzo[d]thiazol-6-yl)methyl)-3H-imidazo[4,5-b]pyridin-6-yl)propan-2-ol from Step 1 of this Example for 6-((3H-imidazo[4,5-b]pyridin-3-yl)methyl)-2-(methylthio)benzo[d]thiazole used in Example 3. LCMS (ESI) m/z 387 (M+H)$^+$.

Step 3:

(1R,2R)-2-((6-((6-(2-Hydroxypropan-2-yl)-3H-imidazo[4,5-b]pyridin-3-yl)methyl)benzo[d]thiazol-2-yl)amino)cyclohexanol (17 mg, 11%) was obtained as a solid using a procedure analogous to that described in Step 5 of Example 70, substituting 2-(3-((2-(methylsulfinyl)benzo[d]thiazol-6-yl)methyl)-3H-imidazo[4,5-b]pyridin-6-yl)propan-2-ol from Step 2 of this Example for 6-((6-fluoro-3H-imidazo[4,5-b]pyridin-3-yl)methyl)-2-(methylsulfinyl)benzo[d]thiazole used in Example 70. $^1$H NMR (300 MHz, DMSO-d$_6$) δ 8.54 (s, 1H), 8.53 (d, J=3.0 Hz, 1H), 8.10 (d, J=3.0 Hz, 1H), 7.97 (d, J=6.0 Hz, 1H), 7.66 (m, 1H), 7.19-7.30 (m, 2H), 5.46 (s, 2H), 5.22 (br s, 1H), 4.76 (br d, J=3.0 Hz, 1H), 3.50 (m, 1H), 3.30 (m, 1H), 2.03 (m, 1H), 1.86 (m, 1H), 1.60-1.70 (m, 2H), 1.51 (s, 6H), 1.15-1.30 (m, 4H); LCMS (ESI) m/z 438 (M+H)$^+$.

Example 110

Preparation of 1-(1-((2-(((1R,2R)-2-hydroxycyclohexyl)amino)benzo[d]thiazol-6-yl)methyl)-1H-benzo[d]imidazol-5-yl)ethanone

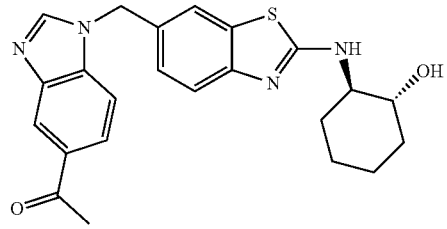 [SMILES: CC(=O)c1ccc2c(c1)ncn2Cc1ccc2nc(N[C@@H]3CCCC[C@H]3O)sc2c1]

A stirred suspension of (1R,2R)-2-((6-((5-bromo-1H-benzo[d]imidazol-1-yl)methyl)benzo[d]thiazol-2-yl)amino)cyclohexanol (150 mg, 0.33 mmol) from Step 5 of Example 108 and tributyl(1-ethoxyvinyl)tin (177 mg, 0.5 mmol) in DMA (1.5 mL) was purged with a stream of argon for 5 min. To the mixture was added tetrakis(triphenylphosphine)palladium (0) (57 mg, 0.05 mmol) and argon was bubbled into the mixture for an additional 5 min. The reaction vessel was sealed and the mixture was heated at 110° C. for 3 h. The mixture was cooled to rt. To the mixture was added 0.5 M aq HCl (500 μL) followed by stirring at rt for 12 h. The mixture was filtered, and the filtrate was purified directly by reverse-phase preparative HPLC using a mixture of water (5% CH$_3$CN, 0.05% HCOOH) and CH$_3$CN (0.05% HCOOH) as the mobile phase and a Varian Pursuit XRs C18 column as the stationary phase. The product was further purified by silica gel flash chromatography eluting with 5% MeOH in CH$_2$Cl$_2$ to afford 1-(1-((2-(((1R,2R)-2-hydroxycyclohexyl)amino)benzo[d]thiazol-6-yl)methyl)-1H-benzo[d]imidazol-5-yl)ethanone (11 mg, 8%) as a white powder. $^1$H NMR (300 MHz, DMSO-d$_6$) δ 8.57 (s, 1H), 8.32 (s, 1H), 7.97 (d, J=7.5 Hz, 1H), 7.85 (d, J=8.5 Hz, 1H), 7.64-7.72 (m, 2H), 7.30 (m, 1H), 7.20 (m, 1H), 5.52 (s, 2H), 4.73 (d, J=5.1 Hz, 1H), 3.52 (m, 1H), 3.34 (m, 1H), 2.62 (s, 3H), 2.02 (m, 1H), 1.90 (m, 1H), 1.5-1.69 (m, 2H), 1.10-1.35 (m, 4H); LCMS (ESI) m/z 421 (M+H)$^+$.

Example 111

Preparation of 1-((2-(((1R,2R)-2-hydroxycyclohexyl)amino)benzo[d]thiazol-6-yl)methyl)-1H-benzo[d]imidazole-6-carbonitrile

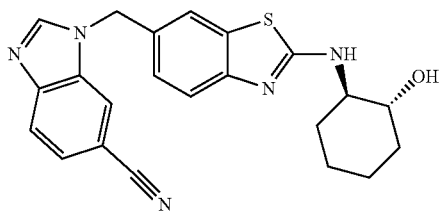 [SMILES: N#Cc1ccc2ncn(Cc3ccc4nc(N[C@@H]5CCCC[C@H]5O)sc4c3)c2c1]

1-((2-(((1R,2R)-2-Hydroxycyclohexyl)amino)benzo[d]thiazol-6-yl)methyl)-1H-benzo[d]imidazole-6-carbonitrile was synthesized as a white powder (23 mg, 13%) using a procedure analogous to that described in Step 6 of Example 108, substituting (1R,2R)-2-((6-((6-bromo-1H-benzo[d]imidazol-1-yl)methyl)benzo[d]thiazol-2-yl)amino)cyclohexanol from Step 6 of Example 107 for (1R,2R)-2-((6-((5-bromo-1H-benzo[d]imidazol-1-yl)methyl)benzo[d]thiazol-2-yl)amino)cyclohexanol used in Example 108. $^1$H NMR (300 MHz, DMSO-$d_6$) δ 8.70 (s, 1H), 8.27 (s, 1H), 8.01 (d, J=7.3 Hz, 1H), 7.83 (d, J=8.3 Hz, 1H), 7.73 (s, 1H), 7.58 (d, J=8.5 Hz, 1H), 7.23-7.35 (m, 2H), 5.53 (s, 2H), 4.76 (d, J=4.5 Hz, 1H), 3.51 (m, 1H), 2.50 (m, 1H), 2.03 (m, 1H), 1.87 (m, 1H), 1.5-1.67 (m, 2H), 1.13-1.31 (m, 4H); LCMS (ESI) m/z 404 (M+H)$^+$.

Example 112

Preparation of (1R,2R)-2-((6-((5-(methylsulfonyl)-1H-benzo[d]imidazol-1-yl)methyl)benzo[d]thiazol-2-yl)amino)cyclohexanol

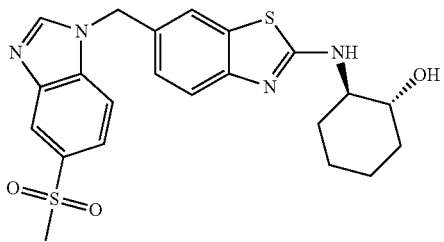 [SMILES: CS(=O)(=O)c1ccc2c(c1)ncn2Cc1ccc2nc(N[C@@H]3CCCC[C@H]3O)sc2c1]

A stirred suspension of (1R,2R)-2-((6-((5-bromo-1H-benzo[d]imidazol-1-yl)methyl)benzo[d]thiazol-2-yl)amino)cyclohexanol (100 mg, 0.22 mmol) (prepared as described in Example 108, steps 1 through 6), sodium methane sulfinate (89 mg, 0.9 mmol) and N,N-dimethylethylenediamine (9.6 µL, 0.9 mmol) was degassed under a stream of argon for 5 min. Copper (I) trifluoromethane-sulfonate benzene complex (22 mg, 0.04 mmol) was added and the mixture was sealed and heated at 125° C. for 7 h. The mixture was cooled to rt, filtered, and the filtrate subjected to purification by reverse-phase preparative HPLC eluting with a mixture of water (5% CH$_3$CN, 0.05% HOAc) and CH$_3$CN (0.05% HOAc) as the mobile phase and a Varian diphenyl column as the stationary phase, to afford (1R,2R)-2-((6-((5-(methylsulfonyl)-1H-benzo[d]imidazol-1-yl)methyl)benzo[d]thiazol-2-yl)amino)cyclohexanol (30 mg, 30%) as a white powder. $^1$H NMR (300 MHz, DMSO-$d_6$) δ 8.69 (s, 1H), 8.20 (s, 1H), 8.06 (d, J=7.5 Hz, 1H), 7.84 (m, 1H), 7.76 (m, 1H), 7.69 (s, 1H), 7.30 (m, 1H), 7.21 (m, 1H), 5.56 (s, 2H), 4.82 (m, 1H), 3.50 (m, 1H), 3.36 (m, 1H), 3.19 (s, 3H), 2.01 (m, 1H), 1.87 (m, 1H), 1.5-1.67 (m, 2H), 1.11-1.31 (m, 4H); LCMS (ESI) m/z 457 (M+H)$^+$.

Example 113

Preparation of (1R,2R)-2-((6-((6-(methylsulfonyl)-1H-benzo[d]imidazol-1-yl)methyl)benzo[d]thiazol-2-yl)amino)cyclohexanol

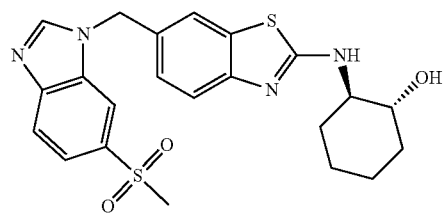 [SMILES: CS(=O)(=O)c1ccc2ncn(Cc3ccc4nc(N[C@@H]5CCCC[C@H]5O)sc4c3)c2c1]

(1R,2R)-2-((6-((6-(Methylsulfonyl)-1H-benzo[d]imidazol-1-yl)methyl)benzo[d]thiazol-2-yl)amino)cyclohexanol was synthesized as a white powder (22 mg, 26%) using a procedure analogous to that described in Example 112, substituting (1R,2R)-2-((6-((6-bromo-1H-benzo[d]imidazol-1-yl)methyl)benzo[d]thiazol-2-yl)amino)cyclohexanol (as prepared in Example 107, steps 1 through 6) for (1R,2R)-2-((6-((5-bromo-1H-benzo[d]imidazol-1-yl)methyl)benzo[d]thiazol-2-yl)amino)cyclohexanol used in Example 112. $^1$H NMR (300 MHz, DMSO-$d_6$) δ 8.69 (s, 1H), 8.21 (s, 1H), 8.01 (d, J=7.3 Hz, 1H), 7.89 (d, J=8.5 Hz, 1H), 7.75 (m, 1H), 7.67 (d, J=1.1 Hz, 1H), 7.32 (m, 1H), 7.20 (m, 1H), 5.60 (s, 2H), 4.76 (d, J=4.3 Hz, 1H), 3.51 (m, 1H), 3.35 (m, 1H), 3.21 (s, 3H), 2.02 (m, 1H), 1.88 (m, 1H), 1.5-1.67 (m, 2H), 1.13-1.34 (m, 4H); LCMS (ESI) m/z 457 (M+H)$^+$.

Example 114

Preparation of (1R,2R)-2-((6-((3H-imidazo[4,5-b]pyridin-3-yl)methyl)thiazolo[4,5-b]pyridin-2-yl)amino)cyclohexanol

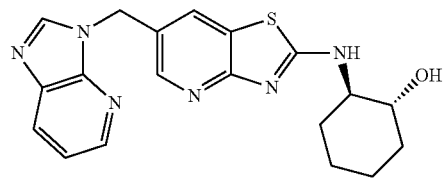

Step 1:

A mixture of ethyl 6-amino-5-bromonicotinate (1.0 g, 4 mmol) and O-ethylxanthic acid potassium salt (785 mg, 4.2 mmol) in DMF (15 mL) was heated at reflux for 6 h. The mixture was cooled to rt and was partitioned between EtOAc (200 mL) and 1 M aq Na$_2$CO$_3$ (150 mL). A solid formed between the two layers and was collected by filtration. The layers were separated and the organic layer was concentrated under reduced pressure until a slurry began to form. The mixture was cooled to 0° C. and the resulting solid was collected by filtration. The two solid batches were combined to afford ethyl 2-mercaptothiazolo[4,5-b]pyridine-6-carboxylate potassium salt (871 mg, 89%), which did not require further purification. $^1$H NMR (300 MHz, DMSO-$d_6$) δ 8.69 (d, J=2.1 Hz, 1H), 8.19 (d, J=2.1 Hz, 1H), 4.29 (q, J=7.0 Hz, 2H), 1.31 (t, J=7.1 Hz, 3H); LCMS (ESI) m/z 241 (M+H)$^+$.

Step 2:

To a stirred mixture of ethyl 2-mercaptothiazolo[4,5-b]pyridine-6-carboxylate potassium salt (1.7 g, 6.6 mmol) from the previous step in DMF (10 mL) at 0° C. was added iodomethane (226 µL, 3.6 mmol). After the mixture was stirred at 0° C. for 2 h, it was allowed to warm slowly to rt. The mixture was partitioned between EtOAc (100 mL) and 0.5 M aq Na$_2$CO$_3$ (50 mL). The organic layer was separated and washed with brine (50 mL), dried over Mg$_2$SO$_4$, filtered, and concentrated under reduced pressure to afford ethyl 2-(methylthio)thiazolo[4,5-b]pyridine-6-carboxylate (724 mg, 82%) as a yellow solid. The material was used in the next step without further purification. $^1$H NMR (300 MHz, DMSO-$d_6$) δ 9.07 (s, 2H), 4.38 (q, J=7.0 Hz, 2H), 2.86 (s, 3H), 1.36 (t, J=7.1 Hz, 3H); LCMS (ESI) m/z 255 (M+H)$^+$.

Step 3:

(2-(Methylthio)thiazolo[4,5-b]pyridin-6-yl)methanol was synthesized as a white solid (404 mg, 67%) using a procedure analogous to that described in Step 3 of Example 36, substituting ethyl 2-(methylthio)thiazolo[4,5-b]pyridine-6-carboxylate from the previous step for ethyl 2-(methylthio)benzo[d]thiazole-6-carboxylate used in Example 36. $^1$H NMR (300 MHz, DMSO-$d_6$) δ 8.51 (d, J=1.9 Hz, 1H), 8.42 (d, J=1.9 Hz, 1H), 5.44 (t, J=5.7 Hz, 1H), 4.63 (d, J=5.7 Hz, 2H), 2.82 (s, 3H); LCMS (ESI) m/z 213 (M+H)$^+$.

Step 4:

To a stirred mixture of (2-(methylthio)thiazolo[4,5-b]pyridin-6-yl)methanol (404 mg, 2 mmol) in anhydrous CH$_2$Cl$_2$ (20 mL) at rt was added SOCl$_2$ (166 µL, 2.4 mmol). After 3 h, the mixture was concentrated under reduced pressure to afford 6-(chloromethyl)-2-(methylthio)thiazolo[4,5-b]pyridine (497 mg) as a white solid. The material was used in the next step without further purification. $^1$H NMR (300 MHz, DMSO-$d_6$) δ 8.65 (d, J=1.9 Hz, 1H), 8.60 (d, J=1.9 Hz, 1H), 4.95 (s, 2H), 2.83 (s, 3H); LCMS (ESI) m/z 231 (M+H)$^+$.

Step 5:

To a stirred mixture of DMF (5 mL) and sodium hydride (60% in mineral oil, 64 mg, 1.6 mmol) at 0° C. under argon, was added 4-azabenzimidazole (204 mg, 1.1 mmol) in one portion. The mixture was stirred for 5 min at 0° C. followed by dropwise addition of a solution of 6-(chloromethyl)-2-(methylthio)thiazolo[4,5-b]pyridine (497 mg, 2.2 mmol) in DMF (2 mL). The mixture was warmed slowly to rt then heated at 70° C. for 18 h. The mixture was cooled to rt, then partitioned between EtOAc (150 mL) and 0.5 M aq Na$_2$CO$_3$ (50 mL). The organic layer was separated and washed with water (50 mL), then brine, dried over Na$_2$SO$_4$, filtered, and concentrated under reduced pressure. The residue was purified by silica gel flash chromatography eluting with a gradient of 100% CH$_2$Cl$_2$ to 5% MeOH in DCM to afford 6-((3H-imidazo[4,5-b]pyridin-3-yl)methyl)-2-(methylthio)thiazolo[4,5-b]pyridine (126 mg, 35%) as a yellow solid. The regiochemistry of the alkylation was determined by 2-dimensional nuclear Overhauser effect (NOE) experiment. $^1$H NMR (300 MHz, DMSO-$d_6$) δ 8.64-8.74 (m, 2H), 8.46 (d, J=2.1 Hz, 1H), 8.38 (dd, J=1.1, 4.7 Hz, 1H), 8.12 (dd, J=1.3, 8.1 Hz, 1H), 7.31 (dd, J=4.7, 8.1 Hz, 1H), 5.67 (s, 2H), 2.80 (s, 3H); LCMS (ESI) m/z 314 (M+H)$^+$.

Step 6:

6-((3H-Imidazo[4,5-b]pyridin-3-yl)methyl)-2-(methylsulfinyl)thiazolo[4,5-b]pyridine was synthesized as a white foam (135 mg) using a procedure analogous to that described in Step 6 of Example 36, substituting 6-((3H-imidazo[4,5-b]pyridin-3-yl)methyl)-2-(methylthio)thiazolo[4,5-b]pyridine from the previous step for 6-((4-bromo-1H-imidazol-1-yl)methyl)-2-(methylthio)benzo[d]thiazole used in Example 36. LCMS (ESI) m/z 330 (M+H)$^+$.

Step 7:

(1R,2R)-2-((6-((3H-Imidazo[4,5-b]pyridin-3-yl)methyl)thiazolo[4,5-b]pyridin-2-yl)amino)cyclohexanol was synthesized as a white powder (80 mg, 53%) using a procedure analogous to that described in Step 7 of Example 36, substituting 6-((3H-imidazo[4,5-b]pyridin-3-yl)methyl)-2-(methylsulfinyl)thiazolo[4,5-b]pyridine from the previous step for 6-((4-bromo-1H-imidazol-1-yl)methyl)-2-(methylsulfinyl)benzo[d]thiazole used in Example 36. $^1$H NMR (300 MHz, DMSO-$d_6$) δ 8.62 (s, 1H), 8.46 (d, J=7.5 Hz, 1H), 8.39 (dd, J=1.2, 4.8 Hz, 1H), 8.33 (d, J=2.1 Hz, 1H), 8.09 (dd, J=1.3, 8.1 Hz, 1H), 8.05 (d, J=2.1 Hz, 1H), 7.30 (m, 1H), 5.50 (s, 2H), 4.82 (d, J=5.3 Hz, 1H), 3.61 (m, 1H), 3.35 (m, 1H), 2.03 (m, 1H), 1.88 (m, 1H), 1.5-1.70 (m, 2H), 1.15-1.33 (m, 4H); LCMS (ESI) m/z 381 (M+H)$^+$.

Example 115

Preparation of (1R,2R)-2-((6-((6-((R,S)-1-hydroxyethyl)-3H-imidazo[4,5-b]pyridin-3-yl)methyl)benzo[d]thiazol-2-yl)amino)cyclohexanol

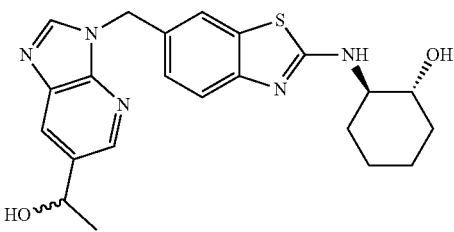 [SMILES: CC(O)c1cnc2c(c1)ncn2Cc1ccc2nc(N[C@@H]3CCCC[C@H]3O)sc2c1]

To a stirred solution of 1-(3-((2-(((1R,2R)-2-hydroxycyclohexyl)amino)benzo[d]thiazol-6-yl)methyl)-3H-imidazo[4,5-b]pyridin-6-yl)ethanone (92 mg, 0.22 mmol) from Example 73, MeOH (5 mL) and DMF (3 mL) at rt was added sodium borohydride (17 mg, 0.44 mmol). The mixture was stirred at rt for 15 min. The reaction mixture was purified directly by reverse-phase HPLC using a mixture of water (5% CH$_3$CN, 0.05% HOAc) and CH$_3$CN (0.05% HOAc) as the mobile phase and Varian Pursuit XRs diphenyl column as the stationary phase to afford (1R,2R)-2-((6-((6-((R,S)-1-hydroxyethyl)-3H-imidazo[4,5-b]pyridin-3-yl)methyl)benzo[d]thiazol-2-yl)amino)cyclohexanol (38 mg, 41%) as a white solid. $^1$H NMR (300 MHz, DMSO-$d_6$) δ 8.55 (s, 1H), 8.37 (d, J=1.5 Hz, 1H), 7.97-8.00 (m, 2H), 7.66 (m, 1H), 7.28 (d, J=6.0 Hz, 1H), 7.20 (dd, J=6.0, 3.0 Hz, 1H), 5.46 (s, 2H), 5.30 (br m, 1H), 4.90 (m, 1H), 4.76 (br m, 1H), 3.50 (m, 1H), 3.30 (m, 1H), 2.03 (m, 1H), 1.87 (m, 1H), 1.5-1.65 (m, 2H), 1.40 (d, J=6.0 Hz, 3H), 1.10-1.30 (m, 4H). LCMS (ESI) m/z 424 (M+H)$^+$.

Example 116

Preparation of 2-(dimethylamino)-1-(3-((2-(((1R,2R)-2-hydroxycyclohexyl)amino)benzo[d]thiazol-6-yl)methyl)-3H-imidazo[4,5-b]pyridin-6-yl)ethanone acetate salt

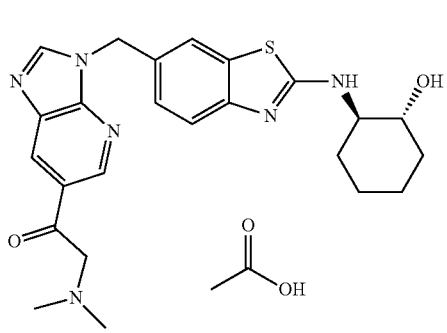

Step 1:

A stirred mixture of (1R,2R)-2-((6-((6-bromo-3H-imidazo[4,5-b]pyridin-3-yl)methyl)benzo[d]thiazol-2-yl)amino)cyclohexanol (693 mg, 1.51 mmol) from Example 29, tributyl (1-ethoxyvinyl)tin (1.10 g, 3.03 mmol) and DMF (10 mL) was purged with argon. To the mixture was added tetrakis(triphenylphosphine)palladium (0) (262 mg, 0.23 mmol). The reaction vessel was sealed and the mixture was heated at 110° C. for 2 h. The mixture was allowed to cool to rt. The mixture was partitioned between water and DCM and the organic layer was separated. The aqueous layer was extracted with additional DCM. The combined organic layers were washed with water then brine, dried over magnesium sulfate, filtered, and concentrated under reduced pressure. The residue was purified by silica gel flash chromatography eluting with 100% DCM to 15% MeOH in DCM to afford (1R,2R)-2-((6-((6-(1-ethoxyvinyl)-3H-imidazo[4,5-b]pyridin-3-yl)methyl)benzo[d]thiazol-2-yl)amino)cyclohexanol (320 mg, 47%) as a solid. LCMS (ESI) m/z 450 (M+H)+.

Step 2:

To a stirred solution of (1R,2R)-2-((6-((6-(1-ethoxyvinyl)-3H-imidazo[4,5-b]pyridin-3-yl)methyl)benzo[d]thiazol-2-yl)amino)cyclohexanol (90 mg, 0.20 mmol) from the previous step in DMF (2 mL) at 0° C. was added N-bromosuccinimide (36 mg, 0.20 mmol), and the mixture was stirred for 15 min. To the mixture was added dimethylamine (2M in THF, 0.90 mL, 1.80 mmol) and stirring was continued at 0° C. for 5 min. The reaction mixture was purified directly by reverse-phase HPLC using a mixture of water (5% $CH_3CN$, 0.05% HOAc) and $CH_3CN$ (0.05% HOAc) as the mobile phase and Varian Pursuit XRs diphenyl column as the stationary phase to afford 2-(dimethylamino)-1-(3-((2-(((1R,2R)-2-hydroxycyclohexyl)amino)benzo[d]thiazol-6-yl)methyl)-3H-imidazo[4,5-b]pyridin-6-yl)ethanone acetate salt (5 mg, 5%) as a white solid. 1H NMR (300 MHz, DMSO-$d_6$) δ 9.01 (d, J=1.7 Hz, 1H), 8.75 (s, 1H), 8.67 (d, J=1.7 Hz, 1H), 8.03 (d, J=7.5 Hz, 1H), 7.68 (s, 1H), 7.20-7.32 (m, 2H), 5.52 (s, 2H), 4.80 (br s, 1H), 3.78 (s, 2H), 3.51 (br m, 1H), 3.30 (br m, 1H), 2.25 (s, 6H), 2.04 (br m, 1H), 1.82-1.86 (m, 4H), 1.59-1.65 (br m, 2H), 1.10-1.60 (m, 4H); LCMS (ESI) m/z 465 (M+H)+.

Example 117

Preparation of 3-((2-(((1R,2R)-2-hydroxycyclohexyl)amino)benzo[d]thiazol-6-yl)methyl)imidazo[1,2-a]pyridine-7-carbonitrile

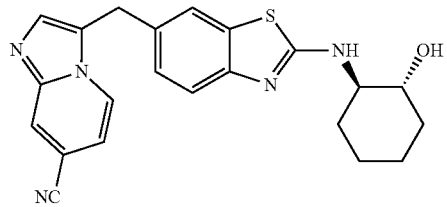 [SMILES: N#Cc1ccn2c(Cc3ccc4nc(N[C@@H]5CCCC[C@H]5O)sc4c3)cnc2c1]

Step 1:

A mixture of 2-fluoro-4-iodoaniline (2.4 g, 10 mmol) and sodium O-ethyl carbonodithioate (3.2 g, 20 mmol) in DMF (8 mL) was stirred at 95° C. for 5 h. The reaction mixture was cooled to rt then diluted with water (25 mL) and 1 N aqueous HCl (20 mL). The mixture was stirred at room temperature for 1 h. The resulting precipitate was collected by filtration and washed with water. The solid was dried to afford 6-iodobenzo[d]thiazole-2-thiol as a light yellow solid (3.3 g, 100%). 1H NMR (300 MHz, $CD_3OD$) δ 7.89 (d, J=1.2 Hz, 1H), 7.67 (dd, J=1.8, 8.7 Hz, 1H), 7.05 (d, J=8.4 Hz, 1H). LCMS (ESI) m/z 294 (M+H)+.

Step 2:

To a stirred mixture of 6-iodobenzo[d]thiazole-2-thiol (0.5 g, 1.7 mmmol) and potassium carbonate (0.23 g, 1.7 mmol) in THF (10 mL) was added methyl iodide (0.12 mL, 1.1 mmol). After stirring at rt overnight, the mixture was concentrated under reduced pressure to give a solid. The solid was partitioned between saturated aq sodium carbonate and DCM. The organic layer was dried over $Na_2SO_4$ and filtered, and concentrated under reduced pressure to give 6-iodo-2-(methylthio)benzo[d]thiazole as a off-white solid (0.4 g, 76%). 1H NMR (300 MHz, $CDCl_3$) δ 8.07 (d, J=1.2 Hz, 1H), 7.69 (dd, J=1.8, 8.4 Hz, 1H), 7.58 (d, J=8.4 Hz, 1H), 2.78 (s, 3H). LCMS (ESI) m/z 308 (M+H)+.

Step 3:

A mixture of 6-iodo-2-(methylthio)benzo[d]thiazole (5.0 g, 16.3 mmol), allyl alcohol (2.2 mL, 32.6 mmol), $Pd(OAc)_2$ (0.36 g, 1.63 mmol), tris(o-tolyl)phosphine (1.0 g, 3.3 mmol) and $NaHCO_3$ (2.8 g, 32.6 mmol) in DMF (75 mL) was stirred at 100° C. under nitrogen atmosphere for 4 h. Then the mixture was cooled to rt and water (300 mL) was added. The mixture was extracted with EtOAc (200 mL×3). The combined organic layers were washed with brine, dried over $Na_2SO_4$, filtered and concentrated under reduced pressure. The residue was purified by silica gel chromatography eluting with 10:1 to 5:1 petroleum ether/EtOAc to afford 3-(2-(methylthio)benzo[d]thiazol-6-yl)propanal as a dark yellow oil (2.0 g, 52%). 1H NMR (300 MHz, $CDCl_3$) δ 9.83 (t, J=1.2 Hz, 1H), 7.78 (d, J=8.4 Hz, 1H), 7.58 (d, J=1.2 Hz, 1H), 7.23 (dd, J=1.8, 8.4 Hz, 1H), 3.05 (t, J=7.5 Hz, 2H), 2.85 (t, J=7.5 Hz, 2H), 2.78 (s, 3H). LCMS (ESI) m/z 238 (M+H)+.

Step 4:

L-proline (0.22 g, 1.9 mmol) was added to a solution of 3-(2-(methylthio)benzo[d]thiazol-6-yl)propanal (2.3 g, 9.7 mmol) in DCM (40 mL) at 0° C. followed by addition of N-chlorosuccinimide (1.4 g, 10 mmol). The reaction mixture was slowly warmed to ambient temperature and stirred overnight. The reaction mixture was concentrated under reduced pressure and purified by silica gel chromatography, eluting with 10:1 to 2:1 petroleum ether/EtOAc to afford 2-chloro-3-(2-(methylthio)benzo[d]thiazol-6-yl)propanal as a yellow oil (2.1 g, 79%). $^1$H NMR (300 MHz, CDCl$_3$) δ 9.56 (dd, J=1.2, 2.1 Hz, 1H), 7.81 (d, J=8.4 Hz, 1H), 7.63 (d, J=0.6 Hz, 1H), 7.28 (d, J=1.5 Hz, 1H), 4.44-4.39 (m, 1H), 3.5-3.44 (m, 1H), 3.20-3.13 (m, 1H), 2.78 (s, 3H). LCMS (ESI) m/z 290 (M+18+H)$^1$.

Step 5:

A mixture of 4-bromopyridin-2-amine (4.9 g, 28.5 mmol), Zn(CN)$_2$ (5.0 g, 42.5 mmol), Pd$_2$(dba)$_3$ (1.3 g, 1.4 mmol) and dppf (1.6 g, 2.8 mmol) in DMF (150 mL) was stirred at 100° C. under nitrogen atmosphere for 1.5 h. The mixture was cooled to rt and water (500 mL) was added. The mixture was extracted with EtOAc (300 mL×3). The combined organic layers were washed with brine, dried over Na$_2$SO$_4$, filtered and concentrated under reduced pressure. The residue was purified by silica gel chromatography eluting with 10:1 to 2:1 petroleum ether/EtOAc to afford 2-aminoisonicotinonitrile as a light yellow solid (2.7 g, 80%). $^1$H NMR (300 MHz, CDCl$_3$) δ 8.19 (d, J=5.1 Hz, 1H), 6.82 (d, J=4.8 Hz, 1H), 6.69 (d, J=0.9 Hz, 1H), 4.72 (br s, 2H). LCMS (ESI) m/z 120 (M+H)$^+$.

Step 6:

A mixture of 2-chloro-3-(2-(methylthio)benzo[d]thiazol-6-yl)propanal (0.35 g, 1.3 mmol) and 2-aminoisonicotinonitrile (0.30 g, 2.6 mmol) in 1-butanol (15 mL) was heated at reflux overnight. After cooling to rt, the formed solid was collected and washed with water, then dried to afford 3-((2-(methylthio)benzo[d]thiazol-6-yl)methyl)imidazo[1,2-a]pyridine-7-carbonitrile as a white solid (0.27 g, 62%). $^1$H NMR (300 MHz, CDCl$_3$) δ 8.45 (d, J=7.2 Hz, 1H), 8.34 (s, 1H), 7.90 (s, 1H), 7.78 (d, J=8.7 Hz, 1H), 7.75 (s, 1H), 7.37 (dd, J=1.2, 7.8 Hz, 1H), 7.20 (dd, J=1.8, 7.2 Hz, 1H), 4.49 (s, 2H), 2.77 (s, 3H). LCMS (ESI) m/z 337 (M+H)$^+$.

Step 7:

To a solution of 3-((2-(methylthio)benzo[d]thiazol-6-yl)methyl)imidazo[1,2-a]pyridine-7-carbonitrile (0.27 g, 0.8 mmol) in DCM (15 mL) was added m-CPBA (0.17 g, 0.9 mmol) at 0° C. The reaction mixture was stirred for 2 h at 0° C., then aq Na$_2$SO$_3$ (15 mL) was added and the mixture was stirred for 0.5 h. The organic layer was separated, dried over Na$_2$SO$_4$, filtered and concentrated under reduced pressure to afford 3-((2-(methylsulfinyl)benzo[d]thiazol-6-yl)methyl)imidazo[1,2-a]pyridine-7-carbonitrile as a yellow solid (0.28 g, 99%). $^1$H NMR (300 MHz, CDCl$_3$) δ 8.46 (d, J=7.2 Hz, 1H), 8.36 (s, 1H), 8.15 (d, J=1.2 Hz, 1H), 8.04 (d, J=8.7 Hz, 1H), 7.78 (s, 1H), 7.55 (dd, J=1.5, 8.4 Hz, 1H), 7.21 (dd, J=1.8, 7.2 Hz, 1H), 4.57 (s, 2H), 3.06 (s, 3H). LCMS (ESI) m/z 353 (M+H)$^+$.

Step 8:

A mixture of 3-((2-(methylsulfinyl)benzo[d]thiazol-6-yl)methyl) imidazo[1,2-a]pyridine-7-carbonitrile (0.20 g, 0.56 mmol), (1R,2R)-2-amino cyclohexanol (97 mg, 0.84 mmol) and DIEA (0.18 g, 1.4 mmol) in DMA (10 mL) was stirred for 2 d at 140° C. The mixture was cooled to rt and water (50 mL) was added. The mixture was extracted with EtOAc (30 mL×3). The combined organic layers were washed with brine, dried over Na$_2$SO$_4$, filtered and concentrated under reduced pressure. The residue was purified by silica gel chromatography eluting with 50:1 to 10:1 DCM/MeOH to afford a solid, which was recrystallized in 10:1 DCM/MeOH (10 mL) to afford 3-((2-(((1R,2R)-2-hydroxycyclohexyl)amino)benzo[d]thiazol-6-yl)methyl)imidazo[1,2-a]pyridine-7-carbonitrile as a white solid (75 mg, 33%). $^1$H NMR (300 MHz, DMSO-d$_6$) δ 8.40 (d, J=6.9 Hz, 1H), 8.32 (s, 1H), 7.88 (d, J=6.9 Hz, 1H), 7.72 (s, 1H), 7.53 (s, 1H), 7.27 (d, J=8.1 Hz, 1H), 7.19 (d, J=6.9 Hz, 1H), 7.09 (d, J=7.5 Hz, 1H), 4.73 (d, J=4.2 Hz, 1H), 4.36 (s, 2H), 3.5-3.50 (m, 1H), 3.37-3.34 (m, 1H), 2.05-2.01 (m, 1H), 1.90-1.86 (m, 1H), 1.65-1.59 (m, 2H), 1.30-1.16 (m, 4H). LCMS (ESI) m/z 404 (M+H)$^+$.

Example 118

Preparation of (1R,2R)-2-((6-((9H-purin-9-yl)methyl)benzo[d]oxazol-2-yl)amino)cyclohexanol

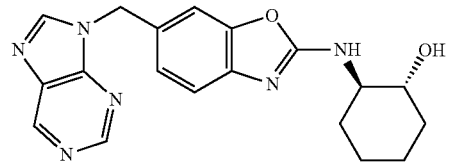 [SMILES: O[C@@H]1CCCC[C@H]1Nc1nc2ccc(Cn3cnc4cncnc43)cc2o1]

Step 1:

A solution of pyrimidine-4,5-diamine (718 mg, 6.53 mmol) and HCOOH (0.36 mL) in triethoxymethane (19 mL) was stirred at 90° C. for 3.5 h. The reaction mixture was concentrated under reduced pressure. The residue was purified by silica gel chromatography eluting with 40:1 DCM/MeOH to give 9H-purine as a brown solid (784 mg, 100%). $^1$H NMR (300 MHz, DMSO-d$_6$) δ 13.40 (br s, 1H), 9.12 (s, 1H), 8.92 (s, 1H), 8.60 (s, 1H). LCMS (ESI) m/z 121 (M+H)$^+$.

Step 2:

To a stirred solution of 9H-purine (784 mg, 6.53 mmol) in DMF (16 mL) was added NaH (60% dispersion in mineral oil, 373 mg, 9.33 mmol,) portionwise at 0° C. After stirring for 30 min, 6-(chloromethyl)-2-(methylthio)benzo[d]oxazole (1.3 g, 6.22 mmol) was added to the mixture. The reaction mixture was allowed to warm to rt and stir for 3 h. The reaction mixture was poured into water (150 mL) and extracted with ethyl acetate (150 mL×4). The combined organic layers were washed with water and brine, dried over Na$_2$SO$_4$, filtered and concentrated under reduced pressure. The residue was purified by silica gel chromatography eluting with 40:1 DCM/MeOH to give 6-((9H-purin-9-yl)methyl)-2-(methylthio)benzo[d]oxazole as a light yellow solid (569 mg, 32.7%). $^1$H NMR (300 MHz, DMSO-d$_6$) δ 9.14 (s, 1H), 8.92 (s, 1H), 8.77 (s, 1H), 7.69 (s, 1H), 7.56 (d, J=7.8 Hz, 1H), 7.35 (d, J=9.0 Hz, 1H), 5.59 (s, 2H), 2.70 (s, 3H). LCMS (ESI) m/z 298 (M+H)$^+$.

Step 3:

A mixture of 6-((9H-purin-9-yl)methyl)-2-(methylthio)benzo[d]oxazole (400 mg, 1.35 mmol) and m-CPBA (289 mg, 1.69 mmol) in DCM (25 mL) was stirred at 0° C. for 6 h. The reaction mixture was washed with aq Na$_2$S$_2$O$_3$ and brine, dried over Na$_2$SO$_4$, filtered and concentrated under reduced pressure. The residue was purified by silica gel chromatography eluting with 1:5 petroleum ether/ethyl acetate to give 6-((9H-purin-9-yl)methyl)-2-(methylsulfinyl)benzo[d]oxazole as a light yellow solid (143 mg, 33.89%). $^1$H NMR (300 MHz, CDCl$_3$) δ 9.18 (s, 1H), 9.03 (s, 1H), 8.13 (s, 1H), 7.82 (d, J=8.4 Hz, 1H), 7.66 (s, 1H), 7.44 (d, J=9.9 Hz, 1H), 5.62 (s, 2H), 3.18 (s, 3H). LCMS (ESI) m/z 314 (M+H)$^+$.

Step 4:

A mixture of 6-((9H-purin-9-yl)methyl)-2-(methylsulfinyl)benzo[d]oxazole (106 mg, 0.34 mmol), (1R,2R)-2- aminocyclohexanol (77 mg, 0.51 mg) and DIEA (132 mg, 1.02 mmol) in DMA (3 mL) was stirred at 135° C. for 2 h. The reaction mixture was cooled to rt, poured into water (30 mL) and extracted with ethyl acetate (20 mL×2). The combined organic layers were washed with brine, dried over Na$_2$SO$_4$, filtered and concentrated under reduced pressure. The residue was purified by silica gel chromatography eluting with 1:6 petroleum ether/ethyl acetate to give crude product, which was washed with 10:1 petroleum ether/ethyl acetate to afford (1R,2R)-2-((6-((9H-purin-9-yl)methyl)benzo[d]oxazol-2-yl)amino)cyclohexanol as a light yellow solid (68 mg, 48.57%). $^1$H NMR (300 MHz, DMSO-d$_6$) δ 9.16 (s, 1H), 8.96 (s, 1H), 8.73 (s, 1H), 7.79 (d, J=7.8 Hz, 1H), 7.42 (s, 1H), 7.16 (d, J=1.2 Hz, 1H), 7.14 (d, J=8.1 Hz, 1H) 5.51 (s, 2H), 4.66 (d, J=4.2 Hz, 1H), 3.34 (br s, 2H), 1.90 (br s, 2H), 1.60 (br s, 2H), 1.22 (br s, 4H). LCMS (ESI) m/z 365 (M+H)$^+$.

Example 119

Preparation of (1R,2R)-2-((6-((5,6-dimethyl-1H-benzo[d]imidazol-1-yl)methyl)benzo[d]thiazol-2-yl)amino)cyclohexanol

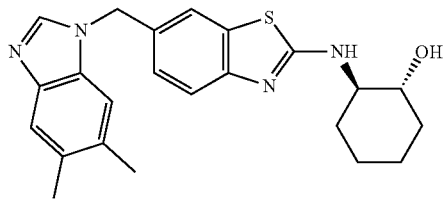 [SMILES: Cc1cc2ncn(Cc3ccc4nc(N[C@@H]5CCCC[C@H]5O)sc4c3)c2cc1C]

Step 1:

To a stirred mixture of anhydrous DMF (15 mL) and sodium hydride (60% dispersion in mineral oil, 105 mg, 2.63 mmol) at 0° C. under nitrogen, was added portionwise 5,6-dimethyl-1H-benzo[d]imidazole (215 mg, 1.4 mmol). The reaction mixture was stirred for 5 min. A solution of 6-(chloromethyl)-2-(methylthio)benzo[d]thiazole (320 mg, 1.4 mmol) from Step 4 of Example 36 in anhydrous DMF (2 mL) was added dropwise. The reaction mixture was allowed to warm to rt and stir for 1 h. The reaction solution was poured into ice-water and extracted with EtOAc (50 mL×3). The combined organic layers were further washed with water (20 mL), then brine (20 mL). The organic layer was separated, dried over Na$_2$SO$_4$, filtered, and concentrated under reduced pressure to afford 6-((5,6-dimethyl-1H-benzo[d]imidazol-1-yl)methyl)-2-(methylthio)benzo[d]thiazole (450 mg, 96%) as a yellow solid which was not purified further. $^1$H NMR (300 MHz, CDCl$_3$) δ 7.86 (s, 1H), 7.81 (d, J=8.4 Hz, 1H), 7.59 (s, 1H), 7.46 (s, 1H), 7.24-7.26 (m, 1H), 7.03 (s, 1H), 5.40 (s, 2H), 2.77 (s, 3H), 2.37 (s, 3H), 2.32 (s, 3H); LCMS (ESI) m/z 340 (M+H)'.

Step 2:

To a stirred solution of 6-((5,6-dimethyl-1H-benzo[d]imidazol-1-yl)methyl)-2-(methylthio)benzo[d]thiazole (450 mg, 1.32 mmol) from the previous step in DCM (20 mL) at 0° C. was added a solution of meta-chloroperbenzoic acid (270 mg, 1.32 mmol) in DCM (3 mL). After stirring for 2 h at 0° C., the reaction solution was diluted with EtOAc (100 mL) and washed sequentially with saturated aq Na$_2$S$_2$O$_3$, saturated aq NaHCO$_3$, and brine. The organic layer was dried over Na$_2$SO$_4$, filtered, and concentrated under reduced pressure to afford 6-((5,6-dimethyl-1H-benzo[d]imidazol-1-yl)methyl)-2-(methylsulfinyl)benzo[d]thiazole (460 mg, 98%) as a colorless solid which was not purified further. $^1$H NMR (300 MHz, CDCl$_3$) δ 8.01 (d, J=8.4 Hz, 1H), 7.90 (s, 1H), 7.72 (s, 1H), 7.60 (s, 1H), 7.37 (m, 1H), 7.02 (s, 1H), 5.48 (s, 2H), 3.06 (s, 3H), 2.37 (s, 3H), 2.32 (s, 3H); LCMS (ESI) m/z 356 (M+H)$^+$.

Step 3:

A stirred mixture of 6-((5,6-dimethyl-1H-benzo[d]imidazol-1-yl)methyl)-2-(methylsulfinyl)benzo[d]thiazole (150 mg, 0.42 mmol) from the previous step, (1R,2R)-2-aminocyclohexanol (140 mg, 1.2 mmol), DIEA (540 mg, 4.2 mmol) and NMP (2 mL) was heated at 130° C. for 12 h. The reaction mixture was cooled to rt, diluted with EtOAc (30 mL) and washed with water (10 mL×2). The organic layer was separated, dried over Na$_2$SO$_4$, filtered, and concentrated under reduced pressure. The residue was purified by silica gel flash chromatography eluting with 3% MeOH in DCM to afford (1R,2R)-2-((6-((5,6-dimethyl-1H-benzo[d]imidazol-1-yl)methyl)benzo[d]thiazol-2-yl)amino)cyclohexanol (80 mg, 47%) as a white solid. $^1$H NMR (300 MHz, DMSO-d$_6$) δ 8.22 (s, 1H), 7.92 (d, J=6.0 Hz, 1H), 7.58 (m, 1H), 7.41 (s, 1H), 7.26-7.31 (m, 2H), 7.14 (m, 1H), 5.40 (s, 2H), 4.71 (d, J=3.0 Hz, 1H), 3.50 (m, 1H), 3.35 (m, 1H), 2.30 (s, 6H), 2.02 (m, 1H), 1.88 (m, 1H), 1.86-1.90 (m, 2H), 1.12-1.27 (m, 4H); LCMS (ESI) m/z 407 (M+H)$^+$.

Example 120

Preparation of 1-(1-((2-(((1R,2R)-2-hydroxycyclohexyl)amino)benzo[d]thiazol-6-yl)methyl)-1H-benzo[d]imidazol-6-yl)ethanone

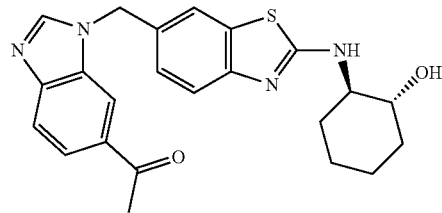 [SMILES: CC(=O)c1ccc2ncn(Cc3ccc4nc(N[C@@H]5CCCC[C@H]5O)sc4c3)c2c1]

1-(1-((2-(((1R,2R)-2-Hydroxycyclohexyl)amino)benzo[d]thiazol-6-yl)methyl)-1H-benzo[d]imidazol-6-yl)ethanone was synthesized as a white powder (8 mg, 6%) using a procedure analogous to that described in Example 110, substituting (1R,2R)-2-((6-((6-bromo-1H-benzo[d]imidazol-1-yl)methyl)benzo[d]thiazol-2-yl)amino)cyclohexanol from Step 6 of Example 107 for (1R,2R)-2-((6-((5-bromo-1H-benzo[d]imidazol-1-yl)methyl)benzo[d]thiazol-2-yl)amino)cyclohexanol used in Example 110. $^1$H NMR (300 MHz, DMSO-d$_6$) δ 8.60 (s, 1H), 8.24 (s, 1H), 7.99 (d, J=7.5 Hz, 1H), 7.82 (m, 1H), 7.74 (m, 1H), 7.68 (s, 1H), 7.31 (m, 1H), 7.21 (m, 1H), 5.58 (s, 2H), 4.75 (d, J=5.1 Hz, 1H), 3.51 (m, 1H), 3.35 (m, 1H), 2.61 (s, 3H), 2.02 (m, 1H), 1.87 (m, 1H), 1.5-1.67 (m, 2H), 1.10-1.34 (m, 4H); LCMS (ESI) m/z 421 (M+H)$^+$.

Example 121

Preparation of (1R,2R)-2-((6-((5-ethynyl-1H-benzo[d]imidazol-1-yl)methyl)benzo[d]thiazol-2-yl)amino)cyclohexanol

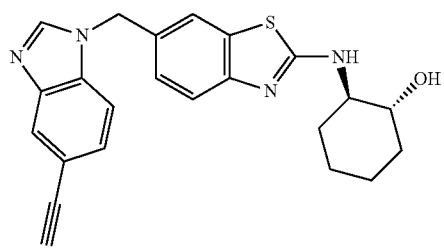 [SMILES: C#Cc1ccc2c(c1)ncn2Cc1ccc2nc(N[C@@H]3CCCC[C@H]3O)sc2c1]

Step 1:

A stirred mixture of (1R,2R)-2-((6-((5-bromo-1H-benzo[d]imidazol-1-yl)methyl)benzo[d]thiazol-2-yl)amino)cyclohexanol (109 mg, 0.24 mmol) from Step 6 of Example 108, (trimethylsilyl)acetylene (68 µL, 0.48 mmol), and DIEA (62 µL, 0.36 mmol) in $CH_3CN$ (2 mL), was purged with a stream of argon for 5 min. To the mixture was added tetrakis(triphenylphosphine)palladium (0) (57 mg, 0.05 mmol) and argon was bubbled into the mixture for an additional 5 min. The reaction vessel was sealed and the mixture was heated at 80° C. for 5 h. The mixture was cooled to rt and was partitioned between EtOAc (100 mL) and 1 M aq $NaHCO_3$ (50 mL). The organic layer was washed with brine (50 mL), dried over $Mg_2SO_4$, filtered, and concentrated under reduced pressure. The residue was purified by silica gel flash chromatography eluting with 5% MeOH in DCM to afford (1R,2R)-24645-((trimethylsilyl)ethynyl)-1H-benzo[d]imidazol-1-yl)methyl)benzo[d]thiazol-2-yl)amino)cyclohexanol (61 mg, 54%) as an amber oil. LCMS (ESI) m/z 476 (M+H)⁺.

Step 2:

A mixture of (1R,2R)-2-((6-((5-((trimethylsilyl)ethynyl)-1H-benzo[d]imidazol-1-yl)methyl)benzo[d]thiazol-2-yl)amino)cyclohexanol (61 mg, 0.13 mmole) and $Na_2CO_3$ (177 mg, 1.3 mmole) in MeOH (2 mL) was stirred at rt for 2 h. The mixture was filtered and the filtrate was concentrated under reduced pressure. The residue was purified by reverse-phase preparative HPLC using a mixture of water (5% $CH_3CN$, 0.05% HCOOH) and $CH_3CN$ (0.05% HCOOH) as the mobile phase and a Varian Pursuit XRs C18 column as the stationary phase to afford (1R,2R)-2-((6-((5-ethynyl-1H-benzo[d]imidazol-1-yl)methyl)benzo[d]thiazol-2-yl)amino)cyclohexanol (8 mg, 17%) as a white powder. ¹H NMR (300 MHz, DMSO-$d_6$) δ 8.49 (s, 1H), 8.01 (d, J=7.3 Hz, 1H), 7.76 (s, 1H), 7.65 (s, 1H), 7.57 (d, J=8.3 Hz, 1H), 7.27-7.33 (m, 2H), 7.19 (m, 1H), 5.48 (s, 2H), 4.78 (d, J=4.9 Hz, 1H), 4.03 (s, 1H), 3.51 (m, 1H), 3.35 (m, 1H), 2.03 (m, 1H), 1.87 (m, 1H), 1.5-1.69 (m, 2H), 1.11-1.31 (m, 4H); LCMS (ESI) m/z 405 (M+H)⁺.

Example 122

Preparation of (1R,2R)-2-((6-((6-ethynyl-1H-benzo[d]imidazol-1-yl)methyl)benzo[d]thiazol-2-yl)amino)cyclohexanol

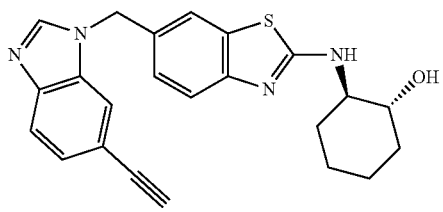 [SMILES: C#Cc1ccc2ncn(Cc3ccc4nc(N[C@@H]5CCCC[C@H]5O)sc4c3)c2c1]

Step 1:

(1R,2R)-2-((6-((6-((Trimethylsilyl)ethynyl)-1H-benzo[d]imidazol-1-yl)methyl)benzo[d]thiazol-2-yl)amino)cyclohexanol was synthesized as an oil (46 mg, 41%) using a procedure analogous to that described in Step 1 of Example 121, substituting (1R,2R)-2-((6-((6-bromo-1H-benzo[d]imidazol-1-yl)methyl)benzo[d]thiazol-2-yl)amino)cyclohexanol from Step 6 of Example 107 for (1R,2R)-2-((6-((5-bromo-1H-benzo[d]imidazol-1-yl)methyl)benzo[d]thiazol-2-yl)amino)cyclohexanol used in Example 121. LCMS (ESI) m/z 476 (M+H)⁺.

Step 2:

(1R,2R)-2-((6-((6-Ethynyl-1H-benzo[d]imidazol-1-yl)methyl)benzo[d]thiazol-2-yl)amino)cyclohexanol was synthesized as a powder (7 mg, 18%) using a procedure analogous to that described in Step 2 of Example 121, substituting (1R,2R)-2-((6-((6-((trimethylsilyl)ethynyl)-1H-benzo[d]imidazol-1-yl)methyl)benzo[d]thiazol-2-yl)amino)cyclohexanol from the previous step for (1R,2R)-2-((6-((5-((trimethylsilyl)ethynyl)-1H-benzo[d]imidazol-1-yl)methyl)benzo[d]thiazol-2-yl)amino)cyclohexanol used in Example 121. ¹H NMR (300 MHz, DMSO-$d_6$) δ 8.50 (s, 1H), 8.03 (d, J=7.2 Hz, 1H), 7.74 (s, 1H), 7.60-7.68 (m, 2H), 7.16-7.34 (m, 3H), 5.48 (s, 2H), 4.80 (d, J=4.0 Hz, 1H), 4.10 (s, 1H), 3.51 (m, 1H), 3.35 (m, 1H), 2.02 (m, 1H), 1.87 (m, 1H), 1.5-1.67 (m, 2H), 1.11-1.34 (m, 4H); LCMS (ESI) m/z 405 (M+H)⁺.

Example 123

Preparation of (1R,2R)-2-((6-((6-bromo-5-methoxy-3H-imidazo[4,5-b]pyridin-3-yl)methyl)benzo[d]thiazol-2-yl)amino)cyclohexanol

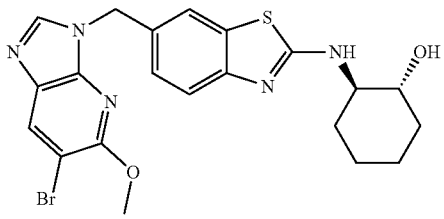 [SMILES: COc1nc2c(cc1Br)ncn2Cc1ccc2nc(N[C@@H]3CCCC[C@H]3O)sc2c1]

Step 1:

To a stirred solution of 6-methoxy-3-nitropyridin-2-amine (1.56 g, 9.2 mmol) in 15 mL of DMF at rt was added N-bromosuccimide (1.81 g, 10.1 mmol) in portions. The

255 resulting mixture was stirred at rt for 1 h. TLC showed the reaction was complete. The reaction mixture was quenched with water and the reddish brown solid was collected by filtration, washed with water, and dried in a vacuum oven to give 5-bromo-6-methoxy-3-nitropyridin-2-amine (2.1 g, 92%). LCMS (ESI) m/z 248, 250 (M+H)$^+$.

Step 2:

A mixture of acetic anhydride (15.9 mL, 168.7 mmol) and formic acid (6.4 mL, 168.7 mmol) was heated at 60° C. for 3 h. After cooling to rt, 5-bromo-6-methoxy-3-nitropyridin-2-amine (2.1 g, 8.4 mmol) from Step 1 of this Example was added in portions. The resulting mixture was heated at 60° C. for 1 h, then at 70° C. for 1 h. LCMS analysis showed that the reaction was complete. The volume was condensed under reduced pressure, and the precipitated solid was collected by filtration to give N-(5-bromo-6-methoxy-3-nitropyridin-2-yl)formamide as a light yellow solid (2.2 g, 94%). LCMS (ESI) m/z 276, 278 (M+H)$^+$.

Step 3:

Crude N-(5-bromo-6-methoxy-3-nitropyridin-2-yl)-N-((2-(methylthio)benzo[d]thiazol-6-yl)methyl)formamide (950 mg) was obtained as a light yellow solid using a procedure analogous to that described in Step 4 of Example 3, substituting N-(5-bromo-6-methoxy-3-nitropyridin-2-yl)formamide from Step 2 of this Example for 3H-imidazo[4,5-b]pyridine used in Example 3. LCMS (ESI) m/z 469,471 (M+H)$^+$.

Step 4:

To a stirred solution of crude N-(5-bromo-6-methoxy-3-nitropyridin-2-yl)-N-((2-(methylthio)benzo[d]thiazol-6-yl)methyl)formamide (950 mg, 2.0 mmol) in EtOH (8 mL) were added AcOH (2 mL) and iron (169 mg, 3.0 mmol). The resulting mixture was heated at reflux for 1 h. Another portion of iron (169 mg, 3.0 mmol) was added and heating was continued for 1 h at 105° C. LCMS analysis showed that the reaction was complete. The mixture was allowed to cool to rt, and then water was added. Crude 6-((6-bromo-5-methoxy-3H-imidazo[4,5-b]pyridin-3-yl)methyl)-2-(methylthio)benzo[d]thiazole was collected by filtration as a brownish green solid (1.01 g). LCMS (ESI) m/z 421, 423 (M+H)$^+$.

Step 5:

(1R,2R)-2-((6-((6-Bromo-5-methoxy-3H-imidazo[4,5-b]pyridin-3-yl)methyl)benzo[d]thiazol-2-yl)amino)cyclohexanol (115 mg, 23%) was obtained as a light yellow solid using procedures analogous to those described in Step 5 of Example 3 followed by Step 5 of Example 2, substituting 6-((6-bromo-5-methoxy-3H-imidazo[4,5-b]pyridin-3-yl)methyl)-2-(methylthio)benzo[d]thiazole from Step 4 of this Example for 6-((3H-imidazo[4,5-b]pyridin-3-yl)methyl)-2-(methylthio)benzo[d]thiazole used in Example 3, and substituting the product of that reaction for 2-bromo-6-((5,6-dimethoxy-1H-benzo[d]imidazol-1-yl)methyl)benzo[d]thiazole used in Example 2. $^1$H NMR (300 MHz, DMSO-d$_6$) δ 8.41 (s, 1H), 8.35 (s, 1H), 7.97 (d, J=7.5 Hz, 1H), 7.73 (s, 1H), 7.29 (s, 2H), 5.39 (s, 2H), 4.75 (br s, 1H), 4.01 (s, 3H), 3.50 (br s, 2H), 2.04 (br s, 1H), 1.80-1.88 (m, 1H), 1.60 (br s, 2H), 1.22 (d, J=5.8 Hz, 4H). LCMS (ESI) m/z 488, 490 (M+H)$^+$.

256

Example 124

Preparation of 3-((2-(((1R,2R)-2-hydroxycyclohexyl)amino)benzo[d]oxazol-6-yl)methyl)-3H-imidazo[4,5-b]pyridine-6-carbonitrile

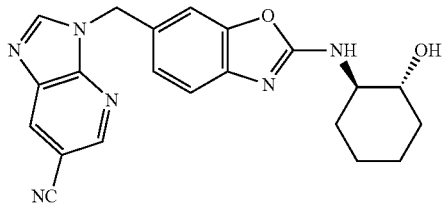

Step 1:

A solution of 5-bromo-pyridine-2,3-diamine (3.0 g, 15.96 mmol) and HCOOH (1.1 mL) in triethoxymethane (48 mL) was stirred at 90° C. for 3 h. The reaction mixture was concentrated under reduced pressure. The residue was purified by silica gel chromatography eluting with 40:1 DCM/MeOH to give 6-bromo-3H-imidazo[4,5-b]pyridine as a light brown solid (2.74 g, 86.7%). $^1$H NMR (300 MHz, DMSO-d$_6$) δ 8.49 (s, 1H), 8.44 (s, 1H), 8.30 (br s, 1H). LCMS (ESI) m/z 198 (M+H)'.

Step 2:

To a stirred solution of 6-bromo-3H-imidazo[4,5-b]pyridine (200 mg, 1.01 mmol) in DMF (16 mL) was added NaH (60% dispersion in mineral oil, 581 mg, 1.44 mmol) portionwise at 0° C. After the mixture was stirred for 30 min, 6-(chloromethyl)-2-(methylthio)benzo[d]oxazole (203 mg, 0.96 mmol) was added. The reaction mixture was allowed to warm to rt and stir for 2 h. The reaction mixture was poured into water (40 mL) and extracted with ethyl acetate (60 mL×4). The combined organic layers were washed with water and brine, dried over Na$_2$SO$_4$, filtered and concentrated under reduced pressure. The residue was purified by preparative TLC eluting with 15:1 DCM/MeOH to give 6-((6-bromo-3H-imidazo[4,5-b]pyridin-3-yl)methyl)-2-(methylthio)benzo[d]oxazole (156 mg, 43.2%) as a light yellow solid. $^1$H NMR (300 MHz, DMSO-d$_6$) δ 8.47 (s, 1H), 8.22 (s, 1H), 8.04 (s, 1H), 7.56 (d, J=8.4 Hz, 1H), 7.40 (s, 1H), 7.26 (d, J=6.6 Hz, 1H), 5.53 (s, 2H), 2.74 (s, 3H). LCMS (ESI) m/z 374 (M+H)$^+$.

Step 3:

A mixture of 6-((6-bromo-3H-imidazo[4,5-b]pyridin-3-yl)methyl)-2-(methylthio)benzo[d]oxazole (522 mg, 1.39 mmol) and m-CPBA (282 mg, 1.39 mmol) in DCM (20 mL) was stirred at 0° C. for 5 h. The reaction mixture was washed with aq Na$_2$S$_2$O$_3$ and brine, dried over Na$_2$SO$_4$, filtered and concentrated under reduced pressure. The residue was purified by silica gel chromatography eluting with 1:1 to 1:5 petroleum ether/ethyl acetate to give 6-((6-bromo-3H-imidazo[4,5-b]pyridin-3-yl)methyl)-2-(methylsulfinyl)benzo[d]oxazole as a light yellow solid (400 mg, 73.7%). $^1$H NMR (300 MHz, DMSO-d$_6$) δ 8.69 (s, 1H), 8.48 (s, 1H), 8.40 (s, 1H), 7.68 (s, 1H), 7.58 (d, J=8.1 Hz, 1H), 7.34 (d, J=9.3 Hz, 1H), 5.60 (s, 2H), 2.73 (s, 3H). LCMS (ESI) m/z 390 (M+H)$^+$.

Step 4:

A mixture of 6-((6-bromo-3H-imidazo[4,5-b]pyridin-3-yl)methyl)-2-(methyl sulfinyl)benzo[d]oxazole (330 mg, 0.84 mmol), (1R,2R)-2-aminocyclohexanol (192 mg, 1.27 mg) and DIEA (327 mg, 2.54 mmol) in DMA (15 mL) was stirred at 135° C. for 1 h. The reaction mixture was cooled to rt, poured into water (100 mL) and extracted with ethyl acetate (50 mL×3). The combined organic layers were washed with water and brine, dried over Na₂SO₄, filtered and concentrated under reduced pressure. The residue was purified by silica gel chromatography eluting with 1:6 petroleum ether/ethyl acetate to give (1R,2R)-2-((6-((6-bromo-3H-imidazo[4,5-b]pyridin-3-yl)methyl)benzo[d]oxazol-2-yl)amino)cyclohexanol as a light yellow solid (373 mg, 100%). ¹H NMR (300 MHz, DMSO-d₆) δ 8.65 (s, 1H), 8.48 (s, 1H), 8.38 (s, 1H), 7.79 (d, J=7.5 Hz, 1H), 7.38 (s, 1H), 7.13 (s, 1H), 5.48 (s, 2H), 4.68 (s, 3H), 3.37 (br s, 2H), 1.92 (br s, 2H), 1.62 (br s, 2H), 1.23 (br s, 4H). LCMS (ESI) m/z 441 (M+H)⁺.

Step 5:

A mixture of (1R,2R)-2-((6-((6-bromo-3H-imidazo[4,5-b]pyridin-3-yl)methyl)benzo[d]oxazol-2-yl)amino)cyclohexanol (276 mg, 0.62 mmol), Zn(CN)₂ (110 mg, 0.94 mmol), Pd₂(dba)₃ (57 mg, 0.062 mmol) and dppf (68.8 mg, 0.124 mmol) in DMF (6 mL) was stirred at 100° C. for 2 h. The reaction mixture was cooled to rt, poured into water (100 mL) and extracted with ethyl acetate (100 mL×2). The combined organic layers were washed with water and brine, dried over Na₂SO₄, filtered and concentrated under reduced pressure. The residue was purified by silica gel chromatography eluting with 15:1 DCM/MeOH to give 3-((2-(((1R,2R)-2-hydroxycyclohexyl)amino)benzo[d]oxazol-6-yl)methyl)-3H-imidazo[4,5-b]pyridine-6-carbonitrile as a light yellow solid (62 mg, 25.8%). ¹H NMR (300 MHz, DMSO-d₆) δ 8.85 (s, 1H), 8.83 (d, J=1.5 Hz, 1H), 8.70 (s, 1H), 7.81 (d, J=7.8 Hz, 1H), 7.41 (s, 1H), 7.14 (m, 2H), 5.54 (s, 2H), 4.68 (d, J=4.8 Hz, 1H), 3.34 (br s, 2H), 1.91 (br s, 2H), 1.62 (br s, 2H), 1.22 (br, 4H). LCMS (ESI) m/z 389 (M+H)⁺.

Example 125

Preparation of (1R,2R)-2-((6-(imidazo[1,2-a]pyrazin-3-ylmethyl)benzo[d]thiazol-2-yl)amino)cyclohexanol

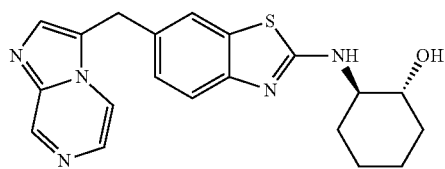

Step 1:

A stirred mixture of 2-chloro-3-(2-(methylthio)benzo[d]thiazol-6-yl)propanal from Step 4 of Example 117 (300 mg, 1.1 mmol) and pyrazin-2-amine (210 mg, 2.2 mmol) in 1-butanol (10 mL) was heated at reflux overnight. The mixture was cooled to rt and water (20 mL) was added. The mixture was extracted with EtOAc (10 mL×3). The combined organic layers were washed with brine, dried over Na₂SO₄, filtered and concentrated under reduced pressure. The residue was purified by silica gel chromatography eluting with 50:1 to 20:1 DCM/MeOH to afford 6-(imidazo[1,2-c]pyrazin-3-ylmethyl)-2-(methylthio)benzo[d]thiazole as a yellow solid (120 mg, 35%). ¹H NMR (300 MHz, CDCl₃) δ 9.10 (d, J=1.2 Hz, 1H), 7.83-7.80 (m, 2H), 7.72-7.68 (m, 2H), 7.50 (d, J=9.0 Hz, 1H), 7.23 (d, J=1.8 Hz, 1H), 4.38 (s, 2H), 2.78 (s, 3H). LCMS (ESI) m/z 313 (M+H)⁺.

Step 2:

To a solution of 6-(imidazo[1,2-c]pyrazin-3-ylmethyl)-2-(methylthio)benzo[d]thiazole (230 mg, 0.74 mmol) from previous step in DCM (14 mL) was added m-CPBA (160 mg, 0.93 mmol) at 0° C. The reaction mixture was stirred for 2 h at 0° C., then aq Na₂S₂O₃ (15 mL) was added and the mixture was stirred for 0.5 h. The organic layer was separated, dried over Na₂SO₄, filtered and concentrated under reduced pressure. The residue was purified by silica gel chromatography, eluting with 50:1 to 20:1 DCM/MeOH, to afford 6-(imidazo[1,2-c]pyrazin-3-ylmethyl)-2-(methylsulfinyl)benzo[d]thiazole as a yellow solid (200 mg, 83%). ¹H NMR (300 MHz, CDCl₃) δ 9.13 (d, J=1.5 Hz, 1H), 8.02 (d, J=8.7 Hz, 1H), 7.85-7.79 (m, 2H), 7.74-7.70 (m, 2H), 7.40 (dd, J=1.5, 8.4 Hz, 1H), 4.46 (s, 2H), 3.07 (s, 3H). LCMS (ESI) m/z 329 (M+H)⁺.

Step 3:

A mixture of 6-(imidazo[1,2-c]pyrazin-3-ylmethyl)-2-(methylsulfinyl)benzo[d]thiazole (350 mg, 1.07 mmol), (1R,2R)-2-aminocyclohexanol (324 mg, 2.14 mmol) and DIEA (414 mg, 3.21 mmol) in NMP (14 mL) was stirred for 2 d at 140° C. The mixture was cooled to rt and water (50 mL) was added. The mixture was extracted with EtOAc (30 mL×3). The combined organic layers were washed with brine, dried over Na₂SO₄, filtered and concentrated under reduced pressure. The residue was purified by silica gel chromatography eluting with 50:1 to 10:1 DCM/MeOH to afford 100 mg of solid. The solid was recrystallized with 10:1 DCM/MeOH to afford (1R,2R)-2-((6-(imidazo[1,2-c]pyrazin-3-ylmethyl)benzo[d]thiazol-2-yl)amino)cyclohexanol as a white solid (70 mg, 17%). ¹H NMR (300 MHz, DMSO-d₆) δ 9.03 (d, J=1.2 Hz, 1H), 8.33 (dd, J=1.8, 4.5 Hz, 1H), 7.88-7.85 (m, 2H), 7.68 (s, 1H), 7.54 (s, 1H), 7.27 (d, J=7.8 Hz, 1H), 7.11 (dd, J=1.5, 7.8 Hz, 1H), 4.71 (d, J=4.8 Hz, 1H), 4.35 (s, 2H), 3.5-3.49 (m, 1H), 3.39-3.36 (m, 1H), 2.05-2.01 (m, 1H), 1.90-1.86 (m, 1H), 1.65-1.59 (m, 2H), 1.30-1.16 (m, 4H). LCMS (ESI) m/z 380 (M+H)⁺.

Example 126

Preparation of 3-((2-(((1R,2R)-2-hydroxycyclohexyl)amino)benzo[d]thiazol-6-yl)methyl)-5-methoxy-3H-imidazo[4,5-b]pyridine-6-carbonitrile

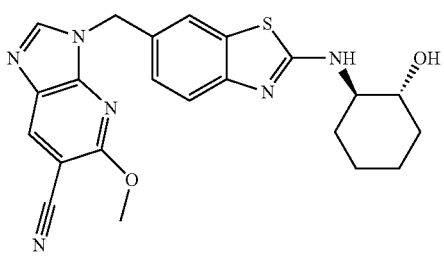

3-((2-(((1R,2R)-2-Hydroxycyclohexyl)amino)benzo[d]thiazol-6-yl)methyl)-5-methoxy-3H-imidazo[4,5-b]pyridine-6-carbonitrile (55 mg, 69%) was obtained as a light yellow solid using a procedures analogous to that described in Example 43, substituting (1R,2R)-2-((6-((6-bromo-5-methoxy-3H-imidazo[4,5-b]pyridin-3-yl)methyl)benzo[d]thiazol-2-yl)amino)cyclohexanol from Example 123 for (1R,2R)-2-((6-((6-bromo-3H-imidazo[4,5-b]pyridin-3-yl)methyl)benzo[d]thiazol-2-yl)amino)cyclohexanol used in Example 43. ¹H NMR (300 MHz, DMSO-d₆) δ 8.60 (d, J=6.6 Hz, 2H), 7.99 (d, J=7.3 Hz, 1H), 7.74 (s, 1H), 7.30 (s, 2H), 5.42 (s, 2H), 4.76 (br s, 1H), 4.07 (s, 3H), 3.5-3.70 (m, 2H), 1.97-2.14 (m, 1H), 1.86 (br s, 1H), 1.62 (d, J=4.5 Hz, 2H), 1.22 (d, J=5.5 Hz, 4H). LCMS (ESI) m/z 435 (M+H)$^+$.

Example 127

Preparation of (1R,2R)-2-((6-((5-methyl-1H-benzo[d]imidazol-1-yl)methyl)benzo[d]thiazol-2-yl)amino)cyclohexanol

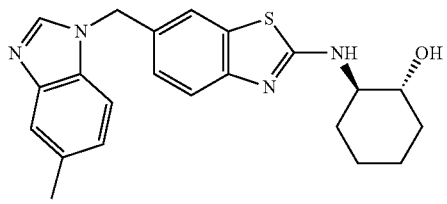 [SMILES: Cc1ccc2c(c1)ncn2Cc1ccc2nc(N[C@@H]3CCCC[C@H]3O)sc2c1]

Step 1:
To a stirred mixture of 4-methyl-2-nitroaniline (1 g, 6.5 mmol) in TFA (15 mL) at 0 to 5° C. was added portionwise sodium triacetoxyborohydride (2.78 g, 13.2 mmol) and the mixture was stirred for 10 min. To the reaction mixture was added portionwise 2-(methylthio)benzo[d]thiazole-6-carbaldehyde (1.44 g, 6.9 mmol) from Step 1 of Example 100. After stirring at rt for 4 h, the mixture was poured into ice-water and extracted with EtOAc (100 mL×3). The combined organic layers were washed with saturated aq NaHCO$_3$ (100 mL×2) and brine (100 mL). The organic layer was separated, dried over Na$_2$SO$_4$, filtered, and concentrated under reduced pressure. The residue was purified by silica gel flash chromatography eluting with 3% EtOAc in petroleum ether to afford 4-methyl-N-((2-(methylthio)benzo[d]thiazol-6-yl)methyl)-2-nitroaniline (0.93 g, 41%) as a yellow solid. $^1$H NMR (300 MHz, CDCl$_3$) δ 8.37 (br s, 1H), 8.01 (s, 1H), 7.83 (d, J=8.4 Hz, 1H), 7.71 (s, 1H), 7.38 (dd, J=8.4, 2.4 Hz, 1H), 7.19 (dd, J=8.7, 2.1 Hz, 1H), 8.71 (d, J=8.7 Hz, 1H), 4.83 (d, J=6.0 Hz, 2H), 2.83 (s, 3H), 2.25 (s, 3H); LCMS (ESI) m/z 346 (M+H)$^+$.

Step 2:
A mixture of 4-methyl-N-((2-(methylthio)benzo[d]thiazol-6-yl)methyl 1)-2-nitroaniline (0.93 g, 2.7 mmol) from the previous step, MeOH (50 mL) and palladium on activated charcoal (100 mg) was stirred under hydrogen at 1 atm pressure at rt for 12 h. The mixture was filtered and the filtrate was concentrated under reduced pressure to afford 4-methyl-N$^1$-((2-(methylthio)benzo[d]thiazol-6-yl)methyl)benzene-1,2-diamine (0.70 g, 85%) as a brown solid which was not purified further. LCMS (ESI) m/z 316 (M+H)$^+$.

Step 3:
A stirred mixture of crude 4-methyl-N$^1$-((2-(methylthio)benzo[d]thiazol-6-yl)methyl)benzene-1,2-diamine (0.7 g, 2.3 mmol), formic acid (0.5 mL) and triethyl orthoformate (5 mL) was heated at 100° C. for 1 h. The reaction mixture was cooled to rt and concentrated under reduced pressure. The residue was purified by silica gel flash chromatography eluting with 3% MeOH in DCM to afford 6-((5-methyl-1H-benzo[d]imidazol-1-yl)methyl)-2-(methylthio)benzo[d]thiazole (0.61 g, 85%) as a yellow solid. $^1$H NMR (300 MHz, CDCl$_3$) δ 7.94 (s, 1H), 7.82 (d, J=8.4 Hz, 1H), 7.62 (s, 1H), 7.49 (s, 1H), 7.26 (m, 1H), 7.14 (d, J=8.1 Hz, 1H), 7.07 (d, J=8.1 Hz, 1H), 5.43 (s, 2H), 2.77 (s, 3H), 2.47 (s, 3H); LCMS (ESI) m/z 326 (M+H)$^+$.

Step 4:
To a stirred solution of 6-((5-methyl-1H-benzo[d]imidazol-1-yl)methyl)-2-(methylthio)benzo[d]thiazole (0.61 g, 1.8 mmol) from the previous step in DCM (20 mL) at 0° C. was added a solution of meta-chloroperbenzoic acid (0.40 g, 1.57 mmol) in DCM (3 mL). After stirring for 2 h at 0° C., the solution was diluted with EtOAc (100 mL) and washed sequentially with saturated aq Na$_2$S$_2$O$_3$, saturated aq NaHCO$_3$, and brine. The organic layer was separated, dried over Na$_2$SO$_4$, filtered, and concentrated under reduced pressure to afford 6-((5-methyl-1H-benzo[d]imidazol-1-yl)methyl)-2-(methylsulfinyl)benzo[d]thiazole (0.57 g, 89%) as a yellow solid which was not purified further.

Step 5:
A stirred mixture of 6-((5-methyl-1H-benzo[d]imidazol-1-yl)methyl)-2-(methylsulfinyl)benzo[d]thiazole (0.26 g, 0.76 mmol) from the previous step, (1R,2R)-2-aminocyclohexanol (0.26 g, 2.2 mmol), DIEA (0.98 g, 7.6 mmol) and NMP (2 mL) was heated at 130° C. for 12 h. The reaction mixture was cooled to rt, diluted with EtOAc (30 mL), and washed with water (10 mL×2). The organic layer was dried over Na$_2$SO$_4$, filtered, and concentrated under reduced pressure. The residue was purified by silica gel flash chromatography eluting with 3% MeOH in DCM to afford (1R,2R)-2-((6-((5-methyl-1H-benzo[d]imidazol-1-yl)methyl)benzo[d]thiazol-2-yl)amino)cyclohexanol (79 mg, 89%) as a white solid. $^1$H NMR (300 MHz, DMSO-d$_6$) δ 8.30 (s, 1H), 7.91 (d, J=7.5 Hz, 1H), 7.61 (d, J=2.0 Hz, 1H), 7.39-7.42 (m, 2H), 7.28 (d, J=8.1 Hz, 1H), 7.16 (dd, J=8.4, 1.8 Hz, 1H), 7.02 (d, J=7.2 Hz, 1H), 5.42 (s, 2H), 4.69 (d, J=5.1 Hz, 1H), 3.39 (m, 1H), 3.33 (m, 1H), 2.38 (s, 3H), 2.03 (m, 1H), 1.86 (m, 1H), 1.5-1.63 (m, 2H), 1.21-1.23 (m, 4H); LCMS (ESI) m/z 393 (M+H)$^+$.

Example 128

Preparation of (1R,2R)-2-((6-((5,6-difluoro-1H-benzo[d]imidazol-1-yl)methyl)benzo[d]thiazol-2-yl)amino)cyclohexanol

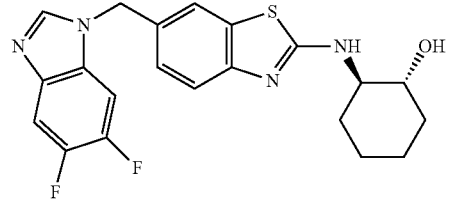 [SMILES: O[C@@H]1CCCC[C@H]1Nc1nc2ccc(Cn3cnc4cc(F)c(F)cc43)cc2s1]

Step 1:
A mixture of 4,5-difluoro-2-nitroaniline (1.73 g, 10 mmol), palladium on activated charcoal (200 mg), and MeOH (50 mL) was stirred under hydrogen (1 atm) at rt for 12 h. The mixture was filtered to remove the catalyst and the filtrate was concentrated under reduced pressure to afford 4,5-difluorobenzene-1,2-diamine (1.42 g, 97%) as a brown solid, which was not purified further. $^1$H NMR (300 MHz, CDCl$_3$) δ 6.50 (m, 2H), 2.75-3.48 (br s, 4H).

Step 2:
A stirred mixture of 4,5-difluorobenzene-1,2-diamine (1.40 g, 9.7 mmol) from the previous step, formic acid (2.0 mL), and triethyl orthoformate (20 mL) was heated at 100° C. for 1 h. The reaction mixture was cooled to rt and concentrated under reduced pressure. The residue was purified by silica gel flash chromatography eluting with 5%

MeOH in DCM to afford 5,6-difluoro-1H-benzo[d]imidazole as (1.12 g, 75%) as a white solid. $^1$H NMR (300 MHz, CDCl$_3$) δ 8.07 (s, 1H), 7.44 (m, 2H); LCMS (ESI) m/z 155 (M+H)$^+$.

Step 3:

To a stirred mixture of sodium hydride (60% dispersion in mineral oil, 0.144 g, 3.0 mmol) in anhydrous DMF (10 mL) at 0° C. under a nitrogen atmosphere was added portionwise 6-difluoro-1H-benzo[d]imidazole (0.475 g, 2.0 mmol) from the previous step. The mixture was stirred at 0° C. for 5 min. To the mixture was added dropwise a solution of 6-(chloromethyl)-2-(methylthio)benzo[d]thiazole (0.32 g, 2.0 mmol) from Step 4 of Example 36 in anhydrous DMF (2 mL). The reaction mixture was allowed to warm to rt and stir for 1 h. The mixture was poured into ice-water and extracted with EtOAc (100 mL×2). The combined organic layers were further washed with water (20 mL) then brine (20 mL). The organic layer was separated and dried over Na$_2$SO$_4$, filtered, and concentrated under reduced pressure to afford 6-((5,6-difluoro-1H-benzo[d]imidazol-1-yl)methyl)-2-(methylthio)benzo[d]thiazole (0.55 g, 76%) as a yellow solid, which was not purified further. $^1$H NMR (300 MHz, CDCl$_3$) δ 7.97 (s, 1H), 7.84 (d, J=8.4 Hz, 1H), 7.59 (m, 1H), 7.50 (s, 1H), 7.24 (m, 1H), 7.02 (m, 1H), 5.40 (s, 2H), 2.78 (s, 3H); LCMS (ESI) m/z 348 (M+H)$^+$.

Step 4:

To a stirred solution of 6-((5,6-difluoro-1H-benzo[d]imidazol-1-yl)methyl)-2-(methylthio)benzo[d]thiazole (0.55 g, 1.58 mmol) from the previous step in DCM (20 mL) at 0° C. was added a solution of meta-chloroperbenzoic acid (0.32 g, 1.58 mmol) in DCM (3 mL). After stirring for 2 h at 0° C., the mixture was diluted with EtOAc (100 mL) and washed sequentially with saturated aq Na$_2$S$_2$O$_3$, saturated aq NaHCO$_3$, and brine. The organic layer was separated, dried over Na$_2$SO$_4$, filtered, and concentrated under reduced pressure to afford 6-((5,6-difluoro-1H-benzo[d]imidazol-1-yl)methyl)-2-(methylsulfinyl)benzo[d]thiazole (0.50 g, 88%) as a white solid, which was not purified further. $^1$H NMR (300 MHz, CDCl$_3$) δ 8.02-8.06 (m, 2H), 7.77 (s, 1H), 7.61 (m, 1H), 7.37 (dd, J=8.4, 1.5 Hz, 1H), 7.01 (m, 1H), 5.48 (s, 2H), 3.07 (s, 3H); LCMS (ESI) m/z 364 (M+H)$^+$.

Step 5:

A stirred mixture of 6-((5,6-difluoro-1H-benzo[d]imidazol-1-yl)methyl)-2-(methylsulfinyl)benzo[d]thiazole (0.20 g, 0.55 mmol), (1R,2R)-2-aminocyclohexanol (0.19 g, 1.6 mmol), DIEA (0.71 g, 5.5 mmol) and NMP (2 mL) was heated at 130° C. for 12 h. The reaction mixture was cooled to rt, diluted with EtOAc (30 mL) and washed with water (10 mL×2). The organic layer was separated, dried over Na$_2$SO$_4$, filtered, and concentrated under reduced pressure. The residue was purified by silica gel flash chromatography eluting with 3% MeOH in DCM to afford (1R,2R)-2-((6-((5,6-difluoro-1H-benzo[d]imidazol-1-yl)methyl)benzo[d]thiazol-2-yl)amino)cyclohexanol (65 mg, 30%) as a white solid. $^1$H NMR (300 MHz, DMSO-d$_6$) δ 8.48 (s, 1H), 7.97 (d, J=7.5 Hz, 1H), 7.69-7.78 (m, 3H), 7.30 (d, J=8.1 Hz, 1H), 7.22 (d, J=8.1 Hz, 1H), 5.44 (s, 2H), 4.74 (d, J=4.8 Hz, 1H), 3.51 (m, 1H), 3.42 (m, 1H), 2.00 (m, 1H), 1.87 (m, 1H), 1.5-1.60 (m, 2H), 1.15-1.25 (m, 4H); LCMS (ESI) m/z 415 (M+H)$^+$.

Example 129

(1R,2R)-2-((6-((5-fluoro-1H-benzo[d]imidazol-1-yl)methyl)benzo[d]thiazol-2-yl)amino)cyclohexanol

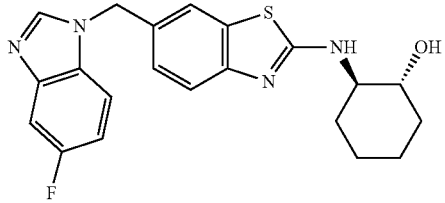 [SMILES: O[C@@H]1CCCC[C@H]1Nc1nc2ccc(Cn3cnc4cc(F)ccc43)cc2s1]

Step 1:

4-Fluoro-N-((2-(methylthio)benzo[d]thiazol-6-yl)methyl)-2-nitro aniline (0.88 g, 66%) was obtained as a yellow solid using a procedure analogous to that described in Step 1 of Example 127, substituting 4-fluoro-2-nitroaniline for 4-methyl-2-nitroaniline used in Example 127. $^1$H NMR (300 MHz, CDCl$_3$) δ 8.37 (br s, 1H), 8.01 (s, 1H), 7.92 (dd, J=9.0, 3.0 Hz, 1H), 7.85 (d, J=9.0 Hz, 1H), 7.37 (dd, J=8.4, 1.5 Hz, 1H), 7.17 (m, 1H), 6.75 (dd, J=9.6, 4.8 Hz, 1H), 4.64 (d, J=5.7 Hz, 2H), 3.78 (s, 3H); LCMS (ESI) m/z 350 (M+H)$^+$.

Step 2:

To a stirred mixture of 4-fluoro-N-((2-(methylthio)benzo[d]thiazol-6-yl)methyl)-2-nitroaniline (1.18 g, 3.3 mmol) from the previous step, acetic acid (3 mL), MeOH (3 mL) and DCM (20 mL) at −10° C. was added portionwise zinc dust (1.7 g, 26 mmol). The reaction mixture was stirred at 10° C. for 0.5 h. The mixture was poured into ice-water and extracted with EtOAc (100 mL×3). The combined organic layers were washed sequentially with water, saturated aq NaHCO$_3$ (100 mL×2), and brine (100 mL). The organic layer was separated, dried over Na$_2$SO$_4$, filtered, and concentrated under reduced pressure to afford 4-fluoro-N$^1$-42-(methylthio)benzo[d]thiazol-6-yl)methyl)benzene-1,2-diamine (0.93 g, yield 87%) as a yellow solid, which was not purified further. $^1$H NMR (300 MHz, CDCl$_3$) δ 7.82 (d, J=8.4 Hz, 1H), 7.76 (s, 1H), 7.42 (dd, J=8.4, 1.8 Hz, 1H), 6.42-6.56 (m, 3H), 4.35 (s, 2H), 3.60 (br s, 2H), 2.79 (s, 3H); LCMS (ESI) m/z 320 (M+H)$^+$.

Step 3:

A stirred mixture of 4-fluoro-N$^1$-((2-(methylthio)benzo[d]thiazol-6-yl)methyl)benzene-1,2-diamine (0.93 g, 2.93 mmol) from the previous step, formic acid (0.5 mL) and triethyl orthoformate (5 mL) was heated at 100° C. for 1 h. The reaction mixture was cooled to rt and concentrated under reduced pressure. The residue was purified by silica gel flash chromatography eluting with 3% MeOH in DCM to afford 6-((5-fluoro-1H-benzo[d]imidazol-1-yl)methyl)-2-(methylthio)benzo[d]thiazole (0.64 g, 67%) as a yellow solid. $^1$H NMR (300 MHz, CDCl$_3$) δ 7.99 (s, 1H), 7.83 (d, J=8.1 Hz, 1H), 7.47-7.51 (m, 2H), 7.26 (m, 1H), 7.17 (m, 1H), 7.00 (dt, J=9.3, 2.4 Hz, 1H), 5.44 (s, 2H), 2.77 (s, 3H); LCMS (ESI) m/z 330 (M+H)$^+$.

Step 4:

To a stirred solution of 6-((5-fluoro-1H-benzo[d]imidazol-1-yl)methyl)-2-(methylthio)benzo[d]thiazole (0.64 g, 1.9 mmol) from the previous step in DCM (20 mL) at 0° C. was added a solution of meta-chloroperbenzoic acid (0.472 g, 2.3 mmol) in DCM (3 mL). The mixture was stirred at 0° C. for 2 h. The solution was diluted with EtOAc (100 mL) and washed sequentially with saturated aq Na$_2$S$_2$O$_3$, saturated aq NaHCO$_3$, and brine. The organic layer was separated, dried over Na$_2$SO$_4$, filtered, and concentrated under reduced pressure to afford 6-((5-fluoro-1H-benzo[d]imidazol-1-yl)methyl)-2-(methylsulfinyl)benzo[d]thiazole (0.63 g, 94%) as a yellow solid, which was not purified further. $^1$H NMR (300 MHz, CDCl$_3$) δ 8.02-8.05 (m, 2H), 7.78 (s, 1H), 7.51 (dd, J=9.6, 2.4 Hz, 1H), 7.38 (dd, J=8.4, 1.8 Hz, 1H), 7.20 (m, 1H), 7.00 (dt, J=9.0, 2.4 Hz, 1H), 5.52 (s, 2H), 3.07 (s, 3H); LCMS (ESI) m/z 346 (M+H)$^+$.

Step 5:

A stirred mixture of 6-((5-fluoro-1H-benzo[d]imidazol-1-yl)methyl)-2-(methylsulfinyl)benzo[d]thiazole (0.20 g, 0.57 mmol) from the previous step, (1R,2R)-2-aminocyclohexanol (0.20 g, 1.7 mmol), DIEA (0.73 g, 5.7 mmol) and NMP (2 mL), was heated at 130° C. for 12 h. The reaction mixture was cooled to rt, diluted with EtOAc (30 mL), and washed with water (10 mL×2). The organic layer was separated, dried over Na$_2$SO$_4$, filtered, and concentrated under reduced pressure. The residue was purified by silica gel flash chromatography eluting with 3% MeOH in DCM to afford (1R,2R)-2-((6-((5-fluoro-1H-benzo[d]imidazol-1-yl)methyl)benzo[d]thiazol-2-yl)amino)cyclohexanol (75 mg, 33%) as a white solid. $^1$H NMR (300 MHz, DMSO-d$_6$) δ 8.45 (s, 1H), 7.93 (d, J=7.2 Hz, 1H), 7.65 (d, J=1.5 Hz, 1H), 7.56 (m, 1H), 7.43 (dd, J=9.6, 2.4 Hz, 1H), 7.28 (m, 1H), 7.19 (dd, J=8.4, 1.8 Hz, 1H), 7.08 (dt, J=9.6, 3.0 Hz, 1H), 5.46 (s, 2H), 4.69 (d, J=5.4 Hz, 1H), 3.51 (m, 1H), 3.37 (m, 1H), 2.01 (m, 1H), 1.87 (m, 1H), 1.5-1.63 (m, 2H), 1.15-1.23 (m, 4H); LCMS (ESI) m/z 397 (M+H)$^+$.

Example 130

Preparation of (1R,2R)-2-((6-((5-(trifluoromethyl)-1H-benzo[d]imidazol-1-yl)methyl)benzo[d]thiazol-2-yl)amino)cyclohexanol

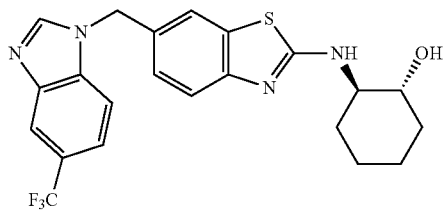

Step 1:

N-((2-(Methylthio)benzo[d]thiazol-6-yl)methyl)-2-nitro-4-(trifluoromethyl)aniline (0.38 g, 49%) was obtained as a yellow solid using a procedure analogous to that described in Step 1 of Example 127, substituting 2-nitro-4-(trifluoromethyl)aniline for 4-methyl-2-nitroaniline used in Example 127. $^1$H NMR (300 MHz, CDCl$_3$) δ 8.64 (br s, 1H), 8.50 (s, 1H), 7.87 (d, J=8.4 Hz, 1H), 7.71 (s, 1H), 7.56 (dd, J=9.0, 2.1 Hz, 1H), 7.38 (dd, J=8.4, 1.8 Hz, 1H), 6.90 (d, J=9.0 Hz, 1H), 4.69 (d, J=5.7 Hz, 2H), 2.79 (s, 3H); LCMS (ESI) m/z 400 (M+H)$^+$.

Step 2:

A mixture of N-((2-(methylthio)benzo[d]thiazol-6-yl)methyl)-2-nitro-4-trifluoromethyl)aniline (0.38 g, 2.0 mmol) from the previous step, MeOH (30 mL) and palladium on activated charcoal (50 mg) was stirred under hydrogen (1 atm) at rt for 12 h. The mixture was filtered to remove the catalyst and the filtrate was concentrated under reduced pressure to afford N$^1$-(2-(methylthio)benzo[d]thiazol-6-yl)methyl)-4-(trifluoromethyl)benzene-1,2-diamine (0.32 g, 91%) as a brown solid, which was not purified further. LCMS (ESI) m/z 370 (M+H)$^+$.

Step 3:

A stirred mixture of N$^1$-(2-(methylthio)benzo[d]thiazol-6-yl)methyl)-4-(trifluoromethyl)benzene-1,2-diamine (0.32 g, 0.86 mmol) from the previous step, formic acid (0.5 mL) and triethyl orthoformate (5 mL) was heated at 100° C. for 1 h. The reaction mixture was cooled to rt and concentrated under reduced pressure. The residue was purified by silica gel flash chromatography eluting with 3% MeOH in DCM to afford 2-(methylthio)-6-((5-(trifluoromethyl)-1H-benzo[d]imidazol-1-yl)methyl)benzo[d]thiazole (0.22 g, 69%) as a yellow solid. $^1$H NMR (300 MHz, CDCl$_3$) δ 8.12 (s, 1H), 8.08 (s, 1H), 7.84 (d, J=8.4 Hz, 1H), 7.48-7.54 (m, 2H), 7.36 (d, J=8.4 Hz, 1H), 7.26 (m, 1H), 5.49 (s, 2H), 2.78 (s, 3H); LCMS (ESI) m/z 380 (M+H)$^+$.

Step 4:

To a stirred solution of 2-(methylthio)-6-((5-(trifluoromethyl)-1H-benzo[d]imidazol-1-yl)methyl)benzo[d]thiazole (0.22 g, 0.58 mmol) from the previous step in DCM (20 mL) at 0° C. was added a solution of meta-chloroperbenzoic acid (0.30 g, 1.5 mmol) in DCM (3 mL). The mixture was stirred at 0° C. for 2 h. The mixture was diluted with EtOAc (100 mL) and washed sequentially with saturated aq Na$_2$S$_2$O$_3$, saturated aq NaHCO$_3$, and brine. The organic layer was separated, dried over Na$_2$SO$_4$, filtered, and concentrated under reduced pressure to afford 2-(methylsulfinyl)-6-((5-(trifluoromethyl)-1H-benzo[d]imidazol-1-yl)methyl)benzo[d]thiazole (0.22 g, 96%) as a yellow solid, which was not purified further. $^1$H NMR (300 MHz, CDCl$_3$) δ 8.12-8.14 (m, 2H), 8.05 (d, J=8.4 Hz, 1H), 7.79 (s, 1H), 7.50 (dd, J=8.7, 1.2 Hz, 1H), 7.37 (t, J=8.4 Hz, 2H), 5.57 (s, 2H), 3.06 (s, 3H); LCMS (ESI) m/z 396 (M+H)$^+$.

Step 5:

A stirred mixture of 2-(methylsulfinyl)-6-((5-(trifluoromethyl)-1H-benzo[d]imidazol-1-yl)methyl)benzo[d]thiazole (0.20 g, 0.50 mmol) from the previous step, (1R,2R)-2-aminocyclohexanol (0.17 g, 1.5 mmol), DIEA (0.59 g, 4.6 mmol) and NMP (2 mL) was heated at 130° C. for 12 h. The reaction mixture was cooled to rt, diluted with EtOAc (30 mL), and washed with water (10 mL×2). The organic layer was separated, dried over Na$_2$SO$_4$, filtered, and concentrated under reduced pressure. The residue was purified by silica gel flash chromatography eluting with 3% MeOH in DCM to afford (1R,2R)-2-((6-((5-(trifluoromethyl)-1H-benzo[d]imidazol-1-yl)methyl)benzo[d]thiazol-2-yl)amino)cyclohexanol (54 mg, 23%) as a white solid. $^1$H NMR (300 MHz, DMSO-d$_6$) δ 8.62 (s, 1H), 8.02 (s, 1H), 7.95 (d, J=7.8 Hz, 1H), 7.79 (d, J=8.7 Hz, 1H), 7.67 (d, J=1.2 Hz, 1H), 7.54 (d, J=8.7 Hz, 1H), 7.29 (d, J=8.4 Hz, 1H), 7.20 (d, J=8.4 Hz, 1H), 5.54 (s, 2H), 4.71 (d, J=5.1 Hz, 1H), 3.51 (m, 1H), 3.39 (m, 1H), 2.01 (m, 1H), 1.80 (m, 1H), 1.5-1.62 (m, 2H), 1.17-1.23 (m, 4H); LCMS (ESI) m/z 447 (M+H)$^+$.

Example 131

Preparation of (1R,2R)-2-((6-(imidazo[1,2-b]pyridazin-3-ylmethyl)benzo[d]thiazol-2-yl)amino)cyclohexanol

Step 1:

A stirred mixture of 2-chloro-3-(2-(methylthio)benzo[d]thiazol-6-yl)propanal (500 mg, 1.8 mmol) from Step 4 of Example 117 and pyridazin-3-amine (350 mg, 3.6 mmol) in 1-butanol (20 mL) was heated at reflux for 15 h. The mixture was cooled to rt and water (40 mL) was added. The mixture was extracted with EtOAc (20 mL×3) and the combined organic layers were washed with brine. The organic layer was separated, dried over $Na_2SO_4$, filtered, and concentrated under reduced pressure. The residue was purified by silica gel flash chromatography eluting with 2 to 5% MeOH in DCM to afford 6-(imidazo[1,2-b]pyridazin-3-ylmethyl)-2-(methylthio)benzo[d]thiazole (460 mg, 80%) as a light brown solid. $^1$H NMR (300 MHz, $CDCl_3$) δ 8.32 (dd, J=4.5, 1.5 Hz, 1H), 7.94 (dd, J=9.3, 1.5 Hz, 1H), 7.79 (d, J=8.7 Hz, 1H), 7.66 (s, 1H), 7.58 (s, 1H), 7.36 (dd, J=8.4, 1.8 Hz, 1H), 7.02 (m, 1H), 4.45 (s, 2H), 2.77 (s, 3H); LCMS (ESI) m/z 313 $(M+H)^+$.

Step 2:

To a stirred solution of 6-(imidazo[1,2-b]pyridazin-3-ylmethyl)-2-(methylthio)benzo[d]thiazole (350 mg, 1.1 mmol) from the previous step in DCM (30 mL) at 0° C. was added meta-chloroperbenzoic acid (194 mg, 1.1 mmol). The reaction mixture was stirred at 0° C. for 2 h. To the mixture was added saturated aq $Na_2S_2O_3$ (15 mL) and the mixture was stirred for a further 0.5 h. The organic layer was separated, dried over $Na_2SO_4$, filtered, and concentrated under reduced pressure. The residue was purified by silica gel flash chromatography eluting with 2 to 5% MeOH in DCM to afford 6-(imidazo[1,2-b]pyridazin-3-ylmethyl)-2-(methylsulfinyl)benzo[d]thiazole (320 mg, 87%) as a yellow solid. $^1$H NMR (300 MHz, $CDCl_3$) δ 8.33 (dd, J=4.5, 1.5 Hz, 1H), 7.91-8.00 (m, 3H), 7.62 (s, 1H), 7.54 (dd, J=8.4, 1.8 Hz, 1H), 7.03 (m, 1H), 4.52 (s, 2H), 3.05 (s, 3H); LCMS (ESI) m/z 329 $(M+H)^+$.

Step 3:

A stirred mixture of 6-(imidazo[1,2-b]pyridazin-3-ylmethyl)-2-(methylsulfinyl)benzo[d]thiazole (260 mg, 0.79 mmol) from the previous step, (1R,2R)-2-aminocyclohexanol hydrochloride (360 mg, 2.38 mmol), DIEA (408 mg, 3.16 mmol) and NMP (10 mL), was heated at 140° C. for 48 h. The mixture was cooled to rt and water (50 mL) was added. The mixture was extracted with EtOAc (30 mL×3) and the combined organic layers were washed with brine. The organic layer was separated, dried over $Na_2SO_4$, filtered, and concentrated under reduced pressure. The residue was purified by silica gel flash chromatography eluting with 2 to 10% MeOH in DCM to afford a solid. The solid was further purified by recrystallization from a 10:1 mixture of DCM: MeOH to afford (1R,2R)-2-((6-(imidazo[1,2-b]pyridazin-3-ylmethyl)benzo[d]thiazol-2-yl)amino)cyclohexanol (80 mg, 27%) as a white solid. $^1$H NMR (300 MHz, DMSO-$d_6$) δ 8.53 (dd, J=4.5, 1.5 Hz, 1H), 8.10 (dd, J=9.3, 1.5 Hz, 1H), 7.83 (d, J=7.8 Hz, 1H), 7.60 (s, 1H), 7.53 (s, 1H), 7.25 (d, J=8.7 Hz, 1H), 7.19 (m, 1H), 7.12 (dd, J=8.4, 1.8 Hz, 1H), 4.71 (d, J=4.8 Hz, 1H), 4.32 (s, 2H), 3.51 (m, 1H), 3.38 (m, 1H), 2.04 (m, 1H), 1.88 (m, 1H), 1.5-1.65 (m, 2H), 1.16-1.30 (m, 4H); LCMS (ESI) m/z 380 $(M+H)^+$.

Example 132

Preparation of (1R,2R)-2-((6-(((6-fluoro-3H-imidazo[4,5-b]pyridin-3-yl)methyl)benzo[d]oxazol-2-yl)amino)cyclohexanol

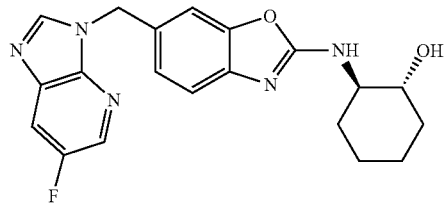

Step 1:

To a stirred solution of 6-fluoro-3H-imidazo[4,5-b]pyridine (502 mg, 3.66 mmol) from Step 2 of Example 70 in anhydrous DMF (10 mL) at 0° C. was added in one portion sodium hydride (60% dispersion in mineral oil, 220 mg, 5.49 mmol), and the mixture was stirred at 0° C. for 30 min. To the reaction mixture was added a solution of 6-(chloromethyl)-2-(methylthio)benzo[d]oxazole (858 mg, 4.03 mmol) from Step 3 of Example 56 in DMF (2 mL). The mixture was allowed to warm to rt and stir for a further 3 h. To the reaction mixture was added water and the mixture was extracted with ethyl acetate (3×100 mL). The combined organic layers were washed sequentially with water and brine, dried over $MgSO_4$, filtered, and concentrated under reduced pressure. The residue was purified by silica gel flash chromatography eluting with 30 to 50% ethyl acetate in petroleum ether to afford 6-((6-fluoro-3H-imidazo[4,5-b]pyridin-3-yl)methyl)-2-(methylthio)benzo[d]oxazole (698 mg, 61%) as a white solid. The regiochemistry of the alkylation was determined by 2-dimensional nuclear Overhauser effect (NOE) experiment. $^1$H NMR (300 MHz, DMSO-$d_6$): δ 8.71 (s, 1H), 8.41 (s, 1H), 8.07 (d, J=6.9 Hz, 1H), 7.68 (s, 1H), 7.58 (d, J=7.8 Hz, 1H), 7.35 (d, J=6.3 Hz, 1H), 5.59 (s, 2H), 2.73 (s, 3H); LCMS (ESI) m/z 315 $(M+H)^+$.

Step 2:

To a stirred solution of 6-((6-fluoro-3H-imidazo[4,5-b]pyridin-3-yl)methyl)-2-(methylthio)benzo[d]oxazole (595 mg, 1.89 mmol) from the previous step in DCM (10 mL) at 0° C. was added 70% meta-chloroperbenzoic acid (425 mg, 2.46 mmol). The reaction mixture was stirred at 0° C. for 2 h. The reaction mixture was washed sequentially with aq sodium sulfite and brine. The organic layer was separated, dried over sodium sulfate, filtered, and concentrated under reduced pressure. The residue was purified by silica gel flash chromatography eluting with 50% ethyl acetate in petroleum ether to afford 6-((6-fluoro-3H-imidazo[4,5-b]pyridin-3-yl)methyl)-2-(methylsulfinyl)benzo[d]oxazole (509 mg, 82%). $^1$H NMR (300 MHz, DMSO-$d_6$): δ 8.73 (s, 1H), 8.40 (s, 2H), 7.53 (d, J=7.2 Hz, 1H), 7.37 (s, 1H), 7.15 (d, J=4.5 Hz, 1H), 5.69 (s, 2H), 3.18 (s, 3H); LCMS (ESI) m/z 331 $(M+H)^+$.

Step 3:

A stirred mixture of 6-((6-fluoro-3H-imidazo[4,5-b]pyridin-3-yl)methyl)-2-(methylsulfinyl)benzo[d]oxazole (220 mg, 0.67 mmol) from the previous step, (1R,2R)-2-aminocyclohexanol (152 mg, 1 mmol), and DIEA (259 mg, 2.01 mmol) in DMA (5 mL) was heated at 135° C. for 2 h. The reaction mixture was cooled to rt, poured into water (30 mL), and extracted with ethyl acetate (50 mL×3). The combined organic layers were washed sequentially with water and brine. The organic layer was separated, dried over sodium sulfate, filtered, and concentrated under reduced pressure. The residue was purified directly by preparative reverse-phase HPLC to afford (1R,2R)-2-((6-((6-fluoro-3H-imidazo[4,5-b]pyridin-3-yl)methyl)benzo[d]oxazol-2-yl)amino)cyclohexanol (68 mg, 27%) as a yellow solid. $^1$H NMR (300 MHz, DMSO-d$_6$): δ 8.67 (s, 1H), 8.41 (m, 1H), 8.06 (m, 1H), 7.79 (m, 1H), 7.39 (s, 1H), 7.13-7.15 (m, 2H), 5.48 (s, 2H), 4.67 (d, J=3.9 Hz, 1H), 3.30-3.35 (m, 2H), 1.86-1.95 (m, 2H), 1.60-1.65 (m, 2H), 1.15-1.35 (m, 4H); LCMS (ESI) m/z 382 (M+H)$^+$.

Example 133

Preparation of ((1R,2R)-2-((6-((6-bromo-3H-imidazo[4,5-b]pyridin-3-yl)methyl)benzo[d]thiazol-2-yl)amino)cyclohexyl)methanol

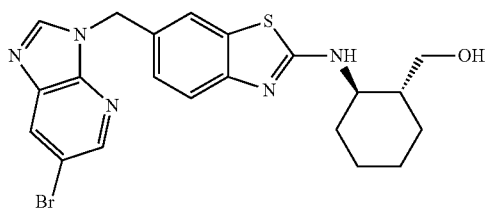 [SMILES: OC[C@@H]1CCCC[C@H]1Nc1nc2ccc(Cn3cnc4cc(Br)cnc43)cc2s1]

Step 1:

To a stirred solution of (1R,2R)-2-aminocyclohexanecarboxylic acid (500 mg, 3.49 mmol) in anhydrous THF (3 mL) at 0° C. was added dropwise a solution of LAH (2M solution in THF, 7 mL, 13.99 mmol). The reaction vessel was sealed and the mixture was stirred at 85° C. for 24 h. The mixture was cooled to 0° C. and diluted with THF (6 mL). To the reaction mixture was added sequentially water (0.5 mL), 1M aq NaOH (0.5 mL), and water (1.5 mL). To the mixture was added MgSO$_4$ and the mixture was stirred at rt for 10 min. The mixture was then diluted with THF (10 mL) and filtered, and the filtrate was concentrated under reduced pressure to afford ((1R,2R)-2-aminocyclohexyl)methanol (326 mg, 70%) as an oil. $^1$H NMR (300 MHz, DMSO-d$_6$) δ 3.27-3.52 (m, 3H), 2.29 (dt, J=10.1, 4.0 Hz, 1H), 1.5-1.78 (m, 4H), 0.98-1.21 (m, 4H), 0.87 (m, 1H).

Step 2:

((1R,2R)-2-((6-((6-Bromo-3H-imidazo[4,5-b]pyridin-3-yl)methyl)benzo[d]thiazol-2-yl)amino)cyclohexyl)methanol (18 mg, 18%) was obtained as a solid using a procedure analogous to that described in Step 5 of Example 70, substituting 6-((6-bromo-3H-imidazo[4,5-b]pyridin-3-yl)methyl)-2-(methylsulfinyl)benzo[d]thiazole from Step 4 of Example 29 for 6-((6-fluoro-3H-imidazo[4,5-b]pyridin-3-yl)methyl)-2-(methylsulfinyl)benzo[d]thiazole used in Example 70, and substituting ((1R,2R)-2-aminocyclohexyl)methanol from Step 1 of this Example for (1R,2R)-2-aminocyclohexanol used in Example 70. $^1$H NMR (500 MHz, DMSO-d$_6$) δ 8.65 (s, 1H), 8.48 (d, J=2.0 Hz, 1H), 8.39 (d, J=2.0 Hz, 1H), 8.00 (d, J=8.4 Hz, 1H), 7.65 (d, J=1.0 Hz, 1H), 7.28 (m, 1H), 7.22 (m, 1H), 5.47 (s, 2H), 4.46 (t, J=5.4 Hz, 1H), 3.55 (br m, 1H), 3.41 (m, 1H), 3.30 (m, 1H), 1.98 (d, J=8.9 Hz, 1H), 1.83 (d, J=10.8 Hz, 1H), 1.62-1.73 (m, 2H), 1.37 (m, 1H), 1.12-1.29 (m, 4H) LCMS (ESI) m/z 472, 474 (M+H)$^+$.

Example 134

Preparation of (1R,2R)-2-((6-((6-(1-methyl-1H-tetrazol-5-yl)-3H-imidazo[4,5-b]pyridin-3-yl)methyl)benzo[d]thiazol-2-yl)amino)cyclohexanol

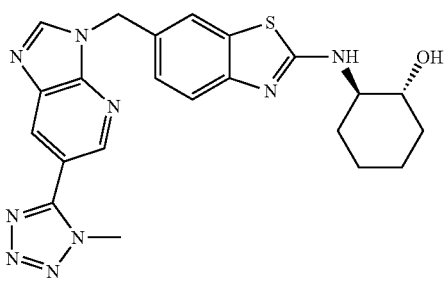 [SMILES: Cn1nnnc1-c1cnc2c(c1)ncn2Cc1ccc2nc(N[C@@H]3CCCC[C@H]3O)sc2c1]

(1R,2R)-2-((6-((6-(1-Methyl-1H-tetrazol-5-yl)-3H-imidazo[4,5-b]pyridin-3-yl)methyl)benzo[d]thiazol-2-yl)amino)cyclohexanol (30 mg, 10%) was obtained as a minor product from the reaction described in Example 94. The regiochemical assignment was consistent with the result from a NMR nuclear Overhauser effect (NOE) experiment. $^1$H NMR (500 MHz, DMSO-d$_6$) δ 8.76-8.84 (m, 2H), 8.60 (d, J=2.0 Hz, 1H), 8.00 (d, J=7.4 Hz, 1H), 7.71 (s, 1H), 7.67 (d, J=19.7 Hz, 1H), 7.28-7.35 (m, 2H), 7.20-7.28 (m, 2H), 5.56 (s, 3H), 4.77 (br s, 1H), 3.50 (br s, 2H), 2.03 (d, J=11.8 Hz, 1H), 1.87 (d, J=11.3 Hz, 1H), 1.5-1.69 (m, 2H), 1.08-1.34 (m, 4H). LCMS (ESI) m/z 462 (M+H)$^+$.

Example 135

Preparation of (1R,2R)-2-((6-((7-(2-hydroxyethoxy)imidazo[1,2-a]pyridin-3-yl)methyl)benzo[d]thiazol-2-yl)amino)cyclohexanol

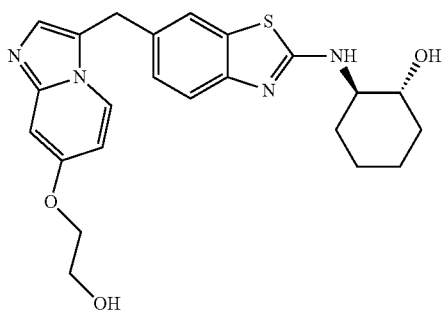 [SMILES: OCCOc1ccn2c(Cc3ccc4nc(N[C@@H]5CCCC[C@H]5O)sc4c3)cnc2c1]

To a stirred solution of (1R,2R)-2-((6-((7-(2-methoxyethoxyl)imidazo[1,2-a]pyridin-3-yl)methyl)benzo[d]thiazol-2-yl)amino)cyclohexanol (45 mg, 0.099 mmol) from Example 153 in 2 mL of DCM at −10° C. was added BBr$_3$ in DCM (1.0 M, 110 μL, 0.11 mmol). The resulting mixture was stirred at rt for 30 min before it was cooled to −10° C. and additional BBr$_3$ in DCM (1.0 M, 100 μL, 0.10 mmol) was added. After stirring at rt overnight, BBr$_3$ in DCM (1.0 M, 100 μL, 0.10 mmol) was added and stirring was continued for 1 d. The resulting mixture was quenched with MeOH and the mixture was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford (1R,2R)-2-((6-((7-(2-hydroxyethoxy)imidazo[1,2-a]pyridin-3-yl)methyl)benzo[d]thiazol-2-yl)amino)cyclohexanol (16 mg, 37%). $^1$H NMR (500 MHz, DMSO-$d_6$) δ 8.00 (d, J=7.9 Hz, 1H), 7.91 (d, J=7.4 Hz, 1H), 7.49 (s, 1H), 7.26 (d, J=8.4 Hz, 1H), 7.22 (s, 1H), 7.06 (d, J=8.4 Hz, 1H), 6.90 (d, J=2.0 Hz, 1H), 6.57 (dd, J=2.5, 7.4 Hz, 1H), 4.79 (br s, 1H), 4.22 (s, 2H), 4.02 (t, J=4.7 Hz, 2H), 3.72 (t, J=4.7 Hz, 2H), 3.50 (br s, 2H), 2.04 (d, J=12.8 Hz, 1H), 1.87 (d, J=11.3 Hz, 1H), 1.5-1.68 (m, 2H), 1.10-1.37 (m, 4H). LCMS (ESI) m/z 439 (M+H)$^+$.

Example 136

Preparation of ((1S,2R)-2-((6-((6-bromo-3H-imidazo[4,5-b]pyridin-3-yl)methyl)benzo[d]thiazol-2-yl)amino)cyclohexyl)methanol

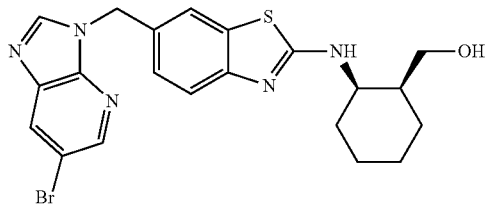 [SMILES: OC[C@H]1CCCC[C@H]1Nc1nc2ccc(Cn3cnc4cc(Br)cnc43)cc2s1]

Step 1:

((1S,2R)-2-Aminocyclohexyl)methanol (460 mg, 64%) was obtained as a solid using a procedure analogous to that described in Step 1 of Example 133, substituting (1S,2R)-2-aminocyclohexanecarboxylic acid hydrochloride for (1R,2R)-2-aminocyclohexanecarboxylic acid used in Example 133. $^1$H NMR (500 MHz, DMSO-$d_6$) δ 3.40 (m, 1H), 3.28 (dd, J=10.6, 6.2 Hz, 1H), 3.04 (q, J=3.4 Hz, 1H), 1.44-1.58 (m, 5H), 1.23-1.43 (m, 6H), 1.17 (m, 1H).

Step 2:

((1S,2R)-2-((6-((6-Bromo-3H-imidazo[4,5-b]pyridin-3-yl)methyl)benzo[d]thiazol-2-yl)amino)cyclohexyl)methanol (7 mg, 19%) was obtained as a solid using a procedure analogous to that described in Step 5 of Example 70, substituting 6-((6-bromo-3H-imidazo[4,5-b]pyridin-3-yl)methyl)-2-(methylsulfinyl)benzo[d]thiazole from Step 4 of Example 29 for 6-((6-fluoro-3H-imidazo[4,5-b]pyridin-3-yl)methyl)-2-(methylsulfinyl)benzo[d]thiazole used in Example 70, and substituting ((1S,2R)-2-aminocyclohexyl)methanol from Step 1 of this Example for (1R,2R)-2-aminocyclohexanol used in Example 70. $^1$H NMR (500 MHz, DMSO-$d_6$) δ 8.66 (s, 1H), 8.48 (d, J=2.0 Hz, 1H), 8.39 (d, J=2.0 Hz, 1H), 7.92 (d, J=8.4 Hz, 1H), 7.65 (d, J=1.0 Hz, 1H), 7.28 (m, 1H), 7.23 (m, 1H), 5.48 (s, 2H), 4.61 (br s, 1H), 4.23 (br s, 1H), 3.27 (m, 1H), 3.21 (m, 1H), 1.81 (m, 1H), 1.74 (m, 1H), 1.63 (m, 1H), 1.39-1.52 (m, 4H), 1.21-1.37 (m, 2H); LCMS (ESI) m/z 472, 474 (M+H)$^+$.

Example 137

Preparation of (1R,2R)-2-((6-((5,6-dichloro-3H-imidazo[4,5-b]pyridin-3-yl)methyl)benzo[d]thiazol-2-yl)amino)cyclohexanol

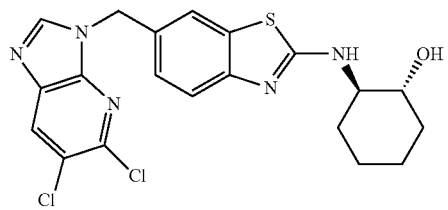 [SMILES: O[C@@H]1CCCC[C@H]1Nc1nc2ccc(Cn3cnc4cc(Cl)c(Cl)nc43)cc2s1]

Step 1:

5,6-Dichloro-N-((2-(methylthio)benzo[d]thiazol-6-yl)methyl)-3-nitropyridin-2-amine (105 mg) was obtained as an yellow solid using a procedure analogous to that described in Step 5 of Example 23, substituting 2,3,6-trichloro-5-nitropyridine for 2-chloro-6-methoxy-3-nitropyridine used in Example 23. LCMS (ESI) m/z 401, 403, 405 (M+H)$^+$.

Step 2:

(1R,2R)-2-((6-((5,6-Dichloro-3H-imidazo[4,5-b]pyridin-3-yl)methyl)benzo[d]thiazol-2-yl)amino)cyclohexanol (35 mg, 31%) was obtained using procedures analogous to those described in Step 6-9 of Example 23, substituting 5,6-dichloro-N-((2-(methylthio)benzo[d]thiazol-6-yl)methyl)-3-nitropyridin-2-amine from Step 1 of this Example for 6-methoxy-$N^2$-((2-(methylthio)benzo[d]thiazol-6-yl)methyl)pyridine-2,3-diamine used in Step 6 of Example 23, and making the analogous substitutions in the subsequent steps. $^1$H NMR (500 MHz, DMSO-$d_6$) δ 8.69 (s, 1H), 8.52 (s, 1H), 7.98 (d, J=7.9 Hz, 1H), 7.63 (s, 1H), 7.30 (d, J=8.4 Hz, 1H), 7.19 (d, J=7.9 Hz, 1H), 5.45 (s, 2H), 4.74 (br s, 1H), 3.51 (br s, 1H), 2.03 (d, J=11.8 Hz, 1H), 1.86 (br s, 1H), 1.5-1.69 (m, 2H), 1.06-1.34 (m, 4H). LCMS (ESI) m/z 448, 450, 452 (M+H)$^+$.

Example 138

Preparation of (1R,2R)-2-((6-((5-ethoxy-1H-benzo[d]imidazol-1-yl)methyl)benzo[d]thiazol-2-yl)amino)cyclohexanol

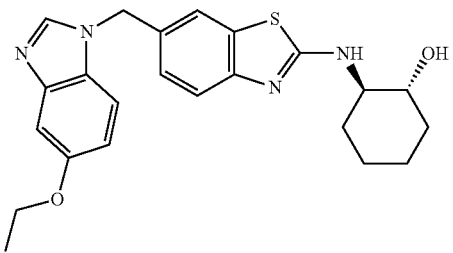 [SMILES: CCOc1ccc2c(c1)ncn2Cc1ccc2nc(N[C@@H]3CCCC[C@H]3O)sc2c1]

A mixture of 1-((2-(((1R,2R)-2-hydroxycyclohexyl)amino)benzo[d]thiazol-6-yl)methyl)-1H-benzo[d]imidazol-5-ol (80 mg, 0.20 mmol) from Example 147, iodoethane (47 mg, 0.30 mmol) and $Cs_2CO_3$ (196 mg, 0.6 mmol) in NMP (3.5 mL) was stirred at rt for 5 h. The mixture was added to water and extracted with DCM. The organic layer was separated, washed sequentially with water and brine, dried over Na₂SO₄, filtered, and concentrated under reduced pressure. The residue was purified by reverse-phase preparative HPLC to afford (1R,2R)-2-((6-((5-ethoxy-1H-benzo[d]imidazol-1-yl)methyl)benzo[d]thiazol-2-yl)amino)cyclohexanol (35 mg, 42%) as a white solid. ¹H NMR (300 MHz, DMSO-d₆) δ 8.30 (s, 1H), 7.96 (d, J=7.5 Hz, 1H), 7.62 (s, 1H), 7.39 (d, J=9.0 Hz, 1H), 7.29 (d, J=8.4 Hz, 1H), 7.14-7.19 (m, 2H), 6.82 (d, J=9.0 Hz, 1H), 5.41 (s, 2H), 4.72 (d, J=4.8 Hz, 1H), 3.97-4.04 (m, 2H), 3.43-3.54 (m, 2H), 2.03 (m, 1H), 1.87 (m, 1H), 1.60-1.65 (br m, 2H), 1.32 (t, J=13.8 Hz, 3H), 1.15-1.24 (m, 4H). LCMS (ESI) m/z 423 (M+H)⁺.

Example 139

Preparation of 3-((2-(((1R,2R)-2-hydroxycyclohexyl)amino)benzo[d]thiazol-6-yl)methyl)-3H-imidazo[4,5-b]pyridine-5,6-dicarbonitrile

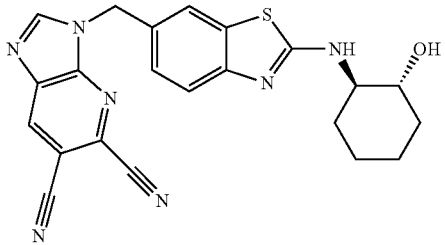 [SMILES: N#Cc1cc2ncn(Cc3ccc4nc(N[C@@H]5CCCC[C@H]5O)sc4c3)c2nc1C#N]

3-((2-(((1R,2R)-2-Hydroxycyclohexyl)amino)benzo[d]thiazol-6-yl)methyl)-3H-imidazo[4,5-b]pyridine-5,6-dicarbonitrile was obtained as a white powder (7 mg, 21%) using a procedures analogous to those described in Example 43, substituting (1R,2R)-2-((6-((5,6-dichloro-3H-imidazo[4,5-b]pyridin-3-yl)methyl)benzo[d]thiazol-2-yl)amino)cyclohexanol from Example 137 for (1R,2R)-2-((6-((6-bromo-3H-imidazo[4,5-b]pyridin-3-yl)methyl)benzo[d]thiazol-2-yl)amino)cyclohexanol used in Example 43. ¹H NMR (500 MHz, DMSO-d₆) δ 9.10 (s, 1H), 9.03 (s, 1H), 8.08 (d, J=7.4 Hz, 1H), 7.66 (s, 1H), 7.27-7.36 (m, 1H), 7.24 (d, J=8.4 Hz, 1H), 5.56 (s, 2H), 4.84 (br s, 1H), 3.46-3.64 (m, 2H), 2.03 (d, J=11.8 Hz, 1H), 1.87 (d, J=10.8 Hz, 1H), 1.5-1.70 (m, 2H), 1.08-1.39 (m, 4H). LCMS (ESI) m/z 430 (M+H)⁺.

Example 140

Preparation of 3-((2-(((1R,2R)-2-(hydroxymethyl)cyclohexyl)amino)benzo[d]thiazol-6-yl)methyl)-3H-imidazo[4,5-b]pyridine-6-carbonitrile

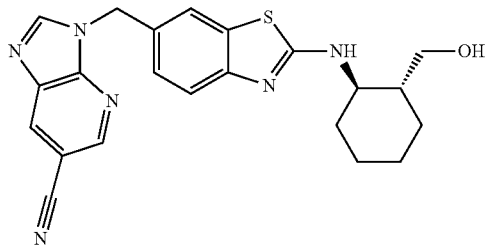 [SMILES: N#Cc1cnc2c(c1)ncn2Cc1ccc2nc(N[C@@H]3CCCC[C@H]3CO)sc2c1]

3-((2-(((1R,2R)-2-(Hydroxymethyl)cyclohexyl)amino)benzo[d]thiazol-6-yl)methyl)-3H-imidazo[4,5-b]pyridine-6-carbonitrile was obtained as a solid (18 mg, 19%) using a procedure analogous to that described in Example 43, substituting ((1R,2R)-2-((6-((6-bromo-3H-imidazo[4,5-b]pyridin-3-yl)methyl)benzo[d]thiazol-2-yl)amino)cyclohexyl)methanol from Example 133 for (1R,2R)-2-((6-((6-bromo-3H-imidazo[4,5-b]pyridin-3-yl)methyl)benzo[d]thiazol-2-yl)amino)cyclohexanol used in Example 43. ¹H NMR (500 MHz, DMSO-d₆) δ 8.84 (s, 1H), 8.82 (d, J=1.5 Hz, 1H), 8.72 (d, J=1.5 Hz, 1H), 8.01 (d, J=8.4 Hz, 1H), 7.67 (s, 1H), 7.28 (m, 1H), 7.24 (m, 1H), 5.53 (s, 2H), 4.46 (br m, 1H), 3.55 (br m, 1H), 3.41 (d, J=9.8 Hz, 1H), 3.30 (m, 1H), 1.98 (m, 1H), 1.83 (d, J=10.8 Hz, 1H), 1.62-1.73 (m, 2H), 1.37 (m, 1H), 1.17-1.27 (m, 4H); LCMS (ESI) m/z 419 (M+H)⁺.

Example 141

Preparation of (1R,2R)-2-((6-((6-(1H-pyrazol-1-yl)-3H-imidazo[4,5-b]pyridin-3-yl)methyl)benzo[d]thiazol-2-yl)amino)cyclohexanol

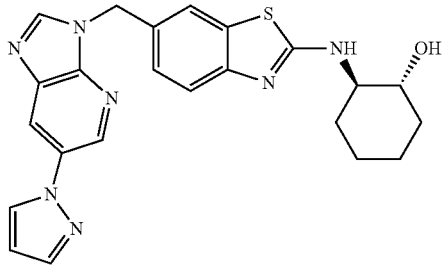 [SMILES: O[C@@H]1CCCC[C@H]1Nc1nc2ccc(Cn3cnc4cc(-n5cccn5)cnc43)cc2s1]

To a stirred solution of CuI (14 mg, 0.0053 mmol), K₂CO₃ (102 mg, 0.74 mmol), and pyrazole (30 mg, 0.44 mmol) in 2 mL of DMF under argon was added (1R,2R)-2-((6-((6-iodo-3H-imidazo[4,5-b]pyridin-3-yl)methyl)benzo[d]thiazol-2-yl)amino)cyclohexanol from Step 2 of Example 96 (150 mg, 0.30 mmol) and trans-N¹,N²-dimethylcyclohexane-1,2-diamine (21 mg, 0.15 mmol). The reaction mixture was then heated at 110° C. overnight. The mixture was cooled to rt, diluted with MeOH, and purified by preparative HPLC using a mixture of water (5% CH₃CN, 0.05% AcOH) and CH₃CN (0.05% AcOH) as the mobile phase and Varian Pursuit XRs Diphenyl column as the stationary phase to afford (1R,2R)-2-((6-((6-(1H-pyrazol-1-yl)-3H-imidazo[4,5-b]pyridin-3-yl)methyl)benzo[d]thiazol-2-yl)amino)cyclohexanol (85 mg, 64%) as a white solid. ¹H NMR (500 MHz, DMSO-d₆) δ 8.92 (d, J=2.0 Hz, 1H), 8.69 (s, 1H), 8.57 (d, J=2.5 Hz, 1H), 8.50 (d, J=2.5 Hz, 1H), 7.96 (d, J=7.4 Hz, 1H), 7.79 (s, 1H), 7.68 (s, 1H), 7.29 (s, 1H), 7.20-7.27 (m, 1H), 6.58 (s, 1H), 5.52 (s, 2H), 4.74 (br s, 1H), 3.51 (br s, 1H), 2.03 (d, J=12.3 Hz, 1H), 1.80-1.95 (m, 1H), 1.5-1.72 (m, 2H), 1.08-1.33 (m, 4H). LCMS (ESI) m/z 446 (M+H)⁺.

Example 142

Preparation of (1R,2R)-2-((6-(imidazo[1,2-b]pyridazin-3-ylmethyl)benzo[d]oxazol-2-yl)amino)cyclohexanol

Step 1:

A mixture of 6-iodobenzo[d]oxazol-2(3H)-one (3.2 g, 12.3 mmmol) in 30 ml, of toluene was heated with Lawesson's reagent (2.7 g, 6.7 mmol) at 100° C. for 4 h. Solvent was then removed under reduced pressure and the residue was cooled to rt and dissolved in 20 mL of DMF. To the mixture was added $K_2CO_3$ (8.4 g, 61.2 mmol) and iodomethane (2.27 mL, 36.7 mmol). The resulting mixture was stirred at rt overnight and heated at 55° C. for 1 h. After cooling to rt, the reaction mixture was partitioned between EtOAc and water, and the organic layer was washed with brine, dried over $Na_2SO_4$, filtered, and evaporated under reduced pressure. The residue was purified on by silica gel column chromatography eluting with 0-25% EtOAc in hexanes to give 6-iodo-2-(methylthio)benzo[d]oxazole as a white solid (1.5 g, 42%). LCMS (ESI) m/z 292 (M+H)$^+$.

Step 2:

Crude 2-chloro-3-(2-(methylthio)benzo[d]oxazol-6-yl) propanal (120 mg) was obtained using procedures analogous to those described in Steps 3-4 of Example 117, substituting 6-iodo-2-(methylthio)benzo[d]oxazole from Step 1 of this Example for 6-iodo-2-(methylthio)benzo[d]thiazole used in Step 3 of Example 117, and making the analogous substitution in Step 4 of Example 117. LCMS (ESI) m/z 256, 258 (M+H)$^+$.

Step 3:

(1R,2R)-2-((6-(Imidazo[1,2-b]pyridazin-3-ylmethyl) benzo[d]oxazol-2-yl)amino)cyclohexanol (20 mg) was obtained as a tan solid using procedures analogous to those described in Steps 1-3 of Example 131, substituting 2-chloro-3-(2-(methylthio)benzo[d]oxazol-6-yl)propanal from Step 2 of this Example for 2-chloro-3-(2-(methylthio) benzo[d]thiazol-6-yl)propanal used in Step 1 of Example 131, and making the analogous substitutions in Steps 2 and 3 of Example 131. $^1$H NMR (500 MHz, DMSO-d$_6$) δ 8.53 (d, J=3.0 Hz, 1H), 8.09 (d, J=9.4 Hz, 1H), 7.74 (d, J=7.4 Hz, 1H), 7.58 (s, 1H), 7.25 (s, 1H), 7.19 (dd, J=4.4, 8.9 Hz, 1H), 7.06-7.13 (m, 1H), 7.03 (d, J=7.9 Hz, 1H), 4.74 (br s, 1H), 4.33 (s, 2H), 1.96 (d, J=9.4 Hz, 1H), 1.88 (d, J=10.3 Hz, 1H), 1.63 (br s, 2H), 1.23 (d, J=6.4 Hz, 4H). LCMS (ESI) m/z 364 (M+H)$^+$.

Example 143

Preparation of 3-((2-(((1R,2R)-2-hydroxycyclohexyl)amino)benzo[d]thiazol-6-yl)methyl)-N-methylimidazo[1,2-b]pyridazine-6-carboxamide

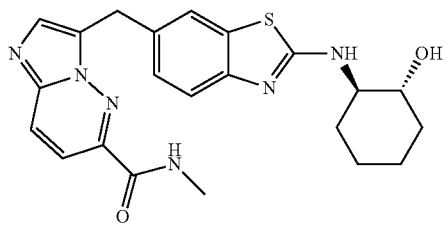 [SMILES: CNC(=O)c1ccc2ncc(Cc3ccc4nc(N[C@@H]5CCCC[C@H]5O)sc4c3)n2n1]

Step 1:

Ethyl 3-((2-(methylthio)benzo[d]thiazol-6-yl)methyl) imidazo[1,2-b]pyridazine-6-carboxylate (272 mg, 54%) was obtained as a white solid using a procedure analogous to that described in Step 6 of Example 117, substituting ethyl 6-aminopyridazine-3-carboxylate for 2-aminoisonicotinitrile used in Example 117. LCMS (ESI) m/z 385 (M+H)$^+$.

Step 2:

Ethyl 3-((2-(methylthio)benzo[d]thiazol-6-yl)methyl) imidazo[1,2-b]pyridazine-6-carboxylate (115 mg, 0.3 mmol) was heated with 2 mL of 2.0 M NH$_2$Me in THF at 85° C. in a sealed tube for 1 h, at 100° C. for 1 h, then at 110° C. overnight. LCMS analysis showed that the reaction was complete. Solvent was evaporated under reduced pressure, and the residue was dried in a vacuum oven to give N-methyl-3-((2-(methylthio)benzo[d]thiazol-6-yl)methyl) imidazo[1,2-b]pyridazine-6-carboxamide, which was used directly for the next step. LCMS (ESI) m/z 370 (M+H)$^+$.

Step 3:

3-((2-(((1R,2R)-2-Hydroxycyclohexyl)amino)benzo[d] thiazol-6-yl)methyl)-N-methylimidazo[1,2-b]pyridazine-6-carboxamide (55 mg, 42%) was obtained as a tan solid using procedures analogous to those described in Step 5 of Example 3 followed by Step 5 of Example 2, substituting N-methyl-3-((2-(methylthio)benzo[d]thiazol-6-yl)methyl) imidazo[1,2-b]pyridazine-6-carboxamide from Step 2 of this Example for 6-((3H-imidazo[4,5-b]pyridin-3-yl) methyl)-2-(methylthio)benzo[d]thiazole used in Example 3, and making the analogous substitution in Step 5 of Example 2. $^1$H NMR (500 MHz, DMSO-d$_6$) δ 8.83 (d, J=4.9 Hz, 1H), 8.20 (d, J=9.4 Hz, 2H), 7.88 (d, J=7.9 Hz, 1H), 7.60-7.71 (m, 3H), 7.24-7.32 (m, 1H), 7.15-7.24 (m, 1H), 4.76 (br s, 1H), 4.44 (s, 2H), 3.51 (br s, 1H), 2.89 (d, J=4.4 Hz, 3H), 2.04 (d, J=11.8 Hz, 1H), 1.87 (d, J=11.3 Hz, 1H), 1.5-1.72 (m, 2H), 1.09-1.40 (m, 4H). LCMS (ESI) m/z 437 (M+H)$^+$.

Example 144

Preparation of (1R,2R)-2-((6-((6-(hydroxymethyl) imidazo[1,2-b]pyridazin-3-yl)methyl)benzo[d]thiazol-2-yl)amino)cyclohexanol

Step 1:

(3-((2-(Methylthio)benzo[d]thiazol-6-yl)methyl)imidazo [1,2-b]pyridazin-6-yl)methanol (48 mg, 34%) was obtained as a white solid using a procedure analogous to that described in Step 2 of Example 2, substituting ethyl 3-((2-(methylthio)benzo[d]thiazol-6-yl)methyl)imidazo[1,2-b] pyridazine-6-carboxylate from Step 1 of Example 143 for ethyl 2-bromobenzo[d]thiazole-6-carboxylate used in Example 2. LCMS (ESI) m/z 343 (M+H)$^+$.

Step 2:

(1R,2R)-2-((6-((6-(Hydroxymethyl)imidazo[1,2-b] pyridazin-3-yl)methyl)benzo[d]thiazol-2-yl)amino)cyclohexanol (15 mg, 26%) was obtained as a yellow powder using procedures analogous to those described in Step 5 of Example 3 followed by Step 5 of Example 2, substituting (3-((2-(methylthio)benzo[d]thiazol-6-yl)methyl)imidazo[1, 2-b]pyridazin-6-yl)methanol from Step 1 of this Example for 6-((3H-imidazo[4,5-b]pyridin-3-yl)methyl)-2-(methylthio)benzo[d]thiazole used in Example 3, and making the analogous substitution in Step 5 of Example 2. $^1$H NMR (500 MHz, DMSO-d$_6$) δ 8.07 (d, J=9.4 Hz, 1H), 7.91 (d, J=7.4 Hz, 1H), 7.55 (s, 1H), 7.50 (s, 1H), 7.21-7.30 (m, 2H), 7.13 (d, J=8.4 Hz, 1H), 4.79 (br s, 1H), 4.60 (s, 2H), 4.28 (s, 2H), 3.50 (br s, 2H), 2.04 (d, J=11.8 Hz, 1H), 1.87 (d, J=10.8 Hz, 1H), 1.5-1.70 (m, 2H), 1.06-1.36 (m, 4H). LCMS (ESI) m/z 410 (M+H)+.

Example 145

Preparation of (1R,2R)-2-((6-((6-(1H-1,2,4-triazol-1-yl)-3H-imidazo[4,5-b]pyridin-3-yl)methyl)benzo[d]thiazol-2-yl)amino)cyclohexanol

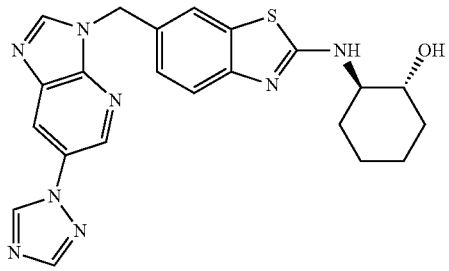

(1R,2R)-2-((6-((6-(1H-1,2,4-Triazol-1-yl)-3H-imidazo[4,5-b]pyridin-3-yl)methyl)benzo[d]thiazol-2-yl)amino)cyclohexanol (48 mg, 45%) was obtained as a yellow powder using a procedure analogous to that described in Example 141, substituting 1,2,4-triazole for pyrazole used in Example 141. $^1$H NMR (500 MHz, DMSO-$d_6$) δ 9.30 (s, 1H), 8.89 (d, J=2.0 Hz, 1H), 8.76 (s, 1H), 8.56 (d, J=2.0 Hz, 1H), 8.29 (s, 1H), 7.99 (d, J=7.4 Hz, 1H), 7.69 (s, 1H), 7.28-7.34 (m, 1H), 7.17-7.26 (m, 1H), 5.54 (s, 2H), 4.76 (br s, 1H), 3.47-3.60 (m, 2H), 2.03 (d, J=11.8 Hz, 1H), 1.86 (m, 1H), 1.5-1.70 (m, 2H), 1.10-1.34 (m, 4H). LCMS (ESI) m/z 447 (M+H)+.

Example 146

Preparation of (1R,2R)-2-((6-((6-iodo-3H-imidazo[4,5-b]pyridin-3-yl)methyl)benzo[d]thiazol-2-yl)amino)cyclohexanol

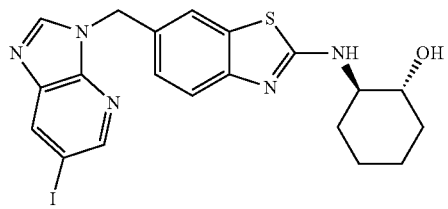

(1R,2R)-2-((6-((6-Iodo-3H-imidazo[4,5-b]pyridin-3-yl)methyl)benzo[d]thiazol-2-yl)amino)cyclohexanol was obtained as an off-white solid using procedures analogous to those described in Steps 4-5 of Example 3 followed by Step 5 of Example 2, substituting 6-iodo-3H-imidazo[4,5-b]pyridine from Step 1 of Example 96 for 3H-imidazo[4,5-b]pyridine used in Step 4 of Example 3, and making the analogous substitutions in Step 5 of Example 3 and Step 5 of Example 2. $^1$H NMR (500 MHz, DMSO-$d_6$) δ 8.59 (s, 1H), 8.56 (s, 1H), 8.49 (s, 1H), 8.06 (d, J=7.4 Hz, 1H), 7.64 (s, 1H), 7.23-7.32 (m, 1H), 7.19 (d, J=8.4 Hz, 1H), 5.46 (s, 2H), 4.84 (br s, 1H), 3.50 (br s, 2H), 2.03 (d, J=11.8 Hz, 1H), 1.86 (d, J=10.8 Hz, 1H), 1.5-1.67 (m, 2H), 1.09-1.36 (m, 4H). LCMS (ESI) m/z 506 (M+H)+.

Example 147

Preparation of 1-((2-(((1R,2R)-2-hydroxycyclohexyl)amino)benzo[d]thiazol-6-yl)methyl)-1H-benzo[d]imidazol-5-ol

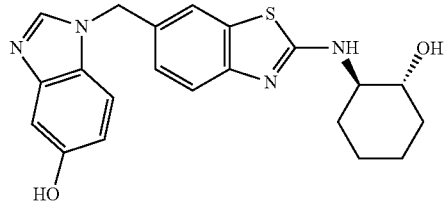 [SMILES: Oc1ccc2c(c1)ncn2Cc1ccc2nc(N[C@@H]3CCCC[C@H]3O)sc2c1]

Step 1:
To a stirred mixture of 4-(benzyloxy)-2-nitroaniline (2.0 g, 8.2 mmol) in TFA (14 mL) at −15° C. was added sodium triacetoxyborohydride (2.84 g, 12 mmol). Then a solution of 2-(methylthio)benzo[d]thiazole-6-carbaldehyde (1.9 g, 9.0 mmol) from Step 1 of Example 100 in DCM (10 mL) was added dropwise. The reaction mixture was allowed to warm to 0° C. and stir for 2 h. The mixture was partitioned between DCM and water. The organic layer was separated and washed sequentially with saturated aq NaHCO$_3$ and brine. The organic layer was separated, dried over Na$_2$SO$_4$, filtered, and concentrated under reduced pressure. The residue was purified by silica gel flash chromatography eluting with a gradient of 10% EtOAc in petroleum ether to 100% EtOAc to afford 4-(benzyloxy)-N-((2-(methylthio)benzo[d]thiazol-6-yl)methyl)-2-nitroaniline (2.3 g, 64%) as a red-brown solid. $^1$H NMR (300 MHz, CDCl$_3$) δ 8.34 (s, 1H), 7.84 (d, J=8.4 Hz, 1H), 7.72-7.77 (m, 2H), 7.33-7.43 (m, 6H), 7.14 (m, 1H), 6.76 (d, J=9.6 Hz, 1H), 5.02 (s, 2H), 4.64 (d, J=5.7 Hz, 2H), 2.79 (s, 3H); LCMS (ESI) m/z 438 (M+H)+.

Step 2:
To a mixture of 4-(benzyloxy)-N-((2-(methylthio)benzo[d]thiazol-6-yl)methyl)-2-nitroaniline (2.8 g, 6.42 mmol) from the previous step, HOAc (7.5 mL), MeOH (7.5 mL) and DCM (50 mL) at 0° C. was added portionwise zinc dust (4.25 g, 65.4 mmol). The reaction mixture was stirred at 5° C. for 1 h. The mixture was filtered and the filtrate was diluted with DCM and washed sequentially with water and saturated aq NaHCO$_3$. The organic layer was separated, dried over Na$_2$SO$_4$, filtered, and concentrated under reduced pressure to afford 4-(benzyloxy)-N$^1$-((2-(methylthio)benzo[d]thiazol-6-yl)methyl)benzene-1,2-diamine (2.49 g, 95%) as a light orange solid which was not purified further. $^1$H NMR (300 MHz, CDCl$_3$) δ 7.83 (d, J=8.4 Hz, 1H), 7.77 (s, 1H), 7.26-7.44 (m, 7H), 6.59 (d, J=8.4 Hz, 1H), 6.46 (s, 1H), 6.38 (m, 1H), 4.97 (s, 2H), 4.34 (s, 2H), 3.54 (br s, 2H), 2.80 (s, 3H). LCMS (ESI) m/z 408 (M+H)+.

Step 3:
A mixture of 4-(benzyloxy)-N$^1$-((2-(methylthio)benzo[d]thiazol-6-yl)methyl)benzene-1,2-diamine (2.49 g, 6.1 mmol) from the previous step, triethylorthoformate (60 mL), and formic acid (1.22 g) was stirred at 90° C. for 2 h. The reaction mixture was cooled to rt, and then concentrated under reduced pressure. The residue was purified by silica gel flash chromatography eluting with a gradient of 50% EtOAc in petroleum ether to 100% EtOAc to afford 6-((5-(benzyloxy)-1H-benzo[d]imidazol-1-yl)methyl)-2-(methylthio)benzo[d]thiazole (1.6 g, 62%) as a light yellow solid. $^1$H NMR (300 MHz, CDCl$_3$) δ 7.93 (s, 1H), 7.82 (d, J=8.4 Hz, 1H), 7.50 (s, 1H), 7.44-7.49 (m, 2H), 7.30-7.40 (m, 4H), 7.26 (m, 1H), 7.13 (d, J=9.0 Hz, 1H), 6.98 (m, 1H), 5.41 (s, 2H), 5.10 (s, 2H), 2.77 (s, 3H); LCMS (ESI) m/z 418 (M+H)⁺.

Step 4:

A mixture of 6-((5-(benzyloxy)-1H-benzo[d]imidazol-1-yl)methyl)-2-(methylthio)benzo[d]thiazole (1.6 g, 3.8 mmol) from the previous step and meta-chloroperbenzoic acid (0.82 g, 4.75 mmol) in DCM (38 mL) was stirred at 0° C. for 2 h. The mixture was diluted with DCM and washed sequentially with aq Na₂S₂O₃, saturated aq NaHCO₃, and water. The organic layer was separated, dried over Na₂SO₄, filtered, and concentrated under reduced pressure to afford 6-((5-(benzyloxy)-1H-benzo[d]imidazol-1-yl)methyl)-2-(methylsulfinyl)benzo[d]thiazole (1.58 g, 96%) as a yellow solid. ¹H NMR (300 MHz, CDCl₃) δ 8.02 (d, J=8.4 Hz, 1H), 7.96 (s, 1H), 7.76 (s, 1H), 7.44-7.47 (m, 2H), 7.31-7.40 (m, 5H), 7.12 (d, J=8.7 Hz, 1H), 6.97 (m, 1H), 5.49 (s, 2H), 5.11 (s, 2H), 3.08 (s, 3H); LCMS (ESI) m/z 434 (M+H)⁺.

Step 5:

A stirred mixture of 6-((5-(benzyloxy)-1H-benzo[d]imidazol-1-yl)methyl)-2-(methylsulfinyl)benzo[d]thiazole (1.48 g, 3.4 mmol) from the previous step, (1R,2R)-2-aminocyclohexanol hydrochloride (1.29 g, 8.5 mmol), and DIEA (2.19 g, 17 mmol) in DMA (44 mL) was heated at 138° C. for 15 h. The reaction mixture was cooled to rt and concentrated under reduced pressure. The residue was purified by silica gel flash chromatography eluting with 2 to 6% MeOH in DCM to afford (1R,2R)-2-((6-((5-(benzyloxy)-1H-benzo[d]imidazol-1-yl)methyl)benzo[d]thiazol-2-yl)amino)cyclohexanol (0.98 g, 59%) as a yellow solid. ¹H NMR (300 MHz, CDCl₃) δ 7.88 (s, 1H), 7.43-7.46 (m, 3H), 7.29-7.39 (m, 4H), 7.25 (s, 1H), 7.13-7.16 (m, 2H), 6.96 (m, 1H), 5.75 (br s, 1H), 5.31 (s, 2H), 5.09 (s, 2H), 3.46-3.56 (m, 2H), 2.07-2.18 (m, 2H), 1.71-1.77 (m, 2H), 1.26-1.40 (m, 4H); LCMS (ESI) m/z 485 (M+H)⁺.

Step 6:

To a stirred mixture of (1R,2R)-2-((6-((5-(benzyloxy)-1H-benzo[d]imidazol-1-yl)methyl)benzo[d]thiazol-2-yl)amino)cyclohexanol (3.4 g, 7.02 mmol) in DCM (40 mL) at −30° C. was added boron tribromide (3.4 mL, 35.4 mmol). The reaction mixture was stirred at −30° C. for 2 h. To the mixture was added water and the pH was adjusted to 8 with aq NH₄OH. The precipitate was collected by filtration to give a light yellow solid (2.45 g). A portion of this solid (150 mg) was purified directly by reverse-phase preparative HPLC to afford 1-((2-(((1R,2R)-2-hydroxycyclohexyl)amino)benzo[d]thiazol-6-yl)methyl)-1H-benzo[d]imidazol-5-ol as a white solid (54 mg). ¹H NMR (300 MHz, DMSO-d₆) δ 8.98 (s, 1H), 8.22 (s, 1H), 7.93 (d, J=7.5 Hz, 1H), 7.61 (s, 1H), 7.30 (s, 1H), 7.27 (s, 1H), 7.17 (m, 1H), 6.94 (s, 1H), 6.69 (m, 1H), 5.37 (s, 2H), 4.71 (d, J=5.4 Hz, 1H), 3.53 (m, 1H), 3.36 (m, 1H), 2.03 (m, 1H), 1.88 (m, 1H), 1.60-1.63 (m, 2H), 1.15-1.29 (m, 4H). LCMS (ESI) m/z 395 (M+H)⁺.

Example 148

Preparation of (1R,2R)-2-((6-((5,7-difluoro-1H-benzo[d]imidazol-1-yl)methyl)benzo[d]thiazol-2-yl)amino)cyclohexanol

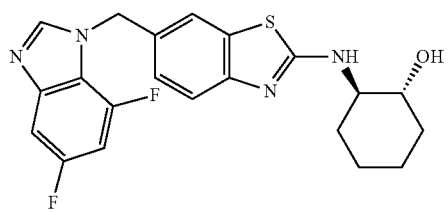 [SMILES: O[C@@H]1CCCC[C@H]1Nc1nc2ccc(Cn3cnc4cc(F)cc(F)c43)cc2s1]

Step 1:

2,4-Difluoro-N-((2-(methylthio)benzo[d]thiazol-6-yl)methyl)-6-nitroaniline (0.8 g, 73%) was obtained as a yellow solid using a procedure analogous to that described in Step 1 of Example 127, substituting 2,4-difluoro-6-nitroaniline for 4-methyl-2-nitroaniline used in Example 127. ¹H NMR (300 MHz, CDCl₃) δ 7.84 (d, J=8.1 Hz, 1H), 7.70-7.74 (m, 2H), 7.36 (dd, J=8.4, 1.8 Hz, 1H), 7.05 (m, 1H), 4.78 (d, J=3.6 Hz, 2H), 2.79 (s, 3H); LCMS (ESI) m/z 368 (M+H)⁺.

Step 2:

4,6-Difluoro-N¹-((2-(methylthio)benzo[d]thiazol-6-yl)methyl)benzene-1,2-diamine (0.29 g, 91%) was obtained as a yellow solid using a procedure analogous to that described in Step 2 of Example 130, substituting 2,4-difluoro-N-((2-(methylthio)benzo[d]thiazol-6-yl)methyl)-6-nitroaniline from Step 1 of this Example for N-((2-(methylthio)benzo[d]thiazol-6-yl)methyl)-2-nitro-4-trifluoromethyl)aniline used in Example 130. ¹H NMR (300 MHz, CDCl₃) δ 7.79 (d, J=8.4 Hz, 1H), 7.70 (s, 1H), 7.35 (dd, J=8.7, 1.8 Hz, 1H), 6.18-6.24 (m, 2H), 4.20 (br s, 2H), 4.13 (s, 2H), 2.79 (s, 3H); LCMS (ESI) m/z 338 (M+H)⁺.

Step 3:

6-((5,7-Difluoro-1H-benzo[d]imidazol-1-yl)methyl)-2-(methylthio)benzo[d]thiazole (0.18 g, 59%) was obtained as a yellow solid using a procedure analogous to that described in Step 3 of Example 130, substituting 4,6-difluoro-N¹-((2-(methylthio)benzo[d]thiazol-6-yl)methyl)benzene-1,2-diamine from Step 2 of this Example for N¹-((2-(methylthio)benzo[d]thiazol-6-yl)methyl)-4-(trifluoromethyl)benzene-1,2-diamine used in Example 130. LCMS (ESI) m/z 348 (M+H)⁺.

Step 4:

6-((5,7-Difluoro-1H-benzo[d]imidazol-1-yl)methyl)-2-(methylsulfinyl)benzo[d]thiazole (0.17 g, 90%) was obtained as a yellow solid using a procedure analogous to that described in Step 4 of Example 130, substituting 6-((5,7-difluoro-1H-benzo[d]imidazol-1-yl)methyl)-2-(methylthio)benzo[d]thiazole from Step 3 of this Example for 2-(methylthio)-6-((5-(trifluoromethyl)-1H-benzo[d]imidazol-1-yl)methyl)benzo[d]thiazole used in Example 130. ¹H NMR (300 MHz, CDCl₃) δ 8.01-8.05 (m, 2H), 7.81 (s, 1H), 7.41 (dd, J=8.7, 1.8 Hz, 1H), 7.32 (dd, J=9.0, 2.1 Hz, 1H), 6.80 (t, J=9.6 Hz, 1H), 5.64 (s, 2H), 3.06 (s, 3H); LCMS (ESI) m/z 364 (M+H)⁺.

Step 5:

((1R,2R)-2-((6-((5,7-Difluoro-1H-benzo[d]imidazol-1-yl)methyl)benzo[d]thiazol-2-yl)amino)cyclohexanol (65 mg, 34.5%) was obtained as a yellow solid using a procedure analogous to that described in Step 5 of Example 130, substituting 6-((5,7-difluoro-1H-benzo[d]imidazol-1-yl)methyl)-2-(methylsulfinyl)benzo[d]thiazole from Step 4 of this Example for 2-(methylsulfinyl)-6-((5-(trifluoromethyl)-1H-benzo[d]imidazol-1-yl)methyl)benzo[d]thiazole used in Example 130. ¹H NMR (300 MHz, DMSO-d₆) δ 8.51 (s, 1H), 7.95 (d, J=7.8 Hz, 1H), 7.54 (s, 1H), 7.36 (dd, J=9.3, 1.5 Hz, 1H), 7.30 (d, J=8.1 Hz, 1H), 7.06-7.15 (m, 2H), 5.51 (s, 2H), 4.71 (d, J=5.1 Hz, 1H), 3.53 (m, 1H), 3.33 (m, 1H), 2.03 (m, 1H), 1.87 (m, 1H), 1.5-1.63 (m, 2H), 1.14-1.29 (m, 4H); LCMS (ESI) m/z 415 (M+H)⁺.

Example 149

Preparation of (1R,2R)-2-((6-((5-(trifluoromethoxy)-1H-benzo[d]imidazol-1-yl)methyl)benzo[d]thiazol-2-yl)amino)cyclohexanol

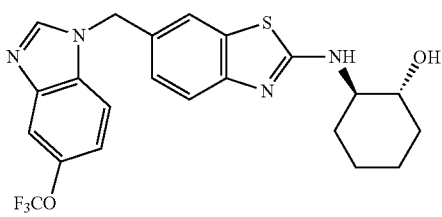

Step 1:
N-((2-(Methylthio)benzo[d]thiazol-6-yl)methyl)-2-nitro-4-(trifluoromethoxy)aniline (0.85 g, 51%) was obtained as a yellow solid using a procedure analogous to that described in Step 1 of Example 127, substituting 2-nitro-4-(trifluoromethoxy)aniline for 4-methyl-2-nitroaniline used in Example 127. $^1$H NMR (300 MHz, CDCl$_3$) δ 8.49 (br s, 1H), 8.28 (d, J=0.6 Hz, 1H), 7.94 (d, J=3.0 Hz, 1H), 7.84 (s, 1H), 7.38 (dd, J=8.4, 1.5 Hz, 1H), 7.29 (m, 1H), 6.83 (d, J=9.0 Hz, 1H), 4.66 (d, J=5.7 Hz, 2H), 2.79 (s, 3H); LCMS (ESI) m/z 416 (M+H)$^+$.

Step 2:
N$^1$-((2-(Methylthio)benzo[d]thiazol-6-yl)methyl)-4-(trifluoromethoxy)benzene-1,2-diamine (0.69 g, 88%) was obtained as a yellow solid using a procedure analogous to that described in Step 2 of Example 130, substituting N-((2-(methylthio)benzo[d]thiazol-6-yl)methyl)-2-nitro-4-(trifluoromethoxy)aniline from Step 1 of this Example for N-((2-(methylthio)benzo[d]thiazol-6-yl)methyl)-2-nitro-4-trifluoromethyl)aniline used in Example 130. $^1$H NMR (300 MHz, CDCl$_3$) δ 7.83 (d, J=8.4 Hz, 1H), 7.75 (s, 1H), 7.41 (dd, J=8.4, 1.5 Hz, 1H), 6.5-6.65 (m, 4H), 4.35 (s, 2H), 3.48 (br s, 2H), 2.77 (s, 3H); LCMS (ESI) m/z 386 (M+H)$^+$.

Step 3:
2-(Methylthio)-6-((5-(trifluoromethoxy)-1H-benzo[d]imidazol-1-yl)methyl)benzo[d]thiazole (0.55 g, 79%) was obtained as a yellow solid using a procedure analogous to that described in Step 3 of Example 130, substituting N$^1$-((2-(methylthio)benzo[d]thiazol-6-yl)methyl)-4-(trifluoromethoxy)benzene-1,2-diamine from Step 2 of this Example for N$^1$-((2-(methylthio)benzo[d]thiazol-6-yl)methyl)-4-(trifluoromethyl)benzene-1,2-diamine used in Example 130. $^1$H NMR (300 MHz, CDCl$_3$) δ 8.03 (s, 1H), 7.83 (d, J=8.4 Hz, 1H), 7.70 (s, 1H), 7.52 (s, 1H), 7.22-7.28 (m, 2H), 7.13 (m, 1H), 5.45 (s, 2H), 2.78 (s, 3H); LCMS (ESI) m/z 396 (M+H)$^+$.

Step 4:
2-(Methylsulfinyl)-6-((5-(trifluoromethoxy)-1H-benzo[d]imidazol-1-yl)methyl)benzo[d]thiazole (0.55 g, 96%) was obtained as a yellow solid using a procedure analogous to that described in Step 4 of Example 130, substituting 2-(methylthio)-6-((5-(trifluoromethoxy)-1H-benzo[d]imidazol-1-yl)methyl)benzo[d]thiazole from Step 3 of this Example for 2-(methylthio)-6-((5-(trifluoromethyl)-1H-benzo[d]imidazol-1-yl)methyl)benzo[d]thiazole used in Example 130. $^1$H NMR (300 MHz, CDCl$_3$) δ 8.08 (s, 1H), 7.04 (d, J=8.4 Hz, 1H), 7.79 (s, 1H), 7.71 (s, 1H), 7.38 (dd, J=8.4, 1.8 Hz, 1H), 7.24 (m, 1H), 7.13 (m, 1H), 5.52 (s, 2H), 3.06 (s, 3H); LCMS (ESI) m/z 412 (M+H)$^+$.

Step 5:
(1R,2R)-2-((6-((5-(Trifluoromethoxy)-1H-benzo[d]imidazol-1-yl)methyl)benzo[d]thiazol-2-yl)amino)cyclohexanol (65 mg, 35%) was obtained as a white solid using a procedure analogous to that described in Step 5 of Example 130, substituting 2-(methylsulfinyl)-6-((5-(trifluoromethoxy)-1H-benzo[d]imidazol-1-yl)methyl)benzo[d]thiazole from Step 4 of this Example for 2-(methylsulfinyl)-6-((5-(trifluoromethyl)-1H-benzo[d]imidazol-1-yl)methyl)benzo[d]thiazole used in Example 130. $^1$H NMR (300 MHz, DMSO-d$_6$) δ 8.54 (s, 1H), 7.93 (d, J=6.6 Hz, 1H), 7.65-7.75 (m, 3H), 7.30 (d, J=8.1 Hz, 1H), 7.21-7.26 (m, 2H), 5.50 (s, 2H), 4.69 (d, J=5.1 Hz, 1H), 3.51 (m, 1H), 3.40 (m, 1H), 2.01 (m, 1H), 1.85 (m, 1H), 1.57-1.60 (m, 2H), 1.20-1.23 (m, 4H); LCMS (ESI) m/z 463 (M+H)$^+$.

Example 150

Preparation of (1R,2R)-2-((6-((6-methoxyimidazo[1,2-b]pyridazin-3-yl)methyl)benzo[d]thiazol-2-yl)amino)cyclohexanol

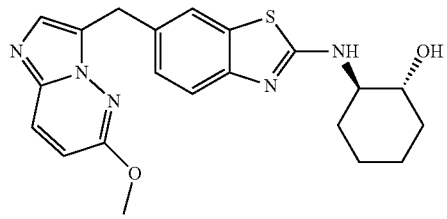 [SMILES: COc1ccc2ncc(Cc3ccc4nc(N[C@@H]5CCCC[C@H]5O)sc4c3)n2n1]

Step 1:
A stirred mixture of 2-chloro-3-(2-(methylthio)benzo[d]thiazol-6-yl)propanal from Step 4 of Example 117 (600 mg, 2.2 mmol) and 6-methoxypyridazin-3-amine (550 mg, 4.4 mmol) in 1-butanol (20 mL) was heated at reflux overnight. The mixture was cooled to rt and water (40 mL) was added. The mixture was extracted with EtOAc (20 mL×3). The combined organic layers were washed with brine, dried over Na$_2$SO$_4$, filtered and concentrated under reduced pressure. The residue was purified by silica gel chromatography eluting with 50:1 to 20:1 DCM/MeOH to afford 6-((6-methoxyimidazo[1,2-b]pyridazin-3-yl)methyl)-2-(methylthio)benzo[d]thiazole as a light brown solid (500 mg, 66%). $^1$H NMR (300 MHz, CDCl$_3$) δ 7.79-7.73 (m, 2H), 7.67 (d, J=1.2 Hz, 1H), 7.43 (s, 1H), 7.38 (dd, J=1.5, 8.4 Hz, 1H), 6.64 (d, J=9.6 Hz, 1H), 4.33 (s, 2H), 3.94 (s, 3H), 2.78 (s, 3H). LCMS (ESI) m/z 343 (M+H)$^+$.

Step 2:
To a solution of 6-((6-methoxyimidazo[1,2-b]pyridazin-3-yl)methyl)-2-(methylthio)benzo[d]thiazole (500 mg, 1.46 mmol) in DCM (30 mL) was added m-CPBA (314 mg, 1.82 mmol) at 0° C. The reaction mixture was stirred for 2 h at 0° C., then aq Na$_2$SO$_3$ (15 mL) was added and the mixture was stirred for 0.5 h. The organic layer was separated, dried over Na$_2$SO$_4$, filtered and concentrated under reduced pressure. The residue was purified by silica gel chromatography eluting with 50:1 to 20:1 DCM/MeOH to afford 6-((6-methoxyimidazo[1,2-b]pyridazin-3-yl)methyl)-2-(methylsulfinyl)benzo[d]thiazole as a yellow solid (500 mg, 95%). $^1$H NMR (300 MHz, CDCl$_3$) δ 7.99-7.93 (m, 2H), 7.76 (d, J=9.6 Hz, 1H), 7.53 (dd, J=1.5, 8.4 Hz, 1H), 7.46 (s, 1H), 6.65 (d, J=9.3 Hz, 1H), 4.42 (s, 2H), 3.94 (s, 3H), 3.06 (s, 3H). LCMS (ESI) m/z 359 (M+H)$^+$.

Step 3:

A mixture of 6-((6-methoxyimidazo[1,2-b]pyridazin-3-yl)methyl)-2-(methylsulfinyl)benzo[d]thiazole (320 mg, 0.89 mmol), (1R,2R)-2-amino cyclohexanol (308 mg, 2.68 mmol) and DIEA (231 mg, 1.79 mmol) in NMP (11 mL) was stirred for 1 d at 140° C. The mixture was cooled to rt and water (50 mL) was added. The mixture was extracted with EtOAc (30 mL×3). The combined organic layers were washed with brine, dried over $Na_2SO_4$, filtered and concentrated under reduced pressure. The residue was purified by silica gel chromatography eluting with 50:1 to 10:1 DCM/MeOH, then further purified by preparative HPLC to afford (1R,2R)-2-((6-((6-methoxyimidazo[1,2-b]pyridazin-3-yl)methyl)benzo[d]thiazol-2-yl)amino)cyclohexanol as a brown solid (120 mg, 33%). $^1$H NMR (300 MHz, DMSO-$d_6$) δ 7.97 (d, J=9.6 Hz, 1H), 7.83 (d, J=7.5 Hz, 1H), 7.61 (s, 1H), 7.44 (s, 1H), 7.26 (d, J=8.4 Hz, 1H), 7.18 (d, J=9.9 Hz, 1H), 6.82 (d, J=9.6 Hz, 1H), 4.72 (d, J=5.4 Hz, 1H), 4.23 (s, 2H), 3.95 (s, 3H), 3.5-3.49 (m, 1H), 3.39-3.36 (m, 1H), 2.05-2.01 (m, 1H), 1.90-1.86 (m, 1H), 1.65-1.59 (m, 2H), 1.28-1.14 (m, 4H). LCMS (ESI) m/z 410 (M+H)$^+$.

Example 151

Preparation of (1R,2R)-2-((6-((5-methoxy-1H-benzo[0]imidazol-1-yl)methyl)benzo[d]oxazol-2-yl)amino)cyclohexanol

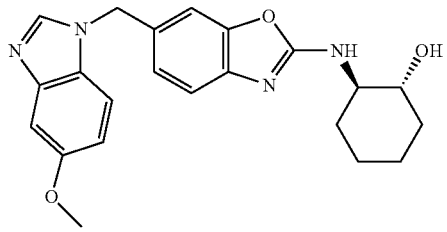 [SMILES: COc1ccc2c(c1)ncn2Cc1ccc2nc(N[C@@H]3CCCC[C@H]3O)oc2c1]

Step 1:

To a solution of 4-methoxy-2-nitroaniline (500 mg, 2.99 mmol) and TFA (3.07 mL) in DCM (15 mL) at 5° C. was added NaBH(OAc)$_3$ (1.9 g, 8.97 mmol). To the resulting mixture at 0° C. was added a solution of 2-(methylthio)benzo[d]oxazole-6-carbaldehyde (630 mg, 3.29 mmol) in DCM (10 mL), and. the mixture was stirred at 0° C. for 2 h. The reaction mixture was diluted with DCM and washed sequentially with $H_2O$, aq NaHCO$_3$ and brine. The organic layer was dried over $Na_2SO_4$ and concentrated under reduced pressure to give 4-methoxy-N-((2-(methylthio)benzo[d]oxazol-6-yl)methyl)-2-nitroaniline as a light brown solid (1.08 g, quantitative). $^1$H NMR (300 MHz, DMSO-$d_6$) δ 8.62 (t, 1H), 7.64 (s, 1H), 7.58 (d, J=8.4 Hz, 1H), 7.52 (s, 1H), 7.37 (d, J=9.3 Hz, 1H), 7.18 (d, J=6.0 Hz, 1H), 6.93 (d, J=9.3 Hz, 1H), 4.71 (d, J=5.7 Hz, 1H), 3.72 (s, 3H), 2.75 (s, 3H). LCMS (ESI) m/z 346 (M+H)$^+$.

Step 2:

To a stirred solution of 4-methoxy-N-((2-(methylthio)benzo[d]oxazol-6-yl)methyl)-2-nitroaniline (1.07 g, 3.11 mmol), HOAc (3.7 mL) and MeOH (3.7 mL) in DCM (40 mL) at 0° C. was added zinc dust (2.02 g, 31.1 mmol) portionwise. After stirring for 2 h, the mixture was filtered. The filtrate was washed with aq NaHCO$_3$ and brine, dried over Na$_2$SO$_4$ and concentrated under reduced pressure to give 4-methoxy-N$^1$-((2-(methylthio)benzo[d]oxazol-6-yl)methyl)benzene-1,2-diamine (775 mg, 79.1%). $^1$H NMR (300 MHz, DMSO-$d_6$) δ 7.60 (s, 1H), 7.55 (d, J=8.4 Hz, 1H), 7.35 (d, J=9.6 Hz, 1H), 6.26 (d, J=8.1 Hz, 1H), 6.21 (s, 1H), 5.97 (d, J=9.0 Hz, 2H), 4.74 (t, 1H), 4.68 (s, 1H), 4.31 (d, J=5.7 Hz, 1H), 3.55 (s, 3H), 2.74 (s, 3H). LCMS (ESI) m/z 316 (M+H)$^+$.

Step 3:

A solution of 4-methoxy-N$^1$-((2-(methylthio)benzo[d]oxazol-6-yl)methyl) benzene-1,2-diamine (755 mg, 2.40 mmol) in triethoxymethane (8 mL) and HCOOH (0.2 mL) was stirred at 90° C. for 40 min. The reaction mixture was concentrated under reduced pressure. The residue was purified by silica gel chromatography eluting with 1:2 petroleum ether/ethyl acetate to give 6-((5-methoxy-1H-benzo[d]imidazol-1-yl)methyl)-2-(methylthio)benzo[d]oxazole as a light brown solid (683 mg, 87.6%). $^1$H NMR (300 MHz, DMSO-$d_6$) δ 8.36 (s, 1H), 7.66 (s, 1H), 7.58 (d, J=7.8 Hz, 1H), 7.43 (d, J=9.0 Hz, 1H), 7.30 (d, J=6.6 Hz, 1H), 7.16 (s, 1H), 6.82 (d, J=6.6 Hz, 1H), 5.54 (s, 2H), 3.75 (s, 3H), 2.73 (s, 3H). LCMS (ESI) m/z 326 (M+H)$^+$.

Step 4:

A solution of 6-((5-methoxy-1H-benzo[d]imidazol-1-yl)methyl)-2-(methyl thio)benzo[d]oxazole (683 mg, 2.1 mmol) and m-CPBA (471 mg, 2.7 mmol) in DCM (10 mL) was stirred at 0° C. for 3.5 h. The reaction mixture was washed with aq Na$_2$S$_2$O$_3$ and brine. The organic layer was dried over Na$_2$SO$_4$, filtered and concentrated under reduced pressure. The residue was purified by silica gel chromatography eluting with 1:1 petroleum ether/ethyl acetate to give 6-((5-methoxy-1H-benzo[d]imidazol-1-yl)methyl)-2-(methylsulfinyl)benzo[d]oxazole (455 mg, 63.6%) as a yellow solid. $^1$H NMR (300 MHz, DMSO-$d_6$) δ 8.40 (s, 1H), 7.88 (m, 2H), 7.44 (m, 2H), 7.18 (s, 1H), 6.83 (s, 1H), 5.63 (s, 2H), 3.75 (s, 3H), 3.18 (s, 3H). LCMS (ESI) m/z 342 (M+H)$^+$.

Step 5:

A mixture of 6-((5-methoxy-1H-benzo[d]imidazol-1-yl)methyl)-2-(methylsulfinyl)benzo[d]oxazole (450 mg, 1.32 mmol), (1R,2R)-2-aminocyclohexanol (228 mg, 1.98 mmol) and DIEA (341 mg, 2.64 mmol) in DMA (10 mL) was stirred at 120° C. for 1.5 h. The reaction mixture was cooled to rt and poured into water (30 mL) and the resulting mixture was extracted with ethyl acetate (30 mL×3). The combined organic layers were washed with water and brine, dried over Na$_2$SO$_4$, filtered and concentrated under reduced pressure. The residue was purified by preparative HPLC to give (1R,2R)-2-((6-((5-methoxy-1H-benzo[d]imidazol-1-yl)methyl)benzo[d]oxazol-2-yl)amino)cyclohexanol as a white solid (155 mg, 29.9%). $^1$HNMR (300 MHz, DMSO-$d_6$) δ 8.32 (s, 1H), 7.80 (d, J=7.8 Hz, 1H), 7.41 (d, J=8.7 Hz, 1H), 7.33 (s, 1H), 7.16-7.08 (m, 3H), 6.82 (dd, J=2.4, 8.7 Hz, 1H), 5.42 (s, 2H), 4.68 (d, J=4.5 Hz, 1H), 3.75 (s, 3H), 3.35 (br s, 2H), 1.90 (m, 2H), 1.62 (br s, 2H), 1.22 (br s, 4H). LCMS (ESI) m/z 393 (M+H)$^+$.

Example 152

Preparation of (1R,2R)-2-((6-((6-methoxy-1H-benzo[0]imidazol-1-yl)methyl)benzo[d]oxazol-2-yl)amino)cyclohexanol

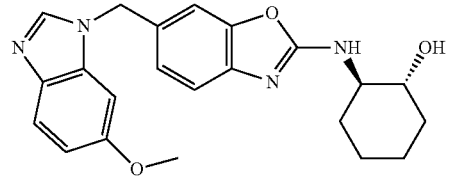 [SMILES: COc1ccc2ncn(Cc3ccc4nc(N[C@@H]5CCCC[C@H]5O)oc4c3)c2c1]

Step 1:

To a solution of 5-methoxy-2-nitroaniline (500 mg, 2.99 mmol) and TFA (3.07 mL) in DCM (15 mL) at 5° C. was added NaBH(OAc)$_3$ (1.9 g, 8.97 mmol). To the resulting mixture at 0° C. was added dropwise a solution of 2-(methylthio)benzo[d]oxazole-6-carbaldehyde (630 mg, 3.29 mmol) in DCM (10 mL) and. the mixture was stirred at 0° C. for 2 h. The reaction mixture was diluted with DCM and washed with H$_2$O, aq NaHCO$_3$ and brine. The organic layer was dried over Na$_2$SO$_4$ and concentrated under reduced pressure to give 5-methoxy-N-((2-(methylthio)benzo[d]oxazol-6-yl)methyl)-2-nitro aniline as a light brown solid (1.06 g, 100%). $^1$H NMR (300 MHz, DMSO-d$_6$) δ 8.90 (t, 1H), 8.04 (d, J=8.7 Hz, 1H), 7.68 (s, 1H), 7.60 (d, J=8.4 Hz, 1H), 7.41 (d, J=7.5 Hz, 1H), 6.28-6.32 (m, 2H), 4.73 (d, J=6 Hz, 2H), 3.72 (s, 3H), 2.74 (s, 3H). LCMS (ESI) m/z 345 (M+H)$^+$.

Step 2:

To a stirred solution of 5-methoxy-N-((2-(methylthio)benzo[d]oxazol-6-yl)methyl)-2-nitroaniline (1.05 g, 3.05 mmol), HOAc (3.6 mL) and methanol (3.6 mL) in DCM (40 mL) at 0° C. was added zinc dust (1.98 g, 30.5 mmol) portionwise. After stirring for 2 h, the mixture was filtered. The filtrate was washed with aq NaHCO$_3$ and brine, dried over Na$_2$SO$_4$ and concentrated under reduced pressure to give 5-methoxy-N$^1$-((2-(methylthio)benzo[d]oxazol-6-yl)methyl)benzene-1,2-diamine as a light yellow solid (920 mg, 95.7%). $^1$H NMR (300 MHz, DMSO-d$_6$) δ 7.5-7.60 (m, 2H), 7.35 (d, J=7.8 Hz, 1H), 6.47 (d, J=8.1 Hz, 1H), 5.93-5.99 (m, 2H), 5.32 (t, 1H), 4.38 (d, J=5.7 Hz, 2H), 4.13 (s, 2H), 3.50 (s, 3H), 2.74 (s, 3H). LCMS (ESI) m/z 316 (M+H)$^+$.

Step 3:

A mixture of 5-methoxy-N$^1$-(2-(methylthio)benzo[d]oxazol-6-yl)methyl) benzene-1,2-diamine (920 mg, 2.92 mmol), triethoxymethane (8.8 mL) and HCOOH (0.2 mL) was stirred at 90° C. for 40 min. The reaction mixture was concentrated under reduced pressure. The residue was purified by silica gel chromatography eluting with 1:2 petroleum ether/ethyl acetate to give 6-((6-methoxy-1H-benzo[d]imidazol-1-yl)methyl)-2-(methylthio)benzo[d]oxazole as a light brown solid (799 mg, 84.1%). $^1$H NMR (300 MHz, DMSO-d$_6$) δ 8.28 (s, 1H), 7.68 (s, 1H), 7.59 (d, J=8.1 Hz, 1H), 7.52 (d, J=9.0 Hz, 1H), 7.33 (d, J=6.6 Hz, 1H), 7.15 (s, 1H), 6.80 (d, J=6.6 Hz, 1H), 5.54 (s, 2H), 3.75 (s, 3H), 2.73 (s, 3H). LCMS (ESI) m/z 326 (M+H)$^+$.

Step 4:

A solution of 6-((6-methoxy-1H-benzo[d]imidazol-1-yl)methyl)-2-(methyl lthio)benzo[d]oxazole (799 mg, 2.46 mmol) and m-CPBA (551 mg, 3.20 mmol) in DCM (18 mL) was stirred at 0° C. for 3.5 h. The reaction mixture was washed with aqueous Na$_2$S$_2$O$_3$ and brine. The organic layer was dried over Na$_2$SO$_4$ and concentrated under reduced pressure. The residue was purified by silica gel chromatography eluting with 1:1 petroleum ether/ethyl acetate to give 6-((6-methoxy-1H-benzo[d]imidazol-1-yl)methyl)-2-(methylsulfinyl)benzo[d]oxazole as a light yellow solid (697 mg, 74.9%). $^1$H NMR (300 MHz, DMSO-d$_6$) δ 8.34 (s, 1H), 7.87-7.92 (m, 2H), 7.47-7.55 (m, 2H), 7.16 (s, 1H), 6.82 (d, J=5.4 Hz, 1H), 5.63 (s, 2H), 3.75 (s, 3H), 3.18 (s, 3H). LCMS (ESI) m/z 342 (M+H)$^+$.

Step 5:

A mixture of 6-((6-methoxy-1H-benzo[d]imidazol-1-yl)methyl)-2-(methyl sulfinyl)benzo[d]oxazole (595 mg, 1.74 mmol), (1R,2R)-2-aminocyclohexanol (301 mg, 2.6 mmol) and DIEA (449 mg, 3.48 mmol) in DMA (12 mL) was stirred at 120° C. for 1.5 h. The reaction mixture was cooled to rt, poured into water (30 mL) and extracted with ethyl acetate (30 mL×3). The combined organic layers were washed with brine, dried over Na$_2$SO$_4$ and concentrated under reduced pressure. The residue was purified by preparative HPLC to give (1R,2R)-2-((6-((6-methoxy-1H-benzo[d]imidazol-1-yl)methyl)benzo[d]oxazol-2-yl)amino)cyclohexanol as a white solid (198 mg, 29.0%). $^1$H NMR (300 MHz, DMSO-d$_6$) δ 8.24 (s, 1H), 7.80 (d, J=6.9 Hz, 1H), 7.50 (d, J=8.7 Hz, 1H), 7.36 (s, 1H), 7.14 (s, 3H), 6.80 (dd, J=2.4, 9.0 Hz, 1H), 5.42 (s, 2H), 4.68 (d, J=3.3 Hz, 1H), 3.76 (s, 3H), 3.33 (br s, 2H), 1.89 (br s, 2H), 1.62 (br s, 2H), 1.22 (br s, 4H). LCMS (ESI) m/z 393 (M+H)$^+$.

Example 153

Preparation of (1R,2R)-2-((6-((7-(2-methoxyethoxyl)imidazo[1,2-a]pyridin-3-yl)methyl)benzo[d]thiazol-2-yl)amino)cyclohexanol

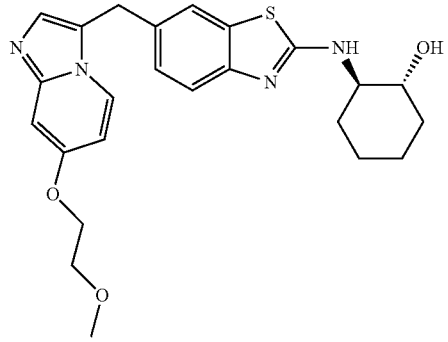 [SMILES: COCCOc1ccn2c(Cc3ccc4nc(N[C@@H]5CCCC[C@H]5O)sc4c3)cnc2c1]

Step 1:

(1R,2R)-2-((6-Iodobenzo[d]thiazol-2-yl)amino)cyclohexanol (1.9 g, 81%) was obtained as a yellow solid using procedures analogous to those described in Step 5 of Example 3 followed by Step 5 of Example 2, substituting 6-iodo-2-(methylthio)benzo[d]thiazole (Ref: US2009/163464 A1, 2009) for 6-((3H-imidazo[4,5-b]pyridin-3-yl)methyl)-2-(methylthio)benzo[d]thiazole used in Example 3, and then making the analogous substitution in Step 5 of Example 2. LCMS (ESI) m/z 375 (M+H)$^+$.

Step 2:

Crude 2-chloro-3-(2-(((1R,2R)-2-hydroxycyclohexyl)amino)benzo[d]thiazol-6-yl)propanal (180 mg) was obtained as a yellow oil using procedures analogous to those described in Steps 3-4 of Example 117, substituting (1R,2R)-2-((6-iodobenzo[d]thiazol-2-yl)amino)cyclohexanol from Step 1 of this Example for 6-iodo-2-(methylthio)benzo[d]thiazole used in Step 3 of Example 117, and making the analogous substitution in Step 4 of Example 117. LCMS (ESI) m/z 339, 341 (M+H)$^+$. In the same reaction, 2-chloro-3-(4-chloro-2-(((1R,2R)-2-hydroxycyclohexyl)amino)benzo[d]thiazol-6-yl)propanal was also present as a minor product.

Step 3:

(1R,2R)-2-((6-((7-(2-Methoxyethoxyl)imidazo[1,2-a]pyridin-3-yl)methyl)benzo[d]thiazol-2-yl)amino)cyclohexanol (28 mg, 18%) was obtained as a yellow powder using a procedure analogous to that described in Step 6 of Example 117, substituting 4-(2-methoxyethoxyl)pyridin-2-amine (Ref: WO2008/121687 A2, 2008) for 2-aminoisonicotinonitrile, and 2-chloro-3-(2-(((1R,2R)-2-hydroxycyclohexyl)amino)benzo[d]thiazol-6-yl)propanal from Step 2 of this Example for 2-chloro-3-(2-(methylthio)benzo[d]thiazol-6-yl)propanal used in Example 117. $^1$H NMR (500 MHz, DMSO-$d_6$) δ 8.00 (d, J=7.4 Hz, 1H), 7.89 (d, J=7.4 Hz, 1H), 7.49 (s, 1H), 7.25 (d, J=8.4 Hz, 1H), 7.23 (s, 1H), 7.06 (d, J=7.9 Hz, 1H), 6.92 (d, J=2.5 Hz, 1H), 6.58 (dd, J=2.5, 7.4 Hz, 1H), 4.77 (d, J=5.9 Hz, 1H), 4.22 (s, 2H), 4.07-4.16 (m, 2H), 3.60-3.72 (m, 2H), 3.50 (br s, 2H), 3.30 (s, 3H), 2.04 (d, J=12.3 Hz, 1H), 1.87 (d, J=11.8 Hz, 1H), 1.5-1.71 (m, 2H), 1.06-1.36 (m, 4H). LCMS (ESI) m/z 453 (M+H)$^+$.

Example 154

Preparation of (1R,2R)-2-((6-((3H-imidazo[4,5-b]pyridin-3-yl)methyl)-5-fluorobenzo[d]thiazol-2-yl)amino)cyclohexanol

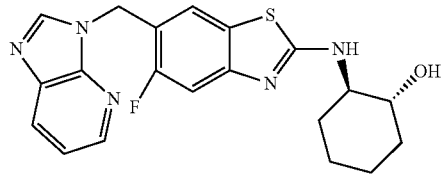 [SMILES: O[C@@H]1CCCC[C@H]1Nc1nc2cc(F)c(Cn3cnc4cccnc43)cc2s1]

Step 1:
A mixture of 4-amino-2,5-difluorobenzonitrile (1.0 g, 6.5 mmol) and O-ethylxanthic acid potassium salt (1.2 g, 7.8 mmol) in DMF (15 mL) was heated at reflux for 6 h. The mixture was cooled to rt and partitioned between EtOAc (200 mL) and 1 M aq $Na_2CO_3$ (100 mL). The organic layer was separated and the aqueous layer was extracted with additional EtOAc (2×200 mL). The combined organic layers were washed with brine (100 mL), dried over $Mg_2SO_4$, filtered, and concentrated under reduced pressure. The residue was purified by silica gel flash chromatography eluting with 2% MeOH in DCM to afford 6-cyano-5-fluorobenzo[d]thiazole-2-thiolate potassium salt (1.94 g) as an orange solid. LCMS (ESI) m/z 211 (M+H)$^+$.

Step 2:
5-Fluoro-2-(methylthio)benzo[d]thiazole-6-carbonitrile was synthesized as an orange solid (1.2 g, 86%) using a procedure analogous to that described in Step 2 of Example 114, substituting 6-cyano-5-fluorobenzo[d]thiazole-2-thiolate potassium salt from the previous step for ethyl 2-mercaptothiazolo[4,5-b]pyridine-6-carboxylate potassium salt used in Example 114. $^1$H NMR (300 MHz, DMSO-$d_6$) δ 8.67 (d, J=6.4 Hz, 1H), 8.01 (d, J=10.5 Hz, 1H), 2.84 (s, 3H); LCMS (ESI) m/z 225 (M+H)$^+$.

Step 3:
To a stirred mixture of 5-fluoro-2-(methylthio)benzo[d]thiazole-6-carbonitrile in anhydrous THF (20 mL) at 20° C. under argon was added dropwise lithium aluminum hydride (2 M solution in THF, 11.7 mL, 5.9 mmol). After 1 h, water (500 µL) and 1 M aq NaOH (500 µL) were added slowly to the reaction mixture. After 5 minutes, additional water (2 mL) was added and the mixture was stirred at rt for 30 minutes. The mixture was filtered and the filtrate was concentrated under reduced pressure. The residue was purified by silica gel flash chromatography eluting with 5% MeOH in $CH_2Cl_2$ to afford (5-fluoro-2-(methylthio)benzo[d]thiazol-6-yl)methanamine (128 mg, 29%) as a colorless oil. $^1$H NMR (500 MHz, DMSO-$d_6$) δ 8.07 (d, J=7.1 Hz, 1H), 7.64 (d, J=11.1 Hz, 1H), 3.83 (s, 2H), 2.78 (s, 3H), 1.80-2.06 (m, 2H); LCMS (ESI) m/z 229 (M+H)$^+$.

Step 4:
To a stirred mixture of (5-fluoro-2-(methylthio)benzo[d]thiazol-6-yl)methanamine (128 mg, 0.6 mmol) and DIEA (195 µL, 1.2 mmol) at 0° C. under argon was added 2-chloro-3-nitropyridine (98 mg, 0.7 mmol) in one portion. The mixture was stirred at rt for 18 h and then concentrated under reduced pressure. The residue was purified by silica gel flash chromatography eluting with a gradient of 100% hexanes to 50% EtOAc in hexanes to afford N-((5-fluoro-2-(methylthio)benzo[d]thiazol-6-yl)methyl)-3-nitropyridin-2-amine (165 mg, 84%) as a yellow oil. LCMS (ESI) m/z 351 (M+H)$^+$.

Step 5:
$N^2$-((5-Fluoro-2-(methylthio)benzo[d]thiazol-6-yl)methyl)pyridine-2,3-diamine was synthesized as a yellow solid (200 mg) using a procedure analogous to that described in Step 2 of Example 41, substituting N-((5-fluoro-2-(methylthio)benzo[d]thiazol-6-yl)methyl)-3-nitropyridin-2-amine from the previous step for 4-bromo-5-methoxy-N-((2-(methylthio)benzo[d]thiazol-6-yl)methyl)-2-nitroaniline used in Example 41. LCMS (ESI) m/z 321 (M+H)$^+$.

Step 6:
6-((3H-Imidazo[4,5-b]pyridin-3-yl)methyl)-5-fluoro-2-(methylthio)benzo[d]thiazole was synthesized as a tan solid (180 mg) using a procedure analogous to that described in Step 3 of Example 41, substituting $N^2$-((5-fluoro-2-(methylthio)benzo[d]thiazol-6-yl)methyl)pyridine-2,3-diamine from the previous step for 4-bromo-5-methoxy-$N^1$-((2-(methylthio)benzo[d]thiazol-6-yl)methyl)benzene-1,2-diamine used in Example 41. LCMS (ESI) m/z 331 (M+H)$^+$.

Step 7:
6-((3H-Imidazo[4,5-b]pyridin-3-yl)methyl)-5-fluoro-2-(methylsulfinyl)benzo[c]thiazole was synthesized as a white foam (314 mg) using a procedure analogous to that described in Step 6 of Example 36, substituting 6-((3H-imidazo[4,5-b]pyridin-3-yl)methyl)-5-fluoro-2-(methylthio)benzo[c]thiazole from the previous step for the 6-((4-bromo-1H-imidazol-1-yl)methyl)-2-(methylthio)benzo[d]thiazole used in Example 36. LCMS (ESI) m/z 347 (M+H)$^+$.

Step 8:
(1R,2R)-2-((6-((3H-Imidazo[4,5-b]pyridin-3-yl)methyl)-5-fluorobenzo[d]thiazol-2-yl)amino)cyclohexanol was synthesized as a white powder (42 mg, 19%) using a procedure analogous to that described in Step 7 of Example 36, substituting 6-((3H-imidazo[4,5-b]pyridin-3-yl)methyl)-5-fluoro-2-(methylsulfinyl)benzo[d]thiazole from the previous step for 6-((4-bromo-1H-imidazol-1-yl)methyl)-2-(methylsulfinyl)benzo[c]thiazole used in Example 36. $^1$H NMR (500 MHz, DMSO-$d_6$) δ 8.50 (s, 1H), 8.36 (dd, J=1.2, 4.7 Hz, 1H), 8.15 (d, J=7.6 Hz, 1H), 8.09 (dd, J=1.1, 8.0 Hz, 1H), 7.60 (d, J=7.4 Hz, 1H), 7.29 (m, 1H), 7.18 (d, J=11.6 Hz, 1H), 5.52 (s, 2H), 4.75 (d, J=5.2 Hz, 1H), 3.51 (m, 1H), 3.32 (m, 1H), 2.01 (m, 1H), 1.89 (m, 1H), 1.5-1.65 (m, 2H), 1.12-1.31 (m, 4H); LCMS (ESI) m/z 398 (M+H)$^+$.

Example 155

Preparation of (1R,2R)-2-((6-((6-morpholinoimidazo[1,2-b]pyridazin-3-yl)methyl)benzo[d]thiazol-2-yl)amino)cyclohexanol

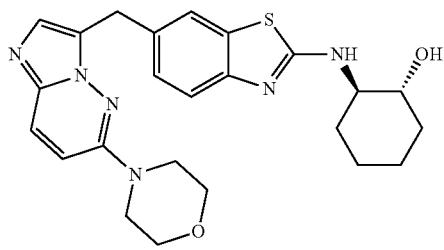 [SMILES: O[C@@H]1CCCC[C@H]1Nc1nc2ccc(Cc3cnc4ccc(N5CCOCC5)nn34)cc2s1]

(1R,2R)-2-((6-((6-Morpholinoimidazo[1,2-b]pyridazin-3-yl)methyl)benzo[d]thiazol-2-yl)amino)cyclohexanol (55 mg, 13%) was obtained as a yellow powder using a procedure analogous to that described in Step 6 of Example 117, substituting 6-morpholinopyridazin-3-amine (Ref: U.S. Pat. No. 4,104,385 A1, 1978) and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. $^1$H NMR (500 MHz, DMSO-$d_6$) δ 7.87 (d, J=7.8 Hz, 1H), 7.81 (d, J=9.9 Hz, 1H), 7.58 (s, 1H), 7.35 (s, 1H), 7.24 (d, J=8.3 Hz, 1H), 7.13 (d, J=8.3 Hz, 1H), 7.09 (d, J=9.9 Hz, 1H), 4.78 (br s, 1H), 4.17 (s, 2H), 3.72 (d, J=4.7 Hz, 4H), 3.50 (br s, 2H), 3.42-3.49 (m, 4H), 2.04 (d, J=11.9 Hz, 1H), 1.87 (d, J=10.4 Hz, 1H), 1.5-1.71 (m, 2H), 1.10-1.37 (m, 4H). LCMS (ESI) m/z 465 (M+H)$^+$.

Example 156

Preparation of (1R,2R)-2-((4-chloro-6-((6-morpholinoimidazo[1,2-b]pyridazin-3-yl)methyl)benzo[d]thiazol-2-yl)amino)cyclohexanol

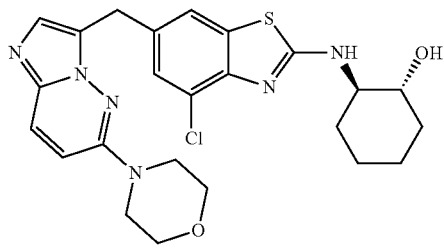 [SMILES: O[C@@H]1CCCC[C@H]1Nc1nc2c(Cl)cc(Cc3cnc4ccc(N5CCOCC5)nn34)cc2s1]

(1R,2R)-2-((4-Chloro-6-((6-morpholinoimidazo[1,2-b]pyridazin-3-yl)methyl)benzo[d]thiazol-2-yl)amino)cyclohexanol (25 mg, 6%) was obtained as a yellow powder using a procedure analogous to that described in Step 6 of Example 117, substituting 6-morpholinopyridazin-3-amine (Ref: U.S. Pat. No. 4,104,385 A1, 1978) and 2-chloro-3-(4-chloro-2-(((1R,2R)-2-hydroxycyclohexyl)amino)benzo[d]thiazol-6-yl)propanal (minor product from Step 2 of Example 153), respectively, for 2-aminoisonicotinonitrile and 2-chloro-3-(2-(methylthio)benzo[d]thiazol-6-yl)propanal used in Example 117. $^1$H NMR (500 MHz, DMSO-$d_6$) δ 8.20 (d, J=7.3 Hz, 1H), 7.82 (d, J=9.9 Hz, 1H), 7.56 (s, 1H), 7.40 (s, 1H), 7.27 (s, 1H), 7.10 (d, J=9.9 Hz, 1H), 4.83 (br s, 1H), 4.17 (s, 2H), 3.66-3.80 (m, 4H), 3.44 (d, J=4.7 Hz, 4H), 2.02 (d, J=7.8 Hz, 1H), 1.88 (d, J=11.4 Hz, 1H), 1.63 (br s, 2H), 1.10-1.37 (m, 4H). LCMS (ESI) m/z 499, 501 (M+H)$^+$.

Example 157

Preparation of (1R,2R)-2-((6-(imidazo[2,1-b]thiazol-5-ylmethyl)benzo[d]thiazol-2-yl)amino)cyclohexanol

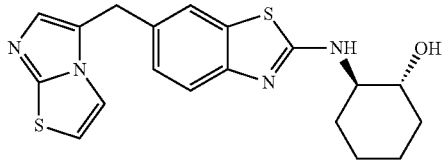 [SMILES: O[C@@H]1CCCC[C@H]1Nc1nc2ccc(Cc3cnc4sccn34)cc2s1]

Step 1:

A stirred mixture of 2-chloro-3-(2-(methylthio)benzo[d]thiazol-6-yl)propanal from Step 4 of Example 117 (500 mg, 1.84 mmol) and thiazol-2-amine (370 mg, 3.68 mmol) in 1-butanol (22 mL) was heated at reflux overnight. The mixture was cooled to rt and water (120 mL) was added. The mixture was extracted with EtOAc (60 mL×3). The combined organic layers were washed with brine, dried over Na$_2$SO$_4$, filtered and concentrated under reduced pressure. The residue was purified by silica gel chromatography eluting with 50:1 to 20:1 DCM/MeOH to afford 6-(imidazo[2,1-b]thiazol-5-ylmethyl)-2-(methylthio)benzo[d]thiazole as a yellow solid (350 mg, 60%). $^1$H NMR (300 MHz, CDCl$_3$) δ 7.80 (d, J=8.4 Hz, 1H), 7.55 (d, J=1.2 Hz, 1H), 7.29 (d, J=1.8 Hz, 1H), 7.16 (d, J=0.9 Hz, 1H), 6.99 (d, J=4.5 Hz, 1H), 6.71 (dd, J=0.9 Hz, J=4.5 Hz, 1H), 4.24 (s, 2H), 2.78 (s, 3H). LCMS (ESI) m/z 318 (M+H)$^+$.

Step 2:

To a solution of 6-(imidazo[2,1-b]thiazol-5-ylmethyl)-2-(methylthio)benzo[d]thiazole (350 mg, 1.1 mmol) in DCM (20 mL) was added m-CPBA (240 mg, 1.4 mmol) at 0° C. The reaction mixture was stirred for 2 h at 0° C., then aq Na$_2$S$_2$O$_3$ (20 mL) was added and the mixture was stirred for 0.5 h. The organic layer was separated and dried over Na$_2$SO$_4$, filtered and concentrated under reduced pressure. The residue was purified by silica gel chromatography eluting with 50:1 to 20:1 DCM/MeOH to afford 6-(imidazo[2,1-b]thiazol-5-ylmethyl)-2-(methylsulfinyl)benzo[d]thiazole as a yellow solid (310 mg, 85%). $^1$H NMR (300 MHz, CDCl$_3$) δ 8.00 (d, J=8.4 Hz, 1H), 7.82 (d, J=0.9 Hz, 1H), 7.43 (dd, J=1.5, 8.4 Hz, 1H), 7.18 (s, 1H), 7.03 (d, J=4.5 Hz, 1H), 6.75 (dd, J=0.9, 4.5 Hz, 1H), 4.32 (s, 2H), 3.07 (s, 3H). LCMS (ESI) m/z 334 (M+H)$^+$.

Step 3:

A mixture of 6-(imidazo[2,1-b]thiazol-5-ylmethyl)-2-(methylsulfinyl)benzo[d]thiazole (310 mg, 0.93 mmol), (1R,2R)-2-aminocyclohexanol (321 mg, 2.79 mmol) and DIEA (240 mg, 1.86 mmol) in NMP (10 mL) was stirred for 1 d at 130° C. The mixture was cooled to rt and water (50 mL) was added. The mixture was extracted with EtOAc (100 mL×3). The combined organic layers were washed with brine, dried over Na$_2$SO$_4$, filtered and concentrated under reduced pressure. The residue was purified by silica gel chromatography eluting with 50:1 to 10:1 DCM/MeOH, and the product was further purified by preparative HPLC to afford (1R,2R)-2-((6-(imidazo[2,1-b]thiazol-5-ylmethyl)benzo[d]thiazol-2-yl)amino)cyclohexanol as a brown solid (100 mg, 28%). ¹H NMR (300 MHz, DMSO-d₆) δ 7.84 (d, J=7.2 Hz, 1H), 7.68 (d, J=4.5 Hz, 1H), 7.54 (d, J=1.8 Hz, 1H), 7.27 (d, J=8.1 Hz, 1H), 7.20 (dd, J=0.9, 4.2 Hz, 1H), 7.10 (dd, J=1.8, 8.4 Hz, 1H), 7.02 (s, 1H), 4.71 (d, J=4.8 Hz, 1H), 4.15 (s, 2H), 3.5-3.49 (m, 1H), 3.39-3.36 (m, 1H), 2.05-2.01 (m, 1H), 1.90-1.86 (m, 1H), 1.65-1.59 (m, 2H), 1.30-1.16 (m, 4H). LCMS (ESI) m/z 385 (M+H)⁺.

Example 158

Preparation of (1R,2R)-2-((6-((6-chloroimidazo[1,2-b]pyridazin-3-yl)methyl)benzo[d]thiazol-2-yl)amino)cyclohexanol

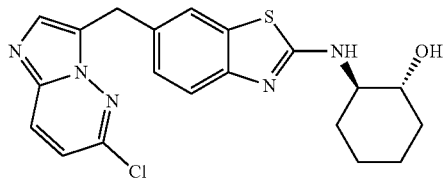 [SMILES: O[C@@H]1CCCC[C@H]1Nc1nc2ccc(Cc3cnc4ccc(Cl)nn34)cc2s1]

Step 1:
A mixture of 2-chloro-3-(2-(methylthio)benzo[d]thiazol-6-yl)propanal from Step 4 of Example 117 (1.5 g, 5.5 mmol) and 6-chloropyridazin-3-amine (1.4 g, 11 mmol) in 1-butanol (60 mL) was heated at reflux overnight. Then the mixture was cooled to rt and water (120 mL) was added. The mixture was extracted with EtOAc (60 mL×3). The combined organic layers were washed with brine, dried over Na₂SO₄, filtered and concentrated under reduced pressure. The residue was purified by silica gel chromatography eluting with 50:1 to 20:1 DCM/MeOH to afford 6-((6-chloroimidazo[1,2-b]pyridazin-3-yl)methyl)-2-(methylthio)benzo[d]thiazole as a yellow solid (1.6 g, 84%). ¹H NMR (300 MHz, CDCl₃) δ 7.89 (d, J=9.6 Hz, 1H), 7.81 (d, J=8.4 Hz, 1H), 7.68 (dd, J=0.6, 1.2 Hz, 1H), 7.53 (s, 1H), 7.37 (dd, J=1.8, 8.4 Hz, 1H), 7.03 (d, J=9.3 Hz, 1H), 4.40 (s, 2H), 2.78 (s, 3H). LCMS (ESI) m/z 347 (M+H)⁺.

Step 2:
To a solution of 6-((6-chloroimidazo[1,2-b]pyridazin-3-yl)methyl)-2-(methylthio)benzo[d]thiazole (1.6 g, 4.6 mmol) in DCM (90 mL) was added m-CPBA (1.0 g, 5.8 mmol) at 0° C. The reaction mixture was stirred for 2 h at 0° C., then aq Na₂S₂O₃ (45 mL) was added and the mixture was stirred for 0.5 h. The organic layer was separated, dried over Na₂SO₄, filtered and concentrated under reduced pressure. The residue was purified by silica gel chromatography eluting with 50:1 to 20:1 DCM/MeOH to afford 6-((6-chloroimidazo[1,2-b]pyridazin-3-yl)methyl)-2-(methylsulfinyl)benzo[d]thiazole as a yellow solid (1.68 g, 100%). ¹H NMR (300 MHz, CDCl₃) δ 8.00 (d, J=8.4 Hz, 1H), 7.92 (d, J=3.6 Hz, 1H), 7.89 (s, 1H), 7.58 (s, 1H), 7.53 (dd, J=2.1, 8.7 Hz, 1H), 7.05 (d, J=9.3 Hz, 1H), 4.48 (s, 2H), 3.07 (s, 3H). LCMS (ESI) m/z 363 (M+H)⁺.

Step 3:
A mixture of 6-((6-chloroimidazo[1,2-b]pyridazin-3-yl)methyl)-2-(methylsulfinyl)benzo[d]thiazole (1.0 g, 2.7 mmol), (1R,2R)-2-aminocyclohexanol (0.93 g, 8.1 mmol) and DIEA (697 mg, 5.4 mmol) in NMP (40 mL) was stirred for 2 d at 140° C. The mixture was cooled to rt and water (150 mL) was added. The mixture was extracted with EtOAc (100 mL×3). The combined organic layers were washed with brine, dried over Na₂SO₄, filtered and concentrated under reduced pressure. The residue was purified by silica gel chromatography eluting with 50:1 to 10:1 DCM/MeOH to afford (1R,2R)-2-((6-((6-chloroimidazo[1,2-b]pyridazin-3-yl)methyl)benzo[d]thiazol-2-yl)amino)cyclohexanol as a brown solid (530 mg, 46%). ¹H NMR (300 MHz, DMSO-d₆) δ 8.20 (d, J=9.6 Hz, 1H), 7.86 (d, J=7.2 Hz, 1H), 7.63 (s, 1H), 7.54 (d, J=1.8 Hz, 1H), 7.32 (d, J=9.9 Hz, 1H), 7.27 (d, J=1.8 Hz, 1H), 7.12 (dd, J=1.5, 8.4 Hz, 1H), 4.73 (d, J=5.1 Hz, 1H), 4.29 (s, 2H), 3.5-3.49 (m, 1H), 3.39-3.36 (m, 1H), 2.05-2.01 (m, 1H), 1.90-1.86 (m, 1H), 1.65-1.59 (m, 2H), 1.30-1.16 (m, 4H). LCMS (ESI) m/z 414 (M+H)⁺.

Example 159

Preparation of (1R,2R)-2-((6-((6-(1H-pyrazol-1-yl)imidazo[1,2-a]pyridin-3-yl)methyl)benzo[d]thiazol-2-yl)amino)cyclohexanol

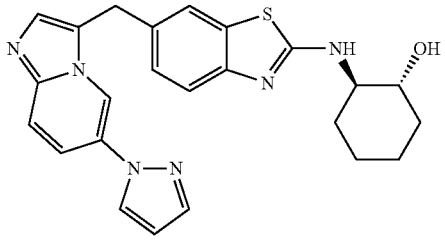 [SMILES: O[C@@H]1CCCC[C@H]1Nc1nc2ccc(Cc3cnc4ccc(-n5cccn5)cn34)cc2s1]

Step 1:
(1R,2R)-2-((6-((6-Iodoimidazo[1,2-a]pyridin-3-yl)methyl)benzo[d]thiazol-2-yl)amino)cyclohexanol (50 mg, 13%) was obtained as a light brown solid using a procedure analogous to that described in Step 6 of Example 117, substituting 5-iodopyridin-2-amine and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. LCMS (ESI) m/z 505 (M+H)⁺.

Step 2:
(1R,2R)-2-((6-((6-(1H-Pyrazol-1-yl)imidazo[1,2-a]pyridin-3-yl)methyl)benzo[d]thiazol-2-yl)amino)cyclohexanol (7 mg, 16%) was obtained as a light tan solid using a procedure analogous to that described in Example 141, substituting (1R,2R)-2-((6-((6-iodoimidazo[1,2-a]pyridin-3-yl)methyl)benzo[d]thiazol-2-yl)amino)cyclohexanol from Step 1 of this Example for (1R,2R)-2-((6-((6-iodo-3H-imidazo[4,5-b]pyridin-3-yl)methyl)benzo[d]thiazol-2-yl)amino)cyclohexanol used in Example 141. ¹H NMR (500 MHz, DMSO-d₆) δ 8.70 (br s, 1H), 8.48 (d, J=2.1 Hz, 1H), 7.92 (d, J=7.3 Hz, 1H), 7.76 (br s, 2H), 7.73 (br s, 1H), 7.54 (s, 1H), 7.28 (d, J=8.3 Hz, 1H), 7.12 (d, J=8.3 Hz, 1H), 6.57 (s, 1H), 4.79 (br s, 1H), 4.36 (s, 2H), 3.49 (d, J=6.7 Hz, 2H), 2.04 (d, J=11.4 Hz, 1H), 1.87 (d, J=10.4 Hz, 1H), 1.5-1.71 (m, 2H), 1.08-1.36 (m, 4H). LCMS (ESI) m/z 445 (M+H)⁺.

Example 160

Preparation of (1R,2R)-2-((6-((5-(1H-pyrazol-1-yl)-1H-benzo[d]imidazol-1-yl)methyl)benzo[d]thiazol-2-yl)amino)cyclohexanol

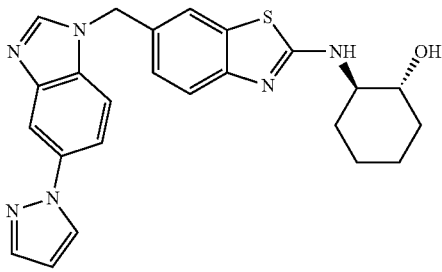 [SMILES: O[C@@H]1CCCC[C@H]1Nc1nc2ccc(Cn3cnc4cc(-n5cccn5)ccc43)cc2s1]

(1R,2R)-2-((6-((5-(1H-pyrazol-1-yl)-1H-benzo[d]imidazol-1-yl)methyl)benzo[d]thiazol-2-yl)amino)cyclohexanol (18 mg, 20%) was obtained as a solid using a procedure analogous to that described in Example 141, substituting (1R,2R)-2-((6-((5-iodo-1H-benzo[d]imidazol-1-yl)methyl)benzo[d]thiazol-2-yl)amino)cyclohexanol from Step 5 of Example 183 for (1R,2R)-2-((6-((6-iodo-3H-imidazo[4,5-b]pyridin-3-yl)methyl)benzo[d]thiazol-2-yl)amino)cyclohexanol used in Example 141. $^1$H NMR (500 MHz, DMSO-$d_6$) δ 8.43-8.53 (m, 2H), 8.06 (d, J=1.6 Hz, 1H), 7.99 (d, J=7.8 Hz, 1H), 7.69-7.75 (m, 2H), 7.64-7.68 (m, 2H), 7.30 (d, J=8.3 Hz, 1H), 7.22 (d, J=8.3 Hz, 1H), 6.51 (d, J=2.1 Hz, 1H), 5.50 (s, 2H), 4.76 (br m, 1H), 3.48-3.56 (br m, 2H), 2.02 (m, 1H), 1.87 (m, 1H), 1.5-1.68 (m, 2H), 1.09-1.35 (m, 4H); LCMS (ESI) m/z 445 (M+H)$^+$.

Example 161

Preparation of (1R,2R)-2-((6-((5-(1H-1,2,4-triazol-1-yl)-1H-benzo[d]imidazol-1-yl)methyl)benzo[d]thiazol-2-yl)amino)cyclohexanol

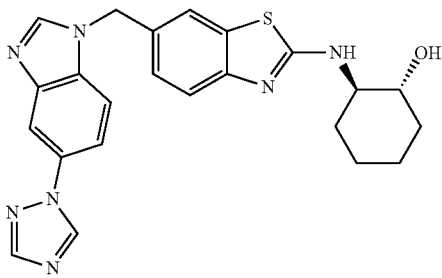 [SMILES: O[C@@H]1CCCC[C@H]1Nc1nc2ccc(Cn3cnc4cc(-n5cncn5)ccc43)cc2s1]

(1R,2R)-2-((6-((5-(1H-1,2,4-Triazol-1-yl)-1H-benzo[d]imidazol-1-yl)methyl)benzo[d]thiazol-2-yl)amino)cyclohexanol (10 mg, 8%) was obtained as a solid using a procedure analogous to that described in Example 141, substituting (1R,2R)-2-((6-((5-iodo-1H-benzo[d]imidazol-1-yl)methyl)benzo[d]thiazol-2-yl)amino)cyclohexanol from Step 5 of Example 183 and 1H-1,2,4-triazole, respectively, for (1R,2R)-2-((6-((6-iodo-3H-imidazo[4,5-b]pyridin-3-yl)methyl)benzo[d]thiazol-2-yl)amino)cyclohexanol and 1H-pyrazole used in Example 141. $^1$H NMR (500 MHz, DMSO-$d_6$) δ 9.23 (s, 1H), 8.54 (s, 1H), 8.20 (s, 1H), 8.12 (s, 1H), 7.97 (d, J=7.3 Hz, 1H), 7.71-7.74 (m, 2H), 7.68 (s, 1H), 7.30 (d, J=8.3 Hz, 1H), 7.22 (d, J=8.3 Hz, 1H), 5.52 (s, 2H), 4.74 (br s, 1H), 3.48-3.56 (br m, 2H), 2.02 (m, 1H), 1.87 (br s, 1H), 1.5-1.72 (m, 2H), 1.10-1.33 (m, 4H); LCMS (ESI) m/z 446 (M+H)$^+$.

Example 162

Preparation of (1S,2R)-2-((6-((6-fluoro-3H-imidazo[4,5-b]pyridin-3-yl)methyl)benzo[d]thiazol-2-yl)amino)cyclohexanol

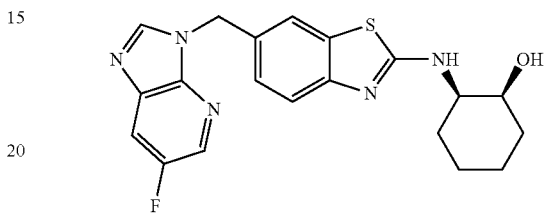

Step 1:

A mixture of acetic anhydride (49 mL, 0.5 mol) and formic acid (19 mL, 0.5 mol) was heated at 60° C. for 3 h. 5-Fluoro-3-nitropyridin-2-amine was added and the mixture was stirred at 60° C. for 1 h. The mixture was concentrated under reduced pressure and the residue was stirred vigorously in diethyl ether (200 mL) for 30 minutes. The solid was collected by filtration to afford N-(5-fluoro-3-nitropyridin-2-yl)formamide (4.5 g, 96%) as an orange solid which did not require further purification. LCMS (ESI) m/z 186 (M+H)$^+$.

Step 2:

N-(5-Fluoro-3-nitropyridin-2-yl)-N-((2-(methylthio)benzo[d]thiazol-6-yl)methyl)formamide was synthesized as an yellow solid (4 g, 82%) using a procedure analogous to that described in Step 3 of Example 47, substituting N-(5-fluoro-3-nitropyridin-2-yl)formamide from the previous step for 5-bromo-6-methoxy-1H-benzo[d]imidazole used in Example 47. LCMS (ESI) m/z 379 (M+H)$^+$.

Step 3:

A stirred mixture of N-(5-fluoro-3-nitropyridin-2-yl)-N-((2-(methylthio)benzo[d]thiazol-6-yl)methyl)formamide and iron powder (6 g, 108 mmol) in EtOH (70 mL) and HOAc (30 mL) was heated at reflux for 2 h. The mixture was cooled to rt, filtered, and the filtrate was concentrated under reduced pressure. The residue was purified by silica gel flash chromatography, eluting with a gradient of 100% hexanes to 100% EtOAc, to afford 6-((6-fluoro-3H-imidazo[4,5-b]pyridin-3-yl)methyl)-2-(methylthio)benzo[d]thiazole (1 g, 28%) as a white foam. $^1$H NMR (500 MHz, DMSO-$d_6$) δ 8.72 (s, 1H), 8.40 (t, J=2.0 Hz, 1H), 8.09 (dd, J=2.6, 9.5 Hz, 1H), 7.99 (s, 1H), 7.80 (d, J=8.4 Hz, 1H), 7.45 (dd, J=1.5, 8.4 Hz, 1H), 5.61 (s, 2H), 2.76 (s, 3H); LCMS (ESI) m/z 331 (M+H)$^+$.

Step 4:

6-((6-Fluoro-3H-imidazo[4,5-b]pyridin-3-yl)methyl)-2-(methylsulfinyl)benzo[d]thiazole was synthesized as a white foam (1.8 g) using a procedure analogous to that described in Step 6 of Example 36, substituting 6-((6-fluoro-3H-imidazo[4,5-b]pyridin-3-yl)methyl)-2-(methylthio)benzo[d]thiazole from the previous step for 6-((4-bromo-1H-imidazol-1-yl)methyl)-2-(methylthio)benzo[d]thiazole used in Example 36. LCMS (ESI) m/z 347 (M+H)$^+$.

Step 5:

To a suspension of 6-((6-fluoro-3H-imidazo[4,5-b]pyridin-3-yl)methyl)-2-(methylsulfinyl)benzo[d]thiazole (1.0 g, 3.0 mmol) and (1S,2R)-2-aminocyclohexanol hydrochloride (916 mg, 6 mmol) in anhydrous DMA (12 mL) was added DIEA (1.6 mL, 9.0 mmol). The mixture was heated in a sealed tube at 110° C. for 12 h. The mixture was cooled to rt and additional (1S,2R)-2-aminocyclohexanol hydrochloride (458 mg, 3 mmol) and DIEA (530 µL, 3 mmol) were added. The mixture was further heated in a sealed tube at 120° C. for 12 h. The mixture was cooled to rt and partitioned between EtOAc (200 mL) and 0.5 M aq $K_2CO_3$ (100 mL). The organic layer was separated, washed with brine (100 mL), dried over $Na_2SO_4$, filtered, and concentrated under reduced pressure. The residue was purified by silica gel flash chromatography, eluting with 5% MeOH in $CH_2Cl_2$, then by reverse-phase preparative HPLC using a mixture of water (5% $CH_3CN$, 0.05% HCOOH) and $CH_3CN$ (0.05% HCOOH) as the mobile phase and Varian Pursuit XRs C18 column as the stationary phase to afford (1S,2R)-2-((6-((6-fluoro-3H-imidazo[4,5-b]pyridin-3-yl)methyl)benzo[d]thiazol-2-yl)amino)cyclohexanol (89 mg, 7%) as a white powder. $^1$H NMR (500 MHz, DMSO-$d_6$) δ 8.67 (s, 1H), 8.41 (s, 1H), 8.06 (dd, J=2.5, 9.5 Hz, 1H), 7.85 (d, J=7.5 Hz, 1H), 7.66 (s, 1H), 7.29 (d, J=8.0 Hz, 1H), 7.21 (dd, J=1.3, 8.3 Hz, 1H), 5.47 (s, 2H), 4.67 (m, 1H), 3.90 (m, 1H), 3.84 (m, 1H), 1.64-1.74 (m, 2H), 1.43-1.63 (m, 4H), 1.25-1.34 (m, 2H); LCMS (ESI) m/z 398 (M+H)$^+$.

Example 163

Preparation of trans-4-((6-((6-fluoro-3H-imidazo[4,5-b]pyridin-3-yl)methyl)benzo[d]thiazol-2-yl)amino)cyclohexanol

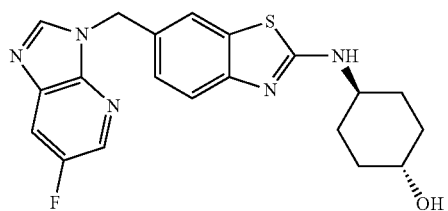 [SMILES: O[C@H]1CC[C@H](Nc2nc3ccc(Cn4cnc5cc(F)cnc54)cc3s2)CC1]

To a stirred suspension of 6-((6-fluoro-3H-imidazo[4,5-b]pyridin-3-yl)methyl)-2-(methylsulfinyl)benzo[d]thiazole (119 g, 0.3 mmol) from Step 4 of Example 162 and trans-4-aminocyclohexanol (119 mg, 1.0 mmol) in anhydrous DMA (1 mL) was added DIEA (180 µL, 1.0 mmol). The mixture was heated in a sealed tube at 110° C. for 15 h. The mixture was cooled to rt and was purified by reverse-phase preparative HPLC using a mixture of water (5% $CH_3CN$, 0.05% HCOOH) and $CH_3CN$ (0.05% HCOOH) as the mobile phase and Varian Pursuit XRs C18 column as the stationary phase to afford trans-4-((6-((6-fluoro-3H-imidazo[4,5-b]pyridin-3-yl)methyl)benzo[c]thiazol-2-yl)amino)cyclohexanol (50 mg, 37%) as a white powder. $^1$H NMR (500 MHz, DMSO-$d_6$) δ 8.67 (s, 1H), 8.41 (s, 1H), 8.06 (dd, J=2.6, 9.3 Hz, 1H), 7.92 (d, J=7.3 Hz, 1H), 7.66 (s, 1H), 7.32 (d, J=8.3 Hz, 1H), 7.23 (d, J=8.0 Hz, 1H), 5.48 (s, 2H), 4.55 (m, 1H), 3.60 (m, 1H), 3.40 (m, 1H), 1.93-2.03 (m, 2H), 1.78-1.87 (m, 2H), 1.19-1.30 (m, 4H); LCMS (ESI) m/z 398 (M+H)$^+$.

Example 164

Preparation of (1R,2R)-2-((6-((3H-imidazo[4,5-b]pyridin-3-yl)methyl)-7-fluorobenzo[d]thiazol-2-yl)amino)cyclohexanol

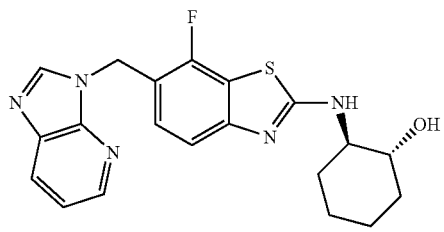 [SMILES: O[C@@H]1CCCC[C@H]1Nc1nc2ccc(Cn3cnc4cccnc43)c(F)c2s1]

Step 1:

6-(Methoxycarbonyl)-7-fluorobenzo[d]thiazole-2-thiolate potassium salt was synthesized as a brown oil (1.2 g) using a procedure analogous to that described in Step 1 of Example 114, substituting methyl 4-amino-2,3-difluorobenzoate for ethyl 6-amino-5-bromonicotinate used in Example 114. The material was used in the next step without further purification. LCMS (ESI) m/z 243 (M+H)$^+$.

Step 2:

Methyl 7-fluoro-2-(methylthio)benzo[d]thiazole-6-carboxylate was synthesized as a clear oil (400 mg, 29%) using a procedure analogous to that described in Step 2 of Example 114, substituting 6-(methoxycarbonyl)-7-fluorobenzo[d]thiazole-2-thiolate potassium salt from the previous step for ethyl 2-mercaptothiazolo[4,5-b]pyridine-6-carboxylate potassium salt used in Example 114. $^1$H NMR (500 MHz, DMSO-$d_6$) δ 7.96 (m, 1H), 7.77 (d, J=8.6 Hz, 1H), 3.89 (s, 3H), 2.85 (s, 3H); LCMS (ESI) m/z 258 (M+H)$^+$.

Step 3:

(7-Fluoro-2-(methylthio)benzo[d]thiazol-6-yl)methanol was synthesized as a white solid (249 mg, 69%) using a procedure analogous to that described in Step 3 of Example 36, substituting methyl 7-fluoro-2-(methylthio)benzo[d]thiazole-6-carboxylate from the previous step for ethyl 2-(methylthio)benzo[d]thiazole-6-carboxylate used in Example 36. $^1$H NMR (500 MHz, DMSO-$d_6$) δ 7.70 (d, J=8.4 Hz, 1H), 7.56 (t, J=7.8 Hz, 1H), 5.39 (t, J=5.8 Hz, 1H), 4.64 (d, J=5.7 Hz, 2H), 2.81 (s, 3H); LCMS (ESI) m/z 230 (M+H)$^+$.

Step 4:

6-(Chloromethyl)-7-fluoro-2-(methylthio)benzo[d]thiazole was synthesized as a white solid (258 mg) using a procedure analogous to that described in Step 4 of Example 114, substituting methyl (7-fluoro-2-(methylthio)benzo[d]thiazol-6-yl)methanol from the previous step for (2-(methylthio)thiazolo[4,5-b]pyridin-6-yl)methanol used in Example 114. LCMS (ESI) m/z 248 (M+H)$^+$.

Step 5:

6-((3H-Imidazo[4,5-b]pyridin-3-yl)methyl)-7-fluoro-2-(methylthio)benzo[d]thiazole was synthesized as a yellow solid (200 mg, 61%) using a procedure analogous to that described in Step 5 of Example 114, substituting 6-(chloromethyl)-7-fluoro-2-(methylthio)benzo[d]thiazole from the previous step for 6-(chloromethyl)-2-(methylthio)thiazolo[4,5-b]pyridine used in Example 114. The regiochemistry of the alkylation was determined by 2-dimensional nuclear Overhauser effect (NOE) experiment. $^1$H NMR (500 MHz, DMSO-$d_6$) δ 8.60 (s, 1H), 8.36 (dd, J=1.0, 4.7 Hz, 1H), 8.10 (dd, J=1.1, 8.0 Hz, 1H), 7.67 (d, J=8.4 Hz, 1H), 7.42 (t, J=8.0

Hz, 1H), 7.29 (dd, J=4.8, 8.0 Hz, 1H), 5.68 (s, 2H), 2.80 (s, 3H); LCMS (ESI) m/z 331 (M+H)+.

Step 6:

6-((3H-Imidazo[4,5-b]pyridin-3-yl)methyl)-7-fluoro-2-(methylsulfinyl)benzo[d]thiazole was synthesized as a yellow solid (350 mg) using a procedure analogous to that described in Step 6 of Example 36, substituting 6-((3H-imidazo[4,5-b]pyridin-3-yl)methyl)-7-fluoro-2-(methylthio)benzo[c]thiazole from the previous step for 6-((4-bromo-1H-imidazol-1-yl)methyl)-2-(methylthio)benzo[d]thiazole used in Example 36. LCMS (ESI) m/z 347 (M+H)+.

Step 7:

(1R,2R)-2-((6-((3H-Imidazo[4,5-b]pyridin-3-yl)methyl)-7-fluorobenzo[c]thiazol-2-yl)amino)cyclohexanol was synthesized as a white powder (75 mg, 31%) using a procedure analogous to that described in Step 7 of Example 36, substituting 6-((3H-imidazo[4,5-b]pyridin-3-yl)methyl)-7-fluoro-2-(methylsulfinyl)benzo[c]thiazole from the previous step for 6-((4-bromo-1H-imidazol-1-yl)methyl)-2-(methylsulfinyl)benzo[d]thiazole used in Example 36. $^1$H NMR (500 MHz, DMSO-$d_6$) δ 8.53 (s, 1H), 8.37 (dd, J=1.2, 4.7 Hz, 1H), 8.26 (d, J=7.6 Hz, 1H), 8.09 (dd, J=1.2, 8.1 Hz, 1H), 7.29 (dd, J=4.8, 8.0 Hz, 1H), 7.11-7.23 (m, 2H), 5.56 (s, 2H), 4.77 (d, J=4.9 Hz, 1H), 3.50 (m, 1H), 3.32 (m, 1H), 2.03 (m, 1H), 1.88 (m, 1H), 1.5-1.68 (m, 2H), 1.12-1.32 (m, 4H); LCMS (ESI) m/z 398 (M+H)+.

Example 165

Preparation of (1R,2R)-2-((6-((6-methoxyimidazo[1,2-a]pyridin-3-yl)methyl)benzo[d]thiazol-2-yl)amino)cyclohexanol

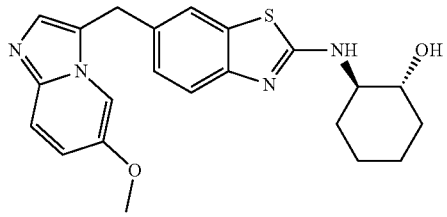 [SMILES: COc1ccc2ncc(Cc3ccc4nc(N[C@@H]5CCCC[C@H]5O)sc4c3)n2c1]

(1R,2R)-2-((6-((6-Methoxyimidazo[1,2-a]pyridin-3-yl)methyl)benzo[d]thiazol-2-yl)amino)cyclohexanol (58 mg, 6%) was obtained as a light tan solid using a procedure analogous to that described in Step 6 of Example 117, substituting 5-methoxypyridin-2-amine and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. $^1$H NMR (500 MHz, DMSO-$d_6$) δ 7.88 (d, J=7.4 Hz, 1H), 7.78 (s, 1H), 7.55 (s, 1H), 7.47 (d, J=9.8 Hz, 1H), 7.30 (s, 1H), 7.28 (d, J=8.4 Hz, 1H), 7.13 (d, J=8.4 Hz, 1H), 7.00 (dd, J=2.0, 9.8 Hz, 1H), 4.76 (br s, 1H), 4.26 (s, 2H), 3.74 (s, 3H), 3.51 (br s, 2H), 2.04 (d, J=12.8 Hz, 1H), 1.87-1.92 (m, 1H), 1.5-1.71 (m, 2H), 1.11-1.35 (m, 4H). LCMS (ESI) m/z 409 (M+H)+.

Example 166

Preparation of (1R,2R)-2-((6-((3H-imidazo[4,5-b]pyridin-3-yl)methyl)-4-bromobenzo[d]thiazol-2-yl)amino)cyclohexanol

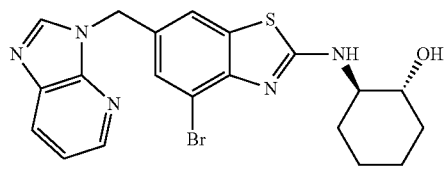 [SMILES: O[C@@H]1CCCC[C@H]1Nc1nc2c(Br)cc(Cn3cnc4cccnc43)cc2s1]

Step 1:

To a stirred mixture of 4-amino-3-fluorobenzonitrile (5 g, 37 mmol) in anhydrous CH$_2$Cl$_2$ (40 mL) under Ar at rt was added dropwise N-bromosuccinimide (6.5 g, 37 mmol). After 15 h, the mixture was concentrated under reduced pressure. The residue was purified by silica gel flash chromatography eluting with a gradient of 100% hexanes to 50% EtOAc in hexanes to afford 4-amino-3-bromo-5-fluorobenzonitrile (6.4 g, 81%) as a tan solid. $^1$H NMR (500 MHz, DMSO-$d_6$) δ 7.76 (s, 1H), 7.62 (dd, J=1.5, 11.1 Hz, 1H), 6.44 (s, 2H); LCMS (ESI) m/z 214, 216 (M+H)+.

Step 2:

4-Bromo-6-cyanobenzo[d]thiazole-2-thiolate potassium salt was synthesized as a brown oil (9.3 g) using a procedure analogous to that described in Step 1 of Example 154, substituting 4-amino-3-bromo-5-fluorobenzonitrile from the previous step for 4-amino-2,5-difluorobenzonitrile used in Example 154 and omitting the chromatography used in Step 1 of Example 154. LCMS (ESI) m/z 269, 271 (M+H)+.

Step 3:

4-Bromo-2-(methylthio)benzo[d]thiazole-6-carbonitrile was synthesized as a yellow solid (1.0 g, 12%) using a procedure analogous to that described in Step 2 of Example 114, substituting 4-bromo-6-cyanobenzo[d]thiazole-2-thiolate potassium salt from the previous step for ethyl 2-mercaptothiazolo[4,5-b]pyridine-6-carboxylate potassium salt used in Example 114. LCMS (ESI) m/z 284, 286 (M+H)+.

Step 4:

(4-Bromo-2-(methylthio)benzo[d]thiazol-6-yl)methanamine was synthesized as a clear oil (794 mg, 79%) using a procedure analogous to that described in Step 3 of Example 154, substituting 4-bromo-2-(methylthio)benzo[d]thiazole-6-carbonitrile from the previous step for 5-fluoro-2-(methylthio)benzo[d]thiazole-6-carbonitrile used in Example 154. LCMS (ESI) m/z 288, 290 (M+H)+.

Step 5:

N-((4-Bromo-2-(methylthio)benzo[d]thiazol-6-yl)methyl)-3-nitropyridin-2-amine was synthesized as a yellow solid (115 mg, 39%) using a procedure analogous to that described in Step 4 of Example 154, substituting (4-bromo-2-(methylthio)benzo[d]thiazol-6-yl)methanamine from the previous step for (5-fluoro-2-(methylthio)benzo[d]thiazol-6-yl)methanamine used in Example 154. LCMS (ESI) m/z 410, 412 (M+H)+.

Step 6:

N$^2$-((4-Bromo-2-(methylthio)benzo[d]thiazol-6-yl)methyl)pyridine-2,3-diamine was synthesized as a red solid (120 mg) using a procedure analogous to that described in Step 2 of Example 41, substituting N-((4-bromo-2-(methylthio)benzo[d]thiazol-6-yl)methyl)-3-nitropyridin-2-amine from the previous step for 4-bromo-5-methoxy-N-((2-

(methylthio)benzo[d]thiazol-6-yl)methyl)-2-nitroaniline used in Example 41. LCMS (ESI) m/z 380, 382 (M+H)+.

Step 7:
6-((3H-Imidazo[4,5-b]pyridin-3-yl)methyl)-4-bromo-2-(methylthio)benzo[d]thiazole was synthesized as an orange solid (180 mg) using a procedure analogous to that described in Step 3 of Example 41, substituting $N^2$-((4-bromo-2-(methylthio)benzo[d]thiazol-6-yl)methyl)pyridine-2,3-diamine from the previous step for 4-bromo-5-methoxy-$N^1$-((2-(methylthio)benzo[d]thiazol-6-yl)methyl)benzene-1,2-diamine used in Example 41. LCMS (ESI) m/z 390, 392 (M+H)+.

Step 8:
6-((3H-Imidazo[4,5-b]pyridin-3-yl)methyl)-4-bromo-2-(methylsulfinyl)benzo[d]thiazole was synthesized as a yellow foam (211 mg) using a procedure analogous to that described in Step 6 of Example 36, substituting 6-((3H-imidazo[4,5-b]pyridin-3-yl)methyl)-4-bromo-2-(methylthio)benzo[d]thiazole from the previous step for 6-((4-bromo-1H-imidazol-1-yl)methyl)-2-(methylthio)benzo[d]thiazole used in Example 36. LCMS (ESI) m/z 406, 408 (M+H)+.

Step 9:
(1R,2R)-2-((6-((3H-imidazo[4,5-b]pyridin-3-yl)methyl)-4-bromobenzo[d]thiazol-2-yl)amino)cyclohexanol was synthesized as a white powder (9 mg, 7%) using a procedure analogous to that described in Step 7 of Example 36, substituting 6-((3H-imidazo[4,5-b]pyridin-3-yl)methyl)-4-bromo-2-(methylsulfinyl)benzo[d]thiazole from the previous step for 6-((4-bromo-1H-imidazol-1-yl)methyl)-2-(methylsulfinyl)benzo[d]thiazole used in Example 36. $^1$H NMR (500 MHz, DMSO-d$_6$) δ 8.61 (s, 1H), 8.29-8.41 (m, 2H), 8.09 (dd, J=1.2, 8.1 Hz, 1H), 7.68 (s, 1H), 7.49 (d, J=1.2 Hz, 1H), 7.30 (m, 1H), 5.47 (s, 2H), 4.85 (m, 1H), 3.35 (m, 1H), 1.99 (m, 1H), 1.88 (m, 1H), 1.60-1.66 (m, 2H), 1.13-1.33 (m, 5H); LCMS (ESI) m/z 457, 459 (M+H)+.

Example 167

Preparation of (1R,2R)-2-((6-((7-(1H-pyrazol-1-yl)imidazo[1,2-a]pyridin-3-yl)methyl)benzo[d]thiazol-2-yl)amino)cyclohexanol

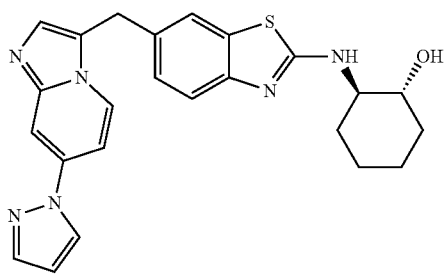 [SMILES: O[C@@H]1CCCC[C@H]1Nc1nc2ccc(Cc3cnc4cc(-n5cccn5)ccn34)cc2s1]

Step 1:
(1R,2R)-2-((6-((7-Iodoimidazo[1,2-a]pyridin-3-yl)methyl)benzo[d]thiazol-2-yl)amino)cyclohexanol (50 mg, 13%) was obtained as a light brown solid using a procedure analogous to that described in Step 6 of Example 117, substituting 4-iodopyridin-2-amine and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. LCMS (ESI) m/z 505 (M+H)+.

Step 2:
(1R,2R)-2-((6-((7-(1H-Pyrazol-1-yl)imidazo[1,2-a]pyridin-3-yl)methyl)benzo[d]thiazol-2-yl)amino)cyclohexanol (7 mg, 16%) was obtained as a light tan solid using a procedure analogous to that described in Example 141, substituting (1R,2R)-2-((6-((7-iodoimidazo[1,2-a]pyridin-3-yl)methyl)benzo[d]thiazol-2-yl)amino)cyclohexanol from Step 1 of this Example for (1R,2R)-2-((6-((6-iodo-3H-imidazo[4,5-b]pyridin-3-yl)methyl)benzo[d]thiazol-2-yl)amino)cyclohexanol used in Example 141. $^1$H NMR (500 MHz, DMSO-d$_6$) δ 8.64 (d, J=2.6 Hz, 1H), 8.32 (d, J=6.7 Hz, 1H), 7.98 (br s, 1H), 7.87 (d, J=7.3 Hz, 1H), 7.79 (s, 1H), 7.54 (s, 2H), 7.44 (br s, 1H), 7.28 (d, J=8.3 Hz, 1H), 7.12 (d, J=7.3 Hz, 1H), 6.59 (s, 1H), 4.74 (br s, 1H), 4.31 (s, 2H), 3.48-3.57 (m, 2H), 2.03 (d, J=10.9 Hz, 1H), 1.87 (d, J=10.4 Hz, 1H), 1.5-1.71 (m, 2H), 1.09-1.38 (m, 4H). LCMS (ESI) m/z 445 (M+H)+.

Example 168

Preparation of (1R,2R)-2-((6-((3H-imidazo[4,5-b]pyridin-3-yl)methyl)-4,7-difluorobenzo[d]thiazol-2-yl)amino)cyclohexanol

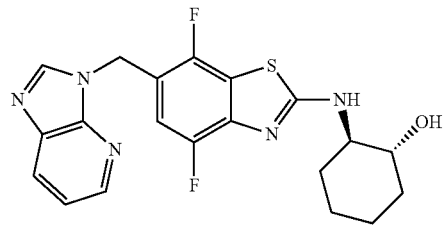 [SMILES: O[C@@H]1CCCC[C@H]1Nc1nc2c(F)cc(Cn3cnc4cccnc43)c(F)c2s1]

Step 1:
4-Amino-3-bromo-2,5-difluorobenzonitrile was synthesized as a yellow solid (2.4 g, 73%) using a procedure analogous to that described in Step 1 of Example 166, substituting 4-amino-2,5-difluorobenzonitrile for 4-amino-3-fluorobenzonitrile used in Example 166. $^1$H NMR (500 MHz, DMSO-d$_6$) δ 7.71 (dd, J=5.9, 11.1 Hz, 1H), 6.89 (br s, 2H); LCMS (ESI) m/z 232, 234 (M+H)+.

Step 2:
6-Cyano-4,7-difluorobenzo[d]thiazole-2-thiolate potassium salt was synthesized as a brown oil (3.93 g) using a procedure analogous to that described in Step 1 of Example 154, substituting 4-amino-3-bromo-2,5-difluorobenzonitrile from the previous step for 4-amino-2,5-difluorobenzonitrile used in Example 154. LCMS (ESI) m/z 228 (M+H)+.

Step 3:
4,7-Difluoro-2-(methylthio)benzo[d]thiazole-6-carbonitrile was synthesized as a yellow solid (1.0 g, 37%) using a procedure analogous to that described in Step 2 of Example 114, substituting 6-cyano-4,7-difluorobenzo[d]thiazole-2-thiolate potassium salt from the previous step for ethyl 2-mercaptothiazolo[4,5-b]pyridine-6-carboxylate potassium salt used in Example 114. $^1$H NMR (500 MHz, DMSO-d$_6$) δ 8.04 (m, 1H), 2.88 (s, 3H); LCMS (ESI) m/z 243 (M+H)+.

Step 4:
(4,7-Difluoro-2-(methylthio)benzo[d]thiazol-6-yl)methanamine was synthesized as a clear oil (646 mg, 64%) using a procedure analogous to that described in Step 3 of Example 154, substituting 4,7-difluoro-2-(methylthio)benzo[d]thiazole-6-carbonitrile from the previous step for 5-fluoro-2-(methylthio)benzo[d]thiazole-6-carbonitrile used in Example 154. LCMS (ESI) m/z 247 (M+H)+.

Step 5:

N-((4,7-Difluoro-2-(methylthio)benzo[d]thiazol-6-yl)methyl)-3-nitropyridin-2-amine was synthesized as a yellow oil (187 mg, 39%) using a procedure analogous to that described in Step 4 of Example 154, substituting (4,7-difluoro-2-(methylthio)benzo[d]thiazol-6-yl)methanamine from the previous step for (5-fluoro-2-(methylthio)benzo[d]thiazol-6-yl)methanamine used in Example 154. $^1$H NMR (500 MHz, CDCl$_3$) δ 8.99 (t, J=6.0 Hz, 1H), 8.40-8.48 (m, 2H), 7.36 (dd, J=5.5, 11.0 Hz, 1H), 6.80 (dd, J=4.4, 8.4 Hz, 1H), 4.91 (d, J=6.2 Hz, 2H), 2.82 (s, 3H); LCMS (ESI) m/z 369 (M+H)+.

Step 6:

N$^2$-((4,7-Difluoro-2-(methylthio)benzo[d]thiazol-6-yl)methyl)pyridine-2,3-diamine was synthesized as a yellow solid (190 mg) using a procedure analogous to that described in Step 2 of Example 41, substituting N-((4,7-difluoro-2-(methylthio)benzo[d]thiazol-6-yl)methyl)-3-nitropyridin-2-amine from the previous step for 4-bromo-5-methoxy-N-((2-(methylthio)benzo[d]thiazol-6-yl)methyl)-2-nitroaniline used in Example 41. LCMS (ESI) m/z 339 (M+H)+.

Step 7:

6-((3H-Imidazo[4,5-b]pyridin-3-yl)methyl)-4,7-difluoro-2-(methylthio)benzo[d]thiazole was synthesized as a orange solid (220 mg) using a procedure analogous to that described in Step 3 of Example 41, substituting N$^2$-((4,7-difluoro-2-(methylthio)benzo[d]thiazol-6-yl)methyl)pyridine-2,3-diamine from the previous step for 4-bromo-5-methoxy-N$^1$-((2-(methylthio)benzo[d]thiazol-6-yl)methyl)benzene-1,2-diamine used in Example 41. LCMS (ESI) m/z 349 (M+H)+.

Step 8:

6-((3H-Imidazo[4,5-b]pyridin-3-yl)methyl)-4,7-difluoro-2-(methylsulfinyl)benzo[d]thiazole was synthesized as a yellow foam (200 mg) using a procedure analogous to that described in Step 6 of Example 36, substituting 6-((3H-imidazo[4,5-b]pyridin-3-yl)methyl)-4,7-difluoro-2-(methylthio)benzo[d]thiazole from the previous step for 6-(4-bromo-1H-imidazol-1-yl)methyl)-2-(methylthio)benzo[d]thiazole used in Example 36. LCMS (ESI) m/z 364 (M+H)+.

Step 9:

(1R,2R)-2-((6-((3H-Imidazo[4,5-b]pyridin-3-yl)methyl)-4,7-difluorobenzo[d]thiazol-2-yl)amino)cyclohexanol was synthesized as a white powder (58 mg, 25%) using a procedure analogous to that described in Step 7 of Example 36, substituting 6-((3H-imidazo[4,5-b]pyridin-3-yl)methyl)-4,7-difluoro-2-(methylsulfinyl)benzo[d]thiazole from the previous step for 6-((4-bromo-1H-imidazol-1-yl)methyl)-2-(methylsulfinyl)benzo[d]thiazole used in Example 36. $^1$H NMR (500 MHz, DMSO-d$_6$) δ 8.45-8.58 (m, 2H), 8.38 (d, J=4.7 Hz, 1H), 8.09 (d, J=8.0 Hz, 1H), 7.29 (dd, J=4.7, 8.0 Hz, 1H), 7.16 (dd, J=5.8, 10.8 Hz, 1H), 5.54 (s, 2H), 4.80 (d, J=5.2 Hz, 1H), 3.51 (m, 1H), 3.35 (m, 1H), 2.02 (m, 1H), 1.88 (m, 1H), 1.5-1.67 (m, 2H), 1.17-1.32 (m, 4H). LCMS (ESI) m/z 416 (M+H)+.

Example 169

Preparation of (1R,2R)-2-((6-((7-(1H-1,2,4-triazol-1-yl)imidazo[1,2-a]pyridin-3-yl)methyl)benzo[d]thiazol-2-yl)amino)cyclohexanol

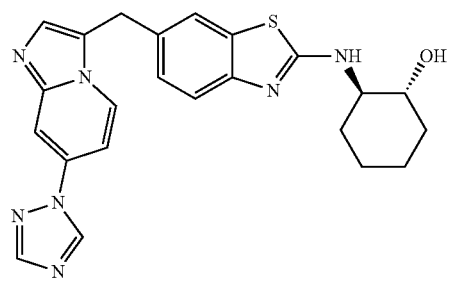 [SMILES: O[C@@H]1CCCC[C@H]1Nc1nc2ccc(Cc3cnc4cc(-n5cncn5)ccn34)cc2s1]

(1R,2R)-2-((6-((7-(1H-1,2,4-triazol-1-yl)imidazo[1,2-a]pyridin-3-yl)methyl)benzo[d]thiazol-2-yl)amino)cyclohexanol (50 mg, 57%) was obtained as a light yellow powder using a procedure analogous to that described in Example 141, substituting (1R,2R)-2-((6-((7-iodoimidazo[1,2-a]pyridin-3-yl)methyl)benzo[d]thiazol-2-yl)amino)cyclohexanol from Step 1 of Example 167 and 1H-1,2,4-triazole, respectively, for (1R,2R)-2-((6-((6-iodo-3H-imidazo[4,5-b]pyridin-3-yl)methyl)benzo[d]thiazol-2-yl)amino)cyclohexanol and pyrazole used in Example 141. $^1$H NMR (500 MHz, DMSO-d$_6$) δ 9.41 (s, 1H), 8.40 (d, J=7.3 Hz, 1H), 8.28 (s, 1H), 8.08 (s, 1H), 7.90 (d, J=7.3 Hz, 1H), 7.54 (s, 1H), 7.50 (s, 1H), 7.48 (d, J=5.7 Hz, 1H), 7.28 (d, J=8.3 Hz, 1H), 7.11 (d, J=8.3 Hz, 1H), 4.76 (br s, 1H), 4.34 (s, 2H), 3.48-3.56 (m, 2H), 2.04 (d, J=11.4 Hz, 1H), 1.88-1.93 (m, 1H), 1.5-1.70 (m, 2H), 1.08-1.36 (m, 4H). LCMS (ESI) m/z 446 (M+H)+.

Example 170

Preparation of 1-((2-(((1R,2R)-2-hydroxycyclohexyl)amino)benzo[d]oxazol-6-yl)methyl)-1H-benzo[d]imidazole-5-carbonitrile

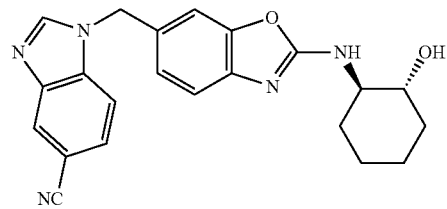

Step 1:

To a solution of 4-bromo-2-nitroaniline (400 mg, 1.84 mmol) and TFA (1.89 mL) in DCM (8 mL) at −5° C. was added NaBH(OAc)$_3$ (1.17 g, 5.52 mmol). Then to the mixture at 0° C. was added a solution of 2-(methylthio)benzo[d]oxazole-6-carbaldehyde (391 mg, 2.03 mmol) in DCM (7 mL), and the mixture was stirred at 0° C. for 2 h. The mixture was diluted with DCM and washed with H$_2$O, aq NaHCO$_3$ and brine. The organic layer was dried over Na$_2$SO$_4$, filtered and concentrated under reduced pressure. The residue was purified by silica gel chromatography eluting with 20:1 to 10:1 petroleum ether/ethyl acetate to give 4-bromo-N-((2-(methylthio)benzo[d]oxazol-6-yl)methyl)-2-nitroaniline as a yellow solid (704 mg, 97.4%). ¹H NMR (300 MHz, DMSO-d₆) δ 8.80 (t, 1H), 8.15 (s, 1H), 7.64 (s, 1H), 7.5-7.60 (m, 2H), 7.35 (d, J=8.4 Hz, 1H), 6.90 (d, J=9.3 Hz, 1H), 4.72 (d, J=6.6 Hz, 1H), 2.73 (s, 3H). LCMS (ESI) m/z 394 (M+H)⁺.

Step 2:
To a stirred solution of 4-bromo-N-((2-(methylthio)benzo[d]oxazol-6-yl)methyl)-2-nitroaniline (704 mg, 1.79 mmol), HOAc (2.1 mL) and methanol (2.1 mL) in DCM (18 mL) at 0° C. was added zinc dust (1.16 g, 17.9 mmol) portionwise. After stirring for 2 h, the mixture was filtered. The filtrate was washed with aq NaHCO₃ and brine. The organic layer was dried over NaSO₄, filtered and concentrated under reduced pressure to give 4-bromo-N¹-((2-(methylthio)benzo[d]oxazol-6-yl)methyl)benzene-1,2-diamine (469 mg, 71.9%) as a yellow solid. ¹H NMR (300 MHz, DMSO-d₆) δ 7.72-7.60 (m, 2H), 7.53 (d, J=5.4 Hz, 1H), 6.68 (s, 1H), 6.49 (d, J=1.8 Hz, 1H), 6.23 (d, J=8.1 Hz, 1H), 5.36 (t, 1H), 4.90 (s, 2H), 4.38 (d, J=6.0 Hz, 2H), 2.74 (s, 3H). LCMS (ESI) m/z 365 (M+H)⁺.

Step 3:
A mixture of 4-bromo-N¹-((2-(methylthio)benzo[d]oxazol-6-yl)methyl) benzene-1,2-diamine (465 mg, 2.40 mmol), triethyl orthoformate (3.8 mL), and HCOOH (0.06 mL) was stirred at 90° C. for 40 min. The reaction mixture was concentrated under reduced pressure. The residue was purified by silica gel chromatography eluting with 1:1 petroleum ether/ethyl acetate to give 6-((5-bromo-1H-benzo[d]imidazol-1-yl)methyl)-2-(methylthio)benzo[d]oxazole as a light brown solid (327 mg, 68.3%). ¹H NMR (300 MHz, DMSO-d₆) δ 8.50 (s, 1H), 7.85 (s, 1H), 7.68 (s, 1H), 7.5-7.60 (m, 2H), 7.30-7.37 (m, 2H), 5.60 (s, 2H), 2.73 (s, 3H). LCMS (ESI) m/z 375 (M+H)⁺.

Step 4:
A solution of 6-((5-bromo-1H-benzo[d]imidazol-1-yl)methyl)-2-(methylthio)benzo[d]oxazole (327 mg, 0.87 mmol) and m-CPBA (226 mg, 1.31 mmol) in DCM (6 mL) was stirred at 0° C. for 3.5 h. The mixture was washed with aq Na₂S₂O₃ and brine. The organic layer was dried over Na₂SO₄, filtered and concentrated under reduced pressure. The residue was purified by silica gel chromatography eluting with 1:5 petroleum ether/ethyl acetate to give 6-((5-bromo-1H-benzo[d]imidazol-1-yl)methyl)-2-(methylsulfinyl)benzo[d]oxazole (256 mg, 75.52%) as a yellow solid. ¹H NMR (300 MHz, DMSO-d₆) δ 8.54 (s, 1H), 7.97 (s, 1H), 7.87-7.89 (m, 2H), 7.57 (d, J=9.0 Hz, 1H), 7.46 (d, J=9.6 Hz, 1H), 7.36 (d, J=6.6 Hz, 1H), 5.68 (s, 2H), 3.18 (s, 3H). LCMS (ESI) m/z 391 (M+H)⁺.

Step 5:
A mixture of 6-((5-bromo-1H-benzo[d]imidazol-1-yl)methyl)-2-(methyl sulfinyl)benzo[d]oxazole (206 mg, 0.53 mmol), (1R,2R)-2-aminocyclohexanol (91 mg, 0.79 mmol) and DIEA (136 mg, 1.06 mmol) in DMA (4 mL) was stirred at 120° C. for 2 h. The reaction mixture was cooled to rt, poured into water (30 mL) and extracted with ethyl acetate (30 mL×3). The combined organic layers were washed with brine, dried over Na₂SO₄, filtered and concentrated under reduced pressure. The residue was purified by preparative HPLC to give (1R,2R)-2-((6-((5-bromo-1H-benzo[d]imidazol-1-yl)methyl)benzo[d]oxazol-2-yl)amino)cyclohexanol as a light yellow solid (175 mg, 74.8%). ¹H NMR (300 MHz, DMSO-d₆) δ 8.46 (s, 1H), 7.81-7.84 (m, 2H), 7.56 (d, J=8.7 Hz, 1H), 7.33-7.36 (m, 1H), 7.12 (s, 2H), 5.48 (s, 1H), 4.68 (d, J=4.2 Hz, 1H), 3.35 (br s, 2H), 1.90 (br s, 2H), 1.62 (br s, 2H), 1.22 (br s, 4H). LCMS (ESI) m/z 442 (M+H)⁺.

Step 6:
A mixture of (1R,2R)-2-((6-((5-bromo-1H-benzo[d]imidazol-1-yl)methyl)benzo[d]oxazol-2-yl)amino)cyclohexanol (126 mg, 0.29 mmol), Zn(CN)₂ (134 mg, 1.14 mmol), Pd₂(dba)₃ (53 mg, 0.06 mmol) and dppf (63 mg, 0.12 mmol) in DMF (4 mL) was stirred at 130° C. for 6 h. The reaction mixture was cooled to rt, poured into water (20 mL) and extracted with ethyl acetate (20 mL×2). The combined organic layers were washed with water and brine, dried over Na₂SO₄, filtered and concentrated under reduced pressure. The residue was purified by preparative HPLC to give 1-((2-(((1R,2R)-2-hydroxycyclohexyl)amino)benzo[d]oxazol-6-yl)methyl)-1H-benzo[d]imidazole-5-carbonitrile as a white solid (40 mg, 35.7%). ¹H NMR (300 MHz, DMSO-d₆) δ 8.67 (s, 1H), 8.20 (s, 1H), 7.83-7.78 (m, 2H), 7.61 (d, J=6.9 Hz, 1H), 7.41 (s, 1H), 7.14 (s, 1H), 5.54 (s, 2H), 4.68 (d, 1H), 3.32 (br s, 2H), 1.91 (br s, 2H), 1.62 (br s, 2H), 1.22 (br s, 4H). LCMS (ESI) m/z 388 (M+H)⁺.

Example 171

Preparation of (1R,2R)-2-((6-((5-(2-morpholinoethoxy)-1H-benzo[d]imidazol-1-yl)methyl)benzo[d]thiazol-2-yl)amino)cyclohexanol

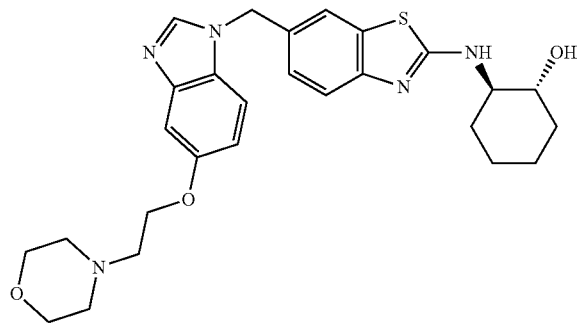 [SMILES: O[C@@H]1CCCC[C@H]1Nc1nc2ccc(Cn3cnc4cc(OCCN5CCOCC5)ccc43)cc2s1]

Step 1:
To a mixture of 1-((2-(((1R,2R)-2-hydroxycyclohexyl)amino)benzo[d]thiazol-6-yl)methyl)-1H-benzo[d]imidazol-5-ol (2.4 g, 6.07 mmol) from Example 147 and 2,2-dimethoxypropane (8 g, 76.81 mmol) in 1,4-dioxane (200 mL) was added para-toluenesulfonic acid (0.15 g, 0.8 mmol). The reaction mixture was heated at 100° C. for 15 h. The mixture was partitioned between saturated aq NaHCO₃ and DCM. The organic layer was separated, dried over Na₂SO₄, filtered, and concentrated under reduced pressure. The residue was purified by silica gel flash chromatography eluting with 2 to 10% MeOH in DCM to afford 1-((2-((3aR,7aR)-2,2-dimethylhexahydrobenzo[d]oxazol-3(2H)-yl)benzo[d]thiazol-6-yl)methyl)-1H-benzo[c]imidazol-5-ol (0.9 g, 34%) as a yellow solid. ¹H NMR (300 MHz, DMSO-d₆) δ 8.99 (s, 1H), 8.24 (s, 1H), 7.79 (s, 1H), 7.50 (d, J=8.4 Hz, 1H), 7.24-7.30 (m, 2H), 6.94 (s, 1H), 6.68 (m, 1H), 5.43 (s, 2H), 3.68 (m, 1H), 3.05 (m, 1H), 2.67 (m, 1H), 2.04 (m, 1H), 1.76-1.78 (m, 2H), 1.70 (s, 3H), 1.53 (s, 3H), 1.26-1.39 (m, 4H); LCMS (ESI) m/z 435 (M+H)⁺.

Step 2:
A stirred mixture of 4-(2-chloroethyl)morpholine (1 g, 5.4 mmol) and KI (4.5 g 26.8 mmol) in acetone (15 mL) was heated at 75° C. for 24 h. The mixture was diluted with saturated aq NaHCO₃ and extracted with DCM. The organic layer was separated, dried over Na₂SO₄, filtered, and concentrated under reduced pressure to afford 4-(2-iodoethyl)

morpholine (0.8 g, 62%) as a pale yellow oil which was not purified further. $^1$H NMR (300 MHz, CDCl$_3$) δ 3.71 (t, J=9.0 Hz, 4H), 3.20 (t, J=7.8 Hz, 2H), 2.72 (t, J=7.8 Hz, 2H), 2.49 (t, J=9.3 Hz, 4H). LCMS (ESI) m/z 242 (M+H)$^+$.

Step 3:

A mixture of 1-((2-((3aR,7aR)-2,2-dimethylhexahydrobenzo[d]oxazol-3(2H)-yl)benzo[d]thiazol-6-yl)methyl)-1H-benzo[d]imidazol-5-ol (100 mg, 0.23 mmol) from Step 1 of this Example, 4-(2-iodoethyl)morpholine (111 mg, 0.46 mmol) from Step 2 of this Example, Cs$_2$CO$_3$ (250 mg, 0.69 mmol), and NMP (2 mL) was stirred at rt for 3 h. The mixture was diluted with EtOAc and washed with brine. The organic layer was separated, dried over Na$_2$SO$_4$, filtered, and concentrated under reduced pressure. The residue was purified by silica gel flash chromatography, eluting with a gradient of 33% DCM in THF to 100% THF, to afford (3aR,7aR)-2,2-dimethyl-3-(6-((5-(2-morpholinoethoxy)-1H-benzo[d]imidazol-1-yl)methyl)benzo[d]thiazol-2-yl)octahydrobenzo[d]oxazole (84 mg, 67%) as a yellow solid. $^1$H NMR (300 MHz, CDCl$_3$) δ 7.90 (s, 1H), 7.58 (d, J=8.1 Hz, 1H), 7.40 (s, 1H), 7.29 (s, 1H), 7.14-7.19 (m, 2H), 6.90 (m, 1H), 5.35 (s, 2H), 4.11-4.17 (m, 2H), 3.70-3.75 (m, 4H), 3.65 (m, 1H), 3.08 (m, 1H), 2.76-2.84 (m, 3H), 2.5-2.60 (m, 4H), 2.17 (m, 1H), 1.82-1.92 (m, 2H), 1.78 (s, 3H), 1.46 (s, 3H), 1.33-1.39 (m, 4H); LCMS (ESI) m/z 548 (M+H)$^+$.

Step 4:

To a stirred mixture of (3aR,7aR)-2,2-dimethyl-3-(6-((5-(2-morpholino ethoxy)-1H-benzo[d]imidazol-1-yl)methyl)benzo[d]thiazol-2-yl)octahydrobenzo[d]oxazole (85 mg, 0.15 mmol) from the previous step in DCM (10 mL) at 0° C. was added methanolic HCl (3 drops). The reaction mixture was stirred at 0° C. for 10 min. The mixture was adjusted to pH ~7 by addition of triethylamine and then concentrated under reduced pressure. The residue was purified directly by reverse-phase preparative HPLC to afford (1R,2R)-2-((6-((5-(2-morpholinoethoxy)-1H-benzo[d]imidazol-1-yl)methyl)benzo[d]thiazol-2-yl)amino)cyclohexanol (20 mg, 25%) as a light yellow solid. $^1$H NMR (300 MHz, DMSO-d$_6$) δ 8.30 (s, 1H), 7.97 (m, 1H), 7.62 (s, 1H), 7.39 (d, J=8.4 Hz, 1H), 7.29 (d, J=8.1 Hz, 1H), 7.17 (d, J=6.9 Hz, 2H), 6.83 (m, 1H), 5.41 (s, 2H), 4.73 (d, J=5.4 Hz, 1H), 4.08 (t, J=11.7 Hz, 2H), 3.57 (t, J=9.1 Hz, 4H), 3.47-3.52 (m, 2H), 2.68 (t, J=11.7 Hz, 2H), 2.46 (t, J=9.3 Hz, 4H), 2.02 (m, 1H), 1.87 (m, 1H), 1.5-1.63 (br s, 2H), 1.16-1.28 (m, 4H). LCMS (ESI) m/z 508 (M+H)$^+$.

Example 172

Preparation of (1R,2R)-2-((6-((5-(2-hydroxyethoxy)-1H-benzo[d]imidazol-1-yl)methyl)benzo[d]thiazol-2-yl)amino)cyclohexanol

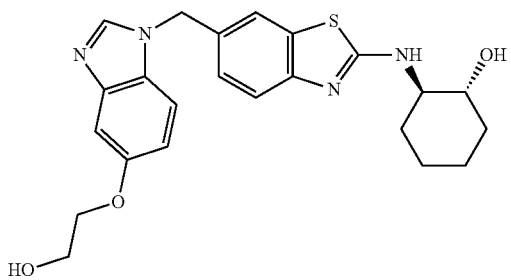 [SMILES: OCCOc1ccc2c(c1)ncn2Cc1ccc2nc(N[C@@H]3CCCC[C@H]3O)sc2c1]

Step 1:

A stirred mixture of 1-((2-((3aR,7aR)-2,2-dimethylhexahydrobenzo[d]oxazol-3(2H)-yl)benzo[d]thiazol-6-yl)methyl)-1H-benzo[d]imidazol-5-ol (60 mg, 0.14 mmol) from Step 1 of Example 171, 2-iodoethanol (60 mg, 0.35 mmol), Cs$_2$CO$_3$ (137 mg, 0.42 mmol), and NMP (2 mL) was heated at 100° C. for 24 h. The mixture was diluted with EtOAc and washed with brine. The organic layer was separated, dried over Na$_2$SO$_4$, filtered, and concentrated under reduced pressure. The residue was purified by preparative TLC to afford 2-((1-((2-((3aR,7aR)-2,2-dimethylhexahydrobenzo[d]oxazol-3(2H)-yl)benzo[d]thiazol-6-yl)methyl)-1H-benzo[d]imidazol-5-yl)oxy)ethanol (26 mg, 39%) as a light yellow solid. $^1$H NMR (300 MHz, CDCl$_3$) δ 7.93 (s, 1H), 7.58 (d, J=8.1 Hz, 1H), 7.40 (s, 1H), 7.32 (s, 1H), 7.16-7.19 (m, 2H), 6.91 (m, 1H), 5.36 (s, 2H), 4.13 (t, J=9.0 Hz, 2H), 3.98 (t, J=9.0 Hz, 2H), 3.65 (m, 1H), 3.08 (m, 1H), 2.80 (m, 1H), 2.14 (m, 1H), 1.84-1.92 (m, 2H), 1.78 (s, 3H), 1.63 (s, 3H), 1.28-1.40 (m, 4H); LCMS (ESI) m/z 479 (M+H)$^+$.

Step 2:

To a stirred mixture of 2-((1-((2-((3aR,7aR)-2,2-dimethylhexahydrobenzo[d]oxazol-3(2H)-yl)benzo[d]thiazol-6-yl)methyl)-1H-benzo[d]imidazol-5-yl)oxy)ethanol (70 mg, 0.15 mmol) from the previous step in DCM (5 mL) at 0° C. was added methanolic HCl (3 drops). The reaction mixture was stirred at 0° C. for 10 min. The mixture was adjusted to pH ~7 by the addition of triethylamine and concentrated under reduced pressure. The residue was purified directly by reverse-phase preparative HPLC to afford ((1R,2R)-2-((6-((5-(2-hydroxyethoxy)-1H-benzo[d]imidazol-1-yl)methyl)benzo[d]thiazol-2-yl)amino)cyclohexanol (30 mg, 47%) as a light yellow solid. $^1$H NMR (300 MHz, DMSO-d$_6$) δ 8.30 (s, 1H), 7.95 (d, J=7.2 Hz, 1H), 7.62 (s, 1H), 7.40 (d, J=9.0 Hz, 1H), 7.29 (d, J=8.1 Hz, 1H), 7.16-7.18 (m, 2H), 6.84 (m, 1H), 5.41 (s, 2H), 4.83 (br s, 1H), 4.72 (d, J=4.5 Hz, 1H), 3.98 (t, J=9.6 Hz, 2H), 3.71 (d, J=4.5 Hz, 2H), 3.52 (m, 1H), 3.33 (br s, 1H), 2.03 (m, 1H), 1.87 (m, 1H), 1.61-1.63 (m, 2H), 1.22-1.28 (m, 4H); LCMS (ESI) m/z 439 (M+H)$^+$.

Example 173

1-((2-(((1R,2R)-2-hydroxycyclohexyl)amino)benzo[d]thiazol-6-yl)methyl)-N-methyl-1H-benzo[d]imidazole-5-carboxamide

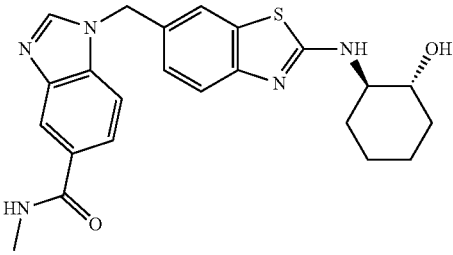 [SMILES: CNC(=O)c1ccc2c(c1)ncn2Cc1ccc2nc(N[C@@H]3CCCC[C@H]3O)sc2c1]

Step 1:

Methyl 4-(((2-(methylthio)benzo[d]thiazol-6-yl)methyl)amino)-3-nitrobenzoate (1.80 g, 91%) was obtained as a yellow solid using a procedure analogous to that described in Step 1 of Example 127, substituting methyl 4-amino-3-nitrobenzoate for 4-methyl-2-nitroaniline used in Example 127. $^1$H NMR (300 MHz, CDCl$_3$) δ 9.15 (br s, 1H), 8.63 (s, 1H), 7.98 (s, 1H), 7.88 (dd, J=9.0, 2.4 Hz, 1H), 7.82 (d, J=8.4 Hz, 1H), 7.47 (dd, J=8.7, 1.8 Hz, 1H), 7.02 (d, J=9.0

Hz, 1H), 4.81 (d, J=5.7 Hz, 2H), 3.80 (s, 3H), 2.77 (s, 3H); LCMS (ESI) m/z 391 (M+H)+.

Step 2:
Methyl 3-amino-4-(((2-(methylthio)benzo[d]thiazol-6-yl)methyl)amino)benzoate (1.01 g, 62%) was obtained as a yellow solid using a procedure analogous to that described in Step 2 of Example 129, substituting 4-(((2-(methylthio)benzo[d]thiazol-6-yl)methyl)amino)-3-nitrobenzoate from Step 1 of this Example for 4-fluoro-N-((2-(methylthio)benzo[d]thiazol-6-yl)methyl)-2-nitroaniline used in Example 129. LCMS (ESI) m/z 360 (M+H)+.

Step 3:
Methyl 1-((2-(methylthio)benzo[d]thiazol-6-yl)methyl)-1H benzo[d]imidazole-5-carboxylate (0.42 g, 42%) was obtained as a yellow solid using a procedure analogous to that described in Step 3 of Example 130, substituting methyl 3-amino-4-(((2-(methylthio)benzo[d]thiazol-6-yl)methyl)amino)benzoate from Step 2 of this Example for $N^1$-((2-(methylthio)benzo[d]thiazol-6-yl)methyl)-4-(trifluoromethyl)benzene-1,2-diamine used in Example 130. $^1$H NMR (300 MHz, CDCl$_3$) δ 8.55 (s, 1H), 8.05 (s, 1H), 7.98 (dd, J=8.7, 1.5 Hz, 1H), 7.83 (d, J=8.4 Hz, 1H), 7.51 (s, 1H), 7.26-7.32 (m, 2H), 5.48 (s, 2H), 3.94 (s, 3H), 2.77 (s, 3H); LCMS (ESI) m/z 370 (M+H)+.

Step 4:
Methyl 1-((2-(methylsulfinyl)benzo[d]thiazol-6-yl)methyl)-1H-benzo[d]imidazole-5-carboxylate (0.40 g, 93%) was obtained as a yellow solid using a procedure analogous to that described in Step 4 of Example 130, substituting methyl 1-((2-(methylthio)benzo[d]thiazol-6-yl)methyl)-1H benzo[d]imidazole-5-carboxylate from Step 3 of this Example for 2-(methylthio)-6-((5-(trifluoromethyl)-1H-benzo[d]imidazol-1-yl)methyl)benzo[d]thiazole used in Example 130. $^1$H NMR (300 MHz, CDCl$_3$) δ 8.56 (s, 1H), 8.09 (s, 1H), 7.91-8.05 (m, 2H), 7.79 (s, 1H), 7.39 (dd, J=8.7, 1.6 Hz, 1H), 7.29 (d, J=8.7 Hz, 1H), 5.56 (s, 2H), 3.94 (s, 3H), 3.06 (s, 3H); LCMS (ESI) m/z 386 (M+H)+.

Step 5:
Methyl 1-((2-(((1R,2R)-2-hydroxycyclohexyl)amino)benzo[d]thiazol-6-yl)ethyl)-1H-benzo[d]imidazole-5-carboxylate (0.27 g, 60%) was obtained as a white solid using a procedure analogous to that described in Step 5 of Example 130, substituting methyl 1-((2-(methylsulfinyl)benzo[d]thiazol-6-yl)methyl)-1H-benzo[d]imidazole-5-carboxylate from Step 4 of this Example for 2-(methylsulfinyl)-6-((5-(trifluoromethyl)-1H-benzo[d]imidazol-1-yl)methyl)benzo[d]thiazole used in Example 130. $^1$H NMR (300 MHz, CDCl$_3$) δ 8.51 (s, 1H), 8.01 (s, 1H), 9.76 (dd, J=8.4, 1.5 Hz, 1H), 7.46 (d, J=8.1 Hz, 1H), 7.30 (d, J=8.4 Hz, 1H), 7.13 (dd, J=8.1, 1.2 Hz, 1H), 7.27 (s, 1H), 5.35 (s, 2H), 3.92 (s, 3H), 3.48-3.51 (m, 2H), 2.01-2.03 (m, 2H), 1.70 (br m, 2H), 1.25-1.32 (m, 4H); LCMS (ESI) m/z 438 (M+H)+.

Step 6:
A mixture of methyl 1-((2-(((1R,2R)-2-hydroxycyclohexyl)amino)benzo[d]thiazol-6-yl)ethyl)-1H-benzo[d]imidazole-5-carboxylate (0.27 g, 0.61 mmol) from the previous step, lithium hydroxide (84 mg, 3.05 mmol), THF (20 mL) and water (4 mL) was stirred at rt for 3 h. The mixture was concentrated under reduced pressure and the pH was adjusted to 4-5. The mixture was extracted with EtOAc (30 mL×3) and the combined organic layers were washed with water (10 mL×2), dried over Na$_2$SO$_4$, filtered, and concentrated under reduced pressure to afford 1-((2-(((1R,2R)-2-hydroxycyclohexyl)amino)benzo[d]thiazol-6-yl)methyl)-1H-benzo[d]imidazole-5-carboxylic acid (0.15 g, 58%) as a white solid which was not purified further. $^1$H NMR (300 MHz, CDCl$_3$) δ 8.25 (s, 1H), 7.94 (s, 1H), 7.81 (d, J=8.4 Hz, 1H), 7.27 (m, 1H), 7.18-7.21 (m, 2H), 7.06 (m, 1H), 5.25 (s, 2H), 3.30-3.39 (m, 2H), 1.98 (m, 1H), 1.86 (m, 1H), 1.5-1.56 (m, 2H), 1.06-1.16 (m, 4H); LCMS (ESI) m/z 424 (M+H)+.

Step 7:
A mixture of 1-((2-(((1R,2R)-2-hydroxycyclohexyl)amino)benzo[d]thiazol-6-yl)methyl)-1H-benzo[d]imidazole-5-carboxylic acid (100 mg, 0.24 mmol) from the previous step, methylamine (1 mL, 22.5 mmol), DIEA (91 mg, 0.35 mmol) and DMF (5 mL) was stirred at rt for 15 min. HATU (180 mg, 0.23 mmol) was added and the mixture was stirred at rt for 15 h. The reaction mixture was diluted with EtOAc (50 mL) and washed sequentially with water (10 mL) and brine (10 mL). The organic layer was separated, dried over Na$_2$SO$_4$, filtered, and concentrated under reduced pressure. The residue was purified directly by reverse-phase preparative HPLC to afford 1-((2-(((1R,2R)-2-hydroxycyclohexyl)amino)benzo[d]thiazol-6-yl)methyl)-N-methyl-1H-benzo[d]imidazole-5-carboxamide (26 mg, 25%) as a white solid. $^1$H NMR (300 MHz, DMSO-d$_6$) δ 8.49 (s, 1H), 8.37 (br s, 1H), 8.16 (s, 1H), 7.95 (d, J=7.5 Hz, 1H), 7.5-7.75 (m, 3H), 7.29 (m, 1H), 7.20 (m, 1H), 5.49 (s, 2H), 4.72 (d, J=5.1 Hz, 1H), 3.50 (m, 1H), 3.35 (m, 1H), 2.50 (s, 3H), 2.04 (m, 1H), 1.88 (m, 1H), 1.60-1.62 (m, 2H), 1.18-1.21 (m, 4H). LCMS (ESI) m/z 436 (M+H)+.

Example 174

Preparation of (1R,2R)-2-((6-((5-(3,6-dihydro-2H-pyran-4-yl)-1H-benzo[d]imidazol-1-yl)methyl)benzo[d]thiazol-2-yl)amino)cyclohexanol

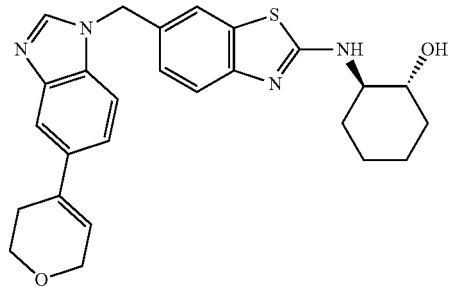 [SMILES: O[C@@H]1CCCC[C@H]1Nc1nc2ccc(Cn3cnc4cc(C5=CCOCC5)ccc43)cc2s1]

A stirred mixture of (1R,2R)-2-((6-((5-iodo-1H-benzo[d]imidazol-1-yl)methyl)benzo[d]thiazol-2-yl)amino)cyclohexanol (300 mg, 0.59 mmol) from Step 5 of Example 183, 2-(3,6-dihydro-2H-pyran-4-yl)-4,4,5,5-tetramethyl-1,3,2-dioxaborolane (188 mg, 0.89 mmol), Na$_2$CO$_3$ (126 mg, 1.19 mmol), 1,4-dioxane (3 mL) and water (0.5 mL) was purged with a stream of nitrogen for 10 min. [1,1'-Bis(diphenylphosphino)ferrocene]dichloropalladium (II) (44 mg, 0.59 mmol) was added and the mixture was heated at 100° C. for 2 h. The reaction mixture was cooled to rt and partitioned between EtOAc and water. The organic layer was separated, dried over Na$_2$SO$_4$, filtered, and concentrated under reduced pressure. The residue was purified by silica gel flash chromatography eluting with 30:1 DCM: MeOH and then by reverse-phase preparative HPLC to afford (1R,2R)-2-((6-((5-(3,6-dihydro-2H-pyran-4-yl)-1H-benzo[d]imidazol-1-yl)methyl)benzo[d]thiazol-2-yl)amino)cyclohexanol (54 mg, 20%) as a white solid. $^1$H NMR (300 MHz, DMSO-d$_6$) δ 8.38 (s, 1H), 7.94 (d, J=7.8 Hz, 1H), 7.67 (d, J=1.5 Hz, 1H), 7.63 (d, J=1.8 Hz, 1H), 7.50 (d, J=8.4 Hz, 1H), 7.35 (m, 1H), 7.29 (d, J=8.1 Hz, 1H), 7.18 (m, 1H), 6.19 (s, 1H), 5.46

(s, 2H), 4.71 (d, J=5.1 Hz, 1H), 4.22 (d, J=2.7 Hz, 2H), 3.81-3.84 (m, 2H), 3.51 (m, 1H), 3.38 (m, 1H), 2.02 (m, 1H), 2.00 (m, 1H), 1.61 (br s, 2H), 1.14-1.29 (m, 4H); LCMS (ESI) m/z 460 (M+H)+.

Example 175

Preparation of (1R,2R)-2-((6-((5-(3,3,3-trifluoroprop-1-en-2-yl)-1H-benzo[d]imidazol-1-yl)methyl) benzo[d]thiazol-2-yl)amino)cyclohexanol

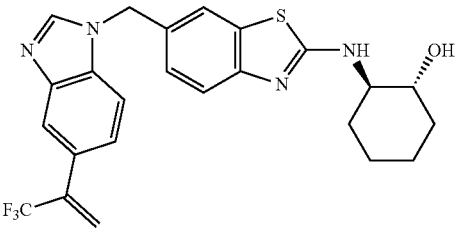 [SMILES: C=C(c1ccc2c(c1)ncn2Cc1ccc2nc(N[C@@H]3CCCC[C@H]3O)sc2c1)C(F)(F)F]

(1R,2R)-2-((6-((5-(3,3,3-Trifluoroprop-1-en-2-yl)-1H-benzo[d]imidazol-1-yl)methyl)benzo[d]thiazol-2-yl)amino) cyclohexanol (71 mg, 25%) was obtained as a white solid using a procedure analogous to that described in Example 174, substituting 4,4,5,5-tetramethyl-2-(3,3,3-trifluoroprop-1-en-2-yl)-1,3,2-dioxaborolane for 2-(3,6-dihydro-2H-pyran-4-yl)-4,4,5,5-tetramethyl-1,3,2-dioxaborolane used in Example 174. $^1$H NMR (300 MHz, DMSO-$d_6$) δ 8.49 (s, 1H), 7.95 (d, J=7.8 Hz, 1H), 7.75 (s, 1H), 7.67 (d, J=1.2 Hz, 1H), 7.63 (d, J=8.4 Hz, 1H), 7.35 (d, J=8.4 Hz, 1H), 7.30 (d, J=8.4 Hz, 1H), 7.20 (m, 1H), 6.04 (t, J=1.8 Hz, 2H), 5.49 (s, 2H), 4.17 (d, J=5.1 Hz, 1H), 3.51 (m, 1H), 3.35 (m, 1H), 2.03 (m, 1H), 1.88 (m, 1H), 1.60-1.64 (m, 2H), 1.18-1.25 (m, 4H); LCMS (ESI) m/z 473 (M+H)+.

Example 176

Preparation of (R)—N-(cyclohex-2-en-1-yl)-6-((6-fluoro-3H-imidazo[4,5-b]pyridin-3-yl)methyl)benzo [d]thiazol-2-amine

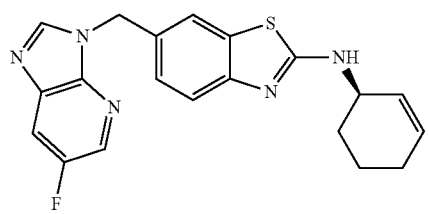 [SMILES: Fc1cnc2c(c1)ncn2Cc1ccc2nc(N[C@H]3C=CCCC3)sc2c1]

To a stirred mixture of (1R,2R)-2-((6-((6-fluoro-3H-imidazo[4,5-b]pyridin-3-yl)methyl)benzo[d]thiazol-2-yl) amino)cyclohexanol (156 mg, 0.4 mmol) from Example 162 in CH$_2$Cl$_2$ (10 mL) at 78° C. under argon was added diethylaminosulfur trifluoride (63 μL, 0.5 mmol). After stirring the mixture for 3 h, additional diethylaminosulfur trifluoride (63 μL, 0.5 mmol) was added. After the mixture was stirred for a further 3 h, it was poured over ice. Additional CH$_2$Cl$_2$ (50 mL) was added and the mixture was stirred until the ice was melted. The layers were separated and the organic layer was washed with brine (50 mL), dried over MgSO$_4$, filtered, and concentrated under reduced pressure. The residue was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford (R)—N-(cyclohex-2-en-1-yl)-6-((6-fluoro-3H-imidazo[4,5-b]pyridin-3-yl)methyl)benzo[d]thiazol-2-amine (5 mg, 3%) as a white powder. $^1$H NMR (500 MHz, DMSO-$d_6$) δ 8.67 (s, 1H), 8.41 (s, 1H), 8.03-8.13 (m, 2H), 7.68 (s, 1H), 7.32 (d, J=8.3 Hz, 1H), 7.24 (dd, J=1.3, 8.3 Hz, 1H), 5.83 (m, 1H), 5.72 (m, 1H), 5.48 (s, 2H), 4.40 (br s, 1H), 1.95-2.03 (m, 2H), 1.90 (m, 1H), 1.70 (m, 1H), 1.5-1.62 (m, 2H); LCMS (ESI) m/z 380 (M+H)+.

Example 177

Preparation of (1R,2R)-2-((6-((6-bromoimidazo[1,2-b]pyridazin-3-yl)methyl)benzo[d]thiazol-2-yl) amino)cyclohexanol

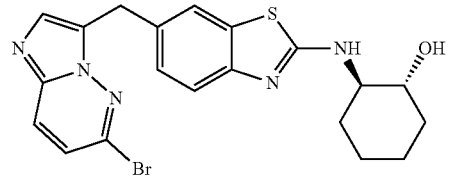

(1R,2R)-2-((6-((6-Bromoimidazo[1,2-b]pyridazin-3-yl)methyl)benzo[d]thiazol-2-yl)amino)cyclohexanol (25 mg, 28%) was obtained as a light tan solid using a procedure analogous to that described in Step 6 of Example 117, substituting 6-bromopyridazin-3-amine and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio) benzo[d]thiazol-6-yl)propanal used in Example 117. $^1$H NMR (500 MHz, DMSO-$d_6$) δ 8.09 (d, J=9.8 Hz, 1H), 7.89 (d, J=7.4 Hz, 1H), 7.59 (s, 1H), 7.54 (s, 1H), 7.39 (d, J=9.4 Hz, 1H), 7.27 (d, J=7.9 Hz, 1H), 7.12 (d, J=8.4 Hz, 1H), 4.76 (br s, 1H), 4.29 (s, 2H), 3.47-3.59 (m, 2H), 2.04 (d, J=11.8 Hz, 1H), 1.86-1.92 (m, 1H), 1.5-1.69 (m, 2H), 1.11-1.34 (m, 4H). LCMS (ESI) m/z 458, 460 (M+H)+.

Example 178

Preparation of (1R,2R)-2-((6-((6-(4-methylpiperazin-1-yl)imidazo[1,2-b]pyridazin-3-yl)methyl) benzo[d]thiazol-2-yl)amino)cyclohexanol

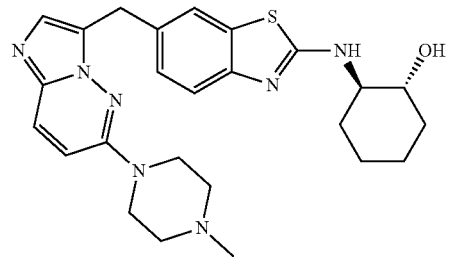 [SMILES: CN1CCN(c2ccc3ncc(Cc4ccc5nc(N[C@@H]6CCCC[C@H]6O)sc5c4)n3n2)CC1]

(1R,2R)-2-((6-((6-(4-Methylpiperazin-1-yl)imidazo[1,2-b]pyridazin-3-yl)methyl)benzo[d]thiazol-2-yl)amino)cyclohexanol (40 mg, 28%) was obtained as a yellow powder using a procedure analogous to that described in Step 6 of Example 117, substituting 6-(1-methylpiperidin-4-yl)pyridazin-3-amine (Ref: U.S. Pat. No. 4,104,385 A1, 1978) and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. $^1$H NMR (500 MHz, DMSO-$d_6$) δ 7.88 (d, J=7.4 Hz, 1H), 7.78 (d, J=9.8 Hz, 1H), 7.58 (s, 1H), 7.33 (br s, 1H), 7.24 (d, J=7.9 Hz, 1H), 7.13 (d, J=8.4 Hz, 1H), 7.10 (d, J=9.8 Hz, 1H), 4.77 (br s, 1H), 4.16 (s, 2H), 3.44-3.51 (m, 4H), 3.34 (td, J=4.6, 9.0 Hz, 2H), 2.37-2.46 (m, 4H), 2.21 (s, 3H), 1.98-2.08 (m, 1H), 1.87-1.94 (m, 1H), 1.5-1.70 (m, 2H), 1.09-1.35 (m, 4H). LCMS (ESI) m/z 478 (M+H)$^+$.

Example 179

Preparation of (trans-4-((6-((6-fluoro-3H-imidazo[4,5-b]pyridin-3-yl)methyl)benzo[d]thiazol-2-yl)amino)cyclohexyl)methanol

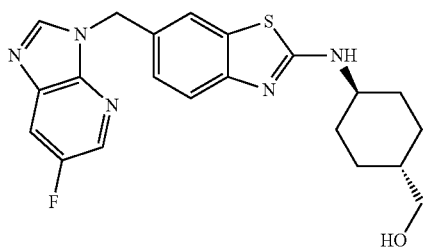 [SMILES: OC[C@H]1CC[C@H](Nc2nc3ccc(Cn4cnc5cc(F)cnc54)cc3s2)CC1]

Step 1:
To a stirred suspension of trans-4-aminocyclohexanecarboxylic acid hydrochloride (0.5 g, 2.8 mmol) in anhydrous THF (10 mL) at 0° C. under argon was added dropwise lithium aluminum hydride (2 M solution in THF, 5.6 mL, 11 mmol). The mixture was stirred for 1 h at 0° C., then allowed to warm to rt and stir for an additional 1 h. The mixture was then heated in a sealed tube at 85° C. for 12 h. The mixture was cooled to 0° C. and H$_2$O (600 μL) was slowly added, followed by a 1 M aq NaOH (1.2 mL) and H$_2$O (1.8 mL). The mixture was diluted with CH$_2$Cl$_2$ (50 mL) and stirred for 30 min at rt. The mixture was filtered, and the filtrate was concentrated under reduced pressure to afford (trans-4-aminocyclohexyl)methanol (323 mg, 90%) as a white solid that did not require further purification.

Step 2:
(trans-4-((6-((6-Fluoro-3H-imidazo[4,5-b]pyridin-3-yl)methyl)benzo[d]thiazol-2-yl)amino)cyclohexyl)methanol was synthesized as a white powder (43 mg, 36%) using a procedure analogous to that described in Step 5 of Example 162, substituting (trans-4-aminocyclohexyl)methanol for (1S,2R)-2-aminocyclohexanol hydrochloride used in Example 162. $^1$H NMR (500 MHz, DMSO-$d_6$) δ 8.68 (s, 1H), 8.41 (t, J=2.0 Hz, 1H), 8.07 (dd, J=2.6, 9.5 Hz, 1H), 7.95 (d, J=7.4 Hz, 1H), 7.66 (d, J=1.2 Hz, 1H), 7.31 (m, 1H), 7.22 (dd, J=1.6, 8.2 Hz, 1H), 5.47 (s, 2H), 4.40 (t, J=5.2 Hz, 1H), 3.58 (m, 1H), 3.22 (m, 2H), 2.00-2.07 (m, 2H), 1.73-1.80 (m, 2H), 1.32 (m, 1H), 1.13-1.25 (m, 2H), 0.92-1.03 (m, 2H); LCMS (ESI) m/z 412 (M+H)$^+$.

Example 180

Preparation of (cis-4-((6-((6-fluoro-3H-imidazo[4,5-b]pyridin-3-yl)methyl)benzo[d]thiazol-2-yl)amino)cyclohexyl)methanol

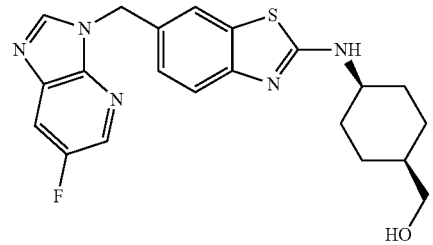 [SMILES: OC[C@H]1CC[C@@H](Nc2nc3ccc(Cn4cnc5cc(F)cnc54)cc3s2)CC1]

Step 1:
(cis-4-Aminocyclohexyl)methanol was synthesized as a white powder (301 mg, 86%) using a procedure analogous to that described in Step 1 of Example 179, substituting cis-4-aminocyclohexanecarboxylic acid for trans-4-aminocyclohexanecarboxylic acid hydrochloride used in Example 179.

Step 2:
(cis-4-((6-((6-Fluoro-3H-imidazo[4,5-b]pyridin-3-yl)methyl)benzo[d]thiazol-2-yl)amino)cyclohexyl)methanol was synthesized as a white powder (26 mg, 21%) using a procedure analogous to that described in Step 5 of Example 162, substituting (cis-4-aminocyclohexyl)methanol from the previous step for (1S,2R)-2-aminocyclohexanol hydrochloride used in Example 162. $^1$H NMR (500 MHz, DMSO-$d_6$) δ 8.67 (s, 1H), 8.41 (t, J=2.0 Hz, 1H), 8.07 (dd, J=2.5, 9.4 Hz, 1H), 7.98 (d, J=7.1 Hz, 1H), 7.66 (d, J=1.0 Hz, 1H), 7.30 (m, 1H), 7.23 (dd, J=1.4, 8.2 Hz, 1H), 5.48 (s, 2H), 4.41 (t, J=4.9 Hz, 1H), 3.96 (m, 1H), 3.26 (t, J=5.4 Hz, 2H), 1.70-1.78 (m, 2H), 1.4-1.60 (m, 5H), 1.28-1.38 (m, 2H); LCMS (ESI) m/z 412 (M+H)$^+$.

Example 181

Preparation of 6-((6-fluoro-3H-imidazo[4,5-b]pyridin-3-yl)methyl)-N-((1R,2R)-2-(methylthio)cyclohexyl)benzo[d]thiazol-2-amine

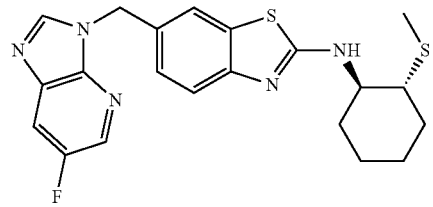 [SMILES: CS[C@@H]1CCCC[C@H]1Nc1nc2ccc(Cn3cnc4cc(F)cnc43)cc2s1]

Step 1:
To a stirred mixture of (1R,2R)-2-((6-((6-fluoro-3H-imidazo[4,5-b]pyridin-3-yl)methyl)benzo[d]thiazol-2-yl)amino)cyclohexanol (517 mg, 1.3 mmol) from Example 162, TEA (194 μL, 1.4 mmol), and CH$_2$Cl$_2$ (15 mL) at rt under argon was added methanesulfonyl chloride (152 μL, 2.0 mmol). After stirring the mixture for 15 h, additional TEA (194 μL, 1.4 mmol) and methanesulfonyl chloride (152 μL, 2.0 mmol) were added. After stirring for an additional 18 h, the mixture was diluted with CH₂Cl₂ and stirred with saturated aq NaHCO₃ (50 mL) for 30 min. The layers were separated and the organic layer was washed with brine (50 mL), dried over MgSO₄, filtered, and concentrated under reduced pressure. The residue was purified by silica gel flash chromatography, eluting with a gradient of 100% hexanes to 100% EtOAc, to afford (1S,2R)-2-((6-((6-fluoro-3H-imidazo[4,5-b]pyridin-3-yl)methyl)benzo[d]thiazol-2-yl)amino)cyclohexyl methanesulfonate (274 mg, 44%) as a clear oil. ¹H NMR (500 MHz, DMSO-d₆) δ 8.66 (s, 1H), 8.39 (t, J=1.8 Hz, 1H), 8.16 (d, J=7.4 Hz, 1H), 8.04 (dd, J=2.6, 9.5 Hz, 1H), 7.66 (d, J=1.0 Hz, 1H), 7.33 (d, J=8.1 Hz, 1H), 7.22 (dd, J=1.4, 8.2 Hz, 1H), 5.46 (s, 2H), 4.98 (m, 1H), 4.06 (m, 1H), 2.99 (s, 3H), 2.01 (m, 1H), 1.5-1.72 (m, 4H), 1.34-1.50 (m, 3H); LCMS (ESI) m/z 476 (M+H)⁺.

Step 2:

A mixture of (1S,2R)-2-((6-((6-fluoro-3H-imidazo[4,5-b]pyridin-3-yl)methyl)benzo[d]thiazol-2-yl)amino)cyclohexyl methanesulfonate (100 mg, 0.2 mmol) and sodium thiomethoxide (74 mg, 1.0 mmol) in DMF (1.0 mL) was stirred at rt for 2 h. The mixture was purified directly by reverse-phase preparative HPLC using a mixture of water (5% CH₃CN, 0.05% HCOOH) and CH₃CN (0.05% HCOOH) as the mobile phase and Varian Pursuit XRs C18 column as the stationary phase to afford 6-((6-fluoro-3H-imidazo[4,5-b]pyridin-3-yl)methyl)-N-((1R,2R)-2-(methylthio)cyclohexyl)benzo[d]thiazol-2-amine (5 mg, 4%) as a white powder. ¹H NMR (500 MHz, DMSO-d₆) δ 8.68 (s, 1H), 8.41 (t, J=1.8 Hz, 1H), 8.04-8.11 (m, 2H), 7.67 (s, 1H), 7.30 (m, 1H), 7.23 (m, 1H), 5.48 (s, 2H), 3.72 (m, 1H), 2.56 (m, 1H), 1.99-2.08 (m, 5H), 1.63-1.71 (m, 2H), 1.41-1.51 (m, 1H), 1.21-1.36 (m, 3H); LCMS (ESI) m/z 428 (M+H)⁺.

Example 182

Preparation of (1R,2R)-2-((6-((5-(oxetan-3-yloxy)-1H-benzo[d]imidazol-1-yl)methyl)benzo[d]thiazol-2-yl)amino)cyclohexanol

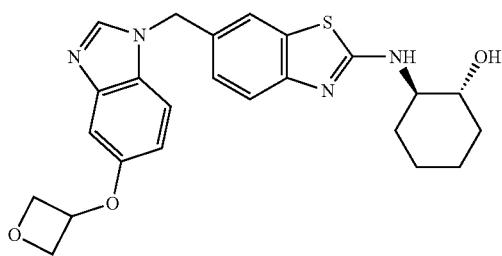 [SMILES: O[C@@H]1CCCC[C@H]1Nc1nc2ccc(Cn3cnc4cc(OC5COC5)ccc43)cc2s1]

Step 1:

To a stirred mixture of oxetan-3-ol (0.85 g, 11.5 mmol) in DCM (38 mL) were added TEA (3.3 mL, 23 mmol) and 4-methylbenzene-1-sulfonyl chloride (2.7 g, 13.8 mmol). The reaction mixture was stirred at rt for 15 h. The mixture was partitioned between water and DCM. The organic layer was separated, dried over Na₂SO₄, filtered, and concentrated under reduced pressure. The residue was purified by silica gel flash chromatography eluting with a gradient of 30% DCM in petroleum ether to 100% DCM to afford oxetan-3-yl 4-methylbenzenesulfonate (1.3 g, 50%) as a white solid. ¹H NMR (300 MHz, CDCl₃) δ 7.77 (d, J=8.4 Hz, 2H), 7.35 (d, J=8.7 Hz, 2H), 5.30 (m, 1H), 4.66-4.74 (m, 4H), 2.46 (s, 3H); LCMS (ESI) m/z 229 (M+H)⁺.

Step 2:

A stirred mixture of 1-((2-((3aR,7aR)-2,2-dimethylhexahydrobenzo[d]oxazol-3(2H)-yl)benzo[d]thiazol-6-yl)methyl)-1H-benzo[d]imidazol-5-ol (100 mg, 0.23 mmol) from Step 1 of Example 171, oxetan-3-yl 4-methylbenzenesulfonate (420 mg, 1.84 mmol) from the previous step, Cs₂CO₃ (225 mg, 0.69 mmol), sodium iodide (276 mg, 0.69 mmol) and NMP (4 mL) was heated at 145° C. for 15 h. The mixture was diluted with EtOAc and washed with brine. The organic layer was dried over Na₂SO₄, filtered, and concentrated under reduced pressure. The residue was purified by silica gel flash chromatography eluting with 40:1 DCM/MeOH to afford (3aR,7aR)-2,2-dimethyl-3-(6-((5-(oxetan-3-yloxy)-1H-benzo[d]imidazol-1-yl)methyl)benzo[d]thiazol-2-yl)octahydrobenzo[d]oxazole (35 mg, 31%) as a yellow solid. ¹H NMR (300 MHz, CDCl₃) δ 7.90 (s, 1H), 7.58 (d, J=8.4 Hz, 1H), 7.40 (s, 1H), 7.17-7.20 (m, 2H), 6.94 (s, 1H), 6.84 (m, 1H), 5.35 (s, 2H), 5.24 (m, 1H), 5.00 (m, 2H), 4.79 (m, 2H), 3.66 (m, 1H), 3.08 (m, 1H), 2.81 (m, 1H), 2.15 (m, 1H), 1.84-1.92 (m, 2H), 1.78 (s, 3H), 1.63 (s, 3H), 1.30-1.45 (m, 4H); LCMS (ESI) m/z 491 (M+H)⁺.

Step 3:

(1R,2R)-2-((6-((5-(Oxetan-3-yloxy)-1H-benzo[d]imidazol-1-yl)methyl)benzo[d]thiazol-2-yl)amino)cyclohexanol (20 mg, 50%) was obtained as a yellow solid using a procedure analogous to that described in Step 2 of Example 172, substituting (3aR,7aR)-2,2-dimethyl-3-(6-((5-(oxetan-3-yloxy)-1H-benzo[d]imidazol-1-yl)methyl)benzo[d]thiazol-2-yl)octahydrobenzo[d]oxazole from Step 2 of this Example for 2-((1-((2-((3aR,7aR)-2,2-dimethylhexahydrobenzo[d]oxazol-3(2H)-yl)benzo[d]thiazol-6-yl)methyl)-1H-benzo[d]imidazol-5-yl)oxy)ethanol used in Example 172. ¹H NMR (300 MHz, DMSO-d₆) δ 8.21 (s, 1H), 7.49 (s, 1H), 7.34-7.37 (m, 2H), 7.19 (m, 1H), 6.82-6.89 (m, 2H), 5.44 (s, 2H), 5.28 (t, J=8.4 Hz, 1H), 5.00-5.04 (m, 2H), 4.67-4.71 (m, 2H), 3.57 (m, 1H), 3.44 (m, 1H), 2.08 (m, 1H), 2.00 (m, 1H), 1.70-1.77 (m, 2H), 1.29-1.41 (m, 4H); LCMS (ESI) m/z 451 (M+H)⁺.

Example 183

Preparation of (1R,2R)-2-((6-((5-vinyl-1H-benzo[d]imidazol-1-yl)methyl)benzo[d]thiazol-2-yl)amino)cyclohexanol

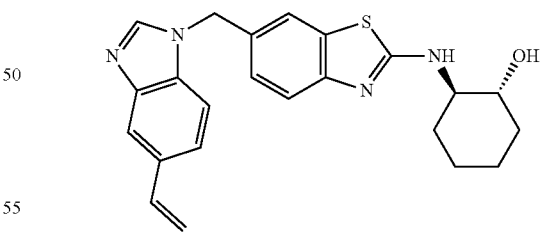

Step 1:

4-Iodo-N-((2-(methylthio)benzo[d]thiazol-6-yl)methyl)-2-nitroaniline (5.7 g, 66%) was obtained as a yellow solid using a procedure analogous to that described in Step 1 of Example 127, substituting 4-iodo-2-nitroaniline for 4-methyl-2-nitroaniline used in Example 127. ¹H NMR (300 MHz, CDCl₃) δ 8.50 (d, J=2.1 Hz, 1H), 8.46 (br s, 1H), 7.85 (d, J=8.7 Hz, 1H), 7.70 (s, 1H), 7.57 (d, J=9.0 Hz, 1H), 7.36 (d, J=8.4 Hz, 1H), 6.58 (d, J=9.0 Hz, 1H), 4.63 (d, J=5.7 Hz, 2H), 2.79 (s, 3H); LCMS (ESI) m/z 458 (M+H)²⁺.

Step 2:

4-Iodo-N¹-((2-(methylthio)benzo[d]thiazol-6-yl)methyl)benzene-1,2-diamine (4.89 g, 92%) was obtained as a yellow solid using a procedure analogous to that described in Step 2 of Example 129, substituting 4-iodo-N-((2-(methylthio)benzo[d]thiazol-6-yl)methyl)-2-nitroaniline from Step 1 of this Example for 4-fluoro-N-((2-(methylthio)benzo[d]thiazol-6-yl)methyl)-2-nitroaniline used in Example 129. LCMS (ESI) m/z 428 (M+H)⁺.

Step 3:

6-((5-Iodo-1H-benzo[d]imidazol-1-yl)methyl)-2-(methylthio)benzo[d]thiazole (3 g, 60%) was obtained as a orange solid using a procedure analogous to that described in Step 3 of Example 130, substituting 4-iodo-N¹-(2-(methylthio)benzo[d]thiazol-6-yl)methyl)benzene-1,2-diamine from Step 2 of this Example for N¹-((2-(methylthio)benzo[d]thiazol-6-yl)methyl)-4-(trifluoromethyl)benzene-1,2-diamine used in Example 130. ¹H NMR (300 MHz, CDCl₃) δ 8.18 (s, 1H), 7.91 (s, 1H), 7.82 (d, J=8.4 Hz, 1H), 7.48-7.53 (m, 2H), 7.24 (d, J=9.0 Hz, 1H), 7.04 (d, J=8.4 Hz, 1H), 5.43 (s, 2H), 2.78 (s, 3H); LCMS (ESI) m/z 438 (M+H)⁺.

Step 4:

6-((5-Iodo-1H-benzo[d]imidazol-1-yl)methyl)-2-(methylsulfinyl)benzo[d]thiazole (2.79 g, 90%) was obtained as a tan solid using a procedure analogous to that described in Step 4 of Example 130, substituting 6-((5-iodo-1H-benzo[d]imidazol-1-yl)methyl)-2-(methylthio)benzo[d]thiazole from Step 3 of this Example for 2-(methylthio)-6-((5-(trifluoromethyl)-1H-benzo[d]imidazol-1-yl)methyl)benzo[d]thiazole used in Example 130. ¹H NMR (300 MHz, CDCl₃) δ 8.20 (s, 1H), 8.03 (d, J=8.4 Hz, 1H), 7.96 (s, 1H), 7.76 (s, 1H), 7.52 (d, J=8.4 Hz, 1H), 7.36 (d, J=8.4 Hz, 1H), 7.03 (d, J=8.4 Hz, 1H), 5.51 (s, 2H), 3.07 (s, 3H); LCMS (ESI) m/z 454 (M+H)⁺.

Step 5:

(1R,2R)-2-((6-((5-Iodo-1H-benzo[d]imidazol-1-yl)methyl)benzo[d]thiazol-2-yl)amino)cyclohexanol (1.78 g, 57%) was obtained as a brown solid using a procedure analogous to that described in Step 5 of Example 130, substituting 6-((5-iodo-1H-benzo[d]imidazol-1-yl)methyl)-2-(methylsulfinyl)benzo[d]thiazole from Step 4 of this Example for 2-(methylsulfinyl)-6-((5-(trifluoromethyl)-1H-benzo[d]imidazol-1-yl)methyl)benzo[d]thiazole used in Example 130. ¹H NMR (300 MHz, CDCl₃) δ 8.13 (s, 1H), 7.87 (s, 1H), 7.46 (d, J=8.45 Hz, 1H), 7.44 (d, J=9.9 Hz, 1H), 7.19 (s, 1H), 7.08 (d, J=8.4 Hz, 1H), 7.03 (d, J=8.4 Hz, 1H), 5.28 (s, 2H), 3.52 (m, 1H), 3.44 (m, 1H), 2.04-2.16 (m, 2H), 1.68-2.73 (m, 2H), 1.18-1.42 (m, 4H); LCMS (ESI) m/z 505 (M+H)⁺.

Step 6:

(1R,2R)-2-((6-((5-Vinyl-1H-benzo[d]imidazol-1-yl)methyl)benzo[d]thiazol-2-yl)amino)cyclohexanol (64 mg, 20%) was obtained as a white solid using a procedure analogous to that described in Example 174, substituting 4,4,5,5-tetramethyl-2-vinyl-1,3,2-dioxaborolane for 2-(3,6-dihydro-2H-pyran-4-yl)-4,4,5,5-tetramethyl-1,3,2-dioxaborolane used in Example 174. ¹H NMR (300 MHz, DMSO-d₆) δ 8.39 (s, 1H), 7.95 (d, J=7.5 Hz, 1H), 7.72 (s, 1H), 7.64 (s, 1H), 7.51 (d, J=8.4 Hz, 1H), 7.38 (d, J=8.4 Hz, 1H), 7.28 (d, J=8.4 Hz, 1H), 7.19 (d, J=8.4 Hz, 1H), 6.81 (m, 1H), 5.77 (d, J=18.0 Hz, 1H), 5.45 (s, 2H), 5.16 (d, J=11.1 Hz, 1H), 4.73 (d, J=8.4 Hz, 1H), 3.53 (m, 1H), 3.27 (m, 1H), 2.02 (m, 1H), 1.87 (m, 1H), 1.60-1.62 (m, 2H), 1.20-1.24 (m, 4H); LCMS (ESI) m/z 405 (M+H)⁺.

Example 184

Preparation of (1R,2R)-2-((6-((5-(cyclohex-1-en-1-yl)-1H-benzo[d]imidazol-1-yl)methyl)benzo[d]thiazol-2-yl)amino)cyclohexanol

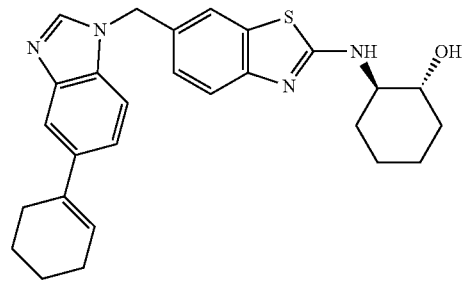 [SMILES: O[C@@H]1CCCC[C@H]1Nc1nc2ccc(Cn3cnc4cc(C5=CCCCC5)ccc43)cc2s1]

(1R,2R)-2-((6-((5-(Cyclohex-1-en-1-yl)-1H-benzo[d]imidazol-1-yl)methyl)benzo[d]thiazol-2-yl)amino)cyclohexanol (80 mg, 30%) was obtained as a white solid using a procedure analogous to that described in Example 174, substituting 2-(cyclohex-1-en-1-yl)-4,4,5,5-tetramethyl-1,3,2-dioxaborolane for 2-(3,6-dihydro-2H-pyran-4-yl)-4,4,5,5-tetramethyl-1,3,2-dioxaborolane used in Example 174. ¹H NMR (300 MHz, DMSO-d₆) δ 8.35 (s, 1H), 7.94 (d, J=8.1 Hz, 1H), 7.60 (d, J=8.7 Hz, 2H), 7.45 (d, J=8.4 Hz, 1H), 7.29 (d, J=8.1 Hz, 2H), 7.18 (m, 1H), 6.08 (d, J=4.5 Hz, 1H), 5.44 (s, 2H), 4.72 (d, J=5.4 Hz, 1H), 3.51 (m, 1H), 3.37 (m, 1H), 2.39-2.45 (m, 2H), 2.13-2.20 (m, 2H), 2.04 (m, 1H), 1.89 (m, 1H), 1.80-1.83 (m, 2H), 1.5-1.66 (m, 4H), 1.11-1.36 (m, 4H); LCMS (ESI) m/z 459 (M+H)⁺.

Example 185

Preparation of (1R,2R)-2-((6-((5-(1-methyl-3-(trifluoromethyl)-1H-pyrazol-4-yl)-1H-benzo[d]imidazol-1-yl)methyl)benzo[d]thiazol-2-yl)amino)cyclohexanol

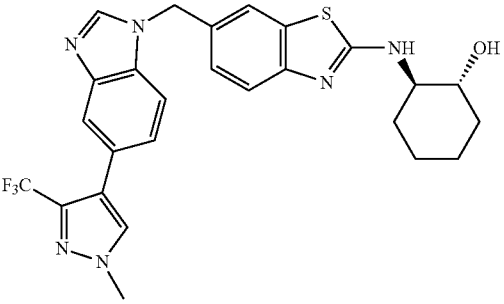 [SMILES: Cn1cc(-c2ccc3c(c2)ncn3Cc2ccc3nc(N[C@@H]4CCCC[C@H]4O)sc3c2)c(C(F)(F)F)n1]

(1R,2R)-2-((6-((5-(1-Methyl-3-(trifluoromethyl)-1H-pyrazol-4-yl)-1H-benzo[d]imidazol-1-yl)methyl)benzo[d]thiazol-2-yl)amino)cyclohexanol (71 mg, 25%) was obtained as a white solid using a procedure analogous to that described in Example 174, substituting (1-methyl-3-(trifluoromethyl)-1H-pyrazol-4-yl)boronic acid for 2-(3,6-dihydro-2H-pyran-4-yl)-4,4,5,5-tetramethyl-1,3,2-dioxaborolane used in Example 174. ¹H NMR (300 MHz, DMSO-d₆) δ 8.44 (s, 1H), 8.10 (s, 1H), 7.95 (m, 1H), 7.69 (s, 1H), 7.63 (s, 1H), 7.60 (d, J=8.7 Hz, 1H), 7.30 (d, J=8.4 Hz, 1H), 7.23-7.75 (m, 2H), 5.48 (s, 2H), 4.70 (m, 1H), 3.96 (s, 3H), 3.51 (m, 1H), 3.32 (m, 1H), 2.03 (m, 1H), 1.84 (m, 1H), 1.5-1.62 (m, 2H), 1.15-1.29 (m, 4H); LCMS (ESI) m/z 527 (M+H)⁺.

Example 186

Preparation of (1R,2R)-2-((6-((5-fluoroimidazo[1,2-a]pyridin-3-yl)methyl)benzo[d]thiazol-2-yl)amino)cyclohexanol

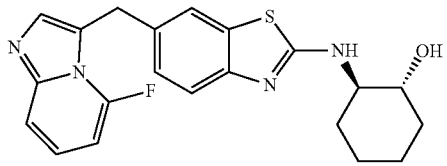 [SMILES: O[C@@H]1CCCC[C@H]1Nc1nc2ccc(Cc3cnc4cccc(F)n34)cc2s1]

(1R,2R)-2-((6-((5-Fluoroimidazo[1,2-a]pyridin-3-yl)methyl)benzo[d]thiazol-2-yl)amino)cyclohexanol (5 mg, 10%) was obtained as a yellow powder using a procedure analogous to that described in Step 6 of Example 117, substituting 6-fluoropyridin-2-amine and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. ¹H NMR (500 MHz, DMSO-d₆) δ 7.92 (d, J=7.4 Hz, 1H), 7.42 (d, J=3.9 Hz, 1H), 7.35-7.40 (m, 1H), 7.26 (d, J=8.4 Hz, 1H), 7.22 (dd, J=7.1, 15.5 Hz, 1H), 6.99 (d, J=7.9 Hz, 1H), 6.66 (t, J=7.1 Hz, 1H), 4.80 (br s, 1H), 4.39 (br s, 2H), 3.50 (br s, 2H), 2.04 (d, J=11.8 Hz, 1H), 1.87 (d, J=10.8 Hz, 1H), 1.5-1.70 (m, 2H), 1.10-1.37 (m, 4H). LCMS (ESI) m/z 397 (M+H)⁺.

Example 187

Preparation of (1R,2R)-2-((6-((7-morpholinoimidazo[1,2-a]pyridin-3-yl)methyl)benzo[d]thiazol-2-yl)amino)cyclohexanol

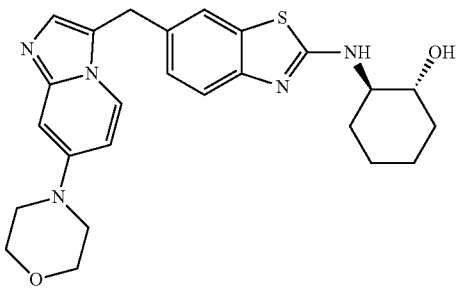 [SMILES: O[C@@H]1CCCC[C@H]1Nc1nc2ccc(Cc3cnc4cc(N5CCOCC5)ccn34)cc2s1]

Step 1:
A mixture of 4-chloropyridin-2-amine (400 mg, 3.1 mmol) and morpholine (2 mL) in 2 mL of DMA was heated at 200° C. for 5 min in a microwave reactor. LCMS analysis indicated completion of the reaction. The mixture was partitioned between EtOAc and brine, and the organic layer was dried over Na₂SO₄ and concentrated under reduced pressure to give crude 4-morpholinopyridin-2-amine as a yellow solid (350 mg). LCMS (ESI) m/z 180 (M+H)⁺.

Step 2:
(1R,2R)-2-((6-((7-Morpholinoimidazo[1,2-a]pyridin-3-yl)methyl)benzo[d]thiazol-2-yl)amino)cyclohexanol (50 mg, 31%) was obtained as a yellow powder using a procedure analogous to that described in Step 6 of Example 117, substituting 4-morpholinopyridin-2-amine from Step 1 of this Example and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. ¹H NMR (500 MHz, DMSO-d₆) δ 7.94 (d, J=7.9 Hz, 1H), 7.88 (d, J=7.4 Hz, 1H), 7.48 (s, 1H), 7.25 (d, J=7.9 Hz, 1H), 7.18 (s, 1H), 7.06 (d, J=8.4 Hz, 1H), 6.79 (dd, J=2.2, 7.6 Hz, 1H), 6.67 (d, J=2.0 Hz, 1H), 4.75 (br s, 1H), 4.20 (s, 2H), 3.67-3.79 (m, 4H), 3.50 (br s, 2H), 3.09-3.16 (m, 4H), 2.03 (d, J=11.8 Hz, 1H), 1.86 (br s, 1H), 1.5-1.71 (m, 2H), 1.12-1.38 (m, 4H). LCMS (ESI) m/z 464 (M+H)⁺.

Example 188

Preparation of (1R,2R)-2-((6-((7-(4-methylpiperazin-1-yl)imidazo[1,2-a]pyridin-3-yl)methyl)benzo[d]thiazol-2-yl)amino)cyclohexanol

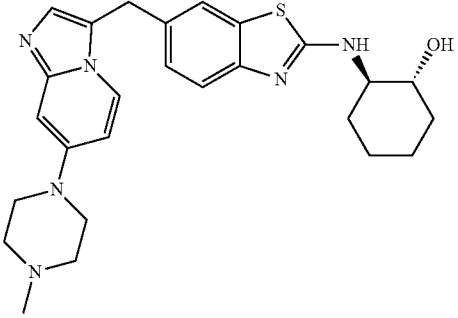 [SMILES: CN1CCN(c2ccn3c(Cc4ccc5nc(N[C@@H]6CCCC[C@H]6O)sc5c4)cnc3c2)CC1]

Step 1:
A mixture of 4-chloropyridin-2-amine (400 mg, 3.1 mmol) and N-methylpiperizine (2 mL) in DMA (2 mL) was heated at 200° C. for 5 min in a microwave reactor. LCMS analysis indicated completion of the reaction. The reaction mixture was partitioned between EtOAc and brine, and the organic layer was dried over Na₂SO₄ and concentrated under reduced pressure to give crude 4-(4-methylpiperazin-1-yl)pyridin-2-amine as a brown solid (350 mg). LCMS (ESI) m/z 193 (M+H)⁺.

Step 2:
(1R,2R)-2-((6-((7-(4-Methylpiperazin-1-yl)imidazo[1,2-a]pyridin-3-yl)methyl)benzo[d]thiazol-2-yl)amino)cyclohexanol (17 mg, 9%) was obtained as a yellow solid using a procedure analogous to that described in Step 6 of Example 117, substituting 4-(4-methylpiperazin-1-yl)pyridin-2-amine from Step 1 of this Example, and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. ¹H NMR (500 MHz, DMSO-d₆) δ 7.90 (d, J=7.4 Hz, 1H), 7.87 (d, J=7.4 Hz, 1H), 7.47 (s, 1H), 7.25 (d, J=8.4 Hz, 1H), 7.17 (s, 1H), 7.06 (d, J=6.9 Hz, 1H), 6.72-6.81 (m, 2H), 6.64 (s, 1H), 4.19 (s, 2H), 3.51 (br s, 1H), 3.31-3.37 (m, 2H), 3.16 (d, J=4.4 Hz, 4H), 2.42 (d, J=4.4 Hz, 4H), 2.21 (s, 3H), 2.03

(d, J=11.8 Hz, 1H), 1.83-1.87 (m, 1H), 1.5-1.70 (m, 2H), 1.10-1.35 (m, 4H). LCMS (ESI) m/z 477 (M+H)+.

Example 189

Preparation of ((1R,2R)-2-((6-((5,7-dimethyl-1H-benzo[d]imidazol-1-yl)methyl)benzo[d]thiazol-2-yl)amino)cyclohexanol

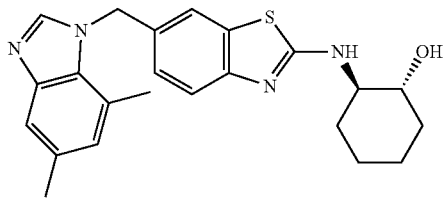 [SMILES: Cc1cc(C)c2c(c1)ncn2Cc1ccc2nc(N[C@@H]3CCCC[C@H]3O)sc2c1]

Step 1:
N-(2,4-Dimethyl-6-nitrophenyl)formamide (746 mg, 64%) was obtained as a solid using a procedure analogous to that described in Step 1 of Example 203, substituting 4,6-dimethyl-2-nitroaniline for 4-bromo-2-fluoro-6-nitroaniline used in Example 203. LCMS (ESI) m/z 195 (M+H)+.

Step 2:
N-(2,4-Dimethyl-6-nitrophenyl)-N-((2-(methylthio)benzo[d]thiazol-6-yl)methyl)formamide (1.29 g, 87%) was obtained as a yellow solid using a procedure analogous to that described in Step 2 of Example 203, substituting N-(2,4-dimethyl-6-nitrophenyl)formamide from the previous step for N-(4-bromo-2-fluoro-6-nitrophenyl)formamide used in Example 203. LCMS (ESI) m/z 388 (M+H)+.

Step 3:
6-((5,7-Dimethyl-1H-benzo[d]imidazol-1-yl)methyl)-2-(methylthio)benzo[d]thiazole (696 mg, 62%) was obtained as a solid using a procedure analogous to that described in Step 3 of Example 203, substituting N-(2,4-dimethyl-6-nitrophenyl)-N-((2-(methylthio)benzo[d]thiazol-6-yl)methyl)formamide from the previous step for N-(4-bromo-2-fluoro-6-nitrophenyl)-N-((2-(methylthio)benzo[d]thiazol-6-yl)methyl)formamide used in Example 203. 1H NMR (500 MHz, DMSO-d6) δ 8.25 (s, 1H), 7.80 (d, J=8.4 Hz, 1H), 7.60 (d, J=0.8 Hz, 1H), 7.29 (s, 1H), 7.08 (dd, J=8.4, 1.6 Hz, 1H), 6.74 (s, 1H), 5.75 (s, 2H), 2.75 (s, 3H), 2.33 (s, 3H), 2.33 (s, 3H); LCMS (ESI) m/z 340 (M+H)+.

Step 4:
6-((5,7-Dimethyl-1H-benzo[d]imidazol-1-yl)methyl)-2-(methylsulfinyl)benzo[d]thiazole (600 mg, 83%) was obtained as a solid using a procedure analogous to that described in Step 4 of Example 203, substituting 6-((5,7-dimethyl-1H-benzo[d]imidazol-1-yl)methyl)-2-(methylthio)benzo[d]thiazole from the previous step for 6-((5-bromo-7-fluoro-1H-benzo[d]imidazol-1-yl)methyl)-2-(methylsulfinyl)benzo[d]thiazole used in Example 203. 1H NMR (500 MHz, DMSO-d6) δ 8.28 (s, 1H), 8.07 (d, J=8.5 Hz, 1H), 7.83 (m, 1H), 7.31 (m, 1H), 7.28 (dd, J=8.6, 1.6 Hz, 1H), 6.74 (m, 1H), 5.83 (s, 2H), 3.05 (s, 3H), 2.33 (s, 3H), 2.33 (s, 3H); LCMS (ESI) m/z 356 (M+H)+.

Step 5:
((1R,2R)-2-((6-((5,7-Dimethyl-1H-benzo[d]imidazol-1-yl)methyl)benzo[d]thiazol-2-yl)amino)cyclohexanol (50 mg, 29%) was obtained as a solid using a procedure analogous to that described in Step 5 of Example 203, substituting 6-((5,7-dimethyl-1H-benzo[d]imidazol-1-yl)methyl)-2-(methylsulfinyl)benzo[d]thiazole from the previous step for 6-((5-bromo-7-fluoro-1H-benzo[d]imidazol-1-yl)methyl)-2-(methylsulfinyl)benzo[d]thiazole used in Example 203. 1H NMR (500 MHz, DMSO-d6) δ 8.21 (s, 1H), 7.96 (d, J=7.6 Hz, 1H), 7.22-7.30 (m, 3H), 6.81 (dd, J=1.2, 8.4 Hz, 1H), 6.73 (s, 1H), 5.62 (s, 2H), 4.75 (br m, 1H), 3.51 (br m, 1H), 3.30 (br m, 1H), 2.38 (s, 3H), 2.33 (s, 3H), 2.02 (m, 1H), 1.85 (m, 1H), 1.5-1.66 (m, 2H), 1.13-1.30 (m, 4H); LCMS (ESI) m/z 407 (M+H)+.

Example 190

Preparation of (1R,2R)-2-((6-((5-bromo-7-methyl-1H-benzo[d]imidazol-1-yl)methyl)benzo[d]thiazol-2-yl)amino)cyclohexanol

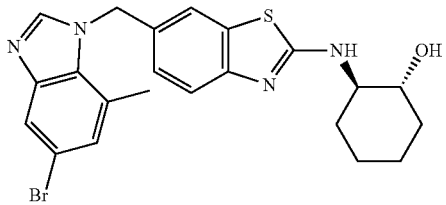 [SMILES: Cc1cc(Br)cc2ncn(Cc3ccc4nc(N[C@@H]5CCCC[C@H]5O)sc4c3)c12]

Step 1:
N-(4-bromo-2-methyl-6-nitrophenyl)formamide (227 mg, 33%) was obtained as a solid using a procedure analogous to that described in Step 1 of Example 203, substituting 4-bromo-2-methyl-6-nitroaniline for 4-bromo-2-fluoro-6-nitroaniline used in Example 203. LCMS (ESI) m/z 259 and 260 (M+H)+.

Step 2:
N-(4-Bromo-2-methyl-6-nitrophenyl)-N-((2-(methylthio)benzo[d]thiazol-6-yl)methyl)formamide (377 mg, 95%) was obtained as an oil using a procedure analogous to that described in Step 2 of Example 203, substituting N-(4-bromo-2-methyl-6-nitrophenyl)formamide from the previous step for N-(4-bromo-2-fluoro-6-nitrophenyl)formamide used in Example 203. LCMS (ESI) m/z 452 and 454 (M+H)+.

Step 3:
6-((5-Bromo-7-methyl-1H-benzo[d]imidazol-1-yl)methyl)-2-(methylthio)benzo[d]thiazole (100 mg, 30%) was obtained as a solid using a procedure analogous to that described in Step 3 of Example 203, substituting N-(4-bromo-2-methyl-6-nitrophenyl)-N-((2-(methylthio)benzo[d]thiazol-6-yl)methyl)formamide from the previous step for N-(4-bromo-2-fluoro-6-nitrophenyl)-N-((2-(methylthio)benzo[d]thiazol-6-yl)methyl)formamide used in Example 203. 1H NMR (500 MHz, DMSO-d6) δ 8.38 (s, 1H), 7.81 (d, J=8.4 Hz, 1H), 7.72 (m, 1H), 7.62 (m, 1H), 7.10-7.11 (m, 2H), 5.79 (s, 2H), 2.76 (s, 3H), 2.37 (s, 3H); LCMS (ESI) m/z 404 and 406 (M+H)+.

Step 4:
6-((5-Bromo-7-methyl-1H-benzo[d]imidazol-1-yl)methyl)-2-(methylsulfinyl)benzo[d]thiazole (60 mg, 58%) was obtained as a solid using a procedure analogous to that described in Step 4 of Example 203, substituting 6-((5-bromo-7-methyl-1H-benzo[d]imidazol-1-yl)methyl)-2-(methylthio)benzo[d]thiazole from the previous step for 6-((5-bromo-7-fluoro-1H-benzo[d]imidazol-1-yl)methyl)-2-(methylsulfinyl)benzo[d]thiazole used in Example 203. 1H NMR (500 MHz, DMSO-d6) δ 8.42 (s, 1H), 8.09 (d, J=8.5 Hz, 1H), 7.85 (m, 1H), 7.73 (m, 1H), 7.31 (dd, J=8.6, 1.6 Hz, 1H), 7.12 (m, 1H), 5.87 (s, 2H), 3.05 (s, 3H), 2.37 (s, 3H); LCMS (ESI) m/z 420 and 422 (M+H)⁺.

Step 5:

(1R,2R)-2-((6-((5-Bromo-7-methyl-1H-benzo[d]imidazol-1-yl)methyl)benzo[d]thiazol-2-yl)amino)cyclohexanol (9 mg, 13%) was obtained as a solid using a procedure analogous to that described in Step 5 of Example 203, substituting 6-((5-bromo-7-methyl-1H-benzo[d]imidazol-1-yl)methyl)-2-(methylsulfinyl)benzo[d]thiazole from the previous step for 6-((5-bromo-7-fluoro-1H-benzo[d]imidazol-1-yl)methyl)-2-(methylsulfinyl)benzo[d]thiazole used in Example 203. ¹H NMR (500 MHz, DMSO-d₆) δ 8.34 (s, 1H), 7.98 (d, J=7.6 Hz, 1H), 7.70 (d, J=1.0 Hz, 1H), 7.25-7.31 (m, 2H), 7.10 (s, 1H), 6.83 (dd, J=1.2, 8.1 Hz, 1H), 5.66 (s, 2H), 4.76 (br m, 1H), 3.51 (br m, 1H), 3.30 (br m, 1H), 2.42 (s, 3H), 2.03 (m, 1H), 1.87 (m, 1H), 1.5-1.66 (m, 2H), 1.13-1.32 (m, 4H); LCMS (ESI) m/z 471 and 473 (M+H)⁺.

Example 191

Preparation of 6-((6-fluoro-3H-imidazo[4,5-b]pyridin-3-yl)methyl)-N-phenylbenzo[d]thiazol-2-amine

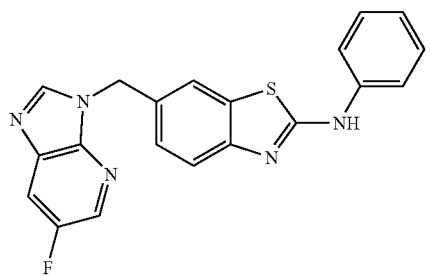 [SMILES: Fc1cnc2c(c1)ncn2Cc1ccc2nc(Nc3ccccc3)sc2c1]

6-((6-Fluoro-3H-imidazo[4,5-b]pyridin-3-yl)methyl)-N-phenylbenzo[d]thiazol-2-amine was synthesized as a white powder (38 mg, 23%) using a procedure analogous to that described in Step 5 of Example 162, substituting aniline for (1S,2R)-2-aminocyclohexanol hydrochloride used in Example 162 and increasing the reaction temperature to 130° C. ¹H NMR (500 MHz, DMSO-d₆) δ 10.50 (br s, 1H), 8.71 (s, 1H), 8.42 (m, 1H), 8.09 (dd, J=2.5, 9.4 Hz, 1H), 7.80 (s, 1H), 7.73-7.77 (m, 2H), 7.55 (d, J=8.4 Hz, 1H), 7.32-7.37 (m, 3H), 7.01 (t, J=7.4 Hz, 1H), 5.55 (s, 2H); LCMS (ESI) m/z 376 (M+H)⁺.

Example 192

Preparation of ((1R,3R)-3-((6-((6-fluoro-3H-imidazo[4,5-b]pyridin-3-yl)methyl)benzo[d]thiazol-2-yl)amino)cyclohexyl)methanol

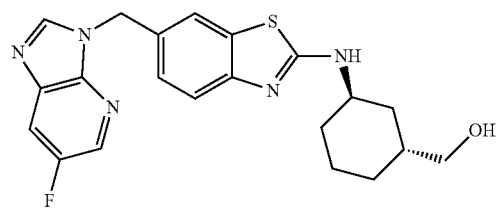 [SMILES: OC[C@@H]1CCC[C@@H](Nc2nc3ccc(Cn4cnc5cc(F)cnc54)cc3s2)C1]

Step 1:

A mixture of (1R,3R)-3-((tert-butoxycarbonyl)amino)cyclohexanecarboxylic acid in a 1:1 solution of TFA:CH₂Cl₂ (6 mL) was stirred at rt for 3 h. The mixture was concentrated under reduced pressure. The residue was triturated in ethyl ether (50 mL) and the resulting solid was collected by filtration to afford (1R,3R)-3-aminocyclohexanecarboxylic acid trifluoroacetate (253 mg, 86%) as a white solid that did not require further purification.

Step 2:

((1R,3R)-3-Aminocyclohexyl)methanol was synthesized as a white powder (213 mg, 75%) using a procedure analogous to that described in Step 1 of Example 179, substituting (1R,3R)-3-aminocyclohexanecarboxylic acid trifluoroacetate from the previous step for trans-4-aminocyclohexanecarboxylic acid hydrochloride used in Example 179.

Step 3:

((1R,3R)-3-((6-((6-Fluoro-3H-imidazo[4,5-b]pyridin-3-yl)methyl)benzo[d]thiazol-2-yl)amino)cyclohexyl)methanol was synthesized as a white powder (17 mg, 10%) using a procedure analogous to that described in Step 5 of Example 162, substituting ((1R,3R)-3-aminocyclohexyl)methanol from the previous step for (1S,2R)-2-aminocyclohexanol hydrochloride used in Example 162. ¹H NMR (500 MHz, DMSO-d₆) δ 8.68 (s, 1H), 8.41 (t, J=1.8 Hz, 1H), 8.07 (dd, J=2.5, 9.4 Hz, 1H), 7.96 (d, J=7.6 Hz, 1H), 7.66 (s, 1H), 7.31 (m, 1H), 7.23 (dd, J=1.5, 8.4 Hz, 1H), 5.48 (s, 2H), 4.43 (m 1H), 3.65 (m, 1H), 3.17-3.28 (m, 2H), 1.95-2.10 (m, 2H), 1.61-1.79 (m, 2H), 1.49 (m, 1H), 1.31 (m, 1H), 1.08 (m, 1H), 0.75-0.90 (m, 2H); LCMS (ESI) m/z 412 (M+H)⁺.

Example 193

Preparation of (1R,2S,3R)-3-((6-((6-fluoro-3H-imidazo[4,5-b]pyridin-3-yl)methyl)benzo[d]thiazol-2-yl)amino)cyclohexane-1,2-diol

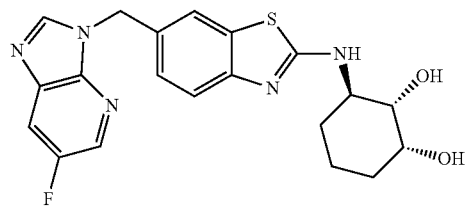 [SMILES: O[C@@H]1[C@H](O)CCC[C@H]1Nc1nc2ccc(Cn3cnc4cc(F)cnc43)cc2s1]

(1R,2S,3R)-3-((6-((6-Fluoro-3H-imidazo[4,5-b]pyridin-3-yl)methyl)benzo[d]thiazol-2-yl)amino)cyclohexane-1,2-diol was synthesized as a white powder (15 mg, 14%) using a procedure analogous to that described in Step 5 of Example 232, substituting 6-((6-fluoro-3H-imidazo[4,5-b]pyridin-3-yl)methyl)-2-(methylsulfinyl)benzo[d]thiazole from Step 4 of Example 70 for 6-((5-iodo-1H-benzo[d]imidazol-1-yl)methyl)-2-(methylsulfinyl)benzo[d]thiazole used in Example 232. ¹H NMR (500 MHz, DMSO-d₆) δ 8.68 (s, 1H), 8.41 (t, J=2.0 Hz, 1H), 8.07 (dd, J=2.5, 9.4 Hz, 1H), 7.94 (d, J=7.9 Hz, 1H), 7.66 (d, J=1.0 Hz, 1H), 7.29 (m, 1H), 7.22 (dd, J=1.4, 8.2 Hz, 1H), 5.48 (s, 2H), 4.54 (br s, 1H), 4.44 (br s, 1H), 3.93 (m, 1H), 3.79 (m, 1H), 3.39 (m, 1H), 1.91 (m, 1H), 1.5-1.69 (m, 2H), 1.33-1.43 (m, 2H), 1.19 (m, 1H); LCMS (ESI) m/z 414 (M+H)+.

Example 194

Preparation of ((1S,3R)-3-((6-((6-fluoro-3H-imidazo[4,5-b]pyridin-3-yl)methyl)benzo[d]thiazol-2-yl)amino)cyclohexyl)methanol

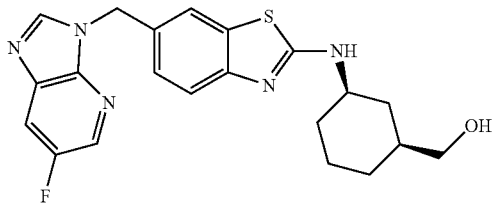 [SMILES: OC[C@H]1CCC[C@@H](Nc2nc3ccc(Cn4cnc5cc(F)cnc54)cc3s2)C1]

Step 1:
(1S,3R)-3-Aminocyclohexanecarboxylic acid trifluoroacetate was synthesized as a white powder (275 mg, 94%) using a procedure analogous to that described in Step 1 of Example 192, substituting (1S,3R)-3-((tert-butoxycarbonyl)amino)cyclohexanecarboxylic acid for (1R,3R)-3-((tert-butoxycarbonyl)amino)cyclohexanecarboxylic acid used in Example 192.

Step 2:
((1S,3R)-3-Aminocyclohexyl)methanol was synthesized as a white powder (157 mg, 59%) using a procedure analogous to that described in Step 1 of Example 179, substituting (1S,3R)-3-aminocyclohexanecarboxylic acid trifluoroacetate from the previous step for trans-4-aminocyclohexanecarboxylic acid hydrochloride used in Example 179.

Step 3:
((1S,3R)-3-((6-((6-Fluoro-3H-imidazo[4,5-b]pyridin-3-yl)methyl)benzo[d]thiazol-2-yl)amino)cyclohexyl)methanol was synthesized as a white powder (15 mg, 8%) using a procedure analogous to that described in Step 5 of Example 162, substituting ((1S,3R)-3-aminocyclohexyl)methanol from the previous step for (1S,2R)-2-aminocyclohexanol hydrochloride used in Example 162. 1H NMR (500 MHz, DMSO-d6) δ 8.68 (s, 1H), 8.41 (t, J=1.8 Hz, 1H), 8.07 (dd, J=2.5, 9.4 Hz, 1H), 7.96 (d, J=7.6 Hz, 1H), 7.66 (s, 1H), 7.31 (m, 1H), 7.23 (dd, J=1.5, 8.4 Hz, 1H), 5.48 (s, 2H), 4.43 (m 1H), 3.65 (m, 1H), 3.17-3.28 (m, 2H), 1.95-2.10 (m, 2H), 1.61-1.79 (m, 2H), 1.49 (m, 1H), 1.31 (m, 1H), 1.08 (m, 1H), 0.75-0.90 (m, 2H); LCMS (ESI) m/z 412 (M+H)+.

Example 195

Preparation of 6-chloro-1-((2-(((1R,2R)-2-hydroxycyclohexyl)amino)benzo[d]oxazol-6-yl)methyl)-1H-benzo[d]imidazole-5-carbonitrile

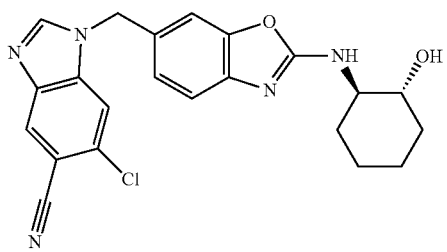 [SMILES: N#Cc1cc2ncn(Cc3ccc4nc(N[C@@H]5CCCC[C@H]5O)oc4c3)c2cc1Cl]

Step 1:
A mixture of 5-chloro-2-nitroaniline (6.0 g, 34.88 mmol) and NBS (6.06 g, 34.0 mmol) in HOAc (240 mL) was stirred at 130° C. for 1 h. The reaction mixture was poured into water. The precipitate was collected by filtration and washed with petroleum ether to give 4-bromo-5-chloro-2-nitroaniline as a light brown solid (8.25 g, 96.5%). 1H NMR (300 MHz, DMSO-d6) δ 8.24 (s, 1H), 7.62 (br s, 2H), 7.29 (s, 1H). LCMS (ESI) m/z 251 (M+H)+.

Step 2:
To a solution of 4-bromo-5-chloro-2-nitroaniline (550 mg, 2.19 mmol) from the previous step and TFA (2.26 mL) in DCM (10 mL) at −15° C. was added NaBH(OAc)3 (1.39 g, 5.37 mmol). Then a solution of 2-(methylthio)benzo[d]oxazole-6-carbaldehyde (465 mg, 2.41 mmol) in DCM (6 mL) was added to the mixture. After complete addition, the mixture was stirred at −10° C. to 0° C. for 2 h. The reaction mixture was diluted with DCM and washed sequentially with H2O, aq NaHCO3 and brine. The organic layer was dried over Na2SO4, filtered and concentrated under reduced pressure. The residue was purified by silica gel chromatography eluting with 5:1 to 2:1 petroleum ether/DCM to give 4-bromo-5-chloro-N-((2-(methylthio)benzo[d]oxazol-6-yl)methyl)-2-nitroaniline as a yellow solid (451 mg, 48.2%). 1H NMR (300 MHz, DMSO-d6) δ 8.81 (t, 1H), 8.34 (s, 1H), 7.66 (s, 1H), 7.60 (d, J=8.1 Hz, 1H), 7.37 (d, J=6.9 Hz, 1H), 7.19 (s, 1H), 4.76 (d, J=6.3 Hz, 2H), 2.74 (s, 3H). LCMS (ESI) m/z 428 (M+H)+.

Step 3:
To a stirred solution of 4-bromo-5-chloro-N-((2-(methylthio)benzo[d]oxazol-6-yl)methyl)-2-nitroaniline (451 mg, 1.06 mmol) in methanol (80 mL) and DCM (80 mL) was added palladium on activated charcoal (100 mg). The mixture was stirred under hydrogen for 2 h, filtered and concentrated under reduced pressure to give 4-bromo-5-chloro-N1-((2-(methylthio)benzo[d]oxazol-6-yl)methyl)benzene-1,2-diamine as a light yellow solid (415 mg, 98.6%). 1H NMR (300 MHz, DMSO-d6) δ 7.5-7.60 (m, 2H), 7.35 (d, J=8.1 Hz, 1H), 6.81 (s, 1H), 6.41 (s, 1H), 5.64 (t, 1H), 5.03 (s, 2H), 4.40 (d, J=6.0 Hz, 2H), 2.74 (s, 3H). LCMS (ESI) m/z 399 (M+H)+.

Step 4:
A mixture of 4-bromo-5-chloro-N1-((2-(methylthio)benzo[d]oxazol-6-yl)methyl)benzene-1,2-diamine (622 mg, 2.40 mmol), triethoxymethane (5 mL) and HCOOH (0.08 mL) was stirred at 90° C. for 2 h. The reaction mixture was concentrated under reduced pressure. The residue was purified by silica gel chromatography, eluting with 1:1 petroleum ether/ethyl acetate to give 6-((5-bromo-6-chloro-1H-benzo[d]imidazol-1-yl)methyl)-2-(methylthio)benzo[d]oxazole as a light brown solid (607 mg, 84.5%). 1H NMR (300 MHz, DMSO-d6) δ 8.56 (s, 1H), 8.07 (s, 1H), 8.02 (s, 1H), 7.72 (s, 1H), 7.60 (d, J=8.4 Hz, 1H), 7.34 (d, J=6.6 Hz, 1H), 5.60 (s, 2H), 2.73 (s, 3H). LCMS (ESI) m/z 408 (M+H)+.

Step 5:
A solution of 6-((5-bromo-6-chloro-1H-benzo[d]imidazol-1-yl)methyl)-2-(methylthio)benzo[d]oxazole (554 mg, 1.80 mmol) and m-CPBA (403 mg, 2.34 mmol) in DCM (18 mL) was stirred at 0° C. for 3 h. The reaction mixture was washed with aqueous Na2S2O3 and brine. The organic layer was dried over Na2SO4, filtered and concentrated under reduced pressure. The residue was purified by silica gel chromatography eluting with 1:5 petroleum ether/ethyl acetate to give 6-((5-bromo-6-chloro-1H-benzo[d]imidazol-1-yl)methyl)-2-(methylsulfinyl)benzo[d]oxazole (510 mg, 87.5%) as a yellow solid. 1H NMR (300 MHz, DMSO-d6)

δ 8.59 (s, 1H), 8.08 (s, 1H), 8.04 (s, 1H), 7.97 (s, 1H), 7.90 (d, J=8.7 Hz, 1H), 7.50 (d, J=9.3 Hz, 1H), 5.69 (s, 2H), 3.18 (s, 3H). LCMS (ESI) m/z 424 (M+H)+.

Step 6:

A mixture of 6-((5-bromo-6-chloro-1H-benzo[d]imidazol-1-yl)methyl)-2-(methylsulfinyl)benzo[d]oxazole (460 mg, 1.08 mmol), (1R,2R)-2-aminocyclohexanol (245 mg, 2.13 mmol) and DIEA (366 mg, 2.84 mmol) in DMA (10 mL) was stirred at 120° C. for 1 h. The reaction mixture was cooled to rt, poured into water (30 mL) and extracted with ethyl acetate (100 mL×3). The combined organic layers were washed with brine, dried over Na2SO4, filtered and concentrated under reduced pressure. The residue was purified by silica gel chromatography eluting with 1:5 petroleum ether/ethyl acetate to give (1R,2R)-2-((6-((5-bromo-6-chloro-1H-benzo[d]imidazol-1-yl)methyl)benzo[d]oxazol-2-yl)amino)cyclohexanol as a light yellow solid (470 mg, 82.3%). 1H NMR (300 MHz, CDCl3) δ 8.52 (s, 1H), 8.06 (s, 1H), 8.00 (s, 1H), 7.82 (d, J=7.8 Hz, 1H), 7.41 (s, 1H), 7.14 (s, 1H), 5.48 (s, 2H), 4.68 (d, J=4.2 Hz, 1H), 3.33 (br s, 2H), 1.91 (br s, 2H), 1.63 (br s, 2H), 1.25 (br s, 4H). LCMS (ESI) m/z 477 (M+H)+.

Step 7:

A mixture of (1R,2R)-2-((6-((5-bromo-6-chloro-1H-benzo[d]imidazol-1-yl)methyl)benzo[d]oxazol-2-yl)amino)cyclohexanol (215 mg, 0.45 mmol), Zn(CN)2 (327 mg, 2.71 mmol), Pd2(dba)3 (82 mg, 0.09 mmol) and dppf (100 mg, 0.18 mmol) in DMA (10 mL) was stirred at 100° C. for 16 h. The reaction mixture was cooled to room temperature, poured into water (20 mL) and extracted with ethyl acetate (50 mL×2). The combined organic layers were washed with water and brine, dried over Na2SO4, filtered and concentrated under reduced pressure. The residue was purified by preparative HPLC to give 6-chloro-1-((2-(((1R,2R)-2-hydroxycyclohexyl)amino)benzo[d]oxazol-6-yl)methyl)-1H-benzo[d]imidazole-5-carbonitrile as a white solid (25 mg, 13.5%). 1H NMR (300 MHz, DMSO-d6): δ 8.69 (s, 1H), 8.36 (s, 1H), 8.13 (s, 1H), 7.82 (d, J=7.8 Hz, 1H), 7.45 (s, 1H), 7.16 (s, 1H), 5.53 (s, 2H), 4.68 (d, J=4.5 Hz, 1H), 3.38-3.31 (m, 2H), 1.92-1.86 (m, 2H), 1.65-1.60 (m, 2H), 1.27-1.19 (m, 4H). LCMS (ESI) m/z 422 (M+H)+.

Example 196

Preparation of 2-((1-((2-(((1R,2R)-2-hydroxycyclohexyl)amino)benzo[d]thiazol-6-yl)methyl)-1H-benzo[d]imidazol-5-yl)oxy)acetonitrile

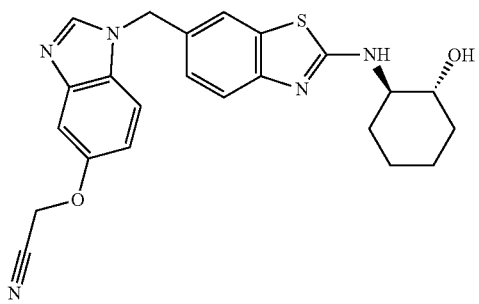 [SMILES: N#CCOc1ccc2c(c1)ncn2Cc1ccc2nc(N[C@@H]3CCCC[C@H]3O)sc2c1]

Step 1:

2-((1-((2-43aR,7aR)-2,2-Dimethylhexahydrobenzo[d]oxazol-3(2H)-yl)benzo[d]thiazol-6-yl)methyl)-1H-benzo[d]imidazol-5-yl)oxy)acetonitrile (42 mg, 25%) was obtained as a yellow solid using a procedure analogous to that described in Step 3 of Example 171, substituting iodoacetonitrile for 4-(2-iodoethyl)morpholine used in Example 171. 1H NMR (300 MHz, CDCl3) δ 7.99 (s, 1H), 7.58 (d, J=8.1 Hz, 1H), 7.30-7.40 (m, 2H), 7.16-7.26 (m, 2H), 6.95 (m, 1H), 5.38 (s, 2H), 4.79 (s, 2H), 3.65 (m, 1H), 3.08 (m, 1H), 2.80 (m, 1H), 2.17 (m, 1H), 1.82-1.92 (m, 2H), 1.78 (s, 3H), 1.64 (s, 3H), 1.33-1.39 (m, 4H).

Step 2:

2-((1-((2-(((1R,2R)-2-Hydroxycyclohexyl)amino)benzo[d]thiazol-6-yl)methyl)-1H-benzo[d]imidazol-5-yl)oxy)acetonitrile (31 mg, 68%) was obtained as a white solid using a procedure analogous to that described in Step 4 of Example 171, substituting 2-((1-((2-((3aR,7aR)-2,2-dimethylhexahydrobenzo[d]oxazol-3 (2H)-yl)benzo[d]thiazol-6-yl)methyl)-1H-benzo[d]imidazol-5-yl)oxy)acetonitrile for (3aR,7aR)-2,2-dimethyl-3-(6-((5-(2-morpholino ethoxy)-1H-benzo[d]imidazol-1-yl)methyl)benzo[d]thiazol-2-yl)octahydrobenzo[d]oxazole used in Example 171. 1H NMR (300 MHz, CDCl3) δ 7.95 (s, 1H), 7.48 (d, J=8.4 Hz, 1H), 7.40 (d, J=2.1 Hz, 1H), 7.29 (m, 1H), 7.20 (d, J=8.1 Hz, 1H), 7.16 (dd, J=8.1, 1.5 Hz, 1H), 6.96 (dd, J=8.7, 2.4 Hz, 1H), 5.36 (s, 2H), 5.21 (m, 1H), 4.80 (s, 2H), 3.83 (br m, 1H), 3.61 (br m, 1H), 3.47 (m, 1H), 2.08-2.18 (m, 2H), 1.75-1.79 (m, 2H), 1.24-1.44 (m, 4H). LCMS (ESI) m/z 434 (M+H)+.

Example 197

Preparation of 6-((6-fluoro-3H-imidazo[4,5-b]pyridin-3-yl)methyl)-N-(2-methoxyphenyl)benzo[d]thiazol-2-amine

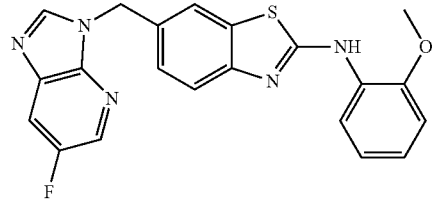 [SMILES: COc1ccccc1Nc1nc2ccc(Cn3cnc4cc(F)cnc43)cc2s1]

6-((6-Fluoro-3H-imidazo[4,5-b]pyridin-3-yl)methyl)-N-(2-methoxyphenyl)benzo[d]thiazol-2-amine was synthesized as a white powder (45 mg, 15%) using a procedure analogous to that described in Example 191, substituting 2-methoxyaniline for aniline used in Example 191. 1H NMR (500 MHz, CDCl3) δ 9.84 (s, 1H), 8.71 (s, 1H), 8.35-8.46 (m, 2H), 8.08 (dd, J=2.6, 9.5 Hz, 1H), 7.78 (s, 1H), 7.50 (d, J=8.4 Hz, 1H), 7.31 (dd, J=1.5, 8.4 Hz, 1H), 6.91-7.10 (m, 3H), 5.53 (s, 2H), 3.85 (s, 3H); LCMS (ESI) m/z 407 (M+H)+.

Example 198

Preparation of N-((1R,2R)-2-chlorocyclohexyl)-6-((6-fluoro-3H-imidazo[4,5-b]pyridin-3-yl)methyl)benzo[d]thiazol-2-amine

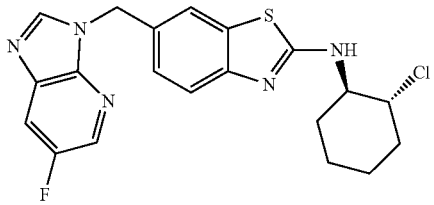 [SMILES: Fc1cnc2c(c1)ncn2Cc1ccc2nc(N[C@@H]3CCCC[C@H]3Cl)sc2c1]

To a stirred mixture of (1S,2R)-2-((6-((6-fluoro-3H-imidazo[4,5-b]pyridin-3-yl)methyl)benzo[d]thiazol-2-yl)amino)cyclohexanol (282 mg, 0.7 mmol) from Example 162, DIEA (247 µL, 1.4 mmol), and $CH_2Cl_2$(15 mL) at 0° C. under argon was added sulfuryl chloride (142 mg, 2.0 mmol). The mixture was warmed to rt and stirred for 15 h, and then stirred at 60° C. for 15 h. The mixture was cooled to rt and purified directly by reverse-phase preparative HPLC using a mixture of water (5% $CH_3CN$, 0.05% HCOOH) and $CH_3CN$ (0.05% HCOOH) as the mobile phase and Varian Pursuit XRs C18 column as the stationary phase. The product was further purified by triturating in $CH_2Cl_2$ (5 mL) to afford N-((1R,2R)-2-chlorocyclohexyl)-6-((6-fluoro-3H-imidazo[4,5-b]pyridin-3-yl)methyl)benzo[d]thiazol-2-amine (29 mg, 10%) as a white solid. $^1$H NMR (500 MHz, $CDCl_3$) δ 8.68 (s, 1H), 8.41 (s, 1H), 8.24 (d, J=8.4 Hz, 1H), 8.07 (dd, J=2.6, 9.5 Hz, 1H), 7.68 (s, 1H), 7.33 (d, J=8.4 Hz, 1H), 7.24 (dd, J=1.4, 8.2 Hz, 1H), 5.48 (s, 2H), 4.02 (m, 1H), 3.87 (m, 1H), 2.20 (m, 1H), 2.07 (m, 1H), 1.63-1.75 (m, 3H), 1.29-1.41 (m, 3H); LCMS (ESI) m/z 416 (M+H)$^+$.

Example 199

Preparation of 1-(3-((2-(((1R,2R)-2-hydroxycyclohexyl)amino)benzo[d]thiazol-6-yl)methyl)imidazo[1,2-a]pyridin-7-yl)piperidin-4-ol

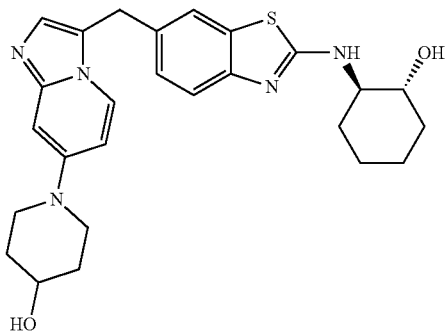 [SMILES: OC1CCN(c2ccn3c(Cc4ccc5nc(N[C@@H]6CCCC[C@H]6O)sc5c4)cnc3c2)CC1]

1-(3-((2-(((1R,2R)-2-Hydroxycyclohexyl)amino)benzo[d]thiazol-6-yl)methyl)imidazo[1,2-a]pyridin-7-yl)piperidin-4-ol (30 mg, 22%) was obtained as a yellow solid using a procedure analogous to that described in Step 6 of Example 117, substituting 4-(2-aminopyridin-4-yl)cyclohexanol and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. $^1$H NMR (500 MHz, DMSO-$d_6$) δ 7.88 (d, J=7.4 Hz, 2H), 7.47 (s, 1H), 7.25 (d, J=8.4 Hz, 1H), 7.15 (s, 1H), 7.06 (d, J=8.4 Hz, 1H), 6.76 (dd, J=2.2, 7.6 Hz, 1H), 6.63 (s, 1H), 4.74 (br s, 1H), 4.18 (s, 2H), 3.63 (dd, J=4.2, 8.6 Hz, 1H), 3.54 (d, J=12.8 Hz, 2H), 3.31-3.37 (m, 4H), 2.80-2.93 (m, 2H), 2.04 (d, J=11.8 Hz, 1H), 1.88-1.92 (m, 1H), 1.74-1.83 (m, 2H), 1.5-1.70 (m, 2H), 1.38-1.50 (m, 2H), 1.10-1.37 (m, 4H). LCMS (ESI) m/z 478 (M+H)$^+$.

Example 200

Preparation of 1-(3-((2-(((1R,2R)-2-hydroxycyclohexyl)amino)benzo[d]thiazol-6-yl)methyl)imidazo[1,2-a]pyridin-7-yl)ethanone

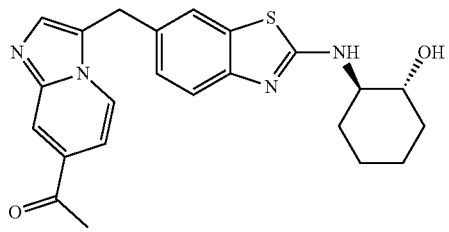 [SMILES: CC(=O)c1ccn2c(Cc3ccc4nc(N[C@@H]5CCCC[C@H]5O)sc4c3)cnc2c1]

Step 1:
1-(2-Aminopyridin-4-yl)ethanone was obtained as a yellow solid (398 mg, 64%) using a procedure analogous to that described in Example 73, substituting 4-iodopyridin-2-amine for (1R,2R)-2-((6-((6-bromo-3H-imidazo[4,5-b]pyridin-3-yl)methyl)benzo[d]thiazol-2-yl)amino)cyclohexanol used in Example 73. LCMS (ESI) m/z 137 (M+H)$^+$.

Step 2:
1-(3-((2-(((1R,2R)-2-Hydroxycyclohexyl)amino)benzo[d]thiazol-6-yl)methyl)imidazo[1,2-a]pyridin-7-yl)ethanone (80 mg, 35%) was obtained as a yellow powder using a procedure analogous to that described in Step 6 of Example 117, substituting 1-(2-aminopyridin-4-yl)ethanone from Step 1 of this Example and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. $^1$H NMR (500 MHz, DMSO-$d_6$) δ 8.32 (s, 1H), 8.29 (d, J=6.9 Hz, 1H), 7.87 (d, J=7.4 Hz, 1H), 7.67 (s, 1H), 7.53 (s, 1H), 7.28 (br s, 1H), 7.27 (d, J=7.9 Hz, 1H), 7.09 (d, J=8.4 Hz, 1H), 4.72 (d, J=4.9 Hz, 1H), 4.35 (s, 2H), 3.51 (br s, 1H), 2.62 (s, 3H), 2.03 (d, J=11.3 Hz, 1H), 1.87 (d, J=10.8 Hz, 1H), 1.5-1.70 (m, 2H), 1.09-1.35 (m, 4H). LCMS (ESI) m/z 421 (M+H)$^+$.

Example 201

Preparation of (1R,2R)-2-((6-((7-(1-hydroxyethyl)imidazo[1,2-a]pyridin-3-yl)methyl)benzo[d]thiazol-2-yl)amino)cyclohexanol

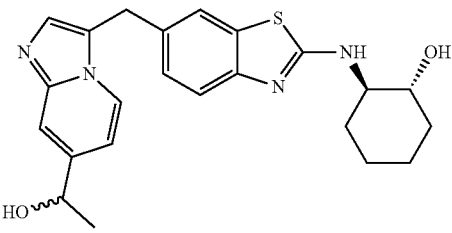 [SMILES: CC(O)c1ccn2c(Cc3ccc4nc(N[C@@H]5CCCC[C@H]5O)sc4c3)cnc2c1]

To a stirred solution of 1-(3-((2-(((1R,2R)-2-hydroxycyclohexyl)amino)benzo[d]thiazol-6-yl)methyl)imidazo[1,2-a]pyridin-7-yl)ethanone (40 mg, 0.095 mmol) from Example 200 in MeOH at rt was added $NaBH_4$. After 30 min, 3N HCl was added and the mixture was purified by reverse-phase HPLC using a mixture of water (5% $CH_3CN$, 0.05% HCOOH) and CH₃CN (0.05% HCOOH) as the mobile phase and Varian Pursuit XRs C18 column as the stationary phase to afford (1R,2R)-2-((6-((7-(1-hydroxyethyl)imidazo[1,2-a]pyridin-3-yl)methyl)benzo[d]thiazol-2-yl)amino)cyclohexanol (23 mg, 58%) as white powder. $^1$H NMR (500 MHz, DMSO-d₆) δ 8.11 (d, J=7.4 Hz, 1H), 7.87 (d, J=7.9 Hz, 1H), 7.50 (s, 1H), 7.41 (s, 1H), 7.37 (s, 1H), 7.26 (d, J=8.4 Hz, 1H), 7.07 (d, J=7.9 Hz, 1H), 6.84 (d, J=7.4 Hz, 1H), 5.30 (br s, 1H), 4.72 (q, J=6.4 Hz, 2H), 4.26 (s, 2H), 3.50 (br s, 1H), 2.03 (d, J=11.8 Hz, 1H), 1.82-1.87 (m, 1H), 1.5-1.69 (m, 2H), 1.32 (d, J=6.9 Hz, 3H), 1.10-1.30 (m, 4H). LCMS (ESI) m/z 423 (M+H)⁺.

Example 202

Preparation of 1-(3-((2-(((1R,2R)-2-hydroxycyclohexyl)amino)benzo[d]thiazol-6-yl)methyl)imidazo[1,2-a]pyridin-7-yl)ethanone oxime

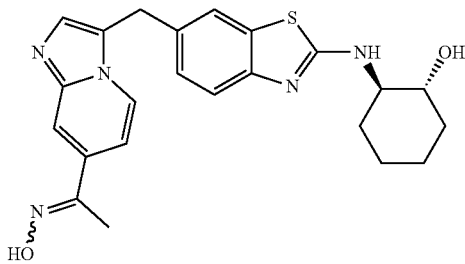 [SMILES: CC(=NO)c1ccn2c(Cc3ccc4nc(N[C@@H]5CCCC[C@H]5O)sc4c3)cnc2c1]

To a stirred solution of 1-(3-((2-(((1R,2R)-2-hydroxycyclohexyl)amino)benzo[d]thiazol-6-yl)methyl)imidazo[1,2-a]pyridin-7-yl)ethanone (40 mg, 0.095 mmol) from Example 200 in EtOH (2 mL) at rt were added hydroxylamine hydrochloride (120 mg, excess) and pyridine (200 μL, excess). The mixture was heated at 90° C. for 1 h, and then cooled to rt. Purification by reverse-phase HPLC using a mixture of water (5% CH₃CN, 0.05% HCOOH), CH₃CN (0.05% HCOOH) as the mobile phase and Varian Pursuit XRs C18 column as the stationary phase afforded 1-(3-((2-(((1R,2R)-2-hydroxycyclohexyl)amino)benzo[d]thiazol-6-yl)methyl)imidazo[1,2-a]pyridin-7-yl)ethanone oxime (23 mg, 61%) as yellow powder. $^1$H NMR (500 MHz, DMSO-d₆) δ 11.46 (br s, 1H), 8.13 (d, J=7.4 Hz, 1H), 7.90 (d, J=7.4 Hz, 1H), 7.72 (s, 1H), 7.51 (s, 1H), 7.45 (s, 1H), 7.08 (d, J=8.4 Hz, 1H), 6.44-6.58 (m, 1H), 5.89 (s, 1H), 4.78 (d, J=2.5 Hz, 1H), 4.29 (s, 2H), 3.50 (br s, 1H), 2.18 (s, 3H), 2.04 (d, J=12.3 Hz, 1H), 1.87 (d, J=10.8 Hz, 1H), 1.5-1.67 (m, 2H), 1.15-1.32 (m, 4H). LCMS (ESI) m/z 436 (M+H)⁺.

Example 203

Preparation of (1R,2R)-2-((6-((5-bromo-7-fluoro-1H-benzo[d]imidazol-1-yl)methyl)benzo[d]thiazol-2-yl)amino)cyclohexanol

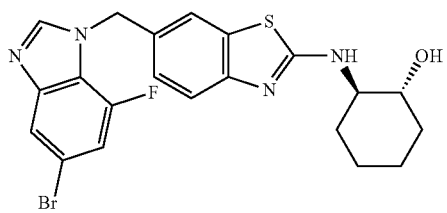 [SMILES: O[C@@H]1CCCC[C@H]1Nc1nc2ccc(Cn3cnc4cc(Br)cc(F)c43)cc2s1]

Step 1:
A stirred mixture of acetic anhydride (20 mL, 213 mmol) and formic acid (8 mL, 213 mmol) was heated at 60° C. for 3 h. The mixture was cooled to rt, -bromo-2-fluoro-6-nitroaniline (2.5 g, 10.64 mmol) was added. The mixture was heated at 60° C. for 15 h, cooled to rt and concentrated under reduced pressure. The residue was partitioned between saturated aq NaHCO₃ and DCM. The organic layer was separated, dried over MgSO₄, filtered, and concentrated under reduced pressure to afford N-(4-bromo-2-fluoro-6-nitrophenyl)formamide (2.79 g, 100%) as a brown solid that was not purified further. LCMS (ESI) m/z 285 and 287 (M+H+Na)⁺.

Step 2:
To a stirred solution of N-(4-bromo-2-fluoro-6-nitrophenyl)formamide (2.79 g, 10.61 mmol) from the previous step in anhydrous DMF (40 mL) at 0° C. was added sodium hydride (60% dispersion in mineral oil, 485 mg, 12.13 mmol). The mixture was stirred at 0° C. for 15 min, then allowed to warm to rt. To the reaction mixture was added a solution of 6-(chloromethyl)-2-(methylthio)benzo[d]thiazole (3.04 g, 13.24 mmol) from Step 3 of Example 3 in DMF (10 mL), and the mixture was stirred at rt for 15 h. The mixture was partitioned between water and DCM and the organic layer was separated and washed sequentially with water and brine. The organic layer was separated, dried over MgSO₄, filtered, and concentrated under reduced pressure to afford N-(4-bromo-2-fluoro-6-nitrophenyl)-N-((2-(methylthio)benzo[d]thiazol-6-yl)methyl)formamide (4.8 g, 98%) as an oil, which was not purified further. LCMS (ESI) m/z 456 and 458 (M+H)⁺.

Step 3:
To a stirred mixture of N-(4-bromo-2-fluoro-6-nitrophenyl)-N-((2-(methylthio)benzo[d]thiazol-6-yl)methyl)formamide (4.8 g, 10.55 mmol) from the previous step, HOAc (15 mL) and EtOH (50 mL) at rt was added portionwise iron powder (1.77 g, 31.65 mmol). The mixture was heated at 80° C. for 2.5 h. After cooling to rt, the mixture was partitioned between saturated aq NaHCO₃ and a 10:1 mixture of EtOAc and MeOH. The biphasic mixture was filtered through Celite, and the layers of the filtrate were separated. The aqueous layer was extracted with a 10:1 mixture of EtOAc and MeOH. The combined organic layers were dried over MgSO₄, filtered, and concentrated under reduced pressure. The residual solid was purified by trituration with diethyl ether to afford 6-((5-bromo-7-fluoro-1H-benzo[d]imidazol-1-yl)methyl)-2-(methylthio)benzo[d]thiazole (1.39 mg, 39%) as a white solid. $^1$H NMR (500 MHz, DMSO-d₆) δ 8.56 (s, 1H), 7.87 (m, 1H), 7.80 (d, J=8.4 Hz, 1H), 7.75 (m, 1H), 7.30-7.34 (m, 2H), 5.66 (s, 2H), 2.76 (s, 3H); LCMS (ESI) m/z 408 and 410 (M+H)+.

Step 4:
6-((5-Bromo-7-fluoro-1H-benzo[d]imidazol-1-yl)methyl)-2-(methylsulfinyl)benzo[d]thiazole (1.33 g, 92%) was obtained as a white solid using a procedure analogous to that described in Step 4 of Example 130, substituting 6-((5-bromo-7-fluoro-1H-benzo[d]imidazol-1-yl)methyl)-2-(methylthio)benzo[d]thiazole from Step 3 of this Example for 2-(methylthio)-6-((5-(trifluoromethyl)-1H-benzo[d]imidazol-1-yl)methyl)benzo[d]thiazole used in Example 130. $^1$H NMR (500 MHz, DMSO-d₆) δ 8.58 (s, 1H), 8.10 (m, 1H), 8.07 (d, J=10.6 Hz, 1H), 7.76 (m, 1H), 7.48 (dd, J=8.5, 1.7 Hz, 1H), 7.32 (dd, J=10.6, 1.7 Hz, 1H), 5.75 (s, 2H), 3.05 (s, 3H); LCMS (ESI) m/z 424 and 426 (M+H)+.

Step 5:

A stirred mixture of 6-((5-bromo-7-fluoro-1H-benzo[d]imidazol-1-yl)methyl)-2-(methylsulfinyl)benzo[d]thiazole (1.33 g, 3.14 mmol), (1R,2R)-2-aminocyclohexanol (1.09 g, 9.43 mmol), DIEA (1.62 g, 12.58 mmol) and DMA (40 mL) was heated in a sealed vial at 110° C. for 15 h. The mixture was cooled to rt and then partitioned between water and EtOAc. The organic layer was separated and washed sequentially with water and brine. The organic layer was separated, dried over MgSO₄, filtered, and concentrated under reduced pressure. The residual solid was purified by trituration with a 6:1 mixture of diethyl ether and DCM to afford (1R,2R)-2-((6-((5-bromo-7-fluoro-1H-benzo[d]imidazol-1-yl)methyl)benzo[d]thiazol-2-yl)amino)cyclohexanol (952 mg, 64%) as a tan solid. A 90 mg portion was further purified by reverse-phase preparative HPLC using a mixture of water (5% CH₃CN, 0.05% HOAc) and CH₃CN (0.05% HOAc) as the mobile phase and Varian Pursuit XRs diphenyl column as the stationary phase to afford (1R,2R)-2-((6-((5-bromo-7-fluoro-1H-benzo[d]imidazol-1-yl)methyl)benzo[d]thiazol-2-yl)amino)cyclohexanol (15 mg) as a white solid. $^1$H NMR (500 MHz, DMSO-$d_6$) δ 8.52 (s, 1H), 7.98 (d, J=10.0 Hz, 1H), 7.74 (d, J=5.0 Hz, 1H), 7.54 (m, 1H), 7.33 (m, 1H), 7.29 (d, J=10.0 Hz, 1H), 7.08 (m, 1H), 5.52 (s, 2H), 4.75 (d, J=5.0 Hz, 1H), 3.51 (m, 1H), 3.33 (m, 1H), 2.02 (m, 1H), 1.87 (m, 1H), 1.5-1.64 (m, 2H), 1.16-1.30 (m, 4H); LCMS (ESI) m/z 475 and 477 (M+H)+.

Example 204

Preparation of 1-(3-((2-(((1R,2R)-2-hydroxycyclohexyl)amino)benzo[d]thiazol-6-yl)methyl)imidazo[1,2-a]pyridin-7-yl)ethanone O-methyl oxime

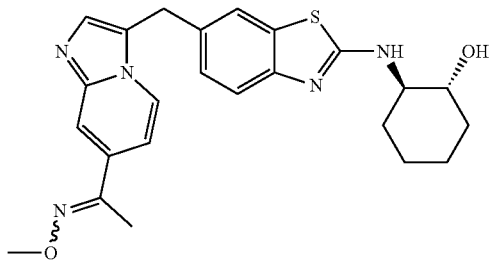 [SMILES: CON=C(C)c1ccn2c(Cc3ccc4nc(N[C@@H]5CCCC[C@H]5O)sc4c3)cnc2c1]

1-(3-((2-(((1R,2R)-2-Hydroxycyclohexyl)amino)benzo[d]thiazol-6-yl)methyl)imidazo[1,2-a]pyridin-7-yl)ethanone O-methyl oxime was obtained as yellow powder (23 mg, 59%) using a procedure analogous to that described in Example 202, substituting O-methylhydroxylamine hydrochloride for hydroxylamine hydrochloride used in Example 202. $^1$H NMR (500 MHz, DMSO-$d_6$) δ 8.17 (d, J=7.4 Hz, 1H), 7.92 (d, J=7.4 Hz, 1H), 7.79 (s, 1H), 7.51 (s, 1H), 7.46 (s, 1H), 7.27 (d, J=8.4 Hz, 2H), 7.08 (d, J=7.9 Hz, 1H), 4.78 (br s, 1H), 4.30 (s, 2H), 3.94 (s, 3H), 3.50 (br s, 1H), 2.21 (s, 3H), 2.04 (d, J=11.8 Hz, 1H), 1.85-1.93 (m, 1H), 1.5-1.69 (m, 2H), 1.09-1.35 (m, 4H). LCMS (ESI) m/z 450 (M+H)+.

Example 205

Preparation of (1R,2R)-2-((6-((9H-benzo[d]imidazo[1,2-a]imidazol-3-yl)methyl)benzo[d]thiazol-2-yl)amino)cyclohexanol

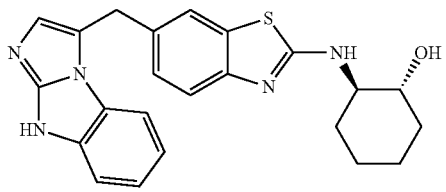 [SMILES: O[C@@H]1CCCC[C@H]1Nc1nc2ccc(Cc3cnc4[nH]c5ccccc5n34)cc2s1]

(1R,2R)-2-((6-((9H-Benzo[d]imidazo[1,2-a]imidazol-3-yl)methyl)benzo[d]thiazol-2-yl)amino)cyclohexanol (17 mg, 7%) was obtained as a solid using a procedure analogous to that described in Step 3 Example 153, using 2-chloro-3-(2-(((1R,2R)-2-hydroxycyclohexyl)amino)benzo[d]thiazol-6-yl)prop anal from Step 2 of Example 153 and substituting 1H-benzo[d]imidazol-2-amine for 4-(2-methoxyethoxyl)pyridin-2-amine used in Step 3 of Example 153. $^1$H NMR (500 MHz, DMSO-$d_6$) δ 11.66 (br s, 1H), 7.87 (d, J=7.4 Hz, 1H), 7.54 (s, 1H), 7.35 (dd, J=3.4, 7.9 Hz, 2H), 7.28 (d, J=8.4 Hz, 1H), 7.08-7.17 (m, 2H), 6.84-6.95 (m, 2H), 4.74 (br s, 1H), 4.32 (s, 2H), 3.50 (br s, 1H), 3.33 (m, 1H), 2.02 (m, 1H), 1.87 (m, 1H), 1.5-1.67 (m, 2H), 1.12-1.33 (m, 4H); LCMS (ESI) m/z 418 (M+H)+.

Example 206

Preparation of 7-fluoro-1-((2-(((1R,2R)-2-hydroxycyclohexyl)amino)benzo[d]thiazol-6-yl)methyl)-1H-benzo[d]imidazole-5-carbonitrile

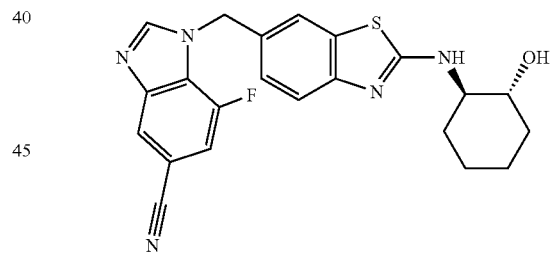

A stirred mixture of (1R,2R)-2-((6-((5-bromo-7-fluoro-1H-benzo[d]imidazol-1-yl)methyl)benzo[d]thiazol-2-yl)amino)cyclohexanol (150 mg, 0.316 mmol) from Example 203, zinc cyanide (111 mg, 0.948 mmol), 1,1'-bis(diphenylphosphino)ferrocene (35 mg, 0.0632 mmol) and anhydrous DMF (2 mL) was purged with a stream of argon. To the mixture was added palladium(trisdibenzylideneacetone) (0) (29 mg, 0.0316 mmol) and the mixture was heated in a sealed tube 100° C. for 6 h. The mixture was cooled and additional zinc cyanide (111 mg, 0.948 mmol), 1,1'-bis(diphenylphosphino)ferrocene (35 mg, 0.0632 mmol), and palladium(trisdibenzylideneacetone) (0) (29 mg, 0.0316 mmol) were added, and heating in a sealed tube was continued at 100° C. for 15 h. The mixture was cooled to rt and purified directly by reverse-phase preparative HPLC using a mixture of water (5% CH₃CN, 0.05% HOAc) and CH₃CN (0.05% HOAc) as the mobile phase and Varian Pursuit XRs diphenyl column as the stationary phase to afford (7-fluoro-1-((2-(((1R,2R)-2-hydroxycyclohexyl)amino)benzo[d]thiazol-6-yl)methyl)-1H-benzo[d]imidazole-5-carbonitrile (2.6 mg, 2%) as a white solid. $^1$H NMR (500 MHz, DMSO-$d_6$) δ 8.70 (s, 1H), 8.13 (s, 1H), 8.02 (d, J=7.6 Hz, 1H), 7.63 (d, J=11.1 Hz, 1H), 7.57 (s, 1H), 7.29 (d, J=8.1 Hz, 1H), 7.10 (d, J=8.1 Hz, 1H), 5.58 (s, 2H), 4.77 (br s, 1H), 3.50 (br m, 1H), 3.30 (br m, 1H), 2.02 (m, 1H), 1.87 (m, 1H), 1.5-1.67 (m, 2H), 1.12-1.32 (m, 4H); LCMS (ESI) m/z 422 (M+H)$^+$.

Example 207

Preparation of (1R,2R)-2-((6-((7-fluoro-5-vinyl-1H-benzo[d]imidazol-1-yl)methyl)benzo[d]thiazol-2-yl)amino)cyclohexanol

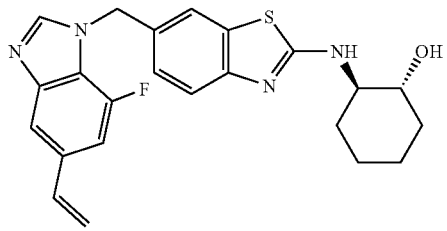 [SMILES: C=Cc1cc(F)c2c(c1)ncn2Cc1ccc2nc(N[C@@H]3CCCC[C@H]3O)sc2c1]

A stirred mixture of (1R,2R)-2-((6-((5-bromo-7-fluoro-1H-benzo[d]imidazol-1-yl)methyl)benzo[d]thiazol-2-yl)amino)cyclohexanol (150 mg, 0.316 mmol) from Example 203, vinyl boronic acid pinacol ester (97 mg, 0.632 mmol), sodium carbonate (67 mg, 0.0632 mmol), 1,4-dioxane (2 mL), and water (0.5 mL) was purged with a stream of argon. To the mixture was added dichloro[1,1'-bis(diphenylphosphino)ferrocene]palladium (II) DCM adduct (35 mg, 0.0474 mmol) and the mixture was heated in a sealed reaction vessel at 100° C. for 2.5 h. The mixture was cooled to rt and purified directly by reverse-phase preparative HPLC using a mixture of water (5% CH$_3$CN, 0.05% HOAc) and CH$_3$CN (0.05% HOAc) as the mobile phase and Varian Pursuit XRs diphenyl column as the stationary phase to afford (1R,2R)-2-((6-((7-fluoro-5-vinyl-1H-benzo[d]imidazol-1-yl)methyl)benzo[d]thiazol-2-yl)amino)cyclohexanol (23 mg, 17%) as a white solid. $^1$H NMR (500 MHz, DMSO-$d_6$) δ 8.44 (s, 1H), 7.98 (d, J=7.6 Hz, 1H), 7.55 (d, J=6.9 Hz, 2H), 7.23-7.31 (m, 2H), 7.09 (m, 1H), 6.79 (dd, J=11.0, 17.6 Hz, 1H), 5.83 (d, J=17.5 Hz, 1H), 5.51 (s, 2H), 5.22 (d, J=11.1 Hz, 1H), 4.74 (d, J=4.4 Hz, 1H), 3.51 (br m, 1H), 3.30 (br m, 1H), 2.03 (m, 1H), 1.87 (m, 1H), 1.5-1.67 (m, 2H), 1.14-1.32 (m, 4H); LCMS (ESI) m/z 423 (M+H)$^+$.

Example 208

Preparation of (1R,2R)-2-((6-((5-(3,6-dihydro-2H-pyran-4-yl)-7-fluoro-1H-benzo[d]imidazol-1-yl)methyl)benzo[d]thiazol-2- yl)amino)cyclohexanol

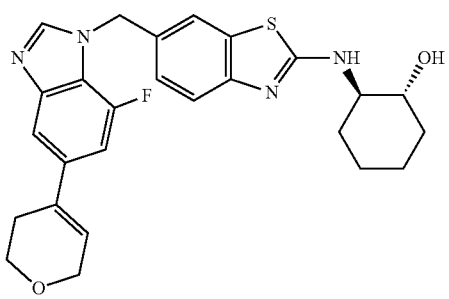 [SMILES: O[C@@H]1CCCC[C@H]1Nc1nc2ccc(Cn3cnc4cc(C5=CCOCC5)cc(F)c43)cc2s1]

A stirred mixture of (1R,2R)-2-((6-((5-bromo-7-fluoro-1H-benzo[d]imidazol-1-yl)methyl)benzo[d]thiazol-2-yl)amino)cyclohexanol (150 mg, 0.316 mmol) from Example 203, 3,6-dihydro-2H-pyran-4-boronic acid pinacol ester (133 mg, 0.632 mmol), sodium carbonate (67 mg, 0.0632 mmol), 1,4-dioxane (2 mL), and water (0.5 mL) was purged with a stream of argon. To the mixture was added dichloro[1,1'-bis(diphenylphosphino)ferrocene]palladium (II) DCM adduct (35 mg, 0.0474 mmol) and the mixture was heated in a sealed vessel at 100° C. for 3 h. The mixture was cooled to rt and purified directly by reverse-phase preparative HPLC using a mixture of water (5% CH$_3$CN, 0.05% HOAc) and CH$_3$CN (0.05% HOAc) as the mobile phase and Varian Pursuit XRs diphenyl column as the stationary phase to afford (1R,2R)-2-((6-((5-(3,6-dihydro-2H-pyran-4-yl)-7-fluoro-1H-benzo[d]imidazol-1-yl)methyl)benzo[d]thiazol-2-yl)amino)cyclohexanol (55 mg, 36%) as a white solid. $^1$H NMR (500 MHz, DMSO-$d_6$) δ 8.43 (s, 1H), 7.95 (d, J=7.6 Hz, 1H), 7.49-7.56 (m, 2H), 7.29 (d, J=8.1 Hz, 1H), 7.21 (d, J=13.0 Hz, 1H), 7.09 (m, 1H), 6.27 (br m, 1H), 5.51 (s, 2H), 4.72 (d, J=5.2 Hz, 1H), 4.21 (d, J=2.5 Hz, 2H), 4.06 (m, 1H), 3.81 (t, J=5.4 Hz, 2H), 3.61 (m, 1H), 3.51 (br m, 1H), 3.30 (br m, 1H), 2.00 (m, 1H), 1.88 (m, 1H), 1.5-1.67 (m, 2H), 1.11-1.32 (m, 4H); LCMS (ESI) m/z 479 (M+H)$^+$.

Example 209

Preparation of (1R,2R)-2-((6-((5-morpholino-1H-benzo[d]imidazol-1-yl)methyl)benzo[d]thiazol-2-yl)amino)cyclohexanol

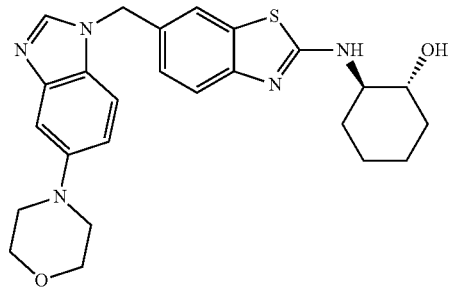 [SMILES: O[C@@H]1CCCC[C@H]1Nc1nc2ccc(Cn3cnc4cc(N5CCOCC5)ccc43)cc2s1]

(1R,2R)-2-((6-((5-Morpholino-1H-benzo[d]imidazol-1-yl)methyl)benzo[d]thiazol-2-yl)amino)cyclohexanol (10 mg, 7%) was obtained as a solid using a procedure analogous to that described in Example 97, substituting (1R,2R)-2-((6-((5-iodo-1H-benzo[d]imidazol-1-yl)methyl)benzo[d]thiazol-2-yl)amino)cyclohexanol from Step 5 of Example 183 for (1R,2R)-2-((6-((6-iodo-3H-imidazo[4,5-b]pyridin-3-yl)methyl)benzo[d]thiazol-2-yl)amino)cyclohexanol from Example 97. $^1$H NMR (500 MHz, DMSO-$d_6$) δ 8.42 (br s, 1H), 7.62 (br s, 1H), 7.57 (s, 1H), 7.47 (br s, 1H), 7.29 (d, J=8.4 Hz, 1H), 7.15 (d, J=7.9 Hz, 2H), 6.94 (d, J=8.9 Hz, 1H), 5.40 (s, 2H), 4.42 (br s, 1H), 3.70-3.81 (m, 4H), 3.52 (m, 1H), 3.41 (br s, 1H), 3.06-3.11 (m, 4H), 2.07 (m, 1H), 1.90 (m, 1H), 1.60-1.70 (m, 2H), 1.20-1.36 (m, 4H); LCMS (ESI) m/z 464 (M+H)$^+$.

Example 210

Preparation of 1-(1-((2-(((1R,2R)-2-hydroxycyclohexyl)amino)benzo[d]thiazol-6-yl)methyl)-1H-benzo[d]imidazol-5-yl)piperidin-2-one

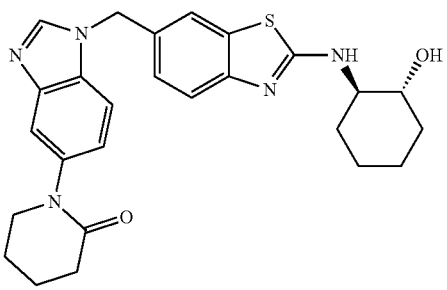 [SMILES: O=C1CCCCN1c1ccc2c(c1)ncn2Cc1ccc2nc(N[C@@H]3CCCC[C@H]3O)sc2c1]

To a stirred mixture of copper iodide (23 mg, 0.12 mmol) and tripotassium phosphate (190 mg, 0.90 mmol) in DMSO (3 mL) were added (1R,2R)-2-((6-((5-iodo-1H-benzo[d]imidazol-1-yl)methyl)benzo[d]thiazol-2-yl)amino)cyclohexanol (150 mg, 0.30 mmol) from Step 5 of Example 183 and piperidin-2-one (200 mg, 2.02 mmol). The mixture was flushed with argon and heated in a sealed reaction vessel at 125° C. for 15 h. The reaction mixture was cooled to rt and filtered, and the filtrate was purified directly by reverse-phase preparative HPLC using a mixture of water (5% CH₃CN, 0.05% HOAc) and CH₃CN (0.05% HOAc) as the mobile phase and Varian Pursuit XRs diphenyl column as the stationary phase to afford 1-(1-((2-(((1R,2R)-2-Hydroxycyclohexyl)amino)benzo[d]thiazol-6-yl)methyl)-1H-benzo[d]imidazol-5-yl)piperidin-2-one (3 mg, 7%) as a solid. $^1$H NMR (500 MHz, DMSO-d$_6$) δ 8.31 (br s, 1H), 7.69 (br s, 1H), 7.62 (s, 1H), 7.44-7.53 (m, 2H), 7.30 (d, J=8.4 Hz, 1H), 7.18 (d, J=8.4 Hz, 1H), 7.08 (d, J=8.9 Hz, 1H), 5.45 (s, 2H), 3.62 (t, J=5.4 Hz, 2H), 3.51 (br s, 1H), 3.37-3.46 (m, 2H), 2.36-2.43 (m, 2H), 2.06 (m, 1H), 1.82-1.93 (m, 5H), 1.61-1.70 (m, 2H), 1.20-1.36 (m, 4H); LCMS (ESI) m/z 476 (M+H)$^+$.

Example 211

Preparation of (1R,2R)-2-((6-((5-(1H-pyrazol-3-yl)-1H-benzo[d]imidazol-1-yl)methyl)benzo[d]thiazol-2-yl)amino)cyclohexanol

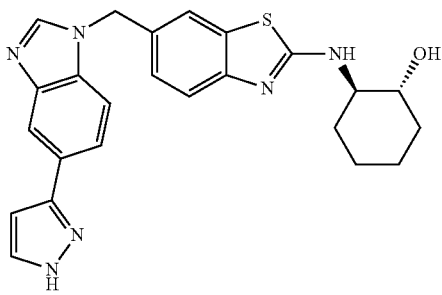 [SMILES: O[C@@H]1CCCC[C@H]1Nc1nc2ccc(Cn3cnc4cc(-c5cc[nH]n5)ccc43)cc2s1]

To a stirred solution of (1R,2R)-2-((6-((5-iodo-1H-benzo[d]imidazol-1-yl)methyl)benzo[d]thiazol-2-yl)amino)cyclohexanol (100 mg, 0.20 mmol) from Step 5 of Example 183 in DMF (2 mL) were added (1H-pyrazol-3-yl)boronic acid (90 mg, 0.80 mmol), NaHCO₃ (100 mg 1.2 mmol), bis(triphenylphosphine)palladium(II) dichloride (28 mg, 0.04 mmol), and water (0.4 mL). The mixture was flushed with argon and heated in a sealed vessel at 90° C. for 15 h. The reaction mixture was cooled to rt and partitioned between DCM and water. The aqueous layer was extracted twice with DCM and the combined organic phases were washed three times with a 1:1 mixture of water and brine. The organic phases were then dried over MgSO₄, filtered, and concentrated under reduced pressure. The residue was purified by silica gel flash chromatography eluting with 100% DCM to 10% MeOH/DCM to afford (1R,2R)-2-((6-((5-(1H-pyrazol-3-yl)-1H-benzo[d]imidazol-1-yl)methyl)benzo[d]thiazol-2-yl)amino)cyclohexanol (4 mg, 5%) as a solid. $^1$H NMR (500 MHz, DMSO-d$_6$) δ 12.92 (br s, 1H), 12.53 (br s, 1H), 8.29 (br s, 1H), 8.03 (m, 1H), 7.5-7.74 (m, 3H), 7.53 (d, J=7.9 Hz, 1H), 7.31 (d, J=7.9 Hz, 1H), 7.20 (d, J=8.4 Hz, 1H), 6.63 (br s, 1H), 5.47 (s, 2H), 4.42 (d, J=4.4 Hz, 1H), 3.51 (br s, 1H), 3.41 (tt, J=4.5, 8.8 Hz, 1H), 2.06 (m, 1H), 1.90 (d, J=11.8 Hz, 1H), 1.5-1.71 (m, 2H), 1.19-1.36 (m, 4H); LCMS (ESI) m/z 445 (M+H)$^+$.

Example 212

Preparation of (1R,2R)-2-((6-((6-(trifluoromethyl)-3H-imidazo[4,5-b]pyridin-3-yl)methyl)benzo[d]thiazol-2-yl)amino)cyclohexanol

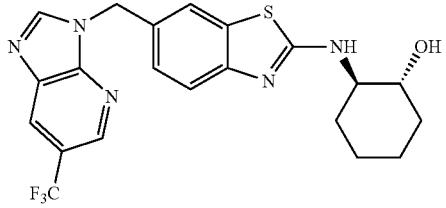 [SMILES: O[C@@H]1CCCC[C@H]1Nc1nc2ccc(Cn3cnc4cc(C(F)(F)F)cnc43)cc2s1]

Step 1:
A mixture of 2-chloro-3-nitro-5-(trifluoromethyl)pyridine (500 mg, 2.21 mmol), (2-(methylthio)benzo[d]thiazol-6-yl)methanamine from Step 4 of Example 23 (583 mg, 2.76 mmol), and triethylamine (837 mg, 8.29 mmol) in DMF (10 mL) was stirred at rt overnight. The reaction mixture was diluted with EtOAc and washed with water. The organic layer was dried over Na₂SO₄, filtered and concentrated under reduced pressure. The residue was purified by silica gel chromatography eluting with 1:0 to 10:1 petroleum ether/EtOAc to give N-((2-(methylthio)benzo[d]thiazol-6-yl)methyl)-3-nitro-5-(trifluoromethyl)pyridin-2-amine as a yellow solid (150 mg, 84.7%). $^1$H NMR (300 MHz, DMSO-d$_6$) δ 9.46 (t, J=1.8 Hz, 1H), 8.78 (d, J=2.1 Hz, 1H), 8.66 (d, J=2.4 Hz, 1H), 7.97 (s, 1H), 7.78 (d, J=8.4 Hz, 1H), 7.49-7.45 (m, 1H), 4.95 (d, J=6.6 Hz, 2H), 2.77 (s, 3H); LCMS (ESI) m/z 401 (M+H)$^+$.

Step 2:
To a mixture of N-((2-(methylthio)benzo[d]thiazol-6-yl)methyl)-3-nitro-5-(trifluoromethyl)pyridin-2-amine (0.97 g, 2.42 mmol), HOAc (4 mL), and MeOH (4 mL) in DCM (30 mL) cooled in ice-water bath was slowly added zinc dust (1.6 g, 24.2 mmol). The reaction mixture was stirred at 0° C. for 2 h. The mixture was filtered and the filtrate was diluted with DCM and then washed with water and aq NaHCO₃. The organic layer was dried over Na₂SO₄, filtered and concentrated under reduced pressure to afford N$^2$-((2-(methylthio)benzo[d]thiazol-6-yl)methyl)-5-(trifluoromethyl)pyridine-2,3-diamine (0.89 g, 100%). $^1$H NMR (300 MHz, DMSO-d$_6$) δ 8.05 (s, 1H), 7.82 (d, J=8.4 Hz, 1H), 7.77 (s, 1H), 7.44-7.41 (m, 1H), 7.03 (d, J=1.8 Hz, 1H), 4.84 (br s, 1H), 4.78 (d, J=5.1 Hz, 2H), 3.29 (br s, 2H), 2.79 (s, 3H). LCMS (ESI) m/z 371 (M+H)⁺.

Step 3:

A mixture of N²-((2-(methylthio)benzo[d]thiazol-6-yl)methyl)-5-(trifluoromethyl)pyridine-2,3-diamine (0.89 g, 2.39 mmol), triethoxymethane (30 mL) and HCOOH (0.6 g) was stirred at 90° C. for 2 h. The mixture was concentrated under reduced pressure. The residue was purified by silica gel chromatography eluting with 2:1 to 0:1 petroleum ether/EtOAc to afford 2-(methylthio)-6-((6-(trifluoromethyl)-3H-imidazo[4,5-b]pyridin-3-yl)methyl)benzo[d]thiazole as a light yellow solid (0.77 g, 79.3%). ¹H NMR (300 MHz, DMSO-d₆) δ 8.88 (s, 1H), 8.77 (d, J=1.2 Hz, 1H), 8.57 (d, J=1.8 Hz, 1H), 8.00 (d, J=1.2 Hz, 1H), 7.81 (d, J=8.4 Hz, 1H), 7.49-7.46 (m, 1H), 5.68 (s, 2H), 2.77 (s, 3H). LCMS (ESI) m/z 381 (M+H)⁺.

Step 4:

A mixture of 2-(methylthio)-6-((6-(trifluoromethyl)-3H-imidazo[4,5-b]pyridin-3-yl)methyl)benzo[d]thiazole (200 mg, 0.53 mmol) and m-CPBA (114 mg, 0.66 mmol) in DCM (5 mL) was stirred in an ice-water bath for 2 h. The mixture was diluted with DCM and washed with aq Na₂S₂O₃, aq NaHCO₃ and water. The organic layer was dried over Na₂SO₄, filtered and concentrated under reduced pressure to afford 2-(methylsulfinyl)-6-((6-(trifluoromethyl)-3H-imidazo[4,5-b]pyridin-3-yl)methyl)benzo[d]thiazole as a yellow solid (180 mg, 87.8%). ¹H NMR (300 MHz, DMSO-d₆) δ 8.91 (s, 1H), 8.77 (s, 1H), 8.59 (s, 1H), 8.23 (s, 1H), 8.08 (d, J=8.1 Hz, 1H), 7.66-7.62 (m, 1H), 5.77 (s, 2H), 3.06 (s, 3H). LCMS (ESI) m/z 397 (M+H)⁺.

Step 5:

A mixture of 2-(methylsulfinyl)-6-((6-(trifluoromethyl)-3H-imidazo[4,5-b]pyridin-3-yl)methyl)benzo[d]thiazole (180 mg, 0.45 mmol), (1R,2R)-2-aminocyclohexanol (112 mg, 0.97 mmol) and DIEA (261 mg, 2 mmol) in DMA (2 mL) was stirred at 130° C. overnight. The reaction mixture was diluted with EtOAc and washed with brine. The organic layer was dried over NaSO₄, filtered and concentrated under reduced pressure. The residue was purified by preparative HPLC to afford (1R,2R)-2-((6-((6-(trifluoromethyl)-3H-imidazo[4,5-b]pyridin-3-yl)methyl)benzo[d]thiazol-2-yl)amino)cyclohexanol as a yellow solid (64 mg, 31.8%). ¹H NMR (300 MHz, DMSO-d₆) δ 8.84 (s, 1H), 8.78 (d, J=1.2 Hz, 1H), 8.55 (d, J=1.5 Hz, 1H), 7.95 (d, J=7.8 Hz, 1H), 7.68 (d, J=1.5 Hz, 1H), 7.29 (d, J=7.8 Hz, 1H), 7.25-7.22 (m, 1H), 5.55 (s, 2H), 4.71 (d, J=5.1 Hz, 1H), 3.5-3.50 (m, 1H), 3.37-3.33 (m, 1H), 2.08-2.01 (m, 1H), 1.87-1.85 (m, 1H), 1.64-1.60 (m, 2H), 1.29-1.19 (m, 4H). LCMS (ESI) m/z 448 (M+H)⁺.

Example 213

Preparation of (1S,2S)-2-((6-((6-fluoro-3H-imidazo[4,5-b]pyridin-3-yl)methyl)benzo[d]thiazol-2-yl)amino)cyclohexanol

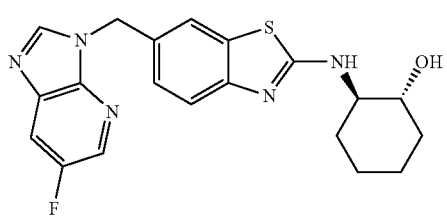 [SMILES: O[C@@H]1CCCC[C@H]1Nc1nc2ccc(Cn3cnc4cc(F)cnc43)cc2s1]

(1S,2S)-2-((6-((6-Fluoro-3H-imidazo[4,5-b]pyridin-3-yl)methyl)benzo[c]thiazol-2-yl)amino)cyclohexanol was synthesized as a white powder (48 mg, 42%) using a procedure analogous to that described in Step 5 of Example 162, substituting (1S,2S)-2-aminocyclohexanol for (1S,2R)-2-aminocyclohexanol hydrochloride used in Example 162. ¹H NMR (500 MHz, DMSO-d₆) δ 8.67 (s, 1H), 8.41 (t, J=2.0 Hz, 1H), 8.07 (dd, J=2.6, 9.5 Hz, 1H), 7.95 (d, J=7.6 Hz, 1H), 7.66 (d, J=1.2 Hz, 1H), 7.28 (m, 1H), 7.22 (dd, J=1.5, 8.4 Hz, 1H), 5.48 (s, 2H), 4.72 (d, J=5.2 Hz, 1H), 3.51 (m, 1H), 3.33 (m, 1H), 2.02 (m, 1H), 1.87 (m, 1H), 1.5-1.65 (m, 2H), 1.15-1.29 (m, 4H); LCMS (ESI) m/z 399 (M+H)⁺.

Example 214

Preparation of (1R,2R)-2-((6-((7-(1H-imidazol-1-yl)imidazo[1,2-a]pyridin-3-yl)methyl)benzo[d]thiazol-2-yl)amino)cyclohexanol

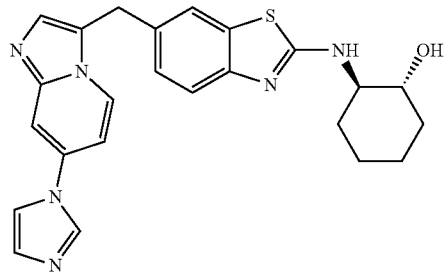

(1R,2R)-2-((6-((7-(1H-Imidazol-1-yl)imidazo[1,2-a]pyridin-3-yl)methyl)benzo[d]thiazol-2-yl)amino)cyclohexanol (27 mg, 47%) was obtained as a light tan solid using a procedure analogous to that described in Example 141, substituting (1R,2R)-2-((6-((7-iodoimidazo[1,2-a]pyridin-3-yl)methyl)benzo[d]thiazol-2-yl)amino)cyclohexanol from Step 1 of Example 167 and imidazole, respectively, for (1R,2R)-2-((6-((6-iodo-3H-imidazo[4,5-b]pyridin-3-yl)methyl)benzo[d]thiazol-2-yl)amino)cyclohexanol and pyrazole used in Example 141. ¹H NMR (500 MHz, DMSO-d₆) δ 8.42 (br s, 1H), 8.34 (d, J=6.9 Hz, 1H), 7.93 (br s, 1H), 7.90 (d, J=7.4 Hz, 2H), 7.54 (s, 1H), 7.49 (br s, 1H), 7.33 (d, J=7.4 Hz, 1H), 7.27 (d, J=8.4 Hz, 1H), 7.01-7.19 (m, 2H), 4.77 (br s, 1H), 4.33 (s, 2H), 3.51 (br s, 1H), 3.31-3.34 (m, 2H), 2.04 (d, J=11.8 Hz, 1H), 1.87 (d, J=10.8 Hz, 1H), 1.5-1.70 (m, 2H), 1.06-1.36 (m, 4H). LCMS (ESI) m/z 445 (M+H)⁺.

Example 215

Preparation of (1R,2R)-2-((6-((7-(2H-1,2,3-triazol-2-yl)imidazo[1,2-a]pyridin-3-yl)methyl)benzo[d]thiazol-2-yl)amino)cyclohexanol

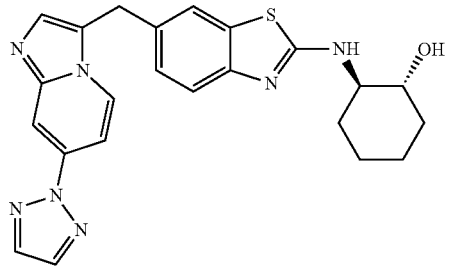

(1R,2R)-2-((6-((7-(2H-1,2,3-Triazol-2-yl)imidazo[1,2-a]pyridin-3-yl)methyl)benzo[d]thiazol-2-yl)amino)cyclohexanol (13 mg, 23%) was obtained as a light tan solid using a procedure analogous to that described in Example 141, substituting (1R,2R)-2-((6-((7-iodoimidazo[1,2-a]pyridin-3-yl)methyl)benzo[d]thiazol-2-yl)amino)cyclohexanol from Step 1 of Example 167 and 1,2,3-triazole, respectively, for (1R,2R)-2-((6-((6-iodo-3H-imidazo[4,5-b]pyridin-3-yl)methyl)benzo[d]thiazol-2-yl)amino)cyclohexanol and pyrazole used in Example 141. $^1$H NMR (500 MHz, DMSO-$d_6$) δ 8.40 (d, J=7.4 Hz, 1H), 8.18 (s, 2H), 8.04 (s, 1H), 7.90 (d, J=7.9 Hz, 1H), 7.63 (dd, J=2.0, 7.4 Hz, 1H), 7.54 (s, 1H), 7.51 (s, 1H), 7.28 (d, J=8.4 Hz, 1H), 7.11 (d, J=6.9 Hz, 1H), 4.77 (br s, 1H), 4.34 (s, 2H), 3.51 (br s, 3H), 2.04 (d, J=11.8 Hz, 1H), 1.87 (d, J=11.3 Hz, 1H), 1.5-1.69 (m, 2H), 1.10-1.36 (m, 4H). LCMS (ESI) m/z 446 (M+H)$^+$.

Example 216

Preparation of (1R,2R)-2-((6-((7-vinylimidazo[1,2-a]pyridin-3-yl)methyl)benzo[d]thiazol-2-yl)amino)cyclohexanol

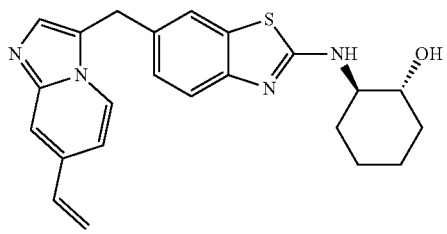 [SMILES: C=Cc1ccn2c(Cc3ccc4nc(N[C@@H]5CCCC[C@H]5O)sc4c3)cnc2c1]

Step 1:
Crude 4-vinylpyridin-2-amine (200 mg) was obtained as a light tan solid using a procedure analogous to that described in Example 98, substituting 4-iodopyridin-2-amine for (1R,2R)-2-((6-((6-bromo-3H-imidazo[4,5-b]pyridin-3-yl)methyl)benzo[d]thiazol-2-yl)amino)cyclohexanol used in Example 98. LCMS (ESI) m/z 121 (M+H)$^+$.

Step 2:
(1R,2R)-2-((6-((7-Vinylimidazo[1,2-a]pyridin-3-yl)methyl)benzo[d]thiazol-2-yl)amino)cyclohexanol (13 mg, 8%) was obtained as a light tan solid using a procedure analogous to that described in Step 6 of Example 117, substituting 4-vinylpyridin-2-amine from Step 1 of this Example and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. $^1$H NMR (500 MHz, DMSO-$d_6$) δ 8.14 (d, J=6.9 Hz, 1H), 7.86 (d, J=7.4 Hz, 1H), 7.52 (d, J=3.4 Hz, 2H), 7.40 (s, 1H), 7.26 (d, J=7.9 Hz, 1H), 7.13 (d, J=5.9 Hz, 1H), 7.09 (d, J=6.9 Hz, 1H), 6.77 (dd, J=10.8, 17.7 Hz, 1H), 5.91 (d, J=17.7 Hz, 1H), 5.34 (d, J=11.3 Hz, 1H), 4.72 (d, J=3.4 Hz, 1H), 4.28 (s, 2H), 3.52 (d, J=8.4 Hz, 2H), 2.03 (d, J=10.8 Hz, 1H), 1.87 (d, J=11.3 Hz, 1H), 1.5-1.70 (m, 2H), 1.11-1.36 (m, 4H). LCMS (ESI) m/z 405 (M+H)$^+$.

Example 217

Preparation of (1R,2R)-2-((6-((7-(allyloxy)imidazo[1,2-a]pyridin-3-yl)methyl)benzo[d]thiazol-2-yl)amino)cyclohexanol

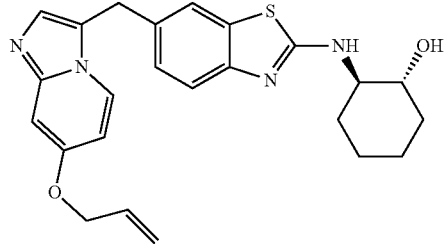 [SMILES: C=CCOc1ccn2c(Cc3ccc4nc(N[C@@H]5CCCC[C@H]5O)sc4c3)cnc2c1]

Step 1:
To a stirred solution of 2-aminopyridin-4-ol (500 mg, 4.5 mmol) in DMF (5 mL) at rt was added K$_2$CO$_3$ (940 mg, 6.8 mmol). The resulting mixture was stirred at rt for 20 min before allyl bromide (393 μL, 4.5 mmol) was added. The mixture was then stirred at rt overnight and heated at 60° C. for 2 h. After cooling to rt, the mixture was partitioned between EtOAc and water, and the organic layer was washed with brine, dried over Na$_2$SO$_4$, and evaporated under reduced pressure. The residue was purified by silica gel chromatography eluting with EtOAc in hexanes to give 4-(allyloxy)pyridin-2-amine (110 mg, 16%) as a white solid. LCMS (ESI) m/z 151 (M+H)$^+$.

Step 2:
(1R,2R)-2-((6-((7-(Allyloxy)imidazo[1,2-a]pyridin-3-yl)methyl)benzo[d]thiazol-2-yl)amino)cyclohexanol (56 mg, 34%) was obtained as a light tan solid using a procedure analogous to that described in Step 6 of Example 117, substituting 4-(allyloxy)pyridin-2-amine from Step 1 of this Example and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. $^1$H NMR (500 MHz, DMSO-$d_6$) δ 8.02 (d, J=7.4 Hz, 1H), 7.88 (d, J=7.9 Hz, 1H), 7.49 (s, 1H), 7.26 (d, J=7.9 Hz, 1H), 7.23 (s, 1H), 7.07 (d, J=8.4 Hz, 1H), 6.92 (d, J=2.5 Hz, 1H), 6.60 (dd, J=2.5, 7.4 Hz, 1H), 5.96-6.10 (m, 1H), 5.42 (d, J=17.2 Hz, 1H), 5.28 (d, J=10.3 Hz, 1H), 4.75 (br s, 1H), 4.61 (d, J=5.4 Hz, 2H), 4.22 (s, 2H), 3.51 (br s, 2H), 2.04 (d, J=11.8 Hz, 1H), 1.87-1.94 (m, 1H), 1.5-1.69 (m, 2H), 1.11-1.36 (m, 4H). LCMS (ESI) m/z 435 (M+H)$^+$.

Example 218

Preparation of (1R,2R)-2-((6-((7-(1H-1,2,3-triazol-1-yl)imidazo[1,2-a]pyridin-3-yl)methyl)benzo[d]thiazol-2-yl)amino)cyclohexanol

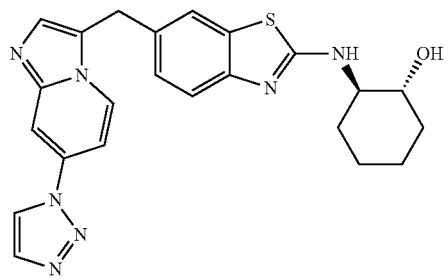 [SMILES: O[C@@H]1CCCC[C@H]1Nc1nc2ccc(Cc3cnc4cc(-n5ccnn5)ccn34)cc2s1]

(1R,2R)-2-((6-((7-(1H-1,2,3-triazol-1-yl)imidazo[1,2-a]pyridin-3-yl)methyl)benzo[d]thiazol-2-yl)amino)cyclohexanol (6 mg, 11%) was obtained as a light tan solid using a procedure analogous to that described in Example 141, substituting (1R,2R)-2-((6-((7-iodoimidazo[1,2-a]pyridin-3-yl)methyl)benzo[d]thiazol-2-yl)amino)cyclohexanol from Step 1 of Example 167 and 1,2,3-triazole, respectively, for (1R,2R)-2-((6-((6-iodo-3H-imidazo[4,5-b]pyridin-3-yl)methyl)benzo[d]thiazol-2-yl)amino)cyclohexanol and pyrazole used in Example 141. $^1$H NMR (500 MHz, DMSO-$d_6$) δ 8.98 (s, 1H), 8.44 (d, J=7.4 Hz, 1H), 8.17 (s, 1H), 8.01 (s, 1H), 7.96 (d, J=7.4 Hz, 1H), 7.58 (d, J=7.4 Hz, 1H), 7.55 (br s, 2H), 7.28 (d, J=8.4 Hz, 1H), 7.11 (d, J=8.4 Hz, 1H), 4.83 (br s, 1H), 4.35 (s, 2H), 3.50 (br s, 3H), 2.04 (d, J=11.8 Hz, 1H), 1.87 (d, J=10.8 Hz, 1H), 1.5-1.67 (m, 2H), 1.08-1.33 (m, 4H). LCMS (ESI) m/z 446 (M+H)$^+$.

Example 219

Preparation of N-((1R,2S)-2-chlorocyclohexyl)-6-((6-fluoro-3H-imidazo[4,5-b]pyridin-3-yl)methyl)benzo[d]thiazol-2-amine

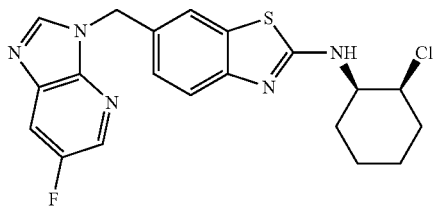 [SMILES: Fc1cnc2c(c1)ncn2Cc1ccc2nc(N[C@@H]3CCCC[C@@H]3Cl)sc2c1]

N-((1R,2S)-2-Chlorocyclohexyl)-6-((6-fluoro-3H-imidazo[4,5-b]pyridin-3-yl)methyl)benzo[d]thiazol-2-amine was synthesized as a white powder (6 mg, 2%) using a procedure analogous to that described in Example 198, substituting (1R,2R)-2-((6-((6-fluoro-3H-imidazo[4,5-b]pyridin-3-yl)methyl)benzo[d]thiazol-2-yl)amino)cyclohexanol for (1S,2R)-2-((6-((6-fluoro-3H-imidazo[4,5-b]pyridin-3-yl)methyl)benzo[d]thiazol-2-yl)amino)cyclohexanol used in Example 198. $^1$H NMR (500 MHz, CDCl$_3$) δ 8.68 (s, 1H), 8.41 (s, 1H), 8.24 (d, J=8.4 Hz, 1H), 8.07 (dd, J=2.6, 9.5 Hz, 1H), 7.68 (s, 1H), 7.33 (d, J=8.4 Hz, 1H), 7.24 (dd, J=1.4, 8.2 Hz, 1H), 5.48 (s, 2H), 4.02 (m, 1H), 3.87 (m, 1H), 2.20 (m, 1H), 2.07 (m, 1H), 1.63-1.75 (m, 3H), 1.29-1.41 (m, 3H); LCMS (ESI) m/z 416 (M+H)$^+$.

Example 220

Preparation of 3-amino-1-((2-(((1R,2R)-2-hydroxycyclohexyl)amino)benzo[d]thiazol-6-yl)methyl)pyrazin-2(1H)-one acetate salt

Step 1:
To a stirred mixture of sodium iodide (4.89 g, 32.67 mmol) and 2-iodo-3-methoxypyrazine (2.57 g, 10.89 mmol) in acetonitrile (30 mL) at rt was added trimethylsilyl chloride (3.55 g, 32.67 mmol). The mixture was heated at 70° C. for 1.5 h. The mixture was cooled to rt and partitioned between a mixture of DCM, MeOH, and aq 2 M HCl. The organic layer was separated and the aqueous layer was extracted with additional DCM/MeOH mixture. The combined organic layers were dried over MgSO$_4$, filtered, and concentrated under reduced pressure to afford 3-iodopyrazin-2(1H)-one (1.21 g, 50%) as a brown solid that did not require further purification. $^1$H NMR (500 MHz, DMSO-$d_6$) δ 12.54 (br s, 1H), 7.42 (d, J=3.7 Hz, 1H), 7.17 (d, J=3.7 Hz, 1H); LCMS (ESI) m/z 223 (M+H)$^+$.

Step 2:
3-Iodo-1-((2-(methylthio)benzo[d]thiazol-6-yl)methyl)pyrazin-2(1H)-one (1 g) was obtained as a brown solid using a procedure analogous to that described in Step 2 of Example 203, substituting 3-iodopyrazin-2(1H)-one from Step 1 of this Example for N-(4-bromo-2-fluoro-6-nitrophenyl)formamide used in Example 203. $^1$H NMR (500 MHz, DMSO-$d_6$) δ 7.98 (s, 1H), 7.81-7.85 (m, 2H), 7.45 (m, 1H), 7.23 (m, 1H), 5.19 (s, 2H), 2.77 (s, 3H); LCMS (ESI) m/z 416 (M+H)$^+$.

Step 3:
A stirred mixture of 3-iodo-1-((2-(methylthio)benzo[d]thiazol-6-yl)methyl)pyrazin-2(1H)-one (750 mg, 1.81 mmol), ammonia (7 M solution in MeOH, 2 mL, 14 mmol), and DMSO (1.5 mL), was heated in a Biotage Microwave Synthesizer at 150° C. for 15 min. The mixture was cooled to and partitioned between EtOAc and a 1:1 mixture of water and brine. The organic layer was separated, dried over MgSO$_4$, filtered, and concentrated under reduced pressure. The residue was purified by silica gel flash chromatography eluting with a gradient of 100% DCM to 2% MeOH in DCM to afford 3-amino-1-((2-(methylthio)benzo[d]thiazol-6-yl)methyl)pyrazin-2(1H)-one (149 mg) as a yellow solid. $^1$H NMR (500 MHz, DMSO-$d_6$) δ 7.96 (s, 1H), 7.82 (d, J=8.4 Hz, 1H), 7.43 (dd, J=1.5, 8.4 Hz, 1H), 6.92 (d, J=4.7 Hz, 1H), 6.65-6.67 (br m, 3H), 5.11 (s, 2H), 2.78 (s, 3H); LCMS (ESI) m/z 305 (M+H)$^+$.

Step 4:
3-Amino-1-((2-(methylsulfinyl)benzo[d]thiazol-6-yl)methyl)pyrazin-2(1H)-one (84 mg, 54%) was obtained as a yellow solid using a procedure analogous to that described in Step 4 of Example 130, substituting 3-amino-1-((2-(methylthio)benzo[d]thiazol-6-yl)methyl)pyrazin-2(1H)-one from Step 3 of this Example for 2-(methylthio)-6-((5-(trifluoromethyl)-1H-benzo[d]imidazol-1-yl)methyl)benzo[d]thiazole used in Example 130. $^1$H NMR (500 MHz, DMSO-$d_6$) δ 8.20 (s, 1H), 8.08 (d, J=8.6 Hz, 1H), 7.59 (dd, J=1.5, 8.4 Hz, 1H), 6.94 (d, J=4.7 Hz, 1H), 6.69 (d, J=4.4 Hz, 3H), 5.19 (s, 2H), 3.07 (s, 3H); LCMS (ESI) m/z 321 (M+H)+.

Step 5:
3-Amino-1-((2-(((1R,2R)-2-hydroxycyclohexyl)amino)benzo[d]thiazol-6-yl)methyl)pyrazin-2(1H)-one acetate salt (19 mg, 17%) was obtained as a solid using a procedure analogous to that described in Step 5 of Example 203, substituting 3-amino-1-((2-(methylsulfinyl)benzo[d]thiazol-6-yl)methyl)pyrazin-2(1H)-one from Step 4 of this Example for 6-((5-bromo-7-fluoro-1H-benzo[d]imidazol-1-yl)methyl)-2-(methylsulfinyl)benzo[d]thiazole used in Example 130. $^1$H NMR (500 MHz, DMSO-$d_6$) δ 7.99 (d, J=7.4 Hz, 1H), 7.62 (s, 1H), 7.30 (d, J=8.1 Hz, 1H), 7.19 (dd, J=1.5, 8.1 Hz, 1H), 6.87 (d, J=4.7 Hz, 1H), 6.60-6.80 (m, 3H), 4.99 (s, 2H), 3.20-3.60 (m, 4H), 2.04 (m, 1H), 1.88 (s, 3H), 1.5-1.67 (m, 2H), 1.12-1.33 (m, 4H); LCMS (ESI) m/z 372 (M+H)+.

Example 221

Preparation of 3-((2-(((1R,2R)-2-hydroxycyclohexyl)amino)benzo[d]thiazol-6-yl)methyl)imidazo[1,2-b]pyridazine-6-carbonitrile

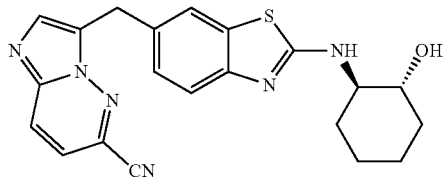

Step 1:
A stirred mixture of 2-chloro-3-(2-(methylthio)benzo[d]thiazol-6-yl)propanal from Step 4 of Example 117 (1.3 g, 4.8 mmol) and 6-aminopyridazine-3-carbonitrile (0.8 g, 7.2 mmol) in 1-butanol (48 mL) was heated at reflux overnight. The mixture was cooled to rt and water (100 mL) was added. The mixture was extracted with EtOAc (3×60 mL, and the combined organic layers were washed with brine, dried over Na$_2$SO$_4$, filtered and concentrated under reduced pressure. The residue was purified by silica gel chromatography eluting with 50:1 to 20:1 DCM/MeOH to afford 3-((2-(methylthio)benzo[d]thiazol-6-yl)methyl)imidazo[1,2-b]pyridazine-6-carbonitrile as a yellow solid (0.7 g, 44%). $^1$H NMR (300 MHz, CDCl$_3$) δ 8.09 (d, J=9.0 Hz, 1H), 7.83-7.78 (m, 2H), 7.69 (s, 1H), 7.36 (d, J=8.4 Hz, 1H), 7.29 (d, J=9.3 Hz, 1H), 4.46 (s, 2H), 2.78 (s, 3H). LCMS (ESI) m/z 338 (M+H)+.

Step 2:
To a solution of 3-((2-(methylthio)benzo[d]thiazol-6-yl)methyl)imidazo[1,2-b]pyridazine-6-carbonitrile (0.7 g, 2.1 mmol) in DCM (30 mL) at 0° C. was slowly added m-CPBA (0.4 g, 2.1 mmol). The reaction mixture was stirred at 0° C. for 2 h, then aq Na$_2$SO$_3$ (25 mL) was added and the mixture was stirred for 0.5 h. The organic layer was separated and dried over Na$_2$SO$_4$, filtered and concentrated under reduced pressure. The residue was purified by silica gel chromatography eluting with 50:1 to 20:1 DCM/MeOH to afford 3-((2-(methylsulfinyl)benzo[d]thiazol-6-yl)methyl)imidazo[1,2-b]pyridazine-6-carbonitrile as a yellow solid (0.7 g, 96%). $^1$H NMR (300 MHz, CDCl$_3$) δ 8.11 (d, J=9.3 Hz, 1H), 8.02 (d, J=8.4 Hz, 1H), 7.92 (s, 1H), 7.82 (s, 1H), 7.51 (d, J=8.4 Hz, 1H), 7.31 (d, J=9.3 Hz, 1H), 4.54 (s, 2H), 3.07 (s, 3H). LCMS (ESI) m/z 354 (M+H)+.

Step 3:
A mixture of 3-((2-(methylsulfinyl)benzo[d]thiazol-6-yl)methyl)imidazo[1,2-b]pyridazine-6-carbonitrile (300 mg, 0.9 mmol), (1R,2R)-2-aminocyclohexanol (293 mg, 2.5 mmol) and DIEA (219 mg, 1.7 mmol) in NMP (16 mL) was stirred at 135° C. overnight. The mixture was cooled to rt and water (40 mL) was added. The mixture was extracted with EtOAc (3×30 mL). The combined organic layers were washed with brine, dried over Na$_2$SO$_4$, filtered and concentrated under reduced pressure. The residue was purified by silica gel chromatography eluting with 50:1 to 20:1 DCM/MeOH to afford 3-((2-(((1R,2R)-2-hydroxycyclohexyl)amino)benzo[d]thiazol-6-yl)methyl)imidazo[1,2-b]pyridazine-6-carbonitrile as a brown solid (100 mg, 30%).

1H NMR (300 MHz, DMSO-d$_6$) δ 8.40 (d, J=9.3 Hz, 1H), 7.87-7.84 (m, 2H), 7.70 (d, J=9.3 Hz, 1H), 7.55 (d, J=1.5 Hz, 1H), 7.28 (d, J=8.1 Hz, 1H), 7.13 (dd, J=1.5, 8.1 Hz, 1H), 4.72 (d, J=5.1 Hz, 1H), 4.36 (s, 2H), 3.5-3.51 (m, 1H), 3.39-3.36 (m, 1H), 2.06-2.02 (m, 1H), 1.90-1.86 (m, 1H), 1.65-1.59 (m, 2H), 1.31-1.17 (m, 4H). LCMS (ESI) m/z 405 (M+H)+.

Example 222

Preparation of 1-((2-(((1R,2R)-2-hydroxycyclohexyl)amino)benzo[d]thiazol-6-yl)methyl)-3-morpholinopyrazin-2(1H)-one

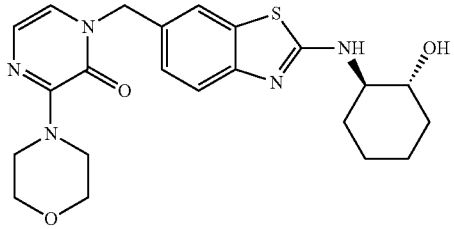 [SMILES: O=c1c(N2CCOCC2)nccn1Cc1ccc2nc(N[C@@H]3CCCC[C@H]3O)sc2c1]

Step 1:
A mixture of 2,3-dichloropyrazine (894 mg, 6 mmol), morpholine (523 mg, 6 mmol) and DIEA (1.55 g, 12 mmol) in DMSO (8 mL) was stirred at 70° C. for 2 h. The reaction mixture was poured into water (30 mL) and extracted with ethyl acetate (3×20 mL). The combined organic layers were washed with 2N aq HCl (30 mL), water (2×30 mL) and brine, dried over Na$_2$SO$_4$, filtered and concentrated under reduced pressure to give 4-(3-chloropyrazin-2-yl)morpholine as a light yellow solid (1.01 g, 92.8%). $^1$H NMR (300 MHz, DMSO-d$_6$) δ 8.11 (d, J=2.4 Hz, 1H), 7.90 (d, J=2.7 Hz, 1H), 3.86 (t, J=9.3 Hz, 4H), 3.45 (t, J=9.6 Hz, 4H). LCMS (ESI) m/z 200 (M+H)+.

Step 2:
A mixture of 4-(3-chloropyrazin-2-yl)morpholine (894 mg, 6 mmol) and aq NaOH (13 mL, 52 mmol) in DMSO (18 mL) was stirred at 80° C. for 2 h. The reaction mixture was poured into water (30 mL) and extracted with ethyl acetate (3×20 mL). The combined organic layers were washed with brine, dried over Na$_2$SO$_4$, filtered and concentrated under reduced pressure to give 3-morpholinopyrazin-2(1H)-one as a light yellow solid (807 mg, 92.9%). $^1$H NMR (300 MHz, CDCl$_3$) δ 11.80 (br s, 1H), 7.05 (d, J=4.2 Hz, 1H), 6.73 (d, J=4.2 Hz, 1H), 3.84 (s, 8H). LCMS (ESI) m/z 182 (M+H)+.

Step 3:
To a stirred solution of 3-morpholinopyrazin-2(1H)-one (317 mg, 1.75 mmol) in DMF (8 mL) at 0° C. was added NaH (60% in mineral oil, 105 mg, 2.63 mmol). After stirring for 20 min, a solution of 6-(chloromethyl)-2-(methylthio)benzo[d]thiazole (400 mg, 1.75 mmol) in DMF (2 mL) was added dropwise, and the mixture was stirred at rt for 2 h. The mixture was poured into water and extracted with ethyl acetate (3×20 mL). The combined organic layers were washed with brine, dried over Na$_2$SO$_4$, filtered and concentrated under reduced pressure to give 1-((2-(methylthio)benzo[d]thiazol-6-yl)methyl)-3-morpholinopyrazin-2(1H)-one as a light yellow solid (625 mg, 95.4%). $^1$H NMR (300 MHz, CDCl$_3$) δ 7.82 (d, J=8.4 Hz, 1H), 7.71 (s, 1H), 7.36 (d, J=6.6 Hz, 1H), 6.92 (d, J=4.2 Hz, 1H), 6.71 (d, J=4.2 Hz, 1H), 5.10 (s, 2H), 3.81 (s, 8H), 2.80 (s, 3H). LCMS (ESI) m/z 375 (M+H)+.

Step 4:

A solution of 1-((2-(methylthio)benzo[d]thiazol-6-yl)methyl)-3-morpholinopyrazin-2(1H)-one (752 mg, 2.0 mmol) and m-CPBA (449 mg, 2.6 mmol) in DCM (20 mL) was stirred at 0° C. for 4 h. The reaction mixture was washed with aqueous Na$_2$S$_2$O$_3$ and brine. The organic layer was dried over Na$_2$SO$_4$, filtered and concentrated under reduced pressure. The residue was purified by silica gel chromatography eluting with 1:3 petroleum ether/ethyl acetate to give 1-((2-(methylsulfinyl)benzo[d]thiazol-6-yl)methyl)-3-morpholinopyrazin-2(1H)-one as a light yellow solid (430 mg, 55.1%). $^1$H NMR (300 MHz, DMSO-d$_6$) δ 8.20 (s, 1H), 8.08 (d, J=8.4 Hz, 1H), 7.59 (d, J=6.9 Hz, 1H), 7.29 (d, J=4.5 Hz, 1H), 6.96 (d, J=4.2 Hz, 1H), 5.20 (s, 2H), 3.65 (s, 8H), 3.07 (s, 3H). LCMS (ESI) m/z 391 (M+H)$^+$.

Step 5:

A mixture of 1-((2-(methylsulfinyl)benzo[d]thiazol-6-yl)methyl)-3-morpholino pyrazin-2(1H)-one (250 mg, 0.64 mmol), (1R,2R)-2-aminocyclohexanol (221 mg, 1.92 mmol) and DIEA (248 mg, 1.92 mmol) in DMA (6.6 mL) was stirred at 130° C. for 16 h. The reaction mixture was cooled to rt and poured into water (30 mL). The mixture extracted with ethyl acetate (3×100 mL) and the combined organic layers were washed with brine, dried over Na$_2$SO$_4$, filtered and concentrated under reduced pressure. The residue was purified by silica gel chromatography eluting with 1:5 petroleum ether/ethyl acetate to give 1-((2-(((1R,2R)-2-hydroxycyclohexyl)amino)benzo[d]thiazol-6-yl)methyl)-3-morpholinopyrazin-2(1H)-one as a light yellow solid (120 mg, 26.5%). $^1$H NMR (300 MHz, DMSO-d$_6$) δ 7.96 (d, J=7.2 Hz, 1H), 7.63 (s, 1H), 7.30 (d, J=8.4 Hz, 1H), 7.18-7.22 (m, 2H), 6.90 (d, J=4.8 Hz, 1H), 5.01 (s, 2H), 4.72 (d, J=5.1 Hz, 1H), 3.65 (s, 8H), 3.5-3.52 (m, 1H), 3.36-3.31 (m, 1H), 2.07-2.02 (m, 1H), 1.90-1.86 (m, 1H), 1.63-1.62 (m, 2H), 1.30-1.22 (m, 4H). LCMS (ESI) m/z 442 (M+H)$^+$.

Example 223

Preparation of (3-((2-(((1R,2R)-2-hydroxycyclohexyl)amino)benzo[d]thiazol-6-yl)methyl)imidazo[1,2-a]pyridin-7-yl)(pyrrolidin-1-yl)methanone

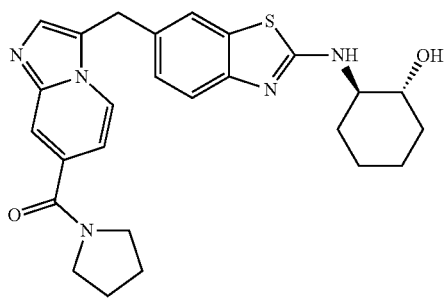 [SMILES: O=C(c1ccn2c(Cc3ccc4nc(N[C@@H]5CCCC[C@H]5O)sc4c3)cnc2c1)N1CCCC1]

(3-((2-(((1R,2R)-2-Hydroxycyclohexyl)amino)benzo[d]thiazol-6-yl)methyl)imidazo[1,2-a]pyridin-7-yl)(pyrrolidin-1-yl)methanone (65 mg, 46%) was obtained as a light tan solid using a procedure analogous to that described in Step 6 of Example 117, substituting (2-aminopyridin-4-yl)(pyrrolidin-1-yl)methanone and 2-chloro-3-(2-(((1R,2R)-2-hydroxycyclohexyl)amino)benzo[d]thiazol-6-yl)propanal from Step 2 of Example 153, respectively, for 2-aminoisonicotinonitrile and 2-chloro-3-(2-(methylthio)benzo[d]thiazol-6-yl)propanal used in Example 117. $^1$H NMR (500 MHz, DMSO-d$_6$) δ 8.24 (d, J=6.9 Hz, 1H), 8.01 (d, J=7.4 Hz, 1H), 7.72 (s, 1H), 7.53 (s, 2H), 7.31 (br s, 1H), 7.27 (d, J=7.9 Hz, 1H), 7.10 (d, J=8.4 Hz, 1H), 6.99 (d, J=6.9 Hz, 1H), 6.78 (br s, 1H), 4.88 (br s, 1H), 4.31 (s, 2H), 3.43-3.58 (m, 6H), 2.04 (d, J=12.3 Hz, 1H), 1.76-1.94 (m, 5H), 1.5-1.68 (m, 2H), 1.10-1.27 (m, 4H). LCMS (ESI) m/z 476 (M+H)$^+$.

Example 224

Preparation of (E)-3-(1-((2-(((1R,2R)-2-hydroxycyclohexyl)amino)benzo[d]thiazol-6-yl)methyl)-1H-benzo[d]imidazol-5-yl)acrylic acid

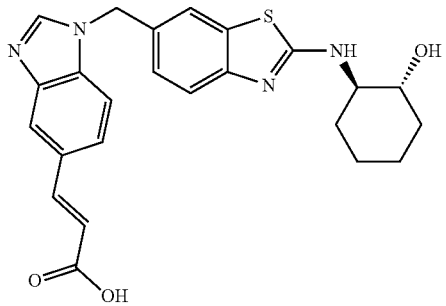 [SMILES: O=C(O)/C=C/c1ccc2c(c1)ncn2Cc1ccc2nc(N[C@@H]3CCCC[C@H]3O)sc2c1]

Step 1:

To a stirred solution of (1R,2R)-2-((6-((5-iodo-1H-benzo[d]imidazol-1-yl)methyl)benzo[d]thiazol-2-yl)amino)cyclohexanol (150 mg, 0.30 mmol) from Step 5 of Example 183 in DMF (2 mL) were added ethyl acrylate (0.036 mL, 0.33 mmol), palladium (II) acetate (7 mg 0.03 mmol), and triethylamine (0.088 mL, 0.63 mmol). The mixture was flushed with argon and heated in a sealed vessel at 120° C. for 3 h. The mixture was cooled to rt and partitioned between EtOAc and water. The separated aqueous layer was extracted twice with EtOAc and the combined organic phases were washed three times with a 1:1 mixture of water and brine, dried over MgSO$_4$, filtered, and concentrated under reduced pressure to afford (E)-ethyl 3-(1-((2-(((1R,2R)-2-hydroxycyclohexyl)amino)benzo[d]thiazol-6-yl)methyl)-1H-benzo[d]imidazol-5-yl)acrylate (187 mg) as a solid. The product was used directly in the next step. LCMS (ESI) m/z 477 (M+H)$^+$.

Step 2:

To a stirred solution of (E)-ethyl 3-(1-((2-(((1R,2R)-2-hydroxycyclohexyl)amino)benzo[d]thiazol-6-yl)methyl)-1H-benzo[d]imidazol-5-yl)acrylate from the previous step in THF (2 mL) was added 1M aq LiOH (2 mL) and the mixture was stirred at rt for 48 h. The mixture was then acidified and concentrated under reduced pressure. The residue was purified directly by reverse-phase preparative HPLC using a mixture of water (5% CH$_3$CN, 0.05% HOAc) and CH$_3$CN (0.05% HOAc) as the mobile phase and Varian Pursuit XRs diphenyl column as the stationary phase to afford (E)-3-(1-((2-(((1R,2R)-2-hydroxycyclohexyl)amino)benzo[d]thiazol-6-yl)methyl)-1H-benzo[d]imidazol-5-yl)acrylic acid as a solid (22 mg, 16%). $^1$H NMR (500 MHz, DMSO-d$_6$) δ 8.46 (s, 1H), 7.90-8.01 (m, 2H), 7.68 (d, J=15.8 Hz, 1H), 7.66 (d, J=1.0 Hz, 1H), 7.58 (s, 2H), 7.29 (d, J=10 Hz, 1H), 7.20 (dd, J=1.2, 8.1 Hz, 1H), 6.48 (d, J=15.8 Hz, 1H), 5.48 (s, 2H), 4.73 (br s, 1H), 3.47-3.57 (br m, 2H), 2.02

(m, 1H), 1.86 (m, 1H), 1.5-1.67 (m, 2H), 1.12-1.32 (m, 4H). LCMS (ESI) m/z 449 (M+H)⁺.

Example 225

Preparation of (1R,2R)-2-((6-((5-(1,2,3,6-tetrahydropyridin-4-yl)-1H-benzo[d]imidazol-1-yl)methyl)benzo[d]thiazol-2-yl)amino)cyclohexanol

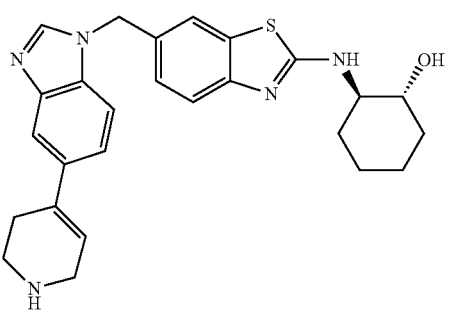 [SMILES: O[C@@H]1CCCC[C@H]1Nc1nc2ccc(Cn3cnc4cc(C5=CCNCC5)ccc43)cc2s1]

Step 1:
To a stirred solution of (1R,2R)-2-((6-((5-iodo-1H-benzo[d]imidazol-1-yl)methyl)benzo[d]thiazol-2-yl)amino)cyclohexanol (100 mg, 0.20 mmol) from Step 5 of Example 183 in DMF (2 mL) were added N-Boc-1,2,5,6-tetrahydropyridine-4-boronic acid pinacol ester (93 mg, 0.30 mmol), potassium carbonate (55 mg 0.40 mmol), bis-triphenylphosphine palladium (II) chloride (6.3 mg, 0.009 mmol), and 1,1'-bis(diphenylphosphino)ferrocene (5 mg, 0.009 mmol). The mixture was flushed with argon and heated in a sealed vessel at 80° C. for 15 h. The reaction mixture was purified directly by reverse-phase preparative HPLC using a mixture of water (5% CH₃CN, 0.05% HOAc) and CH₃CN (0.05% HOAc) as the mobile phase and Varian Pursuit XRs diphenyl column as the stationary phase to afford tert-butyl 4-(1-((2-(((1R,2R)-2-hydroxycyclohexyl)amino)benzo[d]thiazol-6-yl)methyl)-1H-benzo[d]imidazol-5-yl)-5,6-dihydropyridine-1(2H-carboxylate as a solid (35 mg, 31%). ¹H NMR (500 MHz, DMSO-d₆) δ 8.38 (s, 1H), 7.97 (d, J=7.9 Hz, 1H), 7.66 (s, 1H), 7.63 (s, 1H), 7.49 (d, J=8.4 Hz, 1H), 7.33 (m, 1H), 7.28 (d, J=8.4 Hz, 1H), 7.18 (dd, J=1.2, 8.1 Hz, 1H), 6.09 (br s, 1H), 5.45 (s, 2H), 4.75 (d, J=3.9 Hz, 1H), 3.98 (br s, 2H), 3.46-3.59 (m, 4H), 3.36-3.42 (m, 2H), 2.02 (m, 1H), 1.87 (m, 1H), 1.5-1.67 (m, 2H), 1.38-1.48 (m, 9H), 1.13-1.32 (m, 4H); LCMS (ESI) m/z 560 (M+H)⁺.

Step 2:
To a stirred solution of tert-butyl 4-(1-((2-(((1R,2R)-2-hydroxycyclohexyl)amino)benzo[d]thiazol-6-yl)methyl)-1H-benzo[d]imidazol-5-yl)-5,6-dihydropyridine-1(2H-carboxylate (30 mg, 0.05 mmol) from the previous step in DCM (3 mL) at 0° C. was added 4M HCl in 1,4-dioxane (0.3 mL), and the mixture was stirred at 0° C. for 5 min. The mixture concentrated under reduced pressure and the residue was purified by reverse-phase preparative HPLC using a mixture of water (5% CH₃CN, 0.05% HOAc) and CH₃CN (0.05% HOAc) as the mobile phase and Phenomenex Luna C-18 column as the stationary phase to afford (1R,2R)-2-((6-((5-(1,2,3,6-tetrahydropyridin-4-yl)-1H-benzo[d]imidazol-1-yl)methyl)benzo[d]thiazol-2-yl)amino)cyclohexanol as a solid (1.38 mg, 5%). ¹H NMR (500 MHz, DMSO-d₆) δ 8.36 (s, 1H), 8.00 (d, J=7.4 Hz, 1H), 7.62 (d, J=5.9 Hz, 2H), 7.47 (d, J=8.9 Hz, 1H), 7.31 (d, J=8.4 Hz, 1H), 7.28 (d, J=8.4 Hz, 1H), 7.18 (dd, J=1.2, 8.1 Hz, 1H), 6.14 (br s, 1H), 5.44 (s, 2H), 3.47-3.57 (br m, 2H), 2.94 (t, J=5.4 Hz, 2H), 2.40 (br s, 2H), 2.02 (d, J=11.8 Hz, 1H), 1.85-1.87 (m, 6H), 1.5-1.66 (m, 2H), 1.12-1.30 (m, 4H); LCMS (ESI) m/z 460 (M+H)⁺.

Example 226

Preparation of (1R,2R)-2-((6-((5-(1H-imidazol-1-yl)-1H-benzo[d]imidazol-1-yl)methyl)benzo[d]thiazol-2-yl)amino)cyclohexanol

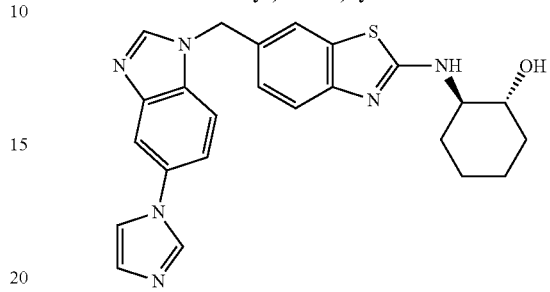

A stirred mixture of (1R,2R)-2-((6-((5-iodo-1H-benzo[d]imidazol-1-yl)methyl)benzo[d]thiazol-2-yl)amino)cyclohexanol (250 mg, 0.50 mmol) from Step 5 of Example 183, imidazole (80 mg, 1.18 mmol), potassium carbonate (82 mg, 0.59 mmol), trans-N,N-dimethylcyclohexane-1,2-diamine (9 mg, 0.063 mmol), copper (I) iodide (30 mg, 0.158 mmol) and DMF (2 mL) was heated at 120° C. for 3 h. The reaction mixture was cooled to rt and partitioned between EtOAc and water. The organic layer was separated, dried over Na₂SO₄, filtered, and concentrated under reduced pressure. The residue was purified by silica gel flash chromatography, eluting with 20:1 DCM: MeOH, to afford (1R,2R)-2-((6-((5-(1H-imidazol-1-yl)-1H-benzo[d]imidazol-1-yl)methyl)benzo[d]thiazol-2-yl)amino)cyclohexanol (78 mg, 35%) as a white solid. ¹H NMR (300 MHz, DMSO-d₆) δ 8.52 (s, 1H), 8.18 (s, 1H), 7.91-7.96 (m, 2H), 7.72-7.86 (m, 3H), 7.47 (dd, J=8.4, 1.8 Hz, 1H), 7.30 (d, J=8.1 Hz, 1H), 7.21 (dd, J=8.1, 1.5 Hz, 1H), 7.07 (d, J=1.2 Hz, 1H), 5.52 (s, 2H), 4.71 (d, J=5.1 Hz, 1H), 3.51 (m, 1H), 3.38 (m, 1H), 2.02 (m, 1H), 1.88 (m, 1H), 1.60-1.80 (m, 2H), 1.15-1.28 (m, 4H); LCMS (ESI) m/z 445 (M+H)⁺.

Example 227

Preparation of (1R,2R)-2-((6-((5-(2-methyl-2H-tetrazol-5-yl)-1H-benzo[d]imidazol-1-yl)methyl)benzo[d]thiazol-2-yl)amino)cyclohexanol

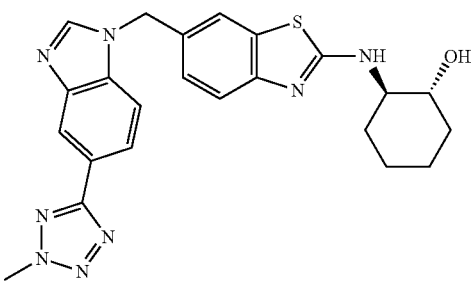 [SMILES: Cn1nnc(-c2ccc3c(c2)ncn3Cc2ccc3nc(N[C@@H]4CCCC[C@H]4O)sc3c2)n1]

(1R,2R)-2-((6-((5-(2-Methyl-2H-tetrazol-5-yl)-1H-benzo[d]imidazol-1-yl)methyl)benzo[d]thiazol-2-yl)amino)cyclohexanol (18 mg, 18%) was obtained as a solid using a procedure analogous to that described in Step 5 of Example 203, substituting 6-((5-(2-methyl-2H-tetrazol-5-yl)-1H-benzo[d]imidazol-1-yl)methyl)-2-(methylsulfinyl)benzo[d]

thiazole from Step 6 of Example 236 for 6-((5-bromo-7-fluoro-1H-benzo[d]imidazol-1-yl)methyl)-2-(methylsulfinyl)benzo[d]thiazole used in Example 203. ¹H NMR (300 MHz, DMSO-d₆) δ 8.53 (s, 1H), 8.29 (s, 1H), 7.91-7.97 (m, 2H), 7.68-7.76 (m, 2H), 7.21-7.32 (m, 2H), 5.52 (s, 2H), 4.72 (d, J=5.1 Hz, 1H), 4.42 (s, 3H), 3.51 (m, 1H), 3.38 (m, 1H), 2.02 (m, 1H), 1.88 (m, 1H), 1.60-1.80 (m, 2H), 1.15-1.28 (m, 4H); LCMS (ESI) m/z 461 (M+H)⁺.

Example 228

Preparation of (1S,2R,3R)-3-((6-((6-fluoro-3H-imidazo[4,5-b]pyridin-3-yl)methyl)benzo[d]thiazol-2-yl)amino)cyclohexane-1,2-diol

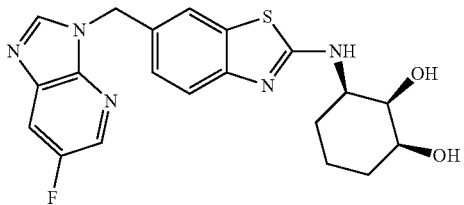 [SMILES: O[C@H]1[C@@H](O)CCC[C@H]1Nc1nc2ccc(Cn3cnc4cc(F)cnc43)cc2s1]

To a stirred mixture of NMO in tert-butanol (5 mL), THF (1.5 mL), H₂O (0.5 mL), and a 4% wt solution of OsO₄ in H₂O (10 μL, 0.3 mmol) at rt was added portionwise (R)—N-(cyclohex-2-en-1-yl)-6-((6-fluoro-3H-imidazo[4,5-b]pyridin-3-yl)methyl)benzo[d]thiazol-2-amine (142 mg, 0.4 mmol) from Example 176. After the mixture was stirred at rt for 18 h, it was partitioned between EtOAc (200 mL) and 0.5 M aq K₂CO₃ (100 mL). The organic layer was separated, washed with brine (100 mL), dried over MgSO₄, filtered, and concentrated under reduced pressure. The residue was purified twice by reverse-phase preparative HPLC eluting with a mixture of water (5% CH₃CN, 0.05% HCOOH) and CH₃CN (0.05% HCOOH) as the mobile phase and Varian Pursuit XRs C18 column as the stationary phase to afford (1S,2R,3R)-3-((6-((6-fluoro-3H-imidazo[4,5-b]pyridin-3-yl)methyl)benzo[d]thiazol-2-yl)amino)cyclohexane-1,2-diol (7 mg, 2%) as a white powder. ¹H NMR (500 MHz, DMSO-d₆) δ 8.67 (s, 1H), 8.40 (m, 1H), 8.07 (dd, J=2.6, 9.5 Hz, 1H), 7.95 (d, J=7.9 Hz, 1H), 7.66 (d, J=1.2 Hz, 1H), 7.29 (d, J=8.4 Hz, 1H), 7.21 (dd, J=1.6, 8.2 Hz, 1H), 5.47 (s, 2H), 4.45-4.70 (m, 2H), 3.88 (br s, 1H), 3.76 (m, 1H), 3.43 (m, 1H), 1.40-1.62 (m, 5H), 1.25 (m, 1H); LCMS (ESI) m/z 414 (M+H)⁺.

Example 229

Preparation of (1R,2S,3R)-3-((6-((7-(1H-pyrazol-1-yl)imidazo[1,2-a]pyridin-3-yl)methyl)benzo[d]thiazol-2-yl)amino)cyclohexane-1,2-diol

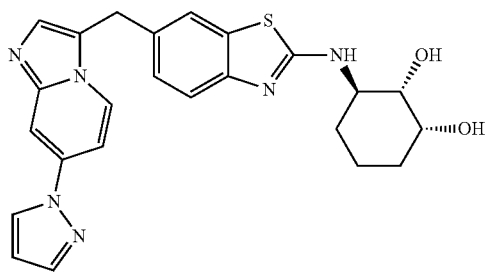 [SMILES: O[C@@H]1[C@H](O)CCC[C@H]1Nc1nc2ccc(Cc3cnc4cc(-n5cccn5)ccn34)cc2s1]

Step 1:
A 20 mL reaction vessel was charged with 4-iodopyridin-2-amine (1.5 g, 6.8 mmol) and 1H-pyrazole (4.0 g, 58.9 mmol). Concentrated hydrochloric acid (1.5 ml) and 1,4-dioxane (1.5 mL) were added, and the reaction vessel was sealed. The mixture was irradiated in a microwave oven at 120° C. for 45 min and then at 130° C. for 60 min. The mixture was cooled to rt and then diethyl ether (6 ml) and ethanol (3 ml) were added. The mixture was sonicated for 10 min, and the solid was collected by filtration and washed with diethyl ether and n-hexane to give 4-(1H-pyrazol-1-yl)pyridin-2-amine hydrochloride (1.2 g, 90%) as a white solid. LCMS (ESI) m/z 161 (M+H)⁺.

Step 2:
6-((7-(1H-pyrazol-1-yl)imidazo[1,2-a]pyridin-3-yl)methyl)-2-(methylthio)benzo[d]thiazole (176 mg, 63%) was obtained as a yellow solid using a procedure analogous to that described in Step 6 of Example 117, substituting 4-(1H-pyrazol-1-yl)pyridin-2-amine hydrochloride from Step 1 of this Example for 2-aminoisonicotinonitrile used in Example 117, and adding NaHCO₃ to the reaction mixture. LCMS (ESI) m/z 378 (M+H)⁺.

Step 3:
(1R,2S,3R)-3-((6-((7-(1H-Pyrazol-1-yl)imidazo[1,2-a]pyridin-3-yl)methyl)benzo[d]thiazol-2-yl)amino)cyclohexane-1,2-diol (25 mg, 12%) was obtained as a light tan solid using procedures analogous to those described in Steps 7-8 of Example 117, substituting 6-((7-(1H-pyrazol-1-yl)imidazo[1,2-a]pyridin-3-yl)methyl)-2-(methylthio)benzo[d]thiazole for 3-((2-(methylthio)benzo[d]thiazol-6-yl)methyl)imidazo[1,2-a]pyridine-7-carbonitrile used in Step 7 of Example 117, and substituting the product of that reaction and (1R,2S,3R)-3-aminocyclohexane-1,2-diol hydrochloride, respectively, for 3-((2-(methylsulfinyl)benzo[d]thiazol-6-yl)methyl) imidazo[1,2-a]pyridine-7-carbonitrile and (1R,2R)-2-amino cyclohexanol used in Step 8 of Example 117. ¹H NMR (500 MHz, DMSO-d₆) δ 8.66 (d, J=2.5 Hz, 1H), 8.32 (d, J=7.4 Hz, 1H), 7.99 (s, 1H), 7.85 (d, J=7.9 Hz, 1H), 7.79 (s, 1H), 7.54 (s, 1H), 7.53 (d, J=2.0 Hz, 1H), 7.43 (s, 1H), 7.28 (d, J=7.9 Hz, 1H), 7.12 (d, J=8.4 Hz, 1H), 6.59 (s, 1H), 4.53 (d, J=5.9 Hz, 1H), 4.43 (d, J=3.9 Hz, 1H), 4.31 (s, 2H), 3.93 (d, J=3.9 Hz, 1H), 3.80 (br s, 1H), 3.37-3.45 (m, 1H), 1.92 (dd, J=3.4, 11.8 Hz, 1H), 1.65 (dd, J=5.2, 16.5 Hz, 1H), 1.5-1.61 (m, 1H), 1.32-1.48 (m, 2H), 1.14-1.29 (m, 1H). LCMS (ESI) m/z 461 (M+H)⁺.

Example 230

Preparation of (1R,2S,3R)-3-((6-((5-methoxy-1H-benzo[d]imidazol-1-yl)methyl)benzo[d]thiazol-2-yl)amino)cyclohexane-1,2-diol

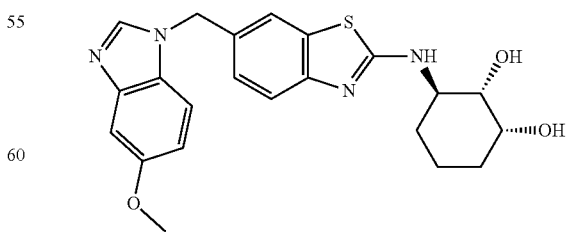

Step 1:
4-Methoxy-N-((2-(methylthio)benzo[d]thiazol-6-yl)methyl)-2-nitroaniline (5.2 g, 92%) was obtained as a red solid using a procedure analogous to that described in Step 1 of Example 127, substituting 4-methoxy-2-nitroaniline for 4-methyl-2-nitroaniline used in Example 127. $^1$H NMR (500 MHz, DMSO-$d_6$) δ 8.64 (t, J=6.1 Hz, 1H), 7.98 (m, 1H), 7.80 (d, J=8.4 Hz, 1H), 7.52 (d, J=3.1 Hz, 1H), 7.45 (dd, J=8.4, 1.5 Hz, 1H), 7.18 (dd, J=9.4, 3.1 Hz, 1H), 6.91 (d, J=9.5 Hz, 1H), 4.72 (d, J=6.1 Hz, 2H), 3.72 (s, 3H), 2.77 (s, 3H); LCMS (ESI) m/z 362 (M+H)$^+$.

Step 2:

4-Methoxy-N$^1$-((2-(methylthio)benzo[d]thiazol-6-yl) methyl)benzene-1,2-diamine (4 g, 84%) was obtained as an oil using a procedure analogous to that described in Step 2 of Example 129, substituting 4-methoxy-N-((2-(methylthio) benzo[d]thiazol-6-yl)methyl)-2-nitroaniline from the previous step for 4-fluoro-N-((2-(methylthio)benzo[d]thiazol-6-yl)methyl)-2-nitroaniline used in Example 129. LCMS (ESI) m/z 332 (M+H)$^+$.

Step 3:

6-((5-Methoxy-1H-benzo[d]imidazol-1-yl)methyl)-2-(methylthio)benzo[d]thiazole (1.12 g, 27%) was obtained as a solid using a procedure analogous to that described in Step 3 of Example 129, substituting 4-methoxy-N$^1$-((2-(methylthio)benzo[d]thiazol-6-yl)methyl)benzene-1,2-diamine from the previous step for 4-fluoro-N$^1$-((2-(methylthio)benzo[d]thiazol-6-yl)methyl) benzene-1,2-diamine used in Example 129. $^1$H NMR (500 MHz, DMSO-$d_6$) δ 8.35 (s, 1H), 7.97 (d, J=1.2 Hz, 1H), 7.79 (d, J=8.4 Hz, 1H), 7.38-7.41 (m, 2H), 7.18 (d, J=2.3 Hz, 1H), 6.82 (dd, J=8.8, 2.3 Hz, 1H), 5.55 (s, 2H), 3.75 (s, 3H), 2.76 (s, 3H); LCMS (ESI) m/z 342 (M+H)$^+$.

Step 4:

6-((5-Methoxy-1H-benzo[d]imidazol-1-yl)methyl)-2-(methylsulfinyl)benzo[d]thiazole (986 mg, 84%) was obtained as a solid using a procedure analogous to that described in Step 4 of Example 129, substituting 6-((5-methoxy-1H-benzo[d]imidazol-1-yl)methyl)-2-(methylthio) benzo[d]thiazole from the previous step for 6-((5-fluoro-1H-benzo[d]imidazol-1-yl)methyl)-2-(methylthio)benzo[d] thiazole used in Example 129. $^1$H NMR (500 MHz, DMSO-$d_6$) δ 8.38 (s, 1H), 8.21 (d, J=1.2 Hz, 1H), 8.06 (d, J=8.4 Hz, 1H), 7.55 (dd, J=8.5, 1.6 Hz, 1H), 7.38 (d, J=8.8 Hz, 1H), 7.19 (d, J=2.3 Hz, 1H), 6.83 (dd, J=8.8, 2.3 Hz, 1H), 5.64 (s, 2H), 3.75 (s, 3H), 3.05 (s, 3H); LCMS (ESI) m/z 358 (M+H)$^+$.

Step 5:

(1R,2S,3R)-3-((6-((5-Methoxy-1H-benzo[d]imidazol-1-yl)methyl)benzo[d]thiazol-2-yl)amino)cyclohexane-1,2-diol (53 mg, 15%) was obtained as a solid using a procedure analogous to that described in Step 5 of Example 232, substituting 6-((5-methoxy-1H-benzo[d]imidazol-1-yl) methyl)-2-(methylsulfinyl)benzo[d]thiazole, prepared as described in the previous step for 6-((5-iodo-1H-benzo[d] imidazol-1-yl)methyl)-2-(methylsulfinyl)benzo[d]thiazole from Example 232. $^1$H NMR (500 MHz, DMSO-$d_6$) δ 8.31 (s, 1H), 7.92 (d, J=7.9 Hz, 1H), 7.62 (s, 1H), 7.40 (d, J=8.9 Hz, 1H), 7.29 (d, J=8.1 Hz, 1H), 7.13-7.20 (m, 2H), 6.82 (dd, J=2.1, 8.7 Hz, 1H), 5.41 (s, 2H), 4.52 (d, J=5.9 Hz, 1H), 4.43 (d, J=3.7 Hz, 1H), 3.93 (d, J=4.4 Hz, 1H), 3.79 (m, 1H), 3.75 (s, 3H), 3.40 (m, 1H), 1.91 (dd, J=3.8, 12.4 Hz, 1H), 1.5-1.70 (m, 2H), 1.32-1.45 (m, 2H), 1.20 (m, 1H); LCMS (ESI) m/z 425 (M+H)$^+$.

Example 231

Preparation of (1R,2S,3R)-3-((6-((7-(2H-1,2,3-triazol-2-yl)imidazo[1,2-a]pyridin-3-yl)methyl)benzo [d]thiazol-2-yl)amino)cyclohexane-1,2-diol

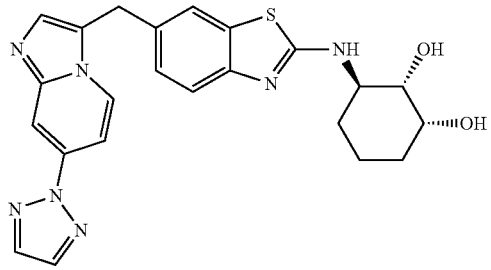

Step 1:

4-(2H-1,2,3-triazol-2-yl)pyridin-2-amine (370 mg, 39%) was obtained as a white solid using a procedure analogous to that described in Example 141, substituting 4-iodopyridin-2-amine and 1,2,3-triazole, respectively, for (1R,2R)-2-((6-((6-iodo-3H-imidazo[4,5-b]pyridin-3-yl)methyl)benzo [d]thiazol-2-yl)amino)cyclohexanol and pyrazole used in Example 141. LCMS (ESI) m/z 162 (M+H)$^+$.

Step 2:

6-((7-(2H-1,2,3-Triazol-2-yl)imidazo[1,2-a]pyridin-3-yl) methyl)-2-(methylthio)benzo[d]thiazole (87 mg, 31%) was obtained as a yellow solid using a procedure analogous to that described in Step 6 of Example 117, substituting 4-(2H-1,2,3-triazol-2-yl)pyridin-2-amine from Step 1 of this Example for 2-aminoisonicotinonitrile used in Example 117, and adding NaHCO$_3$ to the reaction mixture. LCMS (ESI) m/z 379 (M+H)$^+$.

Step 3:

(1R,2S,3R)-3-((6-((7-(2H-1,2,3-Triazol-2-yl)imidazo[1, 2-a]pyridin-3-yl)methyl)benzo[d]thiazol-2-yl)amino)cyclohexane-1,2-diol (35 mg, 33%) was obtained as a light tan solid using procedures analogous to those described in Steps 7-8 of Example 117, substituting 6-((7-(2H-1,2,3-triazol-2-yl)imidazo[1,2-a]pyridin-3-yl)methyl)-2-(methylthio)benzo [d]thiazole from Step 2 of this Example for 3-((2-(methylthio)benzo[d]thiazol-6-yl)methyl)imidazo[1,2-a]pyridine-7-carbonitrile used in Step 7 of Example 117, and substituting the product of that reaction and (1R,2S,3R)-3-aminocyclohexane-1,2-diol hydrochloride, respectively, for 3-((2-(methylsulfinyl)benzo[d]thiazol-6-yl)methyl) imidazo[1,2-a]pyridine-7-carbonitrile and (1R,2R)-2-amino cyclohexanol used in Step 8 of Example 117. $^1$H NMR (500 MHz, DMSO-$d_6$) δ 8.40 (d, J=7.4 Hz, 1H), 8.19 (s, 2H), 8.04 (s, 1H), 7.85 (d, J=7.9 Hz, 1H), 7.63 (dd, J=2.0, 7.4 Hz, 1H), 7.54 (s, 1H), 7.51 (s, 1H), 7.29 (d, J=8.4 Hz, 1H), 7.12 (d, J=8.4 Hz, 1H), 4.49-4.69 (m, 1H), 4.43 (br s, 1H), 4.34 (s, 2H), 3.93 (d, J=3.9 Hz, 1H), 3.80 (br s, 1H), 3.40 (d, J=8.4 Hz, 2H), 1.92 (dd, J=3.9, 12.3 Hz, 1H), 1.66 (dd, J=5.4, 10.8 Hz, 1H), 1.5-1.61 (m, 1H), 1.31-1.48 (m, 2H), 1.12-1.29 (m, 1H). LCMS (ESI) m/z 461 (M+H)$^+$.

Example 232

Preparation of (1R,2S,3R)-3-((6-((5-vinyl-1H-benzo[d]imidazol-1-yl)methyl)benzo[d]thiazol-2-yl)amino)cyclohexane-1,2-diol

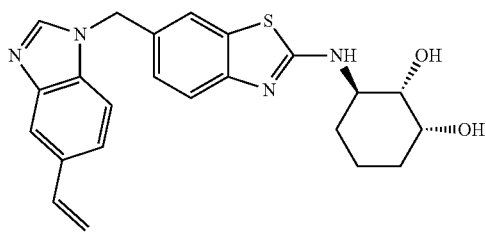 [SMILES: C=Cc1ccc2c(c1)ncn2Cc1ccc2nc(N[C@@H]3CCC[C@@H](O)[C@H]3O)sc2c1]

Step 1:
N-(4-Iodo-2-nitrophenyl)formamide was synthesized as a black solid (7.4 g, 71%) using a procedure analogous to that described in Step 1 of Example 162, substituting 4-iodo-2-nitroaniline for 5-fluoro-3-nitropyridin-2-amine used in Example 162. LCMS (ESI) m/z 293 (M+H)$^+$.

Step 2:
N-(4-Iodo-2-nitrophenyl)-N-((2-(methylthio)benzo[d]thiazol-6-yl)methyl)formamide was synthesized as an brown solid (9.7 g, 82%) using a procedure analogous to that described in Step 3 of Example 47, substituting N-(4-Iodo-2-nitrophenyl)formamide from the previous step for 5-bromo-6-methoxy-1H-benzo[d]imidazole used in Example 47. LCMS (ESI) m/z 486 (M+H)$^+$.

Step 3:
A stirred mixture of N-(4-iodo-2-nitrophenyl)-N-((2-(methylthio)benzo[d]thiazol-6-yl)methyl)formamide and iron powder (16.7 g, 20 mmol) in EtOH (140 mL) and HOAc (60 mL) was heated at reflux for 1 h. The mixture was cooled to rt and filtered, and the filtrate was concentrated under reduced pressure. The residue was partitioned between EtOAc (200 mL) and 0.5 M aq Na$_2$CO$_3$ (100 mL). The organic layer was separated and further washed with brine (100 mL), dried over MgSO$_4$, filtered, and concentrated under reduced pressure to afford 6-((5-iodo-1H-benzo[d]imidazol-1-yl)methyl)-2-(methylthio)benzo[d]thiazole (5.9 g, 68%) as a yellow solid that did not require further purification. $^1$H NMR (500 MHz, DMSO-d$_6$) δ 8.44 (s, 1H), 8.03 (d, J=1.0 Hz, 1H), 7.97 (s, 1H), 7.80 (d, J=8.4 Hz, 1H), 7.49 (dd, J=1.4, 8.5 Hz, 1H), 7.37-7.43 (m, 2H), 5.60 (s, 2H), 2.76 (s, 3H); LCMS (ESI) m/z 438 (M+H)$^+$.

Step 4:
6-((5-Iodo-1H-benzo[d]imidazol-1-yl)methyl)-2-(methylsulfinyl)benzo[d]thiazole was synthesized as a white foam (2.9 g, 94%) using a procedure analogous to that described in Step 6 of Example 36, substituting 6-((5-iodo-1H-benzo[d]imidazol-1-yl)methyl)-2-(methylthio)benzo[d]thiazole from the previous step for the 6-((4-bromo-1H-imidazol-1-yl)methyl)-2-(methylthio)benzo[d]thiazole used in Example 36. $^1$H NMR (500 MHz, DMSO-d$_6$) δ 8.47 (s, 1H), 8.21 (s, 1H), 8.02-8.10 (m, 2H), 7.56 (dd, J=1.4, 8.5 Hz, 1H), 7.50 (dd, J=1.2, 8.4 Hz, 1H), 7.40 (d, J=8.6 Hz, 1H), 5.69 (s, 2H), 3.05 (s, 3H); LCMS (ESI) m/z 454 (M+H)$^+$.

Step 5:
To a suspension of 6-((5-iodo-1H-benzo[d]imidazol-1-yl)methyl)-2-(methylsulfinyl)benzo[d]thiazole (350 mg, 0.8 mmol) and (1R,2S,3R)-3-aminocyclohexane-1,2-diol hydrochloride (258 mg, 1.6 mmol), prepared as described in Gauthier Errasti, et al, *Org. Lett.* 2009, 13, 2912-2915, in anhydrous DMA (1.5 mL) was added DIEA (402 μL, 2.4 mmol). The mixture was heated in a sealed tube at 120° C. for 15 h. The mixture was cooled to rt and partitioned between EtOAc (150 mL) and 0.5 M aq K$_2$CO$_3$ (100 mL). The organic layer was separated and washed with brine (100 mL), dried over Na$_2$SO$_4$, filtered, and concentrated under reduced pressure. The residue was purified by silica gel flash chromatography eluting with 5% MeOH in DCM to afford (1R,2S,3R)-3-((6-((5-iodo-1H-benzo[d]imidazol-1-yl)methyl)benzo[d]thiazol-2-yl)amino)cyclohexane-1,2-diol (127 mg, 32%) as a yellow solid. LCMS (ESI) m/z 521 (M+H)$^+$.

Step 6:
A suspension of (1R,2S,3R)-3-((6-((5-iodo-1H-benzo[d]imidazol-1-yl)methyl)benzo[d]thiazol-2-yl)amino)cyclohexane-1,2-diol (120 mg, 0.2 mmol), vinylboronic acid pinacol ester (71 mg, 0.5 mmol), and K$_2$CO$_3$ (64 mg, 0.5 mmol) in 6:1 dioxane:water (3.5 mL) was purged with argon for 5 min. [1,1'-Bis(diphenylphosphino)ferrocene]dichloropalladium (II) (19 mg, 0.02 mmol) was added to the mixture, the mixture was purged with argon for an additional 5 min and then heated in a sealed tube at 100° C. for 6 h. The mixture was cooled to rt and partitioned between EtOAc (150 mL) and 0.5 M aq K$_2$CO$_3$ (100 mL). The organic layer was separated and washed with brine (100 mL), dried over Na$_2$SO$_4$, filtered, and concentrated under reduced pressure. The residue was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase to afford the nearly pure compound. This was further purified by silica gel flash chromatography, eluting isocratically with 5% MeOH in CH$_2$Cl$_2$, to afford (1R,2S,3R)-3-((6-((5-vinyl-1H-benzo[d]imidazol-1-yl)methyl)benzo[d]thiazol-2-yl)amino)cyclohexane-1,2-diol (5 mg, 5%) as a white powder. $^1$H NMR (500 MHz, MeOH-d$_4$) δ 8.28 (br s, 1H), 7.69 (s, 1H), 7.54 (m, 1H), 7.41-7.43 (m, 2H), 7.37 (d, J=8.1 Hz, 1H), 7.22 (m, 1H), 6.81-6.86 (m, 2H), 5.76 (d, J=17.7 Hz, 1H), 5.49 (s, 2H), 5.19 (d, J=11.1 Hz, 1H), 3.99-4.02 (m, 2H), 3.50 (m, 1H), 2.08 (m, 1H), 1.72-1.85 (m, 2H), 1.48-1.55 (m, 2H), 1.28-1.39 (m, 2H); LCMS (ESI) m/z 421 (M+H)$^+$.

Example 233

Preparation of (1R,2S,3R)-3-((6-((5-(oxetan-3-yloxy)-1H-benzo[d]imidazol-1-yl)methyl)benzo[d]thiazol-2-yl)amino)cyclohexane-1,2-diol

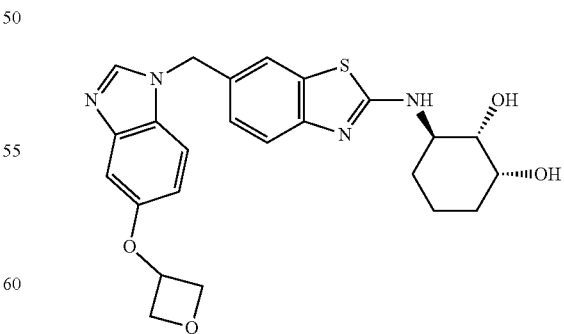

Step 1:
To a stirred solution of 4-amino-3-nitrophenol (1.37 g, 8.91 mmol) in DMF (15 mL) at rt was added cesium carbonate (5.79 g, 17.82 mmol) and the mixture was stirred for 30 min. Oxetan-3-yl-4-methylbenzenesulfonate (3.05 g, 13.36 mmol) was added and the mixture was heated at 80° C. for 6 h. The mixture was cooled to rt and partitioned between EtOAc and water. The organic layer was separated, and the aqueous layer was extracted with additional EtOAc. The combined organic layers were washed with brine. The organic layer was separated, dried over MgSO$_4$, filtered, and concentrated under reduced pressure. The solid residue was purified by trituration with diethyl ether to afford 2-nitro-4-(oxetan-3-yloxy)aniline (1.33 g, 71%) as a brown solid. $^1$H NMR (500 MHz, DMSO-d$_6$) δ 7.29 (br s, 2H), 7.15 (dd, J=9.2, 3.0 Hz, 1H), 7.10 (d, J=3.0 Hz, 1H), 7.02 (d, J=9.2 Hz, 1H), 5.24 (pentet, J=4.9 Hz, 1H), 4.87-4.93 (m, 2H), 4.5-4.53 (m, 2H); LCMS (ESI) m/z 211 (M+H)$^+$.

Step 2:

A stirred mixture of acetic anhydride (15 mL, 161 mmol) and formic acid (6 mL, 161 mmol) was heated at 60° C. for 5 h. The mixture was cooled to rt, then 2-nitro-4-(oxetan-3-yloxy)aniline (1.69 g, 8.02 mmol) was added and the mixture was heated at 70° C. for 15 h. The mixture was cooled to rt and concentrated under reduced pressure. The residue was partitioned between EtOAc and saturated aq NaHCO$_3$. The organic layer was separated, dried over MgSO$_4$, filtered, and concentrated under reduced pressure. The residue was purified by silica gel flash chromatography eluting with a gradient of 20% EtOAc in hexanes to 100% EtOAc to afford N-(2-nitro-4-(oxetan-3-yloxy)phenyl)formamide (967 mg, 51%) as a yellow solid. $^1$H NMR (500 MHz, DMSO-d$_6$) δ 10.36 (br s, 1H), 8.29 (m, 1H), 7.85 (d, J=8.9 Hz, 1H), 7.36 (d, J=1.8 Hz, 1H), 7.24 (dd, J=9.0, 3.0 Hz, 1H), 5.38 (pentet, J=4.9 Hz, 1H), 4.92-4.94 (m, 2H), 4.5-4.56 (m, 2H).

Step 3:

N-((2-(Methylthio)benzo[d]thiazol-6-yl)methyl)-N-(2-nitro-4-(oxetan-3-yloxy)phenyl)formamide (1.71 g) was obtained as an oil using a procedure analogous to that described in Step 2 of Example 203, substituting N-(2-nitro-4-(oxetan-3-yloxy)phenyl)formamide from Step 2 of this Example for N-(4-bromo-2-fluoro-6-nitrophenyl)formamide used in Example 203. LCMS (ESI) m/z 432 (M+H)$^+$.

Step 4:

2-(Methylthio)-6-((5-(oxetan-3-yloxy)-1H-benzo[d]imidazol-1-yl)methyl)benzo[d]thiazole (640 mg, 41% from N-(2-nitro-4-(oxetan-3-yloxy)phenyl)formamide) was obtained as a solid using a procedure analogous to that described in Step 3 of Example 203, substituting N-((2-(methylthio)benzo[d]thiazol-6-yl)methyl)-N-(2-nitro-4-(oxetan-3-yloxy)phenyl)formamide from the previous step for N-(4-bromo-2-fluoro-6-nitrophenyl)-N-((2-(methylthio)benzo[d]thiazol-6-yl)methyl)formamide used in Example 203. $^1$H NMR (500 MHz, DMSO-d$_6$) δ 8.38 (s, 1H), 7.98 (d, J=1.4 Hz, 1H), 7.79 (d, J=8.4 Hz, 1H), 7.43 (d, J=8.8 Hz, 1H), 7.40 (dd, J=8.4, 1.8 Hz, 1H), 6.93 (d, J=2.3 Hz, 1H), 6.79 (dd, J=8.8, 2.3 Hz, 1H), 5.55 (s, 2H), 5.27 (pentet, J=5.6 Hz, 1H), 4.91-4.94 (m, 2H), 4.5-4.55 (m, 2H), 2.76 (s, 3H); LCMS (ESI) m/z 384 (M+H)$^+$.

Step 5:

2-(Methylsulfinyl)-6-((5-(oxetan-3-yloxy)-1H-benzo[d]imidazol-1-yl)methyl)benzo[d]thiazole (496 mg, 74%) was obtained as a white solid using a procedure analogous to that described in Step 4 of Example 130, substituting 2-(methylthio)-6-((5-(oxetan-3-yloxy)-1H-benzo[d]imidazol-1-yl)methyl)benzo[d]thiazole from the previous step for 2-(methylthio)-6-((5-(trifluoromethyl)-1H-benzo[d]imidazol-1-yl)methyl)benzo[d]thiazole used in Example 130. $^1$H NMR (500 MHz, DMSO-d$_6$) δ 8.41 (s, 1H), 8.22 (m, 1H), 8.07 (d, J=10.0 Hz, 1H), 7.56 (m, 1H), 7.42 (d, J=10.0 Hz, 1H), 6.95 (d, J=5.0 Hz, 1H), 6.80 (m, 1H), 5.64 (s, 2H), 5.27 (pentet, J=5.0 Hz, 1H), 4.92-4.95 (m, 2H), 4.5-4.55 (m, 2H), 3.05 (s, 3H); LCMS (ESI) m/z 400 (M+H)+.

Step 6:

(1R,2S,3R)-3-((6-((5-(Oxetan-3-yloxy)-1H-benzo[d]imidazol-1-yl)methyl)benzo[d]thiazol-2-yl)amino)cyclohexane-1,2-diol (68 mg, 12%) was obtained as a solid using a procedure analogous to that described in Step 5 of Example 232, substituting 2-(methylsulfinyl)-6-((5-(oxetan-3-yloxy)-1H-benzo[d]imidazol-1-yl)methyl)benzo[d]thiazole from the previous step for 6-((5-iodo-1H-benzo[d]imidazol-1-yl)methyl)-2-(methylsulfinyl)benzo[d]thiazole used in Example 232. $^1$H NMR (500 MHz, DMSO-d$_6$) δ 8.34 (s, 1H), 7.92 (d, J=7.9 Hz, 1H), 7.63 (d, J=1.5 Hz, 1H), 7.43 (d, J=8.8 Hz, 1H), 7.28 (d, J=8.2 Hz, 1H), 7.18 (dd, J=8.2, 1.6 Hz, 1H), 6.91 (d, J=2.3 Hz, 1H), 6.79 (dd, J=8.8, 2.4 Hz, 1H), 5.41 (s, 2H), 5.27 (pentet, J=5.2 Hz, 1H), 4.91-4.94 (m, 2H), 4.5-4.54 (m, 2H), 4.43 (d, J=3.8 Hz, 1H), 3.92 (br m, 1H), 3.79 (m, 1H), 3.38 (m, 1H), 3.31 (m, 1H), 1.91 (m, 1H), 1.5-1.67 (m, 2H), 1.34-1.42 (m, 2H), 1.21 (m, 1H); LCMS (ESI) m/z 467 (M+H)$^+$.

Example 234

Preparation of (1R,2S,3R)-3-((6-((6-(1H-1,2,4-triazol-1-yl)-3H-imidazo[4,5-b]pyridin-3-yl)methyl)benzo[d]thiazol-2-yl)amino)cyclohexane-1,2-diol

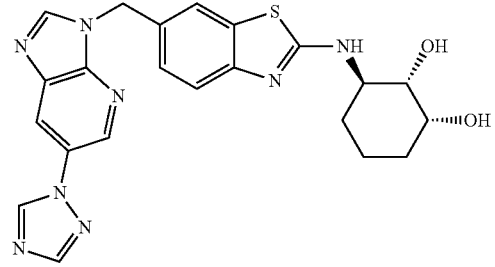 [SMILES: O[C@@H]1[C@H](O)CCC[C@H]1Nc1nc2ccc(Cn3cnc4cc(-n5cncn5)cnc43)cc2s1]

Step 1:

6-((6-(1H-1,2,4-Triazol-1-yl)-3H-imidazo[4,5-b]pyridin-3-yl)methyl)-2-(methylthio)benzo[d]thiazole (108 mg, 19%) was obtained as a yellow solid using a procedure analogous to that described in Example 141, substituting 6-((6-iodo-3H-imidazo[4,5-b]pyridin-3-yl)methyl)-2-(methylthio)benzo[d]thiazole, prepared as an intermediate product in Step 2 of Example 96, and 1,2,4-triazole, respectively, for (1R,2R)-2-((6-((6-iodo-3H-imidazo[4,5-b]pyridin-3-yl)methyl)benzo[d]thiazol-2-yl)amino)cyclohexanol and pyrazole used in Example 141. LCMS (ESI) m/z 380 (M+H)$^+$.

Step 2:

(1R,2S,3R)-3-((6-((6-(1H-1,2,4-Triazol-1-yl)-3H-imidazo[4,5-b]pyridin-3-yl)methyl)benzo[d]thiazol-2-yl)amino)cyclohexane-1,2-diol (53 mg, 41%) was obtained as a yellow solid using procedures analogous to those described in Steps 7-8 of Example 117, substituting 6-((6-(1H-1,2,4-triazol-1-yl)-3H-imidazo[4,5-b]pyridin-3-yl)methyl)-2-(methylthio)benzo[d]thiazole from Step 1 of this Example for 3-((2-(methylthio)benzo[d]thiazol-6-yl)methyl)imidazo[1,2-a]pyridine-7-carbonitrile used in Step 7 of Example 117, and substituting the product of that reaction and (1R,2S,3R)-3-aminocyclohexane-1,2-diol hydrochloride, respectively, for 3-((2-(methylsulfinyl)benzo[d]thiazol-6-yl)methyl)imidazo[1,2-a]pyridine-7-carbonitrile and (1R,2R)-2-amino cyclohexanol used in Step 8 of Example 117. $^1$H NMR (500 MHz, DMSO-d$_6$) δ 9.30 (s, 1H), 8.89 (d, J=2.0 Hz, 1H), 8.76 (s, 1H), 8.56 (d, J=2.0 Hz, 1H), 8.29 (s, 1H), 8.21 (s, 1H), 7.93 (d, J=7.9 Hz, 1H), 7.69 (s, 1H), 7.27-7.32 (m, 1H), 7.20-7.27 (m, 1H), 5.54 (s, 2H), 4.44 (d, J=4.9 Hz, 2H), 3.93 (d, J=4.4 Hz, 1H), 3.79 (br s, 1H), 3.39 (d, J=8.4 Hz, 2H), 1.92 (dd, J=3.4, 12.8 Hz, 1H), 1.61-1.71 (m, 1H), 1.5-1.61 (m, 1H), 1.30-1.47 (m, 2H), 1.12-1.29 (m, 1H). LCMS (ESI) m/z 463 (M+H)$^+$.

Example 235

Preparation of (1R,2S,3R)-3-((6-((5-morpholino-1H-benzo[d]imidazol-1-yl)methyl)benzo[d]thiazol-2-yl)amino)cyclohexane-1,2-diol

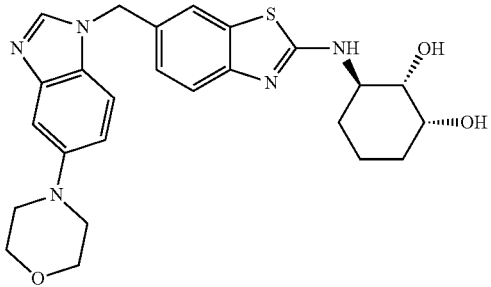 [SMILES: O[C@@H]1[C@H](O)CCC[C@H]1Nc1nc2ccc(Cn3cnc4cc(N5CCOCC5)ccc43)cc2s1]

A suspension of (1R,2S,3R)-3-((6-((5-iodo-1H-benzo[d]imidazol-1-yl)methyl)benzo[d]thiazol-2-yl)amino)cyclohexane-1,2-diol (262 mg, 0.5 mmol) from Step 5 of Example 232, morpholine (264 µL, 3.0 mmol), L-proline (23 mg, 0.2 mmol), and K$_2$CO$_3$ (209 mg, 1.5 mmol) in DMSO (2.0 mL) was purged with argon for 5 min. Copper (I) iodide (19 mg, 0.02 mmol) was added, and the mixture was purged for an additional 5 min, then heated in a sealed tube at 110° C. for 2 h. The mixture was cooled to rt and filtered through Celite, and the filtrate was purified by reverse-phase preparative HPLC using a mixture of water (5% CH$_3$CN, 0.05% HCOOH) and CH$_3$CN (0.05% HCOOH) as the mobile phase and Varian Pursuit XRs C18 column as the stationary phase, followed by silica gel flash chromatography eluting with 5% MeOH in CH$_2$Cl$_2$ to afford (1R,2S,3R)-3-((6-((5-morpholino-1H-benzo[d]imidazol-1-yl)methyl)benzo[d]thiazol-2-yl)amino)cyclohexane-1,2-diol (2 mg, 1%) as a white powder. $^1$H NMR (500 MHz, MeOH-d$_4$) δ 8.19 (s, 1H), 7.50 (s, 1H), 7.31-7.39 (m, 2H), 7.16-7.23 (m, 2H), 7.05 (dd, J=2.0, 8.9 Hz, 1H), 5.44 (s, 2H), 3.95-4.06 (m, 2H), 3.80-3.88 (m, 4H), 3.50 (dd, J=2.6, 9.2 Hz, 1H), 3.06-3.14 (m, 4H), 2.09 (m, 1H), 1.77-1.86 (m, 2H), 1.48-1.53 (m, 2H), 1.33 (m, 1H); LCMS (ESI) m/z 480 (M+H)$^+$.

Example 236

Preparation of (1R,2S,3R)-3-((6-((5-(2-methyl-2H-tetrazol-5-yl)-1H-benzo[d]imidazol-1-yl)methyl)benzo[d]thiazol-2-yl)amino)cyclohexane-1,2-diol

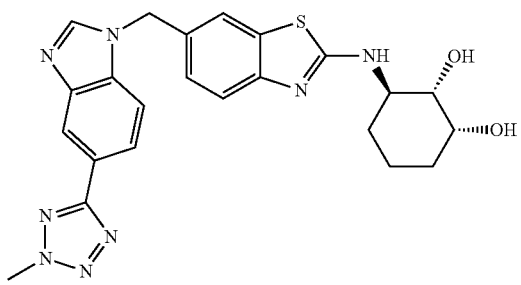 [SMILES: Cn1nnc(-c2ccc3c(c2)ncn3Cc2ccc3nc(N[C@@H]4CCC[C@@H](O)[C@H]4O)sc3c2)n1]

Step 1:
N-(4-Cyano-2-nitrophenyl)formamide was synthesized as a white solid (4.8 g, 100%) using a procedure analogous to that described in Step 1 of Example 162, substituting 4-cyano-2-nitroaniline for 5-fluoro-3-nitropyridin-2-amine used in Example 162. LCMS (ESI) m/z 192 (M+H)$^+$.

Step 2:
N-(4-Cyano-2-nitrophenyl)-N-((2-(methylthio)benzo[d]thiazol-6-yl)methyl)formamide was synthesized as an yellow foam (920 mg, 92%) using a procedure analogous to that described in Step 3 of Example 47, substituting N-(4-cyano-2-nitrophenyl)formamide from the previous step for 5-bromo-6-methoxy-1H-benzo[d]imidazole used in Example 47. LCMS (ESI) m/z 385 (M+H)$^+$.

Step 3:
1-((2-(Methylthio)benzo[d]thiazol-6-yl)methyl)-1H-benzo[d]imidazole-5-carbonitrile was synthesized as a white solid (694 mg, 86%) using a procedure analogous to that described in Step 3 of Example 232, substituting N-(4-cyano-2-nitrophenyl)-N-((2-(methylthio)benzo[d]thiazol-6-yl)methyl)formamide from the previous step for N-(4-iodo-2-nitrophenyl)-N-((2-(methylthio)benzo[d]thiazol-6-yl)methyl)formamide used in Example 232. LCMS (ESI) m/z 337 (M+H)$^+$.

Step 4:
A suspension of 1-((2-(methylthio)benzo[d]thiazol-6-yl)methyl)-1H-benzo[d]imidazole-5-carbonitrile (694 mg, 2.1 mmol), sodium azide (403 mg, 6.3 mmol), and ammonium chloride (331 mg, 6.3 mmol) in DMF (3 mL) was heated in a sealed tube at 125° C. for 15 h. The mixture was cooled to rt and a precipitate formed. The solid was collected by filtration to afford 6-((5-(2H-tetrazol-5-yl)-1H-benzo[d]imidazol-1-yl)methyl)-2-(methylthio)benzo[d]thiazole (796 mg, 100%) as a yellow solid that did not require further purification. $^1$H NMR (500 MHz, DMSO-d$_6$) δ 8.41 (s, 1H), 8.19 (s, 1H), 8.02 (s, 1H), 7.88 (dd, J=1.0, 8.4 Hz, 1H), 7.81 (d, J=8.6 Hz, 1H), 7.52 (d, J=8.4 Hz, 1H), 7.45 (dd, J=1.4, 8.5 Hz, 1H), 7.15-7.30 (br s, 2H), 5.60 (s, 2H), 2.76 (s, 3H); LCMS (ESI) m/z 380 (M+H)$^+$.

Step 5:
To a stirred mixture of 6-((5-(2H-tetrazol-5-yl)-1H-benzo[d]imidazol-1-yl)methyl)-2-(methylthio)benzo[d]thiazole (796 mg, 2.1 mmol), Cs$_2$CO$_3$ (673 mg, 2.1 mmol), and DMF (10 mL) was added iodomethane (129 µL, 2.1 mmol). The mixture was heated at 60° C. for 6 h. Additional iodomethane (30 µL, 0.5 mmol) was added and the mixture was stirred at 60° C. for an additional 4 h. The mixture was cooled to rt and partitioned between EtOAc (200 mL) and 0.5 M aq Na$_2$CO$_3$ (100 mL). The organic layer was separated and washed with brine (100 mL), dried over MgSO$_4$, filtered and concentrated under reduced pressure. The residue was purified by silica gel flash chromatography, eluting with 2% MeOH in CH$_2$Cl$_2$, to afford 6-((5-(2-methyl-2H-tetrazol-5-yl)-1H-benzo[d]imidazol-1-yl)methyl)-2-(methylthio)benzo[d]thiazole (318 mg, 39%) as a white solid. The regiochemistry of the alkylation was determined by 2-dimensional nuclear Overhauser effect (NOE) experiment. $^1$H NMR (500 MHz, DMSO-d$_6$) δ 8.58 (s, 1H), 8.31 (s, 1H), 8.03 (s, 1H), 7.93 (dd, J=1.0, 8.4 Hz, 1H), 7.82 (d, J=8.4 Hz, 1H), 7.73 (d, J=8.6 Hz, 1H), 7.46 (dd, J=1.2, 8.4 Hz, 1H), 5.66 (s, 2H), 4.41 (s, 3H), 2.76 (s, 3H); LCMS (ESI) m/z 394 (M+H)$^+$.

Step 6:
6-((5-(2-Methyl-2H-tetrazol-5-yl)-1H-benzo[d]imidazol-1-yl)methyl)-2-(methylsulfinyl)benzo[d]thiazole was synthesized as a white foam (390 mg) using a procedure analogous to that described in Step 6 of Example 36, substituting 6-((5-(2-methyl-2H-tetrazol-5-yl)-1H-benzo[d]imidazol-1-yl)methyl)-2-(methylthio)benzo[d]thiazole from the previous step for 6-((4-bromo-1H-imidazol-1-yl)methyl)-2-(methylthio)benzo[d]thiazole used in Example 36. LCMS (ESI) m/z 410 (M+H)+.

Step 7:

To a suspension of 6-((5-(2-methyl-2H-tetrazol-5-yl)-1H-benzo[d]imidazol-1-yl)methyl)-2-(methylsulfinyl)benzo[d]thiazole (330 mg, 0.8 mmol) and (1R,2S,3R)-3-aminocyclohexane-1,2-diol hydrochloride (391 mg, 2.4 mmol), prepared as described in Gauthier Errasti, et al, *Org. Lett.* 2009, 13, 2912-2915, in anhydrous NMP (3.0 mL) was added DIEA (703 µL, 4.0 mmol). The mixture was heated in a sealed tube at 120° C. for 15 h. Additional (1R,2S,3R)-3-aminocyclohexane-1,2-diol hydrochloride (258 mg, 1.6 mmol) and DIEA (703 µL, 4.0 mmol) were added, and the mixture was heated at 140° C. for a further 15 h. The mixture was cooled to rt and was purified by reverse-phase preparative HPLC using a mixture of water (5% $CH_3CN$, 0.05% HCOOH) and $CH_3CN$ (0.05% HCOOH) as the mobile phase and Varian Pursuit XRs C18 column as the stationary phase to afford (1R,2S,3R)-3-((6-((5-(2-methyl-2H-tetrazol-5-yl)-1H-benzo[d]imidazol-1-yl)methyl)benzo[d]thiazol-2-yl)amino)cyclohexane-1,2-diol (37 mg, 10%) as a white powder. $^1$H NMR (500 MHz, DMSO-$d_6$) δ 8.53 (s, 1H), 8.29 (s, 1H), 7.90-7.98 (m, 2H), 7.74 (d, J=8.4 Hz, 1H), 7.69 (s, 1H), 7.31 (m, 1H), 7.23 (dd, J=1.5, 8.4 Hz, 1H), 5.52 (s, 2H), 4.41 (s, 3H), 3.93 (m, 1H), 3.79 (m, 1H), 3.25 (m, 1H), 1.91 (m, 1H), 1.5-1.69 (m, 3H), 1.32-1.44 (m, 2H), 1.15-1.25 (m, 2H); LCMS (ESI) m/z 477 (M+H)+.

Example 237

M-NFS-60 Cell Proliferation Assay

The compounds disclosed herein were tested in an M-NFS-60 cell proliferation assay to determine their cellular potency against CSF1R. M-NFS-60s are mouse monocytic cells that depend on the binding of the ligand M-CSF to its receptor, CSF1R, to proliferate Inhibition of CSF1R kinase activity will cause reduced growth and/or cell death. This assay assesses the potency of compounds as CSF1R inhibitors by measuring the reduction of Alamar Blue reagent by viable cells.

On day one of the experiment, M-NFS-60 cells were maintained in RPMI complete medium (Omega Scientific) plus 10% FBS supplemented with 20 ng/mL of M-CSF (R&D Systems). 96-well TC-treated, flat bottom plates were seeded at 10,000 cell/well at a volume of 100 µL per well. The cells were cultured overnight at 37° C. under 5% $CO_2$.

On day two, compounds were added to the cells at 9 different concentrations, with half-log intervals alongside a control reference compound serving as a positive control. Final DMSO concentration was kept at 0.5% for a final volume of 200 µL. The compounds were allowed to incubate with the cells for 72 hours at 37° C. under 5% $CO_2$.

On day five of the experiment, 40 µl of Alamar Blue reagent was added to each well and allowed to incubate for 3 hours. Alamar Blue fluorescence was read using SoftMax Pro software at 560 nm (excitation) and 590 nm (emission). $IC_{50}$s were generated as an average of duplicates and represents the concentration of test compound that achieves 50% inhibition of cellular proliferation compared to control.

In one embodiment, the compounds provided herein were found to have $IC_{50}$ of about or less than about 5, 4, 3, 2, 1, 0.5, 0.1, 0.05 or 0.01 µM. In another embodiment, the compounds provided herein were found to have activity IC50 of about or less than about 2000, 1000, 500, 300, 100, 50, 40, 30 or 20 nM. In another embodiment, the compounds provided herein were found to have activity IC50 of less than about 200 or 100 nM.

Example 238

HEK293 CSF1R Phosphorylation MSD Assay

The compounds disclosed herein were tested in a CSF1R phosphorylation assay to determine their cellular potency against CSF1R. A HEK293 cell line expressing CSF1R fused to FK506 binding protein (FKBP) as a molecular tag was generated. Inhibition of CSF1R kinase activity will prevent ligand-stimulated autophosphorylation of the CSF1R-FKBP in intact cells. Subsequent cell lysates are assayed in a sandwich ELISA employing the electrochemiluminescent Meso Scale Discovery (MSD) technology for the presence of the phosphorylated (p)CSF1R-FKBP. This assay determines the potency of compounds as CSF1R inhibitors by measuring the reduction in the amount of pCSF1R with increasing doses of compounds added to the cells prior to M-CSF stimulation.

On day one of the experiment, HEK293-CSF1R-FKPB cells, maintained in DMEM, with L-glutamine (Mediatech), 10% FBS, and 100 units/mL Penicillin/Streptomycin, were seeded at 50,000 cell/well in a volume of 100 µL per well in 96-well Cell Bind plates (Costar). The cells were cultured overnight at 37° C. under 5% $CO_2$. To prepare the plates used in the MSD assay, a 330 nM biotin-FK506 (in TBS pH 7.2) solution was added at 30 µL, per well to streptavidin-coated 96-well plates (MSD), and incubated overnight at room temperature, shaking at 500 rpm on an orbital shaker.

On day two, compounds diluted in DMSO were added to the cells in duplicate plates at 9 different concentrations with half-log intervals, plus DMSO only control, alongside a reference compound serving as a positive control. Final DMSO concentration was 0.5% in a volume of 200 µL, per well. The compounds were allowed to incubate with the cells for 2 h at 37° C. under 5% $CO_2$. At the end of the incubation, human M-CSF (R&D Systems) was added for 5 min to a final concentration of 50 ng/mL to stimulate CSF1R phosphorylation. Cells were lysed for 20 min, and the lysates were applied to the washed, FK506-coated MSD plates, and incubated overnight at 4° C. shaking at 500 rpm.

On day three, the MSD plates were washed, and the captured CSF1R-FKBP was assayed sequentially for phosphorylation using mouse anti-phosphotyrosine antibody (Millipore) and Sulfo-TAG goat anti-mouse IgG antibody (MSD), and detected on a Sector Imager 6000 instrument (MSD).

A single IC50 value for each compound was determined by averaging the $IC_{50}$s of the duplicates calculated using Igor Pro 6 software, and represents the compound concentration that achieves a 50% inhibition of ligand-induced CSF1R phosphorylation compared to DMSO control.

Example 239

Competition Binding Assay to Determine Selectivity Scores and Binding Constants (Kd) of the Compounds Against a Panel of Kinases Competition binding assays used herein were developed, validated and performed as described in Fabian et al., *Nature Biotechnology* 2005, 23, 329-336. Kinases were produced as fusions to T7 phage (See, Fabian et al. or WO04/015142) or alternatively, the kinases were expressed in HEK-293 cells and subsequently tagged with DNA for PCR detection (See, WO08/005310). For the binding assays, streptavidin-coated magnetic beads were treated with biotinylated affinity ligands for 30 min at room temperature to generate affinity resins. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinase, liganded affinity beads, and test compounds in 1× binding buffer (20% SeaBlock, 0.17×PBS, 0.05% Tween 20, 6 mM DTT). Test compounds were prepared as 100× stocks in DMSO and diluted into the aqueous environment. Kds were determined using an eleven point threefold serial dilutions. DMSO or control compounds were was added to control assays lacking a test compound. Primary screen assays were performed in polypropylene 384-well plates in a final volume of 20-40 μL, while Kd determinations were performed in polystyrene 96-well plates in a final volume of 135 pt. The assay plates were incubated at room temperature with shaking for 1 hour to allow the binding reactions to reach equilibrium, and the affinity beads were washed extensively with wash buffer (1×PBS, 0.05% Tween 20) to remove unbound protein. The beads were then resuspended in elution buffer (1×PBS, 0.05% Tween 20, 0.5 μM non-biotinylated affinity ligand) and incubated at room temperature with shaking for 30 min. The kinase concentration in the eluates was measured by quantitative PCR.

A selectivity score (S10) is a quantitative measure of selectivity of a compound against a panel of kinases. An S10 was calculated for a compound by dividing the number of kinases found to have a percent of control (DMSO) less than 10 by the total number of distinct kinases tested (excluding mutant variants). Percent of control (POC) is calculated by subtracting the signal of the control compound (POC=0) from the signal of the test compound and dividing the outcome by the signal of DMSO (POC=100) minus the signal of the control compound. For the compounds disclosed herein, S10 scores were obtained by testing the compounds at 10 μM concentration in a kinase panel containing either 386 or 392 distinct kinases.

In one embodiment, the compounds provided herein were found to have S10 score of about or less than about 0.1, 0.08, 0.06, 0.04, 0.03, or 0.02.

The compounds provided herein were found to have the following activity shown in Table 1:

TABLE 1

| Ex. # | CSF1R Kd (nM) | FLT3 Kd (nM) | KIT Kd (nM) | PDGFRβ Kd (nM) | CSF1R M-NFS-60 CTB:IC$_{50}$ (nM) | HEK293 pCSF1R M-CSF MSD:IC$_{50}$ (nM) | Kinase specificity S(10) |
|---|---|---|---|---|---|---|---|
| 1 | B | C | B | B | B | B | ND |
| 2 | B | B | B | B | B | A | ND |
| 3 | A | C | B | B | B | B | B |
| 4 | A | B | B | B | B | A | ND |
| 5 | D | D | D | D | D | D | ND |
| 6 | B | A | B | B | B | B | ND |
| 7 | B | B | B | A | C | B | ND |
| 8 | B | C | C | C | D | C | ND |
| 9 | C | C | C | C | D | C | ND |
| 10 | B | C | C | B | C | C | ND |
| 11 | B | B | B | B | C | C | ND |
| 12 | D | C | D | D | D | C | ND |
| 13 | B | C | B | B | C | B | ND |
| 14 | D | C | D | C | D | D | ND |
| 15 | C | D | C | D | D | C | ND |
| 16 | C | B | B | C | D | C | ND |
| 17 | B | B | D | B | C | C | ND |
| 18 | A | A | A | A | B | A | ND |
| 19 | A | C | B | B | B | B | ND |
| 20 | C | C | D | D | D | C | ND |
| 21 | D | D | D | D | D | C | ND |
| 22 | B | C | B | D | C | B | ND |
| 23 | A | A | A | B | B | A | ND |
| 24 | D | D | D | D | D | D | ND |
| 25 | D | D | D | D | D | D | ND |
| 26 | B | B | D | D | D | D | ND |
| 27 | B | C | B | B | B | B | ND |
| 28 | B | A | A | A | B | B | ND |
| 29 | B | B | A | B | B | A | ND |
| 30 | A | C | A | B | B | B | ND |
| 31 | A | C | B | B | D | D | ND |
| 32 | D | B | D | D | D | D | ND |
| 33 | B | B | A | A | B | B | C |
| 34 | B | A | B | B | B | B | C |
| 35 | A | A | A | A | B | A | C |
| 36 | B | D | C | D | B | B | A |
| 37 | D | D | D | D | D | D | A |
| 38 | C | D | C | D | C | C | A |
| 39 | A | A | A | A | A | A | C |
| 40 | A | A | A | A | A | A | B |
| 41 | B | B | B | C | B | B | A |
| 42 | A | C | A | A | B | B | B |
| 43 | B | C | B | B | B | B | B |
| 44 | B | D | C | C | B | B | A |
| 45 | A | B | A | A | A | A | B |
| 46 | A | C | B | A | B | B | B |
| 47 | B | B | A | B | A | B | B |
| 48 | B | D | C | B | B | B | A |
| 49 | B | C | C | C | B | C | A |
| 50 | A | A | A | A | A | A | C |
| 51 | A | A | A | A | A | A | C |
| 52 | A | A | A | B | B | A | C |
| 53 | B | C | B | B | A | A | B |
| 54 | C | D | B | B | B | B | A |
| 55 | B | C | A | A | A | A | B |
| 56 | B | B | A | A | B | B | C |
| 57 | A | B | A | A | B | B | C |
| 58 | A | C | A | A | B | B | B |
| 59 | B | C | B | B | B | B | C |
| 60 | B | C | B | A | B | B | B |
| 61 | B | A | A | A | A | A | C |
| 62 | A | B | A | A | A | A | C |
| 63 | B | A | A | A | B | B | C |
| 64 | B | B | A | A | B | C | C |
| 65 | B | C | C | D | B | B | B |
| 66 | B | D | C | B | C | B | A |
| 67 | B | C | A | B | B | B | B |
| 68 | B | C | B | B | A | A | A |
| 69 | A | C | B | A | B | B | ND |
| 70 | A | C | A | B | B | A | ND |
| 71 | B | D | D | C | C | C | ND |
| 72 | B | D | D | C | C | B | ND |
| 73 | B | C | B | A | B | A | A |
| 74 | B | A | B | B | B | B | B |
| 75 | B | C | A | A | B | B | C |
| 76 | A | A | A | A | B | B | C |
| 77 | B | C | C | C | C | B | A |
| 78 | B | A | A | A | A | A | ND |
| 79 | B | B | A | A | A | A | ND |
| 80 | B | B | A | A | A | A | B |
| 81 | C | C | B | B | D | D | B |
| 82 | B | C | C | B | C | C | A |
| 83 | A | A | C | B | B | B | A |
| 84 | B | C | B | B | B | A | A |
| 85 | A | B | A | A | A | A | B |
| 86 | B | B | A | A | B | A | C |
| 87 | A | B | A | A | A | A | B |
| 88 | A | B | A | B | A | B | ND |

TABLE 1-continued

| Ex. # | CSF1R Kd (nM) | FLT3 Kd (nM) | KIT Kd (nM) | PDGFRβ Kd (nM) | CSF1R M-NFS-60 CTB:IC$_{50}$ (nM) | HEK293 pCSF1R M-CSF MSD:IC$_{50}$ (nM) | Kinase specificity S(10) |
|---|---|---|---|---|---|---|---|
| 89 | B | C | A | A | B | B | ND |
| 90 | B | C | B | B | B | B | ND |
| 91 | D | A | B | B | B | B | D |
| 92 | B | C | A | A | B | B | ND |
| 93 | B | B | A | A | D | D | ND |
| 94 | B | B | B | B | A | A | ND |
| 95 | A | D | C | A | B | B | ND |
| 96 | B | A | A | A | A | A | C |
| 97 | B | B | A | A | A | A | B |
| 98 | B | B | A | A | A | A | B |
| 99 | D | C | D | C | D | C | A |
| 100 | B | C | B | B | B | B | A |
| 101 | C | B | C | B | B | B | B |
| 102 | B | B | A | A | A | A | B |
| 103 | B | D | D | B | B | B | ND |

In Table 1,
CSF1R Kd (nM): A≤5, 5<B≤20, 20<C≤50, D>50; and ND=no data;
FLT3 Kd (nM): A≤200, 200<B≤1000, 1000<C≤5000, D>5000; and ND=no data;
KIT Kd (nM): A≤100, 100<B≤500, 500<C≤2000, D>2000; and ND=no data;
PDGFRβ Kd (nM): A≤50, 50<B≤500, 500<C≤2000, D>2000; and ND=no data;
CSF1R Cell Proliferation Assay (M-NSF-60) IC$_{50}$ (nM): A≤50, 50<B≤400, 400<C≤1500, D>1500; and ND=no data;
HEK293 pCSF1R Assay (M-CSF MSD) IC$_{50}$ (nM): A≤50, 50<B≤200, 200<C≤500, D>500; and ND=no data; and
S score: A≤0.01, 0.01<B≤0.02, C>0.02; and ND=no data.
Additional compounds provided herein were found to have the following activity shown in Table 2:

TABLE 2

| Ex. # | CSF1R Kd (nM) | FLT3 Kd (nM) | KIT Kd (nM) | PDGFRβ Kd (nM) | CSF1R M-NFS-60 CTB:IC$_{50}$ (nM) | HEK293 pCSF1R M-CSF MSD:IC$_{50}$ (nM) | Kinase specificity S(10) |
|---|---|---|---|---|---|---|---|
| 104 | A | A | A | A | A | A | A |
| 105 | B | B | C | C | C | C | A |
| 106 | C | B | C | C | D | D | A |
| 107 | B | C | B | B | B | B | B |
| 108 | B | D | C | C | B | B | A |
| 109 | C | C | B | B | B | B | A |
| 110 | A | C | B | B | B | A | A |
| 111 | B | C | C | C | B | B | A |
| 112 | C | C | C | C | D | C | A |
| 113 | C | C | C | D | D | C | A |
| 114 | D | C | B | C | B | B | A |
| 115 | D | C | C | B | B | B | A |
| 116 | B | B | B | B | D | B | ND |
| 117 | B | D | D | B | C | D | A |
| 118 | C | C | B | Q | C | D | A |
| 119 | B | B | A | A | B | B | A |
| 120 | B | C | B | B | B | B | B |
| 121 | B | C | B | B | B | B | A |
| 122 | B | B | B | B | B | B | B |
| 123 | B | B | A | B | B | B | B |
| 124 | B | B | A | A | B | B | B |
| 125 | B | C | C | B | B | B | B |
| 126 | B | B | B | B | B | A | A |
| 127 | B | C | B | A | B | A | A |
| 128 | B | D | B | B | C | B | B |
| 129 | A | C | A | A | B | A | B |
| 130 | B | C | B | A | B | C | A |
| 131 | A | A | A | A | A | A | B |
| 132 | A | A | A | A | B | B | C |
| 133 | B | C | B | A | B | B | A |
| 134 | B | B | B | A | B | A | A |
| 135 | B | D | C | C | B | B | ND |
| 136 | B | C | A | A | B | B | B |
| 137 | A | B | A | A | A | A | A |
| 138 | A | B | A | A | A | A | A |
| 139 | C | B | B | B | C | C | A |
| 140 | B | D | C | B | C | C | A |
| 141 | A | B | A | A | A | A | B |
| 142 | A | A | A | A | B | A | C |
| 143 | B | C | C | C | C | C | B |
| 144 | A | B | B | B | B | B | B |
| 145 | A | C | B | A | B | A | A |
| 146 | B | B | A | A | B | A | B |
| 147 | A | B | A | A | B | A | A |
| 148 | A | C | A | B | B | B | A |
| 149 | B | B | B | A | B | C | A |
| 150 | A | B | A | A | B | B | B |
| 151 | B | B | A | A | B | A | B |
| 152 | B | A | A | B | B | A | A |
| 153 | B | C | C | B | B | A | A |
| 154 | B | C | C | C | B | B | A |
| 155 | A | A | A | B | B | A | B |
| 156 | B | C | D | C | C | C | A |
| 157 | C | D | D | C | C | D | A |
| 158 | A | B | A | A | A | A | B |
| 159 | B | C | C | C | C | C | A |
| 160 | A | B | A | A | A | A | A |
| 161 | B | C | B | B | B | A | A |
| 162 | A | C | B | B | B | A | A |
| 163 | D | D | B | B | D | D | A |
| 164 | B | C | D | C | C | D | A |
| 165 | B | D | C | C | C | D | A |
| 166 | B | B | C | D | C | D | A |
| 167 | A | C | B | B | A | A | A |
| 168 | B | C | D | D | C | D | A |
| 169 | B | C | C | B | B | B | A |
| 170 | B | D | D | C | D | D | A |
| 171 | B | B | A | A | B | A | C |
| 172 | A | B | B | B | B | A | B |
| 173 | B | B | B | B | B | B | B |
| 174 | A | A | A | A | A | A | B |
| 175 | B | B | B | B | B | B | A |
| 176 | B | C | B | B | C | C | B |
| 177 | A | A | A | A | A | A | C |
| 178 | B | B | C | C | C | C | B |
| 179 | B | C | A | A | C | C | B |
| 180 | C | C | B | B | D | D | A |
| 181 | B | C | B | A | C | C | B |
| 182 | A | B | B | B | B | A | A |
| 183 | B | B | A | A | A | A | B |
| 184 | B | B | A | B | B | C | A |
| 185 | B | A | A | A | B | B | A |
| 186 | B | A | B | B | C | C | B |
| 187 | B | D | D | C | C | B | A |
| 188 | B | C | D | C | C | B | A |
| 189 | B | B | C | C | B | C | A |
| 190 | C | B | C | C | B | D | A |
| 191 | C | C | B | C | D | D | A |
| 192 | B | C | B | A | C | C | B |
| 193 | B | C | A | A | A | A | A |
| 194 | B | C | B | A | B | B | A |
| 195 | C | C | C | C | C | C | A |
| 196 | A | B | B | B | B | A | A |
| 197 | B | D | B | B | C | D | A |
| 198 | A | C | B | A | B | C | A |
| 199 | B | D | D | D | D | C | A |
| 200 | B | B | C | B | B | B | A |
| 201 | C | C | C | C | D | C | A |
| 202 | B | C | B | B | B | B | A |
| 203 | B | B | A | B | B | B | A |
| 204 | B | C | B | B | B | B | A |

TABLE 2-continued

| Ex. # | CSF1R Kd (nM) | FLT3 Kd (nM) | KIT Kd (nM) | PDGFRβ Kd (nM) | CSF1R M-NFS-60 CTB:IC$_{50}$ (nM) | HEK293 pCSF1R M-CSF MSD:IC$_{50}$ (nM) | Kinase specificity S(10) |
|---|---|---|---|---|---|---|---|
| 205 | B | B | C | B | C | D | B |
| 206 | B | B | B | B | B | B | A |
| 207 | B | A | A | A | A | B | B |
| 208 | A | A | A | A | A | B | B |
| 209 | B | B | B | B | B | B | A |
| 210 | C | D | C | C | D | C | A |
| 211 | A | A | A | A | A | A | C |
| 212 | B | B | A | A | B | B | A |
| 213 | A | B | A | A | B | B | B |
| 214 | A | D | B | B | B | A | B |
| 215 | B | C | C | C | B | B | A |
| 216 | B | C | C | B | B | B | A |
| 217 | B | C | C | B | B | B | A |
| 218 | B | C | C | B | B | A | A |
| 219 | B | C | B | A | C | B | B |
| 220 | C | D | D | B | D | D | A |
| 221 | A | A | A | A | A | A | B |
| 222 | C | D | D | C | D | D | A |
| 223 | B | C | B | B | B | B | A |
| 224 | B | B | A | B | D | D | A |
| 225 | A | B | A | A | C | B | ND |
| 226 | A | B | A | A | A | A | B |
| 227 | B | C | B | B | A | A | B |
| 228 | D | D | C | B | D | D | A |
| 229 | B | B | A | A | B | A | A |
| 230 | B | B | A | A | A | A | A |
| 231 | B | C | C | B | A | A | A |
| 232 | A | A | A | A | A | A | A |
| 233 | A | B | A | A | B | A | A |
| 234 | B | B | A | A | B | B | A |
| 235 | B | B | A | A | B | B | A |
| 236 | B | B | B | B | B | B | A |

In Table 2,
CSF1R Kd (nM): A≤5, 5<B≤20, 20<C≤50, D>50; and ND=no data;
FLT3 Kd (nM): A≤200, 200<B≤1000, 1000<C≤5000, D>5000; and ND=no data;
KIT Kd (nM): A≤100, 100<B≤500, 500<C≤2000, D>2000; and ND=no data;
PDGFRβ Kd (nM): A≤50, 50<B≤500, 500<C≤2000, D>2000; and ND=no data;
CSF1R Cell Proliferation Assay (M-NSF-60) IC$_{50}$ (nM): A≤50, 50<B≤400, 400<C≤1500, D>1500; and ND=no data;
HEK293 pCSF1R Assay (M-CSF MSD) IC$_{50}$ (nM): A≤50, 50<B≤200, 200<C≤500, D>500; and ND=no data; and
S score: A≤0.01, 0.01<B≤0.02, C>0.02; and ND=no data.

Example 240

In Vivo Inhibition of the Growth and Survival of M-NFS-60 Tumor Cells in Mice 1×10$^7$ M-NFS-60 cells suspended in PBS were injected into the peritoneal cavity of athymic nu/nu mice (Harlan Research Labs) in all study groups except the nave group, on Day 0. On Days 1-3, Compound A having the Formula I suspended in 0.5% hydroxypropylmethylcellulose (HPMC) was dosed orally at 100, 30, and 10 and 3 mg/kg once a day (QD) in the treatment group and compound Ki20227 suspended in Pharmatek#6 was dosed orally at 30 mg/kg once a day (QD) to the positive control group. The vehicle control group received Pharmatek#6 once a day (QD) and the naive group was untreated. On Day 4, the peritoneal cavity was flushed with 5 mL sterile PBS containing 40 units/mL sodium heparin and the peritoneal cells were counted via the Vi-cell cell counter. FIG. 1 shows the decrease in the number of tumor cells in the groups that were administered Compound A.

Figure 2:
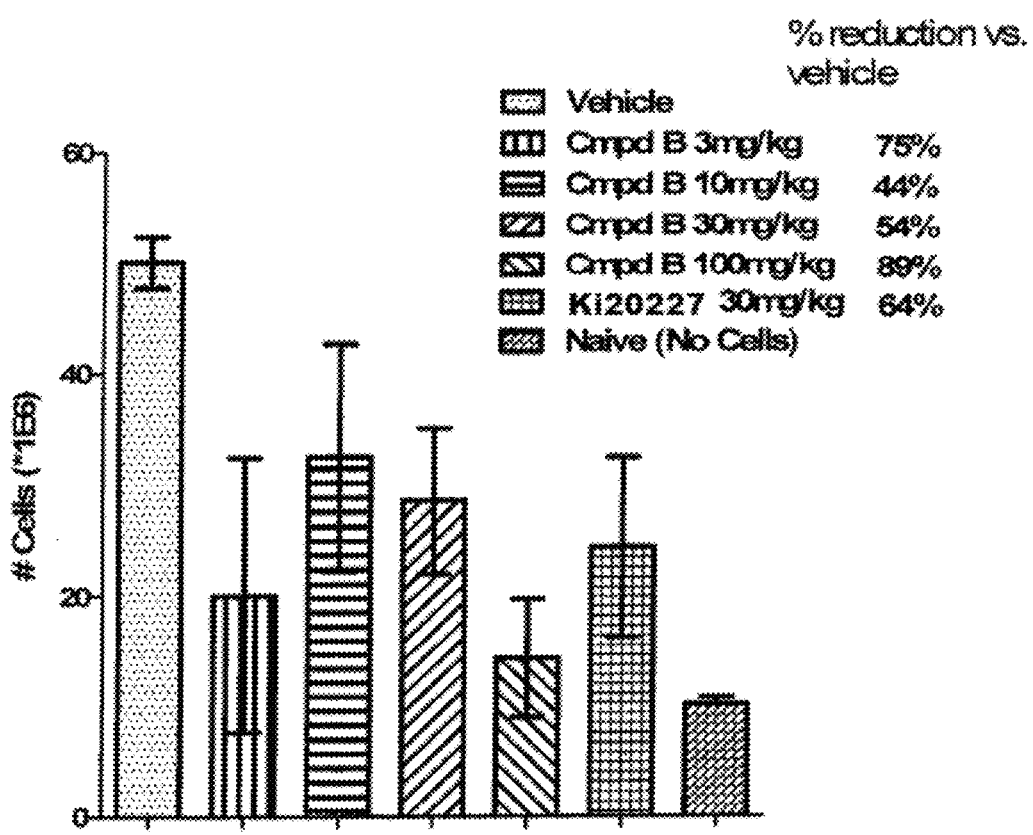
FIG. 2 depicts the in vivo inhibition of CSF-1 dependent M-NFS-60 tumor cell proliferation in the peritoneal cavity of athymic nu/nu mice from the administration of one of the compounds provided herein having the Formula I (Compound B).

The same study was conducted using Compound B of having the Formula I, which was administered in the same formulation at the same dose and schedule. FIG. 2 shows the decrease in the number of tumor cells in the groups that were administered Compound B.

Example 241

In Vivo Inhibition of PTHrP-Induced Hypercalemia

Hypercalcemia of malignancy is a significant complication of advanced breast and lung cancer, and multiple myeloma. Production of humoral factors by the primary tumor is the mechanism responsible for 80% of cases. The vast majority of HHM is caused by tumor-produced parathyroid hormone-related protein, which acts through PTH/PTHrP receptors in the bone and kidney to stimulate osteoclastic bone resorption and calcium resorption. Transforming growth factor-β (TGF-β), which is stored in bone matrix and released by osteoclastic bone resorption, brings about enhanced PTHrP production of tumor cells in bone. Increased production of PTHrP accelerates further bone resorption and provides more space for tumor cell proliferation. Suppression of osteoclast-mediated bone resorption may therefore be effective against bone metastasis. M-CSF has been shown to induce osteoclast generation and bone resorption and therefore CSF1R inhibition may be an effective mechanism against one metastasis.

In this humoral hypercalcemia of malignancy model; 3-day-old BDF1 mice (Charles River Laboratories) in all groups except naïve were challenged twice daily (morning and evening, by subcutaneous injection) with 0.5 mg/kg recombinant PTHrP (Bachem, Torrance, Calif.) for seven days. The treatment group was administered Compound A of Formula I suspended in 0.5% hydroxypropylmethylcellulose (HPMC) at 100, 30, and 10 and 3 mg/kg orally once a day (QD) for seven days On day 1, rPTHrP was injected immediately prior to dosing of Compound A or Vehicle Control. The positive control group was administered compound Ki20227 suspended in Pharmatek#6 and was dosed orally at 30 mg/kg once a day (QD) while the vehicle control group received 1% hydroxypropylmethylcellulose orally once daily for seven days. The study groups are summarized in Table 3 below. Mandibular blood was drawn exactly 3 hr after last dose to monitor changes in blood ionized calcium and TRAPC5b levels (a bone resorption marker). Blood ionized calcium levels were determined using a QuantiChrom Calcium Assay Kit (DICA-500) for Quantitative Colorimetric Calcium Determination at 612 nm. TRAPC5b levels were determined using mouse TRAP assay (Immunodiagnosticsystems Inc. # SB-TR103). Mice were sacrificed on Day8 and the tibiae were harvested for bone TRAP5b and H&E staining.

TABLE 3

| Group | N | Treatment | Route/frequency |
|---|---|---|---|
| 1 Naive | 4 | none | n/a |
| 2 PTHrP | 4 | 0.5 mg/kg PTHrP | SC BID |
| 3 vehicle control | 4 | 0.5 mg/kg PTHrP + 1% HPMC | SC BID and PO QD |
| 4 positive control | 4 | 0.5 mg/kg PTHrP + Ki20227 30 mg/kg | SC BID and PO |
| 5 | 5 | 0.5 mg/kg PTHrP + | SC BID and |

TABLE 3-continued

| Group | N | Treatment | Route/frequency |
|---|---|---|---|
| experimental | | 100 mg/kg Compound A | PO QD |
| 6 experimental | 5 | 0.5 mg/kg PTHrP + 30 mg/kg Compound A | SC BID and POQD |
| 7 experimental | 5 | 0.5 mg/kg PTHrP + 10 mg/kg Compound A | SC BID and PO QD |
| 8 experimental | 5 | 0.5 mg/kg PTHrP + 3 mg/kg Compound A | SC BID and PO QD |

Figure 3:
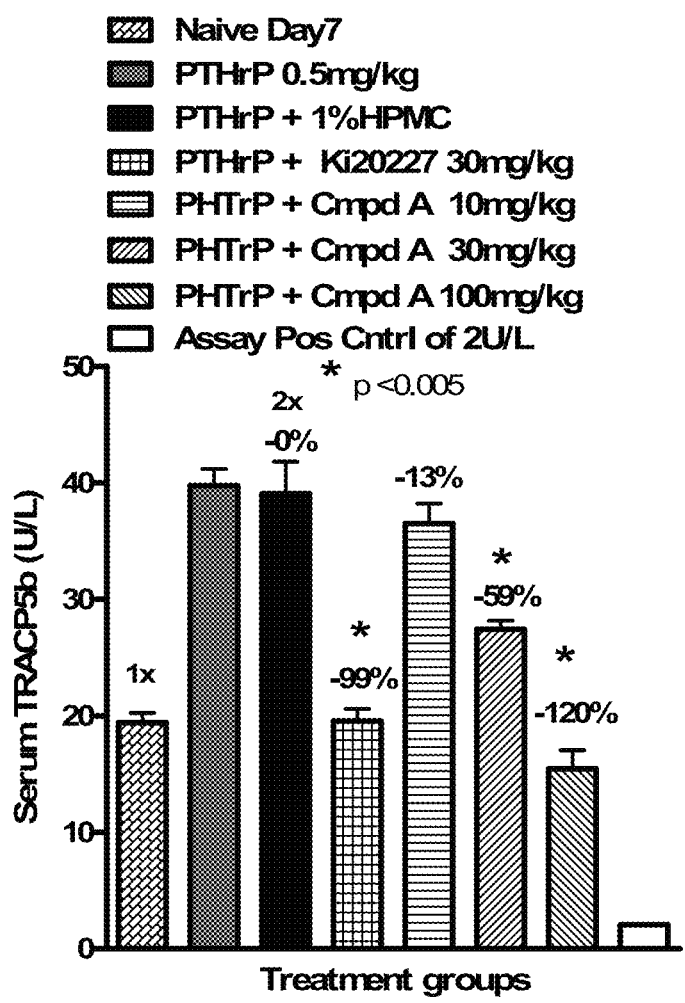
FIG. 3 depicts the in vivo inhibition of PTHrP-induced hypercalcemia from the administration of Compound A having the Formula I, in BDF1 mice challenged twice daily for seven days with 0.5 mg/kg recombinant PTHrP, as measured by serum TRAPC5B levels, a bone resorption marker.

The results show that CSF1R inhibitors can be effective in this HHM model. FIG. 3 shows Compound A reduced serum TRAP5b levels in a dose related manner and at the highest dose, reduced TRAP5b levels below that of naïve animals.

Figure 4:
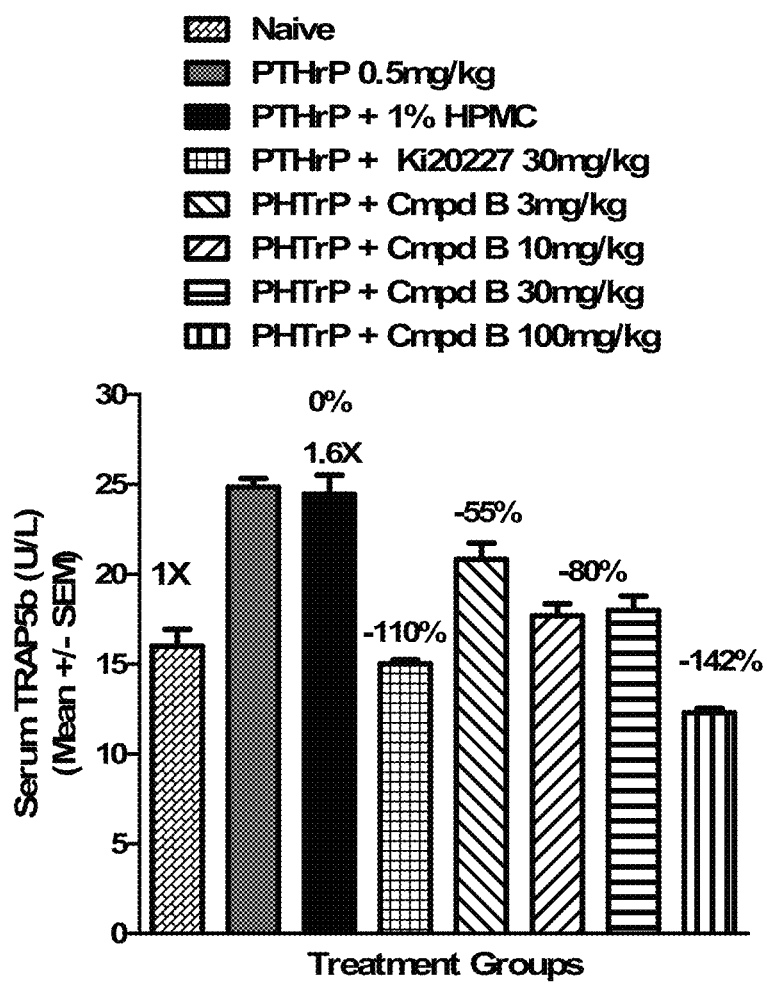
FIG. 4 depicts the in vivo inhibition of PTHrP-induced hypercalcemia from the administration of Compound B having the Formula I, in BDF1 mice challenged twice daily for seven days with 0.5 mg/kg recombinant PTHrP, as measured by serum TRAPC5B levels, a bone resorption marker.

The same study was conducted using Compound B having the Formula I, which was administered in the same formulation at the same dose and schedule. FIG. 4 shows Compound B reduced serum TRAP5b levels in a dose related manner and at the highest dose, reduced TRAP5b levels below that of naïve animals.

Example 242

In Vivo Inhibition of MCP-1 Induction

MCP-1 (monocyte chemo-attractant protein 1) is a chemokine that regulates migration and infiltration of monocytes/macrophages and is implicated in the development of tumor metastasis. It was demonstrated in prior experiments that M-CSF stimulation of human monocytes, peripheral blood mononuclear cells (PBMC) or whole blood, induced levels of MCP-1. This experiment was conducted to see whether the same observations may be made in vivo.

In this study, 55-day old Balb/c mice (Harlan Laboratories) were grouped according to Table 4. One hour prior to M-CSF stimulation, animals were dosed orally with either Compound A, GW-2580 or vehicle. One hour post dose, animals were administered 0.8 μg each M-CSF resuspended in 200 μL sterile saline I.V. Two hours after administration of M-CSF, blood was collected via the maxillary vein and processed for MCP-1 ELISA (R&D Systems # MJE00) according to the manufacturer's instructions.

TABLE 4

| Group | N | Treatment | MCSF | Therapy (Dose) |
|---|---|---|---|---|
| 1 | 3 | Vehicle + sterile saline | Saline IV | 1% HPMC |
| 2 | 3 | Vehicle + 0.8 μg/ms rM-CSF-CF | 200 μL IV | 1% HPMC |
| 3 | 4 | 0.8 μg/ms rM-CSF-CF in saline | 200 μL IV | Cmpd A (1 mg/kg) |
| 4 | 4 | 0.8 μg/ms rM-CSF-CF in saline | 200 μL IV | Cmpd A (3 mg/kg) |
| 5 | 4 | 0.8 μg/ms rM-CSF-CF in saline | 200 μL IV | Cmpd A (10 mg/kg) |
| 6 | 4 | 0.8 μg/ms rM-CSF-CF in saline | 200 μL IV | Cmpd A (30 mg/kg) |
| 7 | 4 | 0.8 μg/ms rM-CSF-CF in saline | 200 μL IV | Cmpd A (100 mg/kg) |
| 8 | 4 | 0.8 μg/ms rM-CSF-CF in saline | 200 μL IV | GW-2580 (160 mg/kg) |
| 9 | 3 | Naïve for base line | none | none |

Figure 5:
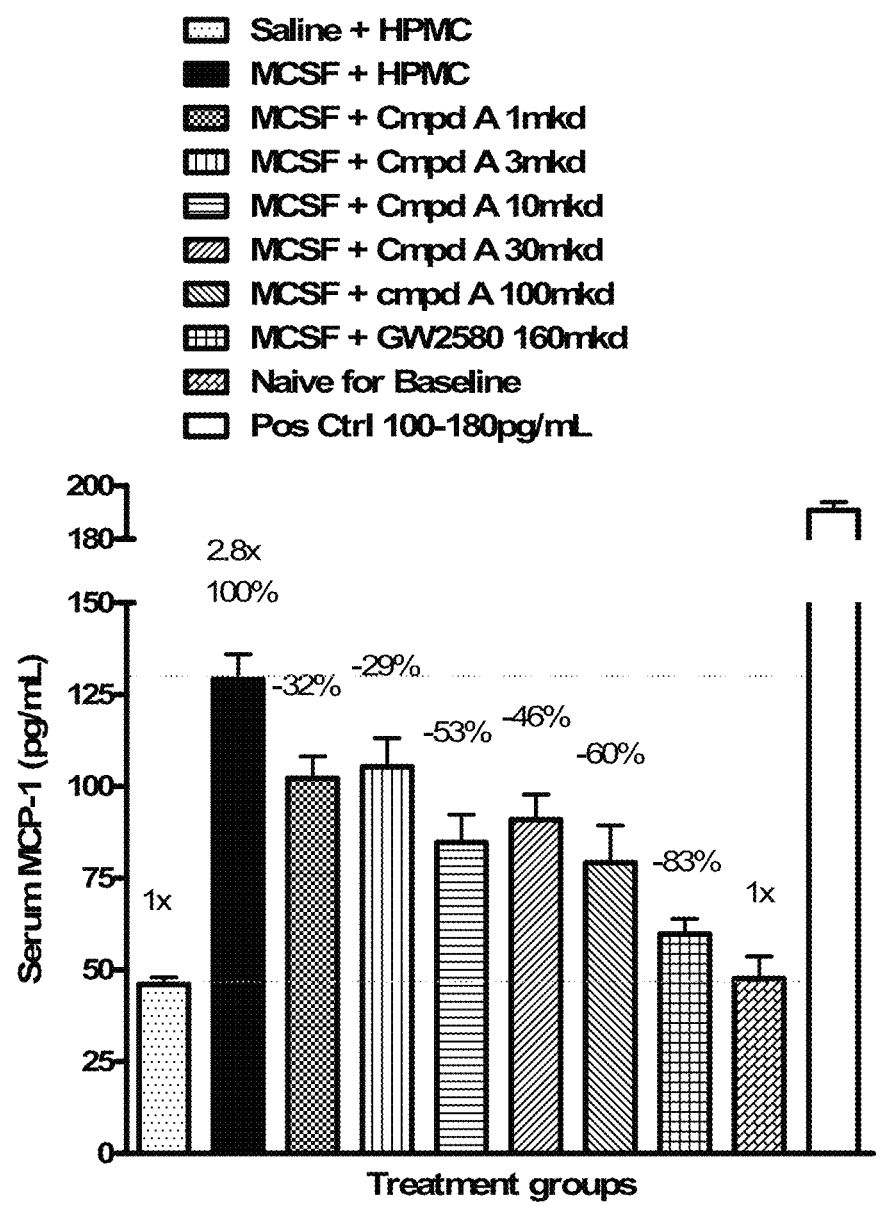
FIG. 5 depicts the in vivo inhibition of MCP-1 induction in Balb/c mice treated with Compound A having the Formula I, prior to M-CSF stimulation.
Figure 6:
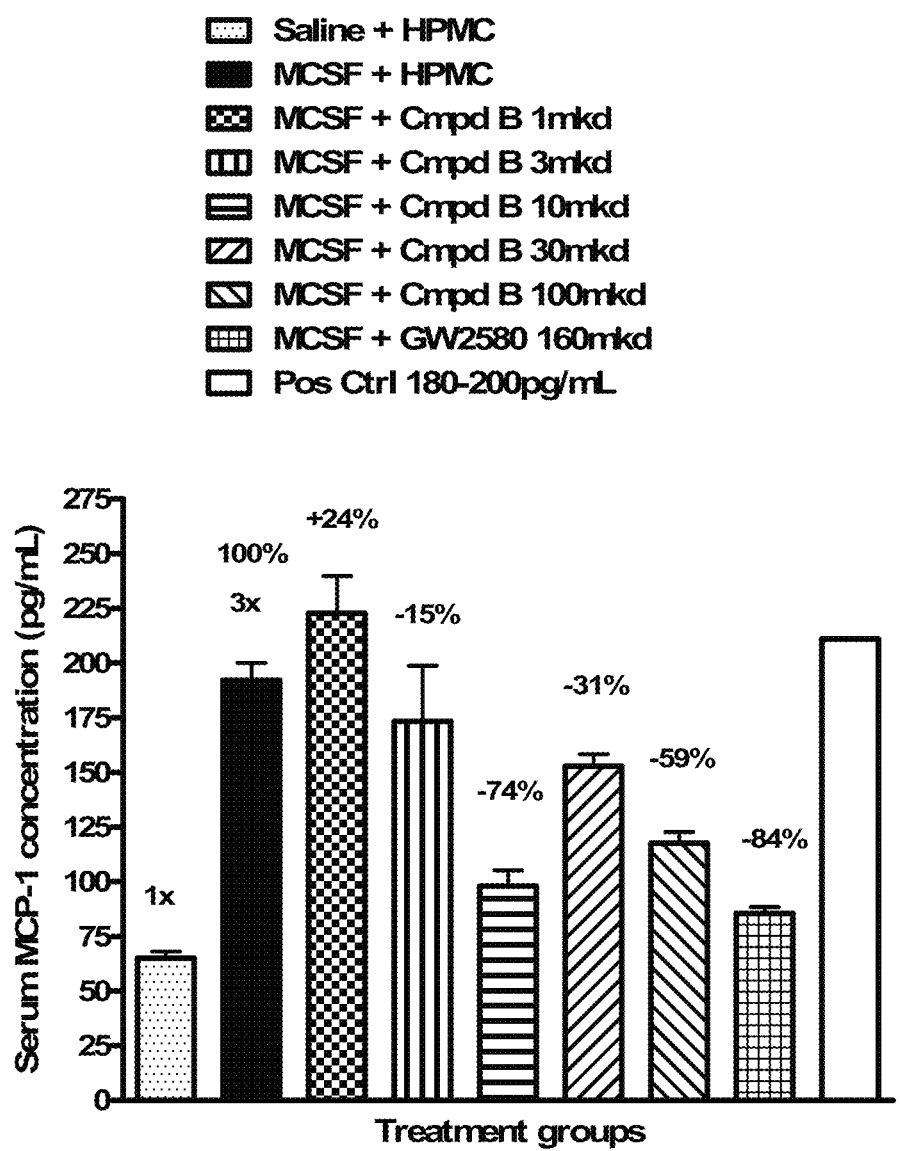
FIG. 6 depicts the in vivo inhibition of MCP-1 induction in Balb/c mice treated with Compound B having the Formula I, prior to M-CSF stimulation.

FIG. 5 shows that IV injection of M-CSF in mice induces the level of MCP-1 approximately three-fold. The most potent MCP-1 reduction was observed at 60% at 100 mg/kg, and activity was reduced but comparable at the 30 and 10 mg/kg (46 and 53%, respectively) by pretreatment with Compound A. The same study was conducted using Compound B having the Formula I, which was administered in the same formulation at the same dose and schedule. FIG. 6 also shows IV injection of M-CSF inducing a three-fold increase in MCP-1 levels. A dose response was less evident, but maximal activity was again observed at 100 mg/kg, and the % reduction (59%) was nearly identical to that measured for Compound A.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

Since modifications will be apparent to those of skill in the art, it is intended that the claimed subject matter be limited only by the scope of the appended claims.

What is claimed is:

1. A method for treatment of a disease selected from myeloid leukemia, cancer of the head and neck, prostate cancer, breast cancer, melanoma, lung cancer, arthritis, and Alzheimer's disease, comprising administering a therapeutically effective amount of a compound having formula IV:

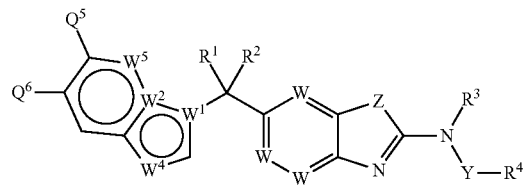

or a pharmaceutically acceptable salt, solvate, hydrate, stereoiomer, mixture of stereoisomers or racemic mixture of stereoisomers thereof, wherein:

$R^1$ and $R^2$ are each independently selected from hydrogen or halogen;

$R^3$ is hydrogen or alkyl;

$R^4$ is phenyl or cyclohexyl, where $R^4$ is optionally substituted with one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^u OR^x$, —$R^u OR^u N(R^y)(R^z)$, —$R^u N(R^y)(R^z)$, —$R^u SR^x$, —$R^u C(J)R^x$, —$R^u C(J)OR^x$, —$R^u C(J)N(R^y)(R^z)$, —$R^u S(O)_r R^w$, —$R^u N(R^x)C(J)R^x$, —$R^u N(R^x)C(J)OR^x$, —$R^u N(R^x)S(O)_r R^w$, =$NOR^d$, or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one to three $Q^3$ groups; each $Q^3$ is independently selected from deuterium, halo, hydroxyl, alkyl, haloalkyl and hydroxyalkyl;

Y is —$(CR^5 R^6)_q$—;

$R^5$ and $R^6$ are each independently hydrogen, halo, alkyl, haloalkyl or hydroxyalkyl;

Z is O, S, or NH;

each W is independently CR$^8$ or N;

$R^8$ is hydrogen, halo, haloalkyl or alkyl;

$W^1$ is N or C;

$W^2$ is N or CR$^{9b}$, $R^{9b}$ is hydrogen or $Q^2$;

W⁴ is N or CR¹¹ᵇ,
W⁵ is N or CR¹³;
R¹¹ᵇ and R¹³ are each independently hydrogen or Q²;
Q² is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —RᵘORˣ, —RᵘORᵘORˣ, —RᵘORᵘN(Rʸ)(Rᶻ), —RᵘN(Rʸ)(Rᶻ), —RᵘSRˣ, —RᵘC(J)Rˣ, —RᵘC(J)ORˣ, —Rᵘ(J)N(Rʸ)(Rᶻ), —RᵘC(J)RᵘN(Rʸ)(Rᶻ), —RᵘC(J)N(Rʸ)ORˣ, —C(=NORˣ)Rˣ, —RᵘS(O)ₜRʷ, —RᵘN(Rˣ)C(J)Rˣ, —RᵘN(Rˣ)C(J)ORˣ, —RᵘN(Rˣ)S(O)ₜRʷ or —C(=NRʸ)N(Rʸ)ORˣ, where the alkyl, haloalkyl, aminoalkyl, alkenyl, alkynyl, cycloalkyl, cycloalkenyl, aryl, heteroaryl, and heterocyclyl groups are optionally substituted with one to three Q⁴ groups, each Q⁴ is independently selected from halo, deuterium, hydroxyl, alkyl, haloalkyl and hydroxyalkyl;
Q⁵ and Q⁶ are each independently hydrogen, deuterium, halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —RᵘORˣ, —RᵘORˣ, —RᵘORᵘN(Rʸ)(Rᶻ), —RᵘN(Rʸ)(Rᶻ), —RᵘSRˣ, —RᵘC(J)Rˣ, —RᵘC(J)ORˣ, —RᵘC(J)N(Rʸ)(Rᶻ), —RᵘC(J)RᵘN(Rʸ)(Rᶻ), —RᵘC(J)N(Rʸ)ORˣ, —C(=NORˣ)Rˣ, —RᵘS(O)ₜRʷ, —RᵘN(Rˣ)C(J)Rˣ, —RᵘN(Rˣ)C(J)ORˣ, —RᵘN(Rˣ)S(O)ₜRʷ or —C(=NRʸ)N(Rʸ)ORˣ, where the alkyl, haloalkyl, aminoalkyl, alkenyl, alkynyl, cycloalkyl, cycloalkenyl, aryl, heteroaryl, and heterocyclyl groups are optionally substituted with one or more Q⁸ groups; each Q⁸ is independently selected from halo, deuterium, hydroxyl, alkyl, haloalkyl and hydroxyalkyl;
each Rᵈ is independently hydrogen or alkyl;
Rᵈ is hydrogen or alkyl;
each Rᵘ is independently alkylene, alkenylene or a direct bond;
Rʷ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;
each Rˣ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;
Rʸ and Rᶻ are each independently selected from (i) or (ii) below:
(i) Rʸ and Rᶻ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or
(ii) Rʸ and Rᶻ, together with the nitrogen atom to which they are attached, form a heterocyclyl or heteroaryl, optionally substituted with one, two or three Q⁷ groups; each Q⁷ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;
J is O, NRˣ or S;
each t is independently an integer from 0-2; and
q is an integer from 0-4.

2. The method of claim 1, where R⁴ is cyclohexyl, optionally substituted with one, two or three groups selected from Q¹; each Q¹ is independently halo, oxo, alkyl, haloalkyl, hydroxyalkyl, cycloalkyl, =NOH, —RᵘORˣ or —RᵘC(O)Rˣ, each Rᵘ is independently alkylene or a direct bond; and each Rˣ is independently hydrogen or alkyl.

3. The method of claim 1, where Y is direct bond, —CH₂—, —CH(CH₃)— or —CH(CH₂OH)—.

4. The compound method of claim 1, where each W is independently CR⁸ or N; and R⁸ is hydrogen, haloalkyl or alkyl.

5. The method of claim 1, wherein the compound has Formula V or a pharmaceutically acceptable salt, solvate, hydrate, single stereoiomer, mixture of stereoisomers or racemic mixture of stereoisomers thereof, wherein:
R¹ and R² are each independently selected from hydrogen or halogen;
R³ is hydrogen or alkyl;
R⁴ is phenyl or cyclohexyl, where R⁴ is optionally substituted with one, two or three groups selected from Q¹;
each Q¹ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —RᵘORˣ, —RᵘORᵘN(Rʸ)(Rᶻ), —RᵘN(Rʸ)(Rᶻ), —RᵘSRˣ, —RᵘC(J)Rˣ, —RᵘC(J)ORˣ, —RᵘC(J)N(Rʸ)(Rᶻ), —RᵘS(O)ₜRʷ, —RᵘN(Rˣ)C(J)Rˣ, —RᵘN(Rˣ)C(J)ORˣ, —RᵘN(Rˣ)S(O)ₜRʷ, =NORᵈ, or —C(=NRʸ)N(Rʸ)ORˣ, where the alkyl, haloalkyl, aminoalkyl, alkenyl, alkynyl, cycloalkyl, cycloalkenyl, aryl, heteroaryl, and heterocyclyl groups are optionally substituted with one to three Q³ groups; each Q³ is independently selected from deuterium, halo, hydroxyl, alkyl, haloalkyl and hydroxyalkyl;
Y is —(CR⁵R⁶)ᵩ—;
R⁵ and R⁶ are each independently hydrogen, halo, alkyl, haloalkyl or hydroxyalkyl;
Z is O, S, or NH;
each W is independently CR⁸ or N;
R⁸ is hydrogen, halo, haloalkyl or alkyl;
W⁴ is N or CR¹¹ᵇ;
W⁵ is N or CR¹³;
R¹¹ᵇ and R¹³ are each independently hydrogen or Q²;
Q² is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —RᵘORˣ, —RᵘORᵘORˣ, —RᵘORᵘN(Rʸ)(Rᶻ), RᵘN(Rʸ)(Rᶻ), —RᵘSRˣ, —RᵘC(J)Rˣ, —RᵘC(J)ORˣ, —RᵘC(J)N(Rʸ)(Rᶻ), —RᵘC(J)RᵘN(Rʸ)(Rᶻ), —RᵘC(J)N(Rʸ)ORˣ, —C(=NORˣ)Rˣ, —RᵘS(O)ₜRʷ, —RᵘN(Rˣ)C(J)Rˣ, —RᵘN(Rˣ)C(J)ORˣ, —RᵘN(Rˣ)S(O)ₜRʷ or —C(=NRʸ)N(Rʸ)ORˣ, where the alkyl, haloalkyl, aminoalkyl, alkenyl, alkynyl, cycloalkyl, cycloalkenyl, aryl, heteroaryl, and heterocyclyl groups are optionally substituted with one to three $Q^4$ groups, each $Q^4$ is independently selected from halo, deuterium, hydroxyl, alkyl, haloalkyl and hydroxyalkyl;

$Q^5$ and $Q^6$ are each independently hydrogen, deuterium, halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

each $R^d$ is independently hydrogen or alkyl;
each $R^u$ is independently alkylene, alkenylene or a direct bond;
$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;
each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;
$R^y$ and $R^z$ are each independently selected from (i) or (ii) below:
(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or
(ii) $R^y$ and $R^z$, together with the nitrogen atom to which they are attached, form a heterocyclyl or heteroaryl, optionally substituted with one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;
$R^y$ and $R^z$ are each independently hydrogen or alkyl;
J is O, NR$^x$ or S;
each t is independently an integer from 0-2; and
q is an integer from 0-4.

6. The method of claim 1, wherein the compound has Formula VI

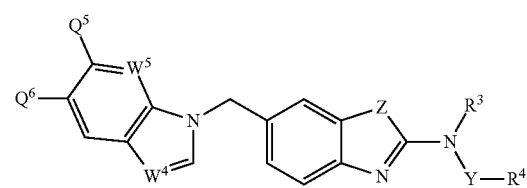

VI or a pharmaceutically acceptable salt, solvate, hydrate, single stereoiomer, mixture of stereoisomers or racemic mixture of stereoisomers thereof, wherein
$R^3$ is hydrogen or alkyl;
$R^4$ is phenyl or cyclohexyl, where $R^4$ is optionally substituted with one, two or three groups selected from $Q^1$;
each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"S(O)$_t$R$^w$, —R"N(R$^x$)C(J)R$^x$, —R"N(R$^x$)C(J)OR$^x$, —R"N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one to three $Q^3$ groups; each $Q^3$ is independently selected from deuterium, halo, hydroxyl, alkyl, haloalkyl and hydroxyalkyl;
Y is —(CR$^5$R$^6$)$_q$—;
$R^5$ and $R^6$ are each independently hydrogen, halo, alkyl, haloalkyl or hydroxyalkyl;
Z is O, S, or NH;
$W^5$ is N or CH;
$W^4$ is N or CR$^{11b}$;
$R^{11b}$ is hydrogen or $Q^2$;
$Q^2$ is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one to three $Q^4$ groups, each $Q^4$ is independently selected from halo, deuterium, hydroxyl, alkyl, haloalkyl and hydroxyalkyl;
$Q^5$ and $Q^6$ are each independently hydrogen, deuterium, halo, cyano, oxo, thioxo, alkyl, haloalkyl, aminoalkyl, alkenyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"C(J)R$^x$, —R"C(J)OR$^x$, —R$_u$C(J)N(R$^y$)(R$^z$), —R"C(J)R"N(R$^y$)(R$^z$), —R"C(J)N(R$^y$)OR$^x$, —C(=NOR$^x$)R$^x$, —R"S(O)$_t$R$^w$, —R"N(R$^x$)C(J)R$^x$, —R"N(R$^x$)C(J)OR$^x$, —R"N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl; $Q^5$ and $Q^6$ are each independently hydrogen, deuterium, halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R"OR$^x$, —R"OR"OR$^x$, —R"OR"N(R$^y$)(R$^z$), —R"N(R$^y$)(R$^z$), —R"SR$^x$, —R"C(J)R$^x$, —R"C(J)OR$^x$, —R"C(J)N(R$^y$)

(R$^z$), —R$^u$C(J)R$^u$N(R$^y$)(R$^z$), —R$^u$C(J)N(R$^y$)OR$^x$, —C(=NOR$^x$)R$^x$, —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^8$ groups; each Q$^8$ is independently selected from halo, deuterium, hydroxyl, alkyl, haloalkyl and hydroxyalkyl;

each R$^d$ is independently hydrogen or alkyl;

each R$^u$ is independently alkylene, alkenylene or a direct bond;

R$^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each R$^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

R$^y$ and R$^z$ are each independently selected from (i) or (ii) below:

(i) R$^y$ and R$^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) R$^y$ and R$^z$, together with the nitrogen atom to which they are attached, form a heterocyclyl or heteroaryl, optionally substituted with one, two or three Q$^7$ groups; each Q$^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, NR$^x$ or S;

each t is independently an integer from 0-2; and q is an integer from 0-4.

7. The method of claim 1, where each Q$^1$ is independently halo, oxo, alkyl, haloalkyl, hydroxyalkyl, cycloalkyl, =NOH, —R$^u$OR$^x$ or —R$^u$C(O)R$^x$; each R$^u$ is independently alkylene or a direct bond; and each R$^x$ is independently hydrogen or alkyl.

8. The method of claim 1, wherein the compound has Formula IX

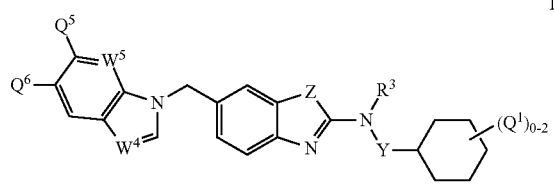

IX or a pharmaceutically acceptable salt, solvate, hydrate, single stereoiomer, mixture of stereoisomers or racemic mixture of stereoisomers thereof, wherein:

R$^3$ is hydrogen or alkyl;

each Q$^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$^u$OR$^x$, —R$^u$OR$^u$N(R$^y$)(R$^z$), —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$, =NOR$^d$, or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one to three Q$^3$ groups; each Q$^3$ is independently selected from deuterium, halo, hydroxyl, alkyl, haloalkyl and hydroxyalkyl;

Y is —(CR$^5$R$^6$)$_q$—;

R$^5$ and R$^6$ are each independently hydrogen, halo, alkyl, haloalkyl or hydroxyalkyl;

Z is O, S, or NH;

W$^4$ is N or CR$^{11b}$;

W$^5$ is N or CR$^{13}$;

R$^{11b}$ and R$^{13}$ are each independently hydrogen or Q$^2$;

each Q$^2$ is independently halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —R$^u$OR$^x$, —R$^u$OR$^u$OR$^x$, —R$^u$OR$^u$N(R$^y$)(R$^z$), —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$C(J)R$^u$N(R$^y$)(R$^z$), —R$^u$C(J)N(R$^y$)OR$^x$, —C(=NOR$^x$)R$^x$, —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one to three Q$^4$ groups, each Q$^4$ is independently selected from halo, deuterium, hydroxyl, alkyl, haloalkyl and hydroxyalkyl;

Q$^5$ and Q$^6$ are each independently hydrogen, halo, cyano, alkyl, haloalkyl, aminoalkyl, alkenyl, alkynyl, cycloalkyl, heteroaryl, heteroaralkyl, heterocyclyl, heterocyclylalkyl, —R$^u$OR$^x$, —R$^u$N(R$^y$)(R$^z$), —R$^u$SR$^x$, —R$^u$C(J)R$^x$, —R$^u$C(J)OR$^x$, —R$^u$C(J)N(R$^y$)(R$^z$), —R$^u$S(O)$_t$R$^w$, —R$^u$N(R$^x$)C(J)R$^x$, —R$^u$N(R$^x$)C(J)OR$^x$, —R$^u$N(R$^x$)S(O)$_t$R$^w$ or —C(=NR$^y$)N(R$^y$)OR$^x$, where the alkyl, haloalkyl, aminoalkyl, alkenyl, alkynyl, cycloalkyl, cycloalkenyl, aryl, heteroaryl, and heterocyclyl groups are optionally substituted with one or more Q$^8$ groups; each Q$^8$ is independently selected from halo, deuterium, hydroxyl, alkyl, haloalkyl and hydroxyalkyl;

R$^d$ is hydrogen or alkyl;

each R$^u$ is independently alkylene, alkenylene or a direct bond;

R$^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each R$^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

R$^y$ and R$^z$ are each independently selected from (i) or (ii) below:

(i) R$^y$ and R$^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) R$^y$ and R$^z$, together with the nitrogen atom to which they are attached, form a heterocyclyl or heteroaryl, optionally substituted with one, two or three Q⁷ groups;
each Q⁷ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;
J is O, NR$^x$ or S;
each t is independently an integer from 0-2;
n is 1 or 2; and
q is an integer from 0-4.

9. The method of claim 8, wherein Q⁵ and Q⁶ are each independently hydrogen, halo, alkoxy, tetrazole or pyrazole, where the tetrazole and pyrazole rings are optionally substituted with one or two alkyl groups.

10. The method of claim 8, wherein, Q⁵ and Q⁶ are each independently hydrogen, chloro, fluoro, bromo or methoxy.

11. The method of claim 1, wherein the compound has Formula XI

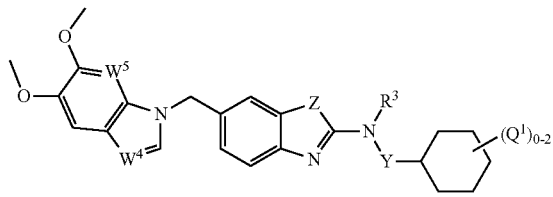

XI or a pharmaceutically acceptable salt, solvate, hydrate, single stereoiomer, mixture of stereoisomers or racemic mixture of stereoisomers thereof, wherein:
R³ is hydrogen or alkyl;
each Q¹ is independently halo, oxo, alkyl, haloalkyl, hydroxyalkyl, cycloalkyl, =NOH, —R$^u$OR$^x$ or —R$^u$C(O)R$^x$;
each R$^u$ is independently alkylene or a direct bond;
each R$^x$ is independently hydrogen or alkyl;
Y is —(CR⁵R⁶)$_q$—;
R⁵ and R⁶ are each independently hydrogen, halo, alkyl, haloalkyl or hydroxyalkyl;
Z is O, S, or NH;
W⁴ is N or CR$^{11b}$;
R$^{11b}$ is hydrogen, halo or alkyl;
W⁵ is N or CR$^{13}$;
R$^{13}$ is hydrogen, halo or alkyl; and
q is an integer from 0-4.

12. The method of claim 1, wherein the compound is selected from:
2-((6-((1H-benzo[d]imidazol-1-yl)methyl)benzo[d]thiazol-2-yl)amino)cyclohexanol,
(1R,2R)-2-((6-((5,6-dimethoxy-1H-benzo[d]imidazol-1-yl)methyl)benzo[d]thiazol-2-yl)amino)cyclohexanol,
2-((6-((5,6-dimethoxy-1H-benzo[d]imidazol-1-yl)methyl)benzo[d]thiazol-2-yl)amino)cyclohexanol,
(1R,2R)-2-((6-((3H-imidazo[4,5-b]pyridin-3-yl)methyl)benzo[d]thiazol-2-yl)amino)cyclohexanol methanesulfonic acid,
(1R,2R)-2-((6-((3H-imidazo[4,5-b]pyridin-3-yl)methyl)benzo[d]thiazol-2-yl)amino)cyclohexanol
2-((6-((3H-imidazo[4,5-b]pyridin-3-yl)methyl)benzo[d]thiazol-2-yl)amino)cyclohexanol
(1R,2R)-2-((6-((6-methoxy-1H-benzo[d]imidazol-1-yl)methyl)benzo[d]thiazol-2-yl)amino)cyclohexanol,
2-((6-((6-methoxy-1H-benzo[d]imidazol-1-yl)methyl)benzo[d]thiazol-2-yl)amino)cyclohexanol,
(1R,2R)-2-((6-((5-methoxy-1H-benzo[d]imidazol-1-yl)methyl)benzo[d]thiazol-2-yl)amino)cyclohexanol,
2-((6-((5-methoxy-1H-benzo[d]imidazol-1-yl)methyl)benzo[d]thiazol-2-yl)amino)cyclohexanol,
(1R,2R)-2-((6-((1H-benzo[d]imidazol-1-yl)methyl)benzo[d]thiazol-2-yl)amino)cyclohexanol,
(1S,2S)-2-((6-((1H-benzo[d]imidazol-1-yl)methyl)benzo[d]thiazol-2-yl)amino)cyclohexanol,
2-((6-((1H-benzo[d]imidazol-1-yl)methyl)benzo[d]thiazol-2-yl)amino)cyclohexanol,
N-benzyl-6-((5,6-dimethoxy-1H-benzo[d]imidazol-1-yl)methyl)benzo[d]thiazol-2-amine,
N-cyclohexyl-6-((5,6-dimethoxy-1H-benzo[d]imidazol-1-yl)methyl)-N-methylbenzo[d]thiazol-2-amine,
N-cyclohexyl-6-((5,6-dimethoxy-1H-benzo[d]imidazol-1-yl)methyl)benzo[d]thiazol-2-amine,
6-((5,6-dimethoxy-1H-benzo[d]imidazol-1-yl)methyl)-N-phenylbenzo[d]thiazol-2-amine,
(1R,2R)-2-((6-((5-methoxy-3H-imidazo[4,5-b]pyridin-3-yl)methyl)benzo[d]thiazol-2-yl)amino)cyclohexanol,
2-((6-((5-methoxy-3H-imidazo[4,5-b]pyridin-3-yl)methyl)benzo[d]thiazol-2-yl)amino)cyclohexanol,
6-((5,6-dimethoxy-1H-benzo[d]imidazol-1-yl)methyl)-N-(2-ethoxyphenyl)benzo[d]thiazol-2-amine,
N-(cyclohexylmethyl)-6-((5,6-dimethoxy-1H-benzo[d]imidazol-1-yl)methyl)benzo[d]thiazol-2-amine,
(1R,2R)-2-((6-((6-bromo-3H-imidazo[4,5-b]pyridin-3-yl)methyl)benzo[d]thiazol-2-yl)amino)cyclohexanol,
2-((6-((6-bromo-3H-imidazo[4,5-b]pyridin-3-yl)methyl)benzo[d]thiazol-2-yl)amino)cyclohexanol,
6-((5,6-dimethoxy-1H-benzo[d]imidazol-1-yl)methyl)-N-(2-methoxyphenyl)benzo[d]thiazol-2-amine,
2-((6-((5,6-dimethoxy-1H-benzo[d]imidazol-1-yl)methyl)benzo[d]thiazol-2-yl)amino)phenol,
(S)—N-(1-cyclohexylethyl)-6-((5,6-dimethoxy-1H-benzo[d]imidazol-1-yl)methyl)benzo[d]thiazol-2-amine,
N-(1-cyclohexylethyl)-6-((5,6-dimethoxy-1H-benzo[d]imidazol-1-yl)methyl)benzo[d]thiazol-2-amine,
(1R,2R)-2-((6-((5,6-dimethoxy-1H-benzo[d]imidazol-1-yl)methyl)benzo[d]oxazol-2-yl)amino)cyclohexanol,
2-((6-((5,6-dimethoxy-1H-benzo[d]imidazol-1-yl)methyl)benzo[d]oxazol-2-yl)amino)cyclohexanol,
N-(cyclohexylmethyl)-6-((5,6-dimethoxy-1H-benzo[d]imidazol-1-yl)methyl)benzo[d]oxazol-2-amine,
(1R,2R)-2-((6-(imidazo[1,2-a]pyridin-3-ylmethyl)benzo[d]thiazol-2-yl)amino)cyclohexanol,
2-((6-(imidazo[1,2-a]pyridin-3-ylmethyl)benzo[d]thiazol-2-yl)amino)cyclohexanol,
(1R,2R)-2-((6-((6-(1-methyl-1H-pyrazol-4-yl)-3H-imidazo[4,5-b]pyridin-3-yl)methyl)benzo[d]thiazol-2-yl)amino)cyclohexanol,
2-((6-((6-(1-methyl-1H-pyrazol-4-yl)-3H-imidazo[4,5-b]pyridin-3-yl)methyl)benzo[d]thiazol-2-yl)amino)cyclohexanol,
(1R,2R)-2-((6-((6-(pyridin-3-yl)-3H-imidazo[4,5-b]pyridin-3-yl)methyl)benzo[d]thiazol-2-yl)amino)cyclohexanol,
2-((6-((6-(pyridin-3-yl)-3H-imidazo[4,5-b]pyridin-3-yl)methyl)benzo[d]thiazol-2-yl)amino)cyclohexanol,
(1R,2R)-2-((6-((5-bromo-6-methoxy-1H-benzo[d]imidazol-1-yl)methyl)benzo[d]thiazol-2-yl)amino)cyclohexanol,
2-((6-((5-bromo-6-methoxy-1H-benzo[d]imidazol-1-yl)methyl)benzo[d]thiazol-2-yl)amino)cyclohexanol, 3-((2-(((1R,2R)-2-hydroxycyclohexyl)amino)benzo[d]thiazol-6-yl)methyl)-3H-imidazo[4,5-b]pyridine-6-carbonitrile,
3-((2-((2-hydroxycyclohexyl)amino)benzo[d]thiazol-6-yl)methyl)-3H-imidazo[4,5-b]pyridine-6-carbonitrile,
(1R,2R)-2-((6-((7-methoxyimidazo[1,2-a]pyridin-3-yl)methyl)benzo[d]thiazol-2-yl)amino)cyclohexanol,
2-((6-((7-methoxyimidazo[1,2-a]pyridin-3-yl)methyl)benzo[d]thiazol-2-yl)amino)cyclohexanol,
(1R,2R)-2-((6-((6-cyclopropyl-3H-imidazo[4,5-b]pyridin-3-yl)methyl)benzo[d]thiazol-2-yl)amino)cyclohexanol,
2-((6-((6-cyclopropyl-3H-imidazo[4,5-b]pyridin-3-yl)methyl)benzo[d]thiazol-2-yl)amino)cyclohexanol,
(1R,2R)-2-((6-((6-bromo-5-methoxy-1H-benzo[d]imidazol-1-yl)methyl)benzo[d]thiazol-2-yl)amino)cyclohexanol,
2-((6-((6-bromo-5-methoxy-1H-benzo[d]imidazol-1-yl)methyl)benzo[d]thiazol-2-yl)amino)cyclohexanol,
(1R,2R)-2-((6-((6-methoxy-5-(1-methyl-1H-pyrazol-4-yl)-1H-benzo[d]imidazol-1-yl)methyl)benzo[d]thiazol-2-yl)amino)cyclohexanol,
2-((6-((6-methoxy-5-(1-methyl-1H-pyrazol-4-yl)-1H-benzo[d]imidazol-1-yl)methyl)benzo[d]thiazol-2-yl)amino)cyclohexanol,
(1R,2R)-2-((6-((5-methoxy-6-(1-methyl-1H-pyrazol-4-yl)-1H-benzo[d]imidazol-1-yl)methyl)benzo[d]thiazol-2-yl)amino)cyclohexanol,
2-((6-((5-methoxy-6-(1-methyl-1H-pyrazol-4-yl)-1H-benzo[d]imidazol-1-yl)methyl)benzo[d]thiazol-2-yl)amino)cyclohexanol,
1-((2-(((1R,2R)-2-hydroxycyclohexyl)amino)benzo[d]thiazol-6-yl)methyl)-5-methoxy-1H-benzo[d]imidazole-6-carbonitrile,
1-((2-((2-hydroxycyclohexyl)amino)benzo[d]thiazol-6-yl)methyl)-5-methoxy-1H-benzo[d]imidazole-6-carbonitrile,
(R)-2-((6-((3H-imidazo[4,5-b]pyridin-3-yl)methyl)benzo[d]thiazol-2-yl)amino)cyclohexanone,
2-((6-((3H-imidazo[4,5-b]pyridin-3-yl)methyl)benzo[d]thiazol-2-yl)amino)cyclohexanone,
(1R,2R)-2-((6-((6-chloro-3H-imidazo[4,5-b]pyridin-3-yl)methyl)benzo[d]thiazol-2-yl)amino)cyclohexanol,
2-((6-((6-chloro-3H-imidazo[4,5-b]pyridin-3-yl)methyl)benzo[d]thiazol-2-yl)amino)cyclohexanol,
(1R,2R)-2-((6-((3H-imidazo[4,5-b]pyridin-3-yl)methyl)benzo[d]oxazol-2-yl)amino)cyclohexanol,
2-((6-((3H-imidazo[4,5-b]pyridin-3-yl)methyl)benzo[d]oxazol-2-yl)amino)cyclohexanol,
(R)-2-((6-((3H-imidazo[4,5-b]pyridin-3-yl)methyl)benzo[d]thiazol-2-yl)amino)cyclohexanone oxime,
2-((6-((3H-imidazo[4,5-b]pyridin-3-yl)methyl)benzo[d]thiazol-2-yl)amino)cyclohexanone oxime,
(1S,2R)-2-((6-((3H-imidazo[4,5-b]pyridin-3-yl)methyl)benzo[d]thiazol-2-yl)amino)-1-methylcyclohexanol,
(1R,2R)-2-((6-((3H-imidazo[4,5-b]pyridin-3-yl)methyl)benzo[d]thiazol-2-yl)amino)-1-methylcyclohexanol,
2-((6-((3H-imidazo[4,5-b]pyridin-3-yl)methyl)benzo[d]thiazol-2-yl)amino)-1-methylcyclohexanol,
(1R,2R)-2-((6-((6-bromo-3H-imidazo[4,5-b]pyridin-3-yl)methyl)benzo[d]oxazol-2-yl)amino)cyclohexanol,
2-((6-((6-bromo-3H-imidazo[4,5-b]pyridin-3-yl)methyl)benzo[d]oxazol-2-yl)amino)cyclohexanol,
(S)-2-((6-((3H-imidazo[4,5-b]pyridin-3-yl)methyl)benzo[d]thiazol-2-yl)amino)-2-cyclohexylethanol,
2-((6-((3H-imidazo[4,5-b]pyridin-3-yl)methyl)benzo[d]thiazol-2-yl)amino)-2-cyclohexylethanol,
(R)-2-((6-((3H-imidazo[4,5-b]pyridin-3-yl)methyl)benzo[d]thiazol-2-yl)amino)-2-cyclohexylethanol,
1-((2-(((1R,2R)-2-hydroxycyclohexyl)amino)benzo[d]thiazol-6-yl)methyl)-6-methoxy-1H-benzo[d]imidazole-5-carbonitrile,
1-((2-((2-hydroxycyclohexyl)amino)benzo[d]thiazol-6-yl)methyl)-6-methoxy-1H-benzo[d]imidazole-5-carbonitrile,
((1R,2R)-2-((6-((3H-imidazo[4,5-b]pyridin-3-yl)methyl)benzo[d]thiazol-2-yl)amino)cyclohexyl)methanol,
2-((6-((3H-imidazo[4,5-b]pyridin-3-yl)methyl)benzo[d]thiazol-2-yl)amino)cyclohexyl)methanol,
(1R,2R)-2-((6-((6-methoxy-1H-benzo[d]imidazol-1-yl)methyl)benzo[d]thiazol-2-yl)amino)cyclohexanol,
2-((6-((6-methoxy-1H-benzo[d]imidazol-1-yl)methyl)benzo[d]thiazol-2-yl)amino)cyclohexanol,
(1R,2R)-2-((6-((5-methoxy-1H-benzo[d]imidazol-1-yl)methyl)benzo[d]thiazol-2-yl)amino)cyclohexanol,
2-((6-((5-methoxy-1H-benzo[d]imidazol-1-yl)methyl)benzo[d]thiazol-2-yl)amino)cyclohexanol,
(1R,2R)-2-((6-((6-fluoro-3H-imidazo[4,5-b]pyridin-3-yl)methyl)benzo[d]thiazol-2-yl)amino)cyclohexanol,
2-((6-((6-fluoro-3H-imidazo[4,5-b]pyridin-3-yl)methyl)benzo[d]thiazol-2-yl)amino)cyclohexanol,
1-(3-((2-(((1R,2R)-2-hydroxycyclohexyl)amino)benzo[d]thiazol-6-yl)methyl)-3H-imidazo[4,5-b]pyridin-6-yl)ethanone,
1-(3-((2-((2-hydroxycyclohexyl)amino)benzo[d]thiazol-6-yl)methyl)-3H-imidazo[4,5-b]pyridin-6-yl)ethanone,
(1R,2R)-2-((6-((6-(methylsulfonyl)-3H-imidazo[4,5-b]pyridin-3-yl)methyl)benzo[d]thiazol-2-yl)amino)cyclohexanol,
2-((6-((6-(methylsulfonyl)-3H-imidazo[4,5-b]pyridin-3-yl)methyl)benzo[d]thiazol-2-yl)amino)cyclohexanol,
1-(((6-((3H-imidazo[4,5-b]pyridin-3-yl)methyl)benzo[d]thiazol-2-yl)amino)methyl)cyclohexanol,
(1-(((6-((3H-imidazo[4,5-b]pyridin-3-yl)methyl)benzo[d]thiazol-2-yl)amino)methyl)cyclohexyl)methanol,
(1R,2R)-2-((6-((5-bromo-3H-imidazo[4,5-b]pyridin-3-yl)methyl)benzo[d]thiazol-2-yl)amino)cyclohexanol,
2-((6-((5-bromo-3H-imidazo[4,5-b]pyridin-3-yl)methyl)benzo[d]thiazol-2-yl)amino)cyclohexanol,
methyl 3-((2-(((1R,2R)-2-hydroxycyclohexyl)amino)benzo[d]thiazol-6-yl)methyl)-3H-imidazo[4,5-b]pyridine-6-carboxylate,
methyl 3-((2-((2-hydroxycyclohexyl)amino)benzo[d]thiazol-6-yl)methyl)-3H-imidazo[4,5-b]pyridine-6-carboxylate,
3-((2-(((1R,2R)-2-hydroxycyclohexyl)amino)benzo[d]thiazol-6-yl)methyl)-3H-imidazo[4,5-b]pyridine-6-carboxylic acid,
3-((2-((2-hydroxycyclohexyl)amino)benzo[d]thiazol-6-yl)methyl)-3H-imidazo[4,5-b]pyridine-6-carboxylic acid,
(1R,2R)-2-((6-((6-(morpholinomethyl)-3H-imidazo[4,5-b]pyridin-3-yl)methyl)benzo[d]thiazol-2-yl)amino)cyclohexanol,
2-((6-((6-(morpholinomethyl)-3H-imidazo[4,5-b]pyridin-3-yl)methyl)benzo[d]thiazol-2-yl)amino)cyclohexanol,
(1R,2R)-2-((6-((6-(hydroxymethyl)-3H-imidazo[4,5-b]pyridin-3-yl)methyl)benzo[d]thiazol-2-yl)amino)cyclohexanol,
2-((6-((6-(hydroxymethyl)-3H-imidazo[4,5-b]pyridin-3-yl)methyl)benzo[d]thiazol-2-yl)amino)cyclohexanol, (1R,2R)-2-((6-((6-(methylthio)-3H-imidazo[4,5-b]pyridin-3-yl)methyl)benzo[d]thiazol-2-yl)amino)cyclohexanol,
2-((6-((6-(methylthio)-3H-imidazo[4,5-b]pyridin-3-yl)methyl)benzo[d]thiazol-2-yl)amino)cyclohexanol,
(1R,2R)-2-((6-((6-((methylthio)methyl)-3H-imidazo[4,5-b]pyridin-3-yl)methyl)benzo[d]thiazol-2-yl)amino)cyclohexanol,
2-((6-((6-((methylthio)methyl)-3H-imidazo[4,5-b]pyridin-3-yl)methyl)benzo[d]thiazol-2-yl)amino)cyclohexanol,
3-((2-(((1R,2R)-2-hydroxycyclohexyl)amino)benzo[d]thiazol-6-yl)methyl)-3H-imidazo[4,5-b]pyridine-5-carbonitrile,
3-((2-((2-hydroxycyclohexyl)amino)benzo[d]thiazol-6-yl)methyl)-3H-imidazo[4,5-b]pyridine-5-carbonitrile,
1-(3-((2-(((1R,2R)-2-hydroxycyclohexyl)amino)benzo[d]thiazol-6-yl)methyl)-3H-imidazo[4,5-b]pyridin-5-yl)ethanone,
1-(3-((2-((2-hydroxycyclohexyl)amino)benzo[d]thiazol-6-yl)methyl)-3H-imidazo[4,5-b]pyridin-5-yl)ethanone,
3-((2-(((1R,2R)-2-hydroxycyclohexyl)amino)benzo[d]thiazol-6-yl)methyl)-N-methyl-3H-imidazo[4,5-b]pyridine-6-carboxamide,
3-((2-((2-hydroxycyclohexyl)amino)benzo[d]thiazol-6-yl)methyl)-N-methyl-3H-imidazo[4,5-b]pyridine-6-carboxamide,
N-hydroxy-3-((2-(((1R,2R)-2-hydroxycyclohexyl)amino)benzo[d]thiazol-6-yl)methyl)-3H-imidazo[4,5-b]pyridine-6-carboximidamide,
(1R,2R)-2-((6-((6-(aminomethyl)-3H-imidazo[4,5-b]pyridin-3-yl)methyl)benzo[d]thiazol-2-yl)amino)cyclohexanol acetic acid,
(1R,2R)-2-((6-((6-(aminomethyl)-3H-imidazo[4,5-b]pyridin-3-yl)methyl)benzo[d]thiazol-2-yl)amino)cyclohexanol,
2-((6-((6-(aminomethyl)-3H-imidazo[4,5-b]pyridin-3-yl)methyl)benzo[d]thiazol-2-yl)amino)cyclohexanol,
3-((2-(((1R,2R)-2-hydroxycyclohexyl)amino)benzo[d]thiazol-6-yl)methyl)-N,N-dimethyl-3H-imidazo[4,5-b]pyridine-6-carboxamide,
3-((2-((2-hydroxycyclohexyl)amino)benzo[d]thiazol-6-yl)methyl)-N,N-dimethyl-3H-imidazo[4,5-b]pyridine-6-carboxamide,
(1R,2R)-2-((6-((6-(2H-tetrazol-5-yl)-3H-imidazo[4,5-b]pyridin-3-yl)methyl)benzo[d]thiazol-2-yl)amino)cyclohexanol,
2-((6-((6-(2H-tetrazol-5-yl)-3H-imidazo[4,5-b]pyridin-3-yl)methyl)benzo[d]thiazol-2-yl)amino)cyclohexanol,
(1R,2R)-2-((6-((6-(2-methyl-2H-tetrazol-5-yl)-3H-imidazo[4,5-b]pyridin-3-yl)methyl)benzo[d]thiazol-2-yl)amino)cyclohexanol,
2-((6-((6-(2-methyl-2H-tetrazol-5-yl)-3H-imidazo[4,5-b]pyridin-3-yl)methyl)benzo[d]thiazol-2-yl)amino)cyclohexanol,
(1R,2R)-2-((6-((6-(1-methyl-1H-tetrazol-5-yl)-3H-imidazo[4,5-b]pyridin-3-yl)methyl)benzo[d]thiazol-2-yl)amino)cyclohexanol,
2-((6-((6-(1-methyl-1H-tetrazol-5-yl)-3H-imidazo[4,5-b]pyridin-3-yl)methyl)benzo[d]thiazol-2-yl)amino)cyclohexanol,
(1R,2R)-2-((6-((6-(ethynyl-3H-imidazo[4,5-b]pyridin-3-yl)methyl)benzo[d]thiazol-2-yl)amino)cyclohexanol,
2-((6-((6-(ethynyl-3H-imidazo[4,5-b]pyridin-3-yl)methyl)benzo[d]thiazol-2-yl)amino)cyclohexanol,
(1R,2R)-2-((6-((6-morpholino-3H-imidazo[4,5-b]pyridin-3-yl)methyl)benzo[d]thiazol-2-yl)amino)cyclohexanol,
2-((6-((6-morpholino-3H-imidazo[4,5-b]pyridin-3-yl)methyl)benzo[d]thiazol-2-yl)amino)cyclohexanol,
(1R,2R)-2-((6-((6-vinyl-3H-imidazo[4,5-b]pyridin-3-yl)methyl)benzo[d]thiazol-2-yl)amino)cyclohexanol,
2-((6-((6-vinyl-3H-imidazo[4,5-b]pyridin-3-yl)methyl)benzo[d]thiazol-2-yl)amino)cyclohexanol,
N-((3-((2-(((1R,2R)-2-hydroxycyclohexyl)amino)benzo[d]thiazol-6-yl)methyl)-3H-imidazo[4,5-b]pyridin-6-yl)methyl)acetamide,
N-((3-((2-((2-hydroxycyclohexyl)amino)benzo[d]thiazol-6-yl)methyl)-3H-imidazo[4,5-b]pyridin-6-yl)methyl)acetamide,
(1R,2R)-2-((6-((5-bromo-1H-benzo[d]imidazol-1-yl)methyl)benzo[d]thiazol-2-yl)amino)cyclohexanol,
2-((6-((5-bromo-1H-benzo[d]imidazol-1-yl)methyl)benzo[d]thiazol-2-yl)amino)cyclohexanol,
(1R,2R)-2-((6-((6-ethyl-3H-imidazo[4,5-b]pyridin-3-yl)methyl)benzo[d]thiazol-2-yl)amino)cyclohexanol,
2-((6-((6-ethyl-3H-imidazo[4,5-b]pyridin-3-yl)methyl)benzo[d]thiazol-2-yl)amino)cyclohexanol,
(1R,2R)-2-((6-((6-(3-hydroxy-3-methylbut-1-yn-1-yl)-3H-imidazo[4,5-b]pyridin-3-yl)methyl)benzo[d]thiazol-2-yl)amino)cyclohexanol,
2-((6-((6-(3-hydroxy-3-methylbut-1-yn-1-yl)-3H-imidazo[4,5-b]pyridin-3-yl)methyl)benzo[d]thiazol-2-yl)amino)cyclohexanol;
(1R,2R)-2-((6-((6-(5-(methylsulfonyl)-3H-imidazo[4,5-b]pyridin-3-yl)methyl)benzo[d]thiazol-2-yl)amino)cyclohexanol;
2-((6-((5-(methylsulfonyl)-3H-imidazo[4,5-b]pyridin-3-yl)methyl)benzo[d]thiazol-2-yl)amino)cyclohexanol;
(1R,2R)-2-((6-((6-bromo-1H-benzo[d]imidazol-1-yl)methyl)benzo[d]thiazol-2-yl)amino)cyclohexanol;
2-((6-((6-bromo-1H-benzo[d]imidazol-1-yl)methyl)benzo[d]thiazol-2-yl)amino)cyclohexanol;
1-((2-(((1R,2R)-2-hydroxycyclohexyl)amino)benzo[d]thiazol-6-yl)methyl)-1H-benzo[d]imidazole-5-carbonitrile;
1-((2-((2-hydroxycyclohexyl)amino)benzo[d]thiazol-6-yl)methyl)-1H-benzo[d]imidazole-5-carbonitrile;
(1R,2R)-2-((6-((6-(2-hydroxypropan-2-yl)-3H-imidazo[4,5-b]pyridin-3-yl)methyl)benzo[d]thiazol-2-yl)amino)cyclohexanol;
2-((6-((6-(2-hydroxypropan-2-yl)-3H-imidazo[4,5-b]pyridin-3-yl)methyl)benzo[d]thiazol-2-yl)amino)cyclohexanol;
1-(1-((2-(((1R,2R)-2-hydroxycyclohexyl)amino)benzo[d]thiazol-6-yl)methyl)-1H-benzo[d]imidazol-5-yl)ethanone;
1-(1-((2-((2-hydroxycyclohexyl)amino)benzo[d]thiazol-6-yl)methyl)-1H-benzo[d]imidazol-5-yl)ethanone;
1-((2-(((1R,2R)-2-hydroxycyclohexyl)amino)benzo[d]thiazol-6-yl)methyl)-1H-benzo[d]imidazole-6-carbonitrile;
1-((2-((2-hydroxycyclohexyl)amino)benzo[d]thiazol-6-yl)methyl)-1H-benzo[d]imidazole-6-carbonitrile;
(1R,2R)-2-((6-((5-(methylsulfonyl)-1H-benzo[d]imidazol-1-yl)methyl)benzo[d]thiazol-2-yl)amino)cyclohexanol;
2-((6-((5-(methylsulfonyl)-1H-benzo[d]imidazol-1-yl)methyl)benzo[d]thiazol-2-yl)amino)cyclohexanol;
(1R,2R)-2-((6-((6-(methylsulfonyl)-1H-benzo[d]imidazol-1-yl)methyl)benzo[d]thiazol-2-yl)amino)cyclohexanol;

2-((6-((6-(methylsulfonyl)-1H-benzo[d]imidazol-1-yl)
methyl)benzo[d]thiazol-2-yl)amino)cyclohexanol;
(1R,2R)-2-((6-((6-((R,S)-1-hydroxyethyl)-3H-imidazo[4,
5-b]pyridin-3-yl)methyl)benzo[d]thiazol-2-yl)amino)
cyclohexanol;
2-((6-((6-(1-hydroxyethyl)-3H-imidazo[4,5-b]pyridin-3-
yl)methyl)benzo[d]thiazol-2-yl)amino)cyclohexanol;
2-(dimethylamino)-1-(3-((2-(((1R,2R)-2-hydroxycyclo-
hexyl)amino)benzo[d]thiazol-6-yl)methyl)-3H-imi-
dazo[4,5-b]pyridin-6-yl)ethanone acetate salt;
2-(dimethylamino)-1-(3-((2-((2-hydroxycyclohexyl)
amino)benzo[d]thiazol-6-yl)methyl)-3H-imidazo[4,5-
b]pyridin-6-yl)ethanone;
2-(dimethylamino)-1-(3-((2-(((1R,2R)-2-hydroxycyclo-
hexyl)amino)benzo[d]thiazol-6-yl)methyl)-3H-imi-
dazo[4,5-b]pyridin-6-yl)ethanone;
3-((2-(((1R,2R)-2-hydroxycyclohexyl)amino)benzo[d]
thiazol-6-yl)methyl)imidazo[1,2-a]pyridine-7-carboni-
trile;
3-((2-((2-hydroxycyclohexyl)amino)benzo[d]thiazol-6-
yl)methyl)imidazo[1,2-a]pyridine-7-carbonitrile;
(1R,2R)-2-((6-((5,6-dimethyl-1H-benzo[d]imidazol-1-yl)
methyl)benzo[d]thiazol-2-yl)amino)cyclohexanol;
2-((6-((5,6-dimethyl-1H-benzo[d]imidazol-1-yl)methyl)
benzo[d]thiazol-2-yl)amino)cyclohexanol;
1-(1-((2-(((1R,2R)-2-hydroxycyclohexyl)amino)benzo
[d]thiazol-6-yl)methyl)-1H-benzo[d]imidazol-6-yl)
ethanone;
1-(1-((2-((2-hydroxycyclohexyl)amino)benzo[d]thiazol-
6-yl)methyl)-1H-benzo[d]imidazol-6-yl)ethanone;
(1R,2R)-2-((6-((5-ethynyl-1H-benzo[d]imidazol-1-yl)
methyl)benzo[d]thiazol-2-yl)amino)cyclohexanol;
2-((6-((5-ethynyl-1H-benzo[d]imidazol-1-yl)methyl)
benzo[d]thiazol-2-yl)amino)cyclohexanol;
(1R,2R)-2-((6-((6-ethynyl-1H-benzo[d]imidazol-1-yl)
methyl)benzo[d]thiazol-2-yl)amino)cyclohexanol;
2-((6-((6-ethynyl-1H-benzo[d]imidazol-1-yl)methyl)
benzo[d]thiazol-2-yl)amino)cyclohexanol;
(1R,2R)-2-((6-((6-bromo-5-methoxy-3H-imidazo[4,5-b]
pyridin-3-yl)methyl)benzo[d]thiazol-2-yl)amino)cy-
clohexanol;
2-((6-((6-bromo-5-methoxy-3H-imidazo[4,5-b]pyridin-
3-yl)methyl)benzo[d]thiazol-2-yl)amino)cyclohexa-
nol;
3-(((2(((1R,2R)-2-hydroxycyclohexyl)amino)benzo[d]
oxazol-6-yl)methyl)-3H-imidazo[4,5-b]pyridine-6-car-
bonitrile;
3-((2-((2-hydroxycyclohexyl)amino)benzo[d]oxazol-6-
yl)methyl)-3H-imidazo[4,5-b]pyridine-6-carbonitrile;
3-((2-(((1R,2R)-2-hydroxycyclohexyl)amino)benzo[d]
thiazol-6-yl)methyl)-5-methoxy-3H-imidazo[4,5-b]
pyridine-6-carbonitrile;
3-((2-((2-hydroxycyclohexyl)amino)benzo[d]thiazol-6-
yl)methyl)-5-methoxy-3H-imidazo[4,5-b]pyridine-6-
carbonitrile;
(1R,2R)-2-((6-((5-methyl-1H-benzo[d]imidazol-1-yl)
methyl)benzo[d]thiazol-2-yl)amino)cyclohexanol;
2-((6-((5-methyl-1H-benzo[d]imidazol-1-yl)methyl)
benzo[d]thiazol-2-yl)amino)cyclohexanol;
(1R,2R)-2-((6-((5,6-difluoro-1H-benzo[d]imidazol-1-yl)
methyl)benzo[d]thiazol-2-yl)amino)cyclohexanol;
2-((6-((5,6-difluoro-1H-benzo[d]imidazol-1-yl)methyl)
benzo[d]thiazol-2-yl)amino)cyclohexanol;
(1R,2R)-2-((6-((5-fluoro-1H-benzo[d]imidazol-1-yl)
methyl)benzo[d]thiazol-2-yl)amino)cyclohexanol;
2-((6-((5-fluoro-1H-benzo[d]imidazol-1-yl)methyl)benzo
[d]thiazol-2-yl)amino)cyclohexanol;
(1R,2R)-2-((6-((5-(trifluoromethyl)-1H-benzo[d]imida-
zol-1-yl)methyl)benzo[d]thiazol-2-yl)amino)cyclo-
hexanol;
2-((6-((5-(trifluoromethyl)-1H-benzo[d]imidazol-1-yl)
methyl)benzo[d]thiazol-2-yl)amino)cyclohexanol;
(1R,2R)-2-((6-(imidazo[1,2-b]pyridazin-3-ylmethyl)
benzo[d]thiazol-2-yl)amino)cyclohexanol;
2-((6-(imidazo[1,2-b]pyridazin-3-ylmethyl)benzo[d]thi-
azol-2-yl)amino)cyclohexanol;
(1R,2R)-2-((6-((6-fluoro-3H-imidazo[4,5-b]pyridin-3-yl)
methyl)benzo[d]oxazol-2-yl)amino)cyclohexanol;
2-((6-((6-fluoro-3H-imidazo[4,5-b]pyridin-3-yl)methyl)
benzo[d]oxazol-2-yl)amino)cyclohexanol;
((1R,2R)-2-((6-((6-bromo-3H-imidazo[4,5-b]pyridin-3-
yl)methyl)benzo[d]thiazol-2-yl)amino)cyclohexyl)
methanol;
2-((6-((6-bromo-3H-imidazo[4,5-b]pyridin-3-yl)methyl)
benzo[d]thiazol-2-yl)amino)cyclohexyl)methanol;
(1R,2R)-2-((6-((6-(1-methyl-1H-tetrazol-5-yl)-3H-imi-
dazo[4,5-b]pyridin-3-yl)methyl)benzo[d]thiazol-2-yl)
amino)cyclohexanol;
2-((6-((6-(1-methyl-1H-tetrazol-5-yl)-3H-imidazo[4,5-b]
pyridin-3-yl)methyl)benzo[d]thiazol-2-yl)amino)cy-
clohexanol;
(1R,2R)-2-((6-((7-(2-hydroxyethoxy)imidazo[1,2-a]pyri-
din-3-yl)methyl)benzo[d]thiazol-2-yl)amino)cyclo-
hexanol;
2-((6-((7-(2-hydroxyethoxy)imidazo[1,2-a]pyridin-3-yl)
methyl)benzo[d]thiazol-2-yl)amino)cyclohexanol;
((1S,2R)-2-((6-((6-bromo-3H-imidazo[4,5-b]pyridin-3-
yl)methyl)benzo[d]thiazol-2-yl)amino)cyclohexyl)
methanol;
2-((6-((6-bromo-3H-imidazo[4,5-b]pyridin-3-yl)methyl)
benzo[d]thiazol-2-yl)amino)cyclohexyl)methanol;
(1R,2R)-2-((6-((5,6-dichloro-3H-imidazo[4,5-b]pyridin-
3-yl)methyl)benzo[d]thiazol-2-yl)amino)cyclohexa-
nol;
2-((6-((5,6-dichloro-3H-imidazo[4,5-b]pyridin-3-yl)
methyl)benzo[d]thiazol-2-yl)amino)cyclohexanol;
(1R,2R)-2-((6-((5-ethoxy-1H-benzo[d]imidazol-1-yl)
methyl)benzo[d]thiazol-2-yl)amino)cyclohexanol;
2-((6-((5-ethoxy-1H-benzo[d]imidazol-1-yl)methyl)
benzo[d]thiazol-2-yl)amino)cyclohexanol;
3-((2-(((1R,2R)-2-hydroxycyclohexyl)amino)benzo[d]
thiazol-6-yl)methyl)-3H-imidazo[4,5-b]pyridine-5,6-
dicarbonitrile;
3-((2-((2-hydroxycyclohexyl)amino)benzo[d]thiazol-6-
yl)methyl)-3H-imidazo[4,5-b]pyridine-5,6-dicarboni-
trile;
3-((2-(((1R,2R)-2-(hydroxymethyl)cyclohexyl)amino)
benzo[d]thiazol-6-yl)methyl)-3H-imidazo[4,5-b]pyri-
dine-6-carbonitrile;
3-((2-((2-(hydroxymethyl)cyclohexyl)amino)benzo[d]
thiazol-6-yl)methyl)-3H-imidazo[4,5-b]pyridine-6-car-
bonitrile;
(1R,2R)-2-((6-((6-(1H-pyrazol-1-yl)-3H-imidazo[4,5-b]
pyridin-3-yl)methyl)benzo[d]thiazol-2-yl)amino)cy-
clohexanol;
2-((6-((6-(1H-pyrazol-1-yl)-3H-imidazo[4,5-b]pyridin-3-
yl)methyl)benzo[d]thiazol-2-yl)amino)cyclohexanol;
(1R,2R)-2-((6-(imidazo[1,2-b]pyridazin-3-ylmethyl)
benzo[d]oxazol-2-yl)amino)cyclohexanol;
2-((6-(imidazo[1,2-b]pyridazin-3-ylmethyl)benzo[d]ox-
azol-2-yl)amino)cyclohexanol;
3-((2-(((1R,2R)-2-hydroxycyclohexyl)amino)benzo[d]
thiazol-6-yl)methyl)-N-methylimidazo[1,2-b]
pyridazine-6-carboxamide;

3-((2-((2-hydroxycyclohexyl)amino)benzo[d]thiazol-6-yl)methyl)-N-methylimidazo[1,2-b]pyridazine-6-carboxamide;
(1R,2R)-2-((6-((6-(hydroxymethyl)imidazo[1,2-b]pyridazin-3-yl)methyl)benzo[d]thiazol-2-yl)amino)cyclohexanol;
2-((6-((6-(hydroxymethyl)imidazo[1,2-b]pyridazin-3-yl)methyl)benzo[d]thiazol-2-yl)amino)cyclohexanol;
(1R,2R)-2-((6-((6-(1H-1,2,4-triazol-1-yl)-3H-imidazo[4,5-b]pyridin-3-yl)methyl)benzo[d]thiazol-2-yl)amino)cyclohexanol;
2-((6-((6-(1H-1,2,4-triazol-1-yl)-3H-imidazo[4,5-b]pyridin-3-yl)methyl)benzo[d]thiazol-2-yl)amino)cyclohexanol;
(1R,2R)-2-((6-((6-iodo-3H-imidazo[4,5-b]pyridin-3-yl)methyl)benzo[d]thiazol-2-yl)amino)cyclohexanol;
2-((6-((6-iodo-3H-imidazo[4,5-b]pyridin-3-yl)methyl)benzo[d]thiazol-2-yl)amino)cyclohexanol;
1-((2-(((1R,2R)-2-hydroxycyclohexyl)amino)benzo[d]thiazol-6-yl)methyl)-1H-benzo[d]imidazol-5-ol;
1-((2-((2-hydroxycyclohexyl)amino)benzo[d]thiazol-6-yl)methyl)-1H-benzo[d]imidazol-5-ol;
(1R,2R)-2-((6-((5,7-difluoro-1H-benzo[d]imidazol-1-yl)methyl)benzo[d]thiazol-2-yl)amino)cyclohexanol;
2-((6-((5,7-difluoro-1H-benzo[d]imidazol-1-yl)methyl)benzo[d]thiazol-2-yl)amino)cyclohexanol;
(1R,2R)-2-((6-((5-(trifluoromethoxy)-1H-benzo[d]imidazol-1-yl)methyl)benzo[d]thiazol-2-yl)amino)cyclohexanol;
2-((6-((5-(trifluoromethoxy)-1H-benzo[d]imidazol-1-yl)methyl)benzo[d]thiazol-2-yl)amino)cyclohexanol;
(1R,2R)-2-((6-((6-methoxyimidazo[1,2-b]pyridazin-3-yl)methyl)benzo[d]thiazol-2-yl)amino)cyclohexanol;
2-((6-((6-methoxyimidazo[1,2-b]pyridazin-3-yl)methyl)benzo[d]thiazol-2-yl)amino)cyclohexanol;
(1R,2R)-2-((6-((5-methoxy-1H-benzo[d]imidazol-1-yl)methyl)benzo[d]oxazol-2-yl)amino)cyclohexanol;
2-((6-((5-methoxy-1H-benzo[d]imidazol-1-yl)methyl)benzo[d]oxazol-2-yl)amino)cyclohexanol;
(1R,2R)-2-((6-((6-methoxy-1H-benzo[d]imidazol-1-yl)methyl)benzo[d]oxazol-2-yl)amino)cyclohexanol;
2-((6-((6-methoxy-1H-benzo[d]imidazol-1-yl)methyl)benzo[d]oxazol-2-yl)amino)cyclohexanol;
(1R,2R)-2-((6-((7-(2-methoxyethoxy)imidazo[1,2-a]pyridin-3-yl)methyl)benzo[d]thiazol-2-yl)amino)cyclohexanol;
2-((6-((7-(2-methoxyethoxy)imidazo[1,2-a]pyridin-3-yl)methyl)benzo[d]thiazol-2-yl)amino)cyclohexanol;
(1R,2R)-2-((6-((3H-imidazo[4,5-b]pyridin-3-yl)methyl)-5-fluorobenzo[d]thiazol-2-yl)amino)cyclohexanol;
2-((6-((3H-imidazo[4,5-b]pyridin-3-yl)methyl)-5-fluorobenzo[d]thiazol-2-yl)amino)cyclohexanol;
(1R,2R)-2-((6-((6-morpholinoimidazo[1,2-b]pyridazin-3-yl)methyl)benzo[d]thiazol-2-yl)amino)cyclohexanol;
2-((6-((6-morpholinoimidazo[1,2-b]pyridazin-3-yl)methyl)benzo[d]thiazol-2-yl)amino)cyclohexanol;
(1R,2R)-2-((4-chloro-6-((6-morpholinoimidazo[1,2-b]pyridazin-3-yl)methyl)benzo[d]thiazol-2-yl)amino)cyclohexanol;
2-((4-chloro-6-((6-morpholinoimidazo[1,2-b]pyridazin-3-yl)methyl)benzo[d]thiazol-2-yl)amino)cyclohexanol;
(1R,2R)-2-((6-((6-chloroimidazo[1,2-b]pyridazin-3-yl)methyl)benzo[d]thiazol-2-yl)amino)cyclohexanol;
2-((6-((6-chloroimidazo[1,2-b]pyridazin-3-yl)methyl)benzo[d]thiazol-2-yl)amino)cyclohexanol;
(1R,2R)-2-((6-((6-(1H-pyrazol-1-yl)imidazo[1,2-a]pyridin-3-yl)methyl)benzo[d]thiazol 2-yl)amino)cyclohexanol;
2-((6-((6-(1H-pyrazol-1-yl)imidazo[1,2-a]pyridin-3-yl)methyl)benzo[d]thiazol-2-yl)amino)cyclohexanol;
(1R,2R)-2-((6-((5-(1H-pyrazol-1-yl)-1H-benzo[d]imidazol-1-yl)methyl)benzo[d]thiazol-2-yl)amino)cyclohexanol;
2-((6-((5-(1H-pyrazol-1-yl)-1H-benzo[d]imidazol-1-yl)methyl)benzo[d]thiazol-2-yl)amino)cyclohexanol;
(1R,2R)-2-((6-((5-(1H-1,2,4-triazol-1-yl)-1H-benzo[d]imidazol-1-yl)methyl)benzo[d]thiazol-2-yl)amino)cyclohexanol;
2-((6-((5-(1H-1,2,4-triazol-1-yl)-1H-benzo[d]imidazol-1-yl)methyl)benzo[d]thiazol-2-yl)amino)cyclohexanol;
(1S,2R)-2-((6-((6-fluoro-3H-imidazo[4,5-b]pyridin-3-yl)methyl)benzo[d]thiazol-2-yl)amino)cyclohexanol;
2-((6-((6-fluoro-3H-imidazo[4,5-b]pyridin-3-yl)methyl)benzo[d]thiazol-2-yl)amino)cyclohexanol;
trans-4-((6-((6-fluoro-3H-imidazo[4,5-b]pyridin-3-yl)methyl)benzo[d]thiazol-2-yl)amino)cyclohexanol;
4-((6-((6-fluoro-3H-imidazo[4,5-b]pyridin-3-yl)methyl)benzo[d]thiazol-2-yl)amino)cyclohexanol;
(1R,2R)-2-((6-((3H-imidazo[4,5-b]pyridin-3-yl)methyl)-7-fluorobenzo[d]thiazol-2-yl)amino)cyclohexanol;
2-((6-((3H-imidazo[4,5-b]pyridin-3-yl)methyl)-7-fluorobenzo[d]thiazol-2-yl)amino)cyclohexanol;
(1R,2R)-2-((6-((6-methoxyimidazo[1,2-a]pyridin-3-yl)methyl)benzo[d]thiazol-2-yl)amino)cyclohexanol;
2-((6-((6-methoxyimidazo[1,2-a]pyridin-3-yl)methyl)benzo[d]thiazol-2-yl)amino)cyclohexanol;
(1R,2R)-2-((6-((3H-imidazo[4,5-b]pyridin-3-yl)methyl)-4-bromobenzo[d]thiazol-2-yl)amino)cyclohexanol;
2-((6-((3H-imidazo[4,5-b]pyridin-3-yl)methyl)-4-bromobenzo[d]thiazol-2-yl)amino)cyclohexanol;
(1R,2R)-2-((6-((7-(1H-pyrazol-1-yl)imidazo[1,2-a]pyridin-3-yl)methyl)benzo[d]thiazol-2-yl)amino)cyclohexanol;
2-((6-((7-(1H-pyrazol-1-yl)imidazo[1,2-a]pyridin-3-yl)methyl)benzo[d]thiazol-2-yl)amino)cyclohexanol;
(1R,2R)-2-((6-((3H-imidazo[4,5-b]pyridin-3-yl)methyl)-4,7-difluorobenzo[d]thiazol-2-yl)amino)cyclohexanol;
2-((6-((3H-imidazo[4,5-b]pyridin-3-yl)methyl)-4,7-difluorobenzo[d]thiazol-2-yl)amino)cyclohexanol;
1-((2-(((1R,2R)-2-hydroxycyclohexyl)amino)benzo[d]oxazol-6-yl)methyl)-1H-benzo[d]imidazole-5-carbonitrile;
1-((2-((2-hydroxycyclohexyl)amino)benzo[d]oxazol-6-yl)methyl)-1H-benzo[d]imidazole-5-carbonitrile;
(1R,2R)-2-((6-((5-(2-morpholinoethoxy)-1H-benzo[d]imidazol-1-yl)methyl)benzo[d]thiazol-2-yl)amino)cyclohexanol;
2-((6-((5-(2-morpholinoethoxy)-1H-benzo[d]imidazol-1-yl)methyl)benzo[d]thiazol-2-yl)amino)cyclohexanol;
(1R,2R)-2-((6-((5-(2-hydroxyethoxy)-1H-benzo[d]imidazol-1-yl)methyl)benzo[d]thiazol-2-yl)amino)cyclohexanol;
2-((6-((5-(2-hydroxyethoxy)-1H-benzo[d]imidazol-1-yl)methyl)benzo[d]thiazol-2-yl)amino)cyclohexanol;
1-((2-(((1R,2R)-2-hydroxycyclohexyl)amino)benzo[d]thiazol-6-yl)methyl)-N-methyl-1H-benzo[d]imidazole-5-carboxamide;
1-((2-((2-hydroxycyclohexyl)amino)benzo[d]thiazol-6-yl)methyl)-N-methyl-1H-benzo[d]imidazole-5-carboxamide;

(1R,2R)-2-((6-((5-(3,6-dihydro-2H-pyran-4-yl)-1H-benzo[d]imidazol-1-yl)methyl)benzo[d]thiazol-2-yl)amino)cyclohexanol;
2-((6-((5-(3,6-dihydro-2H-pyran-4-yl)-1H-benzo[d]imidazol-1-yl)methyl)benzo[d]thiazol-2-yl)amino)cyclohexanol;
(1R,2R)-2-((6-((5-(3,3,3-trifluoroprop-1-en-2-yl)-1H-benzo[d]imidazol-1-yl)methyl)benzo[d]thiazol-2-yl)amino)cyclohexanol;
2-((6-((5-(3,3,3-trifluoroprop-1-en-2-yl)-1H-benzo[d]imidazol-1-yl)methyl)benzo[d]thiazol-2-yl)amino)cyclohexanol;
(1R,2R)-2-((6-((6-bromoimidazo[1,2-b]pyridazin-3-yl)methyl)benzo[d]thiazol-2-yl)amino)cyclohexanol;
2-((6-((6-bromoimidazo[1,2-b]pyridazin-3-yl)methyl)benzo[d]thiazol-2-yl)amino)cyclohexanol;
(1R,2R)-2-((6-((6-(4-methylpiperazin-1-yl)imidazo[1,2-b]pyridazin-3-yl)methyl)benzo[d]thiazol-2-yl)amino)cyclohexanol;
2-((6-((6-(4-methylpiperazin-1-yl)imidazo[1,2-b]pyridazin-3-yl)methyl)benzo[d]thiazol-2-yl)amino)cyclohexanol;
(trans-4-((6-((6-fluoro-3H-imidazo[4,5-b]pyridin-3-yl)methyl)benzo[d]thiazol-2-yl)amino)cyclohexyl)methanol;
(cis-4-((6-((6-fluoro-3H-imidazo[4,5-b]pyridin-3-yl)methyl)benzo[d]thiazol-2-yl)amino)cyclohexyl)methanol;
4-((6-((6-fluoro-3H-imidazo[4,5-b]pyridin-3-yl)methyl)benzo[d]thiazol-2-yl)amino)cyclohexyl)methanol;
6-((6-fluoro-3H-imidazo[4,5-b]pyridin-3-yl)methyl)-N-((1R,2R)-2-(methylthio)cyclohexyl)benzo[d]thiazol-2-amine;
6-((6-fluoro-3H-imidazo[4,5-b]pyridin-3-yl)methyl)-N-(2-(methylthio)cyclohexyl)benzo[d]thiazol-2-amine;
(1R,2R)-2-((6-((5-(oxetan-3-yloxy)-1H-benzo[d]imidazol-1-yl)methyl)benzo[d]thiazol-2-yl)amino)cyclohexanol;
2-((6-((5-(oxetan-3-yloxy)-1H-benzo[d]imidazol-1-yl)methyl)benzo[d]thiazol-2-yl)amino)cyclohexanol;
(1R,2R)-2-((6-((5-vinyl-1H-benzo[d]imidazol-1-yl)methyl)benzo[d]thiazol-2-yl)amino)cyclohexanol;
2-((6-((5-vinyl-1H-benzo[d]imidazol-1-yl)methyl)benzo[d]thiazol-2-yl)amino)cyclohexanol;
(1R,2R)-2-((6-((5-(cyclohex-1-en-1-yl)-1H-benzo[d]imidazol-1-yl)methyl)benzo[d]thiazol-2-yl)amino)cyclohexanol;
2-((6-((5-(cyclohex-1-en-1-yl)-1H-benzo[d]imidazol-1-yl)methyl)benzo[d]thiazol-2-yl)amino)cyclohexanol;
(1R,2R)-2-((6-((5-(1-methyl-3-(trifluoromethyl)-1H-pyrazol-4-yl)-1H-benzo[d]imidazol-1-yl)methyl)benzo[d]thiazol-2-yl)amino)cyclohexanol;
2-((6-((5-(1-methyl-3-(trifluoromethyl)-1H-pyrazol-4-yl)-1H-benzo[d]imidazol-1-yl)methyl)benzo[d]thiazol-2-yl)amino)cyclohexanol;
(1R,2R)-2-((6-((5-fluoroimidazo[1,2-a]pyridin-3-yl)methyl)benzo[d]thiazol-2-yl)amino)cyclohexanol;
2-((6-((5-fluoroimidazo[1,2-a]pyridin-3-yl)methyl)benzo[d]thiazol-2-yl)amino)cyclohexanol;
(1R,2R)-2-((6-((7-morpholinoimidazo[1,2-a]pyridin-3-yl)methyl)benzo[d]thiazol-2-yl)amino)cyclohexanol;
2((6-((7-morpholinoimidazo[1,2-a]pyridin-3-yl)methyl)benzo[d]thiazol-2-yl)amino)cyclohexanol;
((1R,2R)-2-((6-((5,7-dimethyl-1H-benzo[d]imidazol-1-yl)methyl)benzo[d]thiazol-2-yl)amino)cyclohexanol;
2-((6-((5,7-dimethyl-1H-benzo[d]imidazol-1-yl)methyl)benzo[d]thiazol-2-yl)amino)cyclohexanol;
(1R,2R)-2-((6-((5-bromo-7-methyl-1H-benzo[d]imidazol-1-yl)methyl)benzo[d]thiazol-2-yl)amino)cyclohexanol;
2-((6-((5-bromo-7-methyl-1H-benzo[d]imidazol-1-yl)methyl)benzo[d]thiazol-2-yl)amino)cyclohexanol;
((1R,3R)-3-((6-((6-fluoro-3H-imidazo[4,5-b]pyridin-3-yl)methyl)benzo[d]thiazol-2-yl)amino)cyclohexyl)methanol;
3-((6-((6-fluoro-3H-imidazo[4,5-b]pyridin-3-yl)methyl)benzo[d]thiazol-2-yl)amino)cyclohexyl)methanol;
(1R,2S,3R)-3-((6-((6-fluoro-3H-imidazo[4,5-b]pyridin-3-yl)methyl)benzo[d]thiazol-2-yl)amino)cyclohexane-1,2-diol;
3-((6-((6-fluoro-3H-imidazo[4,5-b]pyridin-3-yl)methyl)benzo[d]thiazol-2-yl)amino)cyclohexane-1,2-diol;
((1S,3R)-3-((6-((6-fluoro-3H-imidazo[4,5-b]pyridin-3-yl)methyl)benzo[d]thiazol-2-yl)amino)cyclohexyl)methanol;
3-((6-((6-fluoro-3H-imidazo[4,5-b]pyridin-3-yl)methyl)benzo[d]thiazol-2-yl)amino)cyclohexyl)methanol;
6-chloro-1-((2-(((1R,2R)-2-hydroxycyclohexyl)amino)benzo[d]oxazol-6-yl)methyl)-1H-benzo[d]imidazole-5-carbonitrile;
6-chloro-1-((2-((2-hydroxycyclohexyl)amino)benzo[d]oxazol-6-yl)methyl)-1H-benzo[d]imidazole-5-carbonitrile;
2-((1-((2-(((1R,2R)-2-hydroxycyclohexyl)amino)benzo[d]thiazol-6-yl)methyl)-1H-benzo[d]imidazol-5-yl)oxy)acetonitrile;
2-((1-((2-((2-hydroxycyclohexyl)amino)benzo[d]thiazol-6-yl)methyl)-1H-benzo[d]imidazol-5-yl)oxy)acetonitrile;
6-((6-fluoro-3H-imidazo[4,5-b]pyridin-3-yl)methyl)-N-(2-methoxyphenyl)benzo[d]thiazol-2-amine;
N-((1R,2R)-2-chlorocyclohexyl)-6-((6-fluoro-3H-imidazo[4,5-b]pyridin-3-yl)methyl)benzo[d]thiazol-2-amine;
N-(2-chlorocyclohexyl)-6-((6-fluoro-3H-imidazo[4,5-b]pyridin-3-yl)methyl)benzo[d]thiazol-2-amine;
1-(3-((2-(((1R,2R)-2-hydroxycyclohexyl)amino)benzo[d]thiazol-6-yl)methyl)imidazo[1,2-a]pyridin-7-yl)piperidin-4-ol;
1-(3-((2-((2-hydroxycyclohexyl)amino)benzo[d]thiazol-6-yl)methyl)imidazo[1,2-a]pyridin-7-yl)piperidin-4-ol;
1-(3-((2-(((1R,2R)-2-hydroxycyclohexyl)amino)benzo[d]thiazol-6-yl)methyl)imidazo[1,2-a]pyridin-7-yl)ethanone;
1-(3-((2-((2-hydroxycyclohexyl)amino)benzo[d]thiazol-6-yl)methyl)imidazo[1,2-a]pyridin-7-yl)ethanone;
(1R,2R)-2-((6-((7-(1-hydroxyethyl)imidazo[1,2-a]pyridin-3-yl)methyl)benzo[d]thiazol-2-yl)amino)cyclohexanol;
2-((6-((7-(1-hydroxyethyl)imidazo[1,2-a]pyridin-3-yl)methyl)benzo[d]thiazol-2-yl)amino)cyclohexanol;
1-(3-((2-(((1R,2R)-2-hydroxycyclohexyl)amino)benzo[d]thiazol-6-yl)methyl)imidazo[1,2-a]pyridin-7-yl)ethanone oxime;
1-(3-((2-((2-hydroxycyclohexyl)amino)benzo[d]thiazol-6-yl)methyl)imidazo[1,2-a]pyridin-7-yl)ethanone oxime;
(1R,2R)-2-((6-((5-bromo-7-fluoro-1H-benzo[d]imidazol-1-yl)methyl)benzo[d]thiazol-2-yl)amino)cyclohexanol;
2-((6-((5-bromo-7-fluoro-1H-benzo[d]imidazol-1-yl)methyl)benzo[d]thiazol-2-yl)amino)cyclohexanol;

1-(3-((2-(((1R,2R)-2-hydroxycyclohexyl)amino)benzo[d]thiazol-6-yl)methyl)imidazo[1,2-a]pyridin-7-yl)ethanone O-methyl oxime;

1-(3-((2-((2-hydroxycyclohexyl)amino)benzo[d]thiazol-6-yl)methyl)imidazo[1,2-a]pyridin-7-yl)ethanone O-methyl oxime;

7-fluoro-1-((2-(((1R,2R)-2-hydroxycyclohexyl)amino)benzo[d]thiazol-6-yl)methyl)-1H-benzo[d]imidazole-5-carbonitrile;

7-fluoro-1-((2-((2-hydroxycyclohexyl)amino)benzo[d]thiazol-6-yl)methyl)-1H-benzo[d]imidazole-5-carbonitrile;

(1R,2R)-2-((6-((7-fluoro-5-vinyl-1H-benzo[d]imidazol-1-yl)methyl)benzo[d]thiazol-2-yl)amino)cyclohexanol;

2-((6-((7-fluoro-5-vinyl-1H-benzo[d]imidazol-1-yl)methyl)benzo[d]thiazol-2-yl)amino)cyclohexanol;

(1R,2R)-2-((6-((5-(3,6-dihydro-2H-pyran-4-yl)-7-fluoro-1H-benzo[d]imidazol-1-yl)methyl)benzo[d]thiazol-2-yl)amino)cyclohexanol;

2-((6-((5-(3,6-dihydro-2H-pyran-4-yl)-7-fluoro-1H-benzo[d]imidazol-1-yl)methyl)benzo[d]thiazol-2-yl)amino)cyclohexanol;

(1R,2R)-2-((6-((5-morpholino-1H-benzo[d]imidazol-1-yl)methyl)benzo[d]thiazol-2-yl)amino)cyclohexanol;

2-((6-((5-morpholino-1H-benzo[d]imidazol-1-yl)methyl)benzo[d]thiazol-2-yl)amino)cyclohexanol;

1-(1-((2-(((1R,2R)-2-hydroxycyclohexyl)amino)benzo[d]thiazol-6-yl)methyl)-1H-benzo[d]imidazol-5-yl)piperidin-2-one;

1-(1-((2-((2-hydroxycyclohexyl)amino)benzo[d]thiazol-6-yl)methyl)-1H-benzo[d]imidazol-5-yl)piperidin-2-one;

(1R,2R)-2-((6-((5-(1H-pyrazol-3-yl)-1H-benzo[d]imidazol-1-yl)methyl)benzo[d]thiazol-2-yl)amino)cyclohexanol;

2-((6-((5-(1H-pyrazol-3-yl)-1H-benzo[d]imidazol-1-yl)methyl)benzo[d]thiazol-2-yl)amino)cyclohexanol;

(1R,2R)-2-((6-((6-(trifluoromethyl)-3H-imidazo[4,5-b]pyridin-3-yl)methyl)benzo[d]thiazol-2-yl)amino)cyclohexanol;

2-((6-((6-(trifluoromethyl)-3H-imidazo[4,5-b]pyridin-3-yl)methyl)benzo[d]thiazol-2-yl)amino)cyclohexanol;

(1S,2S)-2-((6-((6-fluoro-3H-imidazo[4,5-b]pyridin-3-yl)methyl)benzo[d]thiazol-2-yl)amino)cyclohexanol;

2-((6-((6-fluoro-3H-imidazo[4,5-b]pyridin-3-yl)methyl)benzo[d]thiazol-2-yl)amino)cyclohexanol;

(1R,2R)-2-((6-((7-(1H-imidazol-1-yl)imidazo[1,2-a]pyridin-3-yl)methyl)benzo[d]thiazol-2-yl)amino)cyclohexanol;

2-((6-((7-(1H-imidazol-1-yl)imidazo[1,2-a]pyridin-3-yl)methyl)benzo[d]thiazol-2-yl)amino)cyclohexanol;

(1R,2R)-2-((6-((7-(2H-1,2,3-triazol-2-yl)imidazo[1,2-a]pyridin-3-yl)methyl)benzo[d]thiazol-2-yl)amino)cyclohexanol;

2-((6-((7-(2H-1,2,3-triazol-2-yl)imidazo[1,2-a]pyridin-3-yl)methyl)benzo[d]thiazol-2-yl)amino)cyclohexanol;

(1R,2R)-2-((6-((7-vinylimidazo[1,2-a]pyridin-3-yl)methyl)benzo[d]thiazol-2-yl)amino)cyclohexanol;

2-((6-((7-vinylimidazo[1,2-a]pyridin-3-yl)methyl)benzo[d]thiazol-2-yl)amino)cyclohexanol;

(1R,2R)-2-((6-((7-(allyloxy)imidazo[1,2-a]pyridin-3-yl)methyl)benzo[d]thiazol-2-yl)amino)cyclohexanol;

2-((6-((7-(allyloxy)imidazo[1,2-a]pyridin-3-yl)methyl)benzo[d]thiazol-2-yl)amino)cyclohexanol;

(1R,2R)-2-((6-((7-(1H-1,2,3-triazol-1-yl)imidazo[1,2-a]pyridin-3-yl)methyl)benzo[d]thiazol-2-yl)amino)cyclohexanol;

2-((6-((7-(1H-1,2,3-triazol-1-yl)imidazo[1,2-a]pyridin-3-yl)methyl)benzo[d]thiazol-2-yl)amino)cyclohexanol;

N-((1R,2S)-2-chlorocyclohexyl)-6-((6-fluoro-3H-imidazo[4,5-b]pyridin-3-yl)methyl)benzo[d]thiazol-2-amine;

N-(2-chlorocyclohexyl)-6-((6-fluoro-3H-imidazo[4,5-b]pyridin-3-yl)methyl)benzo[d]thiazol-2-amine;

3-((2-(((1R,2R)-2-hydroxycyclohexyl)amino)benzo[d]thiazol-6-yl)methyl)imidazo[1,2-b]pyridazine-6-carbonitrile;

3-((2-((2-hydroxycyclohexyl)amino)benzo[d]thiazol-6-yl)methyl)imidazo[1,2-b]pyridazine-6-carbonitrile;

(E)-3-(1-((2-(((1R,2R)-2-hydroxycyclohexyl)amino)benzo[d]thiazol-6-yl)methyl)-1H-benzo[d]imidazol-5-yl)acrylic acid;

(E)-3-(1-((2-((2-hydroxycyclohexyl)amino)benzo[d]thiazol-6-yl)methyl)-1H-benzo[d]imidazol-5-yl)acrylic acid;

3-(1-((2-((2-hydroxycyclohexyl)amino)benzo[d]thiazol-6-yl)methyl)-1H-benzo[d]imidazol-5-yl)acrylic acid;

(1R,2R)-2-((6-((5-(1,2,3,6-tetrahydropyridin-4-yl)-1H-benzo[d]imidazol-1-yl)methyl)benzo[d]thiazol-2-yl)amino)cyclohexanol;

2-((6-((5-(1,2,3,6-tetrahydropyridin-4-yl)-1H-benzo[d]imidazol-1-yl)methyl)benzo[d]thiazol-2-yl)amino)cyclohexanol;

(1R,2R)-2-((6-((5-(1H-imidazol-1-yl)-1H-benzo[d]imidazol-1-yl)methyl)benzo[d]thiazol-2-yl)amino)cyclohexanol;

2-((6-((5-(1H-imidazol-1-yl)-1H-benzo[d]imidazol-1-yl)methyl)benzo[d]thiazol-2-yl)amino)cyclohexanol;

(1R,2R)-2-((6-((5-(2-methyl-2H-tetrazol-5-yl)-1H-benzo[d]imidazol-1-yl)methyl)benzo[d]thiazol-2-yl)amino)cyclohexanol;

2-((6-((5-(2-methyl-2H-tetrazol-5-yl)-1H-benzo[d]imidazol-1-yl)methyl)benzo[d]thiazol-2-yl)amino)cyclohexanol;

(1S,2R,3R)-3-((6-((6-fluoro-3H-imidazo[4,5-b]pyridin-3-yl)methyl)benzo[d]thiazol-2-yl)amino)cyclohexane-1,2-diol;

3-((6-((6-fluoro-3H-imidazo[4,5-b]pyridin-3-yl)methyl)benzo[d]thiazol-2-yl)amino)cyclohexane-1,2-diol;

(1R,2S,3R)-3-((6-((7-(1H-pyrazol-1-yl)imidazo[1,2-a]pyridin-3-yl)methyl)benzo[d]thiazol-2-yl)amino)cyclohexane-1,2-diol;

3-((6-((7-(1H-pyrazol-1-yl)imidazo[1,2-a]pyridin-3-yl)methyl)benzo[d]thiazol-2-yl)amino)cyclohexane-1,2-diol;

(1R,2S,3R)-3-((6-((5-methoxy-1H-benzo[d]imidazol-1-yl)methyl)benzo[d]thiazol-2-yl)amino)cyclohexane-1,2-diol;

3-((6-((5-methoxy-1H-benzo[d]imidazol-1-yl)methyl)benzo[d]thiazol-2-yl)amino)cyclohexane-1,2-diol;

(1R,2S,3R)-3-((6-((7-(2H-1,2,3-triazol-2-yl)imidazo[1,2-a]pyridin-3-yl)methyl)benzo[d]thiazol-2-yl)amino)cyclohexane-1,2-diol;

3-((6-((7-(2H-1,2,3-triazol-2-yl)imidazo[1,2-a]pyridin-3-yl)methyl)benzo[d]thiazol-2-yl)amino)cyclohexane-1,2-diol;

(1R,2S,3R)-3-((6-((5-vinyl-1H-benzo[d]imidazol-1-yl)methyl)benzo[d]thiazol-2-yl)amino)cyclohexane-1,2-diol;

3-((6-((5-vinyl-1H-benzo[d]imidazol-1-yl)methyl)benzo[d]thiazol-2-yl)amino)cyclohexane-1,2-diol;

(1R,2S,3R)-3-((6-((5-(oxetan-3-yloxy)-1H-benzo[d]imidazol-1-yl)methyl)benzo[d]thiazol-2-yl)amino)cyclohexane-1,2-diol;

3-((6-((5-(oxetan-3-yloxy)-1H-benzo[d]imidazol-1-yl)methyl)benzo[d]thiazol-2-yl)amino)cyclohexane-1,2-diol;

(1R,2S,3R)-3-((6-((6-(1H-1,2,4-triazol-1-yl)-3H-imidazo[4,5-b]pyridin-3-yl)methyl)benzo[d]thiazol-2-yl)amino)cyclohexane-1,2-diol;

3-((6-((6-(1H-1,2,4-triazol-1-yl)-3H-imidazo[4,5-b]pyridin-3-yl)methyl)benzo[d]thiazol-2-yl)amino)cyclohexane-1,2-diol;

(1R,2S,3R)-3-((6-((5-morpholino-1H-benzo[d]imidazol-1-yl)methyl)benzo[d]thiazol-2-yl)amino)cyclohexane-1,2-diol;

3-((6-((5-morpholino-1H-benzo[d]imidazol-1-yl)methyl)benzo[d]thiazol-2-yl)amino)cyclohexane-1,2-diol;

(1R,2S,3R)-3-((6-((5-(2-methyl-2H-tetrazol-5-yl)-1H-benzo[d]imidazol-1-yl)methyl)benzo[d]thiazol-2-yl)amino)cyclohexane-1,2-diol; and 3-((6-((5-(2-methyl-2H-tetrazol-5-yl)-1H-benzo[d]imidazol-1-yl)methyl)benzo[d]thiazol-2-yl)amino)cyclohexane-1,2-diol.

13. The method of claim 1, wherein the disease is modulated by CSF1R, FLT3, KIT, and/or PDGFRβ kinase.

14. The method of claim 13, wherein the disease is modulated by wild type or mutant CSF1R, FLT3, KIT, and/or PDGFRβ kinase.

15. The method of claim 14 further comprising administering a second pharmaceutical agent selected from anti-proliferative agent, anti-inflammatory agent, immunomodulatory agent and immunosuppressive agent.

16. A method of modulating a CSF1R, FLT3, KIT, and/or PDGFRβ kinase by administering a compound of formula IV:

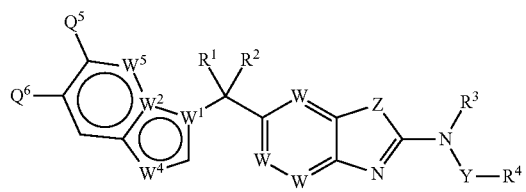

IV or a pharmaceutically acceptable salt, solvate, hydrate, stereoiomer, mixture of stereoisomers or racemic mixture of stereoisomers thereof, wherein:

$R^1$ and $R^2$ are each independently selected from hydrogen or halogen;

$R^3$ is hydrogen or alkyl;

$R^4$ is phenyl or cyclohexyl, where $R^4$ is optionally substituted with one, two or three groups selected from $Q^1$;

each $Q^1$ is independently deuterium, halo, cyano, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uS(O)_tR^w$, —$R^uN(R^x)C(J)R^x$, —$R^uN(R^x)C(J)OR^x$, —$R^uN(R^x)S(O)_tR^w$, =$NOR^d$, or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one to three $Q^3$ groups; each $Q^3$ is independently selected from deuterium, halo, hydroxyl, alkyl, haloalkyl and hydroxyalkyl;

Y is —$(CR^5R^6)_q$—;

$R^5$ and $R^6$ are each independently hydrogen, halo, alkyl, haloalkyl or hydroxyalkyl;

Z is O, S, or NH;

each W is independently $CR^8$ or N;

$R^8$ is hydrogen, halo, haloalkyl or alkyl;

$W^1$ is N or C;

$W^2$ is N or $CR^{9b}$, $R^{9b}$ is hydrogen or $Q^2$;

$W^4$ is N or $CR^{11b}$, $W^5$ is N or $CR^{13}$;

$R^{11b}$ and $R^{13}$ are each independently hydrogen or $Q^2$;

$Q^2$ is halo, deuterium, cyano, oxo, thioxo, alkyl, haloalkyl, haloalkenyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)R^uN(R^y)(R^z)$, —$R^uC(J)N(R^y)OR^x$, —$C(=NOR^x)R^x$, —$R^uS(O)_tR^w$, —$R^uN(R^x)C(J)R^x$, —$R^uN(R^x)C(J)OR^x$, —$R^uN(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one to three $Q^4$ groups, each $Q^4$ is independently selected from halo, deuterium, hydroxyl, alkyl, haloalkyl and hydroxyalkyl;

$Q^5$ and $Q^6$ are each independently hydrogen, deuterium, halo, cyano, oxo, thioxo, alkyl, haloalkyl, aminoalkyl, alkenyl, haloalkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, —$R^uOR^x$, —$R^uOR^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)R^uN(R^y)(R^z)$, —$R^uC(J)N(R^y)OR^x$, —$C(=NOR^x)R^x$, —$R^uS(O)_tR^w$, —$R^uN(R^x)C(J)R^x$, —$R^uN(R^x)C(J)OR^x$, —$R^uN(R^x)S(O)_tR^w$ or —$C(=NR^y)N(R^y)OR^x$, where the alkyl, haloalkyl, aminoalkyl, alkenyl, alkynyl, cycloalkyl, cycloalkenyl, aryl, heteroaryl, and heterocyclyl groups are optionally substituted with one or more $Q^8$ groups; each $Q^8$ is independently selected from halo, deuterium, hydroxyl, alkyl, haloalkyl and hydroxyalkyl;

each $R^d$ is independently hydrogen or alkyl;

$R^d$ is hydrogen or alkyl;

each $R^u$ is independently alkylene, alkenylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, cyanoalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one, two or three $Q^7$ groups; each $Q^7$ is independently selected from halo, deuterium, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^x$ or S;

each t is independently an integer from 0-2; and q is an integer from 0-4.

17. The method of claim 1, wherein the disease is acute myeloid leukemia, chronic myeloid leukemia, prostate cancer, breast cancer, melanoma, rheumatoid arthritis or Alzheimer's disease.

18. The method of claim 1, wherein the disease is Alzheimer's disease.

19. The method of claim 1, wherein the disease is acute myeloid leukemia.

20. The method of claim 1, wherein arthritis is osteoarthritis or rheumatoid arthritis.

* * * * *